United States Patent
Andersen et al.

(10) Patent No.: US 11,001,836 B2
(45) Date of Patent: May 11, 2021

(54) LIBRARY PREPARATION METHODS AND COMPOSITIONS AND USES THEREFOR

(71) Applicant: LIFE TECHNOLOGIES CORPORATION, Carlsbad, CA (US)

(72) Inventors: Mark Andersen, Carlsbad, CA (US); Daniel Mazur, San Diego, CA (US); Sihong Chen, Vista, CA (US); Guobin Luo, Oceanside, CA (US); Xinzhan Peng, Carlsbad, CA (US)

(73) Assignee: Life Technologies Corporation, Carlsbad, CA (US)

( * ) Notice: Subject to any disclaimer, the term of this patent is extended or adjusted under 35 U.S.C. 154(b) by 205 days.

(21) Appl. No.: 16/024,175

(22) Filed: Jun. 29, 2018

(65) Prior Publication Data
US 2019/0002872 A1    Jan. 3, 2019

Related U.S. Application Data

(60) Provisional application No. 62/527,893, filed on Jun. 30, 2017, provisional application No. 62/614,362, (Continued)

(51) Int. Cl.
| | |
|---|---|
| C12N 15/10 | (2006.01) |
| C12Q 1/6806 | (2018.01) |
| C12Q 1/6853 | (2018.01) |
| C12Q 1/6855 | (2018.01) |
| C12Q 1/686 | (2018.01) |
| C40B 20/04 | (2006.01) |

(Continued)

(52) U.S. Cl.
CPC ..... *C12N 15/1068* (2013.01); *C12N 15/1065* (2013.01); *C12Q 1/6806* (2013.01); *C12Q 1/6853* (2013.01); *C12Q 1/6855* (2013.01); *C12Q 1/686* (2013.01); *C40B 20/04* (2013.01); *C40B 40/06* (2013.01); *C40B 50/06* (2013.01)

(58) Field of Classification Search
None
See application file for complete search history.

(56) References Cited

FOREIGN PATENT DOCUMENTS

WO    WO-2013081864 A1    6/2013

OTHER PUBLICATIONS

International Search Report and Written Opinion for PCT Application No. PCT/US2018/040432 dated Oct. 17, 2018, 13 pages.
(Continued)

*Primary Examiner* — Kaijiang Zhang

(57) ABSTRACT

Provided are methods for preparing a library of target nucleic acid sequences, as well as compositions and uses therefor. Methods comprise contacting a nucleic acid sample with a plurality of adaptors capable of amplification of one or more target nucleic acid sequences under conditions wherein the target nucleic acid(s) undergo a first amplification; digesting the resulting first amplification products; repairing the digested target amplicons; and amplifying the repaired products in a second amplification, thereby producing a library of target nucleic acid sequence. Each of the plurality of adaptor compositions comprise a handle and a targeted nucleic acid sequence and optionally one or more tag sequences. Provided methods may be carried out in a single, addition only workflow reaction, allowing for rapid production of highly multiplexed targeted libraries, optionally including unique tag sequences. Resulting library compositions are useful for a variety of applications, including sequencing applications.

20 Claims, 10 Drawing Sheets
Specification includes a Sequence Listing.

Related U.S. Application Data filed on Jan. 6, 2018, provisional application No. 62/685,424, filed on Jun. 15, 2018.

(51) Int. Cl.
    *C40B 50/06*     (2006.01)
    *C40B 40/06*     (2006.01)

(56) References Cited

OTHER PUBLICATIONS

Varley K.E, et al., "Nested Patch PCR Enables Highly Multiplexed Mutation Discovery in Candidate Genes", Genome Research, Cold Spring Harbor Laboratory Press, US, vol. 18, No. 11, Nov. 1, 2008 (Nov. 1, 2008), pp. 1844-1850, XP002678933, DOI: 10.1101/GR. 078204.108, Retrieved from the Internet: URL: http://genome.cshlp.org/content/18/11/1844 [retrieved on Oct. 10, 2008].

SEQUENCE LISTING

<160> NUMBER OF SEQ ID NOS: 1785

<210> SEQ ID NO 1
<211> LENGTH: 50
<212> TYPE: DNA
<213> ORGANISM: Artificial Sequence
<220> FEATURE:
<223> OTHER INFORMATION: Synthetic DNA/RNA, Forward Adaptor
<220> FEATURE:
<221> NAME/KEY: misc_feature
<222> LOCATION: (21)..(23)
<223> OTHER INFORMATION: n is a, c, g, t or u
<220> FEATURE:
<221> NAME/KEY: misc_feature
<222> LOCATION: (27)..(29)
<223> OTHER INFORMATION: n is a, c, g, t or u

<400> SEQUENCE: 1
tctgtacggt gacaaggcgu nnnactnnnt gaugaggacc gucgctuggt        50

<210> SEQ ID NO 2
<211> LENGTH: 61
<212> TYPE: DNA
<213> ORGANISM: Artificial Sequence
<220> FEATURE:
<223> OTHER INFORMATION: Synthetic DNA/RNA, Rev Adaptor B
<220> FEATURE:
<221> NAME/KEY: misc_feature
<222> LOCATION: (22)..(24)
<223> OTHER INFORMATION: n is a, c, g, t or u
<220> FEATURE:
<221> NAME/KEY: misc_feature
<222> LOCATION: (28)..(30)
<223> OTHER INFORMATION: n is a, c, g, t or u

<400> SEQUENCE: 2
ctctatgggc agtcggtgat unnnactnnn tgauccttct gcauggtatt ctttctctuc     60
c                                                                    61

<210> SEQ ID NO 3
<211> LENGTH: 60
<212> TYPE: DNA
<213> ORGANISM: Artificial Sequence
<220> FEATURE:
<223> OTHER INFORMATION: Synthetic DNA/RNA, Rev Adaptor C
<220> FEATURE:

```
<221> NAME/KEY: misc_feature
<222> LOCATION: (21)..(23)
<223> OTHER INFORMATION: n is a, c, g, t or u
<220> FEATURE:
<221> NAME/KEY: misc_feature
<222> LOCATION: (27)..(29)
<223> OTHER INFORMATION: n is a, c, g, t or u

<400> SEQUENCE: 3
tctagtcggt cagtcacggu nnnactnnnt gauccttctg cauggtattc tttctctucc    60

<210> SEQ ID NO 4
<211> LENGTH: 60
<212> TYPE: DNA
<213> ORGANISM: Artificial Sequence
<220> FEATURE:
<223> OTHER INFORMATION: Synthetic DNA/RNA, Rev Adaptor D
<220> FEATURE:
<221> NAME/KEY: misc_feature
<222> LOCATION: (21)..(23)
<223> OTHER INFORMATION: n is a, c, g, t or u
<220> FEATURE:
<221> NAME/KEY: misc_feature
<222> LOCATION: (27)..(29)
<223> OTHER INFORMATION: n is a, c, g, t or u

<400> SEQUENCE: 4
tctagtgctg cagtcacggu nnnactnnnt gauccttctg cauggtattc tttctctucc    60

<210> SEQ ID NO 5
<211> LENGTH: 60
<212> TYPE: DNA
<213> ORGANISM: Artificial Sequence
<220> FEATURE:
<223> OTHER INFORMATION: Synthetic DNA/RNA, Rev Adaptor E
<220> FEATURE:
<221> NAME/KEY: misc_feature
<222> LOCATION: (21)..(23)
<223> OTHER INFORMATION: n is a, c, g, t or u
<220> FEATURE:
<221> NAME/KEY: misc_feature
<222> LOCATION: (27)..(29)
<223> OTHER INFORMATION: n is a, c, g, t or u

<400> SEQUENCE: 5
tgacaaggcg tagtcacggu nnnactnnnt gauccttctg cauggtattc tttctctucc    60

<210> SEQ ID NO 6
<211> LENGTH: 19
<212> TYPE: DNA
<213> ORGANISM: Artificial Sequence
<220> FEATURE:
<223> OTHER INFORMATION: Synthetic Primer, Forward

<400> SEQUENCE: 6
tctgtacggt gacaaggcg                                                 19

<210> SEQ ID NO 7
<211> LENGTH: 20
<212> TYPE: DNA
<213> ORGANISM: Artificial Sequence
<220> FEATURE:
<223> OTHER INFORMATION: Synthetic Primer, Reverse

<400> SEQUENCE: 7
ctctatgggc agtcggtgat                                                20

<210> SEQ ID NO 8
<211> LENGTH: 22
```

```
<212> TYPE: DNA
<213> ORGANISM: Artificial Sequence
<220> FEATURE:
<223> OTHER INFORMATION: Synthetic DNA/RNA primer, F1

<400> SEQUENCE: 8
gctcccaggc acutgatgau ac                                              22

<210> SEQ ID NO 9
<211> LENGTH: 23
<212> TYPE: DNA
<213> ORGANISM: Artificial Sequence
<220> FEATURE:
<223> OTHER INFORMATION: Synthetic DNA/RNA primer, F2

<400> SEQUENCE: 9
tgttgccatt ucagggtttc uga                                             23

<210> SEQ ID NO 10
<211> LENGTH: 25
<212> TYPE: RNA
<213> ORGANISM: Artificial Sequence
<220> FEATURE:
<223> OTHER INFORMATION: Synthetic Primer, F3

<400> SEQUENCE: 10
accaaugcga ggaagaaaaa caauc                                           25

<210> SEQ ID NO 11
<211> LENGTH: 24
<212> TYPE: DNA
<213> ORGANISM: Artificial Sequence
<220> FEATURE:
<223> OTHER INFORMATION: Synthetic DNA/RNA primer, F4

<400> SEQUENCE: 11
tcttcagaau cttgttggcu gcat                                            24

<210> SEQ ID NO 12
<211> LENGTH: 23
<212> TYPE: DNA
<213> ORGANISM: Artificial Sequence
<220> FEATURE:
<223> OTHER INFORMATION: Synthetic DNA/RNA primer, F5

<400> SEQUENCE: 12
agagttgcau ccttcccttc uct                                             23

<210> SEQ ID NO 13
<211> LENGTH: 21
<212> TYPE: DNA
<213> ORGANISM: Artificial Sequence
<220> FEATURE:
<223> OTHER INFORMATION: Synthetic DNA/RNA primer, F6

<400> SEQUENCE: 13
ctggcaugac gcagtttctu c                                               21

<210> SEQ ID NO 14
<211> LENGTH: 25
<212> TYPE: DNA
<213> ORGANISM: Artificial Sequence
<220> FEATURE:
<223> OTHER INFORMATION: Synthetic DNA/RNA primer, F7

<400> SEQUENCE: 14
```
gatcaaagag acgaaguctc tugca                                    25

<210> SEQ ID NO 15
<211> LENGTH: 22
<212> TYPE: DNA
<213> ORGANISM: Artificial Sequence
<220> FEATURE:
<223> OTHER INFORMATION: Synthetic DNA/RNA primer, F8

<400> SEQUENCE: 15
cttgccuaga cagcaccgua at                                       22

<210> SEQ ID NO 16
<211> LENGTH: 23
<212> TYPE: DNA
<213> ORGANISM: Artificial Sequence
<220> FEATURE:
<223> OTHER INFORMATION: Synthetic DNA/RNA primer, F9

<400> SEQUENCE: 16
tggtttctgg ugggaccatt aug                                      23

<210> SEQ ID NO 17
<211> LENGTH: 27
<212> TYPE: DNA
<213> ORGANISM: Artificial Sequence
<220> FEATURE:
<223> OTHER INFORMATION: Synthetic DNA/RNA primer, F10

<400> SEQUENCE: 17
ttgaaagaga acacacutac tcuccac                                  27

<210> SEQ ID NO 18
<211> LENGTH: 27
<212> TYPE: DNA
<213> ORGANISM: Artificial Sequence
<220> FEATURE:
<223> OTHER INFORMATION: Synthetic DNA/RNA primer, F11

<400> SEQUENCE: 18
ctctaccaga gutaatcaac tgaugca                                  27

<210> SEQ ID NO 19
<211> LENGTH: 26
<212> TYPE: DNA
<213> ORGANISM: Artificial Sequence
<220> FEATURE:
<223> OTHER INFORMATION: Synthetic DNA/RNA primer, F12

<400> SEQUENCE: 19
tatcaactgt ccutgttggc aaauca                                   26

<210> SEQ ID NO 20
<211> LENGTH: 27
<212> TYPE: DNA
<213> ORGANISM: Artificial Sequence
<220> FEATURE:
<223> OTHER INFORMATION: Synthetic DNA/RNA primer, F13

<400> SEQUENCE: 20
gcaaatgact ugctattatt gauggca                                  27

<210> SEQ ID NO 21
<211> LENGTH: 28
<212> TYPE: DNA
<213> ORGANISM: Artificial Sequence

```
<220> FEATURE:
<223> OTHER INFORMATION: Synthetic DNA/RNA primer, F14

<400> SEQUENCE: 21
gtgggatcat autcatctac aaaguggt                                              28

<210> SEQ ID NO 22
<211> LENGTH: 20
<212> TYPE: DNA
<213> ORGANISM: Artificial Sequence
<220> FEATURE:
<223> OTHER INFORMATION: Synthetic DNA/RNA primer, F15

<400> SEQUENCE: 22
ggaggtcaug gcatcgagut                                                       20

<210> SEQ ID NO 23
<211> LENGTH: 22
<212> TYPE: DNA
<213> ORGANISM: Artificial Sequence
<220> FEATURE:
<223> OTHER INFORMATION: Synthetic DNA/RNA primer, F16

<400> SEQUENCE: 23
gtgaggcagu ctttacucac ct                                                    22

<210> SEQ ID NO 24
<211> LENGTH: 22
<212> TYPE: DNA
<213> ORGANISM: Artificial Sequence
<220> FEATURE:
<223> OTHER INFORMATION: Synthetic DNA/RNA primer, F17

<400> SEQUENCE: 24
gggaaatgug agccctugag at                                                    22

<210> SEQ ID NO 25
<211> LENGTH: 22
<212> TYPE: DNA
<213> ORGANISM: Artificial Sequence
<220> FEATURE:
<223> OTHER INFORMATION: Synthetic DNA/RNA primer, F18

<400> SEQUENCE: 25
actcttgcuc cttccatcct ug                                                    22

<210> SEQ ID NO 26
<211> LENGTH: 22
<212> TYPE: DNA
<213> ORGANISM: Artificial Sequence
<220> FEATURE:
<223> OTHER INFORMATION: Synthetic DNA/RNA primer, F19

<400> SEQUENCE: 26
cccaaugcag cgaacaatgt uc                                                    22

<210> SEQ ID NO 27
<211> LENGTH: 22
<212> TYPE: DNA
<213> ORGANISM: Artificial Sequence
<220> FEATURE:
<223> OTHER INFORMATION: Synthetic DNA/RNA primer, F20

<400> SEQUENCE: 27
gatcagggcu tccaugagga aa                                                    22
```

<210> SEQ ID NO 28
<211> LENGTH: 24
<212> TYPE: DNA
<213> ORGANISM: Artificial Sequence
<220> FEATURE:
<223> OTHER INFORMATION: Synthetic DNA/RNA primer, F21

<400> SEQUENCE: 28
ctcaagagug agccacttct uacc                                      24

<210> SEQ ID NO 29
<211> LENGTH: 33
<212> TYPE: DNA
<213> ORGANISM: Artificial Sequence
<220> FEATURE:
<223> OTHER INFORMATION: Synthetic DNA/RNA primer, F22

<400> SEQUENCE: 29
agaataaaac acauacaagt tggaaatttc ugg                            33

<210> SEQ ID NO 30
<211> LENGTH: 22
<212> TYPE: DNA
<213> ORGANISM: Artificial Sequence
<220> FEATURE:
<223> OTHER INFORMATION: Synthetic DNA/RNA primer, F23

<400> SEQUENCE: 30
accugagcca aggactttua cc                                        22

<210> SEQ ID NO 31
<211> LENGTH: 27
<212> TYPE: DNA
<213> ORGANISM: Artificial Sequence
<220> FEATURE:
<223> OTHER INFORMATION: Synthetic DNA/RNA primer, F24

<400> SEQUENCE: 31
tgtcaattag cuggaacatc ugaaact                                   27

<210> SEQ ID NO 32
<211> LENGTH: 24
<212> TYPE: DNA
<213> ORGANISM: Artificial Sequence
<220> FEATURE:
<223> OTHER INFORMATION: Synthetic DNA/RNA primer, F25

<400> SEQUENCE: 32
gtgccctatu acctcaatca ucct                                      24

<210> SEQ ID NO 33
<211> LENGTH: 22
<212> TYPE: DNA
<213> ORGANISM: Artificial Sequence
<220> FEATURE:
<223> OTHER INFORMATION: Synthetic DNA/RNA primer, F26

<400> SEQUENCE: 33
ccagacagaa aagcggcugt ua                                        22

<210> SEQ ID NO 34
<211> LENGTH: 32
<212> TYPE: DNA
<213> ORGANISM: Artificial Sequence
<220> FEATURE:
<223> OTHER INFORMATION: Synthetic DNA/RNA primer, F27

<400> SEQUENCE: 34
cctagtagaa tgttuactac caaatggaau ga                          32

<210> SEQ ID NO 35
<211> LENGTH: 27
<212> TYPE: DNA
<213> ORGANISM: Artificial Sequence
<220> FEATURE:
<223> OTHER INFORMATION: Synthetic DNA/RNA primer, F28

<400> SEQUENCE: 35
tttttgauga aacaagacga ctttgug                                27

<210> SEQ ID NO 36
<211> LENGTH: 27
<212> TYPE: DNA
<213> ORGANISM: Artificial Sequence
<220> FEATURE:
<223> OTHER INFORMATION: Synthetic DNA/RNA primer, F29

<400> SEQUENCE: 36
cacagcuaca ccatatatga auggaga                                27

<210> SEQ ID NO 37
<211> LENGTH: 29
<212> TYPE: DNA
<213> ORGANISM: Artificial Sequence
<220> FEATURE:
<223> OTHER INFORMATION: Synthetic DNA/RNA primer, F30

<400> SEQUENCE: 37
gatctatgtu cgaacaggta tcuaccatg                              29

<210> SEQ ID NO 38
<211> LENGTH: 28
<212> TYPE: DNA
<213> ORGANISM: Artificial Sequence
<220> FEATURE:
<223> OTHER INFORMATION: Synthetic DNA/RNA primer, F31

<400> SEQUENCE: 38
gggaagaaaa gugttttgaa atgtgtut                               28

<210> SEQ ID NO 39
<211> LENGTH: 24
<212> TYPE: DNA
<213> ORGANISM: Artificial Sequence
<220> FEATURE:
<223> OTHER INFORMATION: Synthetic DNA/RNA primer, F32

<400> SEQUENCE: 39
tttgaatctt uggccagtac cuca                                   24

<210> SEQ ID NO 40
<211> LENGTH: 31
<212> TYPE: DNA
<213> ORGANISM: Artificial Sequence
<220> FEATURE:
<223> OTHER INFORMATION: Synthetic DNA/RNA primer, F33

<400> SEQUENCE: 40
gactagcuag agacaatgaa tuaagggaaa a                           31

<210> SEQ ID NO 41

<211> LENGTH: 27
<212> TYPE: DNA
<213> ORGANISM: Artificial Sequence
<220> FEATURE:
<223> OTHER INFORMATION: Synthetic DNA/RNA primer, F34

<400> SEQUENCE: 41
ctgagatgca caauaaaaca gtuagcc					27

<210> SEQ ID NO 42
<211> LENGTH: 26
<212> TYPE: DNA
<213> ORGANISM: Artificial Sequence
<220> FEATURE:
<223> OTHER INFORMATION: Synthetic DNA/RNA primer, F35

<400> SEQUENCE: 42
gacaucucua aacaggagaa gaagga					26

<210> SEQ ID NO 43
<211> LENGTH: 25
<212> TYPE: DNA
<213> ORGANISM: Artificial Sequence
<220> FEATURE:
<223> OTHER INFORMATION: Synthetic DNA/RNA primer, F36

<400> SEQUENCE: 43
tcttttctca agutggcctg aauca					25

<210> SEQ ID NO 44
<211> LENGTH: 30
<212> TYPE: DNA
<213> ORGANISM: Artificial Sequence
<220> FEATURE:
<223> OTHER INFORMATION: Synthetic DNA/RNA primer, F37

<400> SEQUENCE: 44
caatcttttg augacattgc atacatucga				30

<210> SEQ ID NO 45
<211> LENGTH: 21
<212> TYPE: DNA
<213> ORGANISM: Artificial Sequence
<220> FEATURE:
<223> OTHER INFORMATION: Synthetic DNA/RNA primer, F38

<400> SEQUENCE: 45
gtatgcaggc aucctcagcu a						21

<210> SEQ ID NO 46
<211> LENGTH: 20
<212> TYPE: DNA
<213> ORGANISM: Artificial Sequence
<220> FEATURE:
<223> OTHER INFORMATION: Synthetic DNA/RNA primer, F39

<400> SEQUENCE: 46
cuggugaccg aggacaacgt						20

<210> SEQ ID NO 47
<211> LENGTH: 20
<212> TYPE: DNA
<213> ORGANISM: Artificial Sequence
<220> FEATURE:
<223> OTHER INFORMATION: Synthetic DNA/RNA primer, F40

<400> SEQUENCE: 47

```
gtccugggag tcucaggaca                                           20

<210> SEQ ID NO 48
<211> LENGTH: 22
<212> TYPE: DNA
<213> ORGANISM: Artificial Sequence
<220> FEATURE:
<223> OTHER INFORMATION: Synthetic DNA/RNA primer, F41

<400> SEQUENCE: 48
ccagttaccu gtcctggtca ut                                        22

<210> SEQ ID NO 49
<211> LENGTH: 26
<212> TYPE: DNA
<213> ORGANISM: Artificial Sequence
<220> FEATURE:
<223> OTHER INFORMATION: Synthetic DNA/RNA primer, F42

<400> SEQUENCE: 49
agtgaaaaac aagcuctcat gtcuga                                    26

<210> SEQ ID NO 50
<211> LENGTH: 29
<212> TYPE: DNA
<213> ORGANISM: Artificial Sequence
<220> FEATURE:
<223> OTHER INFORMATION: Synthetic DNA/RNA primer, F43

<400> SEQUENCE: 50
ggaaaaattg ugaagatctg tgacttugg                                 29

<210> SEQ ID NO 51
<211> LENGTH: 23
<212> TYPE: DNA
<213> ORGANISM: Artificial Sequence
<220> FEATURE:
<223> OTHER INFORMATION: Synthetic DNA/RNA primer, F44

<400> SEQUENCE: 51
agcactctga cauatggcca tut                                       23

<210> SEQ ID NO 52
<211> LENGTH: 23
<212> TYPE: DNA
<213> ORGANISM: Artificial Sequence
<220> FEATURE:
<223> OTHER INFORMATION: Synthetic DNA/RNA primer, F45

<400> SEQUENCE: 52
ggcacggtug aatgtaaggc tua                                       23

<210> SEQ ID NO 53
<211> LENGTH: 24
<212> TYPE: DNA
<213> ORGANISM: Artificial Sequence
<220> FEATURE:
<223> OTHER INFORMATION: Synthetic DNA/RNA primer, F46

<400> SEQUENCE: 53
cccacagaaa cccaugtaug aagt                                      24

<210> SEQ ID NO 54
<211> LENGTH: 23
<212> TYPE: DNA
```

```
<213> ORGANISM: Artificial Sequence
<220> FEATURE:
<223> OTHER INFORMATION: Synthetic DNA/RNA primer, F47

<400> SEQUENCE: 54
tugacagaac gggaagcccu cat                                              23

<210> SEQ ID NO 55
<211> LENGTH: 23
<212> TYPE: DNA
<213> ORGANISM: Artificial Sequence
<220> FEATURE:
<223> OTHER INFORMATION: Synthetic DNA/RNA primer, F48

<400> SEQUENCE: 55
ccttactcau ggtcggauca caa                                              23

<210> SEQ ID NO 56
<211> LENGTH: 26
<212> TYPE: DNA
<213> ORGANISM: Artificial Sequence
<220> FEATURE:
<223> OTHER INFORMATION: Synthetic DNA/RNA primer, F49

<400> SEQUENCE: 56
ccaatattat ggaucccaac tgccua                                           26

<210> SEQ ID NO 57
<211> LENGTH: 26
<212> TYPE: DNA
<213> ORGANISM: Artificial Sequence
<220> FEATURE:
<223> OTHER INFORMATION: Synthetic DNA/RNA primer, F50

<400> SEQUENCE: 57
gctactttga uttctccact uccaac                                           26

<210> SEQ ID NO 58
<211> LENGTH: 22
<212> TYPE: DNA
<213> ORGANISM: Artificial Sequence
<220> FEATURE:
<223> OTHER INFORMATION: Synthetic DNA/RNA primer, F51

<400> SEQUENCE: 58
aaaggcaugg agcatctgua ca                                               22

<210> SEQ ID NO 59
<211> LENGTH: 24
<212> TYPE: DNA
<213> ORGANISM: Artificial Sequence
<220> FEATURE:
<223> OTHER INFORMATION: Synthetic DNA/RNA primer, F52

<400> SEQUENCE: 59
gttatgtccu cattgcccuc aaca                                             24

<210> SEQ ID NO 60
<211> LENGTH: 22
<212> TYPE: DNA
<213> ORGANISM: Artificial Sequence
<220> FEATURE:
<223> OTHER INFORMATION: Synthetic DNA/RNA primer, F53

<400> SEQUENCE: 60
cgagggcaaa uacagcttug gt                                               22
```

<210> SEQ ID NO 61
<211> LENGTH: 29
<212> TYPE: DNA
<213> ORGANISM: Artificial Sequence
<220> FEATURE:
<223> OTHER INFORMATION: Synthetic DNA/RNA primer, F54

<400> SEQUENCE: 61
tgatggagau gtgataattu caggaaaca                                29

<210> SEQ ID NO 62
<211> LENGTH: 26
<212> TYPE: DNA
<213> ORGANISM: Artificial Sequence
<220> FEATURE:
<223> OTHER INFORMATION: Synthetic DNA/RNA primer, F55

<400> SEQUENCE: 62
gagacatgca ugaacatttt tcucca                                   26

<210> SEQ ID NO 63
<211> LENGTH: 22
<212> TYPE: DNA
<213> ORGANISM: Artificial Sequence
<220> FEATURE:
<223> OTHER INFORMATION: Synthetic DNA/RNA primer, F56

<400> SEQUENCE: 63
gcctctuaca cccaguggag aa                                       22

<210> SEQ ID NO 64
<211> LENGTH: 24
<212> TYPE: DNA
<213> ORGANISM: Artificial Sequence
<220> FEATURE:
<223> OTHER INFORMATION: Synthetic DNA/RNA primer, F57

<400> SEQUENCE: 64
ccttctcuct ctgtcauagg gact                                     24

<210> SEQ ID NO 65
<211> LENGTH: 21
<212> TYPE: DNA
<213> ORGANISM: Artificial Sequence
<220> FEATURE:
<223> OTHER INFORMATION: Synthetic DNA/RNA primer, F58

<400> SEQUENCE: 65
ctccaggaag ccuacgtgau g                                        21

<210> SEQ ID NO 66
<211> LENGTH: 23
<212> TYPE: DNA
<213> ORGANISM: Artificial Sequence
<220> FEATURE:
<223> OTHER INFORMATION: Synthetic DNA/RNA primer, F59

<400> SEQUENCE: 66
caggaacgua ctggugaaaa cac                                      23

<210> SEQ ID NO 67
<211> LENGTH: 22
<212> TYPE: DNA
<213> ORGANISM: Artificial Sequence
<220> FEATURE:

<223> OTHER INFORMATION: Synthetic DNA/RNA primer, F60

<400> SEQUENCE: 67
gcttgtaagu gcccgaagtg ua                                    22

<210> SEQ ID NO 68
<211> LENGTH: 23
<212> TYPE: DNA
<213> ORGANISM: Artificial Sequence
<220> FEATURE:
<223> OTHER INFORMATION: Synthetic DNA/RNA primer, F61

<400> SEQUENCE: 68
cgcagtgcua accaagttct tuc                                   23

<210> SEQ ID NO 69
<211> LENGTH: 23
<212> TYPE: DNA
<213> ORGANISM: Artificial Sequence
<220> FEATURE:
<223> OTHER INFORMATION: Synthetic DNA/RNA primer, F62

<400> SEQUENCE: 69
cagtcaaggu tgctgatttu ggt                                   23

<210> SEQ ID NO 70
<211> LENGTH: 20
<212> TYPE: DNA
<213> ORGANISM: Artificial Sequence
<220> FEATURE:
<223> OTHER INFORMATION: Synthetic DNA/RNA primer, F63

<400> SEQUENCE: 70
cgaatcgcua ccctgctgut                                       20

<210> SEQ ID NO 71
<211> LENGTH: 17
<212> TYPE: DNA
<213> ORGANISM: Artificial Sequence
<220> FEATURE:
<223> OTHER INFORMATION: Synthetic DNA/RNA primer, F64

<400> SEQUENCE: 71
taccgauacc gugcggg                                          17

<210> SEQ ID NO 72
<211> LENGTH: 22
<212> TYPE: DNA
<213> ORGANISM: Artificial Sequence
<220> FEATURE:
<223> OTHER INFORMATION: Synthetic DNA/RNA primer, F65

<400> SEQUENCE: 72
ctgtccucca caggcatttt ug                                    22

<210> SEQ ID NO 73
<211> LENGTH: 22
<212> TYPE: DNA
<213> ORGANISM: Artificial Sequence
<220> FEATURE:
<223> OTHER INFORMATION: Synthetic DNA/RNA primer, F66

<400> SEQUENCE: 73
ccatcccuga ctgtgagauc aa                                    22

```
<210> SEQ ID NO 74
<211> LENGTH: 29
<212> TYPE: DNA
<213> ORGANISM: Artificial Sequence
<220> FEATURE:
<223> OTHER INFORMATION: Synthetic DNA/RNA primer, F67

<400> SEQUENCE: 74
tcagtggaaa aauagcctca attctuacc                                       29

<210> SEQ ID NO 75
<211> LENGTH: 29
<212> TYPE: DNA
<213> ORGANISM: Artificial Sequence
<220> FEATURE:
<223> OTHER INFORMATION: Synthetic DNA/RNA primer, F68

<400> SEQUENCE: 75
tattatgact ugtcacaatg ucaccacat                                       29

<210> SEQ ID NO 76
<211> LENGTH: 26
<212> TYPE: DNA
<213> ORGANISM: Artificial Sequence
<220> FEATURE:
<223> OTHER INFORMATION: Synthetic DNA/RNA primer, F69

<400> SEQUENCE: 76
ttccutagtc tttcttugaa gcagca                                          26

<210> SEQ ID NO 77
<211> LENGTH: 26
<212> TYPE: DNA
<213> ORGANISM: Artificial Sequence
<220> FEATURE:
<223> OTHER INFORMATION: Synthetic DNA/RNA primer, F70

<400> SEQUENCE: 77
tctgacucca cgagaacttg aucata                                          26

<210> SEQ ID NO 78
<211> LENGTH: 25
<212> TYPE: DNA
<213> ORGANISM: Artificial Sequence
<220> FEATURE:
<223> OTHER INFORMATION: Synthetic DNA/RNA primer, F71

<400> SEQUENCE: 78
caaggcauaa aagctgggaa auagg                                           25

<210> SEQ ID NO 79
<211> LENGTH: 19
<212> TYPE: DNA
<213> ORGANISM: Artificial Sequence
<220> FEATURE:
<223> OTHER INFORMATION: Synthetic DNA/RNA primer, F72

<400> SEQUENCE: 79
ggctauggca ccugcaact                                                  19

<210> SEQ ID NO 80
<211> LENGTH: 20
<212> TYPE: DNA
<213> ORGANISM: Artificial Sequence
<220> FEATURE:
<223> OTHER INFORMATION: Synthetic DNA/RNA primer, F73
```

```
<400> SEQUENCE: 80
ccacagaucc actgugcgac                                              20

<210> SEQ ID NO 81
<211> LENGTH: 22
<212> TYPE: DNA
<213> ORGANISM: Artificial Sequence
<220> FEATURE:
<223> OTHER INFORMATION: Synthetic DNA/RNA primer, F74

<400> SEQUENCE: 81
ccatcctgac cuggtatggu ca                                           22

<210> SEQ ID NO 82
<211> LENGTH: 20
<212> TYPE: DNA
<213> ORGANISM: Artificial Sequence
<220> FEATURE:
<223> OTHER INFORMATION: Synthetic DNA/RNA primer, F75

<400> SEQUENCE: 82
cagctcgtuc atcgggacut                                              20

<210> SEQ ID NO 83
<211> LENGTH: 27
<212> TYPE: DNA
<213> ORGANISM: Artificial Sequence
<220> FEATURE:
<223> OTHER INFORMATION: Synthetic DNA/RNA primer, F76

<400> SEQUENCE: 83
cctccttccu agagagttag aguaact                                      27

<210> SEQ ID NO 84
<211> LENGTH: 24
<212> TYPE: DNA
<213> ORGANISM: Artificial Sequence
<220> FEATURE:
<223> OTHER INFORMATION: Synthetic DNA/RNA primer, F77

<400> SEQUENCE: 84
cactgtgtta cugccatcga ctua                                         24

<210> SEQ ID NO 85
<211> LENGTH: 28
<212> TYPE: DNA
<213> ORGANISM: Artificial Sequence
<220> FEATURE:
<223> OTHER INFORMATION: Synthetic DNA/RNA primer, F78

<400> SEQUENCE: 85
gattcaatca aacugcagag tattuggg                                     28

<210> SEQ ID NO 86
<211> LENGTH: 22
<212> TYPE: DNA
<213> ORGANISM: Artificial Sequence
<220> FEATURE:
<223> OTHER INFORMATION: Synthetic DNA/RNA primer, F79

<400> SEQUENCE: 86
ggcttcttgg ucgtgttctu ca                                           22

<210> SEQ ID NO 87
<211> LENGTH: 22
```

<212> TYPE: DNA
<213> ORGANISM: Artificial Sequence
<220> FEATURE:
<223> OTHER INFORMATION: Synthetic DNA/RNA primer, F80

<400> SEQUENCE: 87
cccagcgucc tcaaaagtua ca                                        22

<210> SEQ ID NO 88
<211> LENGTH: 20
<212> TYPE: DNA
<213> ORGANISM: Artificial Sequence
<220> FEATURE:
<223> OTHER INFORMATION: Synthetic DNA/RNA primer, F81

<400> SEQUENCE: 88
ctctacguct ccuccgacca                                           20

<210> SEQ ID NO 89
<211> LENGTH: 22
<212> TYPE: DNA
<213> ORGANISM: Artificial Sequence
<220> FEATURE:
<223> OTHER INFORMATION: Synthetic DNA/RNA primer, F82

<400> SEQUENCE: 89
cctgtactgg uggatgtccu ca                                        22

<210> SEQ ID NO 90
<211> LENGTH: 20
<212> TYPE: DNA
<213> ORGANISM: Artificial Sequence
<220> FEATURE:
<223> OTHER INFORMATION: Synthetic DNA/RNA primer, F83

<400> SEQUENCE: 90
cgccaggcuc acctctauag                                           20

<210> SEQ ID NO 91
<211> LENGTH: 29
<212> TYPE: DNA
<213> ORGANISM: Artificial Sequence
<220> FEATURE:
<223> OTHER INFORMATION: Synthetic DNA/RNA primer, F84

<400> SEQUENCE: 91
tgtctttgcu gatgtttcaa uaaaaggaa                                 29

<210> SEQ ID NO 92
<211> LENGTH: 22
<212> TYPE: DNA
<213> ORGANISM: Artificial Sequence
<220> FEATURE:
<223> OTHER INFORMATION: Synthetic DNA/RNA primer, F85

<400> SEQUENCE: 92
catgtactgg uccctcatug ca                                        22

<210> SEQ ID NO 93
<211> LENGTH: 29
<212> TYPE: DNA
<213> ORGANISM: Artificial Sequence
<220> FEATURE:
<223> OTHER INFORMATION: Synthetic DNA/RNA primer, F86

<400> SEQUENCE: 93
tacctctatt gtuggatcat attcgucca                                    29

<210> SEQ ID NO 94
<211> LENGTH: 23
<212> TYPE: DNA
<213> ORGANISM: Artificial Sequence
<220> FEATURE:
<223> OTHER INFORMATION: Synthetic DNA/RNA primer, F87

<400> SEQUENCE: 94
cagacactgu acaagctcua cga                                          23

<210> SEQ ID NO 95
<211> LENGTH: 22
<212> TYPE: DNA
<213> ORGANISM: Artificial Sequence
<220> FEATURE:
<223> OTHER INFORMATION: Synthetic DNA/RNA primer, F88

<400> SEQUENCE: 95
ctctgucaca gtggatucga ga                                           22

<210> SEQ ID NO 96
<211> LENGTH: 23
<212> TYPE: DNA
<213> ORGANISM: Artificial Sequence
<220> FEATURE:
<223> OTHER INFORMATION: Synthetic DNA/RNA primer, F89

<400> SEQUENCE: 96
tccutccata gugaccaaga cca                                          23

<210> SEQ ID NO 97
<211> LENGTH: 22
<212> TYPE: DNA
<213> ORGANISM: Artificial Sequence
<220> FEATURE:
<223> OTHER INFORMATION: Synthetic DNA/RNA primer, F90

<400> SEQUENCE: 97
ggttccatug gtagctggug at                                           22

<210> SEQ ID NO 98
<211> LENGTH: 25
<212> TYPE: DNA
<213> ORGANISM: Artificial Sequence
<220> FEATURE:
<223> OTHER INFORMATION: Synthetic DNA/RNA primer, F91

<400> SEQUENCE: 98
tgtaaagaga cagccuttcc tcuga                                        25

<210> SEQ ID NO 99
<211> LENGTH: 21
<212> TYPE: DNA
<213> ORGANISM: Artificial Sequence
<220> FEATURE:
<223> OTHER INFORMATION: Synthetic DNA/RNA primer, F92

<400> SEQUENCE: 99
acacuctuga gggccacaaa g                                            21

<210> SEQ ID NO 100
<211> LENGTH: 20
<212> TYPE: DNA
<213> ORGANISM: Artificial Sequence

```
<220> FEATURE:
<223> OTHER INFORMATION: Synthetic DNA/RNA primer, F93

<400> SEQUENCE: 100
ccgctccutg tagccaauga                                              20

<210> SEQ ID NO 101
<211> LENGTH: 21
<212> TYPE: DNA
<213> ORGANISM: Artificial Sequence
<220> FEATURE:
<223> OTHER INFORMATION: Synthetic DNA/RNA primer, F94

<400> SEQUENCE: 101
ccacutugga acaggaccaa c                                            21

<210> SEQ ID NO 102
<211> LENGTH: 24
<212> TYPE: DNA
<213> ORGANISM: Artificial Sequence
<220> FEATURE:
<223> OTHER INFORMATION: Synthetic DNA/RNA primer, F95

<400> SEQUENCE: 102
ctttcttcca ccuttctcca gcua                                         24

<210> SEQ ID NO 103
<211> LENGTH: 22
<212> TYPE: DNA
<213> ORGANISM: Artificial Sequence
<220> FEATURE:
<223> OTHER INFORMATION: Synthetic DNA/RNA primer, F96

<400> SEQUENCE: 103
tcaagcccuc caacatccua gt                                           22

<210> SEQ ID NO 104
<211> LENGTH: 22
<212> TYPE: DNA
<213> ORGANISM: Artificial Sequence
<220> FEATURE:
<223> OTHER INFORMATION: Synthetic DNA/RNA primer, R1

<400> SEQUENCE: 104
acagaaucac augccacaca gt                                           22

<210> SEQ ID NO 105
<211> LENGTH: 27
<212> TYPE: DNA
<213> ORGANISM: Artificial Sequence
<220> FEATURE:
<223> OTHER INFORMATION: Synthetic DNA/RNA primer, R2

<400> SEQUENCE: 105
ttccttcuaa aaggccatga agatcug                                      27

<210> SEQ ID NO 106
<211> LENGTH: 23
<212> TYPE: DNA
<213> ORGANISM: Artificial Sequence
<220> FEATURE:
<223> OTHER INFORMATION: Synthetic DNA/RNA primer, R3

<400> SEQUENCE: 106
tctgaagaac augtgugagc aca                                          23
```

<210> SEQ ID NO 107
<211> LENGTH: 29
<212> TYPE: DNA
<213> ORGANISM: Artificial Sequence
<220> FEATURE:
<223> OTHER INFORMATION: Synthetic DNA/RNA primer, R4

<400> SEQUENCE: 107
cccaacccac auttccttta tagatgtut                                    29

<210> SEQ ID NO 108
<211> LENGTH: 24
<212> TYPE: DNA
<213> ORGANISM: Artificial Sequence
<220> FEATURE:
<223> OTHER INFORMATION: Synthetic DNA/RNA primer, R5

<400> SEQUENCE: 108
tgttccaaca ggauctgucc aaaa                                         24

<210> SEQ ID NO 109
<211> LENGTH: 22
<212> TYPE: DNA
<213> ORGANISM: Artificial Sequence
<220> FEATURE:
<223> OTHER INFORMATION: Synthetic DNA/RNA primer, R6

<400> SEQUENCE: 109
ccagtgtctg uccttgcctt uc                                           22

<210> SEQ ID NO 110
<211> LENGTH: 28
<212> TYPE: DNA
<213> ORGANISM: Artificial Sequence
<220> FEATURE:
<223> OTHER INFORMATION: Synthetic DNA/RNA primer, R7

<400> SEQUENCE: 110
cuatgacaag aaaauggaca ccaacaag                                     28

<210> SEQ ID NO 111
<211> LENGTH: 23
<212> TYPE: DNA
<213> ORGANISM: Artificial Sequence
<220> FEATURE:
<223> OTHER INFORMATION: Synthetic DNA/RNA primer, R8

<400> SEQUENCE: 111
aggaggauaa agacctgguc cat                                          23

<210> SEQ ID NO 112
<211> LENGTH: 22
<212> TYPE: DNA
<213> ORGANISM: Artificial Sequence
<220> FEATURE:
<223> OTHER INFORMATION: Synthetic DNA/RNA primer, R9

<400> SEQUENCE: 112
gtcctcugga tctcttcaug ca                                           22

<210> SEQ ID NO 113
<211> LENGTH: 24
<212> TYPE: DNA
<213> ORGANISM: Artificial Sequence
<220> FEATURE:
<223> OTHER INFORMATION: Synthetic DNA/RNA primer, R10

```
<400> SEQUENCE: 113
ctgagacatt ccuatgtcct gcuc                                            24

<210> SEQ ID NO 114
<211> LENGTH: 25
<212> TYPE: DNA
<213> ORGANISM: Artificial Sequence
<220> FEATURE:
<223> OTHER INFORMATION: Synthetic DNA/RNA primer, R11

<400> SEQUENCE: 114
tugauacaaa acaagcccac gaact                                           25

<210> SEQ ID NO 115
<211> LENGTH: 30
<212> TYPE: DNA
<213> ORGANISM: Artificial Sequence
<220> FEATURE:
<223> OTHER INFORMATION: Synthetic DNA/RNA primer, R12

<400> SEQUENCE: 115
ccagcctaat ctugttttc ttatgttcug                                       30

<210> SEQ ID NO 116
<211> LENGTH: 28
<212> TYPE: DNA
<213> ORGANISM: Artificial Sequence
<220> FEATURE:
<223> OTHER INFORMATION: Synthetic DNA/RNA primer, R13

<400> SEQUENCE: 116
gttatagatg gugaaacctg tttgtugg                                        28

<210> SEQ ID NO 117
<211> LENGTH: 26
<212> TYPE: DNA
<213> ORGANISM: Artificial Sequence
<220> FEATURE:
<223> OTHER INFORMATION: Synthetic DNA/RNA primer, R14

<400> SEQUENCE: 117
gattactggt tuccaacagg ttctug                                          26

<210> SEQ ID NO 118
<211> LENGTH: 24
<212> TYPE: DNA
<213> ORGANISM: Artificial Sequence
<220> FEATURE:
<223> OTHER INFORMATION: Synthetic DNA/RNA primer, R15

<400> SEQUENCE: 118
tatggtctug gacatccagg auct                                            24

<210> SEQ ID NO 119
<211> LENGTH: 26
<212> TYPE: DNA
<213> ORGANISM: Artificial Sequence
<220> FEATURE:
<223> OTHER INFORMATION: Synthetic DNA/RNA primer, R16

<400> SEQUENCE: 119
taggaaatgc auttcctttc tuccca                                          26

<210> SEQ ID NO 120
```

```
<211> LENGTH: 22
<212> TYPE: DNA
<213> ORGANISM: Artificial Sequence
<220> FEATURE:
<223> OTHER INFORMATION: Synthetic DNA/RNA primer, R17

<400> SEQUENCE: 120
cctgtggcug tcagtattug ga                                              22

<210> SEQ ID NO 121
<211> LENGTH: 21
<212> TYPE: DNA
<213> ORGANISM: Artificial Sequence
<220> FEATURE:
<223> OTHER INFORMATION: Synthetic DNA/RNA primer, R18

<400> SEQUENCE: 121
gttcatccug ctggagcuca t                                               21

<210> SEQ ID NO 122
<211> LENGTH: 29
<212> TYPE: DNA
<213> ORGANISM: Artificial Sequence
<220> FEATURE:
<223> OTHER INFORMATION: Synthetic DNA/RNA primer, R19

<400> SEQUENCE: 122
gtagctgctg aaaaugtaac tttgtaucc                                       29

<210> SEQ ID NO 123
<211> LENGTH: 22
<212> TYPE: DNA
<213> ORGANISM: Artificial Sequence
<220> FEATURE:
<223> OTHER INFORMATION: Synthetic DNA/RNA primer, R20

<400> SEQUENCE: 123
actctgtagg cugcagttcu ca                                              22

<210> SEQ ID NO 124
<211> LENGTH: 23
<212> TYPE: DNA
<213> ORGANISM: Artificial Sequence
<220> FEATURE:
<223> OTHER INFORMATION: Synthetic DNA/RNA primer, R21

<400> SEQUENCE: 124
ctcctcttgu cttctccttu gca                                             23

<210> SEQ ID NO 125
<211> LENGTH: 26
<212> TYPE: DNA
<213> ORGANISM: Artificial Sequence
<220> FEATURE:
<223> OTHER INFORMATION: Synthetic DNA/RNA primer, R22

<400> SEQUENCE: 125
cttgtgagtg gaugggtaaa accuat                                          26

<210> SEQ ID NO 126
<211> LENGTH: 29
<212> TYPE: DNA
<213> ORGANISM: Artificial Sequence
<220> FEATURE:
<223> OTHER INFORMATION: Synthetic DNA/RNA primer, R23

<400> SEQUENCE: 126
```

```
cggactgaaa guataacctt cttcttucc                                    29

<210> SEQ ID NO 127
<211> LENGTH: 26
<212> TYPE: DNA
<213> ORGANISM: Artificial Sequence
<220> FEATURE:
<223> OTHER INFORMATION: Synthetic DNA/RNA primer, R24

<400> SEQUENCE: 127
gcatgtgaac autctgcttt tcaugg                                       26

<210> SEQ ID NO 128
<211> LENGTH: 22
<212> TYPE: DNA
<213> ORGANISM: Artificial Sequence
<220> FEATURE:
<223> OTHER INFORMATION: Synthetic DNA/RNA primer, R25

<400> SEQUENCE: 128
acgccttcac cuttaacacc uc                                           22

<210> SEQ ID NO 129
<211> LENGTH: 22
<212> TYPE: DNA
<213> ORGANISM: Artificial Sequence
<220> FEATURE:
<223> OTHER INFORMATION: Synthetic DNA/RNA primer, R26

<400> SEQUENCE: 129
acttgggagg uatccacauc ct                                           22

<210> SEQ ID NO 130
<211> LENGTH: 28
<212> TYPE: DNA
<213> ORGANISM: Artificial Sequence
<220> FEATURE:
<223> OTHER INFORMATION: Synthetic DNA/RNA primer, R27

<400> SEQUENCE: 130
agattcatct ugaagaagtt gauggagg                                     28

<210> SEQ ID NO 131
<211> LENGTH: 33
<212> TYPE: DNA
<213> ORGANISM: Artificial Sequence
<220> FEATURE:
<223> OTHER INFORMATION: Synthetic DNA/RNA primer, R28

<400> SEQUENCE: 131
gaataggata ttguatcata ccaatttcuc gat                               33

<210> SEQ ID NO 132
<211> LENGTH: 30
<212> TYPE: DNA
<213> ORGANISM: Artificial Sequence
<220> FEATURE:
<223> OTHER INFORMATION: Synthetic DNA/RNA primer, R29

<400> SEQUENCE: 132
cagcatttga cttuacctta tcaatgtcuc                                   30

<210> SEQ ID NO 133
<211> LENGTH: 33
<212> TYPE: DNA
```

```
<213> ORGANISM: Artificial Sequence
<220> FEATURE:
<223> OTHER INFORMATION: Synthetic DNA/RNA primer, R30

<400> SEQUENCE: 133
actgctaaac actaauataa cctttggaaa uat                                33

<210> SEQ ID NO 134
<211> LENGTH: 30
<212> TYPE: DNA
<213> ORGANISM: Artificial Sequence
<220> FEATURE:
<223> OTHER INFORMATION: Synthetic DNA/RNA primer, R31

<400> SEQUENCE: 134 cattttcca gatacuagag tgtctgtgua                                     30

<210> SEQ ID NO 135
<211> LENGTH: 29
<212> TYPE: DNA
<213> ORGANISM: Artificial Sequence
<220> FEATURE:
<223> OTHER INFORMATION: Synthetic DNA/RNA primer, R32

<400> SEQUENCE: 135
cataagagag aagguttgac tgccauaaa                                     29

<210> SEQ ID NO 136
<211> LENGTH: 28
<212> TYPE: DNA
<213> ORGANISM: Artificial Sequence
<220> FEATURE:
<223> OTHER INFORMATION: Synthetic DNA/RNA primer, R33

<400> SEQUENCE: 136
gaatctccat ttuagcactt acctguga                                      28

<210> SEQ ID NO 137
<211> LENGTH: 32
<212> TYPE: DNA
<213> ORGANISM: Artificial Sequence
<220> FEATURE:
<223> OTHER INFORMATION: Synthetic DNA/RNA primer, R34

<400> SEQUENCE: 137
agaatgtcag tuaagttaat gagctttucc at                                 32

<210> SEQ ID NO 138
<211> LENGTH: 25
<212> TYPE: DNA
<213> ORGANISM: Artificial Sequence
<220> FEATURE:
<223> OTHER INFORMATION: Synthetic DNA/RNA primer, R35

<400> SEQUENCE: 138
gcttgatucc aaggaccatg atcug                                         25

<210> SEQ ID NO 139
<211> LENGTH: 27
<212> TYPE: DNA
<213> ORGANISM: Artificial Sequence
<220> FEATURE:
<223> OTHER INFORMATION: Synthetic DNA/RNA primer, R36

<400> SEQUENCE: 139
caattcccaa aaugaaggta gcuacac                                       27
```

<210> SEQ ID NO 140
<211> LENGTH: 27
<212> TYPE: DNA
<213> ORGANISM: Artificial Sequence
<220> FEATURE:
<223> OTHER INFORMATION: Synthetic DNA/RNA primer, R37

<400> SEQUENCE: 140
ggaagatcca auccattttt gttgucc                                        27

<210> SEQ ID NO 141
<211> LENGTH: 19
<212> TYPE: DNA
<213> ORGANISM: Artificial Sequence
<220> FEATURE:
<223> OTHER INFORMATION: Synthetic DNA/RNA primer, R38

<400> SEQUENCE: 141
cgggaagcgg gagauctug                                                 19

<210> SEQ ID NO 142
<211> LENGTH: 18
<212> TYPE: DNA
<213> ORGANISM: Artificial Sequence
<220> FEATURE:
<223> OTHER INFORMATION: Synthetic DNA/RNA primer, R39

<400> SEQUENCE: 142
ggcgtccuac tggcauga                                                  18

<210> SEQ ID NO 143
<211> LENGTH: 21
<212> TYPE: DNA
<213> ORGANISM: Artificial Sequence
<220> FEATURE:
<223> OTHER INFORMATION: Synthetic DNA/RNA primer, R40

<400> SEQUENCE: 143
cctucagcag ctugaagagc t                                              21

<210> SEQ ID NO 144
<211> LENGTH: 26
<212> TYPE: DNA
<213> ORGANISM: Artificial Sequence
<220> FEATURE:
<223> OTHER INFORMATION: Synthetic DNA/RNA primer, R41

<400> SEQUENCE: 144
ggaaactccc aucttgagtc auaagg                                         26

<210> SEQ ID NO 145
<211> LENGTH: 25
<212> TYPE: DNA
<213> ORGANISM: Artificial Sequence
<220> FEATURE:
<223> OTHER INFORMATION: Synthetic DNA/RNA primer, R42

<400> SEQUENCE: 145
catgtgtcca gugaaaatcc ucact                                          25

<210> SEQ ID NO 146
<211> LENGTH: 30
<212> TYPE: DNA
<213> ORGANISM: Artificial Sequence
<220> FEATURE:

<223> OTHER INFORMATION: Synthetic DNA/RNA primer, R43

<400> SEQUENCE: 146
ctgactutag agattaaagu gaaggaggat                                    30

<210> SEQ ID NO 147
<211> LENGTH: 28
<212> TYPE: DNA
<213> ORGANISM: Artificial Sequence
<220> FEATURE:
<223> OTHER INFORMATION: Synthetic DNA/RNA primer, R44

<400> SEQUENCE: 147
cctggacaaa aauaccaatc tattgugg                                      28

<210> SEQ ID NO 148
<211> LENGTH: 28
<212> TYPE: DNA
<213> ORGANISM: Artificial Sequence
<220> FEATURE:
<223> OTHER INFORMATION: Synthetic DNA/RNA primer, R45

<400> SEQUENCE: 148
actgatatgg uagacagagc cuaaacat                                      28

<210> SEQ ID NO 149
<211> LENGTH: 22
<212> TYPE: DNA
<213> ORGANISM: Artificial Sequence
<220> FEATURE:
<223> OTHER INFORMATION: Synthetic DNA/RNA primer, R46

<400> SEQUENCE: 149
actgaccaaa acucagcctg ut                                            22

<210> SEQ ID NO 150
<211> LENGTH: 25
<212> TYPE: DNA
<213> ORGANISM: Artificial Sequence
<220> FEATURE:
<223> OTHER INFORMATION: Synthetic DNA/RNA primer, R47

<400> SEQUENCE: 150
cctgacagac aauaaaaggc agcut                                         25

<210> SEQ ID NO 151
<211> LENGTH: 28
<212> TYPE: DNA
<213> ORGANISM: Artificial Sequence
<220> FEATURE:
<223> OTHER INFORMATION: Synthetic DNA/RNA primer, R48

<400> SEQUENCE: 151
gttgaaacua aaaatccttu gcaggact                                      28

<210> SEQ ID NO 152
<211> LENGTH: 24
<212> TYPE: DNA
<213> ORGANISM: Artificial Sequence
<220> FEATURE:
<223> OTHER INFORMATION: Synthetic DNA/RNA primer, R49

<400> SEQUENCE: 152
acattctgaa gcagcutgga gtut                                          24

```
<210> SEQ ID NO 153
<211> LENGTH: 26
<212> TYPE: DNA
<213> ORGANISM: Artificial Sequence
<220> FEATURE:
<223> OTHER INFORMATION: Synthetic DNA/RNA primer, R50

<400> SEQUENCE: 153
gaggagattg aaaaucttcc tgccut                                        26

<210> SEQ ID NO 154
<211> LENGTH: 20
<212> TYPE: DNA
<213> ORGANISM: Artificial Sequence
<220> FEATURE:
<223> OTHER INFORMATION: Synthetic DNA/RNA primer, R51

<400> SEQUENCE: 154
ttggtccguc tccuccacgg                                               20

<210> SEQ ID NO 155
<211> LENGTH: 28
<212> TYPE: DNA
<213> ORGANISM: Artificial Sequence
<220> FEATURE:
<223> OTHER INFORMATION: Synthetic DNA/RNA primer, R52

<400> SEQUENCE: 155
cttcagtccg gutttatttg catcauag                                      28

<210> SEQ ID NO 156
<211> LENGTH: 24
<212> TYPE: DNA
<213> ORGANISM: Artificial Sequence
<220> FEATURE:
<223> OTHER INFORMATION: Synthetic DNA/RNA primer, R53

<400> SEQUENCE: 156
gactctccaa gaugggatac ucca                                          24

<210> SEQ ID NO 157
<211> LENGTH: 22
<212> TYPE: DNA
<213> ORGANISM: Artificial Sequence
<220> FEATURE:
<223> OTHER INFORMATION: Synthetic DNA/RNA primer, R54

<400> SEQUENCE: 157
cggtgactua ctgcagctgt ut                                            22

<210> SEQ ID NO 158
<211> LENGTH: 22
<212> TYPE: DNA
<213> ORGANISM: Artificial Sequence
<220> FEATURE:
<223> OTHER INFORMATION: Synthetic DNA/RNA primer, R55

<400> SEQUENCE: 158
tccagaccag ggugttgttt uc                                            22

<210> SEQ ID NO 159
<211> LENGTH: 23
<212> TYPE: DNA
<213> ORGANISM: Artificial Sequence
<220> FEATURE:
<223> OTHER INFORMATION: Synthetic DNA/RNA primer, R56
```

```
<400> SEQUENCE: 159
tgtgccaggg accutacctt aua                                          23

<210> SEQ ID NO 160
<211> LENGTH: 24
<212> TYPE: RNA
<213> ORGANISM: Artificial Sequence
<220> FEATURE:
<223> OTHER INFORMATION: Synthetic Primer, R57

<400> SEQUENCE: 160
cacagcaaag cagaaacuca cauc                                         24

<210> SEQ ID NO 161
<211> LENGTH: 21
<212> TYPE: DNA
<213> ORGANISM: Artificial Sequence
<220> FEATURE:
<223> OTHER INFORMATION: Synthetic DNA/RNA primer, R58

<400> SEQUENCE: 161
tgtgtucccg gacatagucc a                                            21

<210> SEQ ID NO 162
<211> LENGTH: 23
<212> TYPE: DNA
<213> ORGANISM: Artificial Sequence
<220> FEATURE:
<223> OTHER INFORMATION: Synthetic DNA/RNA primer, R59

<400> SEQUENCE: 162
gaaaatgcug gctgaccuaa agc                                          23

<210> SEQ ID NO 163
<211> LENGTH: 30
<212> TYPE: DNA
<213> ORGANISM: Artificial Sequence
<220> FEATURE:
<223> OTHER INFORMATION: Synthetic DNA/RNA primer, R60

<400> SEQUENCE: 163
cacaacccac ugaggtatat gtataggguat                                  30

<210> SEQ ID NO 164
<211> LENGTH: 30
<212> TYPE: DNA
<213> ORGANISM: Artificial Sequence
<220> FEATURE:
<223> OTHER INFORMATION: Synthetic DNA/RNA primer, R61

<400> SEQUENCE: 164
ccatggttaa ataaaaugcc acttactgut                                   30

<210> SEQ ID NO 165
<211> LENGTH: 26
<212> TYPE: DNA
<213> ORGANISM: Artificial Sequence
<220> FEATURE:
<223> OTHER INFORMATION: Synthetic DNA/RNA primer, R62

<400> SEQUENCE: 165
cttggtggua aacttttgag ttugca                                       26

<210> SEQ ID NO 166
<211> LENGTH: 19
```

<212> TYPE: DNA
<213> ORGANISM: Artificial Sequence
<220> FEATURE:
<223> OTHER INFORMATION: Synthetic DNA/RNA primer, R63

<400> SEQUENCE: 166
ccaagccuca tggugccat                                              19

<210> SEQ ID NO 167
<211> LENGTH: 20
<212> TYPE: DNA
<213> ORGANISM: Artificial Sequence
<220> FEATURE:
<223> OTHER INFORMATION: Synthetic DNA/RNA primer, R64

<400> SEQUENCE: 167
tacuggcagc aagugcccag                                             20

<210> SEQ ID NO 168
<211> LENGTH: 22
<212> TYPE: DNA
<213> ORGANISM: Artificial Sequence
<220> FEATURE:
<223> OTHER INFORMATION: Synthetic DNA/RNA primer, R65

<400> SEQUENCE: 168
ccctcacuca cagcacatag uc                                          22

<210> SEQ ID NO 169
<211> LENGTH: 20
<212> TYPE: DNA
<213> ORGANISM: Artificial Sequence
<220> FEATURE:
<223> OTHER INFORMATION: Synthetic DNA/RNA primer, R66

<400> SEQUENCE: 169
ccagguacgc ctccagauga                                             20

<210> SEQ ID NO 170
<211> LENGTH: 30
<212> TYPE: DNA
<213> ORGANISM: Artificial Sequence
<220> FEATURE:
<223> OTHER INFORMATION: Synthetic DNA/RNA primer, R67

<400> SEQUENCE: 170
cttcatgaag accucacagt aaaaauaggt                                  30

<210> SEQ ID NO 171
<211> LENGTH: 25
<212> TYPE: DNA
<213> ORGANISM: Artificial Sequence
<220> FEATURE:
<223> OTHER INFORMATION: Synthetic DNA/RNA primer, R68

<400> SEQUENCE: 171
gactcgagtg augattggga gatuc                                       25

<210> SEQ ID NO 172
<211> LENGTH: 27
<212> TYPE: DNA
<213> ORGANISM: Artificial Sequence
<220> FEATURE:
<223> OTHER INFORMATION: Synthetic DNA/RNA primer, R69

<400> SEQUENCE: 172
agatgctcug agaaaggcat uagaaag                                            27

<210> SEQ ID NO 173
<211> LENGTH: 26
<212> TYPE: DNA
<213> ORGANISM: Artificial Sequence
<220> FEATURE:
<223> OTHER INFORMATION: Synthetic DNA/RNA primer, R70

<400> SEQUENCE: 173
tattgttaac cutgcagaat ggucga                                             26

<210> SEQ ID NO 174
<211> LENGTH: 22
<212> TYPE: DNA
<213> ORGANISM: Artificial Sequence
<220> FEATURE:
<223> OTHER INFORMATION: Synthetic DNA/RNA primer, R71

<400> SEQUENCE: 174
cuacctgccu acgcaacaag at                                                 22

<210> SEQ ID NO 175
<211> LENGTH: 21
<212> TYPE: DNA
<213> ORGANISM: Artificial Sequence
<220> FEATURE:
<223> OTHER INFORMATION: Synthetic DNA/RNA primer, R72

<400> SEQUENCE: 175
gggaccucag atgtgctgtu g                                                  21

<210> SEQ ID NO 176
<211> LENGTH: 20
<212> TYPE: DNA
<213> ORGANISM: Artificial Sequence
<220> FEATURE:
<223> OTHER INFORMATION: Synthetic DNA/RNA primer, R73

<400> SEQUENCE: 176
gtggcttgug ggcaaactug                                                    20

<210> SEQ ID NO 177
<211> LENGTH: 22
<212> TYPE: DNA
<213> ORGANISM: Artificial Sequence
<220> FEATURE:
<223> OTHER INFORMATION: Synthetic DNA/RNA primer, R74

<400> SEQUENCE: 177
cctgctucag gacgttgaac uc                                                 22

<210> SEQ ID NO 178
<211> LENGTH: 20
<212> TYPE: DNA
<213> ORGANISM: Artificial Sequence
<220> FEATURE:
<223> OTHER INFORMATION: Synthetic DNA/RNA primer, R75

<400> SEQUENCE: 178
acctggcucc tcttcacgua                                                    20

<210> SEQ ID NO 179
<211> LENGTH: 24
<212> TYPE: DNA
<213> ORGANISM: Artificial Sequence
<220> FEATURE:
<223> OTHER INFORMATION: Synthetic DNA/RNA primer, R76

<400> SEQUENCE: 179
cacccacacu tacacatcac ttug              24

<210> SEQ ID NO 180
<211> LENGTH: 26
<212> TYPE: DNA
<213> ORGANISM: Artificial Sequence
<220> FEATURE:
<223> OTHER INFORMATION: Synthetic DNA/RNA primer, R77

<400> SEQUENCE: 180
tcgagattua gcagccagaa atgtut            26

<210> SEQ ID NO 181
<211> LENGTH: 24
<212> TYPE: DNA
<213> ORGANISM: Artificial Sequence
<220> FEATURE:
<223> OTHER INFORMATION: Synthetic DNA/RNA primer, R78

<400> SEQUENCE: 181
tgatctggug tcagagaugg agat              24

<210> SEQ ID NO 182
<211> LENGTH: 26
<212> TYPE: DNA
<213> ORGANISM: Artificial Sequence
<220> FEATURE:
<223> OTHER INFORMATION: Synthetic DNA/RNA primer, R79

<400> SEQUENCE: 182
cuagcgccug gaagagaaaa ggagat            26

<210> SEQ ID NO 183
<211> LENGTH: 22
<212> TYPE: DNA
<213> ORGANISM: Artificial Sequence
<220> FEATURE:
<223> OTHER INFORMATION: Synthetic DNA/RNA primer, R80

<400> SEQUENCE: 183
ccctccacaa ucattcctgu gt                22

<210> SEQ ID NO 184
<211> LENGTH: 30
<212> TYPE: DNA
<213> ORGANISM: Artificial Sequence
<220> FEATURE:
<223> OTHER INFORMATION: Synthetic DNA/RNA primer, R81

<400> SEQUENCE: 184
cttatttatt ggtcuctcat tctcccaucc        30

<210> SEQ ID NO 185
<211> LENGTH: 22
<212> TYPE: DNA
<213> ORGANISM: Artificial Sequence
<220> FEATURE:
<223> OTHER INFORMATION: Synthetic DNA/RNA primer, R82

<400> SEQUENCE: 185
gcctgtugga catcctggau ac                22

<210> SEQ ID NO 186
<211> LENGTH: 23
<212> TYPE: DNA
<213> ORGANISM: Artificial Sequence
<220> FEATURE:
<223> OTHER INFORMATION: Synthetic DNA/RNA primer, R83

<400> SEQUENCE: 186
aggagcgaug acggaataua agc                                          23

<210> SEQ ID NO 187
<211> LENGTH: 29
<212> TYPE: DNA
<213> ORGANISM: Artificial Sequence
<220> FEATURE:
<223> OTHER INFORMATION: Synthetic DNA/RNA primer, R84

<400> SEQUENCE: 187
agttaaggac tcugaagatg tacctaugg                                    29

<210> SEQ ID NO 188
<211> LENGTH: 28
<212> TYPE: DNA
<213> ORGANISM: Artificial Sequence
<220> FEATURE:
<223> OTHER INFORMATION: Synthetic DNA/RNA primer, R85

<400> SEQUENCE: 188
gtaataatcc agacugtgtt tctcccut                                     28

<210> SEQ ID NO 189
<211> LENGTH: 30
<212> TYPE: DNA
<213> ORGANISM: Artificial Sequence
<220> FEATURE:
<223> OTHER INFORMATION: Synthetic DNA/RNA primer, R86

<400> SEQUENCE: 189
tattataagg ccugctgaaa atgacugaat                                   30

<210> SEQ ID NO 190
<211> LENGTH: 25
<212> TYPE: DNA
<213> ORGANISM: Artificial Sequence
<220> FEATURE:
<223> OTHER INFORMATION: Synthetic DNA/RNA primer, R87

<400> SEQUENCE: 190
gaauaaagag gagcaggtug aggaa                                        25

<210> SEQ ID NO 191
<211> LENGTH: 25
<212> TYPE: DNA
<213> ORGANISM: Artificial Sequence
<220> FEATURE:
<223> OTHER INFORMATION: Synthetic DNA/RNA primer, R88

<400> SEQUENCE: 191
caacatgacg aagauggcaa actuc                                        25

<210> SEQ ID NO 192
<211> LENGTH: 24
<212> TYPE: DNA
<213> ORGANISM: Artificial Sequence
<220> FEATURE:
<223> OTHER INFORMATION: Synthetic DNA/RNA primer, R89

```
<400> SEQUENCE: 192
gggtacauac aaagcagtct gugt                                              24

<210> SEQ ID NO 193
<211> LENGTH: 29
<212> TYPE: DNA
<213> ORGANISM: Artificial Sequence
<220> FEATURE:
<223> OTHER INFORMATION: Synthetic DNA/RNA primer, R90

<400> SEQUENCE: 193
gcccattttt atcuacttcc atcttguca                                         29

<210> SEQ ID NO 194
<211> LENGTH: 26
<212> TYPE: DNA
<213> ORGANISM: Artificial Sequence
<220> FEATURE:
<223> OTHER INFORMATION: Synthetic DNA/RNA primer, R91

<400> SEQUENCE: 194
agttcacaaa uccatcaatg ttgcuc                                            26

<210> SEQ ID NO 195
<211> LENGTH: 24
<212> TYPE: DNA
<213> ORGANISM: Artificial Sequence
<220> FEATURE:
<223> OTHER INFORMATION: Synthetic DNA/RNA primer, R92

<400> SEQUENCE: 195
tgtgattgua gggtctccct ugat                                              24

<210> SEQ ID NO 196
<211> LENGTH: 20
<212> TYPE: DNA
<213> ORGANISM: Artificial Sequence
<220> FEATURE:
<223> OTHER INFORMATION: Synthetic DNA/RNA primer, R93

<400> SEQUENCE: 196
gggtcugacg ggtagagugt                                                   20

<210> SEQ ID NO 197
<211> LENGTH: 25
<212> TYPE: DNA
<213> ORGANISM: Artificial Sequence
<220> FEATURE:
<223> OTHER INFORMATION: Synthetic DNA/RNA primer, R94

<400> SEQUENCE: 197
tcaaagtcgt cauccttcag ttcuc                                             25

<210> SEQ ID NO 198
<211> LENGTH: 22
<212> TYPE: DNA
<213> ORGANISM: Artificial Sequence
<220> FEATURE:
<223> OTHER INFORMATION: Synthetic DNA/RNA primer, R95

<400> SEQUENCE: 198
catcgctgua gaacgcacca ua                                                22

<210> SEQ ID NO 199
```

```
<211> LENGTH: 28
<212> TYPE: DNA
<213> ORGANISM: Artificial Sequence
<220> FEATURE:
<223> OTHER INFORMATION: Synthetic DNA/RNA primer, R96

<400> SEQUENCE: 199
ggaaacttct gtucataccg acatguag                                       28

<210> SEQ ID NO 200
<211> LENGTH: 26
<212> TYPE: DNA
<213> ORGANISM: Artificial Sequence
<220> FEATURE:
<223> OTHER INFORMATION: Synthetic DNA/RNA primer, F97

<400> SEQUENCE: 200
gaggtcgtat ucgtccacaa aauggt                                         26

<210> SEQ ID NO 201
<211> LENGTH: 30
<212> TYPE: DNA
<213> ORGANISM: Artificial Sequence
<220> FEATURE:
<223> OTHER INFORMATION: Synthetic DNA/RNA primer, F98

<400> SEQUENCE: 201
gaaactgctt aguaactagc agaagtgtuc                                     30

<210> SEQ ID NO 202
<211> LENGTH: 28
<212> TYPE: DNA
<213> ORGANISM: Artificial Sequence
<220> FEATURE:
<223> OTHER INFORMATION: Synthetic DNA/RNA primer, F99

<400> SEQUENCE: 202
gacaaagttg ugtgttgtaa guggaaca                                       28

<210> SEQ ID NO 203
<211> LENGTH: 27
<212> TYPE: DNA
<213> ORGANISM: Artificial Sequence
<220> FEATURE:
<223> OTHER INFORMATION: Synthetic DNA/RNA primer, F100

<400> SEQUENCE: 203
gagcaccaat cuttcttctg cctttug                                        27

<210> SEQ ID NO 204
<211> LENGTH: 25
<212> TYPE: RNA
<213> ORGANISM: Artificial Sequence
<220> FEATURE:
<223> OTHER INFORMATION: Synthetic Primer, F101

<400> SEQUENCE: 204 gagggaucccc aaggaagaga aguga                                         25

<210> SEQ ID NO 205
<211> LENGTH: 27
<212> TYPE: DNA
<213> ORGANISM: Artificial Sequence
<220> FEATURE:
<223> OTHER INFORMATION: Synthetic DNA/RNA primer, F102

<400> SEQUENCE: 205
```
gagctactct ccugaactct ctcacuc                                       27

<210> SEQ ID NO 206
<211> LENGTH: 23
<212> TYPE: DNA
<213> ORGANISM: Artificial Sequence
<220> FEATURE:
<223> OTHER INFORMATION: Synthetic DNA/RNA primer, F103

<400> SEQUENCE: 206
gactcccagu tgcaacgtua ggt                                           23

<210> SEQ ID NO 207
<211> LENGTH: 20
<212> TYPE: DNA
<213> ORGANISM: Artificial Sequence
<220> FEATURE:
<223> OTHER INFORMATION: Synthetic DNA/RNA primer, F104

<400> SEQUENCE: 207
gatcacgugt cccctucca                                                20

<210> SEQ ID NO 208
<211> LENGTH: 30
<212> TYPE: DNA
<213> ORGANISM: Artificial Sequence
<220> FEATURE:
<223> OTHER INFORMATION: Synthetic DNA/RNA primer, F105

<400> SEQUENCE: 208
gaacatttgg cugtgacttc uaagaagaaa                                    30

<210> SEQ ID NO 209
<211> LENGTH: 25
<212> TYPE: DNA
<213> ORGANISM: Artificial Sequence
<220> FEATURE:
<223> OTHER INFORMATION: Synthetic DNA/RNA primer, F106

<400> SEQUENCE: 209
gagatgaucc agatgtuagg gcagt                                         25

<210> SEQ ID NO 210
<211> LENGTH: 28
<212> TYPE: DNA
<213> ORGANISM: Artificial Sequence
<220> FEATURE:
<223> OTHER INFORMATION: Synthetic DNA/RNA primer, F107

<400> SEQUENCE: 210
gagcccaaat ugatttcgat gatctuca                                      28

<210> SEQ ID NO 211
<211> LENGTH: 23
<212> TYPE: DNA
<213> ORGANISM: Artificial Sequence
<220> FEATURE:
<223> OTHER INFORMATION: Synthetic DNA/RNA primer, F108

<400> SEQUENCE: 211
gagctcaaga gugagccact uct                                           23

<210> SEQ ID NO 212
<211> LENGTH: 29
<212> TYPE: DNA

```
<213> ORGANISM: Artificial Sequence
<220> FEATURE:
<223> OTHER INFORMATION: Synthetic DNA/RNA primer, F109

<400> SEQUENCE: 212
gaattaacac acaucagtgg aacttcugt                                    29

<210> SEQ ID NO 213
<211> LENGTH: 27
<212> TYPE: RNA
<213> ORGANISM: Artificial Sequence
<220> FEATURE:
<223> OTHER INFORMATION: Synthetic Primer, F110

<400> SEQUENCE: 213
gagcaaucca aaagaauagc agccaaa                                      27

<210> SEQ ID NO 214
<211> LENGTH: 28
<212> TYPE: DNA
<213> ORGANISM: Artificial Sequence
<220> FEATURE:
<223> OTHER INFORMATION: Synthetic DNA/RNA primer, F111

<400> SEQUENCE: 214
gactttgtgg aauagcccat gaagagua                                     28

<210> SEQ ID NO 215
<211> LENGTH: 25
<212> TYPE: DNA
<213> ORGANISM: Artificial Sequence
<220> FEATURE:
<223> OTHER INFORMATION: Synthetic DNA/RNA primer, F112

<400> SEQUENCE: 215
gaacaggaag agcacaguca cttug                                        25

<210> SEQ ID NO 216
<211> LENGTH: 26
<212> TYPE: DNA
<213> ORGANISM: Artificial Sequence
<220> FEATURE:
<223> OTHER INFORMATION: Synthetic DNA/RNA primer, F113

<400> SEQUENCE: 216
gaccatgcag agugaaagga tauccc                                       26

<210> SEQ ID NO 217
<211> LENGTH: 20
<212> TYPE: DNA
<213> ORGANISM: Artificial Sequence
<220> FEATURE:
<223> OTHER INFORMATION: Synthetic DNA/RNA primer, F114

<400> SEQUENCE: 217
gatggagccg cugacaccua                                              20

<210> SEQ ID NO 218
<211> LENGTH: 23
<212> TYPE: DNA
<213> ORGANISM: Artificial Sequence
<220> FEATURE:
<223> OTHER INFORMATION: Synthetic DNA/RNA primer, F115

<400> SEQUENCE: 218
gaggtgucta gcccauggga gaa                                          23
```

<210> SEQ ID NO 219
<211> LENGTH: 23
<212> TYPE: DNA
<213> ORGANISM: Artificial Sequence
<220> FEATURE:
<223> OTHER INFORMATION: Synthetic DNA/RNA primer, F116

<400> SEQUENCE: 219
gagtctgguc cacattgctc uca                                              23

<210> SEQ ID NO 220
<211> LENGTH: 27
<212> TYPE: DNA
<213> ORGANISM: Artificial Sequence
<220> FEATURE:
<223> OTHER INFORMATION: Synthetic DNA/RNA primer, F117

<400> SEQUENCE: 220
gagcaagagu acacactcct cattugg                                          27

<210> SEQ ID NO 221
<211> LENGTH: 24
<212> TYPE: DNA
<213> ORGANISM: Artificial Sequence
<220> FEATURE:
<223> OTHER INFORMATION: Synthetic DNA/RNA primer, F118

<400> SEQUENCE: 221
gactggtttc uggtgggacc atua                                             24

<210> SEQ ID NO 222
<211> LENGTH: 25
<212> TYPE: DNA
<213> ORGANISM: Artificial Sequence
<220> FEATURE:
<223> OTHER INFORMATION: Synthetic DNA/RNA primer, F119

<400> SEQUENCE: 222
gactcccagg cacutgatga tacuc                                            25

<210> SEQ ID NO 223
<211> LENGTH: 21
<212> TYPE: DNA
<213> ORGANISM: Artificial Sequence
<220> FEATURE:
<223> OTHER INFORMATION: Synthetic DNA/RNA primer, F120

<400> SEQUENCE: 223
gagggctugg taacgtccug t                                                21

<210> SEQ ID NO 224
<211> LENGTH: 27
<212> TYPE: DNA
<213> ORGANISM: Artificial Sequence
<220> FEATURE:
<223> OTHER INFORMATION: Synthetic DNA/RNA primer, F121

<400> SEQUENCE: 224
gatgtgtcaa ggagutcgaa gatucac                                          27

<210> SEQ ID NO 225
<211> LENGTH: 21
<212> TYPE: DNA
<213> ORGANISM: Artificial Sequence
<220> FEATURE:

<223> OTHER INFORMATION: Synthetic DNA/RNA primer, F122

<400> SEQUENCE: 225
gaguacagcc agtgtguccg a                                          21

<210> SEQ ID NO 226
<211> LENGTH: 24
<212> TYPE: DNA
<213> ORGANISM: Artificial Sequence
<220> FEATURE:
<223> OTHER INFORMATION: Synthetic DNA/RNA primer, F123

<400> SEQUENCE: 226
gaccatccgg gcuttacgca aaua                                       24

<210> SEQ ID NO 227
<211> LENGTH: 26
<212> TYPE: DNA
<213> ORGANISM: Artificial Sequence
<220> FEATURE:
<223> OTHER INFORMATION: Synthetic DNA/RNA primer, F124

<400> SEQUENCE: 227
gaccccacug aacctctctt acatut                                     26

<210> SEQ ID NO 228
<211> LENGTH: 23
<212> TYPE: DNA
<213> ORGANISM: Artificial Sequence
<220> FEATURE:
<223> OTHER INFORMATION: Synthetic DNA/RNA primer, F125

<400> SEQUENCE: 228
gacccuaaca gccatgcttt cuc                                        23

<210> SEQ ID NO 229
<211> LENGTH: 23
<212> TYPE: DNA
<213> ORGANISM: Artificial Sequence
<220> FEATURE:
<223> OTHER INFORMATION: Synthetic DNA/RNA primer, F126

<400> SEQUENCE: 229
gacggcgaug ctgagaacca aua                                        23

<210> SEQ ID NO 230
<211> LENGTH: 19
<212> TYPE: DNA
<213> ORGANISM: Artificial Sequence
<220> FEATURE:
<223> OTHER INFORMATION: Synthetic DNA/RNA primer, F127

<400> SEQUENCE: 230
gaccgacgut gaccgcauc                                             19

<210> SEQ ID NO 231
<211> LENGTH: 30
<212> TYPE: DNA
<213> ORGANISM: Artificial Sequence
<220> FEATURE:
<223> OTHER INFORMATION: Synthetic DNA/RNA primer, F128

<400> SEQUENCE: 231
gaaaatattu cagtgtccgt ucacacacaa                                 30

```
<210> SEQ ID NO 232
<211> LENGTH: 21
<212> TYPE: DNA
<213> ORGANISM: Artificial Sequence
<220> FEATURE:
<223> OTHER INFORMATION: Synthetic DNA/RNA primer, F129

<400> SEQUENCE: 232
gaccacacug acgtgcctcu c                                                 21

<210> SEQ ID NO 233
<211> LENGTH: 23
<212> TYPE: DNA
<213> ORGANISM: Artificial Sequence
<220> FEATURE:
<223> OTHER INFORMATION: Synthetic DNA/RNA primer, F130

<400> SEQUENCE: 233
gagcgccaca gagaagutgt uga                                               23

<210> SEQ ID NO 234
<211> LENGTH: 27
<212> TYPE: DNA
<213> ORGANISM: Artificial Sequence
<220> FEATURE:
<223> OTHER INFORMATION: Synthetic DNA/RNA primer, F131

<400> SEQUENCE: 234
gaccacaaaa uggatccaga caacugt                                           27

<210> SEQ ID NO 235
<211> LENGTH: 33
<212> TYPE: DNA
<213> ORGANISM: Artificial Sequence
<220> FEATURE:
<223> OTHER INFORMATION: Synthetic DNA/RNA primer, F132

<400> SEQUENCE: 235
gaactgtttc gtauttatag ctgatttgau gga                                    33

<210> SEQ ID NO 236
<211> LENGTH: 23
<212> TYPE: DNA
<213> ORGANISM: Artificial Sequence
<220> FEATURE:
<223> OTHER INFORMATION: Synthetic DNA/RNA primer, F133

<400> SEQUENCE: 236
gacctcautg cccucaacac agt                                               23

<210> SEQ ID NO 237
<211> LENGTH: 23
<212> TYPE: DNA
<213> ORGANISM: Artificial Sequence
<220> FEATURE:
<223> OTHER INFORMATION: Synthetic DNA/RNA primer, F134

<400> SEQUENCE: 237
gacaccacgu accagatgga ugt                                               23

<210> SEQ ID NO 238
<211> LENGTH: 28
<212> TYPE: DNA
<213> ORGANISM: Artificial Sequence
<220> FEATURE:
<223> OTHER INFORMATION: Synthetic DNA/RNA primer, F135
```

<400> SEQUENCE: 238
gaagacatgc augaacattt ttcuccac                                28

<210> SEQ ID NO 239
<211> LENGTH: 22
<212> TYPE: DNA
<213> ORGANISM: Artificial Sequence
<220> FEATURE:
<223> OTHER INFORMATION: Synthetic DNA/RNA primer, F136

<400> SEQUENCE: 239
gatguggagc ctctuacacc ca                                      22

<210> SEQ ID NO 240
<211> LENGTH: 25
<212> TYPE: DNA
<213> ORGANISM: Artificial Sequence
<220> FEATURE:
<223> OTHER INFORMATION: Synthetic DNA/RNA primer, F137

<400> SEQUENCE: 240
gaacgtcttc cutctctctc tguca                                   25

<210> SEQ ID NO 241
<211> LENGTH: 27
<212> TYPE: DNA
<213> ORGANISM: Artificial Sequence
<220> FEATURE:
<223> OTHER INFORMATION: Synthetic DNA/RNA primer, F138

<400> SEQUENCE: 241
gagaatgtga aaautccagt ggccauc                                 27

<210> SEQ ID NO 242
<211> LENGTH: 22
<212> TYPE: DNA
<213> ORGANISM: Artificial Sequence
<220> FEATURE:
<223> OTHER INFORMATION: Synthetic DNA/RNA primer, F139

<400> SEQUENCE: 242
gagggtgtgu ggtctcccau ac                                      22

<210> SEQ ID NO 243
<211> LENGTH: 24
<212> TYPE: DNA
<213> ORGANISM: Artificial Sequence
<220> FEATURE:
<223> OTHER INFORMATION: Synthetic DNA/RNA primer, F140

<400> SEQUENCE: 243
gaggatgagc uacctggagg augt                                    24

<210> SEQ ID NO 244
<211> LENGTH: 27
<212> TYPE: DNA
<213> ORGANISM: Artificial Sequence
<220> FEATURE:
<223> OTHER INFORMATION: Synthetic DNA/RNA primer, F141

<400> SEQUENCE: 244
gaggtcactg uacaccttac acaugaa                                 27

<210> SEQ ID NO 245
<211> LENGTH: 28

```
<212> TYPE: DNA
<213> ORGANISM: Artificial Sequence
<220> FEATURE:
<223> OTHER INFORMATION: Synthetic DNA/RNA primer, F142

<400> SEQUENCE: 245
gacatcacug taaaccugc agacaaac                                           28

<210> SEQ ID NO 246
<211> LENGTH: 25
<212> TYPE: DNA
<213> ORGANISM: Artificial Sequence
<220> FEATURE:
<223> OTHER INFORMATION: Synthetic DNA/RNA primer, F143

<400> SEQUENCE: 246
gagcuucuug gucgtguuct tcaut                                             25

<210> SEQ ID NO 247
<211> LENGTH: 24
<212> TYPE: DNA
<213> ORGANISM: Artificial Sequence
<220> FEATURE:
<223> OTHER INFORMATION: Synthetic DNA/RNA primer, F144

<400> SEQUENCE: 247
gauggaagcc cagccattuc taaa                                              24

<210> SEQ ID NO 248
<211> LENGTH: 19
<212> TYPE: DNA
<213> ORGANISM: Artificial Sequence
<220> FEATURE:
<223> OTHER INFORMATION: Synthetic DNA/RNA primer, F145

<400> SEQUENCE: 248
gagccccuga gcgtcauct                                                    19

<210> SEQ ID NO 249
<211> LENGTH: 19
<212> TYPE: DNA
<213> ORGANISM: Artificial Sequence
<220> FEATURE:
<223> OTHER INFORMATION: Synthetic DNA/RNA primer, F146

<400> SEQUENCE: 249
gagagctggu ggaggcuga                                                    19

<210> SEQ ID NO 250
<211> LENGTH: 22
<212> TYPE: DNA
<213> ORGANISM: Artificial Sequence
<220> FEATURE:
<223> OTHER INFORMATION: Synthetic DNA/RNA primer, F147

<400> SEQUENCE: 250
gagugaccga ggacaacgug at                                                22

<210> SEQ ID NO 251
<211> LENGTH: 22
<212> TYPE: DNA
<213> ORGANISM: Artificial Sequence
<220> FEATURE:
<223> OTHER INFORMATION: Synthetic DNA/RNA primer, F148

<400> SEQUENCE: 251
```

-continued

```
gactcuggga gatctucacg ct                                          22

<210> SEQ ID NO 252
<211> LENGTH: 22
<212> TYPE: DNA
<213> ORGANISM: Artificial Sequence
<220> FEATURE:
<223> OTHER INFORMATION: Synthetic DNA/RNA primer, F149

<400> SEQUENCE: 252
gaggattgca gautgggcct ug                                          22

<210> SEQ ID NO 253
<211> LENGTH: 30
<212> TYPE: DNA
<213> ORGANISM: Artificial Sequence
<220> FEATURE:
<223> OTHER INFORMATION: Synthetic DNA/RNA primer, F150

<400> SEQUENCE: 253
gaataatcca utgcctgtcu aaagaacact                                  30

<210> SEQ ID NO 254
<211> LENGTH: 25
<212> TYPE: DNA
<213> ORGANISM: Artificial Sequence
<220> FEATURE:
<223> OTHER INFORMATION: Synthetic DNA/RNA primer, F151

<400> SEQUENCE: 254
gagacttggu gttgttgaug gcaaa                                       25

<210> SEQ ID NO 255
<211> LENGTH: 27
<212> TYPE: DNA
<213> ORGANISM: Artificial Sequence
<220> FEATURE:
<223> OTHER INFORMATION: Synthetic DNA/RNA primer, F152

<400> SEQUENCE: 255
gaccaacaug acttacttga ucccat                                      27

<210> SEQ ID NO 256
<211> LENGTH: 20
<212> TYPE: DNA
<213> ORGANISM: Artificial Sequence
<220> FEATURE:
<223> OTHER INFORMATION: Synthetic DNA/RNA primer, F153

<400> SEQUENCE: 256
gaacccuggc ctacctgguc                                             20

<210> SEQ ID NO 257
<211> LENGTH: 26
<212> TYPE: DNA
<213> ORGANISM: Artificial Sequence
<220> FEATURE:
<223> OTHER INFORMATION: Synthetic DNA/RNA primer, F154

<400> SEQUENCE: 257
gatgaagcag caaguatgau gagcaa                                      26

<210> SEQ ID NO 258
<211> LENGTH: 25
<212> TYPE: DNA
<213> ORGANISM: Artificial Sequence
```

<220> FEATURE:
<223> OTHER INFORMATION: Synthetic DNA/RNA primer, F155

<400> SEQUENCE: 258
gaggcacggt ugaatgtaag gctua                                    25

<210> SEQ ID NO 259
<211> LENGTH: 23
<212> TYPE: DNA
<213> ORGANISM: Artificial Sequence
<220> FEATURE:
<223> OTHER INFORMATION: Synthetic DNA/RNA primer, F156

<400> SEQUENCE: 259
gaccacaccc ugttcactcc tut                                      23

<210> SEQ ID NO 260
<211> LENGTH: 28
<212> TYPE: DNA
<213> ORGANISM: Artificial Sequence
<220> FEATURE:
<223> OTHER INFORMATION: Synthetic DNA/RNA primer, F157

<400> SEQUENCE: 260
gaaaggtgat cuattttcc ctttcucc                                  28

<210> SEQ ID NO 261
<211> LENGTH: 29
<212> TYPE: DNA
<213> ORGANISM: Artificial Sequence
<220> FEATURE:
<223> OTHER INFORMATION: Synthetic DNA/RNA primer, F158

<400> SEQUENCE: 261 gagcttttttg cuaaaatgca tgttuccaa                               29

<210> SEQ ID NO 262
<211> LENGTH: 29
<212> TYPE: DNA
<213> ORGANISM: Artificial Sequence
<220> FEATURE:
<223> OTHER INFORMATION: Synthetic DNA/RNA primer, F159

<400> SEQUENCE: 262
gacaaagaat ggucctgcac cagtaauat                                29

<210> SEQ ID NO 263
<211> LENGTH: 25
<212> TYPE: DNA
<213> ORGANISM: Artificial Sequence
<220> FEATURE:
<223> OTHER INFORMATION: Synthetic DNA/RNA primer, F160

<400> SEQUENCE: 263
gatcctcatg uactggtccc tcaut                                    25

<210> SEQ ID NO 264
<211> LENGTH: 34
<212> TYPE: DNA
<213> ORGANISM: Artificial Sequence
<220> FEATURE:
<223> OTHER INFORMATION: Synthetic DNA/RNA primer, F161

<400> SEQUENCE: 264
gacagatctg tatutatttc agtgttactu acct                          34

<210> SEQ ID NO 265
<211> LENGTH: 29
<212> TYPE: DNA
<213> ORGANISM: Artificial Sequence
<220> FEATURE:
<223> OTHER INFORMATION: Synthetic DNA/RNA primer, F162

<400> SEQUENCE: 265
gacatgtcaa caucgctcta atucagaga                                  29

<210> SEQ ID NO 266
<211> LENGTH: 25
<212> TYPE: DNA
<213> ORGANISM: Artificial Sequence
<220> FEATURE:
<223> OTHER INFORMATION: Synthetic DNA/RNA primer, F163

<400> SEQUENCE: 266
gatgttacgc agugctaacc aagut                                      25

<210> SEQ ID NO 267
<211> LENGTH: 24
<212> TYPE: DNA
<213> ORGANISM: Artificial Sequence
<220> FEATURE:
<223> OTHER INFORMATION: Synthetic DNA/RNA primer, F164

<400> SEQUENCE: 267
gagctgautt tggtctugcc agag                                       24

<210> SEQ ID NO 268
<211> LENGTH: 27
<212> TYPE: DNA
<213> ORGANISM: Artificial Sequence
<220> FEATURE:
<223> OTHER INFORMATION: Synthetic DNA/RNA primer, F165

<400> SEQUENCE: 268
gacctcacct cuatggtggg atcauat                                    27

<210> SEQ ID NO 269
<211> LENGTH: 24
<212> TYPE: DNA
<213> ORGANISM: Artificial Sequence
<220> FEATURE:
<223> OTHER INFORMATION: Synthetic DNA/RNA primer, F166

<400> SEQUENCE: 269
gattcgcctg ucctcatgta tugg                                       24

<210> SEQ ID NO 270
<211> LENGTH: 25
<212> TYPE: DNA
<213> ORGANISM: Artificial Sequence
<220> FEATURE:
<223> OTHER INFORMATION: Synthetic DNA/RNA primer, F167

<400> SEQUENCE: 270
gagcacuggg actttggtaa tucac                                      25

<210> SEQ ID NO 271
<211> LENGTH: 28
<212> TYPE: DNA
<213> ORGANISM: Artificial Sequence
<220> FEATURE:
<223> OTHER INFORMATION: Synthetic DNA/RNA primer, F168

<400> SEQUENCE: 271
gacagugaaa aacaagcuct catgucug        28

<210> SEQ ID NO 272
<211> LENGTH: 22
<212> TYPE: DNA
<213> ORGANISM: Artificial Sequence
<220> FEATURE:
<223> OTHER INFORMATION: Synthetic DNA/RNA primer, F169

<400> SEQUENCE: 272
gacagtgtgu ccaccgtgau ct        22

<210> SEQ ID NO 273
<211> LENGTH: 30
<212> TYPE: DNA
<213> ORGANISM: Artificial Sequence
<220> FEATURE:
<223> OTHER INFORMATION: Synthetic DNA/RNA primer, F170

<400> SEQUENCE: 273
gatggaatgc cagaacuaca atctttugat        30

<210> SEQ ID NO 274
<211> LENGTH: 23
<212> TYPE: DNA
<213> ORGANISM: Artificial Sequence
<220> FEATURE:
<223> OTHER INFORMATION: Synthetic DNA/RNA primer, F171

<400> SEQUENCE: 274
gagacgcaut tccacagcua cac        23

<210> SEQ ID NO 275
<211> LENGTH: 26
<212> TYPE: DNA
<213> ORGANISM: Artificial Sequence
<220> FEATURE:
<223> OTHER INFORMATION: Synthetic DNA/RNA primer, F172

<400> SEQUENCE: 275
gagctttgaa uctttggcca guacct        26

<210> SEQ ID NO 276
<211> LENGTH: 25
<212> TYPE: DNA
<213> ORGANISM: Artificial Sequence
<220> FEATURE:
<223> OTHER INFORMATION: Synthetic DNA/RNA primer, F173

<400> SEQUENCE: 276
gagatgcagc cautgacctg ttuac        25

<210> SEQ ID NO 277
<211> LENGTH: 24
<212> TYPE: DNA
<213> ORGANISM: Artificial Sequence
<220> FEATURE:
<223> OTHER INFORMATION: Synthetic DNA/RNA primer, F174

<400> SEQUENCE: 277
gagggatuaa agctggctau ggca        24

<210> SEQ ID NO 278

```
<211> LENGTH: 21
<212> TYPE: DNA
<213> ORGANISM: Artificial Sequence
<220> FEATURE:
<223> OTHER INFORMATION: Synthetic DNA/RNA primer, F175

<400> SEQUENCE: 278
gaagcauacg cagcctguac c                                                 21

<210> SEQ ID NO 279
<211> LENGTH: 22
<212> TYPE: DNA
<213> ORGANISM: Artificial Sequence
<220> FEATURE:
<223> OTHER INFORMATION: Synthetic DNA/RNA primer, F176

<400> SEQUENCE: 279
gagctuccag gagcgatcgt ut                                                22

<210> SEQ ID NO 280
<211> LENGTH: 22
<212> TYPE: DNA
<213> ORGANISM: Artificial Sequence
<220> FEATURE:
<223> OTHER INFORMATION: Synthetic DNA/RNA primer, F177

<400> SEQUENCE: 280
gaagctcgtu catcgggact ug                                                22

<210> SEQ ID NO 281
<211> LENGTH: 25
<212> TYPE: DNA
<213> ORGANISM: Artificial Sequence
<220> FEATURE:
<223> OTHER INFORMATION: Synthetic DNA/RNA primer, F178

<400> SEQUENCE: 281
gactggtuac tgaaagcuca gggat                                             25

<210> SEQ ID NO 282
<211> LENGTH: 27
<212> TYPE: DNA
<213> ORGANISM: Artificial Sequence
<220> FEATURE:
<223> OTHER INFORMATION: Synthetic DNA/RNA primer, F179

<400> SEQUENCE: 282
gaggactctg ugagtgggat ttgttut                                           27

<210> SEQ ID NO 283
<211> LENGTH: 26
<212> TYPE: DNA
<213> ORGANISM: Artificial Sequence
<220> FEATURE:
<223> OTHER INFORMATION: Synthetic DNA/RNA primer, F180

<400> SEQUENCE: 283
gacatcccug actgtgagau caagaa                                            26

<210> SEQ ID NO 284
<211> LENGTH: 22
<212> TYPE: DNA
<213> ORGANISM: Artificial Sequence
<220> FEATURE:
<223> OTHER INFORMATION: Synthetic DNA/RNA primer, F181

<400> SEQUENCE: 284
```

```
gaatcaaccu gcttggtgtc ug                                              22
```

<210> SEQ ID NO 285
<211> LENGTH: 21
<212> TYPE: DNA
<213> ORGANISM: Artificial Sequence
<220> FEATURE:
<223> OTHER INFORMATION: Synthetic DNA/RNA primer, F182

<400> SEQUENCE: 285

```
gaacgaggac cugtgggacu c                                               21
```

<210> SEQ ID NO 286
<211> LENGTH: 22
<212> TYPE: DNA
<213> ORGANISM: Artificial Sequence
<220> FEATURE:
<223> OTHER INFORMATION: Synthetic DNA/RNA primer, F183

<400> SEQUENCE: 286

```
gacatucccc aacagctgug gt                                              22
```

<210> SEQ ID NO 287
<211> LENGTH: 22
<212> TYPE: DNA
<213> ORGANISM: Artificial Sequence
<220> FEATURE:
<223> OTHER INFORMATION: Synthetic DNA/RNA primer, F184

<400> SEQUENCE: 287

```
gaccttccuc ctgaaggccu ga                                              22
```

<210> SEQ ID NO 288
<211> LENGTH: 21
<212> TYPE: DNA
<213> ORGANISM: Artificial Sequence
<220> FEATURE:
<223> OTHER INFORMATION: Synthetic DNA/RNA primer, F185

<400> SEQUENCE: 288

```
gaaagtgcut gtgcccugca t                                               21
```

<210> SEQ ID NO 289
<211> LENGTH: 23
<212> TYPE: DNA
<213> ORGANISM: Artificial Sequence
<220> FEATURE:
<223> OTHER INFORMATION: Synthetic DNA/RNA primer, F186

<400> SEQUENCE: 289

```
gaccccucuu ggaccuuaga ugc                                             23
```

<210> SEQ ID NO 290
<211> LENGTH: 24
<212> TYPE: DNA
<213> ORGANISM: Artificial Sequence
<220> FEATURE:
<223> OTHER INFORMATION: Synthetic DNA/RNA primer, F187

<400> SEQUENCE: 290

```
gacgcaugga gaagaaactg caug                                            24
```

<210> SEQ ID NO 291
<211> LENGTH: 25
<212> TYPE: DNA

<213> ORGANISM: Artificial Sequence
<220> FEATURE:
<223> OTHER INFORMATION: Synthetic DNA/RNA primer, F188

<400> SEQUENCE: 291
gatcccctau gtgcaagtcc uaaag                                    25

<210> SEQ ID NO 292
<211> LENGTH: 22
<212> TYPE: DNA
<213> ORGANISM: Artificial Sequence
<220> FEATURE:
<223> OTHER INFORMATION: Synthetic DNA/RNA primer, F189

<400> SEQUENCE: 292
gaccactgug cagaagctcu cc                                       22

<210> SEQ ID NO 293
<211> LENGTH: 19
<212> TYPE: DNA
<213> ORGANISM: Artificial Sequence
<220> FEATURE:
<223> OTHER INFORMATION: Synthetic DNA/RNA primer, F190

<400> SEQUENCE: 293
gacgccggcc ucgtgaguc                                           19

<210> SEQ ID NO 294
<211> LENGTH: 27
<212> TYPE: DNA
<213> ORGANISM: Artificial Sequence
<220> FEATURE:
<223> OTHER INFORMATION: Synthetic DNA/RNA primer, F191

<400> SEQUENCE: 294
gacaaatgcu gaaagctgta ccauacc                                  27

<210> SEQ ID NO 295
<211> LENGTH: 24
<212> TYPE: DNA
<213> ORGANISM: Artificial Sequence
<220> FEATURE:
<223> OTHER INFORMATION: Synthetic DNA/RNA primer, F192

<400> SEQUENCE: 295
gatgaggcag uctttactca ccug                                     24

<210> SEQ ID NO 296
<211> LENGTH: 25
<212> TYPE: DNA
<213> ORGANISM: Artificial Sequence
<220> FEATURE:
<223> OTHER INFORMATION: Synthetic DNA/RNA primer, F193

<400> SEQUENCE: 296
gagcaaagac uggttctcac ucacc                                    25

<210> SEQ ID NO 297
<211> LENGTH: 24
<212> TYPE: DNA
<213> ORGANISM: Artificial Sequence
<220> FEATURE:
<223> OTHER INFORMATION: Synthetic DNA/RNA primer, F194

<400> SEQUENCE: 297
gacgauctgt tcuacacgga accc                                     24

<210> SEQ ID NO 298
<211> LENGTH: 26
<212> TYPE: DNA
<213> ORGANISM: Artificial Sequence
<220> FEATURE:
<223> OTHER INFORMATION: Synthetic DNA/RNA primer, F195

<400> SEQUENCE: 298
gaccagacaa gccuacagta ggaauc                                    26

<210> SEQ ID NO 299
<211> LENGTH: 23
<212> TYPE: DNA
<213> ORGANISM: Artificial Sequence
<220> FEATURE:
<223> OTHER INFORMATION: Synthetic DNA/RNA primer, F196

<400> SEQUENCE: 299
gactccacag acccuctcct ugc                                       23

<210> SEQ ID NO 300
<211> LENGTH: 24
<212> TYPE: DNA
<213> ORGANISM: Artificial Sequence
<220> FEATURE:
<223> OTHER INFORMATION: Synthetic DNA/RNA primer, F197

<400> SEQUENCE: 300
gaagggtgtc uctctgtggc ttua                                      24

<210> SEQ ID NO 301
<211> LENGTH: 25
<212> TYPE: DNA
<213> ORGANISM: Artificial Sequence
<220> FEATURE:
<223> OTHER INFORMATION: Synthetic DNA/RNA primer, F198

<400> SEQUENCE: 301
gagtttcugc agattgactu gcaca                                     25

<210> SEQ ID NO 302
<211> LENGTH: 30
<212> TYPE: DNA
<213> ORGANISM: Artificial Sequence
<220> FEATURE:
<223> OTHER INFORMATION: Synthetic DNA/RNA primer, F199

<400> SEQUENCE: 302
gatcaggaaa caaaaauttg tgctaugcaa                                30

<210> SEQ ID NO 303
<211> LENGTH: 24
<212> TYPE: DNA
<213> ORGANISM: Artificial Sequence
<220> FEATURE:
<223> OTHER INFORMATION: Synthetic DNA/RNA primer, F200

<400> SEQUENCE: 303
gagctggagg agcuagagct ugat                                      24

<210> SEQ ID NO 304
<211> LENGTH: 24
<212> TYPE: DNA
<213> ORGANISM: Artificial Sequence
<220> FEATURE:

<223> OTHER INFORMATION: Synthetic DNA/RNA primer, F201

<400> SEQUENCE: 304
gagggctguc gtggtagact uaga                                      24

<210> SEQ ID NO 305
<211> LENGTH: 30
<212> TYPE: DNA
<213> ORGANISM: Artificial Sequence
<220> FEATURE:
<223> OTHER INFORMATION: Synthetic DNA/RNA primer, F202

<400> SEQUENCE: 305
gaaagacttc ucaaattgtt gccattucag                                30

<210> SEQ ID NO 306
<211> LENGTH: 27
<212> TYPE: DNA
<213> ORGANISM: Artificial Sequence
<220> FEATURE:
<223> OTHER INFORMATION: Synthetic DNA/RNA primer, F203

<400> SEQUENCE: 306
gacgaggaag aaaaacaauc ccactug                                   27

<210> SEQ ID NO 307
<211> LENGTH: 27
<212> TYPE: DNA
<213> ORGANISM: Artificial Sequence
<220> FEATURE:
<223> OTHER INFORMATION: Synthetic DNA/RNA primer, F204

<400> SEQUENCE: 307
gagagatcct tucgaagtca tcgtcut                                   27

<210> SEQ ID NO 308
<211> LENGTH: 25
<212> TYPE: DNA
<213> ORGANISM: Artificial Sequence
<220> FEATURE:
<223> OTHER INFORMATION: Synthetic DNA/RNA primer, F205

<400> SEQUENCE: 308
gagggcaaug tcaattagcu ggaac                                     25

<210> SEQ ID NO 309
<211> LENGTH: 27
<212> TYPE: DNA
<213> ORGANISM: Artificial Sequence
<220> FEATURE:
<223> OTHER INFORMATION: Synthetic DNA/RNA primer, F206

<400> SEQUENCE: 309
gacactgtgt tacugccatc gactuac                                   27

<210> SEQ ID NO 310
<211> LENGTH: 28
<212> TYPE: DNA
<213> ORGANISM: Artificial Sequence
<220> FEATURE:
<223> OTHER INFORMATION: Synthetic DNA/RNA primer, F207

<400> SEQUENCE: 310 gactttacc cucttcagct cagttuct                                   28

```
<210> SEQ ID NO 311
<211> LENGTH: 30
<212> TYPE: DNA
<213> ORGANISM: Artificial Sequence
<220> FEATURE:
<223> OTHER INFORMATION: Synthetic DNA/RNA primer, F208

<400> SEQUENCE: 311
gatctcctcc aaccuaatag tgtatucaca                              30

<210> SEQ ID NO 312
<211> LENGTH: 30
<212> TYPE: DNA
<213> ORGANISM: Artificial Sequence
<220> FEATURE:
<223> OTHER INFORMATION: Synthetic DNA/RNA primer, F209

<400> SEQUENCE: 312
gatttcguaa gtgttacuca agaagcagaa                              30

<210> SEQ ID NO 313
<211> LENGTH: 26
<212> TYPE: DNA
<213> ORGANISM: Artificial Sequence
<220> FEATURE:
<223> OTHER INFORMATION: Synthetic DNA/RNA primer, F210

<400> SEQUENCE: 313
gaatgccccc aagaauccta guagaa                                  26

<210> SEQ ID NO 314
<211> LENGTH: 31
<212> TYPE: DNA
<213> ORGANISM: Artificial Sequence
<220> FEATURE:
<223> OTHER INFORMATION: Synthetic DNA/RNA primer, F211

<400> SEQUENCE: 314
gaagagatga ttgutgaatt ttcctttugg g                            31

<210> SEQ ID NO 315
<211> LENGTH: 23
<212> TYPE: DNA
<213> ORGANISM: Artificial Sequence
<220> FEATURE:
<223> OTHER INFORMATION: Synthetic DNA/RNA primer, F212

<400> SEQUENCE: 315
gacggaacuc gaatcgcuac cct                                     23

<210> SEQ ID NO 316
<211> LENGTH: 23
<212> TYPE: DNA
<213> ORGANISM: Artificial Sequence
<220> FEATURE:
<223> OTHER INFORMATION: Synthetic DNA/RNA primer, F213

<400> SEQUENCE: 316
gactcgatgc ugttcccagg uac                                     23

<210> SEQ ID NO 317
<211> LENGTH: 29
<212> TYPE: DNA
<213> ORGANISM: Artificial Sequence
<220> FEATURE:
<223> OTHER INFORMATION: Synthetic DNA/RNA primer, F214
```

<400> SEQUENCE: 317
gatcatacag acacutcatt tggaguacc                                    29

<210> SEQ ID NO 318
<211> LENGTH: 30
<212> TYPE: DNA
<213> ORGANISM: Artificial Sequence
<220> FEATURE:
<223> OTHER INFORMATION: Synthetic DNA/RNA primer, F215

<400> SEQUENCE: 318
gaaaaaataa agctuggctt caagttguct                                   30

<210> SEQ ID NO 319
<211> LENGTH: 32
<212> TYPE: DNA
<213> ORGANISM: Artificial Sequence
<220> FEATURE:
<223> OTHER INFORMATION: Synthetic DNA/RNA primer, F216

<400> SEQUENCE: 319
gaacattgtg accutaattt tgtgatctct ug                                32

<210> SEQ ID NO 320
<211> LENGTH: 26
<212> TYPE: DNA
<213> ORGANISM: Artificial Sequence
<220> FEATURE:
<223> OTHER INFORMATION: Synthetic DNA/RNA primer, F217

<400> SEQUENCE: 320
gaccccactc augtttagca gatgua                                       26

<210> SEQ ID NO 321
<211> LENGTH: 26
<212> TYPE: DNA
<213> ORGANISM: Artificial Sequence
<220> FEATURE:
<223> OTHER INFORMATION: Synthetic DNA/RNA primer, F218

<400> SEQUENCE: 321
gaggacaggu tttgttgtug aggaag                                       26

<210> SEQ ID NO 322
<211> LENGTH: 35
<212> TYPE: DNA
<213> ORGANISM: Artificial Sequence
<220> FEATURE:
<223> OTHER INFORMATION: Synthetic DNA/RNA primer, F219

<400> SEQUENCE: 322
gaagcaaggt cauaaattat tctccatatt tucca                             35

<210> SEQ ID NO 323
<211> LENGTH: 34
<212> TYPE: DNA
<213> ORGANISM: Artificial Sequence
<220> FEATURE:
<223> OTHER INFORMATION: Synthetic DNA/RNA primer, F220

<400> SEQUENCE: 323
gatcttttta cctuatagat gggaaacaug agag                              34

<210> SEQ ID NO 324
<211> LENGTH: 33

```
<212> TYPE: DNA
<213> ORGANISM: Artificial Sequence
<220> FEATURE:
<223> OTHER INFORMATION: Synthetic DNA/RNA primer, F221

<400> SEQUENCE: 324
gaatgtgtct ttcaugagaa aaacaagatc aut                           33

<210> SEQ ID NO 325
<211> LENGTH: 29
<212> TYPE: DNA
<213> ORGANISM: Artificial Sequence
<220> FEATURE:
<223> OTHER INFORMATION: Synthetic DNA/RNA primer, F222

<400> SEQUENCE: 325
gatagtagct gauccacaga agttcagua                                29

<210> SEQ ID NO 326
<211> LENGTH: 35
<212> TYPE: DNA
<213> ORGANISM: Artificial Sequence
<220> FEATURE:
<223> OTHER INFORMATION: Synthetic DNA/RNA primer, F223

<400> SEQUENCE: 326
gaaagactct gaauaccacc atcaagaata auaaa                         35

<210> SEQ ID NO 327
<211> LENGTH: 25
<212> TYPE: DNA
<213> ORGANISM: Artificial Sequence
<220> FEATURE:
<223> OTHER INFORMATION: Synthetic DNA/RNA primer, F224

<400> SEQUENCE: 327
gaatctacag gccaauggtt cctuc                                    25

<210> SEQ ID NO 328
<211> LENGTH: 29
<212> TYPE: DNA
<213> ORGANISM: Artificial Sequence
<220> FEATURE:
<223> OTHER INFORMATION: Synthetic DNA/RNA primer, F225

<400> SEQUENCE: 328
gagccagtag ucacaaagat ttctuacca                                29

<210> SEQ ID NO 329
<211> LENGTH: 22
<212> TYPE: DNA
<213> ORGANISM: Artificial Sequence
<220> FEATURE:
<223> OTHER INFORMATION: Synthetic DNA/RNA primer, F226

<400> SEQUENCE: 329
gaagaagaut ggguggggcag ac                                      22

<210> SEQ ID NO 330
<211> LENGTH: 33
<212> TYPE: DNA
<213> ORGANISM: Artificial Sequence
<220> FEATURE:
<223> OTHER INFORMATION: Synthetic DNA/RNA primer, F227

<400> SEQUENCE: 330
```
gaaaccactg atacautttt ctactttccu gaa                          33

<210> SEQ ID NO 331
<211> LENGTH: 32
<212> TYPE: DNA
<213> ORGANISM: Artificial Sequence
<220> FEATURE:
<223> OTHER INFORMATION: Synthetic DNA/RNA primer, F228

<400> SEQUENCE: 331
gaagacttct tugagatatt tccatagcuc ac                           32

<210> SEQ ID NO 332
<211> LENGTH: 35
<212> TYPE: DNA
<213> ORGANISM: Artificial Sequence
<220> FEATURE:
<223> OTHER INFORMATION: Synthetic DNA/RNA primer, F229

<400> SEQUENCE: 332 gacattttg tttatgutat tctctctacc ucagc                         35

<210> SEQ ID NO 333
<211> LENGTH: 34
<212> TYPE: DNA
<213> ORGANISM: Artificial Sequence
<220> FEATURE:
<223> OTHER INFORMATION: Synthetic DNA/RNA primer, F230

<400> SEQUENCE: 333
gaagttatag gtaaucgatg catatagctc auct                         34

<210> SEQ ID NO 334
<211> LENGTH: 34
<212> TYPE: DNA
<213> ORGANISM: Artificial Sequence
<220> FEATURE:
<223> OTHER INFORMATION: Synthetic DNA/RNA primer, F231

<400> SEQUENCE: 334
gaaattgttt gtagggutgg ttattagtga cuat                         34

<210> SEQ ID NO 335
<211> LENGTH: 26
<212> TYPE: DNA
<213> ORGANISM: Artificial Sequence
<220> FEATURE:
<223> OTHER INFORMATION: Synthetic DNA/RNA primer, F232

<400> SEQUENCE: 335
gaccactatg uaagacaaag gcuggt                                  26

<210> SEQ ID NO 336
<211> LENGTH: 28
<212> TYPE: DNA
<213> ORGANISM: Artificial Sequence
<220> FEATURE:
<223> OTHER INFORMATION: Synthetic DNA/RNA primer, F233

<400> SEQUENCE: 336
gagtttctgu agcccatact ttggauga                                28

<210> SEQ ID NO 337
<211> LENGTH: 25
<212> TYPE: DNA
<213> ORGANISM: Artificial Sequence

```
<220> FEATURE:
<223> OTHER INFORMATION: Synthetic DNA/RNA primer, F234

<400> SEQUENCE: 337
gacactguga aggcccuuuc uucug                                        25

<210> SEQ ID NO 338
<211> LENGTH: 33
<212> TYPE: DNA
<213> ORGANISM: Artificial Sequence
<220> FEATURE:
<223> OTHER INFORMATION: Synthetic DNA/RNA primer, F235

<400> SEQUENCE: 338
gagcatagga gataaucata ggaatcccaa aut                               33

<210> SEQ ID NO 339
<211> LENGTH: 25
<212> TYPE: DNA
<213> ORGANISM: Artificial Sequence
<220> FEATURE:
<223> OTHER INFORMATION: Synthetic DNA/RNA primer, F236

<400> SEQUENCE: 339
gaagtcactg gaautgttgg gcuac                                        25

<210> SEQ ID NO 340
<211> LENGTH: 23
<212> TYPE: DNA
<213> ORGANISM: Artificial Sequence
<220> FEATURE:
<223> OTHER INFORMATION: Synthetic DNA/RNA primer, F237

<400> SEQUENCE: 340
gactuccagg agccguagag ttt                                          23

<210> SEQ ID NO 341
<211> LENGTH: 31
<212> TYPE: DNA
<213> ORGANISM: Artificial Sequence
<220> FEATURE:
<223> OTHER INFORMATION: Synthetic DNA/RNA primer, F238

<400> SEQUENCE: 341
gaactcttcc tattuttgta gtgacctgtu t                                 31

<210> SEQ ID NO 342
<211> LENGTH: 27
<212> TYPE: DNA
<213> ORGANISM: Artificial Sequence
<220> FEATURE:
<223> OTHER INFORMATION: Synthetic DNA/RNA primer, F239

<400> SEQUENCE: 342
gattcctgau aaagcacagc tgtagug                                      27

<210> SEQ ID NO 343
<211> LENGTH: 21
<212> TYPE: DNA
<213> ORGANISM: Artificial Sequence
<220> FEATURE:
<223> OTHER INFORMATION: Synthetic DNA/RNA primer, F240

<400> SEQUENCE: 343
gattgtucaa gcagcgaguc c                                            21
```

```
<210> SEQ ID NO 344
<211> LENGTH: 23
<212> TYPE: DNA
<213> ORGANISM: Artificial Sequence
<220> FEATURE:
<223> OTHER INFORMATION: Synthetic DNA/RNA primer, F241

<400> SEQUENCE: 344
gacatgaacu acctggaccg cut                                              23

<210> SEQ ID NO 345
<211> LENGTH: 22
<212> TYPE: DNA
<213> ORGANISM: Artificial Sequence
<220> FEATURE:
<223> OTHER INFORMATION: Synthetic DNA/RNA primer, F242

<400> SEQUENCE: 345
gaggtgctgu ctgggaagau gt                                               22

<210> SEQ ID NO 346
<211> LENGTH: 25
<212> TYPE: DNA
<213> ORGANISM: Artificial Sequence
<220> FEATURE:
<223> OTHER INFORMATION: Synthetic DNA/RNA primer, F243

<400> SEQUENCE: 346
gaaaagaggc aguagcatct tcucc                                            25

<210> SEQ ID NO 347
<211> LENGTH: 28
<212> TYPE: DNA
<213> ORGANISM: Artificial Sequence
<220> FEATURE:
<223> OTHER INFORMATION: Synthetic DNA/RNA primer, F244

<400> SEQUENCE: 347
gaaatcctgg agcuttggtg tctaatuc                                         28

<210> SEQ ID NO 348
<211> LENGTH: 21
<212> TYPE: DNA
<213> ORGANISM: Artificial Sequence
<220> FEATURE:
<223> OTHER INFORMATION: Synthetic DNA/RNA primer, F245

<400> SEQUENCE: 348
gatgcagaag cgguttctgu g                                                21

<210> SEQ ID NO 349
<211> LENGTH: 27
<212> TYPE: DNA
<213> ORGANISM: Artificial Sequence
<220> FEATURE:
<223> OTHER INFORMATION: Synthetic DNA/RNA primer, F246

<400> SEQUENCE: 349
gagcctcaga gauaaaggca aagatug                                          27

<210> SEQ ID NO 350
<211> LENGTH: 34
<212> TYPE: DNA
<213> ORGANISM: Artificial Sequence
<220> FEATURE:
<223> OTHER INFORMATION: Synthetic DNA/RNA primer, F247
```

```
<400> SEQUENCE: 350
gaaccattat ttcttugttt tgtttttcct guat                                34

<210> SEQ ID NO 351
<211> LENGTH: 29
<212> TYPE: DNA
<213> ORGANISM: Artificial Sequence
<220> FEATURE:
<223> OTHER INFORMATION: Synthetic DNA/RNA primer, F248

<400> SEQUENCE: 351
gataccaacc aaguttcatu aaccacagt                                      29

<210> SEQ ID NO 352
<211> LENGTH: 30
<212> TYPE: DNA
<213> ORGANISM: Artificial Sequence
<220> FEATURE:
<223> OTHER INFORMATION: Synthetic DNA/RNA primer, F249

<400> SEQUENCE: 352
gaccatgttg gucacttact caaagattut                                     30

<210> SEQ ID NO 353
<211> LENGTH: 24
<212> TYPE: DNA
<213> ORGANISM: Artificial Sequence
<220> FEATURE:
<223> OTHER INFORMATION: Synthetic DNA/RNA primer, F250

<400> SEQUENCE: 353
gaaatgggca agguatggat gugg                                           24

<210> SEQ ID NO 354
<211> LENGTH: 23
<212> TYPE: DNA
<213> ORGANISM: Artificial Sequence
<220> FEATURE:
<223> OTHER INFORMATION: Synthetic DNA/RNA primer, F251

<400> SEQUENCE: 354
gatggcgcau cagatcctag tut                                            23

<210> SEQ ID NO 355
<211> LENGTH: 32
<212> TYPE: DNA
<213> ORGANISM: Artificial Sequence
<220> FEATURE:
<223> OTHER INFORMATION: Synthetic DNA/RNA primer, F252

<400> SEQUENCE: 355
gatgtaacaa ccuaaaggga ataggaagaa ug                                  32

<210> SEQ ID NO 356
<211> LENGTH: 22
<212> TYPE: DNA
<213> ORGANISM: Artificial Sequence
<220> FEATURE:
<223> OTHER INFORMATION: Synthetic DNA/RNA primer, F253

<400> SEQUENCE: 356
gaggcactgg utctcattcc ug                                             22

<210> SEQ ID NO 357
```

```
<211> LENGTH: 25
<212> TYPE: DNA
<213> ORGANISM: Artificial Sequence
<220> FEATURE:
<223> OTHER INFORMATION: Synthetic DNA/RNA primer, F254

<400> SEQUENCE: 357
gaatgactca auaccaaccc cucca                                              25

<210> SEQ ID NO 358
<211> LENGTH: 32
<212> TYPE: DNA
<213> ORGANISM: Artificial Sequence
<220> FEATURE:
<223> OTHER INFORMATION: Synthetic DNA/RNA primer, F255

<400> SEQUENCE: 358
gacataacca tgauattaat aggactccug ct                                      32

<210> SEQ ID NO 359
<211> LENGTH: 29
<212> TYPE: DNA
<213> ORGANISM: Artificial Sequence
<220> FEATURE:
<223> OTHER INFORMATION: Synthetic DNA/RNA primer, F256

<400> SEQUENCE: 359
gatgaacgca aaccugttg aagtuaaaa                                           29

<210> SEQ ID NO 360
<211> LENGTH: 34
<212> TYPE: DNA
<213> ORGANISM: Artificial Sequence
<220> FEATURE:
<223> OTHER INFORMATION: Synthetic DNA/RNA primer, F257

<400> SEQUENCE: 360
gacttaaaaa tgtcaauatc tggcctcaaa uacg                                    34

<210> SEQ ID NO 361
<211> LENGTH: 33
<212> TYPE: DNA
<213> ORGANISM: Artificial Sequence
<220> FEATURE:
<223> OTHER INFORMATION: Synthetic DNA/RNA primer, F258

<400> SEQUENCE: 361
gagggaagca atutgctaca ctttaattua aac                                     33

<210> SEQ ID NO 362
<211> LENGTH: 26
<212> TYPE: DNA
<213> ORGANISM: Artificial Sequence
<220> FEATURE:
<223> OTHER INFORMATION: Synthetic DNA/RNA primer, F259

<400> SEQUENCE: 362
gaacagaagc utctaatccu caacgt                                             26

<210> SEQ ID NO 363
<211> LENGTH: 27
<212> TYPE: DNA
<213> ORGANISM: Artificial Sequence
<220> FEATURE:
<223> OTHER INFORMATION: Synthetic DNA/RNA primer, F260

<400> SEQUENCE: 363
```
gaagttgaug ccaattcaca aucacca                                        27

<210> SEQ ID NO 364
<211> LENGTH: 33
<212> TYPE: DNA
<213> ORGANISM: Artificial Sequence
<220> FEATURE:
<223> OTHER INFORMATION: Synthetic DNA/RNA primer, F261

<400> SEQUENCE: 364
gactgaggtc tatucacttt cttttcatct tug                                 33

<210> SEQ ID NO 365
<211> LENGTH: 30
<212> TYPE: DNA
<213> ORGANISM: Artificial Sequence
<220> FEATURE:
<223> OTHER INFORMATION: Synthetic DNA/RNA primer, F262

<400> SEQUENCE: 365
gactatttgt ttctucccca tggaattguc                                     30

<210> SEQ ID NO 366
<211> LENGTH: 26
<212> TYPE: DNA
<213> ORGANISM: Artificial Sequence
<220> FEATURE:
<223> OTHER INFORMATION: Synthetic DNA/RNA primer, F263

<400> SEQUENCE: 366
gataatcttu gaactgcctg ugcact                                         26

<210> SEQ ID NO 367
<211> LENGTH: 25
<212> TYPE: DNA
<213> ORGANISM: Artificial Sequence
<220> FEATURE:
<223> OTHER INFORMATION: Synthetic DNA/RNA primer, F264

<400> SEQUENCE: 367
gaaagcaaug gcttgggaag uaaga                                          25

<210> SEQ ID NO 368
<211> LENGTH: 35
<212> TYPE: DNA
<213> ORGANISM: Artificial Sequence
<220> FEATURE:
<223> OTHER INFORMATION: Synthetic DNA/RNA primer, F265

<400> SEQUENCE: 368
gatctaaagg tttttcugat ttcctcatta ggaut                               35

<210> SEQ ID NO 369
<211> LENGTH: 31
<212> TYPE: DNA
<213> ORGANISM: Artificial Sequence
<220> FEATURE:
<223> OTHER INFORMATION: Synthetic DNA/RNA primer, F266

<400> SEQUENCE: 369
gatccagtca tttugagaaa gacaactuac t                                   31

<210> SEQ ID NO 370
<211> LENGTH: 34
<212> TYPE: DNA

```
<213> ORGANISM: Artificial Sequence
<220> FEATURE:
<223> OTHER INFORMATION: Synthetic DNA/RNA primer, F267

<400> SEQUENCE: 370
gattcattaa tatttucaga tcaccagttg atug                         34

<210> SEQ ID NO 371
<211> LENGTH: 35
<212> TYPE: DNA
<213> ORGANISM: Artificial Sequence
<220> FEATURE:
<223> OTHER INFORMATION: Synthetic DNA/RNA primer, F268

<400> SEQUENCE: 371
gaattaactg taccuccaac tttcttacta taugc                        35

<210> SEQ ID NO 372
<211> LENGTH: 32
<212> TYPE: DNA
<213> ORGANISM: Artificial Sequence
<220> FEATURE:
<223> OTHER INFORMATION: Synthetic DNA/RNA primer, F269

<400> SEQUENCE: 372
gattaagaaa cuagaaactg tttagacugc ct                           32

<210> SEQ ID NO 373
<211> LENGTH: 23
<212> TYPE: DNA
<213> ORGANISM: Artificial Sequence
<220> FEATURE:
<223> OTHER INFORMATION: Synthetic DNA/RNA primer, F270

<400> SEQUENCE: 373
gatggttctg ucgactaaac ugc                                     23

<210> SEQ ID NO 374
<211> LENGTH: 26
<212> TYPE: DNA
<213> ORGANISM: Artificial Sequence
<220> FEATURE:
<223> OTHER INFORMATION: Synthetic DNA/RNA primer, F271

<400> SEQUENCE: 374
gaacggacac uatgtcctta agcuga                                  26

<210> SEQ ID NO 375
<211> LENGTH: 22
<212> TYPE: DNA
<213> ORGANISM: Artificial Sequence
<220> FEATURE:
<223> OTHER INFORMATION: Synthetic DNA/RNA primer, F272

<400> SEQUENCE: 375
gattggcaug gcttctcuag ct                                      22

<210> SEQ ID NO 376
<211> LENGTH: 22
<212> TYPE: DNA
<213> ORGANISM: Artificial Sequence
<220> FEATURE:
<223> OTHER INFORMATION: Synthetic DNA/RNA primer, F273

<400> SEQUENCE: 376
gacaccttcu accgctcacu gc                                      22
```

<210> SEQ ID NO 377
<211> LENGTH: 24
<212> TYPE: DNA
<213> ORGANISM: Artificial Sequence
<220> FEATURE:
<223> OTHER INFORMATION: Synthetic DNA/RNA primer, F274

<400> SEQUENCE: 377
gaattgacuc tgaatgucgg ccaa                                      24

<210> SEQ ID NO 378
<211> LENGTH: 24
<212> TYPE: DNA
<213> ORGANISM: Artificial Sequence
<220> FEATURE:
<223> OTHER INFORMATION: Synthetic DNA/RNA primer, F275

<400> SEQUENCE: 378
gactctgccc cuagaaacc ugga                                       24

<210> SEQ ID NO 379
<211> LENGTH: 27
<212> TYPE: DNA
<213> ORGANISM: Artificial Sequence
<220> FEATURE:
<223> OTHER INFORMATION: Synthetic DNA/RNA primer, F276

<400> SEQUENCE: 379
gaattactcu aactttcgca ugcacac                                   27

<210> SEQ ID NO 380
<211> LENGTH: 21
<212> TYPE: DNA
<213> ORGANISM: Artificial Sequence
<220> FEATURE:
<223> OTHER INFORMATION: Synthetic DNA/RNA primer, F277

<400> SEQUENCE: 380
gaagugggca gcagtttcug a                                         21

<210> SEQ ID NO 381
<211> LENGTH: 27
<212> TYPE: DNA
<213> ORGANISM: Artificial Sequence
<220> FEATURE:
<223> OTHER INFORMATION: Synthetic DNA/RNA primer, F278

<400> SEQUENCE: 381
gaaaccaact gcutgtatgc tttcugg                                   27

<210> SEQ ID NO 382
<211> LENGTH: 21
<212> TYPE: DNA
<213> ORGANISM: Artificial Sequence
<220> FEATURE:
<223> OTHER INFORMATION: Synthetic DNA/RNA primer, F279

<400> SEQUENCE: 382
gagcagccut acctggtugg a                                         21

<210> SEQ ID NO 383
<211> LENGTH: 22
<212> TYPE: DNA
<213> ORGANISM: Artificial Sequence
<220> FEATURE:

<223> OTHER INFORMATION: Synthetic DNA/RNA primer, F280

<400> SEQUENCE: 383
gattacagcu cgttggugca gt                                    22

<210> SEQ ID NO 384
<211> LENGTH: 26
<212> TYPE: DNA
<213> ORGANISM: Artificial Sequence
<220> FEATURE:
<223> OTHER INFORMATION: Synthetic DNA/RNA primer, F281

<400> SEQUENCE: 384
gaatggaaac ccugacagag tcttug                                26

<210> SEQ ID NO 385
<211> LENGTH: 26
<212> TYPE: DNA
<213> ORGANISM: Artificial Sequence
<220> FEATURE:
<223> OTHER INFORMATION: Synthetic DNA/RNA primer, F282

<400> SEQUENCE: 385
gatgttatga gcutagcacc tugcag                                26

<210> SEQ ID NO 386
<211> LENGTH: 24
<212> TYPE: DNA
<213> ORGANISM: Artificial Sequence
<220> FEATURE:
<223> OTHER INFORMATION: Synthetic DNA/RNA primer, F283

<400> SEQUENCE: 386
gaccagttcu gcagttagag gtug                                  24

<210> SEQ ID NO 387
<211> LENGTH: 30
<212> TYPE: DNA
<213> ORGANISM: Artificial Sequence
<220> FEATURE:
<223> OTHER INFORMATION: Synthetic DNA/RNA primer, F284

<400> SEQUENCE: 387
gatttgattc ttaaucacct aaggauggct                            30

<210> SEQ ID NO 388
<211> LENGTH: 24
<212> TYPE: DNA
<213> ORGANISM: Artificial Sequence
<220> FEATURE:
<223> OTHER INFORMATION: Synthetic DNA/RNA primer, F285

<400> SEQUENCE: 388
gaatccgtac cutccaccaa tcug                                  24

<210> SEQ ID NO 389
<211> LENGTH: 35
<212> TYPE: DNA
<213> ORGANISM: Artificial Sequence
<220> FEATURE:
<223> OTHER INFORMATION: Synthetic DNA/RNA primer, F286

<400> SEQUENCE: 389
gatataacaa tgaaugacca aaaggaaatu aacaa                      35

```
<210> SEQ ID NO 390
<211> LENGTH: 31
<212> TYPE: DNA
<213> ORGANISM: Artificial Sequence
<220> FEATURE:
<223> OTHER INFORMATION: Synthetic DNA/RNA primer, F287

<400> SEQUENCE: 390
gataactttc cataugcaaa cctactggcu a                                      31

<210> SEQ ID NO 391
<211> LENGTH: 23
<212> TYPE: DNA
<213> ORGANISM: Artificial Sequence
<220> FEATURE:
<223> OTHER INFORMATION: Synthetic DNA/RNA primer, F288

<400> SEQUENCE: 391
gaccuggacg tctuggaaaa ggg                                               23

<210> SEQ ID NO 392
<211> LENGTH: 22
<212> TYPE: DNA
<213> ORGANISM: Artificial Sequence
<220> FEATURE:
<223> OTHER INFORMATION: Synthetic DNA/RNA primer, F289

<400> SEQUENCE: 392
gatctggguc aaggauggca ca                                                22

<210> SEQ ID NO 393
<211> LENGTH: 21
<212> TYPE: DNA
<213> ORGANISM: Artificial Sequence
<220> FEATURE:
<223> OTHER INFORMATION: Synthetic DNA/RNA primer, F290

<400> SEQUENCE: 393
gagcccacut cccatcuggg t                                                 21

<210> SEQ ID NO 394
<211> LENGTH: 20
<212> TYPE: DNA
<213> ORGANISM: Artificial Sequence
<220> FEATURE:
<223> OTHER INFORMATION: Synthetic DNA/RNA primer, F291

<400> SEQUENCE: 394
gatccccgcu gctgugcaac                                                   20

<210> SEQ ID NO 395
<211> LENGTH: 21
<212> TYPE: DNA
<213> ORGANISM: Artificial Sequence
<220> FEATURE:
<223> OTHER INFORMATION: Synthetic DNA/RNA primer, F292

<400> SEQUENCE: 395
gacccacatg uccagcaccu t                                                 21

<210> SEQ ID NO 396
<211> LENGTH: 24
<212> TYPE: DNA
<213> ORGANISM: Artificial Sequence
<220> FEATURE:
<223> OTHER INFORMATION: Synthetic DNA/RNA primer, F293
```

<400> SEQUENCE: 396 gagctggguga aacaggtagu gagt                                           24

<210> SEQ ID NO 397
<211> LENGTH: 22
<212> TYPE: DNA
<213> ORGANISM: Artificial Sequence
<220> FEATURE:
<223> OTHER INFORMATION: Synthetic DNA/RNA primer, F294

<400> SEQUENCE: 397
gactccaggu ccttgtguga gc                                              22

<210> SEQ ID NO 398
<211> LENGTH: 23
<212> TYPE: DNA
<213> ORGANISM: Artificial Sequence
<220> FEATURE:
<223> OTHER INFORMATION: Synthetic DNA/RNA primer, F295

<400> SEQUENCE: 398
gacctcacga acugtgctga ugg                                             23

<210> SEQ ID NO 399
<211> LENGTH: 26
<212> TYPE: DNA
<213> ORGANISM: Artificial Sequence
<220> FEATURE:
<223> OTHER INFORMATION: Synthetic DNA/RNA primer, F296

<400> SEQUENCE: 399
gaggattcga gaagugacag gctaug                                          26

<210> SEQ ID NO 400
<211> LENGTH: 25
<212> TYPE: DNA
<213> ORGANISM: Artificial Sequence
<220> FEATURE:
<223> OTHER INFORMATION: Synthetic DNA/RNA primer, F297

<400> SEQUENCE: 400
gaattggtag cuggtgatgt tccuc                                           25

<210> SEQ ID NO 401
<211> LENGTH: 29
<212> TYPE: DNA
<213> ORGANISM: Artificial Sequence
<220> FEATURE:
<223> OTHER INFORMATION: Synthetic DNA/RNA primer, F298

<400> SEQUENCE: 401
gacagctaat ucatctggag aucaaaccc                                       29

<210> SEQ ID NO 402
<211> LENGTH: 30
<212> TYPE: DNA
<213> ORGANISM: Artificial Sequence
<220> FEATURE:
<223> OTHER INFORMATION: Synthetic DNA/RNA primer, F299

<400> SEQUENCE: 402
gatgtcagtt cccuccttt ctattttcuc                                       30

<210> SEQ ID NO 403
<211> LENGTH: 21

```
<212> TYPE: DNA
<213> ORGANISM: Artificial Sequence
<220> FEATURE:
<223> OTHER INFORMATION: Synthetic DNA/RNA primer, F300

<400> SEQUENCE: 403
gatgggcacg guaatgcugc t                                       21

<210> SEQ ID NO 404
<211> LENGTH: 20
<212> TYPE: DNA
<213> ORGANISM: Artificial Sequence
<220> FEATURE:
<223> OTHER INFORMATION: Synthetic DNA/RNA primer, F301

<400> SEQUENCE: 404
gactcugcgg tggtuggcat                                         20

<210> SEQ ID NO 405
<211> LENGTH: 24
<212> TYPE: DNA
<213> ORGANISM: Artificial Sequence
<220> FEATURE:
<223> OTHER INFORMATION: Synthetic DNA/RNA primer, F302

<400> SEQUENCE: 405
gactccaccu ccaggaactt acuc                                    24

<210> SEQ ID NO 406
<211> LENGTH: 29
<212> TYPE: DNA
<213> ORGANISM: Artificial Sequence
<220> FEATURE:
<223> OTHER INFORMATION: Synthetic DNA/RNA primer, F303

<400> SEQUENCE: 406
gagggatctt gugaaatgtc atctgacuc                               29

<210> SEQ ID NO 407
<211> LENGTH: 29
<212> TYPE: DNA
<213> ORGANISM: Artificial Sequence
<220> FEATURE:
<223> OTHER INFORMATION: Synthetic DNA/RNA primer, F304

<400> SEQUENCE: 407
gatcaaccct gtutttctcc ctcttatug                               29

<210> SEQ ID NO 408
<211> LENGTH: 26
<212> TYPE: DNA
<213> ORGANISM: Artificial Sequence
<220> FEATURE:
<223> OTHER INFORMATION: Synthetic DNA/RNA primer, F305

<400> SEQUENCE: 408
gactguacag catgaagugc aagaac                                  26

<210> SEQ ID NO 409
<211> LENGTH: 26
<212> TYPE: DNA
<213> ORGANISM: Artificial Sequence
<220> FEATURE:
<223> OTHER INFORMATION: Synthetic DNA/RNA primer, F306

<400> SEQUENCE: 409
```
gaccattaac auggcctacc agagut                                        26

<210> SEQ ID NO 410
<211> LENGTH: 24
<212> TYPE: DNA
<213> ORGANISM: Artificial Sequence
<220> FEATURE:
<223> OTHER INFORMATION: Synthetic DNA/RNA primer, F307

<400> SEQUENCE: 410
gattgccuag acagcaccgt aaug                                          24

<210> SEQ ID NO 411
<211> LENGTH: 25
<212> TYPE: DNA
<213> ORGANISM: Artificial Sequence
<220> FEATURE:
<223> OTHER INFORMATION: Synthetic DNA/RNA primer, F308

<400> SEQUENCE: 411
gagacgcagu ttcttcttct caucg                                         25

<210> SEQ ID NO 412
<211> LENGTH: 30
<212> TYPE: DNA
<213> ORGANISM: Artificial Sequence
<220> FEATURE:
<223> OTHER INFORMATION: Synthetic DNA/RNA primer, F309

<400> SEQUENCE: 412
gatatcgagt gtgugcatat gtgtatgtug                                    30

<210> SEQ ID NO 413
<211> LENGTH: 27
<212> TYPE: RNA
<213> ORGANISM: Artificial Sequence
<220> FEATURE:
<223> OTHER INFORMATION: Synthetic Primer, F310

<400> SEQUENCE: 413
gaagggaaaa ugacaaagaa cagcuca                                       27

<210> SEQ ID NO 414
<211> LENGTH: 23
<212> TYPE: DNA
<213> ORGANISM: Artificial Sequence
<220> FEATURE:
<223> OTHER INFORMATION: Synthetic DNA/RNA primer, F311

<400> SEQUENCE: 414
gaggcctgcu tttggagtcc uat                                           23

<210> SEQ ID NO 415
<211> LENGTH: 23
<212> TYPE: DNA
<213> ORGANISM: Artificial Sequence
<220> FEATURE:
<223> OTHER INFORMATION: Synthetic DNA/RNA primer, F312

<400> SEQUENCE: 415
gagaagagcc uccaccatcu cca                                           23

<210> SEQ ID NO 416
<211> LENGTH: 26
<212> TYPE: DNA
<213> ORGANISM: Artificial Sequence
<220> FEATURE:
<223> OTHER INFORMATION: Synthetic DNA/RNA primer, F313

<400> SEQUENCE: 416
gacacacaug ccatcattcu aggaag                                26

<210> SEQ ID NO 417
<211> LENGTH: 27
<212> TYPE: DNA
<213> ORGANISM: Artificial Sequence
<220> FEATURE:
<223> OTHER INFORMATION: Synthetic DNA/RNA primer, F314

<400> SEQUENCE: 417
gagaggtttu ccagcactct gacauat                               27

<210> SEQ ID NO 418
<211> LENGTH: 26
<212> TYPE: DNA
<213> ORGANISM: Artificial Sequence
<220> FEATURE:
<223> OTHER INFORMATION: Synthetic DNA/RNA primer, F315

<400> SEQUENCE: 418
gatcttctct guttcagggc augaac                                26

<210> SEQ ID NO 419
<211> LENGTH: 25
<212> TYPE: DNA
<213> ORGANISM: Artificial Sequence
<220> FEATURE:
<223> OTHER INFORMATION: Synthetic DNA/RNA primer, F316

<400> SEQUENCE: 419
gaagattcug ccgaaccaat ggauc                                 25

<210> SEQ ID NO 420
<211> LENGTH: 28
<212> TYPE: DNA
<213> ORGANISM: Artificial Sequence
<220> FEATURE:
<223> OTHER INFORMATION: Synthetic DNA/RNA primer, F317

<400> SEQUENCE: 420
gatatgactu gtcacaatgu caccacat                              28

<210> SEQ ID NO 421
<211> LENGTH: 27
<212> TYPE: DNA
<213> ORGANISM: Artificial Sequence
<220> FEATURE:
<223> OTHER INFORMATION: Synthetic DNA/RNA primer, F318

<400> SEQUENCE: 421
gagtgcccta tuacctcaat catccug                               27

<210> SEQ ID NO 422
<211> LENGTH: 31
<212> TYPE: DNA
<213> ORGANISM: Artificial Sequence
<220> FEATURE:
<223> OTHER INFORMATION: Synthetic DNA/RNA primer, F319

<400> SEQUENCE: 422
gatcagttac taccugaaaa tgacacttug t                          31

```
<210> SEQ ID NO 423
<211> LENGTH: 26
<212> TYPE: DNA
<213> ORGANISM: Artificial Sequence
<220> FEATURE:
<223> OTHER INFORMATION: Synthetic DNA/RNA primer, F320

<400> SEQUENCE: 423
gataaagacc tucttccgtg tgucct                                           26

<210> SEQ ID NO 424
<211> LENGTH: 35
<212> TYPE: DNA
<213> ORGANISM: Artificial Sequence
<220> FEATURE:
<223> OTHER INFORMATION: Synthetic DNA/RNA primer, F321

<400> SEQUENCE: 424
gatacattta tttugagaaa cttgagagaa cutca                                 35

<210> SEQ ID NO 425
<211> LENGTH: 33
<212> TYPE: DNA
<213> ORGANISM: Artificial Sequence
<220> FEATURE:
<223> OTHER INFORMATION: Synthetic DNA/RNA primer, F322

<400> SEQUENCE: 425
gaagatggtg atagaucttt aagagaattg cut                                   33

<210> SEQ ID NO 426
<211> LENGTH: 34
<212> TYPE: DNA
<213> ORGANISM: Artificial Sequence
<220> FEATURE:
<223> OTHER INFORMATION: Synthetic DNA/RNA primer, F323

<400> SEQUENCE: 426
gaagcttttg ataagaguta ggaaatcact aguc                                  34

<210> SEQ ID NO 427
<211> LENGTH: 33
<212> TYPE: DNA
<213> ORGANISM: Artificial Sequence
<220> FEATURE:
<223> OTHER INFORMATION: Synthetic DNA/RNA primer, F324

<400> SEQUENCE: 427
gaaggauaaa aaccagcatt atttattuga gca                                   33

<210> SEQ ID NO 428
<211> LENGTH: 29
<212> TYPE: DNA
<213> ORGANISM: Artificial Sequence
<220> FEATURE:
<223> OTHER INFORMATION: Synthetic DNA/RNA primer, F325

<400> SEQUENCE: 428
gactgaccca uaatcttgca ccattuacc                                        29

<210> SEQ ID NO 429
<211> LENGTH: 29
<212> TYPE: DNA
<213> ORGANISM: Artificial Sequence
<220> FEATURE:
<223> OTHER INFORMATION: Synthetic DNA/RNA primer, F326
```

<400> SEQUENCE: 429
gatttgaaat gaaugttcac gacaaaugc                                         29

<210> SEQ ID NO 430
<211> LENGTH: 31
<212> TYPE: DNA
<213> ORGANISM: Artificial Sequence
<220> FEATURE:
<223> OTHER INFORMATION: Synthetic DNA/RNA primer, F327

<400> SEQUENCE: 430
gaacaaccaa aacaauacac acagagattu t                                      31

<210> SEQ ID NO 431
<211> LENGTH: 30
<212> TYPE: DNA
<213> ORGANISM: Artificial Sequence
<220> FEATURE:
<223> OTHER INFORMATION: Synthetic DNA/RNA primer, F328

<400> SEQUENCE: 431
gaacggaggg ucatgtgtat attaaguaag                                        30

<210> SEQ ID NO 432
<211> LENGTH: 33
<212> TYPE: DNA
<213> ORGANISM: Artificial Sequence
<220> FEATURE:
<223> OTHER INFORMATION: Synthetic DNA/RNA primer, F329

<400> SEQUENCE: 432
gagaattaag ugtgtactac ucccaagaga aaa                                    33

<210> SEQ ID NO 433
<211> LENGTH: 34
<212> TYPE: DNA
<213> ORGANISM: Artificial Sequence
<220> FEATURE:
<223> OTHER INFORMATION: Synthetic DNA/RNA primer, F330

<400> SEQUENCE: 433
gatataggat gaguagctcc aaattaatga augt                                   34

<210> SEQ ID NO 434
<211> LENGTH: 29
<212> TYPE: DNA
<213> ORGANISM: Artificial Sequence
<220> FEATURE:
<223> OTHER INFORMATION: Synthetic DNA/RNA primer, F331

<400> SEQUENCE: 434
gagctgtaga auagtcaaga ggaatugca                                         29

<210> SEQ ID NO 435
<211> LENGTH: 26
<212> TYPE: DNA
<213> ORGANISM: Artificial Sequence
<220> FEATURE:
<223> OTHER INFORMATION: Synthetic DNA/RNA primer, F332

<400> SEQUENCE: 435
gactcagtgc uctaaatcca gagcug                                            26

<210> SEQ ID NO 436

```
<211> LENGTH: 33
<212> TYPE: DNA
<213> ORGANISM: Artificial Sequence
<220> FEATURE:
<223> OTHER INFORMATION: Synthetic DNA/RNA primer, F333

<400> SEQUENCE: 436
gaatgaaata tugtcaactc tctuaggcaa aat                              33

<210> SEQ ID NO 437
<211> LENGTH: 29
<212> TYPE: DNA
<213> ORGANISM: Artificial Sequence
<220> FEATURE:
<223> OTHER INFORMATION: Synthetic DNA/RNA primer, F334

<400> SEQUENCE: 437
gatacttugc aaagctgaat uagacagca                                   29

<210> SEQ ID NO 438
<211> LENGTH: 26
<212> TYPE: DNA
<213> ORGANISM: Artificial Sequence
<220> FEATURE:
<223> OTHER INFORMATION: Synthetic DNA/RNA primer, F335

<400> SEQUENCE: 438
gaacatgagc aucacatttt cctugg                                      26

<210> SEQ ID NO 439
<211> LENGTH: 29
<212> TYPE: DNA
<213> ORGANISM: Artificial Sequence
<220> FEATURE:
<223> OTHER INFORMATION: Synthetic DNA/RNA primer, F336

<400> SEQUENCE: 439
gatgccttat gaauatattc acgcugact                                   29

<210> SEQ ID NO 440
<211> LENGTH: 22
<212> TYPE: RNA
<213> ORGANISM: Artificial Sequence
<220> FEATURE:
<223> OTHER INFORMATION: Synthetic Primer, F337

<400> SEQUENCE: 440
gaaccaggua agcaccgaag uc                                          22

<210> SEQ ID NO 441
<211> LENGTH: 19
<212> TYPE: DNA
<213> ORGANISM: Artificial Sequence
<220> FEATURE:
<223> OTHER INFORMATION: Synthetic DNA/RNA primer, F338

<400> SEQUENCE: 441
gaaccaagcc gcuggtuca                                              19

<210> SEQ ID NO 442
<211> LENGTH: 25
<212> TYPE: DNA
<213> ORGANISM: Artificial Sequence
<220> FEATURE:
<223> OTHER INFORMATION: Synthetic DNA/RNA primer, F339

<400> SEQUENCE: 442
```

```
gaagacccccu ttaactcaag acugc                                           25

<210> SEQ ID NO 443
<211> LENGTH: 27
<212> TYPE: DNA
<213> ORGANISM: Artificial Sequence
<220> FEATURE:
<223> OTHER INFORMATION: Synthetic DNA/RNA primer, F340

<400> SEQUENCE: 443
gagcgaggau atctggaaga aatucga                                          27

<210> SEQ ID NO 444
<211> LENGTH: 19
<212> TYPE: DNA
<213> ORGANISM: Artificial Sequence
<220> FEATURE:
<223> OTHER INFORMATION: Synthetic DNA/RNA primer, F341

<400> SEQUENCE: 444
gautcuccac ggccgacca                                                   19

<210> SEQ ID NO 445
<211> LENGTH: 27
<212> TYPE: DNA
<213> ORGANISM: Artificial Sequence
<220> FEATURE:
<223> OTHER INFORMATION: Synthetic DNA/RNA primer, F342

<400> SEQUENCE: 445
gaaagtcccu caaaatagg aggugct                                           27

<210> SEQ ID NO 446
<211> LENGTH: 27
<212> TYPE: RNA
<213> ORGANISM: Artificial Sequence
<220> FEATURE:
<223> OTHER INFORMATION: Synthetic Primer, F343

<400> SEQUENCE: 446
gagacagauc agcaacaacc gaaaaug                                          27

<210> SEQ ID NO 447
<211> LENGTH: 29
<212> TYPE: DNA
<213> ORGANISM: Artificial Sequence
<220> FEATURE:
<223> OTHER INFORMATION: Synthetic DNA/RNA primer, F344

<400> SEQUENCE: 447
gatttgtcca gagaccuttc taacgtaut                                        29

<210> SEQ ID NO 448
<211> LENGTH: 24
<212> TYPE: DNA
<213> ORGANISM: Artificial Sequence
<220> FEATURE:
<223> OTHER INFORMATION: Synthetic DNA/RNA primer, F345

<400> SEQUENCE: 448
gatttcugaa gaggacttgt ugcg                                             24

<210> SEQ ID NO 449
<211> LENGTH: 32
<212> TYPE: DNA
```

-continued

<213> ORGANISM: Artificial Sequence
<220> FEATURE:
<223> OTHER INFORMATION: Synthetic DNA/RNA primer, F346

<400> SEQUENCE: 449
gagattttuc agttaataat auccccgag ct					32

<210> SEQ ID NO 450
<211> LENGTH: 19
<212> TYPE: DNA
<213> ORGANISM: Artificial Sequence
<220> FEATURE:
<223> OTHER INFORMATION: Synthetic DNA/RNA primer, F347

<400> SEQUENCE: 450
gaaatcgccu ccggauccc					19

<210> SEQ ID NO 451
<211> LENGTH: 34
<212> TYPE: DNA
<213> ORGANISM: Artificial Sequence
<220> FEATURE:
<223> OTHER INFORMATION: Synthetic DNA/RNA primer, F348

<400> SEQUENCE: 451
gagtcattcc ttcutttaa aatggtgctu aagt					34

<210> SEQ ID NO 452
<211> LENGTH: 22
<212> TYPE: DNA
<213> ORGANISM: Artificial Sequence
<220> FEATURE:
<223> OTHER INFORMATION: Synthetic DNA/RNA primer, F349

<400> SEQUENCE: 452
gaggtccccc accuctcttt ug					22

<210> SEQ ID NO 453
<211> LENGTH: 23
<212> TYPE: DNA
<213> ORGANISM: Artificial Sequence
<220> FEATURE:
<223> OTHER INFORMATION: Synthetic DNA/RNA primer, F350

<400> SEQUENCE: 453
gactcuccag gaaggctcac auc					23

<210> SEQ ID NO 454
<211> LENGTH: 21
<212> TYPE: DNA
<213> ORGANISM: Artificial Sequence
<220> FEATURE:
<223> OTHER INFORMATION: Synthetic DNA/RNA primer, F351

<400> SEQUENCE: 454
gatggcatug ccttgtcctu g					21

<210> SEQ ID NO 455
<211> LENGTH: 27
<212> TYPE: DNA
<213> ORGANISM: Artificial Sequence
<220> FEATURE:
<223> OTHER INFORMATION: Synthetic DNA/RNA primer, F352

<400> SEQUENCE: 455
gaggcagaaa accaaaacau tggctua					27

<210> SEQ ID NO 456
<211> LENGTH: 35
<212> TYPE: DNA
<213> ORGANISM: Artificial Sequence
<220> FEATURE:
<223> OTHER INFORMATION: Synthetic DNA/RNA primer, F353

<400> SEQUENCE: 456
gaaattgttc ctcaaguttg tttaaggact uaaaa                              35

<210> SEQ ID NO 457
<211> LENGTH: 29
<212> TYPE: DNA
<213> ORGANISM: Artificial Sequence
<220> FEATURE:
<223> OTHER INFORMATION: Synthetic DNA/RNA primer, F354

<400> SEQUENCE: 457
gaagtggtat cauccccatt taatagcug                                     29

<210> SEQ ID NO 458
<211> LENGTH: 32
<212> TYPE: DNA
<213> ORGANISM: Artificial Sequence
<220> FEATURE:
<223> OTHER INFORMATION: Synthetic DNA/RNA primer, F355

<400> SEQUENCE: 458
gaacaaatac aaaacugtcc acatctatgt ug                                 32

<210> SEQ ID NO 459
<211> LENGTH: 34
<212> TYPE: DNA
<213> ORGANISM: Artificial Sequence
<220> FEATURE:
<223> OTHER INFORMATION: Synthetic DNA/RNA primer, F356

<400> SEQUENCE: 459
gaaacaaacc atagcuataa tgaagaactt gcua                               34

<210> SEQ ID NO 460
<211> LENGTH: 34
<212> TYPE: DNA
<213> ORGANISM: Artificial Sequence
<220> FEATURE:
<223> OTHER INFORMATION: Synthetic DNA/RNA primer, F257

<400> SEQUENCE: 460
gaaatagttg atcauactt gtaacagaau caca                                34

<210> SEQ ID NO 461
<211> LENGTH: 32
<212> TYPE: DNA
<213> ORGANISM: Artificial Sequence
<220> FEATURE:
<223> OTHER INFORMATION: Synthetic DNA/RNA primer, F358

<400> SEQUENCE: 461
gactcatctc cctutaattt tggcacatta ut                                 32

<210> SEQ ID NO 462
<211> LENGTH: 31
<212> TYPE: DNA
<213> ORGANISM: Artificial Sequence
<220> FEATURE:

<223> OTHER INFORMATION: Synthetic DNA/RNA primer, F359

<400> SEQUENCE: 462
gaaactatct uctttggact tcugaagaga c                                    31

<210> SEQ ID NO 463
<211> LENGTH: 34
<212> TYPE: DNA
<213> ORGANISM: Artificial Sequence
<220> FEATURE:
<223> OTHER INFORMATION: Synthetic DNA/RNA primer, F360

<400> SEQUENCE: 463
gaagtaaata atggttuctc cttctcttac ttug                                  34

<210> SEQ ID NO 464
<211> LENGTH: 26
<212> TYPE: DNA
<213> ORGANISM: Artificial Sequence
<220> FEATURE:
<223> OTHER INFORMATION: Synthetic DNA/RNA primer, F361

<400> SEQUENCE: 464
gattcctggu ggcattcaau aaagca                                           26

<210> SEQ ID NO 465
<211> LENGTH: 24
<212> TYPE: DNA
<213> ORGANISM: Artificial Sequence
<220> FEATURE:
<223> OTHER INFORMATION: Synthetic DNA/RNA primer, F362

<400> SEQUENCE: 465
gaaggagcaa cutagggatc uggt                                             24

<210> SEQ ID NO 466
<211> LENGTH: 23
<212> TYPE: DNA
<213> ORGANISM: Artificial Sequence
<220> FEATURE:
<223> OTHER INFORMATION: Synthetic DNA/RNA primer, F363

<400> SEQUENCE: 466
gaacccctaa uctggtcaac cug                                              23

<210> SEQ ID NO 467
<211> LENGTH: 32
<212> TYPE: DNA
<213> ORGANISM: Artificial Sequence
<220> FEATURE:
<223> OTHER INFORMATION: Synthetic DNA/RNA primer, F364

<400> SEQUENCE: 467
gaagaaatag aaaacuacag gacgttaucc ag                                    32

<210> SEQ ID NO 468
<211> LENGTH: 27
<212> TYPE: DNA
<213> ORGANISM: Artificial Sequence
<220> FEATURE:
<223> OTHER INFORMATION: Synthetic DNA/RNA primer, F365

<400> SEQUENCE: 468
gatccgcttt cuaaaatgtc agttguc                                          27

<210> SEQ ID NO 469
<211> LENGTH: 22
<212> TYPE: RNA
<213> ORGANISM: Artificial Sequence
<220> FEATURE:
<223> OTHER INFORMATION: Synthetic Primer, R97

<400> SEQUENCE: 469
gaggcaggag acccuguagg ag                                           22

<210> SEQ ID NO 470
<211> LENGTH: 26
<212> TYPE: DNA
<213> ORGANISM: Artificial Sequence
<220> FEATURE:
<223> OTHER INFORMATION: Synthetic DNA/RNA primer, R98

<400> SEQUENCE: 470
gaggatauat gccauacccc agcaaa                                       26

<210> SEQ ID NO 471
<211> LENGTH: 29
<212> TYPE: DNA
<213> ORGANISM: Artificial Sequence
<220> FEATURE:
<223> OTHER INFORMATION: Synthetic DNA/RNA primer, R99

<400> SEQUENCE: 471
gaccaagaaa ggcutgtgtc tacatttut                                    29

<210> SEQ ID NO 472
<211> LENGTH: 29
<212> TYPE: DNA
<213> ORGANISM: Artificial Sequence
<220> FEATURE:
<223> OTHER INFORMATION: Synthetic DNA/RNA primer, R100

<400> SEQUENCE: 472
gaccaaauca agaaacctgt tugagagaa                                    29

<210> SEQ ID NO 473
<211> LENGTH: 25
<212> TYPE: DNA
<213> ORGANISM: Artificial Sequence
<220> FEATURE:
<223> OTHER INFORMATION: Synthetic DNA/RNA primer, R101

<400> SEQUENCE: 473
gacacttccc utgtgggaat gucaa                                        25

<210> SEQ ID NO 474
<211> LENGTH: 25
<212> TYPE: DNA
<213> ORGANISM: Artificial Sequence
<220> FEATURE:
<223> OTHER INFORMATION: Synthetic DNA/RNA primer, R102

<400> SEQUENCE: 474
gatgcatcag aacccucctt gaauc                                        25

<210> SEQ ID NO 475
<211> LENGTH: 24
<212> TYPE: RNA
<213> ORGANISM: Artificial Sequence
<220> FEATURE:
<223> OTHER INFORMATION: Synthetic Primer, R103

<400> SEQUENCE: 475
gagguccacg gauccagaaa caag                                    24

<210> SEQ ID NO 476
<211> LENGTH: 23
<212> TYPE: DNA
<213> ORGANISM: Artificial Sequence
<220> FEATURE:
<223> OTHER INFORMATION: Synthetic DNA/RNA primer, R104

<400> SEQUENCE: 476
gaggttcctc cuctcctggt cuc                                     23

<210> SEQ ID NO 477
<211> LENGTH: 29
<212> TYPE: DNA
<213> ORGANISM: Artificial Sequence
<220> FEATURE:
<223> OTHER INFORMATION: Synthetic DNA/RNA primer, R105

<400> SEQUENCE: 477
gagctcacta acuaacgtga aagcctuac                               29

<210> SEQ ID NO 478
<211> LENGTH: 29
<212> TYPE: DNA
<213> ORGANISM: Artificial Sequence
<220> FEATURE:
<223> OTHER INFORMATION: Synthetic DNA/RNA primer, R106

<400> SEQUENCE: 478
gaggttttgc acaagutagg tttgtttug                               29

<210> SEQ ID NO 479
<211> LENGTH: 35
<212> TYPE: DNA
<213> ORGANISM: Artificial Sequence
<220> FEATURE:
<223> OTHER INFORMATION: Synthetic DNA/RNA primer, R107

<400> SEQUENCE: 479
gaacctttat atcgtuactc tgaatcttat ctucc                        35

<210> SEQ ID NO 480
<211> LENGTH: 27
<212> TYPE: DNA
<213> ORGANISM: Artificial Sequence
<220> FEATURE:
<223> OTHER INFORMATION: Synthetic DNA/RNA primer, R108

<400> SEQUENCE: 480
gatgactctg tcucctcttg tcttcuc                                 27

<210> SEQ ID NO 481
<211> LENGTH: 28
<212> TYPE: DNA
<213> ORGANISM: Artificial Sequence
<220> FEATURE:
<223> OTHER INFORMATION: Synthetic DNA/RNA primer, R109

<400> SEQUENCE: 481
gaaaacgttt tucaccttag catttugt                                28

<210> SEQ ID NO 482
<211> LENGTH: 30

```
<212> TYPE: DNA
<213> ORGANISM: Artificial Sequence
<220> FEATURE:
<223> OTHER INFORMATION: Synthetic DNA/RNA primer, R110

<400> SEQUENCE: 482
gacaccatcu ccatatcatu gagaccaaat                                    30

<210> SEQ ID NO 483
<211> LENGTH: 29
<212> TYPE: DNA
<213> ORGANISM: Artificial Sequence
<220> FEATURE:
<223> OTHER INFORMATION: Synthetic DNA/RNA primer, R111

<400> SEQUENCE: 483
gacgacagac uactttggtt ctctttugt                                     29

<210> SEQ ID NO 484
<211> LENGTH: 22
<212> TYPE: DNA
<213> ORGANISM: Artificial Sequence
<220> FEATURE:
<223> OTHER INFORMATION: Synthetic DNA/RNA primer, R112

<400> SEQUENCE: 484
gactcacuga caagctccuc gt                                            22

<210> SEQ ID NO 485
<211> LENGTH: 26
<212> TYPE: DNA
<213> ORGANISM: Artificial Sequence
<220> FEATURE:
<223> OTHER INFORMATION: Synthetic DNA/RNA primer, R113

<400> SEQUENCE: 485
gagccttttc ttutgcttcc cttgut                                        26

<210> SEQ ID NO 486
<211> LENGTH: 19
<212> TYPE: RNA
<213> ORGANISM: Artificial Sequence
<220> FEATURE:
<223> OTHER INFORMATION: Synthetic Primer, R114

<400> SEQUENCE: 486
gacaggaccu ggcccugac                                                19

<210> SEQ ID NO 487
<211> LENGTH: 25
<212> TYPE: DNA
<213> ORGANISM: Artificial Sequence
<220> FEATURE:
<223> OTHER INFORMATION: Synthetic DNA/RNA primer, R115

<400> SEQUENCE: 487
gacccaucac acaccataac uccac                                         25

<210> SEQ ID NO 488
<211> LENGTH: 22
<212> TYPE: DNA
<213> ORGANISM: Artificial Sequence
<220> FEATURE:
<223> OTHER INFORMATION: Synthetic DNA/RNA primer, R116

<400> SEQUENCE: 488
```

```
gagctguccc ctcaccatuc ag                                          22

<210> SEQ ID NO 489
<211> LENGTH: 30
<212> TYPE: DNA
<213> ORGANISM: Artificial Sequence
<220> FEATURE:
<223> OTHER INFORMATION: Synthetic DNA/RNA primer, R117

<400> SEQUENCE: 489
gatcacaacc cacugaggta tatgtauagg                                  30

<210> SEQ ID NO 490
<211> LENGTH: 22
<212> TYPE: RNA
<213> ORGANISM: Artificial Sequence
<220> FEATURE:
<223> OTHER INFORMATION: Synthetic Primer, R118

<400> SEQUENCE: 490
gacaugcacc ggaaaagcga ug                                          22

<210> SEQ ID NO 491
<211> LENGTH: 26
<212> TYPE: DNA
<213> ORGANISM: Artificial Sequence
<220> FEATURE:
<223> OTHER INFORMATION: Synthetic DNA/RNA primer, R119

<400> SEQUENCE: 491
gacatttcta ggutacaggc cuggat                                      26

<210> SEQ ID NO 492
<211> LENGTH: 20
<212> TYPE: DNA
<213> ORGANISM: Artificial Sequence
<220> FEATURE:
<223> OTHER INFORMATION: Synthetic DNA/RNA primer, R120

<400> SEQUENCE: 492
gactccaugc ccctcacuca                                             20

<210> SEQ ID NO 493
<211> LENGTH: 26
<212> TYPE: DNA
<213> ORGANISM: Artificial Sequence
<220> FEATURE:
<223> OTHER INFORMATION: Synthetic DNA/RNA primer, R121

<400> SEQUENCE: 493
gaattgaaaa tcutcctgcc tuccct                                      26

<210> SEQ ID NO 494
<211> LENGTH: 26
<212> TYPE: DNA
<213> ORGANISM: Artificial Sequence
<220> FEATURE:
<223> OTHER INFORMATION: Synthetic DNA/RNA primer, R122

<400> SEQUENCE: 494
gagcaaaagt ggucctctct gaauct                                      26

<210> SEQ ID NO 495
<211> LENGTH: 26
<212> TYPE: DNA
<213> ORGANISM: Artificial Sequence
```

```
<220> FEATURE:
<223> OTHER INFORMATION: Synthetic DNA/RNA primer, R123

<400> SEQUENCE: 495
gaatatcauc cagcctgtgt cttucc                                          26

<210> SEQ ID NO 496
<211> LENGTH: 24
<212> TYPE: DNA
<213> ORGANISM: Artificial Sequence
<220> FEATURE:
<223> OTHER INFORMATION: Synthetic DNA/RNA primer, R124

<400> SEQUENCE: 496
gagagggaag gcaggauctc uaac                                            24

<210> SEQ ID NO 497
<211> LENGTH: 25
<212> TYPE: DNA
<213> ORGANISM: Artificial Sequence
<220> FEATURE:
<223> OTHER INFORMATION: Synthetic DNA/RNA primer, R125

<400> SEQUENCE: 497
gaccaggcaa uggaaagggt acaua                                           25

<210> SEQ ID NO 498
<211> LENGTH: 27
<212> TYPE: DNA
<213> ORGANISM: Artificial Sequence
<220> FEATURE:
<223> OTHER INFORMATION: Synthetic DNA/RNA primer, R126

<400> SEQUENCE: 498
gagaauaaag aggagcaggt ugaggaa                                         27

<210> SEQ ID NO 499
<211> LENGTH: 22
<212> TYPE: DNA
<213> ORGANISM: Artificial Sequence
<220> FEATURE:
<223> OTHER INFORMATION: Synthetic DNA/RNA primer, R127

<400> SEQUENCE: 499
gagggcaaau gagcctcuca gt                                              22

<210> SEQ ID NO 500
<211> LENGTH: 29
<212> TYPE: DNA
<213> ORGANISM: Artificial Sequence
<220> FEATURE:
<223> OTHER INFORMATION: Synthetic DNA/RNA primer, R128

<400> SEQUENCE: 500
gatccagatt gaucttggga gtguaaaaa                                       29

<210> SEQ ID NO 501
<211> LENGTH: 25
<212> TYPE: DNA
<213> ORGANISM: Artificial Sequence
<220> FEATURE:
<223> OTHER INFORMATION: Synthetic DNA/RNA primer, R129

<400> SEQUENCE: 501
gagtctttgt gutcccggac auagt                                           25
```

<210> SEQ ID NO 502
<211> LENGTH: 22
<212> TYPE: DNA
<213> ORGANISM: Artificial Sequence
<220> FEATURE:
<223> OTHER INFORMATION: Synthetic DNA/RNA primer, R130

<400> SEQUENCE: 502
gagggtcuga cgggtagagu gt                                                 22

<210> SEQ ID NO 503
<211> LENGTH: 30
<212> TYPE: DNA
<213> ORGANISM: Artificial Sequence
<220> FEATURE:
<223> OTHER INFORMATION: Synthetic DNA/RNA primer, R131

<400> SEQUENCE: 503
gagcttgctc tgauaggaaa atgagatcua                                         30

<210> SEQ ID NO 504
<211> LENGTH: 24
<212> TYPE: DNA
<213> ORGANISM: Artificial Sequence
<220> FEATURE:
<223> OTHER INFORMATION: Synthetic DNA/RNA primer, R132

<400> SEQUENCE: 504
gacctcttcc ucaggattgc ctut                                               24

<210> SEQ ID NO 505
<211> LENGTH: 30
<212> TYPE: DNA
<213> ORGANISM: Artificial Sequence
<220> FEATURE:
<223> OTHER INFORMATION: Synthetic DNA/RNA primer, R133

<400> SEQUENCE: 505
gatcagtccg gtuttatttg catcatagut                                         30

<210> SEQ ID NO 506
<211> LENGTH: 27
<212> TYPE: DNA
<213> ORGANISM: Artificial Sequence
<220> FEATURE:
<223> OTHER INFORMATION: Synthetic DNA/RNA primer, R134

<400> SEQUENCE: 506
gacccaaaga cuctccaaga tgggaua                                            27

<210> SEQ ID NO 507
<211> LENGTH: 24
<212> TYPE: DNA
<213> ORGANISM: Artificial Sequence
<220> FEATURE:
<223> OTHER INFORMATION: Synthetic DNA/RNA primer, R135

<400> SEQUENCE: 507
gatccagacc agggugttgt ttuc                                               24

<210> SEQ ID NO 508
<211> LENGTH: 25
<212> TYPE: DNA
<213> ORGANISM: Artificial Sequence
<220> FEATURE:
<223> OTHER INFORMATION: Synthetic DNA/RNA primer, R136

-continued

<400> SEQUENCE: 508
gagtgccagg gaccutacct tauac                                    25

<210> SEQ ID NO 509
<211> LENGTH: 22
<212> TYPE: DNA
<213> ORGANISM: Artificial Sequence
<220> FEATURE:
<223> OTHER INFORMATION: Synthetic DNA/RNA primer, R137

<400> SEQUENCE: 509
gactgaggut cagagccaug ga                                       22

<210> SEQ ID NO 510
<211> LENGTH: 25
<212> TYPE: DNA
<213> ORGANISM: Artificial Sequence
<220> FEATURE:
<223> OTHER INFORMATION: Synthetic DNA/RNA primer, R138

<400> SEQUENCE: 510
gagucatatc uccccaaacc ccaat                                    25

<210> SEQ ID NO 511
<211> LENGTH: 24
<212> TYPE: DNA
<213> ORGANISM: Artificial Sequence
<220> FEATURE:
<223> OTHER INFORMATION: Synthetic DNA/RNA primer, R139

<400> SEQUENCE: 511
gagccatagg gcauaagctg tguc                                     24

<210> SEQ ID NO 512
<211> LENGTH: 25
<212> TYPE: DNA
<213> ORGANISM: Artificial Sequence
<220> FEATURE:
<223> OTHER INFORMATION: Synthetic DNA/RNA primer, R140

<400> SEQUENCE: 512
gaccttggtc cutcacctaa cctug                                    25

<210> SEQ ID NO 513
<211> LENGTH: 23
<212> TYPE: DNA
<213> ORGANISM: Artificial Sequence
<220> FEATURE:
<223> OTHER INFORMATION: Synthetic DNA/RNA primer, R141

<400> SEQUENCE: 513
gaccctcutt agccauggca agg                                      23

<210> SEQ ID NO 514
<211> LENGTH: 24
<212> TYPE: DNA
<213> ORGANISM: Artificial Sequence
<220> FEATURE:
<223> OTHER INFORMATION: Synthetic DNA/RNA primer, R142

<400> SEQUENCE: 514
gatggtctcu cattctccca uccc                                     24

<210> SEQ ID NO 515

```
<211> LENGTH: 24
<212> TYPE: DNA
<213> ORGANISM: Artificial Sequence
<220> FEATURE:
<223> OTHER INFORMATION: Synthetic DNA/RNA primer, R143

<400> SEQUENCE: 515
gactcctccu gtgatctgca auct                                          24

<210> SEQ ID NO 516
<211> LENGTH: 30
<212> TYPE: DNA
<213> ORGANISM: Artificial Sequence
<220> FEATURE:
<223> OTHER INFORMATION: Synthetic DNA/RNA primer, R144

<400> SEQUENCE: 516
gagatgauga agatgatugg gaaacacaag                                    30

<210> SEQ ID NO 517
<211> LENGTH: 20
<212> TYPE: DNA
<213> ORGANISM: Artificial Sequence
<220> FEATURE:
<223> OTHER INFORMATION: Synthetic DNA/RNA primer, R145

<400> SEQUENCE: 517
gagggctgug cgtcactgua                                               20

<210> SEQ ID NO 518
<211> LENGTH: 20
<212> TYPE: DNA
<213> ORGANISM: Artificial Sequence
<220> FEATURE:
<223> OTHER INFORMATION: Synthetic DNA/RNA primer, R146

<400> SEQUENCE: 518
gaggagccca ggccuttcut                                               20

<210> SEQ ID NO 519
<211> LENGTH: 21
<212> TYPE: DNA
<213> ORGANISM: Artificial Sequence
<220> FEATURE:
<223> OTHER INFORMATION: Synthetic DNA/RNA primer, R147

<400> SEQUENCE: 519
gagcgtccua ctggcaugac c                                             21

<210> SEQ ID NO 520
<211> LENGTH: 21
<212> TYPE: DNA
<213> ORGANISM: Artificial Sequence
<220> FEATURE:
<223> OTHER INFORMATION: Synthetic DNA/RNA primer, R148

<400> SEQUENCE: 520
gaccacucac aggtcgtgug t                                             21

<210> SEQ ID NO 521
<211> LENGTH: 27
<212> TYPE: DNA
<213> ORGANISM: Artificial Sequence
<220> FEATURE:
<223> OTHER INFORMATION: Synthetic DNA/RNA primer, R149

<400> SEQUENCE: 521
```

```
gaacatgatg gaugtcacgt tcucaaa                                        27
```

<210> SEQ ID NO 522
<211> LENGTH: 26
<212> TYPE: DNA
<213> ORGANISM: Artificial Sequence
<220> FEATURE:
<223> OTHER INFORMATION: Synthetic DNA/RNA primer, R150

<400> SEQUENCE: 522

```
gatgttaacc utgcagaatg gucgat                                         26
```

<210> SEQ ID NO 523
<211> LENGTH: 22
<212> TYPE: DNA
<213> ORGANISM: Artificial Sequence
<220> FEATURE:
<223> OTHER INFORMATION: Synthetic DNA/RNA primer, R151

<400> SEQUENCE: 523

```
gacugcagga ttccuaccgg aa                                             22
```

<210> SEQ ID NO 524
<211> LENGTH: 24
<212> TYPE: DNA
<213> ORGANISM: Artificial Sequence
<220> FEATURE:
<223> OTHER INFORMATION: Synthetic DNA/RNA primer, R152

<400> SEQUENCE: 524

```
gaatcaccaa auggcaccau acga                                           24
```

<210> SEQ ID NO 525
<211> LENGTH: 27
<212> TYPE: DNA
<213> ORGANISM: Artificial Sequence
<220> FEATURE:
<223> OTHER INFORMATION: Synthetic DNA/RNA primer, R153

<400> SEQUENCE: 525

```
gaagttcaag cugaagaaga tguggaa                                        27
```

<210> SEQ ID NO 526
<211> LENGTH: 24
<212> TYPE: DNA
<213> ORGANISM: Artificial Sequence
<220> FEATURE:
<223> OTHER INFORMATION: Synthetic DNA/RNA primer, R154

<400> SEQUENCE: 526

```
gactgacacc uagctgtgat ccug                                           24
```

<210> SEQ ID NO 527
<211> LENGTH: 30
<212> TYPE: DNA
<213> ORGANISM: Artificial Sequence
<220> FEATURE:
<223> OTHER INFORMATION: Synthetic DNA/RNA primer, R155

<400> SEQUENCE: 527

```
gaactgatat gguagacaga gccuaaacat                                     30
```

<210> SEQ ID NO 528
<211> LENGTH: 26
<212> TYPE: DNA

<213> ORGANISM: Artificial Sequence
<220> FEATURE:
<223> OTHER INFORMATION: Synthetic DNA/RNA primer, R156

<400> SEQUENCE: 528
gagtctcagt cautagagca ctcugg    26

<210> SEQ ID NO 529
<211> LENGTH: 27
<212> TYPE: DNA
<213> ORGANISM: Artificial Sequence
<220> FEATURE:
<223> OTHER INFORMATION: Synthetic DNA/RNA primer, R157

<400> SEQUENCE: 529
gatttcatac ugaccaaaac ucagcct    27

<210> SEQ ID NO 530
<211> LENGTH: 23
<212> TYPE: DNA
<213> ORGANISM: Artificial Sequence
<220> FEATURE:
<223> OTHER INFORMATION: Synthetic DNA/RNA primer, R158

<400> SEQUENCE: 530
gagacacggc uttacctcca aug    23

<210> SEQ ID NO 531
<211> LENGTH: 29
<212> TYPE: DNA
<213> ORGANISM: Artificial Sequence
<220> FEATURE:
<223> OTHER INFORMATION: Synthetic DNA/RNA primer, R159

<400> SEQUENCE: 531
gaaggcctgc ugaaaatgac tgaatauaa    29

<210> SEQ ID NO 532
<211> LENGTH: 31
<212> TYPE: DNA
<213> ORGANISM: Artificial Sequence
<220> FEATURE:
<223> OTHER INFORMATION: Synthetic DNA/RNA primer, R160

<400> SEQUENCE: 532
gagtaaaagg ugcactgtaa taauccagac t    31

<210> SEQ ID NO 533
<211> LENGTH: 29
<212> TYPE: DNA
<213> ORGANISM: Artificial Sequence
<220> FEATURE:
<223> OTHER INFORMATION: Synthetic DNA/RNA primer, R161

<400> SEQUENCE: 533
gagactctga agaugtacct atggtccua    29

<210> SEQ ID NO 534
<211> LENGTH: 29
<212> TYPE: DNA
<213> ORGANISM: Artificial Sequence
<220> FEATURE:
<223> OTHER INFORMATION: Synthetic DNA/RNA primer, R162

<400> SEQUENCE: 534 gagctttca aaaggctuaa acacaggat    29

<210> SEQ ID NO 535
<211> LENGTH: 29
<212> TYPE: DNA
<213> ORGANISM: Artificial Sequence
<220> FEATURE:
<223> OTHER INFORMATION: Synthetic DNA/RNA primer, R163

<400> SEQUENCE: 535
gagcaaacca caaaaguata ctccauggt                                    29

<210> SEQ ID NO 536
<211> LENGTH: 29
<212> TYPE: DNA
<213> ORGANISM: Artificial Sequence
<220> FEATURE:
<223> OTHER INFORMATION: Synthetic DNA/RNA primer, R164

<400> SEQUENCE: 536
gatctgactt gguggtaaac ttttgagut                                    29

<210> SEQ ID NO 537
<211> LENGTH: 26
<212> TYPE: DNA
<213> ORGANISM: Artificial Sequence
<220> FEATURE:
<223> OTHER INFORMATION: Synthetic DNA/RNA primer, R165

<400> SEQUENCE: 537
gagttcttgc uggtgtgaaa tgacug                                       26

<210> SEQ ID NO 538
<211> LENGTH: 26
<212> TYPE: DNA
<213> ORGANISM: Artificial Sequence
<220> FEATURE:
<223> OTHER INFORMATION: Synthetic DNA/RNA primer, R166

<400> SEQUENCE: 538 gacacccca ggautctuac agaaaa                                        26

<210> SEQ ID NO 539
<211> LENGTH: 27
<212> TYPE: DNA
<213> ORGANISM: Artificial Sequence
<220> FEATURE:
<223> OTHER INFORMATION: Synthetic DNA/RNA primer, R167

<400> SEQUENCE: 539
gacatctctu ggaaactccc atctuga                                      27

<210> SEQ ID NO 540
<211> LENGTH: 26
<212> TYPE: DNA
<213> ORGANISM: Artificial Sequence
<220> FEATURE:
<223> OTHER INFORMATION: Synthetic DNA/RNA primer, R168

<400> SEQUENCE: 540
gaccacatgu gtccagtgaa aaucct                                       26

<210> SEQ ID NO 541
<211> LENGTH: 23
<212> TYPE: DNA
<213> ORGANISM: Artificial Sequence
<220> FEATURE:

<223> OTHER INFORMATION: Synthetic DNA/RNA primer, R169

<400> SEQUENCE: 541
gaagtgaagg aggaugagcc uga                                        23

<210> SEQ ID NO 542
<211> LENGTH: 30
<212> TYPE: DNA
<213> ORGANISM: Artificial Sequence
<220> FEATURE:
<223> OTHER INFORMATION: Synthetic DNA/RNA primer, R170

<400> SEQUENCE: 542
gagtggaaga tccaauccat ttttgttguc                                 30

<210> SEQ ID NO 543
<211> LENGTH: 30
<212> TYPE: DNA
<213> ORGANISM: Artificial Sequence
<220> FEATURE:
<223> OTHER INFORMATION: Synthetic DNA/RNA primer, R171

<400> SEQUENCE: 543
gaagcatcag cauttgactt taccttauca                                 30

<210> SEQ ID NO 544
<211> LENGTH: 29
<212> TYPE: DNA
<213> ORGANISM: Artificial Sequence
<220> FEATURE:
<223> OTHER INFORMATION: Synthetic DNA/RNA primer, R172

<400> SEQUENCE: 544
gacataagag agaagguttg actgccaua                                  29

<210> SEQ ID NO 545
<211> LENGTH: 28
<212> TYPE: DNA
<213> ORGANISM: Artificial Sequence
<220> FEATURE:
<223> OTHER INFORMATION: Synthetic DNA/RNA primer, R173

<400> SEQUENCE: 545
gaagaaaacc atuacttgtc catcguct                                   28

<210> SEQ ID NO 546
<211> LENGTH: 23
<212> TYPE: DNA
<213> ORGANISM: Artificial Sequence
<220> FEATURE:
<223> OTHER INFORMATION: Synthetic DNA/RNA primer, R174

<400> SEQUENCE: 546
gaccttgtug ggacctcaga ugt                                        23

<210> SEQ ID NO 547
<211> LENGTH: 23
<212> TYPE: DNA
<213> ORGANISM: Artificial Sequence
<220> FEATURE:
<223> OTHER INFORMATION: Synthetic DNA/RNA primer, R175

<400> SEQUENCE: 547
gagtgguagc agtggaugca gaa                                        23

```
<210> SEQ ID NO 548
<211> LENGTH: 25
<212> TYPE: DNA
<213> ORGANISM: Artificial Sequence
<220> FEATURE:
<223> OTHER INFORMATION: Synthetic DNA/RNA primer, R176

<400> SEQUENCE: 548
gaaggcccca uacaatttga ugaca                                   25

<210> SEQ ID NO 549
<211> LENGTH: 20
<212> TYPE: DNA
<213> ORGANISM: Artificial Sequence
<220> FEATURE:
<223> OTHER INFORMATION: Synthetic DNA/RNA primer, R177

<400> SEQUENCE: 549
gaccatggug caccugggat                                         20

<210> SEQ ID NO 550
<211> LENGTH: 28
<212> TYPE: DNA
<213> ORGANISM: Artificial Sequence
<220> FEATURE:
<223> OTHER INFORMATION: Synthetic DNA/RNA primer, R178

<400> SEQUENCE: 550
gaactttgcg uggtgtagat atgaucaa                                28

<210> SEQ ID NO 551
<211> LENGTH: 23
<212> TYPE: DNA
<213> ORGANISM: Artificial Sequence
<220> FEATURE:
<223> OTHER INFORMATION: Synthetic DNA/RNA primer, R179

<400> SEQUENCE: 551
gagtcttcac ucacctcgga uga                                     23

<210> SEQ ID NO 552
<211> LENGTH: 22
<212> TYPE: DNA
<213> ORGANISM: Artificial Sequence
<220> FEATURE:
<223> OTHER INFORMATION: Synthetic DNA/RNA primer, R180

<400> SEQUENCE: 552
gacagguacg cctccagaug ag                                      22

<210> SEQ ID NO 553
<211> LENGTH: 21
<212> TYPE: DNA
<213> ORGANISM: Artificial Sequence
<220> FEATURE:
<223> OTHER INFORMATION: Synthetic DNA/RNA primer, R181

<400> SEQUENCE: 553
gaaacucccg caggttuccc t                                       21

<210> SEQ ID NO 554
<211> LENGTH: 22
<212> TYPE: DNA
<213> ORGANISM: Artificial Sequence
<220> FEATURE:
<223> OTHER INFORMATION: Synthetic DNA/RNA primer, R182
```

<400> SEQUENCE: 554
gagtgcctug cccttttgu gg                                              22

<210> SEQ ID NO 555
<211> LENGTH: 20
<212> TYPE: RNA
<213> ORGANISM: Artificial Sequence
<220> FEATURE:
<223> OTHER INFORMATION: Synthetic Primer, R183

<400> SEQUENCE: 555
gaccgggaug ccaggauacg                                                20

<210> SEQ ID NO 556
<211> LENGTH: 22
<212> TYPE: DNA
<213> ORGANISM: Artificial Sequence
<220> FEATURE:
<223> OTHER INFORMATION: Synthetic DNA/RNA primer, R184

<400> SEQUENCE: 556
gagggcugta cctccucaga ga                                             22

<210> SEQ ID NO 557
<211> LENGTH: 21
<212> TYPE: RNA
<213> ORGANISM: Artificial Sequence
<220> FEATURE:
<223> OTHER INFORMATION: Synthetic Primer, R185

<400> SEQUENCE: 557
gaacaggcug cccaagggcu a                                              21

<210> SEQ ID NO 558
<211> LENGTH: 23
<212> TYPE: DNA
<213> ORGANISM: Artificial Sequence
<220> FEATURE:
<223> OTHER INFORMATION: Synthetic DNA/RNA primer, R186

<400> SEQUENCE: 558
gacagugatc agaugagcag cag                                            23

<210> SEQ ID NO 559
<211> LENGTH: 22
<212> TYPE: DNA
<213> ORGANISM: Artificial Sequence
<220> FEATURE:
<223> OTHER INFORMATION: Synthetic DNA/RNA primer, R187

<400> SEQUENCE: 559
gaacgguctu ggaacccaga ga                                             22

<210> SEQ ID NO 560
<211> LENGTH: 24
<212> TYPE: DNA
<213> ORGANISM: Artificial Sequence
<220> FEATURE:
<223> OTHER INFORMATION: Synthetic DNA/RNA primer, R188

<400> SEQUENCE: 560
gagctattga ugtctgcagt cugg                                           24

<210> SEQ ID NO 561
<211> LENGTH: 22

-continued

```
<212> TYPE: DNA
<213> ORGANISM: Artificial Sequence
<220> FEATURE:
<223> OTHER INFORMATION: Synthetic DNA/RNA primer, R189

<400> SEQUENCE: 561
gatugactug ccggaagagc ct                                             22

<210> SEQ ID NO 562
<211> LENGTH: 22
<212> TYPE: DNA
<213> ORGANISM: Artificial Sequence
<220> FEATURE:
<223> OTHER INFORMATION: Synthetic DNA/RNA primer, R190

<400> SEQUENCE: 562
gaagaccucc gagtcactcc ug                                             22

<210> SEQ ID NO 563
<211> LENGTH: 28
<212> TYPE: DNA
<213> ORGANISM: Artificial Sequence
<220> FEATURE:
<223> OTHER INFORMATION: Synthetic DNA/RNA primer, R191

<400> SEQUENCE: 563
gaaaaagact cggaugatgt acctaugg                                       28

<210> SEQ ID NO 564
<211> LENGTH: 26
<212> TYPE: DNA
<213> ORGANISM: Artificial Sequence
<220> FEATURE:
<223> OTHER INFORMATION: Synthetic DNA/RNA primer, R192

<400> SEQUENCE: 564
gattcctttc tucccagaga catugc                                         26

<210> SEQ ID NO 565
<211> LENGTH: 22
<212> TYPE: DNA
<213> ORGANISM: Artificial Sequence
<220> FEATURE:
<223> OTHER INFORMATION: Synthetic DNA/RNA primer, R193

<400> SEQUENCE: 565
gaacatcccu ctctgctcug ca                                             22

<210> SEQ ID NO 566
<211> LENGTH: 30
<212> TYPE: DNA
<213> ORGANISM: Artificial Sequence
<220> FEATURE:
<223> OTHER INFORMATION: Synthetic DNA/RNA primer, R194

<400> SEQUENCE: 566
gaggctggtt autgaaacct tgtttuacat                                     30

<210> SEQ ID NO 567
<211> LENGTH: 25
<212> TYPE: DNA
<213> ORGANISM: Artificial Sequence
<220> FEATURE:
<223> OTHER INFORMATION: Synthetic DNA/RNA primer, R195

<400> SEQUENCE: 567
```

```
gactacccccc guaccaagua caaac                                    25

<210> SEQ ID NO 568
<211> LENGTH: 19
<212> TYPE: DNA
<213> ORGANISM: Artificial Sequence
<220> FEATURE:
<223> OTHER INFORMATION: Synthetic DNA/RNA primer, R196

<400> SEQUENCE: 568
gatcgucgaa gcggcugac                                            19

<210> SEQ ID NO 569
<211> LENGTH: 24
<212> TYPE: DNA
<213> ORGANISM: Artificial Sequence
<220> FEATURE:
<223> OTHER INFORMATION: Synthetic DNA/RNA primer, R197

<400> SEQUENCE: 569
gagactctgu aggctgcagt tcuc                                      24

<210> SEQ ID NO 570
<211> LENGTH: 27
<212> TYPE: DNA
<213> ORGANISM: Artificial Sequence
<220> FEATURE:
<223> OTHER INFORMATION: Synthetic DNA/RNA primer, R198

<400> SEQUENCE: 570
gacttcttcc uacctgtttc ccaugac                                   27

<210> SEQ ID NO 571
<211> LENGTH: 25
<212> TYPE: DNA
<213> ORGANISM: Artificial Sequence
<220> FEATURE:
<223> OTHER INFORMATION: Synthetic DNA/RNA primer, R199

<400> SEQUENCE: 571
gaggacccau tagaaccaac uccat                                     25

<210> SEQ ID NO 572
<211> LENGTH: 23
<212> TYPE: DNA
<213> ORGANISM: Artificial Sequence
<220> FEATURE:
<223> OTHER INFORMATION: Synthetic DNA/RNA primer, R200

<400> SEQUENCE: 572
gaggcttgug ggagacctug aac                                       23

<210> SEQ ID NO 573
<211> LENGTH: 29
<212> TYPE: DNA
<213> ORGANISM: Artificial Sequence
<220> FEATURE:
<223> OTHER INFORMATION: Synthetic DNA/RNA primer, R201

<400> SEQUENCE: 573
gacctggtag tcucaagcag atgttaaug                                 29

<210> SEQ ID NO 574
<211> LENGTH: 29
<212> TYPE: DNA
<213> ORGANISM: Artificial Sequence
```

```
<220> FEATURE:
<223> OTHER INFORMATION: Synthetic DNA/RNA primer, R202

<400> SEQUENCE: 574
gaaacggaca tgaguttgtt ttccttcua                                29

<210> SEQ ID NO 575
<211> LENGTH: 28
<212> TYPE: DNA
<213> ORGANISM: Artificial Sequence
<220> FEATURE:
<223> OTHER INFORMATION: Synthetic DNA/RNA primer, R203

<400> SEQUENCE: 575
gacagccaac aagautctga agaacaug                                 28

<210> SEQ ID NO 576
<211> LENGTH: 24
<212> TYPE: DNA
<213> ORGANISM: Artificial Sequence
<220> FEATURE:
<223> OTHER INFORMATION: Synthetic DNA/RNA primer, R204

<400> SEQUENCE: 576
gatccctagg uagctaaccc cuac                                     24

<210> SEQ ID NO 577
<211> LENGTH: 26
<212> TYPE: DNA
<213> ORGANISM: Artificial Sequence
<220> FEATURE:
<223> OTHER INFORMATION: Synthetic DNA/RNA primer, R205

<400> SEQUENCE: 577
gaaaaacacg gcaugtgaac attcug                                   26

<210> SEQ ID NO 578
<211> LENGTH: 28
<212> TYPE: DNA
<213> ORGANISM: Artificial Sequence
<220> FEATURE:
<223> OTHER INFORMATION: Synthetic DNA/RNA primer, R206

<400> SEQUENCE: 578
gagtattcau cgagattuag cagccaga                                 28

<210> SEQ ID NO 579
<211> LENGTH: 26
<212> TYPE: DNA
<213> ORGANISM: Artificial Sequence
<220> FEATURE:
<223> OTHER INFORMATION: Synthetic DNA/RNA primer, R207

<400> SEQUENCE: 579
gagagagagg acugactatc ggacug                                   26

<210> SEQ ID NO 580
<211> LENGTH: 26
<212> TYPE: DNA
<213> ORGANISM: Artificial Sequence
<220> FEATURE:
<223> OTHER INFORMATION: Synthetic DNA/RNA primer, R208

<400> SEQUENCE: 580
gagactguca agcagagaat ggguac                                   26
```

```
<210> SEQ ID NO 581
<211> LENGTH: 35
<212> TYPE: DNA
<213> ORGANISM: Artificial Sequence
<220> FEATURE:
<223> OTHER INFORMATION: Synthetic DNA/RNA primer, R209

<400> SEQUENCE: 581
gagaatagga tattguatca taccaatttc ucgat                              35

<210> SEQ ID NO 582
<211> LENGTH: 34
<212> TYPE: DNA
<213> ORGANISM: Artificial Sequence
<220> FEATURE:
<223> OTHER INFORMATION: Synthetic DNA/RNA primer, R210

<400> SEQUENCE: 582
gaacgaaaat guaagaagat tcatctugaa gaag                               34

<210> SEQ ID NO 583
<211> LENGTH: 30
<212> TYPE: DNA
<213> ORGANISM: Artificial Sequence
<220> FEATURE:
<223> OTHER INFORMATION: Synthetic DNA/RNA primer, R211

<400> SEQUENCE: 583
gaaaagccat tttuccagat actagagugt                                    30

<210> SEQ ID NO 584
<211> LENGTH: 22
<212> TYPE: RNA
<213> ORGANISM: Artificial Sequence
<220> FEATURE:
<223> OTHER INFORMATION: Synthetic Primer, R212

<400> SEQUENCE: 584
gagggucccc aagacaccua cg                                            22

<210> SEQ ID NO 585
<211> LENGTH: 23
<212> TYPE: DNA
<213> ORGANISM: Artificial Sequence
<220> FEATURE:
<223> OTHER INFORMATION: Synthetic DNA/RNA primer, R213

<400> SEQUENCE: 585
gaccgagaac ugagggtggu aca                                           23

<210> SEQ ID NO 586
<211> LENGTH: 28
<212> TYPE: DNA
<213> ORGANISM: Artificial Sequence
<220> FEATURE:
<223> OTHER INFORMATION: Synthetic DNA/RNA primer, R214

<400> SEQUENCE: 586
gatactagaa cucaaaacac tggctgut                                      28

<210> SEQ ID NO 587
<211> LENGTH: 32
<212> TYPE: DNA
<213> ORGANISM: Artificial Sequence
<220> FEATURE:
<223> OTHER INFORMATION: Synthetic DNA/RNA primer, R215
```

<400> SEQUENCE: 587
gagtaagtct tcacuttcag attttagtug gg     32

<210> SEQ ID NO 588
<211> LENGTH: 27
<212> TYPE: DNA
<213> ORGANISM: Artificial Sequence
<220> FEATURE:
<223> OTHER INFORMATION: Synthetic DNA/RNA primer, R216

<400> SEQUENCE: 588
gatgcttcct gguctttagg atttcut     27

<210> SEQ ID NO 589
<211> LENGTH: 25
<212> TYPE: DNA
<213> ORGANISM: Artificial Sequence
<220> FEATURE:
<223> OTHER INFORMATION: Synthetic DNA/RNA primer, R217

<400> SEQUENCE: 589
gattttactt cugcttggtg gcaug     25

<210> SEQ ID NO 590
<211> LENGTH: 32
<212> TYPE: DNA
<213> ORGANISM: Artificial Sequence
<220> FEATURE:
<223> OTHER INFORMATION: Synthetic DNA/RNA primer, R218

<400> SEQUENCE: 590
gattttaccc tcauggctta gtagcattat ut     32

<210> SEQ ID NO 591
<211> LENGTH: 31
<212> TYPE: DNA
<213> ORGANISM: Artificial Sequence
<220> FEATURE:
<223> OTHER INFORMATION: Synthetic DNA/RNA primer, R219

<400> SEQUENCE: 591
gaaaaaatat ucatccagct ucaggaaaag g     31

<210> SEQ ID NO 592
<211> LENGTH: 25
<212> TYPE: DNA
<213> ORGANISM: Artificial Sequence
<220> FEATURE:
<223> OTHER INFORMATION: Synthetic DNA/RNA primer, R220

<400> SEQUENCE: 592
gaatcagtcu ggtggatggg uaaca     25

<210> SEQ ID NO 593
<211> LENGTH: 35
<212> TYPE: DNA
<213> ORGANISM: Artificial Sequence
<220> FEATURE:
<223> OTHER INFORMATION: Synthetic DNA/RNA primer, R221

<400> SEQUENCE: 593
gactaataat gaataautgg gtatgaggcu acagt     35

<210> SEQ ID NO 594

```
<211> LENGTH: 25
<212> TYPE: DNA
<213> ORGANISM: Artificial Sequence
<220> FEATURE:
<223> OTHER INFORMATION: Synthetic DNA/RNA primer, R222

<400> SEQUENCE: 594
gatgtgagag agcaaucaag gagug                                          25

<210> SEQ ID NO 595
<211> LENGTH: 29
<212> TYPE: DNA
<213> ORGANISM: Artificial Sequence
<220> FEATURE:
<223> OTHER INFORMATION: Synthetic DNA/RNA primer, R223

<400> SEQUENCE: 595
gagtctgaga guagaaggca gattctgua                                      29

<210> SEQ ID NO 596
<211> LENGTH: 26
<212> TYPE: DNA
<213> ORGANISM: Artificial Sequence
<220> FEATURE:
<223> OTHER INFORMATION: Synthetic DNA/RNA primer, R224

<400> SEQUENCE: 596
gaaacttugc ggagatcuga aaacca                                         26

<210> SEQ ID NO 597
<211> LENGTH: 30
<212> TYPE: DNA
<213> ORGANISM: Artificial Sequence
<220> FEATURE:
<223> OTHER INFORMATION: Synthetic DNA/RNA primer, R225

<400> SEQUENCE: 597
gactctaaag aaggaaguga gaacttcucc                                     30

<210> SEQ ID NO 598
<211> LENGTH: 31
<212> TYPE: DNA
<213> ORGANISM: Artificial Sequence
<220> FEATURE:
<223> OTHER INFORMATION: Synthetic DNA/RNA primer, R226

<400> SEQUENCE: 598
gactttcttc acucaaagtg cctatttuga c                                   31

<210> SEQ ID NO 599
<211> LENGTH: 32
<212> TYPE: DNA
<213> ORGANISM: Artificial Sequence
<220> FEATURE:
<223> OTHER INFORMATION: Synthetic DNA/RNA primer, R227

<400> SEQUENCE: 599
gattcttttg agaacugagt gatttaugac ct                                  32

<210> SEQ ID NO 600
<211> LENGTH: 33
<212> TYPE: DNA
<213> ORGANISM: Artificial Sequence
<220> FEATURE:
<223> OTHER INFORMATION: Synthetic DNA/RNA primer, R228

<400> SEQUENCE: 600
```
gaagaagtua gaaacagaac tgtatguaag cat    33

<210> SEQ ID NO 601
<211> LENGTH: 34
<212> TYPE: DNA
<213> ORGANISM: Artificial Sequence
<220> FEATURE:
<223> OTHER INFORMATION: Synthetic DNA/RNA primer, R229

<400> SEQUENCE: 601
gagctatacg aactuagaag tgagaaataa tcut    34

<210> SEQ ID NO 602
<211> LENGTH: 34
<212> TYPE: DNA
<213> ORGANISM: Artificial Sequence
<220> FEATURE:
<223> OTHER INFORMATION: Synthetic DNA/RNA primer, R230

<400> SEQUENCE: 602
gatttctcca gguccaaaat gaataactat tuga    34

<210> SEQ ID NO 603
<211> LENGTH: 25
<212> TYPE: DNA
<213> ORGANISM: Artificial Sequence
<220> FEATURE:
<223> OTHER INFORMATION: Synthetic DNA/RNA primer, R231

<400> SEQUENCE: 603
gaatccagga uaggaagcac acaug    25

<210> SEQ ID NO 604
<211> LENGTH: 34
<212> TYPE: DNA
<213> ORGANISM: Artificial Sequence
<220> FEATURE:
<223> OTHER INFORMATION: Synthetic DNA/RNA primer, R232

<400> SEQUENCE: 604
gattttataa ctagatuttc cttctctcca tucc    34

<210> SEQ ID NO 605
<211> LENGTH: 33
<212> TYPE: DNA
<213> ORGANISM: Artificial Sequence
<220> FEATURE:
<223> OTHER INFORMATION: Synthetic DNA/RNA primer, R233

<400> SEQUENCE: 605
gaaattcata cauttttctc taacugcaaa cat    33

<210> SEQ ID NO 606
<211> LENGTH: 29
<212> TYPE: DNA
<213> ORGANISM: Artificial Sequence
<220> FEATURE:
<223> OTHER INFORMATION: Synthetic DNA/RNA primer, R234

<400> SEQUENCE: 606
gagcagttgu gagattatct tttcauggc    29

<210> SEQ ID NO 607
<211> LENGTH: 34
<212> TYPE: DNA

<210> SEQ ID NO 607
<211> LENGTH: 34
<212> TYPE: DNA
<213> ORGANISM: Artificial Sequence
<220> FEATURE:
<223> OTHER INFORMATION: Synthetic DNA/RNA primer, R235

<400> SEQUENCE: 607 gatgttttc taaugtgtta aagttcatug gaac                        34

<210> SEQ ID NO 608
<211> LENGTH: 24
<212> TYPE: DNA
<213> ORGANISM: Artificial Sequence
<220> FEATURE:
<223> OTHER INFORMATION: Synthetic DNA/RNA primer, R236

<400> SEQUENCE: 608
gaccatgact gucacagtga ccut                                  24

<210> SEQ ID NO 609
<211> LENGTH: 22
<212> TYPE: DNA
<213> ORGANISM: Artificial Sequence
<220> FEATURE:
<223> OTHER INFORMATION: Synthetic DNA/RNA primer, R237

<400> SEQUENCE: 609
gattguggcc caaacaaagc uc                                    22

<210> SEQ ID NO 610
<211> LENGTH: 30
<212> TYPE: DNA
<213> ORGANISM: Artificial Sequence
<220> FEATURE:
<223> OTHER INFORMATION: Synthetic DNA/RNA primer, R238

<400> SEQUENCE: 610
gagtgcttgg aaauggaatg gtttuagaat                            30

<210> SEQ ID NO 611
<211> LENGTH: 28
<212> TYPE: DNA
<213> ORGANISM: Artificial Sequence
<220> FEATURE:
<223> OTHER INFORMATION: Synthetic DNA/RNA primer, R239

<400> SEQUENCE: 611
gactactgua accaagaggt gactucag                              28

<210> SEQ ID NO 612
<211> LENGTH: 21
<212> TYPE: DNA
<213> ORGANISM: Artificial Sequence
<220> FEATURE:
<223> OTHER INFORMATION: Synthetic DNA/RNA primer, R240

<400> SEQUENCE: 612
gaagccgaua tcccugcaga c                                     21

<210> SEQ ID NO 613
<211> LENGTH: 22
<212> TYPE: DNA
<213> ORGANISM: Artificial Sequence
<220> FEATURE:
<223> OTHER INFORMATION: Synthetic DNA/RNA primer, R241

<400> SEQUENCE: 613
gagtcggugt agaugcacag ct                                    22

-continued

<210> SEQ ID NO 614
<211> LENGTH: 22
<212> TYPE: DNA
<213> ORGANISM: Artificial Sequence
<220> FEATURE:
<223> OTHER INFORMATION: Synthetic DNA/RNA primer, R242

<400> SEQUENCE: 614
gatgcccaag guactgcaug gt                                              22

<210> SEQ ID NO 615
<211> LENGTH: 22
<212> TYPE: RNA
<213> ORGANISM: Artificial Sequence
<220> FEATURE:
<223> OTHER INFORMATION: Synthetic Primer, R243

<400> SEQUENCE: 615
gacucacgcc uaaaccagaa cc                                              22

<210> SEQ ID NO 616
<211> LENGTH: 20
<212> TYPE: DNA
<213> ORGANISM: Artificial Sequence
<220> FEATURE:
<223> OTHER INFORMATION: Synthetic DNA/RNA primer, R244

<400> SEQUENCE: 616
gatagctggc uccgcaccut                                                 20

<210> SEQ ID NO 617
<211> LENGTH: 19
<212> TYPE: DNA
<213> ORGANISM: Artificial Sequence
<220> FEATURE:
<223> OTHER INFORMATION: Synthetic DNA/RNA primer, R245

<400> SEQUENCE: 617
gactgcuggg cgccguaac                                                  19

<210> SEQ ID NO 618
<211> LENGTH: 23
<212> TYPE: DNA
<213> ORGANISM: Artificial Sequence
<220> FEATURE:
<223> OTHER INFORMATION: Synthetic DNA/RNA primer, R246

<400> SEQUENCE: 618
gaacccacac aagcgaauct cug                                             23

<210> SEQ ID NO 619
<211> LENGTH: 26
<212> TYPE: DNA
<213> ORGANISM: Artificial Sequence
<220> FEATURE:
<223> OTHER INFORMATION: Synthetic DNA/RNA primer, R247

<400> SEQUENCE: 619
gaactttgcu gccttaatga catucc                                          26

<210> SEQ ID NO 620
<211> LENGTH: 23
<212> TYPE: DNA
<213> ORGANISM: Artificial Sequence
<220> FEATURE:

<223> OTHER INFORMATION: Synthetic DNA/RNA primer, R248

<400> SEQUENCE: 620
gaggtaccug agatggagga guc                                    23

<210> SEQ ID NO 621
<211> LENGTH: 27
<212> TYPE: DNA
<213> ORGANISM: Artificial Sequence
<220> FEATURE:
<223> OTHER INFORMATION: Synthetic DNA/RNA primer, R249

<400> SEQUENCE: 621
gattgagcca cuaagcagta accatuc                                27

<210> SEQ ID NO 622
<211> LENGTH: 23
<212> TYPE: DNA
<213> ORGANISM: Artificial Sequence
<220> FEATURE:
<223> OTHER INFORMATION: Synthetic DNA/RNA primer, R250

<400> SEQUENCE: 622
gacccgaagu tcttctgcag ucc                                    23

<210> SEQ ID NO 623
<211> LENGTH: 23
<212> TYPE: DNA
<213> ORGANISM: Artificial Sequence
<220> FEATURE:
<223> OTHER INFORMATION: Synthetic DNA/RNA primer, R251

<400> SEQUENCE: 623
gagccgaaac gaucaaggug agt                                    23

<210> SEQ ID NO 624
<211> LENGTH: 30
<212> TYPE: DNA
<213> ORGANISM: Artificial Sequence
<220> FEATURE:
<223> OTHER INFORMATION: Synthetic DNA/RNA primer, R252

<400> SEQUENCE: 624
gatcagtaga aagauggtac caaaaugggt                             30

<210> SEQ ID NO 625
<211> LENGTH: 20
<212> TYPE: DNA
<213> ORGANISM: Artificial Sequence
<220> FEATURE:
<223> OTHER INFORMATION: Synthetic DNA/RNA primer, R253

<400> SEQUENCE: 625
gagaccgagc ucgggtguat                                        20

<210> SEQ ID NO 626
<211> LENGTH: 27
<212> TYPE: DNA
<213> ORGANISM: Artificial Sequence
<220> FEATURE:
<223> OTHER INFORMATION: Synthetic DNA/RNA primer, R254

<400> SEQUENCE: 626
gagcctttgt ggucatggga aagtaua                                27

<210> SEQ ID NO 627
<211> LENGTH: 33
<212> TYPE: DNA
<213> ORGANISM: Artificial Sequence
<220> FEATURE:
<223> OTHER INFORMATION: Synthetic DNA/RNA primer, R255

<400> SEQUENCE: 627
gaatttgcct gaaatuacac atagaactttt cug        33

<210> SEQ ID NO 628
<211> LENGTH: 23
<212> TYPE: DNA
<213> ORGANISM: Artificial Sequence
<220> FEATURE:
<223> OTHER INFORMATION: Synthetic DNA/RNA primer, R256

<400> SEQUENCE: 628
gagggatggg ugactgagau ggt        23

<210> SEQ ID NO 629
<211> LENGTH: 22
<212> TYPE: DNA
<213> ORGANISM: Artificial Sequence
<220> FEATURE:
<223> OTHER INFORMATION: Synthetic DNA/RNA primer, R257

<400> SEQUENCE: 629
gagtggacau gcgaauggag ga        22

<210> SEQ ID NO 630
<211> LENGTH: 34
<212> TYPE: DNA
<213> ORGANISM: Artificial Sequence
<220> FEATURE:
<223> OTHER INFORMATION: Synthetic DNA/RNA primer, R258

<400> SEQUENCE: 630
gatttactct gacagcuaaa tgaactcaaa tgua        34

<210> SEQ ID NO 631
<211> LENGTH: 29
<212> TYPE: DNA
<213> ORGANISM: Artificial Sequence
<220> FEATURE:
<223> OTHER INFORMATION: Synthetic DNA/RNA primer, R259

<400> SEQUENCE: 631
gaaggctcag aacacuttac tgaatttug        29

<210> SEQ ID NO 632
<211> LENGTH: 32
<212> TYPE: DNA
<213> ORGANISM: Artificial Sequence
<220> FEATURE:
<223> OTHER INFORMATION: Synthetic DNA/RNA primer, R260

<400> SEQUENCE: 632
gattacttag aagaaaautg ctccttguca ga        32

<210> SEQ ID NO 633
<211> LENGTH: 28
<212> TYPE: DNA
<213> ORGANISM: Artificial Sequence
<220> FEATURE:
<223> OTHER INFORMATION: Synthetic DNA/RNA primer, R261

<400> SEQUENCE: 633
gagtgaagga aaccautcgt gauaaagc                                28

<210> SEQ ID NO 634
<211> LENGTH: 26
<212> TYPE: DNA
<213> ORGANISM: Artificial Sequence
<220> FEATURE:
<223> OTHER INFORMATION: Synthetic DNA/RNA primer, R262

<400> SEQUENCE: 634
gagaaaatug gacccagttc tcugct                                  26

<210> SEQ ID NO 635
<211> LENGTH: 31
<212> TYPE: DNA
<213> ORGANISM: Artificial Sequence
<220> FEATURE:
<223> OTHER INFORMATION: Synthetic DNA/RNA primer, R263

<400> SEQUENCE: 635
gaatctttca acugtaaaat tcactguggg t                            31

<210> SEQ ID NO 636
<211> LENGTH: 27
<212> TYPE: DNA
<213> ORGANISM: Artificial Sequence
<220> FEATURE:
<223> OTHER INFORMATION: Synthetic DNA/RNA primer, R264

<400> SEQUENCE: 636
gaccattctc auatcctagg tcugcct                                 27

<210> SEQ ID NO 637
<211> LENGTH: 23
<212> TYPE: DNA
<213> ORGANISM: Artificial Sequence
<220> FEATURE:
<223> OTHER INFORMATION: Synthetic DNA/RNA primer, R265

<400> SEQUENCE: 637
gagcacucca tttuggacag caa                                     23

<210> SEQ ID NO 638
<211> LENGTH: 34
<212> TYPE: DNA
<213> ORGANISM: Artificial Sequence
<220> FEATURE:
<223> OTHER INFORMATION: Synthetic DNA/RNA primer, R266

<400> SEQUENCE: 638 gagtttatt tctgguttca atagaacaag tuga                          34

<210> SEQ ID NO 639
<211> LENGTH: 34
<212> TYPE: DNA
<213> ORGANISM: Artificial Sequence
<220> FEATURE:
<223> OTHER INFORMATION: Synthetic DNA/RNA primer, R267

<400> SEQUENCE: 639
gatttgaaag gtagautgcc ataatgtatc atug                         34

<210> SEQ ID NO 640
<211> LENGTH: 33

```
<212> TYPE: DNA
<213> ORGANISM: Artificial Sequence
<220> FEATURE:
<223> OTHER INFORMATION: Synthetic DNA/RNA primer, R268

<400> SEQUENCE: 640
gaatgtggaa tctutgttta gttttactcu ggt                                     33

<210> SEQ ID NO 641
<211> LENGTH: 32
<212> TYPE: DNA
<213> ORGANISM: Artificial Sequence
<220> FEATURE:
<223> OTHER INFORMATION: Synthetic DNA/RNA primer, R269

<400> SEQUENCE: 641
gaatggttta gtcugacaca tatttaacac ut                                      32

<210> SEQ ID NO 642
<211> LENGTH: 34
<212> TYPE: DNA
<213> ORGANISM: Artificial Sequence
<220> FEATURE:
<223> OTHER INFORMATION: Synthetic DNA/RNA primer, R270

<400> SEQUENCE: 642
gattttcaag ttauagaaac atgtcatgtt guca                                    34

<210> SEQ ID NO 643
<211> LENGTH: 34
<212> TYPE: DNA
<213> ORGANISM: Artificial Sequence
<220> FEATURE:
<223> OTHER INFORMATION: Synthetic DNA/RNA primer, R271

<400> SEQUENCE: 643
gactagactt ugagacctgc taaataatua gatg                                    34

<210> SEQ ID NO 644
<211> LENGTH: 23
<212> TYPE: RNA
<213> ORGANISM: Artificial Sequence
<220> FEATURE:
<223> OTHER INFORMATION: Synthetic Primer, R272

<400> SEQUENCE: 644
gacaggucca agugaaccag gga                                                23

<210> SEQ ID NO 645
<211> LENGTH: 20
<212> TYPE: DNA
<213> ORGANISM: Artificial Sequence
<220> FEATURE:
<223> OTHER INFORMATION: Synthetic DNA/RNA primer, R273

<400> SEQUENCE: 645
gaagggcacu gaccctggua                                                    20

<210> SEQ ID NO 646
<211> LENGTH: 22
<212> TYPE: DNA
<213> ORGANISM: Artificial Sequence
<220> FEATURE:
<223> OTHER INFORMATION: Synthetic DNA/RNA primer, R274

<400> SEQUENCE: 646
```
gatctgcagg agggugctct ua    22

<210> SEQ ID NO 647
<211> LENGTH: 23
<212> TYPE: DNA
<213> ORGANISM: Artificial Sequence
<220> FEATURE:
<223> OTHER INFORMATION: Synthetic DNA/RNA primer, R275

<400> SEQUENCE: 647
gagggcaacu acacctgcat ugt    23

<210> SEQ ID NO 648
<211> LENGTH: 26
<212> TYPE: DNA
<213> ORGANISM: Artificial Sequence
<220> FEATURE:
<223> OTHER INFORMATION: Synthetic DNA/RNA primer, R276

<400> SEQUENCE: 648
gatgccaaga cagugaagtt caaaug    26

<210> SEQ ID NO 649
<211> LENGTH: 24
<212> TYPE: DNA
<213> ORGANISM: Artificial Sequence
<220> FEATURE:
<223> OTHER INFORMATION: Synthetic DNA/RNA primer, R277

<400> SEQUENCE: 649
gagacaccac cuacttctcc guca    24

<210> SEQ ID NO 650
<211> LENGTH: 31
<212> TYPE: DNA
<213> ORGANISM: Artificial Sequence
<220> FEATURE:
<223> OTHER INFORMATION: Synthetic DNA/RNA primer, R278

<400> SEQUENCE: 650
gaaagaccaa aagagaaugg aaagtacuga c    31

<210> SEQ ID NO 651
<211> LENGTH: 25
<212> TYPE: DNA
<213> ORGANISM: Artificial Sequence
<220> FEATURE:
<223> OTHER INFORMATION: Synthetic DNA/RNA primer, R279

<400> SEQUENCE: 651
gaagaguatc catcuccagg agacg    25

<210> SEQ ID NO 652
<211> LENGTH: 20
<212> TYPE: DNA
<213> ORGANISM: Artificial Sequence
<220> FEATURE:
<223> OTHER INFORMATION: Synthetic DNA/RNA primer, R280

<400> SEQUENCE: 652
gatgtggcuc tccgcccaut    20

<210> SEQ ID NO 653
<211> LENGTH: 28
<212> TYPE: DNA
<213> ORGANISM: Artificial Sequence -continued

```
<220> FEATURE:
<223> OTHER INFORMATION: Synthetic DNA/RNA primer, R281

<400> SEQUENCE: 653
gagctacacc atuagcttca ctgattut                                      28

<210> SEQ ID NO 654
<211> LENGTH: 29
<212> TYPE: DNA
<213> ORGANISM: Artificial Sequence
<220> FEATURE:
<223> OTHER INFORMATION: Synthetic DNA/RNA primer, R282

<400> SEQUENCE: 654
gactggatgg uaagaggagt ttcttcauc                                     29

<210> SEQ ID NO 655
<211> LENGTH: 23
<212> TYPE: DNA
<213> ORGANISM: Artificial Sequence
<220> FEATURE:
<223> OTHER INFORMATION: Synthetic DNA/RNA primer, R283

<400> SEQUENCE: 655
gacctttccc cucccctacc uag                                           23

<210> SEQ ID NO 656
<211> LENGTH: 34
<212> TYPE: DNA
<213> ORGANISM: Artificial Sequence
<220> FEATURE:
<223> OTHER INFORMATION: Synthetic DNA/RNA primer, R284

<400> SEQUENCE: 656
gacaaaacaa agucaaagag aattatgaaa tgug                               34

<210> SEQ ID NO 657
<211> LENGTH: 31
<212> TYPE: DNA
<213> ORGANISM: Artificial Sequence
<220> FEATURE:
<223> OTHER INFORMATION: Synthetic DNA/RNA primer, R285

<400> SEQUENCE: 657
gacagggatt tuggttacta ctttgcuaag a                                  31

<210> SEQ ID NO 658
<211> LENGTH: 26
<212> TYPE: DNA
<213> ORGANISM: Artificial Sequence
<220> FEATURE:
<223> OTHER INFORMATION: Synthetic DNA/RNA primer, R286

<400> SEQUENCE: 658
gattgtcttc uggacacgtt cugaaa                                        26

<210> SEQ ID NO 659
<211> LENGTH: 34
<212> TYPE: DNA
<213> ORGANISM: Artificial Sequence
<220> FEATURE:
<223> OTHER INFORMATION: Synthetic DNA/RNA primer, R287

<400> SEQUENCE: 659
gatattaagc tttcutggaa aattctcttu ccct                               34
```

<210> SEQ ID NO 660
<211> LENGTH: 27
<212> TYPE: DNA
<213> ORGANISM: Artificial Sequence
<220> FEATURE:
<223> OTHER INFORMATION: Synthetic DNA/RNA primer, R288

<400> SEQUENCE: 660
gattcagaag tuaggaaagg aguccag                               27

<210> SEQ ID NO 661
<211> LENGTH: 20
<212> TYPE: RNA
<213> ORGANISM: Artificial Sequence
<220> FEATURE:
<223> OTHER INFORMATION: Synthetic Primer, R289

<400> SEQUENCE: 661
gacaccuguc acccgcacac                                       20

<210> SEQ ID NO 662
<211> LENGTH: 23
<212> TYPE: DNA
<213> ORGANISM: Artificial Sequence
<220> FEATURE:
<223> OTHER INFORMATION: Synthetic DNA/RNA primer, R290

<400> SEQUENCE: 662
gacagtcagu aacgccagug agt                                   23

<210> SEQ ID NO 663
<211> LENGTH: 20
<212> TYPE: DNA
<213> ORGANISM: Artificial Sequence
<220> FEATURE:
<223> OTHER INFORMATION: Synthetic DNA/RNA primer, R291

<400> SEQUENCE: 663
gagucccgtg gugcaaaggc                                       20

<210> SEQ ID NO 664
<211> LENGTH: 32
<212> TYPE: DNA
<213> ORGANISM: Artificial Sequence
<220> FEATURE:
<223> OTHER INFORMATION: Synthetic DNA/RNA primer, R292

<400> SEQUENCE: 664
gaatgtacac tagttccgg aataaacctt ut                          32

<210> SEQ ID NO 665
<211> LENGTH: 20
<212> TYPE: DNA
<213> ORGANISM: Artificial Sequence
<220> FEATURE:
<223> OTHER INFORMATION: Synthetic DNA/RNA primer, R293

<400> SEQUENCE: 665
gactugaccc cugcgagcca                                       20

<210> SEQ ID NO 666
<211> LENGTH: 23
<212> TYPE: DNA
<213> ORGANISM: Artificial Sequence
<220> FEATURE:
<223> OTHER INFORMATION: Synthetic DNA/RNA primer, R294

```
<400> SEQUENCE: 666
gacccacuca agctcagctg uaa                                           23

<210> SEQ ID NO 667
<211> LENGTH: 27
<212> TYPE: DNA
<213> ORGANISM: Artificial Sequence
<220> FEATURE:
<223> OTHER INFORMATION: Synthetic DNA/RNA primer, R295

<400> SEQUENCE: 667
gactgagaat ggcuacctct cgataug                                       27

<210> SEQ ID NO 668
<211> LENGTH: 27
<212> TYPE: DNA
<213> ORGANISM: Artificial Sequence
<220> FEATURE:
<223> OTHER INFORMATION: Synthetic DNA/RNA primer, R296

<400> SEQUENCE: 668
gaggctggag utggtgttat agtucaa                                       27

<210> SEQ ID NO 669
<211> LENGTH: 29
<212> TYPE: DNA
<213> ORGANISM: Artificial Sequence
<220> FEATURE:
<223> OTHER INFORMATION: Synthetic DNA/RNA primer, R297

<400> SEQUENCE: 669
gactcacaca tcutgagccc atttttauc                                     29

<210> SEQ ID NO 670
<211> LENGTH: 25
<212> TYPE: DNA
<213> ORGANISM: Artificial Sequence
<220> FEATURE:
<223> OTHER INFORMATION: Synthetic DNA/RNA primer, R298

<400> SEQUENCE: 670
gactgagagg gugtcacata ccaug                                         25

<210> SEQ ID NO 671
<211> LENGTH: 27
<212> TYPE: DNA
<213> ORGANISM: Artificial Sequence
<220> FEATURE:
<223> OTHER INFORMATION: Synthetic DNA/RNA primer, R299

<400> SEQUENCE: 671
gattcatacc gacaugtagg acctugt                                       27

<210> SEQ ID NO 672
<211> LENGTH: 22
<212> TYPE: DNA
<213> ORGANISM: Artificial Sequence
<220> FEATURE:
<223> OTHER INFORMATION: Synthetic DNA/RNA primer, R300

<400> SEQUENCE: 672
gaacttcuca caccgctgtg ut                                            22

<210> SEQ ID NO 673
```

<211> LENGTH: 22
<212> TYPE: DNA
<213> ORGANISM: Artificial Sequence
<220> FEATURE:
<223> OTHER INFORMATION: Synthetic DNA/RNA primer, R301

<400> SEQUENCE: 673
gacctcaccu ccgtttccug ca            22

<210> SEQ ID NO 674
<211> LENGTH: 21
<212> TYPE: DNA
<213> ORGANISM: Artificial Sequence
<220> FEATURE:
<223> OTHER INFORMATION: Synthetic DNA/RNA primer, R302

<400> SEQUENCE: 674
gatcuggccc cctuaggagg a            21

<210> SEQ ID NO 675
<211> LENGTH: 27
<212> TYPE: DNA
<213> ORGANISM: Artificial Sequence
<220> FEATURE:
<223> OTHER INFORMATION: Synthetic DNA/RNA primer, R303

<400> SEQUENCE: 675
gatcatcctc uccccataga aaagucc            27

<210> SEQ ID NO 676
<211> LENGTH: 25
<212> TYPE: DNA
<213> ORGANISM: Artificial Sequence
<220> FEATURE:
<223> OTHER INFORMATION: Synthetic DNA/RNA primer, R304

<400> SEQUENCE: 676
gatctcugcc atcattuccg gaaag            25

<210> SEQ ID NO 677
<211> LENGTH: 25
<212> TYPE: DNA
<213> ORGANISM: Artificial Sequence
<220> FEATURE:
<223> OTHER INFORMATION: Synthetic DNA/RNA primer, R305

<400> SEQUENCE: 677
gatgcaagga augcgatgaa guaga            25

<210> SEQ ID NO 678
<211> LENGTH: 23
<212> TYPE: DNA
<213> ORGANISM: Artificial Sequence
<220> FEATURE:
<223> OTHER INFORMATION: Synthetic DNA/RNA primer, R306

<400> SEQUENCE: 678
gagtcgcuaa cacgtgtgtg tuc            23

<210> SEQ ID NO 679
<211> LENGTH: 29
<212> TYPE: DNA
<213> ORGANISM: Artificial Sequence
<220> FEATURE:
<223> OTHER INFORMATION: Synthetic DNA/RNA primer, R307

<400> SEQUENCE: 679

```
gatggctaaa ctugaccttt ttactcugc                                    29
```

<210> SEQ ID NO 680
<211> LENGTH: 22
<212> TYPE: DNA
<213> ORGANISM: Artificial Sequence
<220> FEATURE:
<223> OTHER INFORMATION: Synthetic DNA/RNA primer, R308

<400> SEQUENCE: 680

```
gattcctcag caucgacctu gc                                           22
```

<210> SEQ ID NO 681
<211> LENGTH: 32
<212> TYPE: DNA
<213> ORGANISM: Artificial Sequence
<220> FEATURE:
<223> OTHER INFORMATION: Synthetic DNA/RNA primer, R309

<400> SEQUENCE: 681

```
gaaatctata tactucctta cctgggatug ga                                32
```

<210> SEQ ID NO 682
<211> LENGTH: 25
<212> TYPE: DNA
<213> ORGANISM: Artificial Sequence
<220> FEATURE:
<223> OTHER INFORMATION: Synthetic DNA/RNA primer, R310

<400> SEQUENCE: 682

```
gaacatgctg agaucagcca aatuc                                        25
```

<210> SEQ ID NO 683
<211> LENGTH: 27
<212> TYPE: DNA
<213> ORGANISM: Artificial Sequence
<220> FEATURE:
<223> OTHER INFORMATION: Synthetic DNA/RNA primer, R311

<400> SEQUENCE: 683

```
gagcagugaa aagagtcuca aacacaa                                      27
```

<210> SEQ ID NO 684
<211> LENGTH: 21
<212> TYPE: DNA
<213> ORGANISM: Artificial Sequence
<220> FEATURE:
<223> OTHER INFORMATION: Synthetic DNA/RNA primer, R312

<400> SEQUENCE: 684

```
gacccacagg ccutctucga g                                            21
```

<210> SEQ ID NO 685
<211> LENGTH: 25
<212> TYPE: DNA
<213> ORGANISM: Artificial Sequence
<220> FEATURE:
<223> OTHER INFORMATION: Synthetic DNA/RNA primer, R313

<400> SEQUENCE: 685

```
gactgguatg agaaacugca cgagt                                        25
```

<210> SEQ ID NO 686
<211> LENGTH: 27
<212> TYPE: DNA

<210> SEQ ID NO 687
<211> LENGTH: 27
<212> TYPE: DNA
<213> ORGANIZM: Artificial Sequence
<220> FEATURE:
<223> OTHER INFORMATION: Synthetic DNA/RNA primer, R314

<400> SEQUENCE: 686
gaaataccaa tcuattgtgg gctcugg 27

<210> SEQ ID NO 687
<211> LENGTH: 27
<212> TYPE: DNA
<213> ORGANISM: Artificial Sequence
<220> FEATURE:
<223> OTHER INFORMATION: Synthetic DNA/RNA primer, R315

<400> SEQUENCE: 687
gacctccttc ugcatggtat tcttuct 27

<210> SEQ ID NO 688
<211> LENGTH: 26
<212> TYPE: DNA
<213> ORGANISM: Artificial Sequence
<220> FEATURE:
<223> OTHER INFORMATION: Synthetic DNA/RNA primer, R316

<400> SEQUENCE: 688
gaattaaagc agugctcatg atuggg 26

<210> SEQ ID NO 689
<211> LENGTH: 23
<212> TYPE: DNA
<213> ORGANISM: Artificial Sequence
<220> FEATURE:
<223> OTHER INFORMATION: Synthetic DNA/RNA primer, R317

<400> SEQUENCE: 689
gacgggacuc gagtgatgat ugg 23

<210> SEQ ID NO 690
<211> LENGTH: 26
<212> TYPE: DNA
<213> ORGANISM: Artificial Sequence
<220> FEATURE:
<223> OTHER INFORMATION: Synthetic DNA/RNA primer, R318

<400> SEQUENCE: 690
gacttcacct tuaacacctc cagucc 26

<210> SEQ ID NO 691
<211> LENGTH: 30
<212> TYPE: DNA
<213> ORGANISM: Artificial Sequence
<220> FEATURE:
<223> OTHER INFORMATION: Synthetic DNA/RNA primer, R319

<400> SEQUENCE: 691
gactcctcta gcuatcttaa tgactuggac 30

<210> SEQ ID NO 692
<211> LENGTH: 34
<212> TYPE: DNA
<213> ORGANISM: Artificial Sequence
<220> FEATURE:
<223> OTHER INFORMATION: Synthetic DNA/RNA primer, R320

<400> SEQUENCE: 692
gactgctttc atucataggg aaatacauaa gaaa 34

<210> SEQ ID NO 693
<211> LENGTH: 34
<212> TYPE: DNA
<213> ORGANISM: Artificial Sequence
<220> FEATURE:
<223> OTHER INFORMATION: Synthetic DNA/RNA primer, R321

<400> SEQUENCE: 693
gattcaatat tttaaauagt ctggccuaaa cggt                              34

<210> SEQ ID NO 694
<211> LENGTH: 34
<212> TYPE: DNA
<213> ORGANISM: Artificial Sequence
<220> FEATURE:
<223> OTHER INFORMATION: Synthetic DNA/RNA primer, R322

<400> SEQUENCE: 694
gatgatttcc aguattaatt ggcaauaaga gaat                              34

<210> SEQ ID NO 695
<211> LENGTH: 34
<212> TYPE: DNA
<213> ORGANISM: Artificial Sequence
<220> FEATURE:
<223> OTHER INFORMATION: Synthetic DNA/RNA primer, R323

<400> SEQUENCE: 695
gaatgaaagc uaaaacataa gatgaauggg aaaa                              34

<210> SEQ ID NO 696
<211> LENGTH: 33
<212> TYPE: DNA
<213> ORGANISM: Artificial Sequence
<220> FEATURE:
<223> OTHER INFORMATION: Synthetic DNA/RNA primer, R324

<400> SEQUENCE: 696
gaattatttc ttaccacutt tcctttctcc ugt                               33

<210> SEQ ID NO 697
<211> LENGTH: 28
<212> TYPE: DNA
<213> ORGANISM: Artificial Sequence
<220> FEATURE:
<223> OTHER INFORMATION: Synthetic DNA/RNA primer, R325

<400> SEQUENCE: 697
gaattgtgag atuaacagca gggauacc                                    28

<210> SEQ ID NO 698
<211> LENGTH: 35
<212> TYPE: DNA
<213> ORGANISM: Artificial Sequence
<220> FEATURE:
<223> OTHER INFORMATION: Synthetic DNA/RNA primer, R326

<400> SEQUENCE: 698
gagcttcatt gtctugataa aatttatggt atcut                             35

<210> SEQ ID NO 699
<211> LENGTH: 34
<212> TYPE: DNA
<213> ORGANISM: Artificial Sequence
<220> FEATURE:

<223> OTHER INFORMATION: Synthetic DNA/RNA primer, R327

<400> SEQUENCE: 699
gaccagctct tucatatctt aacattuagc aaca         34

<210> SEQ ID NO 700
<211> LENGTH: 33
<212> TYPE: DNA
<213> ORGANISM: Artificial Sequence
<220> FEATURE:
<223> OTHER INFORMATION: Synthetic DNA/RNA primer, R328

<400> SEQUENCE: 700
gagccaaaac atttugtccc tttctataat tug          33

<210> SEQ ID NO 701
<211> LENGTH: 25
<212> TYPE: DNA
<213> ORGANISM: Artificial Sequence
<220> FEATURE:
<223> OTHER INFORMATION: Synthetic DNA/RNA primer, R329

<400> SEQUENCE: 701
gatggacttc aagugatcac ttgug                   25

<210> SEQ ID NO 702
<211> LENGTH: 22
<212> TYPE: DNA
<213> ORGANISM: Artificial Sequence
<220> FEATURE:
<223> OTHER INFORMATION: Synthetic DNA/RNA primer, R330

<400> SEQUENCE: 702
gaagcctgug gtgctttttug cg                     22

<210> SEQ ID NO 703
<211> LENGTH: 29
<212> TYPE: DNA
<213> ORGANISM: Artificial Sequence
<220> FEATURE:
<223> OTHER INFORMATION: Synthetic DNA/RNA primer, R331

<400> SEQUENCE: 703
gaaagtcaaa cuacactcag aaccugaat               29

<210> SEQ ID NO 704
<211> LENGTH: 30
<212> TYPE: DNA
<213> ORGANISM: Artificial Sequence
<220> FEATURE:
<223> OTHER INFORMATION: Synthetic DNA/RNA primer, R332

<400> SEQUENCE: 704
gagcaaaggc caaagauaaa atgcttacug              30

<210> SEQ ID NO 705
<211> LENGTH: 32
<212> TYPE: DNA
<213> ORGANISM: Artificial Sequence
<220> FEATURE:
<223> OTHER INFORMATION: Synthetic DNA/RNA primer, R333

<400> SEQUENCE: 705
gaaagctaca gaaugtgaac agtcttctua aa           32

<210> SEQ ID NO 706
<211> LENGTH: 30
<212> TYPE: DNA
<213> ORGANISM: Artificial Sequence
<220> FEATURE:
<223> OTHER INFORMATION: Synthetic DNA/RNA primer, R334

<400> SEQUENCE: 706
gagaggtaga ugctgtaatt gctgauacaa                                    30

<210> SEQ ID NO 707
<211> LENGTH: 29
<212> TYPE: DNA
<213> ORGANISM: Artificial Sequence
<220> FEATURE:
<223> OTHER INFORMATION: Synthetic DNA/RNA primer, R335

<400> SEQUENCE: 707
gacaaacacc tccugataaa ttggcttug                                     29

<210> SEQ ID NO 708
<211> LENGTH: 23
<212> TYPE: DNA
<213> ORGANISM: Artificial Sequence
<220> FEATURE:
<223> OTHER INFORMATION: Synthetic DNA/RNA primer, R336

<400> SEQUENCE: 708
gaccctacuc caaggagcuc agg                                           23

<210> SEQ ID NO 709
<211> LENGTH: 30
<212> TYPE: DNA
<213> ORGANISM: Artificial Sequence
<220> FEATURE:
<223> OTHER INFORMATION: Synthetic DNA/RNA primer, R337

<400> SEQUENCE: 709
gacccagtua ccataactac tcugagaaaa                                    30

<210> SEQ ID NO 710
<211> LENGTH: 25
<212> TYPE: DNA
<213> ORGANISM: Artificial Sequence
<220> FEATURE:
<223> OTHER INFORMATION: Synthetic DNA/RNA primer, R338

<400> SEQUENCE: 710
gacttgcaga gcuatccccu aaagc                                         25

<210> SEQ ID NO 711
<211> LENGTH: 21
<212> TYPE: DNA
<213> ORGANISM: Artificial Sequence
<220> FEATURE:
<223> OTHER INFORMATION: Synthetic DNA/RNA primer, R339

<400> SEQUENCE: 711
gagctgcacc gagucgtagu c                                             21

<210> SEQ ID NO 712
<211> LENGTH: 21
<212> TYPE: DNA
<213> ORGANISM: Artificial Sequence
<220> FEATURE:
<223> OTHER INFORMATION: Synthetic DNA/RNA primer, R340

<400> SEQUENCE: 712
gagtcgutgt cuccccgaag g                                    21

<210> SEQ ID NO 713
<211> LENGTH: 30
<212> TYPE: DNA
<213> ORGANISM: Artificial Sequence
<220> FEATURE:
<223> OTHER INFORMATION: Synthetic DNA/RNA primer, R341

<400> SEQUENCE: 713
gaatacagtc cuggatgatg atgttttuga                           30

<210> SEQ ID NO 714
<211> LENGTH: 26
<212> TYPE: DNA
<213> ORGANISM: Artificial Sequence
<220> FEATURE:
<223> OTHER INFORMATION: Synthetic DNA/RNA primer, R342

<400> SEQUENCE: 714
gaggacaaga aaagugcaac tuccca                               26

<210> SEQ ID NO 715
<211> LENGTH: 27
<212> TYPE: DNA
<213> ORGANISM: Artificial Sequence
<220> FEATURE:
<223> OTHER INFORMATION: Synthetic DNA/RNA primer, R343

<400> SEQUENCE: 715
gatttcattg utttccaacu ccgggat                              27

<210> SEQ ID NO 716
<211> LENGTH: 30
<212> TYPE: DNA
<213> ORGANISM: Artificial Sequence
<220> FEATURE:
<223> OTHER INFORMATION: Synthetic DNA/RNA primer, R344

<400> SEQUENCE: 716
gattuccaca gaaacaacau cgatttcttc                           30

<210> SEQ ID NO 717
<211> LENGTH: 30
<212> TYPE: DNA
<213> ORGANISM: Artificial Sequence
<220> FEATURE:
<223> OTHER INFORMATION: Synthetic DNA/RNA primer, R345

<400> SEQUENCE: 717
gatgcattug atcatgcatt ugaaacaagt                           30

<210> SEQ ID NO 718
<211> LENGTH: 19
<212> TYPE: DNA
<213> ORGANISM: Artificial Sequence
<220> FEATURE:
<223> OTHER INFORMATION: Synthetic DNA/RNA primer, R346

<400> SEQUENCE: 718
gaagtctgug cgcgctugc                                       19

<210> SEQ ID NO 719
<211> LENGTH: 19

<212> TYPE: DNA
<213> ORGANISM: Artificial Sequence
<220> FEATURE:
<223> OTHER INFORMATION: Synthetic DNA/RNA primer, R347

<400> SEQUENCE: 719
gagtgcgcac gucgcaauc                                                19

<210> SEQ ID NO 720
<211> LENGTH: 26
<212> TYPE: DNA
<213> ORGANISM: Artificial Sequence
<220> FEATURE:
<223> OTHER INFORMATION: Synthetic DNA/RNA primer, R348

<400> SEQUENCE: 720
gaggatgtau acaaaaggcg gatgug                                        26

<210> SEQ ID NO 721
<211> LENGTH: 22
<212> TYPE: DNA
<213> ORGANISM: Artificial Sequence
<220> FEATURE:
<223> OTHER INFORMATION: Synthetic DNA/RNA primer, R349

<400> SEQUENCE: 721
gagccagaga gucccttuca cc                                            22

<210> SEQ ID NO 722
<211> LENGTH: 23
<212> TYPE: DNA
<213> ORGANISM: Artificial Sequence
<220> FEATURE:
<223> OTHER INFORMATION: Synthetic DNA/RNA primer, R350

<400> SEQUENCE: 722
gatgccactc uttgggttga gut                                           23

<210> SEQ ID NO 723
<211> LENGTH: 27
<212> TYPE: DNA
<213> ORGANISM: Artificial Sequence
<220> FEATURE:
<223> OTHER INFORMATION: Synthetic DNA/RNA primer, R351

<400> SEQUENCE: 723
gatttcaaac uggaggctta ucaccaa                                       27

<210> SEQ ID NO 724
<211> LENGTH: 35
<212> TYPE: DNA
<213> ORGANISM: Artificial Sequence
<220> FEATURE:
<223> OTHER INFORMATION: Synthetic DNA/RNA primer, R352

<400> SEQUENCE: 724
gaatacaagc atgaaaauca aaacatatct tcugc                              35

<210> SEQ ID NO 725
<211> LENGTH: 34
<212> TYPE: DNA
<213> ORGANISM: Artificial Sequence
<220> FEATURE:
<223> OTHER INFORMATION: Synthetic DNA/RNA primer, R353

<400> SEQUENCE: 725
gagtaaatgg tagctuttat cataatcacc aguc                                    34

<210> SEQ ID NO 726
<211> LENGTH: 28
<212> TYPE: DNA
<213> ORGANISM: Artificial Sequence
<220> FEATURE:
<223> OTHER INFORMATION: Synthetic DNA/RNA primer, R354

<400> SEQUENCE: 726
gatccattca agacuttagc aggtggua                                           28

<210> SEQ ID NO 727
<211> LENGTH: 32
<212> TYPE: DNA
<213> ORGANISM: Artificial Sequence
<220> FEATURE:
<223> OTHER INFORMATION: Synthetic DNA/RNA primer, R355

<400> SEQUENCE: 727
gagttactct catgugagaa ccatttgaau ga                                      32

<210> SEQ ID NO 728
<211> LENGTH: 35
<212> TYPE: DNA
<213> ORGANISM: Artificial Sequence
<220> FEATURE:
<223> OTHER INFORMATION: Synthetic DNA/RNA primer, R356

<400> SEQUENCE: 728 gagttttttct tatcucttaa aatgtttctg cuaca                                  35

<210> SEQ ID NO 729
<211> LENGTH: 28
<212> TYPE: DNA
<213> ORGANISM: Artificial Sequence
<220> FEATURE:
<223> OTHER INFORMATION: Synthetic DNA/RNA primer, R257

<400> SEQUENCE: 729
gaaagguaca agtuaaggca cacagaag                                           28

<210> SEQ ID NO 730
<211> LENGTH: 27
<212> TYPE: DNA
<213> ORGANISM: Artificial Sequence
<220> FEATURE:
<223> OTHER INFORMATION: Synthetic DNA/RNA primer, R358

<400> SEQUENCE: 730
gatggatctu ggcacaatga uaacagg                                            27

<210> SEQ ID NO 731
<211> LENGTH: 32
<212> TYPE: DNA
<213> ORGANISM: Artificial Sequence
<220> FEATURE:
<223> OTHER INFORMATION: Synthetic DNA/RNA primer, R359

<400> SEQUENCE: 731
gatgctatag taccaguacc ttttaaggtu ca                                      32

<210> SEQ ID NO 732
<211> LENGTH: 23
<212> TYPE: DNA
<213> ORGANISM: Artificial Sequence
<220> FEATURE:
<223> OTHER INFORMATION: Synthetic DNA/RNA primer, R360

<400> SEQUENCE: 732
gaccgtaagg uggcctactt ugc          23

<210> SEQ ID NO 733
<211> LENGTH: 31
<212> TYPE: DNA
<213> ORGANISM: Artificial Sequence
<220> FEATURE:
<223> OTHER INFORMATION: Synthetic DNA/RNA primer, R361

<400> SEQUENCE: 733
gacagcgttt tcutgtattc ctgtattuag c          31

<210> SEQ ID NO 734
<211> LENGTH: 27
<212> TYPE: DNA
<213> ORGANISM: Artificial Sequence
<220> FEATURE:
<223> OTHER INFORMATION: Synthetic DNA/RNA primer, R362

<400> SEQUENCE: 734
gaggaactgt gaaugaactt gtaggug          27

<210> SEQ ID NO 735
<211> LENGTH: 20
<212> TYPE: RNA
<213> ORGANISM: Artificial Sequence
<220> FEATURE:
<223> OTHER INFORMATION: Synthetic Primer, R363

<400> SEQUENCE: 735
gaccugacca gggcgucaaa          20

<210> SEQ ID NO 736
<211> LENGTH: 29
<212> TYPE: DNA
<213> ORGANISM: Artificial Sequence
<220> FEATURE:
<223> OTHER INFORMATION: Synthetic DNA/RNA primer, R364

<400> SEQUENCE: 736
gaagttcatc tucgaagctc aaattucag          29

<210> SEQ ID NO 737
<211> LENGTH: 31
<212> TYPE: DNA
<213> ORGANISM: Artificial Sequence
<220> FEATURE:
<223> OTHER INFORMATION: Synthetic DNA/RNA primer, R365

<400> SEQUENCE: 737
gatacaacaa aaugtttgac ttcaugcagg t          31

<210> SEQ ID NO 738
<211> LENGTH: 28
<212> TYPE: DNA
<213> ORGANISM: Artificial Sequence
<220> FEATURE:
<223> OTHER INFORMATION: Synthetic DNA/RNA primer, F366

<400> SEQUENCE: 738
aaaactcagt aucaacaact accgguac          28

<210> SEQ ID NO 739
<211> LENGTH: 28
<212> TYPE: DNA
<213> ORGANISM: Artificial Sequence
<220> FEATURE:
<223> OTHER INFORMATION: Synthetic DNA/RNA primer, F367

<400> SEQUENCE: 739
ctcagaaaug gaaaaaacct gcaguaaa                                    28

<210> SEQ ID NO 740
<211> LENGTH: 23
<212> TYPE: DNA
<213> ORGANISM: Artificial Sequence
<220> FEATURE:
<223> OTHER INFORMATION: Synthetic DNA/RNA primer, F368

<400> SEQUENCE: 740
gttccctcug cgtgttctca uaa                                         23

<210> SEQ ID NO 741
<211> LENGTH: 27
<212> TYPE: DNA
<213> ORGANISM: Artificial Sequence
<220> FEATURE:
<223> OTHER INFORMATION: Synthetic DNA/RNA primer, F369

<400> SEQUENCE: 741
aagaaccugu gtgaaagtat cuagcac                                     27

<210> SEQ ID NO 742
<211> LENGTH: 25
<212> TYPE: RNA
<213> ORGANISM: Artificial Sequence
<220> FEATURE:
<223> OTHER INFORMATION: Synthetic Primer, F370

<400> SEQUENCE: 742
auaaaccaaa cccaugcaaa aggac                                       25

<210> SEQ ID NO 743
<211> LENGTH: 25
<212> TYPE: DNA
<213> ORGANISM: Artificial Sequence
<220> FEATURE:
<223> OTHER INFORMATION: Synthetic DNA/RNA primer, F371

<400> SEQUENCE: 743
gcattgaugg aaggaagcaa auaca                                       25

<210> SEQ ID NO 744
<211> LENGTH: 25
<212> TYPE: DNA
<213> ORGANISM: Artificial Sequence
<220> FEATURE:
<223> OTHER INFORMATION: Synthetic DNA/RNA primer, F372

<400> SEQUENCE: 744
ccagcttcau agacaaaggt tcuct                                       25

<210> SEQ ID NO 745
<211> LENGTH: 24
<212> TYPE: DNA
<213> ORGANISM: Artificial Sequence
<220> FEATURE:
<223> OTHER INFORMATION: Synthetic DNA/RNA primer, F373

-continued

<400> SEQUENCE: 745
gtggtttctu ccattgacca cauc                                      24

<210> SEQ ID NO 746
<211> LENGTH: 22
<212> TYPE: DNA
<213> ORGANISM: Artificial Sequence
<220> FEATURE:
<223> OTHER INFORMATION: Synthetic DNA/RNA primer, F374

<400> SEQUENCE: 746
caaaugggca ggactctuag gt                                        22

<210> SEQ ID NO 747
<211> LENGTH: 22
<212> TYPE: DNA
<213> ORGANISM: Artificial Sequence
<220> FEATURE:
<223> OTHER INFORMATION: Synthetic DNA/RNA primer, F375

<400> SEQUENCE: 747
gugaggaaac tuctgcagag gt                                        22

<210> SEQ ID NO 748
<211> LENGTH: 22
<212> TYPE: DNA
<213> ORGANISM: Artificial Sequence
<220> FEATURE:
<223> OTHER INFORMATION: Synthetic DNA/RNA primer, F376

<400> SEQUENCE: 748
ggaagcaggg aagcucttca uc                                        22

<210> SEQ ID NO 749
<211> LENGTH: 27
<212> TYPE: DNA
<213> ORGANISM: Artificial Sequence
<220> FEATURE:
<223> OTHER INFORMATION: Synthetic DNA/RNA primer, F377

<400> SEQUENCE: 749
tggttugaag aactttctuc agaagct                                   27

<210> SEQ ID NO 750
<211> LENGTH: 25
<212> TYPE: DNA
<213> ORGANISM: Artificial Sequence
<220> FEATURE:
<223> OTHER INFORMATION: Synthetic DNA/RNA primer, F378

<400> SEQUENCE: 750
agggagacug ugtgtaatat ttgcg                                     25

<210> SEQ ID NO 751
<211> LENGTH: 30
<212> TYPE: DNA
<213> ORGANISM: Artificial Sequence
<220> FEATURE:
<223> OTHER INFORMATION: Synthetic DNA/RNA primer, F379

<400> SEQUENCE: 751
gccagtatug aagaatgttg aagaucaaaa                                30

<210> SEQ ID NO 752

```
<211> LENGTH: 23
<212> TYPE: DNA
<213> ORGANISM: Artificial Sequence
<220> FEATURE:
<223> OTHER INFORMATION: Synthetic DNA/RNA primer, F380

<400> SEQUENCE: 752
gccaaaagga aguctgttuc cac                                            23

<210> SEQ ID NO 753
<211> LENGTH: 27
<212> TYPE: DNA
<213> ORGANISM: Artificial Sequence
<220> FEATURE:
<223> OTHER INFORMATION: Synthetic DNA/RNA primer, F381

<400> SEQUENCE: 753
catgccacac autctctttt tacaugt                                        27

<210> SEQ ID NO 754
<211> LENGTH: 23
<212> TYPE: DNA
<213> ORGANISM: Artificial Sequence
<220> FEATURE:
<223> OTHER INFORMATION: Synthetic DNA/RNA primer, F382

<400> SEQUENCE: 754
gtagagugct acactgucca aca                                            23

<210> SEQ ID NO 755
<211> LENGTH: 28
<212> TYPE: DNA
<213> ORGANISM: Artificial Sequence
<220> FEATURE:
<223> OTHER INFORMATION: Synthetic DNA/RNA primer, F383

<400> SEQUENCE: 755
ctctgagaaa gaaugaaatg gagtugga                                       28

<210> SEQ ID NO 756
<211> LENGTH: 24
<212> TYPE: DNA
<213> ORGANISM: Artificial Sequence
<220> FEATURE:
<223> OTHER INFORMATION: Synthetic DNA/RNA primer, F384

<400> SEQUENCE: 756
aaacaaattt uccagcgctt cuga                                           24

<210> SEQ ID NO 757
<211> LENGTH: 30
<212> TYPE: DNA
<213> ORGANISM: Artificial Sequence
<220> FEATURE:
<223> OTHER INFORMATION: Synthetic DNA/RNA primer, F385

<400> SEQUENCE: 757
agcaataaaa gtguataaat gcctgtaugc                                     30

<210> SEQ ID NO 758
<211> LENGTH: 30
<212> TYPE: DNA
<213> ORGANISM: Artificial Sequence
<220> FEATURE:
<223> OTHER INFORMATION: Synthetic DNA/RNA primer, F386

<400> SEQUENCE: 758
```

-continued tcaacaagtt gacuaaatct cgtacttuct            30

<210> SEQ ID NO 759
<211> LENGTH: 28
<212> TYPE: DNA
<213> ORGANISM: Artificial Sequence
<220> FEATURE:
<223> OTHER INFORMATION: Synthetic DNA/RNA primer, F387

<400> SEQUENCE: 759
cattcttaca uaaaggacac tgugaagg               28

<210> SEQ ID NO 760
<211> LENGTH: 24
<212> TYPE: DNA
<213> ORGANISM: Artificial Sequence
<220> FEATURE:
<223> OTHER INFORMATION: Synthetic DNA/RNA primer, F388

<400> SEQUENCE: 760
cccttacaga uggagtcttt uggc                   24

<210> SEQ ID NO 761
<211> LENGTH: 27
<212> TYPE: DNA
<213> ORGANISM: Artificial Sequence
<220> FEATURE:
<223> OTHER INFORMATION: Synthetic DNA/RNA primer, F389

<400> SEQUENCE: 761
aaagaccttt uggtaactca gacucag                27

<210> SEQ ID NO 762
<211> LENGTH: 32
<212> TYPE: DNA
<213> ORGANISM: Artificial Sequence
<220> FEATURE:
<223> OTHER INFORMATION: Synthetic DNA/RNA primer, F390

<400> SEQUENCE: 762
acattcacug aaaatugtaa agcctataat tg          32

<210> SEQ ID NO 763
<211> LENGTH: 35
<212> TYPE: DNA
<213> ORGANISM: Artificial Sequence
<220> FEATURE:
<223> OTHER INFORMATION: Synthetic DNA/RNA primer, F391

<400> SEQUENCE: 763
ggttgtgctt ttuaaatttc aattttattt tugct       35

<210> SEQ ID NO 764
<211> LENGTH: 19
<212> TYPE: DNA
<213> ORGANISM: Artificial Sequence
<220> FEATURE:
<223> OTHER INFORMATION: Synthetic DNA/RNA primer, F392

<400> SEQUENCE: 764
ggatgucaca accgugtgg                         19

<210> SEQ ID NO 765
<211> LENGTH: 29
<212> TYPE: DNA

<213> ORGANISM: Artificial Sequence
<220> FEATURE:
<223> OTHER INFORMATION: Synthetic DNA/RNA primer, F393

<400> SEQUENCE: 765
agtgaaaacu aaaatggauc aagcagatg                               29

<210> SEQ ID NO 766
<211> LENGTH: 33
<212> TYPE: DNA
<213> ORGANISM: Artificial Sequence
<220> FEATURE:
<223> OTHER INFORMATION: Synthetic DNA/RNA primer, F394

<400> SEQUENCE: 766
aaactagttt tugccagttt ttuaaaataa cct                          33

<210> SEQ ID NO 767
<211> LENGTH: 23
<212> TYPE: DNA
<213> ORGANISM: Artificial Sequence
<220> FEATURE:
<223> OTHER INFORMATION: Synthetic DNA/RNA primer, F395

<400> SEQUENCE: 767
tttttacccc caguggtatg ugg                                     23

<210> SEQ ID NO 768
<211> LENGTH: 27
<212> TYPE: RNA
<213> ORGANISM: Artificial Sequence
<220> FEATURE:
<223> OTHER INFORMATION: Synthetic Primer, F396

<400> SEQUENCE: 768
gaaaacacaa aucaaagaga agcugca                                 27

<210> SEQ ID NO 769
<211> LENGTH: 28
<212> TYPE: DNA
<213> ORGANISM: Artificial Sequence
<220> FEATURE:
<223> OTHER INFORMATION: Synthetic DNA/RNA primer, F397

<400> SEQUENCE: 769
atatttagua gccaggacag uagaagga                                28

<210> SEQ ID NO 770
<211> LENGTH: 28
<212> TYPE: DNA
<213> ORGANISM: Artificial Sequence
<220> FEATURE:
<223> OTHER INFORMATION: Synthetic DNA/RNA primer, F398

<400> SEQUENCE: 770
aaatatttca gugtccgtuc acacacaa                                28

<210> SEQ ID NO 771
<211> LENGTH: 25
<212> TYPE: DNA
<213> ORGANISM: Artificial Sequence
<220> FEATURE:
<223> OTHER INFORMATION: Synthetic DNA/RNA primer, F399

<400> SEQUENCE: 771
gcagaugcaa ggtattctgu aaagg                                   25

<210> SEQ ID NO 772
<211> LENGTH: 30
<212> TYPE: DNA
<213> ORGANISM: Artificial Sequence
<220> FEATURE:
<223> OTHER INFORMATION: Synthetic DNA/RNA primer, F400

<400> SEQUENCE: 772
acctacataa aacuctttcc agaatgtugt                                       30

<210> SEQ ID NO 773
<211> LENGTH: 25
<212> TYPE: DNA
<213> ORGANISM: Artificial Sequence
<220> FEATURE:
<223> OTHER INFORMATION: Synthetic DNA/RNA primer, F401

<400> SEQUENCE: 773
ccctttctgt ugaagctgtc aatuc                                            25

<210> SEQ ID NO 774
<211> LENGTH: 23
<212> TYPE: DNA
<213> ORGANISM: Artificial Sequence
<220> FEATURE:
<223> OTHER INFORMATION: Synthetic DNA/RNA primer, F402

<400> SEQUENCE: 774
agauggtatg tugccaacac gag                                              23

<210> SEQ ID NO 775
<211> LENGTH: 23
<212> TYPE: DNA
<213> ORGANISM: Artificial Sequence
<220> FEATURE:
<223> OTHER INFORMATION: Synthetic DNA/RNA primer, F403

<400> SEQUENCE: 775
gatgtttccg ucaaatcgtg ugg                                              23

<210> SEQ ID NO 776
<211> LENGTH: 27
<212> TYPE: DNA
<213> ORGANISM: Artificial Sequence
<220> FEATURE:
<223> OTHER INFORMATION: Synthetic DNA/RNA primer, F404

<400> SEQUENCE: 776
gtagaactat cugcagacac cucaaac                                          27

<210> SEQ ID NO 777
<211> LENGTH: 27
<212> TYPE: DNA
<213> ORGANISM: Artificial Sequence
<220> FEATURE:
<223> OTHER INFORMATION: Synthetic DNA/RNA primer, F405

<400> SEQUENCE: 777
ccagaaccac cauctttcag taattug                                          27

<210> SEQ ID NO 778
<211> LENGTH: 27
<212> TYPE: DNA
<213> ORGANISM: Artificial Sequence
<220> FEATURE:

<223> OTHER INFORMATION: Synthetic DNA/RNA primer, F406

<400> SEQUENCE: 778
atcataaaat gtuggagcta ggtccut                                    27

<210> SEQ ID NO 779
<211> LENGTH: 27
<212> TYPE: DNA
<213> ORGANISM: Artificial Sequence
<220> FEATURE:
<223> OTHER INFORMATION: Synthetic DNA/RNA primer, F407

<400> SEQUENCE: 779
tatgatggaa ggguagctgt uagaagg                                    27

<210> SEQ ID NO 780
<211> LENGTH: 28
<212> TYPE: DNA
<213> ORGANISM: Artificial Sequence
<220> FEATURE:
<223> OTHER INFORMATION: Synthetic DNA/RNA primer, F408

<400> SEQUENCE: 780
ggttaaaatg tcacuctgag aggauagc                                   28

<210> SEQ ID NO 781
<211> LENGTH: 27
<212> TYPE: DNA
<213> ORGANISM: Artificial Sequence
<220> FEATURE:
<223> OTHER INFORMATION: Synthetic DNA/RNA primer, F409

<400> SEQUENCE: 781
ggaaatttgu aaaatgtgcu ccccaaa                                    27

<210> SEQ ID NO 782
<211> LENGTH: 25
<212> TYPE: DNA
<213> ORGANISM: Artificial Sequence
<220> FEATURE:
<223> OTHER INFORMATION: Synthetic DNA/RNA primer, F410

<400> SEQUENCE: 782
aattccttgt cacucagacc aacuc                                      25

<210> SEQ ID NO 783
<211> LENGTH: 24
<212> TYPE: DNA
<213> ORGANISM: Artificial Sequence
<220> FEATURE:
<223> OTHER INFORMATION: Synthetic DNA/RNA primer, F411

<400> SEQUENCE: 783
actaaggtga ugttcctgag augc                                       24

<210> SEQ ID NO 784
<211> LENGTH: 30
<212> TYPE: DNA
<213> ORGANISM: Artificial Sequence
<220> FEATURE:
<223> OTHER INFORMATION: Synthetic DNA/RNA primer, F412

<400> SEQUENCE: 784
actttccuta atgtcatttu cagcaaaact                                 30

<210> SEQ ID NO 785
<211> LENGTH: 30
<212> TYPE: DNA
<213> ORGANISM: Artificial Sequence
<220> FEATURE:
<223> OTHER INFORMATION: Synthetic DNA/RNA primer, F413

<400> SEQUENCE: 785
cagtctgaac uacttcttca tattctugct                                30

<210> SEQ ID NO 786
<211> LENGTH: 28
<212> TYPE: DNA
<213> ORGANISM: Artificial Sequence
<220> FEATURE:
<223> OTHER INFORMATION: Synthetic DNA/RNA primer, F414

<400> SEQUENCE: 786
ctagttctgc utgaatgttt tcaucact                                  28

<210> SEQ ID NO 787
<211> LENGTH: 28
<212> TYPE: DNA
<213> ORGANISM: Artificial Sequence
<220> FEATURE:
<223> OTHER INFORMATION: Synthetic DNA/RNA primer, F415

<400> SEQUENCE: 787
tggaatgttc tcauttccca tttctcut                                  28

<210> SEQ ID NO 788
<211> LENGTH: 24
<212> TYPE: DNA
<213> ORGANISM: Artificial Sequence
<220> FEATURE:
<223> OTHER INFORMATION: Synthetic DNA/RNA primer, F416

<400> SEQUENCE: 788
gtttcgtugc ctctgaacug agat                                      24

<210> SEQ ID NO 789
<211> LENGTH: 30
<212> TYPE: DNA
<213> ORGANISM: Artificial Sequence
<220> FEATURE:
<223> OTHER INFORMATION: Synthetic DNA/RNA primer, F417

<400> SEQUENCE: 789
ccttgatttt ctuccttttg ttcacatuca                                30

<210> SEQ ID NO 790
<211> LENGTH: 24
<212> TYPE: DNA
<213> ORGANISM: Artificial Sequence
<220> FEATURE:
<223> OTHER INFORMATION: Synthetic DNA/RNA primer, F418

<400> SEQUENCE: 790
tttctatgct ugtttcccga cugt                                      24

<210> SEQ ID NO 791
<211> LENGTH: 24
<212> TYPE: DNA
<213> ORGANISM: Artificial Sequence
<220> FEATURE:
<223> OTHER INFORMATION: Synthetic DNA/RNA primer, F419

<400> SEQUENCE: 791
gaugaaagct cctucaccac agaa                24

<210> SEQ ID NO 792
<211> LENGTH: 25
<212> TYPE: DNA
<213> ORGANISM: Artificial Sequence
<220> FEATURE:
<223> OTHER INFORMATION: Synthetic DNA/RNA primer, F420

<400> SEQUENCE: 792
cctagagtgc uaacttccag uaacg               25

<210> SEQ ID NO 793
<211> LENGTH: 27
<212> TYPE: DNA
<213> ORGANISM: Artificial Sequence
<220> FEATURE:
<223> OTHER INFORMATION: Synthetic DNA/RNA primer, F421

<400> SEQUENCE: 793
cttggaaggc uaggattgac aaatuct             27

<210> SEQ ID NO 794
<211> LENGTH: 25
<212> TYPE: DNA
<213> ORGANISM: Artificial Sequence
<220> FEATURE:
<223> OTHER INFORMATION: Synthetic DNA/RNA primer, F422

<400> SEQUENCE: 794
ttgttactct tcutggctcc agtug               25

<210> SEQ ID NO 795
<211> LENGTH: 27
<212> TYPE: DNA
<213> ORGANISM: Artificial Sequence
<220> FEATURE:
<223> OTHER INFORMATION: Synthetic DNA/RNA primer, F423

<400> SEQUENCE: 795
ttaggtgggc utagatttct acugact             27

<210> SEQ ID NO 796
<211> LENGTH: 26
<212> TYPE: DNA
<213> ORGANISM: Artificial Sequence
<220> FEATURE:
<223> OTHER INFORMATION: Synthetic DNA/RNA primer, F424

<400> SEQUENCE: 796
tgcttatagg tucagctttc gtttug              26

<210> SEQ ID NO 797
<211> LENGTH: 24
<212> TYPE: DNA
<213> ORGANISM: Artificial Sequence
<220> FEATURE:
<223> OTHER INFORMATION: Synthetic DNA/RNA primer, F425

<400> SEQUENCE: 797
ccactatgua agacaaaggc uggt                24

<210> SEQ ID NO 798
<211> LENGTH: 27

-continued

<212> TYPE: DNA
<213> ORGANISM: Artificial Sequence
<220> FEATURE:
<223> OTHER INFORMATION: Synthetic DNA/RNA primer, F426

<400> SEQUENCE: 798
tccgtttggt uagttccctg atttauc                                   27

<210> SEQ ID NO 799
<211> LENGTH: 28
<212> TYPE: DNA
<213> ORGANISM: Artificial Sequence
<220> FEATURE:
<223> OTHER INFORMATION: Synthetic DNA/RNA primer, F427

<400> SEQUENCE: 799
gtattatctg uggctcagta acaaaugc                                  28

<210> SEQ ID NO 800
<211> LENGTH: 24
<212> TYPE: DNA
<213> ORGANISM: Artificial Sequence
<220> FEATURE:
<223> OTHER INFORMATION: Synthetic DNA/RNA primer, F428

<400> SEQUENCE: 800
ttaaagcctc augaggatca cugg                                      24

<210> SEQ ID NO 801
<211> LENGTH: 26
<212> TYPE: DNA
<213> ORGANISM: Artificial Sequence
<220> FEATURE:
<223> OTHER INFORMATION: Synthetic DNA/RNA primer, F429

<400> SEQUENCE: 801
agttcatcac tuctggaaaa ccacuc                                    26

<210> SEQ ID NO 802
<211> LENGTH: 27
<212> TYPE: DNA
<213> ORGANISM: Artificial Sequence
<220> FEATURE:
<223> OTHER INFORMATION: Synthetic DNA/RNA primer, F430

<400> SEQUENCE: 802
gggatcagca tucagatcta cctttut                                   27

<210> SEQ ID NO 803
<211> LENGTH: 28
<212> TYPE: DNA
<213> ORGANISM: Artificial Sequence
<220> FEATURE:
<223> OTHER INFORMATION: Synthetic DNA/RNA primer, F431

<400> SEQUENCE: 803
ttcagccttt tcuacattca ttctguct                                  28

<210> SEQ ID NO 804
<211> LENGTH: 25
<212> TYPE: DNA
<213> ORGANISM: Artificial Sequence
<220> FEATURE:
<223> OTHER INFORMATION: Synthetic DNA/RNA primer, F432

<400> SEQUENCE: 804
tacccugaua cttttctgga ugcct       25

<210> SEQ ID NO 805
<211> LENGTH: 26
<212> TYPE: DNA
<213> ORGANISM: Artificial Sequence
<220> FEATURE:
<223> OTHER INFORMATION: Synthetic DNA/RNA primer, F433

<400> SEQUENCE: 805
gaatccaaac ugatttcatc ccuggt       26

<210> SEQ ID NO 806
<211> LENGTH: 27
<212> TYPE: DNA
<213> ORGANISM: Artificial Sequence
<220> FEATURE:
<223> OTHER INFORMATION: Synthetic DNA/RNA primer, F434

<400> SEQUENCE: 806
agctgccuac cacaaataca aattaug       27

<210> SEQ ID NO 807
<211> LENGTH: 26
<212> TYPE: DNA
<213> ORGANISM: Artificial Sequence
<220> FEATURE:
<223> OTHER INFORMATION: Synthetic DNA/RNA primer, F435

<400> SEQUENCE: 807
cagagttcuc acagttccaa ggtuag       26

<210> SEQ ID NO 808
<211> LENGTH: 31
<212> TYPE: DNA
<213> ORGANISM: Artificial Sequence
<220> FEATURE:
<223> OTHER INFORMATION: Synthetic DNA/RNA primer, F436

<400> SEQUENCE: 808
gaagaagaag aaaacaaaug gtttuaccaa g       31

<210> SEQ ID NO 809
<211> LENGTH: 28
<212> TYPE: DNA
<213> ORGANISM: Artificial Sequence
<220> FEATURE:
<223> OTHER INFORMATION: Synthetic DNA/RNA primer, F437

<400> SEQUENCE: 809
atcaccacgt cauagaaagt aattgugc       28

<210> SEQ ID NO 810
<211> LENGTH: 30
<212> TYPE: DNA
<213> ORGANISM: Artificial Sequence
<220> FEATURE:
<223> OTHER INFORMATION: Synthetic DNA/RNA primer, F438

<400> SEQUENCE: 810
cattcaaact tactugcaaa atatgtgguc       30

<210> SEQ ID NO 811
<211> LENGTH: 31
<212> TYPE: DNA
<213> ORGANISM: Artificial Sequence
<220> FEATURE:
<223> OTHER INFORMATION: Synthetic DNA/RNA primer, F439

<400> SEQUENCE: 811
gcataggaga taaucatagg aatcccaaau t                                          31

<210> SEQ ID NO 812
<211> LENGTH: 30
<212> TYPE: DNA
<213> ORGANISM: Artificial Sequence
<220> FEATURE:
<223> OTHER INFORMATION: Synthetic DNA/RNA primer, F440

<400> SEQUENCE: 812
agttgtagtt gtugaattca gtatcaucct                                            30

<210> SEQ ID NO 813
<211> LENGTH: 28
<212> TYPE: DNA
<213> ORGANISM: Artificial Sequence
<220> FEATURE:
<223> OTHER INFORMATION: Synthetic DNA/RNA primer, F441

<400> SEQUENCE: 813
tgtgcctttc cuaaggaatt tgctaaua                                              28

<210> SEQ ID NO 814
<211> LENGTH: 28
<212> TYPE: DNA
<213> ORGANISM: Artificial Sequence
<220> FEATURE:
<223> OTHER INFORMATION: Synthetic DNA/RNA primer, F442

<400> SEQUENCE: 814
aaaagataau ggaaagggau gacacagc                                              28

<210> SEQ ID NO 815
<211> LENGTH: 24
<212> TYPE: DNA
<213> ORGANISM: Artificial Sequence
<220> FEATURE:
<223> OTHER INFORMATION: Synthetic DNA/RNA primer, F443

<400> SEQUENCE: 815
ctgttaaggc ccagutagat ccuc                                                  24

<210> SEQ ID NO 816
<211> LENGTH: 28
<212> TYPE: DNA
<213> ORGANISM: Artificial Sequence
<220> FEATURE:
<223> OTHER INFORMATION: Synthetic DNA/RNA primer, F444

<400> SEQUENCE: 816
aggcagttcu agaagaatga aaactcut                                              28

<210> SEQ ID NO 817
<211> LENGTH: 24
<212> TYPE: DNA
<213> ORGANISM: Artificial Sequence
<220> FEATURE:
<223> OTHER INFORMATION: Synthetic DNA/RNA primer, F445

<400> SEQUENCE: 817
tgtacctagc autctgcctc auac                                                  24

```
<210> SEQ ID NO 818
<211> LENGTH: 25
<212> TYPE: DNA
<213> ORGANISM: Artificial Sequence
<220> FEATURE:
<223> OTHER INFORMATION: Synthetic DNA/RNA primer, F446

<400> SEQUENCE: 818 tagaccttttt ccuctgccct tauca                                  25

<210> SEQ ID NO 819
<211> LENGTH: 28
<212> TYPE: DNA
<213> ORGANISM: Artificial Sequence
<220> FEATURE:
<223> OTHER INFORMATION: Synthetic DNA/RNA primer, F447

<400> SEQUENCE: 819
cacatuatta cagtggaugg agaagaca                                28

<210> SEQ ID NO 820
<211> LENGTH: 26
<212> TYPE: DNA
<213> ORGANISM: Artificial Sequence
<220> FEATURE:
<223> OTHER INFORMATION: Synthetic DNA/RNA primer, F448

<400> SEQUENCE: 820
cttctttggg ugttttatgc ttggut                                  26

<210> SEQ ID NO 821
<211> LENGTH: 25
<212> TYPE: DNA
<213> ORGANISM: Artificial Sequence
<220> FEATURE:
<223> OTHER INFORMATION: Synthetic DNA/RNA primer, F449

<400> SEQUENCE: 821
gcagagctut atgaagcagu gaaga                                   25

<210> SEQ ID NO 822
<211> LENGTH: 28
<212> TYPE: DNA
<213> ORGANISM: Artificial Sequence
<220> FEATURE:
<223> OTHER INFORMATION: Synthetic DNA/RNA primer, F450

<400> SEQUENCE: 822
tcttaaatgg ucacagggtt attucagt                                28

<210> SEQ ID NO 823
<211> LENGTH: 27
<212> TYPE: DNA
<213> ORGANISM: Artificial Sequence
<220> FEATURE:
<223> OTHER INFORMATION: Synthetic DNA/RNA primer, F451

<400> SEQUENCE: 823
ttccattgca tcuttctcat ctttcuc                                 27

<210> SEQ ID NO 824
<211> LENGTH: 29
<212> TYPE: DNA
<213> ORGANISM: Artificial Sequence
<220> FEATURE:
<223> OTHER INFORMATION: Synthetic DNA/RNA primer, F452
```

<400> SEQUENCE: 824
ttcactucag caaatttta gauccagac                                29

<210> SEQ ID NO 825
<211> LENGTH: 23
<212> TYPE: DNA
<213> ORGANISM: Artificial Sequence
<220> FEATURE:
<223> OTHER INFORMATION: Synthetic DNA/RNA primer, F453

<400> SEQUENCE: 825
tgccccttuc gtctatttgu cag                                    23

<210> SEQ ID NO 826
<211> LENGTH: 28
<212> TYPE: DNA
<213> ORGANISM: Artificial Sequence
<220> FEATURE:
<223> OTHER INFORMATION: Synthetic DNA/RNA primer, F454

<400> SEQUENCE: 826
ggagattttt ctgugttttc tgctaguc                               28

<210> SEQ ID NO 827
<211> LENGTH: 27
<212> TYPE: DNA
<213> ORGANISM: Artificial Sequence
<220> FEATURE:
<223> OTHER INFORMATION: Synthetic DNA/RNA primer, F455

<400> SEQUENCE: 827
tgacauactt tgcaaugaag cagaaaa                                27

<210> SEQ ID NO 828
<211> LENGTH: 27
<212> TYPE: DNA
<213> ORGANISM: Artificial Sequence
<220> FEATURE:
<223> OTHER INFORMATION: Synthetic DNA/RNA primer, F456

<400> SEQUENCE: 828
ggatcctgat augtcttggt caagtuc                                27

<210> SEQ ID NO 829
<211> LENGTH: 24
<212> TYPE: RNA
<213> ORGANISM: Artificial Sequence
<220> FEATURE:
<223> OTHER INFORMATION: Synthetic Primer, F457

<400> SEQUENCE: 829
ggcaccaaau acgaaacacc caua                                   24

<210> SEQ ID NO 830
<211> LENGTH: 28
<212> TYPE: DNA
<213> ORGANISM: Artificial Sequence
<220> FEATURE:
<223> OTHER INFORMATION: Synthetic DNA/RNA primer, F458

<400> SEQUENCE: 830
atatctgtca gtgaauccac taggacug                               28

<210> SEQ ID NO 831

```
<211> LENGTH: 28
<212> TYPE: DNA
<213> ORGANISM: Artificial Sequence
<220> FEATURE:
<223> OTHER INFORMATION: Synthetic DNA/RNA primer, F459

<400> SEQUENCE: 831
tgaagaagca ucugaaactg tatttcct                                              28

<210> SEQ ID NO 832
<211> LENGTH: 31
<212> TYPE: DNA
<213> ORGANISM: Artificial Sequence
<220> FEATURE:
<223> OTHER INFORMATION: Synthetic DNA/RNA primer, F460

<400> SEQUENCE: 832
ggactactac tataugtgca ttgagagttu t                                          31

<210> SEQ ID NO 833
<211> LENGTH: 32
<212> TYPE: DNA
<213> ORGANISM: Artificial Sequence
<220> FEATURE:
<223> OTHER INFORMATION: Synthetic DNA/RNA primer, F461

<400> SEQUENCE: 833
tggcttataa aatatuaatg tgcttctgtt ut                                         32

<210> SEQ ID NO 834
<211> LENGTH: 28
<212> TYPE: DNA
<213> ORGANISM: Artificial Sequence
<220> FEATURE:
<223> OTHER INFORMATION: Synthetic DNA/RNA primer, F462

<400> SEQUENCE: 834
ggtaaaaaug cctattggau ccaaagag                                              28

<210> SEQ ID NO 835
<211> LENGTH: 30
<212> TYPE: DNA
<213> ORGANISM: Artificial Sequence
<220> FEATURE:
<223> OTHER INFORMATION: Synthetic DNA/RNA primer, F463

<400> SEQUENCE: 835
aatctacaaa aaguaagaac uagcaagact                                            30

<210> SEQ ID NO 836
<211> LENGTH: 28
<212> TYPE: DNA
<213> ORGANISM: Artificial Sequence
<220> FEATURE:
<223> OTHER INFORMATION: Synthetic DNA/RNA primer, F464

<400> SEQUENCE: 836
aagtgacaaa atcuccaagg aagttgua                                              28

<210> SEQ ID NO 837
<211> LENGTH: 26
<212> TYPE: DNA
<213> ORGANISM: Artificial Sequence
<220> FEATURE:
<223> OTHER INFORMATION: Synthetic DNA/RNA primer, F465

<400> SEQUENCE: 837
```
gaattcttug ccacgtattt cuagcc							26

<210> SEQ ID NO 838
<211> LENGTH: 27
<212> TYPE: DNA
<213> ORGANISM: Artificial Sequence
<220> FEATURE:
<223> OTHER INFORMATION: Synthetic DNA/RNA primer, F466

<400> SEQUENCE: 838
ggcttcttca uttcagggta ucaaaaa							27

<210> SEQ ID NO 839
<211> LENGTH: 28
<212> TYPE: DNA
<213> ORGANISM: Artificial Sequence
<220> FEATURE:
<223> OTHER INFORMATION: Synthetic DNA/RNA primer, F467

<400> SEQUENCE: 839
aatacauact gtttgcucac agaaggag							28

<210> SEQ ID NO 840
<211> LENGTH: 31
<212> TYPE: DNA
<213> ORGANISM: Artificial Sequence
<220> FEATURE:
<223> OTHER INFORMATION: Synthetic DNA/RNA primer, F468

<400> SEQUENCE: 840
accgaaagac caaaaaucag aactaatuaa c							31

<210> SEQ ID NO 841
<211> LENGTH: 27
<212> TYPE: DNA
<213> ORGANISM: Artificial Sequence
<220> FEATURE:
<223> OTHER INFORMATION: Synthetic DNA/RNA primer, F469

<400> SEQUENCE: 841
tcacagaaug attcugaaga accaact							27

<210> SEQ ID NO 842
<211> LENGTH: 25
<212> TYPE: DNA
<213> ORGANISM: Artificial Sequence
<220> FEATURE:
<223> OTHER INFORMATION: Synthetic DNA/RNA primer, F470

<400> SEQUENCE: 842 attacccccag aagcugattc tcugt							25

<210> SEQ ID NO 843
<211> LENGTH: 28
<212> TYPE: DNA
<213> ORGANISM: Artificial Sequence
<220> FEATURE:
<223> OTHER INFORMATION: Synthetic DNA/RNA primer, F471

<400> SEQUENCE: 843
tatatgatca tgaaaaugcc agcacuct							28

<210> SEQ ID NO 844
<211> LENGTH: 28
<212> TYPE: DNA

```
<213> ORGANISM: Artificial Sequence
<220> FEATURE:
<223> OTHER INFORMATION: Synthetic DNA/RNA primer, F472

<400> SEQUENCE: 844
ttcccatgga aagaaucaa gatgtaug                                          28

<210> SEQ ID NO 845
<211> LENGTH: 27
<212> TYPE: DNA
<213> ORGANISM: Artificial Sequence
<220> FEATURE:
<223> OTHER INFORMATION: Synthetic DNA/RNA primer, F473

<400> SEQUENCE: 845
actgtcaatc cagacuctga agaacut                                          27

<210> SEQ ID NO 846
<211> LENGTH: 25
<212> TYPE: DNA
<213> ORGANISM: Artificial Sequence
<220> FEATURE:
<223> OTHER INFORMATION: Synthetic DNA/RNA primer, F474

<400> SEQUENCE: 846
caggugauaa acaagcaacc caagt                                            25

<210> SEQ ID NO 847
<211> LENGTH: 29
<212> TYPE: DNA
<213> ORGANISM: Artificial Sequence
<220> FEATURE:
<223> OTHER INFORMATION: Synthetic DNA/RNA primer, F475

<400> SEQUENCE: 847
tggcattaga uaatcaaaag aaacugagc                                        29

<210> SEQ ID NO 848
<211> LENGTH: 30
<212> TYPE: DNA
<213> ORGANISM: Artificial Sequence
<220> FEATURE:
<223> OTHER INFORMATION: Synthetic DNA/RNA primer, F476

<400> SEQUENCE: 848
gaatcaggaa gucagtttga atttacucag                                       30

<210> SEQ ID NO 849
<211> LENGTH: 28
<212> TYPE: DNA
<213> ORGANISM: Artificial Sequence
<220> FEATURE:
<223> OTHER INFORMATION: Synthetic DNA/RNA primer, F477

<400> SEQUENCE: 849
gcctgtugaa aaatgactgu aacaaaag                                         28

<210> SEQ ID NO 850
<211> LENGTH: 28
<212> TYPE: DNA
<213> ORGANISM: Artificial Sequence
<220> FEATURE:
<223> OTHER INFORMATION: Synthetic DNA/RNA primer, F478

<400> SEQUENCE: 850
tgaagataac aaauatactg cugccagt                                         28
```

<210> SEQ ID NO 851
<211> LENGTH: 28
<212> TYPE: DNA
<213> ORGANISM: Artificial Sequence
<220> FEATURE:
<223> OTHER INFORMATION: Synthetic DNA/RNA primer, F479

<400> SEQUENCE: 851
aggagggaaa cacucagatu aaagaaga                                         28

<210> SEQ ID NO 852
<211> LENGTH: 27
<212> TYPE: DNA
<213> ORGANISM: Artificial Sequence
<220> FEATURE:
<223> OTHER INFORMATION: Synthetic DNA/RNA primer, F480

<400> SEQUENCE: 852
tttcagactg caagugggaa aaataut                                          27

<210> SEQ ID NO 853
<211> LENGTH: 30
<212> TYPE: DNA
<213> ORGANISM: Artificial Sequence
<220> FEATURE:
<223> OTHER INFORMATION: Synthetic DNA/RNA primer, F481

<400> SEQUENCE: 853
tcttcttaca acuccctata cattctcaut                                       30

<210> SEQ ID NO 854
<211> LENGTH: 27
<212> TYPE: DNA
<213> ORGANISM: Artificial Sequence
<220> FEATURE:
<223> OTHER INFORMATION: Synthetic DNA/RNA primer, F482

<400> SEQUENCE: 854
ccagttggta cuggaaatca actagug                                          27

<210> SEQ ID NO 855
<211> LENGTH: 28
<212> TYPE: DNA
<213> ORGANISM: Artificial Sequence
<220> FEATURE:
<223> OTHER INFORMATION: Synthetic DNA/RNA primer, F483

<400> SEQUENCE: 855
aaaagagcaa gguactagtg aaaucacc                                         28

<210> SEQ ID NO 856
<211> LENGTH: 28
<212> TYPE: DNA
<213> ORGANISM: Artificial Sequence
<220> FEATURE:
<223> OTHER INFORMATION: Synthetic DNA/RNA primer, F484

<400> SEQUENCE: 856
aaaaaccttg ttuctattga gactgugg                                         28

<210> SEQ ID NO 857
<211> LENGTH: 28
<212> TYPE: DNA
<213> ORGANISM: Artificial Sequence
<220> FEATURE:

```
<223> OTHER INFORMATION: Synthetic DNA/RNA primer, F485

<400> SEQUENCE: 857
aattcagcct uagcttttta cacaagut                                28

<210> SEQ ID NO 858
<211> LENGTH: 28
<212> TYPE: DNA
<213> ORGANISM: Artificial Sequence
<220> FEATURE:
<223> OTHER INFORMATION: Synthetic DNA/RNA primer, F486

<400> SEQUENCE: 858
tgacaaaaau catctcuccg aaaaacaa                                28

<210> SEQ ID NO 859
<211> LENGTH: 25
<212> TYPE: DNA
<213> ORGANISM: Artificial Sequence
<220> FEATURE:
<223> OTHER INFORMATION: Synthetic DNA/RNA primer, F487

<400> SEQUENCE: 859
aataattttg agguagggcc accug                                   25

<210> SEQ ID NO 860
<211> LENGTH: 32
<212> TYPE: DNA
<213> ORGANISM: Artificial Sequence
<220> FEATURE:
<223> OTHER INFORMATION: Synthetic DNA/RNA primer, F488

<400> SEQUENCE: 860
tcataactct cuagataatg atgaatguag ca                           32

<210> SEQ ID NO 861
<211> LENGTH: 28
<212> TYPE: DNA
<213> ORGANISM: Artificial Sequence
<220> FEATURE:
<223> OTHER INFORMATION: Synthetic DNA/RNA primer, F489

<400> SEQUENCE: 861
gtatagggaa gcutcataag tcagtcuc                                28

<210> SEQ ID NO 862
<211> LENGTH: 28
<212> TYPE: DNA
<213> ORGANISM: Artificial Sequence
<220> FEATURE:
<223> OTHER INFORMATION: Synthetic DNA/RNA primer, F490

<400> SEQUENCE: 862
agaagatagu accaagcaag tctttucc                                28

<210> SEQ ID NO 863
<211> LENGTH: 25
<212> TYPE: DNA
<213> ORGANISM: Artificial Sequence
<220> FEATURE:
<223> OTHER INFORMATION: Synthetic DNA/RNA primer, F491

<400> SEQUENCE: 863
tagtacagca aguggaaagc aagut                                   25
```

<210> SEQ ID NO 864
<211> LENGTH: 27
<212> TYPE: DNA
<213> ORGANISM: Artificial Sequence
<220> FEATURE:
<223> OTHER INFORMATION: Synthetic DNA/RNA primer, F492

<400> SEQUENCE: 864
caggcttcac cuaaaaacgt aaaaaug							27

<210> SEQ ID NO 865
<211> LENGTH: 32
<212> TYPE: DNA
<213> ORGANISM: Artificial Sequence
<220> FEATURE:
<223> OTHER INFORMATION: Synthetic DNA/RNA primer, F493

<400> SEQUENCE: 865
atgaaataut tcttttuagg agaaccctca at							32

<210> SEQ ID NO 866
<211> LENGTH: 27
<212> TYPE: DNA
<213> ORGANISM: Artificial Sequence
<220> FEATURE:
<223> OTHER INFORMATION: Synthetic DNA/RNA primer, F494

<400> SEQUENCE: 866
atatattutc tccccatugc agcacaa							27

<210> SEQ ID NO 867
<211> LENGTH: 28
<212> TYPE: DNA
<213> ORGANISM: Artificial Sequence
<220> FEATURE:
<223> OTHER INFORMATION: Synthetic DNA/RNA primer, F495

<400> SEQUENCE: 867
aggacatcca utttatcaag tttcugct							28

<210> SEQ ID NO 868
<211> LENGTH: 33
<212> TYPE: DNA
<213> ORGANISM: Artificial Sequence
<220> FEATURE:
<223> OTHER INFORMATION: Synthetic DNA/RNA primer, F496

<400> SEQUENCE: 868
tggctctgat gauagtaaaa ataagattaa uga							33

<210> SEQ ID NO 869
<211> LENGTH: 28
<212> TYPE: DNA
<213> ORGANISM: Artificial Sequence
<220> FEATURE:
<223> OTHER INFORMATION: Synthetic DNA/RNA primer, F497

<400> SEQUENCE: 869
gctgtatacg uatggcgttt cuaaacat							28

<210> SEQ ID NO 870
<211> LENGTH: 25
<212> TYPE: DNA
<213> ORGANISM: Artificial Sequence
<220> FEATURE:
<223> OTHER INFORMATION: Synthetic DNA/RNA primer, R366

<400> SEQUENCE: 870
tcccgtggcu ggtaaatctg aaaua    25

<210> SEQ ID NO 871
<211> LENGTH: 27
<212> TYPE: DNA
<213> ORGANISM: Artificial Sequence
<220> FEATURE:
<223> OTHER INFORMATION: Synthetic DNA/RNA primer, R367

<400> SEQUENCE: 871
ccaaaacatg aaugttctca acaagug    27

<210> SEQ ID NO 872
<211> LENGTH: 25
<212> TYPE: DNA
<213> ORGANISM: Artificial Sequence
<220> FEATURE:
<223> OTHER INFORMATION: Synthetic DNA/RNA primer, R368

<400> SEQUENCE: 872
attcctgcac uaatgtgttc atuct    25

<210> SEQ ID NO 873
<211> LENGTH: 23
<212> TYPE: RNA
<213> ORGANISM: Artificial Sequence
<220> FEATURE:
<223> OTHER INFORMATION: Synthetic Primer, R369

<400> SEQUENCE: 873
guccaaagcg agcaagagaa ucc    23

<210> SEQ ID NO 874
<211> LENGTH: 26
<212> TYPE: DNA
<213> ORGANISM: Artificial Sequence
<220> FEATURE:
<223> OTHER INFORMATION: Synthetic DNA/RNA primer, R370

<400> SEQUENCE: 874
agttccagua gtcctacttu gacact    26

<210> SEQ ID NO 875
<211> LENGTH: 23
<212> TYPE: DNA
<213> ORGANISM: Artificial Sequence
<220> FEATURE:
<223> OTHER INFORMATION: Synthetic DNA/RNA primer, R371

<400> SEQUENCE: 875
agagcacgtu cttctgctgt aug    23

<210> SEQ ID NO 876
<211> LENGTH: 33
<212> TYPE: DNA
<213> ORGANISM: Artificial Sequence
<220> FEATURE:
<223> OTHER INFORMATION: Synthetic DNA/RNA primer, R372

<400> SEQUENCE: 876
agttgaatat ctgttuttca acaagtacat tut    33

<210> SEQ ID NO 877
<211> LENGTH: 21

```
<212> TYPE: DNA
<213> ORGANISM: Artificial Sequence
<220> FEATURE:
<223> OTHER INFORMATION: Synthetic DNA/RNA primer, R373

<400> SEQUENCE: 877
gcctggccug aatgccuaa a                                              21

<210> SEQ ID NO 878
<211> LENGTH: 30
<212> TYPE: DNA
<213> ORGANISM: Artificial Sequence
<220> FEATURE:
<223> OTHER INFORMATION: Synthetic DNA/RNA primer, R374

<400> SEQUENCE: 878
caatttcaac acaagcuaaa ctaguaggat                                    30

<210> SEQ ID NO 879
<211> LENGTH: 26
<212> TYPE: DNA
<213> ORGANISM: Artificial Sequence
<220> FEATURE:
<223> OTHER INFORMATION: Synthetic DNA/RNA primer, R375

<400> SEQUENCE: 879
tcaacaaaag ugccagtagu catttc                                        26

<210> SEQ ID NO 880
<211> LENGTH: 24
<212> TYPE: DNA
<213> ORGANISM: Artificial Sequence
<220> FEATURE:
<223> OTHER INFORMATION: Synthetic DNA/RNA primer, R376

<400> SEQUENCE: 880
ctgttttuag caaaagcguc caga                                          24

<210> SEQ ID NO 881
<211> LENGTH: 22
<212> TYPE: DNA
<213> ORGANISM: Artificial Sequence
<220> FEATURE:
<223> OTHER INFORMATION: Synthetic DNA/RNA primer, R377

<400> SEQUENCE: 881
agtcagcccu tgctcttuga at                                            22

<210> SEQ ID NO 882
<211> LENGTH: 27
<212> TYPE: DNA
<213> ORGANISM: Artificial Sequence
<220> FEATURE:
<223> OTHER INFORMATION: Synthetic DNA/RNA primer, R378

<400> SEQUENCE: 882
ttggccauac aaagtgauaa aggactt                                       27

<210> SEQ ID NO 883
<211> LENGTH: 22
<212> TYPE: DNA
<213> ORGANISM: Artificial Sequence
<220> FEATURE:
<223> OTHER INFORMATION: Synthetic DNA/RNA primer, R379

<400> SEQUENCE: 883
```
tttgcagggu gaagagctag uc                                              22

<210> SEQ ID NO 884
<211> LENGTH: 25
<212> TYPE: DNA
<213> ORGANISM: Artificial Sequence
<220> FEATURE:
<223> OTHER INFORMATION: Synthetic DNA/RNA primer, R380

<400> SEQUENCE: 884
tgtacaaaug ggactaacag gugga                                           25

<210> SEQ ID NO 885
<211> LENGTH: 30
<212> TYPE: DNA
<213> ORGANISM: Artificial Sequence
<220> FEATURE:
<223> OTHER INFORMATION: Synthetic DNA/RNA primer, R381

<400> SEQUENCE: 885
agcataccaa gtcuactgaa taaacactut                                      30

<210> SEQ ID NO 886
<211> LENGTH: 25
<212> TYPE: DNA
<213> ORGANISM: Artificial Sequence
<220> FEATURE:
<223> OTHER INFORMATION: Synthetic DNA/RNA primer, R382

<400> SEQUENCE: 886
cctggagtcg autgattaga gccua                                           25

<210> SEQ ID NO 887
<211> LENGTH: 28
<212> TYPE: DNA
<213> ORGANISM: Artificial Sequence
<220> FEATURE:
<223> OTHER INFORMATION: Synthetic DNA/RNA primer, R383

<400> SEQUENCE: 887
aatgtgttat guggctccat tatuagct                                        28

<210> SEQ ID NO 888
<211> LENGTH: 29
<212> TYPE: DNA
<213> ORGANISM: Artificial Sequence
<220> FEATURE:
<223> OTHER INFORMATION: Synthetic DNA/RNA primer, R384

<400> SEQUENCE: 888
gcatttttac cuacgatatt cctccaaug                                       29

<210> SEQ ID NO 889
<211> LENGTH: 28
<212> TYPE: DNA
<213> ORGANISM: Artificial Sequence
<220> FEATURE:
<223> OTHER INFORMATION: Synthetic DNA/RNA primer, R385

<400> SEQUENCE: 889
accagtaaaa auaaagaacc aggagugg                                        28

<210> SEQ ID NO 890
<211> LENGTH: 28
<212> TYPE: DNA
<213> ORGANISM: Artificial Sequence

```
<220> FEATURE:
<223> OTHER INFORMATION: Synthetic DNA/RNA primer, R386

<400> SEQUENCE: 890
ttatagaggt ttuctactgt tgcugcat                                  28

<210> SEQ ID NO 891
<211> LENGTH: 27
<212> TYPE: DNA
<213> ORGANISM: Artificial Sequence
<220> FEATURE:
<223> OTHER INFORMATION: Synthetic DNA/RNA primer, R387

<400> SEQUENCE: 891
gcagttgtga gautatcttt tcauggc                                   27

<210> SEQ ID NO 892
<211> LENGTH: 24
<212> TYPE: DNA
<213> ORGANISM: Artificial Sequence
<220> FEATURE:
<223> OTHER INFORMATION: Synthetic DNA/RNA primer, R388

<400> SEQUENCE: 892
catcattcac ccutggcaca guaa                                      24

<210> SEQ ID NO 893
<211> LENGTH: 27
<212> TYPE: DNA
<213> ORGANISM: Artificial Sequence
<220> FEATURE:
<223> OTHER INFORMATION: Synthetic DNA/RNA primer, R389

<400> SEQUENCE: 893
aaauattttc taggaatugc gggagga                                   27

<210> SEQ ID NO 894
<211> LENGTH: 26
<212> TYPE: DNA
<213> ORGANISM: Artificial Sequence
<220> FEATURE:
<223> OTHER INFORMATION: Synthetic DNA/RNA primer, R390

<400> SEQUENCE: 894
cagguaaucg gctctaaaga aacatg                                    26

<210> SEQ ID NO 895
<211> LENGTH: 22
<212> TYPE: DNA
<213> ORGANISM: Artificial Sequence
<220> FEATURE:
<223> OTHER INFORMATION: Synthetic DNA/RNA primer, R391

<400> SEQUENCE: 895
cagagagatu cgaggcagag ug                                        22

<210> SEQ ID NO 896
<211> LENGTH: 31
<212> TYPE: DNA
<213> ORGANISM: Artificial Sequence
<220> FEATURE:
<223> OTHER INFORMATION: Synthetic DNA/RNA primer, R392

<400> SEQUENCE: 896
agtaguggat ttugcttctc tgatataaac t                              31
```

<210> SEQ ID NO 897
<211> LENGTH: 32
<212> TYPE: DNA
<213> ORGANISM: Artificial Sequence
<220> FEATURE:
<223> OTHER INFORMATION: Synthetic DNA/RNA primer, R393

<400> SEQUENCE: 897
gctctuagcc aaaatatuag cataaaaatc ag                           32

<210> SEQ ID NO 898
<211> LENGTH: 31
<212> TYPE: DNA
<213> ORGANISM: Artificial Sequence
<220> FEATURE:
<223> OTHER INFORMATION: Synthetic DNA/RNA primer, R394

<400> SEQUENCE: 898
aaaaagcatu gtttttaatc auacctgact t                            31

<210> SEQ ID NO 899
<211> LENGTH: 27
<212> TYPE: DNA
<213> ORGANISM: Artificial Sequence
<220> FEATURE:
<223> OTHER INFORMATION: Synthetic DNA/RNA primer, R395

<400> SEQUENCE: 899
ggtacagaut tgtaaatcuc agggcaa                                 27

<210> SEQ ID NO 900
<211> LENGTH: 20
<212> TYPE: RNA
<213> ORGANISM: Artificial Sequence
<220> FEATURE:
<223> OTHER INFORMATION: Synthetic Primer, R396

<400> SEQUENCE: 900
gagaucacgg gugacagagc                                         20

<210> SEQ ID NO 901
<211> LENGTH: 23
<212> TYPE: DNA
<213> ORGANISM: Artificial Sequence
<220> FEATURE:
<223> OTHER INFORMATION: Synthetic DNA/RNA primer, R397

<400> SEQUENCE: 901
acctacctga uaccccagau ccc                                     23

<210> SEQ ID NO 902
<211> LENGTH: 27
<212> TYPE: DNA
<213> ORGANISM: Artificial Sequence
<220> FEATURE:
<223> OTHER INFORMATION: Synthetic DNA/RNA primer, R398

<400> SEQUENCE: 902
tccagattga ucttgggagt guaaaaa                                 27

<210> SEQ ID NO 903
<211> LENGTH: 28
<212> TYPE: DNA
<213> ORGANISM: Artificial Sequence
<220> FEATURE:
<223> OTHER INFORMATION: Synthetic DNA/RNA primer, R399

<400> SEQUENCE: 903
gtgtgctaga gguaactcat gataaugg                28

<210> SEQ ID NO 904
<211> LENGTH: 26
<212> TYPE: DNA
<213> ORGANISM: Artificial Sequence
<220> FEATURE:
<223> OTHER INFORMATION: Synthetic DNA/RNA primer, R400

<400> SEQUENCE: 904
gaaaggguca acaaaagaat guccat                  26

<210> SEQ ID NO 905
<211> LENGTH: 26
<212> TYPE: DNA
<213> ORGANISM: Artificial Sequence
<220> FEATURE:
<223> OTHER INFORMATION: Synthetic DNA/RNA primer, R401

<400> SEQUENCE: 905
gaaagttccc caautgaaag tugcag                  26

<210> SEQ ID NO 906
<211> LENGTH: 30
<212> TYPE: DNA
<213> ORGANISM: Artificial Sequence
<220> FEATURE:
<223> OTHER INFORMATION: Synthetic DNA/RNA primer, R402

<400> SEQUENCE: 906
aactttgtaa tucaacattc atcgttgugt              30

<210> SEQ ID NO 907
<211> LENGTH: 27
<212> TYPE: DNA
<213> ORGANISM: Artificial Sequence
<220> FEATURE:
<223> OTHER INFORMATION: Synthetic DNA/RNA primer, R403

<400> SEQUENCE: 907
tagatgatag guggtacatg cacagut                 27

<210> SEQ ID NO 908
<211> LENGTH: 29
<212> TYPE: DNA
<213> ORGANISM: Artificial Sequence
<220> FEATURE:
<223> OTHER INFORMATION: Synthetic DNA/RNA primer, R404

<400> SEQUENCE: 908
accugaatta tcactaucag aacaaagca               29

<210> SEQ ID NO 909
<211> LENGTH: 21
<212> TYPE: DNA
<213> ORGANISM: Artificial Sequence
<220> FEATURE:
<223> OTHER INFORMATION: Synthetic DNA/RNA primer, R405

<400> SEQUENCE: 909
gaacaguacc cgttccctug a                       21

<210> SEQ ID NO 910

<211> LENGTH: 22
<212> TYPE: DNA
<213> ORGANISM: Artificial Sequence
<220> FEATURE:
<223> OTHER INFORMATION: Synthetic DNA/RNA primer, R406

<400> SEQUENCE: 910
cttgaggacc ugcgaaaucc ag                                          22

<210> SEQ ID NO 911
<211> LENGTH: 30
<212> TYPE: DNA
<213> ORGANISM: Artificial Sequence
<220> FEATURE:
<223> OTHER INFORMATION: Synthetic DNA/RNA primer, R407

<400> SEQUENCE: 911
tggaaagctt cucaaagtat ttcatttuct                                  30

<210> SEQ ID NO 912
<211> LENGTH: 27
<212> TYPE: DNA
<213> ORGANISM: Artificial Sequence
<220> FEATURE:
<223> OTHER INFORMATION: Synthetic DNA/RNA primer, R408

<400> SEQUENCE: 912
gcagcgttta uagtctgctt ttacauc                                     27

<210> SEQ ID NO 913
<211> LENGTH: 26
<212> TYPE: DNA
<213> ORGANISM: Artificial Sequence
<220> FEATURE:
<223> OTHER INFORMATION: Synthetic DNA/RNA primer, R409

<400> SEQUENCE: 913
aacgggctug gaagaaaata aucaag                                      26

<210> SEQ ID NO 914
<211> LENGTH: 25
<212> TYPE: DNA
<213> ORGANISM: Artificial Sequence
<220> FEATURE:
<223> OTHER INFORMATION: Synthetic DNA/RNA primer, R410

<400> SEQUENCE: 914
tctgctagcu tgttttctuc acagt                                       25

<210> SEQ ID NO 915
<211> LENGTH: 30
<212> TYPE: DNA
<213> ORGANISM: Artificial Sequence
<220> FEATURE:
<223> OTHER INFORMATION: Synthetic DNA/RNA primer, R411

<400> SEQUENCE: 915
aacaatatac ctuctcagtc tacuaggcat                                  30

<210> SEQ ID NO 916
<211> LENGTH: 28
<212> TYPE: DNA
<213> ORGANISM: Artificial Sequence
<220> FEATURE:
<223> OTHER INFORMATION: Synthetic DNA/RNA primer, R412

<400> SEQUENCE: 916
cagataactu agaacagcct augggaag                                              28

<210> SEQ ID NO 917
<211> LENGTH: 27
<212> TYPE: DNA
<213> ORGANISM: Artificial Sequence
<220> FEATURE:
<223> OTHER INFORMATION: Synthetic DNA/RNA primer, R413

<400> SEQUENCE: 917
ggccaaaatu gaatgctatg ctuagat                                               27

<210> SEQ ID NO 918
<211> LENGTH: 30
<212> TYPE: DNA
<213> ORGANISM: Artificial Sequence
<220> FEATURE:
<223> OTHER INFORMATION: Synthetic DNA/RNA primer, R414

<400> SEQUENCE: 918
agcacaatua gccgtaataa catuagagaa                                            30

<210> SEQ ID NO 919
<211> LENGTH: 28
<212> TYPE: DNA
<213> ORGANISM: Artificial Sequence
<220> FEATURE:
<223> OTHER INFORMATION: Synthetic DNA/RNA primer, R415

<400> SEQUENCE: 919
tggactcatt acuccaaata aacaugga                                              28

<210> SEQ ID NO 920
<211> LENGTH: 28
<212> TYPE: DNA
<213> ORGANISM: Artificial Sequence
<220> FEATURE:
<223> OTHER INFORMATION: Synthetic DNA/RNA primer, R416

<400> SEQUENCE: 920
gtctaatatc aagccugtac agacagut                                              28

<210> SEQ ID NO 921
<211> LENGTH: 27
<212> TYPE: DNA
<213> ORGANISM: Artificial Sequence
<220> FEATURE:
<223> OTHER INFORMATION: Synthetic DNA/RNA primer, R417

<400> SEQUENCE: 921
tgcagaatac autcaaggtt ucaaagc                                               27

<210> SEQ ID NO 922
<211> LENGTH: 25
<212> TYPE: DNA
<213> ORGANISM: Artificial Sequence
<220> FEATURE:
<223> OTHER INFORMATION: Synthetic DNA/RNA primer, R418

<400> SEQUENCE: 922
aataaatgtg ugagtcagtg ugcag                                                 25

<210> SEQ ID NO 923
<211> LENGTH: 22
<212> TYPE: DNA

```
<213> ORGANISM: Artificial Sequence
<220> FEATURE:
<223> OTHER INFORMATION: Synthetic DNA/RNA primer, R419

<400> SEQUENCE: 923
aagccttcau ccggagagtg ua                                           22

<210> SEQ ID NO 924
<211> LENGTH: 25
<212> TYPE: DNA
<213> ORGANISM: Artificial Sequence
<220> FEATURE:
<223> OTHER INFORMATION: Synthetic DNA/RNA primer, R420

<400> SEQUENCE: 924
taatgcugaa gaccccaaag atcuc                                        25

<210> SEQ ID NO 925
<211> LENGTH: 27
<212> TYPE: RNA
<213> ORGANISM: Artificial Sequence
<220> FEATURE:
<223> OTHER INFORMATION: Synthetic Primer, R421

<400> SEQUENCE: 925
gccaaaugaa cagacaagua aaagaca                                      27

<210> SEQ ID NO 926
<211> LENGTH: 28
<212> TYPE: DNA
<213> ORGANISM: Artificial Sequence
<220> FEATURE:
<223> OTHER INFORMATION: Synthetic DNA/RNA primer, R422

<400> SEQUENCE: 926
gcaaattgat agutgttcta gcagugaa                                     28

<210> SEQ ID NO 927
<211> LENGTH: 28
<212> TYPE: DNA
<213> ORGANISM: Artificial Sequence
<220> FEATURE:
<223> OTHER INFORMATION: Synthetic DNA/RNA primer, R423

<400> SEQUENCE: 927
cagcagtaua agcaatatgg aacucgaa                                     28

<210> SEQ ID NO 928
<211> LENGTH: 26
<212> TYPE: DNA
<213> ORGANISM: Artificial Sequence
<220> FEATURE:
<223> OTHER INFORMATION: Synthetic DNA/RNA primer, R424

<400> SEQUENCE: 928
ggagcagaat ggucaagtga tgaaua                                       26

<210> SEQ ID NO 929
<211> LENGTH: 32
<212> TYPE: DNA
<213> ORGANISM: Artificial Sequence
<220> FEATURE:
<223> OTHER INFORMATION: Synthetic DNA/RNA primer, R425

<400> SEQUENCE: 929
ttttataact agatttucct tctctccatu cc                                32
```

<210> SEQ ID NO 930
<211> LENGTH: 24
<212> TYPE: DNA
<213> ORGANISM: Artificial Sequence
<220> FEATURE:
<223> OTHER INFORMATION: Synthetic DNA/RNA primer, R426

<400> SEQUENCE: 930
agagcgtccc cucacaaata aaut                                          24

<210> SEQ ID NO 931
<211> LENGTH: 28
<212> TYPE: DNA
<213> ORGANISM: Artificial Sequence
<220> FEATURE:
<223> OTHER INFORMATION: Synthetic DNA/RNA primer, R427

<400> SEQUENCE: 931
gaaagagttc acuccaaatc aguagaga                                      28

<210> SEQ ID NO 932
<211> LENGTH: 24
<212> TYPE: DNA
<213> ORGANISM: Artificial Sequence
<220> FEATURE:
<223> OTHER INFORMATION: Synthetic DNA/RNA primer, R428

<400> SEQUENCE: 932
ggttctgaug actcacatga uggg                                          24

<210> SEQ ID NO 933
<211> LENGTH: 28
<212> TYPE: DNA
<213> ORGANISM: Artificial Sequence
<220> FEATURE:
<223> OTHER INFORMATION: Synthetic DNA/RNA primer, R429

<400> SEQUENCE: 933
ccctgtguga gagaaaagaa tggaauaa                                      28

<210> SEQ ID NO 934
<211> LENGTH: 28
<212> TYPE: DNA
<213> ORGANISM: Artificial Sequence
<220> FEATURE:
<223> OTHER INFORMATION: Synthetic DNA/RNA primer, R430

<400> SEQUENCE: 934
aggcugaatt ctgtaauaaa agcaaaca                                      28

<210> SEQ ID NO 935
<211> LENGTH: 26
<212> TYPE: DNA
<213> ORGANISM: Artificial Sequence
<220> FEATURE:
<223> OTHER INFORMATION: Synthetic DNA/RNA primer, R431

<400> SEQUENCE: 935
agggtagttc ugtttcaaac tugcat                                        26

<210> SEQ ID NO 936
<211> LENGTH: 30
<212> TYPE: DNA
<213> ORGANISM: Artificial Sequence
<220> FEATURE:

```
<223> OTHER INFORMATION: Synthetic DNA/RNA primer, R432

<400> SEQUENCE: 936
tgtatatttt cagctgcttg tgaatttuct                                    30

<210> SEQ ID NO 937
<211> LENGTH: 28
<212> TYPE: DNA
<213> ORGANISM: Artificial Sequence
<220> FEATURE:
<223> OTHER INFORMATION: Synthetic DNA/RNA primer, R433

<400> SEQUENCE: 937
gacagttctg cauacatgta actagugt                                      28

<210> SEQ ID NO 938
<211> LENGTH: 22
<212> TYPE: RNA
<213> ORGANISM: Artificial Sequence
<220> FEATURE:
<223> OTHER INFORMATION: Synthetic Primer, R434

<400> SEQUENCE: 938
gcggauacaa ccucaaaaga cg                                            22

<210> SEQ ID NO 939
<211> LENGTH: 27
<212> TYPE: DNA
<213> ORGANISM: Artificial Sequence
<220> FEATURE:
<223> OTHER INFORMATION: Synthetic DNA/RNA primer, R435

<400> SEQUENCE: 939
tgucaagttt ctctucagga ggaaaag                                       27

<210> SEQ ID NO 940
<211> LENGTH: 32
<212> TYPE: DNA
<213> ORGANISM: Artificial Sequence
<220> FEATURE:
<223> OTHER INFORMATION: Synthetic DNA/RNA primer, R436

<400> SEQUENCE: 940
aaggaaaata acuctcctga acatcuaaaa ga                                 32

<210> SEQ ID NO 941
<211> LENGTH: 30
<212> TYPE: DNA
<213> ORGANISM: Artificial Sequence
<220> FEATURE:
<223> OTHER INFORMATION: Synthetic DNA/RNA primer, R437

<400> SEQUENCE: 941
tgttgaagag cuattgaaaa tcatttgugc                                    30

<210> SEQ ID NO 942
<211> LENGTH: 30
<212> TYPE: DNA
<213> ORGANISM: Artificial Sequence
<220> FEATURE:
<223> OTHER INFORMATION: Synthetic DNA/RNA primer, R438

<400> SEQUENCE: 942
acagctcaaa gutgaactta ttcacuaaga                                    30
```

<210> SEQ ID NO 943
<211> LENGTH: 31
<212> TYPE: DNA
<213> ORGANISM: Artificial Sequence
<220> FEATURE:
<223> OTHER INFORMATION: Synthetic DNA/RNA primer, R439

<400> SEQUENCE: 943
atgtttttct aatgugttaa agttcatugg a                              31

<210> SEQ ID NO 944
<211> LENGTH: 28
<212> TYPE: DNA
<213> ORGANISM: Artificial Sequence
<220> FEATURE:
<223> OTHER INFORMATION: Synthetic DNA/RNA primer, R440

<400> SEQUENCE: 944
gccagtttcc auatgatcca tctauagt                                  28

<210> SEQ ID NO 945
<211> LENGTH: 28
<212> TYPE: DNA
<213> ORGANISM: Artificial Sequence
<220> FEATURE:
<223> OTHER INFORMATION: Synthetic DNA/RNA primer, R441

<400> SEQUENCE: 945
agaaacctta accauactgc cgtataug                                  28

<210> SEQ ID NO 946
<211> LENGTH: 24
<212> TYPE: DNA
<213> ORGANISM: Artificial Sequence
<220> FEATURE:
<223> OTHER INFORMATION: Synthetic DNA/RNA primer, R442

<400> SEQUENCE: 946
gccacttttu gggtatctgc acua                                      24

<210> SEQ ID NO 947
<211> LENGTH: 23
<212> TYPE: DNA
<213> ORGANISM: Artificial Sequence
<220> FEATURE:
<223> OTHER INFORMATION: Synthetic DNA/RNA primer, R443

<400> SEQUENCE: 947
ttcaagaggu gtacaggcau cag                                       23

<210> SEQ ID NO 948
<211> LENGTH: 28
<212> TYPE: DNA
<213> ORGANISM: Artificial Sequence
<220> FEATURE:
<223> OTHER INFORMATION: Synthetic DNA/RNA primer, R444

<400> SEQUENCE: 948
ggtcaggaaa gaauccaagt ttggtaua                                  28

<210> SEQ ID NO 949
<211> LENGTH: 28
<212> TYPE: DNA
<213> ORGANISM: Artificial Sequence
<220> FEATURE:
<223> OTHER INFORMATION: Synthetic DNA/RNA primer, R445

<400> SEQUENCE: 949
cctcagctcc uagactttca gaaataug                28

<210> SEQ ID NO 950
<211> LENGTH: 32
<212> TYPE: DNA
<213> ORGANISM: Artificial Sequence
<220> FEATURE:
<223> OTHER INFORMATION: Synthetic DNA/RNA primer, R446

<400> SEQUENCE: 950
aaactccatc ucaaacaaac aaacaaatua at            32

<210> SEQ ID NO 951
<211> LENGTH: 29
<212> TYPE: DNA
<213> ORGANISM: Artificial Sequence
<220> FEATURE:
<223> OTHER INFORMATION: Synthetic DNA/RNA primer, R447

<400> SEQUENCE: 951
cctcctgaat ttuagtgaat aaggctuct                29

<210> SEQ ID NO 952
<211> LENGTH: 20
<212> TYPE: DNA
<213> ORGANISM: Artificial Sequence
<220> FEATURE:
<223> OTHER INFORMATION: Synthetic DNA/RNA primer, R448

<400> SEQUENCE: 952
gcaaagcacg aacutgcugt                          20

<210> SEQ ID NO 953
<211> LENGTH: 25
<212> TYPE: DNA
<213> ORGANISM: Artificial Sequence
<220> FEATURE:
<223> OTHER INFORMATION: Synthetic DNA/RNA primer, R449

<400> SEQUENCE: 953
gtgauggcca gagagtcuaa aacag                    25

<210> SEQ ID NO 954
<211> LENGTH: 26
<212> TYPE: DNA
<213> ORGANISM: Artificial Sequence
<220> FEATURE:
<223> OTHER INFORMATION: Synthetic DNA/RNA primer, R450

<400> SEQUENCE: 954
tgacatccct ugataaacct tgtucc                   26

<210> SEQ ID NO 955
<211> LENGTH: 26
<212> TYPE: DNA
<213> ORGANISM: Artificial Sequence
<220> FEATURE:
<223> OTHER INFORMATION: Synthetic DNA/RNA primer, R451

<400> SEQUENCE: 955
tttttgtcgc ugctaactgt atgtua                   26

<210> SEQ ID NO 956
<211> LENGTH: 32

-continued

<212> TYPE: DNA
<213> ORGANISM: Artificial Sequence
<220> FEATURE:
<223> OTHER INFORMATION: Synthetic DNA/RNA primer, R452

<400> SEQUENCE: 956
gctccaacta aucataagag atttuaaaag ac                32

<210> SEQ ID NO 957
<211> LENGTH: 26
<212> TYPE: DNA
<213> ORGANISM: Artificial Sequence
<220> FEATURE:
<223> OTHER INFORMATION: Synthetic DNA/RNA primer, R453

<400> SEQUENCE: 957
aagtaagaag gccugatttg gatuct                26

<210> SEQ ID NO 958
<211> LENGTH: 28
<212> TYPE: DNA
<213> ORGANISM: Artificial Sequence
<220> FEATURE:
<223> OTHER INFORMATION: Synthetic DNA/RNA primer, R454

<400> SEQUENCE: 958
gctatttcct ugatactgga ctgucaaa                28

<210> SEQ ID NO 959
<211> LENGTH: 31
<212> TYPE: DNA
<213> ORGANISM: Artificial Sequence
<220> FEATURE:
<223> OTHER INFORMATION: Synthetic DNA/RNA primer, R455

<400> SEQUENCE: 959
attccttgag uttacattaa ctuaccagaa g                31

<210> SEQ ID NO 960
<211> LENGTH: 28
<212> TYPE: DNA
<213> ORGANISM: Artificial Sequence
<220> FEATURE:
<223> OTHER INFORMATION: Synthetic DNA/RNA primer, R456

<400> SEQUENCE: 960
atgacaatta tcaaccucat ctgctcut                28

<210> SEQ ID NO 961
<211> LENGTH: 30
<212> TYPE: DNA
<213> ORGANISM: Artificial Sequence
<220> FEATURE:
<223> OTHER INFORMATION: Synthetic DNA/RNA primer, R457

<400> SEQUENCE: 961
taaattgutt ttctcctgtu gaaccagaca                30

<210> SEQ ID NO 962
<211> LENGTH: 27
<212> TYPE: DNA
<213> ORGANISM: Artificial Sequence
<220> FEATURE:
<223> OTHER INFORMATION: Synthetic DNA/RNA primer, R458

<400> SEQUENCE: 962

-continued

| | |
|---|---|
| cctgcttatt tutctcacat tctuccg | 27 |

<210> SEQ ID NO 963
<211> LENGTH: 29
<212> TYPE: DNA
<213> ORGANISM: Artificial Sequence
<220> FEATURE:
<223> OTHER INFORMATION: Synthetic DNA/RNA primer, R459

<400> SEQUENCE: 963

| | |
|---|---|
| ggttuagaga ctttcucaaa ggcttagat | 29 |

<210> SEQ ID NO 964
<211> LENGTH: 25
<212> TYPE: DNA
<213> ORGANISM: Artificial Sequence
<220> FEATURE:
<223> OTHER INFORMATION: Synthetic DNA/RNA primer, R460

<400> SEQUENCE: 964

| | |
|---|---|
| gtgtttucac tgtctgucac agaag | 25 |

<210> SEQ ID NO 965
<211> LENGTH: 31
<212> TYPE: DNA
<213> ORGANISM: Artificial Sequence
<220> FEATURE:
<223> OTHER INFORMATION: Synthetic DNA/RNA primer, R461

<400> SEQUENCE: 965

| | |
|---|---|
| aaaactatct tcutcagagg tatcuacaac t | 31 |

<210> SEQ ID NO 966
<211> LENGTH: 24
<212> TYPE: DNA
<213> ORGANISM: Artificial Sequence
<220> FEATURE:
<223> OTHER INFORMATION: Synthetic DNA/RNA primer, R462

<400> SEQUENCE: 966

| | |
|---|---|
| gtgacguact gggttttuag caag | 24 |

<210> SEQ ID NO 967
<211> LENGTH: 27
<212> TYPE: DNA
<213> ORGANISM: Artificial Sequence
<220> FEATURE:
<223> OTHER INFORMATION: Synthetic DNA/RNA primer, R463

<400> SEQUENCE: 967

| | |
|---|---|
| ggcttctgat tugctacatt tgaauct | 27 |

<210> SEQ ID NO 968
<211> LENGTH: 31
<212> TYPE: DNA
<213> ORGANISM: Artificial Sequence
<220> FEATURE:
<223> OTHER INFORMATION: Synthetic DNA/RNA primer, R464

<400> SEQUENCE: 968

| | |
|---|---|
| aggtcttttt ctgaaauatt ttggtcacau g | 31 |

<210> SEQ ID NO 969
<211> LENGTH: 26
<212> TYPE: DNA
<213> ORGANISM: Artificial Sequence

```
<220> FEATURE:
<223> OTHER INFORMATION: Synthetic DNA/RNA primer, R465

<400> SEQUENCE: 969
agatattgcc ugctttacug caagaa                                          26

<210> SEQ ID NO 970
<211> LENGTH: 25
<212> TYPE: DNA
<213> ORGANISM: Artificial Sequence
<220> FEATURE:
<223> OTHER INFORMATION: Synthetic DNA/RNA primer, R466

<400> SEQUENCE: 970
tgtatttcca guccacttuc agagg                                           25

<210> SEQ ID NO 971
<211> LENGTH: 32
<212> TYPE: DNA
<213> ORGANISM: Artificial Sequence
<220> FEATURE:
<223> OTHER INFORMATION: Synthetic DNA/RNA primer, R467

<400> SEQUENCE: 971
ttgttttctt ttucaaagtg gatatuaaac ct                                   32

<210> SEQ ID NO 972
<211> LENGTH: 32
<212> TYPE: DNA
<213> ORGANISM: Artificial Sequence
<220> FEATURE:
<223> OTHER INFORMATION: Synthetic DNA/RNA primer, R468

<400> SEQUENCE: 972
cagaaggaat cgucatctat aaaactatau gt                                   32

<210> SEQ ID NO 973
<211> LENGTH: 32
<212> TYPE: DNA
<213> ORGANISM: Artificial Sequence
<220> FEATURE:
<223> OTHER INFORMATION: Synthetic DNA/RNA primer, R469

<400> SEQUENCE: 973
ctgtagtttt tcctuattac attttgcttc ut                                   32

<210> SEQ ID NO 974
<211> LENGTH: 28
<212> TYPE: DNA
<213> ORGANISM: Artificial Sequence
<220> FEATURE:
<223> OTHER INFORMATION: Synthetic DNA/RNA primer, R470

<400> SEQUENCE: 974
tgggattgaa agucagtatc actgtaut                                        28

<210> SEQ ID NO 975
<211> LENGTH: 28
<212> TYPE: DNA
<213> ORGANISM: Artificial Sequence
<220> FEATURE:
<223> OTHER INFORMATION: Synthetic DNA/RNA primer, R471

<400> SEQUENCE: 975
gttacctttg agcutgtctg acatttug                                        28
```

<210> SEQ ID NO 976
<211> LENGTH: 31
<212> TYPE: DNA
<213> ORGANISM: Artificial Sequence
<220> FEATURE:
<223> OTHER INFORMATION: Synthetic DNA/RNA primer, R472

<400> SEQUENCE: 976
ttggattact ctuagatttg tgttttggtu g                              31

<210> SEQ ID NO 977
<211> LENGTH: 26
<212> TYPE: DNA
<213> ORGANISM: Artificial Sequence
<220> FEATURE:
<223> OTHER INFORMATION: Synthetic DNA/RNA primer, R473

<400> SEQUENCE: 977
atggtagagt tcutgaaaat gggtuc                                    26

<210> SEQ ID NO 978
<211> LENGTH: 33
<212> TYPE: DNA
<213> ORGANISM: Artificial Sequence
<220> FEATURE:
<223> OTHER INFORMATION: Synthetic DNA/RNA primer, R474

<400> SEQUENCE: 978
gtattttatc tatatucaag gagatgtccg aut                            33

<210> SEQ ID NO 979
<211> LENGTH: 27
<212> TYPE: DNA
<213> ORGANISM: Artificial Sequence
<220> FEATURE:
<223> OTHER INFORMATION: Synthetic DNA/RNA primer, R475

<400> SEQUENCE: 979 gcctttggc uaggtgttaa attaugg                                    27

<210> SEQ ID NO 980
<211> LENGTH: 22
<212> TYPE: DNA
<213> ORGANISM: Artificial Sequence
<220> FEATURE:
<223> OTHER INFORMATION: Synthetic DNA/RNA primer, R476

<400> SEQUENCE: 980
gtctaccuga ccaatcgaug gg                                        22

<210> SEQ ID NO 981
<211> LENGTH: 24
<212> TYPE: DNA
<213> ORGANISM: Artificial Sequence
<220> FEATURE:
<223> OTHER INFORMATION: Synthetic DNA/RNA primer, R477

<400> SEQUENCE: 981
agcttttugc agagcttcag uaga                                      24

<210> SEQ ID NO 982
<211> LENGTH: 29
<212> TYPE: DNA
<213> ORGANISM: Artificial Sequence
<220> FEATURE:
<223> OTHER INFORMATION: Synthetic DNA/RNA primer, R478

```
<400> SEQUENCE: 982
ggccagataa ttuaagacat atgttgugc                                    29

<210> SEQ ID NO 983
<211> LENGTH: 26
<212> TYPE: DNA
<213> ORGANISM: Artificial Sequence
<220> FEATURE:
<223> OTHER INFORMATION: Synthetic DNA/RNA primer, R479

<400> SEQUENCE: 983
gctccgtttu agtagcagtt aacugt                                       26

<210> SEQ ID NO 984
<211> LENGTH: 30
<212> TYPE: DNA
<213> ORGANISM: Artificial Sequence
<220> FEATURE:
<223> OTHER INFORMATION: Synthetic DNA/RNA primer, R480

<400> SEQUENCE: 984
gtctgtttcc ucataactta gaatguccat                                   30

<210> SEQ ID NO 985
<211> LENGTH: 26
<212> TYPE: DNA
<213> ORGANISM: Artificial Sequence
<220> FEATURE:
<223> OTHER INFORMATION: Synthetic DNA/RNA primer, R481

<400> SEQUENCE: 985
tcactgtgcg aagacuttta tgtcua                                       26

<210> SEQ ID NO 986
<211> LENGTH: 27
<212> TYPE: DNA
<213> ORGANISM: Artificial Sequence
<220> FEATURE:
<223> OTHER INFORMATION: Synthetic DNA/RNA primer, R482

<400> SEQUENCE: 986
tttcactttg uccaaagatt ccttugc                                      27

<210> SEQ ID NO 987
<211> LENGTH: 28
<212> TYPE: DNA
<213> ORGANISM: Artificial Sequence
<220> FEATURE:
<223> OTHER INFORMATION: Synthetic DNA/RNA primer, R483

<400> SEQUENCE: 987
agaattctgc auttctttac acttuggg                                     28

<210> SEQ ID NO 988
<211> LENGTH: 26
<212> TYPE: DNA
<213> ORGANISM: Artificial Sequence
<220> FEATURE:
<223> OTHER INFORMATION: Synthetic DNA/RNA primer, R484

<400> SEQUENCE: 988
ggactgattu gtgtaacaag tugcag                                       26

<210> SEQ ID NO 989
```

```
<211> LENGTH: 32
<212> TYPE: DNA
<213> ORGANISM: Artificial Sequence
<220> FEATURE:
<223> OTHER INFORMATION: Synthetic DNA/RNA primer, R485

<400> SEQUENCE: 989
tcatacaaat aatutcctac ataatcugca gt                                     32

<210> SEQ ID NO 990
<211> LENGTH: 28
<212> TYPE: DNA
<213> ORGANISM: Artificial Sequence
<220> FEATURE:
<223> OTHER INFORMATION: Synthetic DNA/RNA primer, R486

<400> SEQUENCE: 990
caatactggc ucaataccag aaucaagt                                          28

<210> SEQ ID NO 991
<211> LENGTH: 24
<212> TYPE: DNA
<213> ORGANISM: Artificial Sequence
<220> FEATURE:
<223> OTHER INFORMATION: Synthetic DNA/RNA primer, R487

<400> SEQUENCE: 991
aacctgccau aattttcgtt uggc                                              24

<210> SEQ ID NO 992
<211> LENGTH: 28
<212> TYPE: DNA
<213> ORGANISM: Artificial Sequence
<220> FEATURE:
<223> OTHER INFORMATION: Synthetic DNA/RNA primer, R488

<400> SEQUENCE: 992
gaagtttcca aacuaacatc acaaggug                                          28

<210> SEQ ID NO 993
<211> LENGTH: 26
<212> TYPE: DNA
<213> ORGANISM: Artificial Sequence
<220> FEATURE:
<223> OTHER INFORMATION: Synthetic DNA/RNA primer, R489

<400> SEQUENCE: 993
atttcagaaa acacutgtct tgcgut                                            26

<210> SEQ ID NO 994
<211> LENGTH: 28
<212> TYPE: DNA
<213> ORGANISM: Artificial Sequence
<220> FEATURE:
<223> OTHER INFORMATION: Synthetic DNA/RNA primer, R490

<400> SEQUENCE: 994
accacattat augaaaagcc ttttuggg                                          28

<210> SEQ ID NO 995
<211> LENGTH: 26
<212> TYPE: DNA
<213> ORGANISM: Artificial Sequence
<220> FEATURE:
<223> OTHER INFORMATION: Synthetic DNA/RNA primer, R491

<400> SEQUENCE: 995
```

-continued gguttctctt aucaacacga ggaagt    26

<210> SEQ ID NO 996
<211> LENGTH: 28
<212> TYPE: DNA
<213> ORGANISM: Artificial Sequence
<220> FEATURE:
<223> OTHER INFORMATION: Synthetic DNA/RNA primer, R492

<400> SEQUENCE: 996
ctgtcagttc aucatcttcc auaaaagc    28

<210> SEQ ID NO 997
<211> LENGTH: 31
<212> TYPE: DNA
<213> ORGANISM: Artificial Sequence
<220> FEATURE:
<223> OTHER INFORMATION: Synthetic DNA/RNA primer, R493

<400> SEQUENCE: 997
tataccauac ctauagaggg agaacagata t    31

<210> SEQ ID NO 998
<211> LENGTH: 28
<212> TYPE: DNA
<213> ORGANISM: Artificial Sequence
<220> FEATURE:
<223> OTHER INFORMATION: Synthetic DNA/RNA primer, R494

<400> SEQUENCE: 998
gcttgaagat ttutccaaag tcagaugt    28

<210> SEQ ID NO 999
<211> LENGTH: 27
<212> TYPE: DNA
<213> ORGANISM: Artificial Sequence
<220> FEATURE:
<223> OTHER INFORMATION: Synthetic DNA/RNA primer, R495

<400> SEQUENCE: 999
gttttgcttt ugtctgtttt ccuccaa    27

<210> SEQ ID NO 1000
<211> LENGTH: 28
<212> TYPE: DNA
<213> ORGANISM: Artificial Sequence
<220> FEATURE:
<223> OTHER INFORMATION: Synthetic DNA/RNA primer, R496

<400> SEQUENCE: 1000
aggcaaaaat tcaucacaca aattguca    28

<210> SEQ ID NO 1001
<211> LENGTH: 23
<212> TYPE: DNA
<213> ORGANISM: Artificial Sequence
<220> FEATURE:
<223> OTHER INFORMATION: Synthetic DNA/RNA primer, R497

<400> SEQUENCE: 1001
tcattggagg guatgagcca ucc    23

<210> SEQ ID NO 1002
<211> LENGTH: 21
<212> TYPE: DNA

<213> ORGANISM: Artificial Sequence
<220> FEATURE:
<223> OTHER INFORMATION: Synthetic DNA/RNA primer, F499

<400> SEQUENCE: 1002
acaacugcag caaagacugg t                                      21

<210> SEQ ID NO 1003
<211> LENGTH: 28
<212> TYPE: RNA
<213> ORGANISM: Artificial Sequence
<220> FEATURE:
<223> OTHER INFORMATION: Synthetic Primer, F500

<400> SEQUENCE: 1003
aguuaauuuu gguuacaucc cucucugc                               28

<210> SEQ ID NO 1004
<211> LENGTH: 25
<212> TYPE: RNA
<213> ORGANISM: Artificial Sequence
<220> FEATURE:
<223> OTHER INFORMATION: Synthetic Primer, F501

<400> SEQUENCE: 1004
aucgaucugu uagaaaccuc uccag                                  25

<210> SEQ ID NO 1005
<211> LENGTH: 19
<212> TYPE: DNA
<213> ORGANISM: Artificial Sequence
<220> FEATURE:
<223> OTHER INFORMATION: Synthetic DNA/RNA primer, F502

<400> SEQUENCE: 1005
ggacucugua ggcugcagt                                         19

<210> SEQ ID NO 1006
<211> LENGTH: 22
<212> TYPE: RNA
<213> ORGANISM: Artificial Sequence
<220> FEATURE:
<223> OTHER INFORMATION: Synthetic Primer, F503

<400> SEQUENCE: 1006
ugaggcaguc uuuacucacc ug                                     22

<210> SEQ ID NO 1007
<211> LENGTH: 28
<212> TYPE: DNA
<213> ORGANISM: Artificial Sequence
<220> FEATURE:
<223> OTHER INFORMATION: Synthetic DNA/RNA primer, F504

<400> SEQUENCE: 1007
acaagcaaag ucucuauggu gauuaugt                               28

<210> SEQ ID NO 1008
<211> LENGTH: 25
<212> TYPE: DNA
<213> ORGANISM: Artificial Sequence
<220> FEATURE:
<223> OTHER INFORMATION: Synthetic DNA/RNA primer, F505

<400> SEQUENCE: 1008
caacuaccau ccagcaacag aaaat                                  25

<210> SEQ ID NO 1009
<211> LENGTH: 28
<212> TYPE: RNA
<213> ORGANISM: Artificial Sequence
<220> FEATURE:
<223> OTHER INFORMATION: Synthetic Primer, F506

<400> SEQUENCE: 1009
gacagaugag agaaaugcac uuagaaga                                28

<210> SEQ ID NO 1010
<211> LENGTH: 25
<212> TYPE: RNA
<213> ORGANISM: Artificial Sequence
<220> FEATURE:
<223> OTHER INFORMATION: Synthetic Primer, F507

<400> SEQUENCE: 1010
aggaaugugu uucuccauac agguc                                   25

<210> SEQ ID NO 1011
<211> LENGTH: 24
<212> TYPE: RNA
<213> ORGANISM: Artificial Sequence
<220> FEATURE:
<223> OTHER INFORMATION: Synthetic Primer, F508

<400> SEQUENCE: 1011
cuucaagcag ugagaauacg ucca                                    24

<210> SEQ ID NO 1012
<211> LENGTH: 20
<212> TYPE: RNA
<213> ORGANISM: Artificial Sequence
<220> FEATURE:
<223> OTHER INFORMATION: Synthetic Primer, F509

<400> SEQUENCE: 1012
aggguccagg uucuuccaga                                         20

<210> SEQ ID NO 1013
<211> LENGTH: 26
<212> TYPE: RNA
<213> ORGANISM: Artificial Sequence
<220> FEATURE:
<223> OTHER INFORMATION: Synthetic Primer, F510

<400> SEQUENCE: 1013
gauaguuuug agagucguuc gauugc                                  26

<210> SEQ ID NO 1014
<211> LENGTH: 21
<212> TYPE: RNA
<213> ORGANISM: Artificial Sequence
<220> FEATURE:
<223> OTHER INFORMATION: Synthetic Primer, F511

<400> SEQUENCE: 1014
cuccaccacc uccucaaaca g                                       21

<210> SEQ ID NO 1015
<211> LENGTH: 18
<212> TYPE: RNA
<213> ORGANISM: Artificial Sequence
<220> FEATURE:

<223> OTHER INFORMATION: Synthetic Primer, F512

<400> SEQUENCE: 1015
aucagccagg cacaaagc                                                    18

<210> SEQ ID NO 1016
<211> LENGTH: 28
<212> TYPE: DNA
<213> ORGANISM: Artificial Sequence
<220> FEATURE:
<223> OTHER INFORMATION: Synthetic DNA/RNA primer, F513

<400> SEQUENCE: 1016
caucuuuguc aucagcugaa gaugaaat                                         28

<210> SEQ ID NO 1017
<211> LENGTH: 29
<212> TYPE: RNA
<213> ORGANISM: Artificial Sequence
<220> FEATURE:
<223> OTHER INFORMATION: Synthetic Primer, F514

<400> SEQUENCE: 1017
gccuaaagaa ucaaaugaaa accaagaga                                        29

<210> SEQ ID NO 1018
<211> LENGTH: 18
<212> TYPE: RNA
<213> ORGANISM: Artificial Sequence
<220> FEATURE:
<223> OTHER INFORMATION: Synthetic Primer, F515

<400> SEQUENCE: 1018
gugacccgga gcacuucc                                                    18

<210> SEQ ID NO 1019
<211> LENGTH: 26
<212> TYPE: DNA
<213> ORGANISM: Artificial Sequence
<220> FEATURE:
<223> OTHER INFORMATION: Synthetic DNA/RNA primer, F516

<400> SEQUENCE: 1019
ccacauuaca uacuuaccau gccact                                           26

<210> SEQ ID NO 1020
<211> LENGTH: 18
<212> TYPE: RNA
<213> ORGANISM: Artificial Sequence
<220> FEATURE:
<223> OTHER INFORMATION: Synthetic Primer, F517

<400> SEQUENCE: 1020
augggaccca cuccaucg                                                    18

<210> SEQ ID NO 1021
<211> LENGTH: 22
<212> TYPE: RNA
<213> ORGANISM: Artificial Sequence
<220> FEATURE:
<223> OTHER INFORMATION: Synthetic Primer, F518

<400> SEQUENCE: 1021
cccuucuaag gaccccucu uc                                                22

```
-continued

<210> SEQ ID NO 1022
<211> LENGTH: 20
<212> TYPE: DNA
<213> ORGANISM: Artificial Sequence
<220> FEATURE:
<223> OTHER INFORMATION: Synthetic DNA/RNA primer, F519

<400> SEQUENCE: 1022
cucugccggg cuuugaucut                                              20

<210> SEQ ID NO 1023
<211> LENGTH: 19
<212> TYPE: DNA
<213> ORGANISM: Artificial Sequence
<220> FEATURE:
<223> OTHER INFORMATION: Synthetic DNA/RNA primer, F520

<400> SEQUENCE: 1023
uacuaccgcc ucacacgct                                               19

<210> SEQ ID NO 1024
<211> LENGTH: 21
<212> TYPE: RNA
<213> ORGANISM: Artificial Sequence
<220> FEATURE:
<223> OTHER INFORMATION: Synthetic Primer, F521

<400> SEQUENCE: 1024
uucccucucu ccuucugccu c                                            21

<210> SEQ ID NO 1025
<211> LENGTH: 25
<212> TYPE: DNA
<213> ORGANISM: Artificial Sequence
<220> FEATURE:
<223> OTHER INFORMATION: Synthetic Primer, F522

<400> SEQUENCE: 1025
ccagcagaag acaaaaagac aaaca                                        25

<210> SEQ ID NO 1026
<211> LENGTH: 21
<212> TYPE: DNA
<213> ORGANISM: Artificial Sequence
<220> FEATURE:
<223> OTHER INFORMATION: Synthetic DNA/RNA primer, F523

<400> SEQUENCE: 1026
ggagagggag gagagcuaac t                                            21

<210> SEQ ID NO 1027
<211> LENGTH: 22
<212> TYPE: RNA
<213> ORGANISM: Artificial Sequence
<220> FEATURE:
<223> OTHER INFORMATION: Synthetic Primer, F524

<400> SEQUENCE: 1027
agaagcugug cauuuacacc ga                                           22

<210> SEQ ID NO 1028
<211> LENGTH: 24
<212> TYPE: RNA
<213> ORGANISM: Artificial Sequence
<220> FEATURE:
<223> OTHER INFORMATION: Synthetic Primer, F525
```

```
<400> SEQUENCE: 1028
uuuugcugau gcaugcucu ccac                                          24

<210> SEQ ID NO 1029
<211> LENGTH: 19
<212> TYPE: RNA
<213> ORGANISM: Artificial Sequence
<220> FEATURE:
<223> OTHER INFORMATION: Synthetic Primer, F526

<400> SEQUENCE: 1029
cugauccgca agcaugcuc                                               19

<210> SEQ ID NO 1030
<211> LENGTH: 21
<212> TYPE: RNA
<213> ORGANISM: Artificial Sequence
<220> FEATURE:
<223> OTHER INFORMATION: Synthetic Primer, F527

<400> SEQUENCE: 1030
ugagcucgcu cacuugugau g                                            21

<210> SEQ ID NO 1031
<211> LENGTH: 23
<212> TYPE: RNA
<213> ORGANISM: Artificial Sequence
<220> FEATURE:
<223> OTHER INFORMATION: Synthetic Primer, F528

<400> SEQUENCE: 1031
caggauccaa auucguucug ugc                                          23

<210> SEQ ID NO 1032
<211> LENGTH: 25
<212> TYPE: DNA
<213> ORGANISM: Artificial Sequence
<220> FEATURE:
<223> OTHER INFORMATION: Synthetic DNA/RNA primer, F529

<400> SEQUENCE: 1032
uacuaacaac ucuggucugg accat                                        25

<210> SEQ ID NO 1033
<211> LENGTH: 28
<212> TYPE: RNA
<213> ORGANISM: Artificial Sequence
<220> FEATURE:
<223> OTHER INFORMATION: Synthetic Primer, F530

<400> SEQUENCE: 1033
augcuauuug gacaauaaac ucaccuug                                     28

<210> SEQ ID NO 1034
<211> LENGTH: 25
<212> TYPE: RNA
<213> ORGANISM: Artificial Sequence
<220> FEATURE:
<223> OTHER INFORMATION: Synthetic Primer, F531

<400> SEQUENCE: 1034
cuccuuaccu cauacagugc agaaa                                        25

<210> SEQ ID NO 1035
<211> LENGTH: 20
```

```
<212> TYPE: RNA
<213> ORGANISM: Artificial Sequence
<220> FEATURE:
<223> OTHER INFORMATION: Synthetic Primer, F532

<400> SEQUENCE: 1035
cccugagugc agcuucgauc                                                   20

<210> SEQ ID NO 1036
<211> LENGTH: 20
<212> TYPE: RNA
<213> ORGANISM: Artificial Sequence
<220> FEATURE:
<223> OTHER INFORMATION: Synthetic Primer, F533

<400> SEQUENCE: 1036
cgaucaugga uggcggguac                                                   20

<210> SEQ ID NO 1037
<211> LENGTH: 22
<212> TYPE: RNA
<213> ORGANISM: Artificial Sequence
<220> FEATURE:
<223> OTHER INFORMATION: Synthetic Primer, F534

<400> SEQUENCE: 1037
uuuaugaaug gagaggcugc ug                                                22

<210> SEQ ID NO 1038
<211> LENGTH: 26
<212> TYPE: RNA
<213> ORGANISM: Artificial Sequence
<220> FEATURE:
<223> OTHER INFORMATION: Synthetic Primer, F535

<400> SEQUENCE: 1038
accucucacc cuuauaaguc uucuga                                            26

<210> SEQ ID NO 1039
<211> LENGTH: 21
<212> TYPE: RNA
<213> ORGANISM: Artificial Sequence
<220> FEATURE:
<223> OTHER INFORMATION: Synthetic Primer, F536

<400> SEQUENCE: 1039
acuugagcuu cccuaggacc a                                                 21

<210> SEQ ID NO 1040
<211> LENGTH: 20
<212> TYPE: RNA
<213> ORGANISM: Artificial Sequence
<220> FEATURE:
<223> OTHER INFORMATION: Synthetic Primer, F537

<400> SEQUENCE: 1040
gggagacaau acgugucggg                                                   20

<210> SEQ ID NO 1041
<211> LENGTH: 23
<212> TYPE: RNA
<213> ORGANISM: Artificial Sequence
<220> FEATURE:
<223> OTHER INFORMATION: Synthetic Primer, F538

<400> SEQUENCE: 1041
```
aagacaggua gcgauccagg uag                                          23

<210> SEQ ID NO 1042
<211> LENGTH: 21
<212> TYPE: RNA
<213> ORGANISM: Artificial Sequence
<220> FEATURE:
<223> OTHER INFORMATION: Synthetic Primer, F539

<400> SEQUENCE: 1042
cuaggugccc auguccaucu g                                            21

<210> SEQ ID NO 1043
<211> LENGTH: 23
<212> TYPE: RNA
<213> ORGANISM: Artificial Sequence
<220> FEATURE:
<223> OTHER INFORMATION: Synthetic Primer, F540

<400> SEQUENCE: 1043
gauguccaau guaccugagg caa                                          23

<210> SEQ ID NO 1044
<211> LENGTH: 30
<212> TYPE: RNA
<213> ORGANISM: Artificial Sequence
<220> FEATURE:
<223> OTHER INFORMATION: Synthetic Primer, F541

<400> SEQUENCE: 1044
cagcagaaag aggacucaga auagaaaauc                                   30

<210> SEQ ID NO 1045
<211> LENGTH: 24
<212> TYPE: RNA
<213> ORGANISM: Artificial Sequence
<220> FEATURE:
<223> OTHER INFORMATION: Synthetic Primer, F542

<400> SEQUENCE: 1045
agagauucgc uugugugggu uaaa                                         24

<210> SEQ ID NO 1046
<211> LENGTH: 21
<212> TYPE: RNA
<213> ORGANISM: Artificial Sequence
<220> FEATURE:
<223> OTHER INFORMATION: Synthetic Primer, F543

<400> SEQUENCE: 1046
accaggguua ccuugaucuc c                                            21

<210> SEQ ID NO 1047
<211> LENGTH: 24
<212> TYPE: RNA
<213> ORGANISM: Artificial Sequence
<220> FEATURE:
<223> OTHER INFORMATION: Synthetic Primer, F544

<400> SEQUENCE: 1047
acuucucaau ugcuacgggc aauc                                         24

<210> SEQ ID NO 1048
<211> LENGTH: 22
<212> TYPE: DNA
<213> ORGANISM: Artificial Sequence

```
<220> FEATURE:
<223> OTHER INFORMATION: Synthetic DNA/RNA primer, F545

<400> SEQUENCE: 1048
agaucucggu gaacgaugca at                                            22

<210> SEQ ID NO 1049
<211> LENGTH: 24
<212> TYPE: RNA
<213> ORGANISM: Artificial Sequence
<220> FEATURE:
<223> OTHER INFORMATION: Synthetic Primer, F546

<400> SEQUENCE: 1049
uauguggacu gcagaagaac uucg                                          24

<210> SEQ ID NO 1050
<211> LENGTH: 25
<212> TYPE: RNA
<213> ORGANISM: Artificial Sequence
<220> FEATURE:
<223> OTHER INFORMATION: Synthetic Primer, F547

<400> SEQUENCE: 1050 uggguuuau gaacaagcga uuugg                                          25

<210> SEQ ID NO 1051
<211> LENGTH: 24
<212> TYPE: RNA
<213> ORGANISM: Artificial Sequence
<220> FEATURE:
<223> OTHER INFORMATION: Synthetic Primer, F548

<400> SEQUENCE: 1051
gcucauaucg agagguagcc auuc                                          24

<210> SEQ ID NO 1052
<211> LENGTH: 23
<212> TYPE: RNA
<213> ORGANISM: Artificial Sequence
<220> FEATURE:
<223> OTHER INFORMATION: Synthetic Primer, F549

<400> SEQUENCE: 1052
gcagacgagc uugacaucag aaa                                           23

<210> SEQ ID NO 1053
<211> LENGTH: 21
<212> TYPE: RNA
<213> ORGANISM: Artificial Sequence
<220> FEATURE:
<223> OTHER INFORMATION: Synthetic Primer, F550

<400> SEQUENCE: 1053
aagacuucgg gugcucugua c                                             21

<210> SEQ ID NO 1054
<211> LENGTH: 26
<212> TYPE: RNA
<213> ORGANISM: Artificial Sequence
<220> FEATURE:
<223> OTHER INFORMATION: Synthetic Primer, F551

<400> SEQUENCE: 1054
gggacagacu gucauucaaa auagga                                        26
```

```
<210> SEQ ID NO 1055
<211> LENGTH: 22
<212> TYPE: RNA
<213> ORGANISM: Artificial Sequence
<220> FEATURE:
<223> OTHER INFORMATION: Synthetic Primer, F552

<400> SEQUENCE: 1055
ugaagaaagu ccagaccucg ga                                    22

<210> SEQ ID NO 1056
<211> LENGTH: 23
<212> TYPE: RNA
<213> ORGANISM: Artificial Sequence
<220> FEATURE:
<223> OTHER INFORMATION: Synthetic Primer, F553

<400> SEQUENCE: 1056
gucgacugcc ugauaagaca uga                                   23

<210> SEQ ID NO 1057
<211> LENGTH: 26
<212> TYPE: RNA
<213> ORGANISM: Artificial Sequence
<220> FEATURE:
<223> OTHER INFORMATION: Synthetic Primer, F554

<400> SEQUENCE: 1057
uaguuugguu ucucugucug uucgug                                26

<210> SEQ ID NO 1058
<211> LENGTH: 19
<212> TYPE: DNA
<213> ORGANISM: Artificial Sequence
<220> FEATURE:
<223> OTHER INFORMATION: Synthetic DNA/RNA primer, F555

<400> SEQUENCE: 1058
aagccuccau cgcuaccct                                        19

<210> SEQ ID NO 1059
<211> LENGTH: 17
<212> TYPE: DNA
<213> ORGANISM: Artificial Sequence
<220> FEATURE:
<223> OTHER INFORMATION: Synthetic DNA/RNA primer, F556

<400> SEQUENCE: 1059
ucaggcgcca aguaggt                                          17

<210> SEQ ID NO 1060
<211> LENGTH: 21
<212> TYPE: RNA
<213> ORGANISM: Artificial Sequence
<220> FEATURE:
<223> OTHER INFORMATION: Synthetic Primer, F557

<400> SEQUENCE: 1060
aaagcggcug uuagucacug g                                     21

<210> SEQ ID NO 1061
<211> LENGTH: 25
<212> TYPE: RNA
<213> ORGANISM: Artificial Sequence
<220> FEATURE:
<223> OTHER INFORMATION: Synthetic Primer, F558
```

<400> SEQUENCE: 1061
uaaagaucau gucucggcuc aagga                                    25

<210> SEQ ID NO 1062
<211> LENGTH: 24
<212> TYPE: RNA
<213> ORGANISM: Artificial Sequence
<220> FEATURE:
<223> OTHER INFORMATION: Synthetic Primer, F559

<400> SEQUENCE: 1062
gugcacaggu uauucugauu uccc                                     24

<210> SEQ ID NO 1063
<211> LENGTH: 21
<212> TYPE: RNA
<213> ORGANISM: Artificial Sequence
<220> FEATURE:
<223> OTHER INFORMATION: Synthetic Primer, F560

<400> SEQUENCE: 1063
agaagggcua ggccaauuga c                                        21

<210> SEQ ID NO 1064
<211> LENGTH: 24
<212> TYPE: RNA
<213> ORGANISM: Artificial Sequence
<220> FEATURE:
<223> OTHER INFORMATION: Synthetic Primer, F561

<400> SEQUENCE: 1064
gucagccuga acauaacauc cuug                                     24

<210> SEQ ID NO 1065
<211> LENGTH: 20
<212> TYPE: RNA
<213> ORGANISM: Artificial Sequence
<220> FEATURE:
<223> OTHER INFORMATION: Synthetic Primer, F562

<400> SEQUENCE: 1065
gggaccuccg gucagaaaac                                          20

<210> SEQ ID NO 1066
<211> LENGTH: 21
<212> TYPE: RNA
<213> ORGANISM: Artificial Sequence
<220> FEATURE:
<223> OTHER INFORMATION: Synthetic Primer, F563

<400> SEQUENCE: 1066
cucccaacca agcucucuug a                                        21

<210> SEQ ID NO 1067
<211> LENGTH: 27
<212> TYPE: RNA
<213> ORGANISM: Artificial Sequence
<220> FEATURE:
<223> OTHER INFORMATION: Synthetic Primer, F564

<400> SEQUENCE: 1067
cccagaaggu gagaaaguua aaauucc                                  27

<210> SEQ ID NO 1068

```
<211> LENGTH: 21
<212> TYPE: RNA
<213> ORGANISM: Artificial Sequence
<220> FEATURE:
<223> OTHER INFORMATION: Synthetic Primer, F565

<400> SEQUENCE: 1068
agggcaugaa cuacuuggag g                                              21

<210> SEQ ID NO 1069
<211> LENGTH: 21
<212> TYPE: RNA
<213> ORGANISM: Artificial Sequence
<220> FEATURE:
<223> OTHER INFORMATION: Synthetic Primer, F566

<400> SEQUENCE: 1069
gccucucccu cccuccagga a                                              21

<210> SEQ ID NO 1070
<211> LENGTH: 17
<212> TYPE: DNA
<213> ORGANISM: Artificial Sequence
<220> FEATURE:
<223> OTHER INFORMATION: Synthetic DNA/RNA primer, F567

<400> SEQUENCE: 1070
ugccucaccu ccaccgt                                                   17

<210> SEQ ID NO 1071
<211> LENGTH: 21
<212> TYPE: RNA
<213> ORGANISM: Artificial Sequence
<220> FEATURE:
<223> OTHER INFORMATION: Synthetic Primer, F568

<400> SEQUENCE: 1071
aaguguaaga agugcgaagg g                                              21

<210> SEQ ID NO 1072
<211> LENGTH: 26
<212> TYPE: RNA
<213> ORGANISM: Artificial Sequence
<220> FEATURE:
<223> OTHER INFORMATION: Synthetic Primer, F569

<400> SEQUENCE: 1072
gccuuuuuaa cugguagaga uuggug                                         26

<210> SEQ ID NO 1073
<211> LENGTH: 24
<212> TYPE: RNA
<213> ORGANISM: Artificial Sequence
<220> FEATURE:
<223> OTHER INFORMATION: Synthetic Primer, F570

<400> SEQUENCE: 1073
ucaucaccuu ccuuucaugc ucuc                                           24

<210> SEQ ID NO 1074
<211> LENGTH: 22
<212> TYPE: RNA
<213> ORGANISM: Artificial Sequence
<220> FEATURE:
<223> OTHER INFORMATION: Synthetic Primer, F571

<400> SEQUENCE: 1074
```
uccuacgugg ugugugucug aa                                       22

<210> SEQ ID NO 1075
<211> LENGTH: 25
<212> TYPE: RNA
<213> ORGANISM: Artificial Sequence
<220> FEATURE:
<223> OTHER INFORMATION: Synthetic Primer, F572

<400> SEQUENCE: 1075
ugaucaucga auucuccaaa auggc                                    25

<210> SEQ ID NO 1076
<211> LENGTH: 25
<212> TYPE: RNA
<213> ORGANISM: Artificial Sequence
<220> FEATURE:
<223> OTHER INFORMATION: Synthetic Primer, F573

<400> SEQUENCE: 1076
gaugagaugu gguacaagca uucca                                    25

<210> SEQ ID NO 1077
<211> LENGTH: 28
<212> TYPE: DNA
<213> ORGANISM: Artificial Sequence
<220> FEATURE:
<223> OTHER INFORMATION: Synthetic DNA/RNA primer, F574

<400> SEQUENCE: 1077
ccccuacagc auuguuaaga aaguauut                                 28

<210> SEQ ID NO 1078
<211> LENGTH: 20
<212> TYPE: RNA
<213> ORGANISM: Artificial Sequence
<220> FEATURE:
<223> OTHER INFORMATION: Synthetic Primer, F575

<400> SEQUENCE: 1078
cugggacuag caugcugacc                                          20

<210> SEQ ID NO 1079
<211> LENGTH: 20
<212> TYPE: DNA
<213> ORGANISM: Artificial Sequence
<220> FEATURE:
<223> OTHER INFORMATION: Synthetic DNA/RNA primer, F576

<400> SEQUENCE: 1079
cugccugucu cugguucugt                                          20

<210> SEQ ID NO 1080
<211> LENGTH: 22
<212> TYPE: RNA
<213> ORGANISM: Artificial Sequence
<220> FEATURE:
<223> OTHER INFORMATION: Synthetic Primer, F577

<400> SEQUENCE: 1080 acuggagug aguuggaug gg                                         22

<210> SEQ ID NO 1081
<211> LENGTH: 26
<212> TYPE: DNA

```
<213> ORGANISM: Artificial Sequence
<220> FEATURE:
<223> OTHER INFORMATION: Synthetic DNA/RNA primer, F578

<400> SEQUENCE: 1081
uccugaucuc cuuagacaac uaccut                                          26

<210> SEQ ID NO 1082
<211> LENGTH: 22
<212> TYPE: RNA
<213> ORGANISM: Artificial Sequence
<220> FEATURE:
<223> OTHER INFORMATION: Synthetic Primer, F579

<400> SEQUENCE: 1082
uguuccuauu ucagccccac uc                                              22

<210> SEQ ID NO 1083
<211> LENGTH: 23
<212> TYPE: RNA
<213> ORGANISM: Artificial Sequence
<220> FEATURE:
<223> OTHER INFORMATION: Synthetic Primer, F580

<400> SEQUENCE: 1083
ggaaaggguc cucugaucau ugc                                             23

<210> SEQ ID NO 1084
<211> LENGTH: 20
<212> TYPE: RNA
<213> ORGANISM: Artificial Sequence
<220> FEATURE:
<223> OTHER INFORMATION: Synthetic Primer, F581

<400> SEQUENCE: 1084
cgagggccgg uauacauucg                                                 20

<210> SEQ ID NO 1085
<211> LENGTH: 24
<212> TYPE: DNA
<213> ORGANISM: Artificial Sequence
<220> FEATURE:
<223> OTHER INFORMATION: Synthetic DNA/RNA primer, F582

<400> SEQUENCE: 1085
gaaugugaaa auuccagugg ccat                                            24

<210> SEQ ID NO 1086
<211> LENGTH: 21
<212> TYPE: DNA
<213> ORGANISM: Artificial Sequence
<220> FEATURE:
<223> OTHER INFORMATION: Synthetic DNA/RNA primer, F583

<400> SEQUENCE: 1086
auacccucuc agcguacccu t                                               21

<210> SEQ ID NO 1087
<211> LENGTH: 19
<212> TYPE: RNA
<213> ORGANISM: Artificial Sequence
<220> FEATURE:
<223> OTHER INFORMATION: Synthetic Primer, F584

<400> SEQUENCE: 1087
agcgcuuugu ggucaucca                                                  19
```

<210> SEQ ID NO 1088
<211> LENGTH: 22
<212> TYPE: RNA
<213> ORGANISM: Artificial Sequence
<220> FEATURE:
<223> OTHER INFORMATION: Synthetic Primer, F585

<400> SEQUENCE: 1088
aaacuagccc ucaaucccug ac                                           22

<210> SEQ ID NO 1089
<211> LENGTH: 23
<212> TYPE: RNA
<213> ORGANISM: Artificial Sequence
<220> FEATURE:
<223> OTHER INFORMATION: Synthetic Primer, F586

<400> SEQUENCE: 1089
cacaguugga ggacuuccuc uuc                                          23

<210> SEQ ID NO 1090
<211> LENGTH: 22
<212> TYPE: RNA
<213> ORGANISM: Artificial Sequence
<220> FEATURE:
<223> OTHER INFORMATION: Synthetic Primer, F587

<400> SEQUENCE: 1090
cuacaugggu gcuucccauu cc                                           22

<210> SEQ ID NO 1091
<211> LENGTH: 21
<212> TYPE: RNA
<213> ORGANISM: Artificial Sequence
<220> FEATURE:
<223> OTHER INFORMATION: Synthetic Primer, F588

<400> SEQUENCE: 1091
guccucgugg ccaugaauga a                                            21

<210> SEQ ID NO 1092
<211> LENGTH: 22
<212> TYPE: RNA
<213> ORGANISM: Artificial Sequence
<220> FEATURE:
<223> OTHER INFORMATION: Synthetic Primer, F589

<400> SEQUENCE: 1092 cccaauccccc acaccaagua uc                                          22

<210> SEQ ID NO 1093
<211> LENGTH: 25
<212> TYPE: DNA
<213> ORGANISM: Artificial Sequence
<220> FEATURE:
<223> OTHER INFORMATION: Synthetic DNA/RNA primer, F590

<400> SEQUENCE: 1093 auguccucc cucaucucua auggt                                         25

<210> SEQ ID NO 1094
<211> LENGTH: 22
<212> TYPE: RNA
<213> ORGANISM: Artificial Sequence
<220> FEATURE:

-continued

```
<223> OTHER INFORMATION: Synthetic Primer, F591

<400> SEQUENCE: 1094
uggacucgag caacauugau gg                                    22

<210> SEQ ID NO 1095
<211> LENGTH: 21
<212> TYPE: RNA
<213> ORGANISM: Artificial Sequence
<220> FEATURE:
<223> OTHER INFORMATION: Synthetic Primer, F592

<400> SEQUENCE: 1095
gcugaaguac cagaccugcu a                                     21

<210> SEQ ID NO 1096
<211> LENGTH: 23
<212> TYPE: RNA
<213> ORGANISM: Artificial Sequence
<220> FEATURE:
<223> OTHER INFORMATION: Synthetic Primer, F593

<400> SEQUENCE: 1096
ggauuugacc cuccaugauc agg                                   23

<210> SEQ ID NO 1097
<211> LENGTH: 21
<212> TYPE: RNA
<213> ORGANISM: Artificial Sequence
<220> FEATURE:
<223> OTHER INFORMATION: Synthetic Primer, F594

<400> SEQUENCE: 1097
ucacucucuc ucugcgcauu c                                     21

<210> SEQ ID NO 1098
<211> LENGTH: 21
<212> TYPE: DNA
<213> ORGANISM: Artificial Sequence
<220> FEATURE:
<223> OTHER INFORMATION: Synthetic DNA/RNA primer, F595

<400> SEQUENCE: 1098
caugaagugc aagaacgugg t                                     21

<210> SEQ ID NO 1099
<211> LENGTH: 19
<212> TYPE: RNA
<213> ORGANISM: Artificial Sequence
<220> FEATURE:
<223> OTHER INFORMATION: Synthetic Primer, F596

<400> SEQUENCE: 1099
gcggaucaga gccucaaac                                        19

<210> SEQ ID NO 1100
<211> LENGTH: 28
<212> TYPE: DNA
<213> ORGANISM: Artificial Sequence
<220> FEATURE:
<223> OTHER INFORMATION: Synthetic DNA/RNA primer, F597

<400> SEQUENCE: 1100
acuguccugu uuugauaucc cagauuut                              28
```

```
<210> SEQ ID NO 1101
<211> LENGTH: 25
<212> TYPE: RNA
<213> ORGANISM: Artificial Sequence
<220> FEATURE:
<223> OTHER INFORMATION: Synthetic Primer, F598

<400> SEQUENCE: 1101
cugucucaau aucccaaacc cuaag                                         25

<210> SEQ ID NO 1102
<211> LENGTH: 23
<212> TYPE: RNA
<213> ORGANISM: Artificial Sequence
<220> FEATURE:
<223> OTHER INFORMATION: Synthetic Primer, F599

<400> SEQUENCE: 1102
uauuaguaug ccccugcaac gug                                           23

<210> SEQ ID NO 1103
<211> LENGTH: 23
<212> TYPE: RNA
<213> ORGANISM: Artificial Sequence
<220> FEATURE:
<223> OTHER INFORMATION: Synthetic Primer, F600

<400> SEQUENCE: 1103
caacccuccu gccaucauau uga                                           23

<210> SEQ ID NO 1104
<211> LENGTH: 26
<212> TYPE: RNA
<213> ORGANISM: Artificial Sequence
<220> FEATURE:
<223> OTHER INFORMATION: Synthetic Primer, F601

<400> SEQUENCE: 1104
caaccaugac aagauuuucc cuuacc                                        26

<210> SEQ ID NO 1105
<211> LENGTH: 21
<212> TYPE: RNA
<213> ORGANISM: Artificial Sequence
<220> FEATURE:
<223> OTHER INFORMATION: Synthetic Primer, F602

<400> SEQUENCE: 1105
ugccugugga ggaacuuuuc a                                             21

<210> SEQ ID NO 1106
<211> LENGTH: 19
<212> TYPE: RNA
<213> ORGANISM: Artificial Sequence
<220> FEATURE:
<223> OTHER INFORMATION: Synthetic Primer, F603

<400> SEQUENCE: 1106
cuuccucucg cccaucaca                                                19

<210> SEQ ID NO 1107
<211> LENGTH: 20
<212> TYPE: DNA
<213> ORGANISM: Artificial Sequence
<220> FEATURE:
<223> OTHER INFORMATION: Synthetic DNA/RNA primer, F604
```

<400> SEQUENCE: 1107
agugccuccu cucccaucut                                           20

<210> SEQ ID NO 1108
<211> LENGTH: 25
<212> TYPE: RNA
<213> ORGANISM: Artificial Sequence
<220> FEATURE:
<223> OTHER INFORMATION: Synthetic Primer, F605

<400> SEQUENCE: 1108
cacuccuugc uucucagaug aaacc                                     25

<210> SEQ ID NO 1109
<211> LENGTH: 19
<212> TYPE: RNA
<213> ORGANISM: Artificial Sequence
<220> FEATURE:
<223> OTHER INFORMATION: Synthetic Primer, F606

<400> SEQUENCE: 1109
cagguacucc cgcagguug                                            19

<210> SEQ ID NO 1110
<211> LENGTH: 21
<212> TYPE: RNA
<213> ORGANISM: Artificial Sequence
<220> FEATURE:
<223> OTHER INFORMATION: Synthetic Primer, F607

<400> SEQUENCE: 1110
cacgcauacg guuugguuug g                                         21

<210> SEQ ID NO 1111
<211> LENGTH: 24
<212> TYPE: DNA
<213> ORGANISM: Artificial Sequence
<220> FEATURE:
<223> OTHER INFORMATION: Synthetic DNA/RNA primer, F608

<400> SEQUENCE: 1111
cuagaagcuc ucuaucccac acct                                      24

<210> SEQ ID NO 1112
<211> LENGTH: 25
<212> TYPE: RNA
<213> ORGANISM: Artificial Sequence
<220> FEATURE:
<223> OTHER INFORMATION: Synthetic Primer, F609

<400> SEQUENCE: 1112
caaggaaugc cuucaaaaag uuggg                                     25

<210> SEQ ID NO 1113
<211> LENGTH: 23
<212> TYPE: RNA
<213> ORGANISM: Artificial Sequence
<220> FEATURE:
<223> OTHER INFORMATION: Synthetic Primer, F610

<400> SEQUENCE: 1113
agaugaugau cuccagguac agg                                       23

<210> SEQ ID NO 1114
<211> LENGTH: 21

```
<212> TYPE: DNA
<213> ORGANISM: Artificial Sequence
<220> FEATURE:
<223> OTHER INFORMATION: Synthetic DNA/RNA primer, F611

<400> SEQUENCE: 1114
cggcacugca ugcaauuucu t                                     21

<210> SEQ ID NO 1115
<211> LENGTH: 26
<212> TYPE: RNA
<213> ORGANISM: Artificial Sequence
<220> FEATURE:
<223> OTHER INFORMATION: Synthetic Primer, F612

<400> SEQUENCE: 1115
ccauuuauag cugagucucc auccug                                26

<210> SEQ ID NO 1116
<211> LENGTH: 23
<212> TYPE: DNA
<213> ORGANISM: Artificial Sequence
<220> FEATURE:
<223> OTHER INFORMATION: Synthetic DNA/RNA primer, F613

<400> SEQUENCE: 1116
cccaguugug gguaccuuua gat                                   23

<210> SEQ ID NO 1117
<211> LENGTH: 26
<212> TYPE: RNA
<213> ORGANISM: Artificial Sequence
<220> FEATURE:
<223> OTHER INFORMATION: Synthetic Primer, F614

<400> SEQUENCE: 1117
cuuucaaacg agucaagcaa gaaugg                                26

<210> SEQ ID NO 1118
<211> LENGTH: 23
<212> TYPE: DNA
<213> ORGANISM: Artificial Sequence
<220> FEATURE:
<223> OTHER INFORMATION: Synthetic DNA/RNA primer, F615

<400> SEQUENCE: 1118
accacacuuu ccauaaugag gct                                   23

<210> SEQ ID NO 1119
<211> LENGTH: 25
<212> TYPE: RNA
<213> ORGANISM: Artificial Sequence
<220> FEATURE:
<223> OTHER INFORMATION: Synthetic Primer, F616

<400> SEQUENCE: 1119
cuuuuccauc uuuucugugu ugguc                                 25

<210> SEQ ID NO 1120
<211> LENGTH: 25
<212> TYPE: RNA
<213> ORGANISM: Artificial Sequence
<220> FEATURE:
<223> OTHER INFORMATION: Synthetic Primer, F617

<400> SEQUENCE: 1120
```
cagacaaauc ccaaaacaaa ccuga                                    25

<210> SEQ ID NO 1121
<211> LENGTH: 24
<212> TYPE: RNA
<213> ORGANISM: Artificial Sequence
<220> FEATURE:
<223> OTHER INFORMATION: Synthetic Primer, F618

<400> SEQUENCE: 1121
guagcuacag gacucagaua cgug                                     24

<210> SEQ ID NO 1122
<211> LENGTH: 24
<212> TYPE: RNA
<213> ORGANISM: Artificial Sequence
<220> FEATURE:
<223> OTHER INFORMATION: Synthetic Primer, F619

<400> SEQUENCE: 1122
guauuugggc gaaugcaguu uuuc                                     24

<210> SEQ ID NO 1123
<211> LENGTH: 26
<212> TYPE: RNA
<213> ORGANISM: Artificial Sequence
<220> FEATURE:
<223> OTHER INFORMATION: Synthetic Primer, F620

<400> SEQUENCE: 1123
ccagagaaaa gagaguuacu cacaca                                   26

<210> SEQ ID NO 1124
<211> LENGTH: 24
<212> TYPE: RNA
<213> ORGANISM: Artificial Sequence
<220> FEATURE:
<223> OTHER INFORMATION: Synthetic Primer, F621

<400> SEQUENCE: 1124
acuguguuac ugccaucgac uuac                                     24

<210> SEQ ID NO 1125
<211> LENGTH: 22
<212> TYPE: DNA
<213> ORGANISM: Artificial Sequence
<220> FEATURE:
<223> OTHER INFORMATION: Synthetic DNA/RNA primer, F622

<400> SEQUENCE: 1125
gguauucucg gagguugccu ut                                       22

<210> SEQ ID NO 1126
<211> LENGTH: 22
<212> TYPE: RNA
<213> ORGANISM: Artificial Sequence
<220> FEATURE:
<223> OTHER INFORMATION: Synthetic Primer, F623

<400> SEQUENCE: 1126
cuuggucgug uucuucauuc gg                                       22

<210> SEQ ID NO 1127
<211> LENGTH: 19
<212> TYPE: RNA
<213> ORGANISM: Artificial Sequence

```
<220> FEATURE:
<223> OTHER INFORMATION: Synthetic Primer, F624

<400> SEQUENCE: 1127
accacugugg aggcauuug                                                19

<210> SEQ ID NO 1128
<211> LENGTH: 25
<212> TYPE: RNA
<213> ORGANISM: Artificial Sequence
<220> FEATURE:
<223> OTHER INFORMATION: Synthetic Primer, F625

<400> SEQUENCE: 1128
agugaagauc ucccacauua acacc                                         25

<210> SEQ ID NO 1129
<211> LENGTH: 21
<212> TYPE: RNA
<213> ORGANISM: Artificial Sequence
<220> FEATURE:
<223> OTHER INFORMATION: Synthetic Primer, F626

<400> SEQUENCE: 1129
cuugcccaaa gcaaccuucu c                                             21

<210> SEQ ID NO 1130
<211> LENGTH: 19
<212> TYPE: DNA
<213> ORGANISM: Artificial Sequence
<220> FEATURE:
<223> OTHER INFORMATION: Synthetic DNA/RNA primer, F627

<400> SEQUENCE: 1130
auugguugcg gccaucuct                                                19

<210> SEQ ID NO 1131
<211> LENGTH: 20
<212> TYPE: RNA
<213> ORGANISM: Artificial Sequence
<220> FEATURE:
<223> OTHER INFORMATION: Synthetic Primer, F628

<400> SEQUENCE: 1131
accaauuuca uaggcguggc                                               20

<210> SEQ ID NO 1132
<211> LENGTH: 20
<212> TYPE: RNA
<213> ORGANISM: Artificial Sequence
<220> FEATURE:
<223> OTHER INFORMATION: Synthetic Primer, F629

<400> SEQUENCE: 1132
gccuaucgcu cugcucucuc                                               20

<210> SEQ ID NO 1133
<211> LENGTH: 21
<212> TYPE: RNA
<213> ORGANISM: Artificial Sequence
<220> FEATURE:
<223> OTHER INFORMATION: Synthetic Primer, F630

<400> SEQUENCE: 1133
uaacccagcg acgaacuuuc c                                             21
```

```
<210> SEQ ID NO 1134
<211> LENGTH: 18
<212> TYPE: RNA
<213> ORGANISM: Artificial Sequence
<220> FEATURE:
<223> OTHER INFORMATION: Synthetic Primer, F631

<400> SEQUENCE: 1134
gccccugagc gucaucug                                                 18

<210> SEQ ID NO 1135
<211> LENGTH: 17
<212> TYPE: RNA
<213> ORGANISM: Artificial Sequence
<220> FEATURE:
<223> OTHER INFORMATION: Synthetic Primer, F632

<400> SEQUENCE: 1135
cugguggagg cugacga                                                  17

<210> SEQ ID NO 1136
<211> LENGTH: 22
<212> TYPE: RNA
<213> ORGANISM: Artificial Sequence
<220> FEATURE:
<223> OTHER INFORMATION: Synthetic Primer, F633

<400> SEQUENCE: 1136
acaacgugau gaagaucgca ga                                            22

<210> SEQ ID NO 1137
<211> LENGTH: 19
<212> TYPE: RNA
<213> ORGANISM: Artificial Sequence
<220> FEATURE:
<223> OTHER INFORMATION: Synthetic Primer, F634

<400> SEQUENCE: 1137
gggagaucuu cacgcuggg                                                19

<210> SEQ ID NO 1138
<211> LENGTH: 17
<212> TYPE: DNA
<213> ORGANISM: Artificial Sequence
<220> FEATURE:
<223> OTHER INFORMATION: Synthetic DNA/RNA primer, F635

<400> SEQUENCE: 1138
gucugaggag cccgugt                                                  17

<210> SEQ ID NO 1139
<211> LENGTH: 18
<212> TYPE: RNA
<213> ORGANISM: Artificial Sequence
<220> FEATURE:
<223> OTHER INFORMATION: Synthetic Primer, F636

<400> SEQUENCE: 1139
uccucggagc agugaggg                                                 18

<210> SEQ ID NO 1140
<211> LENGTH: 19
<212> TYPE: RNA
<213> ORGANISM: Artificial Sequence
<220> FEATURE:
<223> OTHER INFORMATION: Synthetic Primer, F637
```

<400> SEQUENCE: 1140
agccucucca cgcucccuc                                                      19

<210> SEQ ID NO 1141
<211> LENGTH: 23
<212> TYPE: RNA
<213> ORGANISM: Artificial Sequence
<220> FEATURE:
<223> OTHER INFORMATION: Synthetic Primer, F638

<400> SEQUENCE: 1141
cucacauugc cccugacaac aua                                                 23

<210> SEQ ID NO 1142
<211> LENGTH: 23
<212> TYPE: RNA
<213> ORGANISM: Artificial Sequence
<220> FEATURE:
<223> OTHER INFORMATION: Synthetic Primer, F639

<400> SEQUENCE: 1142
guguccuuuc aggauggugg aug                                                 23

<210> SEQ ID NO 1143
<211> LENGTH: 26
<212> TYPE: RNA
<213> ORGANISM: Artificial Sequence
<220> FEATURE:
<223> OTHER INFORMATION: Synthetic Primer, F640

<400> SEQUENCE: 1143
ggugacauuu ucaaagcagu guaucc                                              26

<210> SEQ ID NO 1144
<211> LENGTH: 22
<212> TYPE: RNA
<213> ORGANISM: Artificial Sequence
<220> FEATURE:
<223> OTHER INFORMATION: Synthetic Primer, F641

<400> SEQUENCE: 1144
ggguauucga ugauccugu gg                                                   22

<210> SEQ ID NO 1145
<211> LENGTH: 19
<212> TYPE: DNA
<213> ORGANISM: Artificial Sequence
<220> FEATURE:
<223> OTHER INFORMATION: Synthetic DNA/RNA primer, F642

<400> SEQUENCE: 1145
ccuccccacc agcauguut                                                      19

<210> SEQ ID NO 1146
<211> LENGTH: 22
<212> TYPE: RNA
<213> ORGANISM: Artificial Sequence
<220> FEATURE:
<223> OTHER INFORMATION: Synthetic Primer, F643

<400> SEQUENCE: 1146
ggcuuuggug agauccauug ac                                                  22

<210> SEQ ID NO 1147

```
<211> LENGTH: 19
<212> TYPE: DNA
<213> ORGANISM: Artificial Sequence
<220> FEATURE:
<223> OTHER INFORMATION: Synthetic DNA/RNA primer, F644

<400> SEQUENCE: 1147
gcauguacug gucccgcat                                              19

<210> SEQ ID NO 1148
<211> LENGTH: 21
<212> TYPE: RNA
<213> ORGANISM: Artificial Sequence
<220> FEATURE:
<223> OTHER INFORMATION: Synthetic Primer, F645

<400> SEQUENCE: 1148
ugguucugga ucagcuggau g                                           21

<210> SEQ ID NO 1149
<211> LENGTH: 23
<212> TYPE: RNA
<213> ORGANISM: Artificial Sequence
<220> FEATURE:
<223> OTHER INFORMATION: Synthetic Primer, R646

<400> SEQUENCE: 1149
ugccaacaug acuuacuuga ucc                                         23

<210> SEQ ID NO 1150
<211> LENGTH: 22
<212> TYPE: DNA
<213> ORGANISM: Artificial Sequence
<220> FEATURE:
<223> OTHER INFORMATION: Synthetic DNA/RNA primer, F647

<400> SEQUENCE: 1150
ggacuaggcg ugggauguuu ut                                          22

<210> SEQ ID NO 1151
<211> LENGTH: 19
<212> TYPE: RNA
<213> ORGANISM: Artificial Sequence
<220> FEATURE:
<223> OTHER INFORMATION: Synthetic Primer, F648

<400> SEQUENCE: 1151
aguggauccc cucuccacc                                              19

<210> SEQ ID NO 1152
<211> LENGTH: 25
<212> TYPE: DNA
<213> ORGANISM: Artificial Sequence
<220> FEATURE:
<223> OTHER INFORMATION: Synthetic DNA/RNA primer, F649

<400> SEQUENCE: 1152
gagguuuucc agcacucuga cauat                                       25

<210> SEQ ID NO 1153
<211> LENGTH: 24
<212> TYPE: RNA
<213> ORGANISM: Artificial Sequence
<220> FEATURE:
<223> OTHER INFORMATION: Synthetic Primer, F650

<400> SEQUENCE: 1153
```
cgguugaaug uaaggcuuac aacg                                          24

<210> SEQ ID NO 1154
<211> LENGTH: 20
<212> TYPE: RNA
<213> ORGANISM: Artificial Sequence
<220> FEATURE:
<223> OTHER INFORMATION: Synthetic Primer, F651

<400> SEQUENCE: 1154
gaacgggaag cccucauguc                                               20

<210> SEQ ID NO 1155
<211> LENGTH: 25
<212> TYPE: RNA
<213> ORGANISM: Artificial Sequence
<220> FEATURE:
<223> OTHER INFORMATION: Synthetic Primer, F652

<400> SEQUENCE: 1155
ccuuacucau ggucggauca caaag                                         25

<210> SEQ ID NO 1156
<211> LENGTH: 20
<212> TYPE: RNA
<213> ORGANISM: Artificial Sequence
<220> FEATURE:
<223> OTHER INFORMATION: Synthetic Primer, F653

<400> SEQUENCE: 1156
cccuuucucc ccacagaaac                                               20

<210> SEQ ID NO 1157
<211> LENGTH: 22
<212> TYPE: RNA
<213> ORGANISM: Artificial Sequence
<220> FEATURE:
<223> OTHER INFORMATION: Synthetic Primer, F654

<400> SEQUENCE: 1157
guagagcaaa uccaucccca ca                                            22

<210> SEQ ID NO 1158
<211> LENGTH: 19
<212> TYPE: RNA
<213> ORGANISM: Artificial Sequence
<220> FEATURE:
<223> OTHER INFORMATION: Synthetic Primer, F655

<400> SEQUENCE: 1158
ugugcuuuua gggcccacc                                                19

<210> SEQ ID NO 1159
<211> LENGTH: 29
<212> TYPE: DNA
<213> ORGANISM: Artificial Sequence
<220> FEATURE:
<223> OTHER INFORMATION: Synthetic DNA/RNA primer, F656

<400> SEQUENCE: 1159
ucuguucaau uuuguugagc uucugaaut                                     29

<210> SEQ ID NO 1160
<211> LENGTH: 27
<212> TYPE: DNA

<213> ORGANISM: Artificial Sequence
<220> FEATURE:
<223> OTHER INFORMATION: Synthetic DNA/RNA primer, F657

<400> SEQUENCE: 1160
ucaguguuac uuaccugucu ugucuut                                27

<210> SEQ ID NO 1161
<211> LENGTH: 24
<212> TYPE: RNA
<213> ORGANISM: Artificial Sequence
<220> FEATURE:
<223> OTHER INFORMATION: Synthetic Primer, F658

<400> SEQUENCE: 1161
ugaauuagcu guaucgucaa ggca                                  24

<210> SEQ ID NO 1162
<211> LENGTH: 25
<212> TYPE: RNA
<213> ORGANISM: Artificial Sequence
<220> FEATURE:
<223> OTHER INFORMATION: Synthetic Primer, F659

<400> SEQUENCE: 1162
uguuucuccc uucucaggau uccua                                 25

<210> SEQ ID NO 1163
<211> LENGTH: 18
<212> TYPE: RNA
<213> ORGANISM: Artificial Sequence
<220> FEATURE:
<223> OTHER INFORMATION: Synthetic Primer, F660

<400> SEQUENCE: 1163
aaacccgcaa uccggaac                                         18

<210> SEQ ID NO 1164
<211> LENGTH: 23
<212> TYPE: RNA
<213> ORGANISM: Artificial Sequence
<220> FEATURE:
<223> OTHER INFORMATION: Synthetic Primer, F661

<400> SEQUENCE: 1164
cccuccaaca uccagucaa cuc                                    23

<210> SEQ ID NO 1165
<211> LENGTH: 22
<212> TYPE: RNA
<213> ORGANISM: Artificial Sequence
<220> FEATURE:
<223> OTHER INFORMATION: Synthetic Primer, F662

<400> SEQUENCE: 1165
gcuagagcuu gaugagcagc ag                                    22

<210> SEQ ID NO 1166
<211> LENGTH: 20
<212> TYPE: RNA
<213> ORGANISM: Artificial Sequence
<220> FEATURE:
<223> OTHER INFORMATION: Synthetic Primer, F663

<400> SEQUENCE: 1166
ccauggaguc gaugagcugg                                       20

<210> SEQ ID NO 1167
<211> LENGTH: 21
<212> TYPE: RNA
<213> ORGANISM: Artificial Sequence
<220> FEATURE:
<223> OTHER INFORMATION: Synthetic Primer, F664

<400> SEQUENCE: 1167
gcccagcucu gagauccuuu c                                              21

<210> SEQ ID NO 1168
<211> LENGTH: 25
<212> TYPE: RNA
<213> ORGANISM: Artificial Sequence
<220> FEATURE:
<223> OTHER INFORMATION: Synthetic Primer, F665

<400> SEQUENCE: 1168
cauuucugac aacugaacug cucuc                                          25

<210> SEQ ID NO 1169
<211> LENGTH: 26
<212> TYPE: RNA
<213> ORGANISM: Artificial Sequence
<220> FEATURE:
<223> OTHER INFORMATION: Synthetic Primer, F666

<400> SEQUENCE: 1169
uuaccagcuu guucaugucu ggauuc                                         26

<210> SEQ ID NO 1170
<211> LENGTH: 26
<212> TYPE: DNA
<213> ORGANISM: Artificial Sequence
<220> FEATURE:
<223> OTHER INFORMATION: Synthetic DNA/RNA primer, F667

<400> SEQUENCE: 1170
acugagcuug uuggaauaag gaugut                                         26

<210> SEQ ID NO 1171
<211> LENGTH: 22
<212> TYPE: RNA
<213> ORGANISM: Artificial Sequence
<220> FEATURE:
<223> OTHER INFORMATION: Synthetic Primer, F668

<400> SEQUENCE: 1171
uuguaagugc ccgaagugua ag                                             22

<210> SEQ ID NO 1172
<211> LENGTH: 25
<212> TYPE: RNA
<213> ORGANISM: Artificial Sequence
<220> FEATURE:
<223> OTHER INFORMATION: Synthetic Primer, F669

<400> SEQUENCE: 1172
uacgcagugc uaaccaaguu cuuuc                                          25

<210> SEQ ID NO 1173
<211> LENGTH: 24
<212> TYPE: RNA
<213> ORGANISM: Artificial Sequence
<220> FEATURE:

<223> OTHER INFORMATION: Synthetic Primer, F670

<400> SEQUENCE: 1173
cagucaaggu ugcugauuuu gguc                                        24

<210> SEQ ID NO 1174
<211> LENGTH: 26
<212> TYPE: RNA
<213> ORGANISM: Artificial Sequence
<220> FEATURE:
<223> OTHER INFORMATION: Synthetic Primer, F671

<400> SEQUENCE: 1174
uauggauguu gccaagcugu auucug                                      26

<210> SEQ ID NO 1175
<211> LENGTH: 25
<212> TYPE: DNA
<213> ORGANISM: Artificial Sequence
<220> FEATURE:
<223> OTHER INFORMATION: Synthetic DNA/RNA primer, F672

<400> SEQUENCE: 1175
ggugguccua ccauacauga aacat                                       25

<210> SEQ ID NO 1176
<211> LENGTH: 25
<212> TYPE: RNA
<213> ORGANISM: Artificial Sequence
<220> FEATURE:
<223> OTHER INFORMATION: Synthetic Primer, F673

<400> SEQUENCE: 1176
gcaagcaaaa aguuugucca cagag                                       25

<210> SEQ ID NO 1177
<211> LENGTH: 23
<212> TYPE: DNA
<213> ORGANISM: Artificial Sequence
<220> FEATURE:
<223> OTHER INFORMATION: Synthetic DNA/RNA primer, F674

<400> SEQUENCE: 1177
acaucucuca ccucaucugu cct                                         23

<210> SEQ ID NO 1178
<211> LENGTH: 20
<212> TYPE: RNA
<213> ORGANISM: Artificial Sequence
<220> FEATURE:
<223> OTHER INFORMATION: Synthetic Primer, F675

<400> SEQUENCE: 1178
ucccuguagu cccggaugag                                             20

<210> SEQ ID NO 1179
<211> LENGTH: 25
<212> TYPE: RNA
<213> ORGANISM: Artificial Sequence
<220> FEATURE:
<223> OTHER INFORMATION: Synthetic Primer, F676

<400> SEQUENCE: 1179
aauuguugcc auuucagggu uucug                                       25

```
<210> SEQ ID NO 1180
<211> LENGTH: 26
<212> TYPE: RNA
<213> ORGANISM: Artificial Sequence
<220> FEATURE:
<223> OTHER INFORMATION: Synthetic Primer, F677

<400> SEQUENCE: 1180
cucaccuauc ucccaggccu aaaaua                                              26

<210> SEQ ID NO 1181
<211> LENGTH: 22
<212> TYPE: RNA
<213> ORGANISM: Artificial Sequence
<220> FEATURE:
<223> OTHER INFORMATION: Synthetic Primer, F678

<400> SEQUENCE: 1181
acaaacgaga ugccucuucc ag                                                  22

<210> SEQ ID NO 1182
<211> LENGTH: 21
<212> TYPE: RNA
<213> ORGANISM: Artificial Sequence
<220> FEATURE:
<223> OTHER INFORMATION: Synthetic Primer, F679

<400> SEQUENCE: 1182
ggcugucgug guagacuuag a                                                   21

<210> SEQ ID NO 1183
<211> LENGTH: 24
<212> TYPE: RNA
<213> ORGANISM: Artificial Sequence
<220> FEATURE:
<223> OTHER INFORMATION: Synthetic Primer, F680

<400> SEQUENCE: 1183
cugaguguau ccuggagguu guug                                                24

<210> SEQ ID NO 1184
<211> LENGTH: 26
<212> TYPE: RNA
<213> ORGANISM: Artificial Sequence
<220> FEATURE:
<223> OTHER INFORMATION: Synthetic Primer, F681

<400> SEQUENCE: 1184
gcuugguucu gauguuugua guguag                                              26

<210> SEQ ID NO 1185
<211> LENGTH: 25
<212> TYPE: DNA
<213> ORGANISM: Artificial Sequence
<220> FEATURE:
<223> OTHER INFORMATION: Synthetic DNA/RNA primer, F682

<400> SEQUENCE: 1185
uccuuguugg uguccauuuu cuugt                                               25

<210> SEQ ID NO 1186
<211> LENGTH: 24
<212> TYPE: RNA
<213> ORGANISM: Artificial Sequence
<220> FEATURE:
<223> OTHER INFORMATION: Synthetic Primer, F683
```

```
<400> SEQUENCE: 1186
acaugccauc auucuaggaa gcuc                                          24

<210> SEQ ID NO 1187
<211> LENGTH: 21
<212> TYPE: RNA
<213> ORGANISM: Artificial Sequence
<220> FEATURE:
<223> OTHER INFORMATION: Synthetic Primer, F684

<400> SEQUENCE: 1187
caggacccgc uucucugaaa g                                             21

<210> SEQ ID NO 1188
<211> LENGTH: 24
<212> TYPE: RNA
<213> ORGANISM: Artificial Sequence
<220> FEATURE:
<223> OTHER INFORMATION: Synthetic Primer, F685

<400> SEQUENCE: 1188
aagaccccuu uaacucaaga cugc                                          24

<210> SEQ ID NO 1189
<211> LENGTH: 19
<212> TYPE: RNA
<213> ORGANISM: Artificial Sequence
<220> FEATURE:
<223> OTHER INFORMATION: Synthetic Primer, F686

<400> SEQUENCE: 1189
ugcuccauga ggagacacc                                                19

<210> SEQ ID NO 1190
<211> LENGTH: 29
<212> TYPE: DNA
<213> ORGANISM: Artificial Sequence
<220> FEATURE:
<223> OTHER INFORMATION: Synthetic DNA/RNA primer, F687

<400> SEQUENCE: 1190
aauguaaccu ugcuaaagga gugauuuct                                     29

<210> SEQ ID NO 1191
<211> LENGTH: 29
<212> TYPE: RNA
<213> ORGANISM: Artificial Sequence
<220> FEATURE:
<223> OTHER INFORMATION: Synthetic Primer, F688

<400> SEQUENCE: 1191
aacuggcaaa uauaucauug agccaaauc                                     29

<210> SEQ ID NO 1192
<211> LENGTH: 26
<212> TYPE: RNA
<213> ORGANISM: Artificial Sequence
<220> FEATURE:
<223> OTHER INFORMATION: Synthetic Primer, F689

<400> SEQUENCE: 1192
ggugugaaau gacugaguac aaacug                                        26

<210> SEQ ID NO 1193
<211> LENGTH: 25
```

```
<212> TYPE: DNA
<213> ORGANISM: Artificial Sequence
<220> FEATURE:
<223> OTHER INFORMATION: Synthetic DNA/RNA primer, F690

<400> SEQUENCE: 1193
auggugaaac cuguuuguug gacat                                         25

<210> SEQ ID NO 1194
<211> LENGTH: 25
<212> TYPE: RNA
<213> ORGANISM: Artificial Sequence
<220> FEATURE:
<223> OTHER INFORMATION: Synthetic Primer, F691

<400> SEQUENCE: 1194
ccugcucaug gucuuugagu auaug                                         25

<210> SEQ ID NO 1195
<211> LENGTH: 19
<212> TYPE: RNA
<213> ORGANISM: Artificial Sequence
<220> FEATURE:
<223> OTHER INFORMATION: Synthetic Primer, F692

<400> SEQUENCE: 1195
gccacacgca acugucuag                                                19

<210> SEQ ID NO 1196
<211> LENGTH: 25
<212> TYPE: RNA
<213> ORGANISM: Artificial Sequence
<220> FEATURE:
<223> OTHER INFORMATION: Synthetic Primer, F693

<400> SEQUENCE: 1196
gacaauccuu gcuuaccuga ggaac                                         25

<210> SEQ ID NO 1197
<211> LENGTH: 23
<212> TYPE: DNA
<213> ORGANISM: Artificial Sequence
<220> FEATURE:
<223> OTHER INFORMATION: Synthetic DNA/RNA primer, F694

<400> SEQUENCE: 1197
gcucgggauc cauauguggu aat                                           23

<210> SEQ ID NO 1198
<211> LENGTH: 22
<212> TYPE: DNA
<213> ORGANISM: Artificial Sequence
<220> FEATURE:
<223> OTHER INFORMATION: Synthetic DNA/RNA primer, F695

<400> SEQUENCE: 1198
ggcccuauac uuaggcccuu ut                                            22

<210> SEQ ID NO 1199
<211> LENGTH: 17
<212> TYPE: DNA
<213> ORGANISM: Artificial Sequence
<220> FEATURE:
<223> OTHER INFORMATION: Synthetic DNA/RNA primer, F696

<400> SEQUENCE: 1199
```
aacucacggu ggcugct                                              17

<210> SEQ ID NO 1200
<211> LENGTH: 25
<212> TYPE: RNA
<213> ORGANISM: Artificial Sequence
<220> FEATURE:
<223> OTHER INFORMATION: Synthetic Primer, F697

<400> SEQUENCE: 1200
uguccugguc auuuauagaa accga                                     25

<210> SEQ ID NO 1201
<211> LENGTH: 28
<212> TYPE: DNA
<213> ORGANISM: Artificial Sequence
<220> FEATURE:
<223> OTHER INFORMATION: Synthetic DNA/RNA primer, F698

<400> SEQUENCE: 1201
ucucaugucu gaacugaaga uaaugact                                  28

<210> SEQ ID NO 1202
<211> LENGTH: 24
<212> TYPE: DNA
<213> ORGANISM: Artificial Sequence
<220> FEATURE:
<223> OTHER INFORMATION: Synthetic DNA/RNA primer, F699

<400> SEQUENCE: 1202
uugguagcuc agcuggacug auat                                      24

<210> SEQ ID NO 1203
<211> LENGTH: 24
<212> TYPE: RNA
<213> ORGANISM: Artificial Sequence
<220> FEATURE:
<223> OTHER INFORMATION: Synthetic Primer, F700

<400> SEQUENCE: 1203
augaagcagg cugauacuac acag                                      24

<210> SEQ ID NO 1204
<211> LENGTH: 23
<212> TYPE: RNA
<213> ORGANISM: Artificial Sequence
<220> FEATURE:
<223> OTHER INFORMATION: Synthetic Primer, F701

<400> SEQUENCE: 1204
uugugaagau cugugacuuu ggc                                       23

<210> SEQ ID NO 1205
<211> LENGTH: 28
<212> TYPE: RNA
<213> ORGANISM: Artificial Sequence
<220> FEATURE:
<223> OTHER INFORMATION: Synthetic Primer, F702

<400> SEQUENCE: 1205
ccuuuggguu auaaauagug cacucaga                                  28

<210> SEQ ID NO 1206
<211> LENGTH: 27
<212> TYPE: DNA
<213> ORGANISM: Artificial Sequence

```
<220> FEATURE:
<223> OTHER INFORMATION: Synthetic DNA/RNA primer, F703

<400> SEQUENCE: 1206
gggaagaaaa guguuugaa augugut                                          27

<210> SEQ ID NO 1207
<211> LENGTH: 23
<212> TYPE: RNA
<213> ORGANISM: Artificial Sequence
<220> FEATURE:
<223> OTHER INFORMATION: Synthetic Primer, F704

<400> SEQUENCE: 1207
uggcuuugaa ucuuggcca gua                                              23

<210> SEQ ID NO 1208
<211> LENGTH: 21
<212> TYPE: RNA
<213> ORGANISM: Artificial Sequence
<220> FEATURE:
<223> OTHER INFORMATION: Synthetic Primer, F705

<400> SEQUENCE: 1208
gucgaggcaa uggaaaagcu c                                               21

<210> SEQ ID NO 1209
<211> LENGTH: 25
<212> TYPE: RNA
<213> ORGANISM: Artificial Sequence
<220> FEATURE:
<223> OTHER INFORMATION: Synthetic Primer, F706

<400> SEQUENCE: 1209
agaacagcuc aaagcaauuu cuaca                                           25

<210> SEQ ID NO 1210
<211> LENGTH: 26
<212> TYPE: RNA
<213> ORGANISM: Artificial Sequence
<220> FEATURE:
<223> OTHER INFORMATION: Synthetic Primer, F707

<400> SEQUENCE: 1210
agcaagaggc uuuggaguau uucaug                                          26

<210> SEQ ID NO 1211
<211> LENGTH: 29
<212> TYPE: DNA
<213> ORGANISM: Artificial Sequence
<220> FEATURE:
<223> OTHER INFORMATION: Synthetic DNA/RNA primer, F708

<400> SEQUENCE: 1211
uguucaugcu guguauguaa uagaaugut                                       29

<210> SEQ ID NO 1212
<211> LENGTH: 28
<212> TYPE: RNA
<213> ORGANISM: Artificial Sequence
<220> FEATURE:
<223> OTHER INFORMATION: Synthetic Primer, F709

<400> SEQUENCE: 1212
cuggaaugcc agaacuacaa ucuuuuga                                        28
```

<210> SEQ ID NO 1213
<211> LENGTH: 28
<212> TYPE: DNA
<213> ORGANISM: Artificial Sequence
<220> FEATURE:
<223> OTHER INFORMATION: Synthetic DNA/RNA primer, F710

<400> SEQUENCE: 1213
cucaagaagc agaaagggaa gaauuuut                                    28

<210> SEQ ID NO 1214
<211> LENGTH: 24
<212> TYPE: RNA
<213> ORGANISM: Artificial Sequence
<220> FEATURE:
<223> OTHER INFORMATION: Synthetic Primer, F711

<400> SEQUENCE: 1214
ugacagccau caucaaagag aucg                                        24

<210> SEQ ID NO 1215
<211> LENGTH: 24
<212> TYPE: RNA
<213> ORGANISM: Artificial Sequence
<220> FEATURE:
<223> OTHER INFORMATION: Synthetic Primer, F712

<400> SEQUENCE: 1215
gggauuuccu gcagaaagac uuga                                        24

<210> SEQ ID NO 1216
<211> LENGTH: 19
<212> TYPE: RNA
<213> ORGANISM: Artificial Sequence
<220> FEATURE:
<223> OTHER INFORMATION: Synthetic Primer, F713

<400> SEQUENCE: 1216
aaggcacaag aggcccuag                                              19

<210> SEQ ID NO 1217
<211> LENGTH: 26
<212> TYPE: DNA
<213> ORGANISM: Artificial Sequence
<220> FEATURE:
<223> OTHER INFORMATION: Synthetic DNA/RNA primer, F714

<400> SEQUENCE: 1217
accaauggcu aagugaagau gacaat                                      26

<210> SEQ ID NO 1218
<211> LENGTH: 26
<212> TYPE: RNA
<213> ORGANISM: Artificial Sequence
<220> FEATURE:
<223> OTHER INFORMATION: Synthetic Primer, F715

<400> SEQUENCE: 1218
agguuaucuu uuuaccacag uugcac                                      26

<210> SEQ ID NO 1219
<211> LENGTH: 25
<212> TYPE: RNA
<213> ORGANISM: Artificial Sequence
<220> FEATURE:
<223> OTHER INFORMATION: Synthetic Primer, F716

```
<400> SEQUENCE: 1219
uuuucugucc accagggagu aacua                                          25

<210> SEQ ID NO 1220
<211> LENGTH: 26
<212> TYPE: RNA
<213> ORGANISM: Artificial Sequence
<220> FEATURE:
<223> OTHER INFORMATION: Synthetic Primer, F717

<400> SEQUENCE: 1220
gacaaguuca uguacuuuga guuccc                                         26

<210> SEQ ID NO 1221
<211> LENGTH: 24
<212> TYPE: RNA
<213> ORGANISM: Artificial Sequence
<220> FEATURE:
<223> OTHER INFORMATION: Synthetic Primer, F718

<400> SEQUENCE: 1221
agcaaauaaa gacaaagcca accg                                           24

<210> SEQ ID NO 1222
<211> LENGTH: 30
<212> TYPE: DNA
<213> ORGANISM: Artificial Sequence
<220> FEATURE:
<223> OTHER INFORMATION: Synthetic DNA/RNA primer, F719

<400> SEQUENCE: 1222
aguuuaagau gagucauauu uguggguuut                                     30

<210> SEQ ID NO 1223
<211> LENGTH: 24
<212> TYPE: RNA
<213> ORGANISM: Artificial Sequence
<220> FEATURE:
<223> OTHER INFORMATION: Synthetic Primer, F720

<400> SEQUENCE: 1223
cugaccaugu ggacauuagg ugug                                           24

<210> SEQ ID NO 1224
<211> LENGTH: 22
<212> TYPE: RNA
<213> ORGANISM: Artificial Sequence
<220> FEATURE:
<223> OTHER INFORMATION: Synthetic Primer, F721

<400> SEQUENCE: 1224
ccuucccucg ggaaaaacug ac                                             22

<210> SEQ ID NO 1225
<211> LENGTH: 26
<212> TYPE: RNA
<213> ORGANISM: Artificial Sequence
<220> FEATURE:
<223> OTHER INFORMATION: Synthetic Primer, F722

<400> SEQUENCE: 1225
guuugguuuu guaggucuug uggaug                                         26

<210> SEQ ID NO 1226
```

```
<211> LENGTH: 21
<212> TYPE: RNA
<213> ORGANISM: Artificial Sequence
<220> FEATURE:
<223> OTHER INFORMATION: Synthetic Primer, F723

<400> SEQUENCE: 1226
gagguggccu gaucuucaca a                                              21

<210> SEQ ID NO 1227
<211> LENGTH: 25
<212> TYPE: DNA
<213> ORGANISM: Artificial Sequence
<220> FEATURE:
<223> OTHER INFORMATION: Synthetic DNA/RNA primer, F724

<400> SEQUENCE: 1227
cgcuuaugca uacucaggau gagut                                          25

<210> SEQ ID NO 1228
<211> LENGTH: 23
<212> TYPE: RNA
<213> ORGANISM: Artificial Sequence
<220> FEATURE:
<223> OTHER INFORMATION: Synthetic Primer, F725

<400> SEQUENCE: 1228
uaagguuccu ucaagcugcc cua                                            23

<210> SEQ ID NO 1229
<211> LENGTH: 25
<212> TYPE: DNA
<213> ORGANISM: Artificial Sequence
<220> FEATURE:
<223> OTHER INFORMATION: Synthetic DNA/RNA primer, F726

<400> SEQUENCE: 1229
caugggagga uguucuuucc cauut                                          25

<210> SEQ ID NO 1230
<211> LENGTH: 25
<212> TYPE: RNA
<213> ORGANISM: Artificial Sequence
<220> FEATURE:
<223> OTHER INFORMATION: Synthetic Primer, F727

<400> SEQUENCE: 1230
uuuucuuccu aagguugcac auagg                                          25

<210> SEQ ID NO 1231
<211> LENGTH: 21
<212> TYPE: DNA
<213> ORGANISM: Artificial Sequence
<220> FEATURE:
<223> OTHER INFORMATION: Synthetic DNA/RNA primer, F728

<400> SEQUENCE: 1231
auuuuuggcu uccuggccuu t                                              21

<210> SEQ ID NO 1232
<211> LENGTH: 21
<212> TYPE: RNA
<213> ORGANISM: Artificial Sequence
<220> FEATURE:
<223> OTHER INFORMATION: Synthetic Primer, F729

<400> SEQUENCE: 1232
```
ggaaagccuc accugucuac g                                        21

<210> SEQ ID NO 1233
<211> LENGTH: 18
<212> TYPE: RNA
<213> ORGANISM: Artificial Sequence
<220> FEATURE:
<223> OTHER INFORMATION: Synthetic Primer, F730

<400> SEQUENCE: 1233
ucaagaaucg cccgagcc                                            18

<210> SEQ ID NO 1234
<211> LENGTH: 20
<212> TYPE: RNA
<213> ORGANISM: Artificial Sequence
<220> FEATURE:
<223> OTHER INFORMATION: Synthetic Primer, F731

<400> SEQUENCE: 1234
uugguucgga cagacaaccc                                          20

<210> SEQ ID NO 1235
<211> LENGTH: 22
<212> TYPE: RNA
<213> ORGANISM: Artificial Sequence
<220> FEATURE:
<223> OTHER INFORMATION: Synthetic Primer, F732

<400> SEQUENCE: 1235
cucugcacag cuccaaugag ac                                       22

<210> SEQ ID NO 1236
<211> LENGTH: 23
<212> TYPE: DNA
<213> ORGANISM: Artificial Sequence
<220> FEATURE:
<223> OTHER INFORMATION: Synthetic DNA/RNA primer, F733

<400> SEQUENCE: 1236
gcuacaagaa cuaccgauac cgt                                      23

<210> SEQ ID NO 1237
<211> LENGTH: 20
<212> TYPE: RNA
<213> ORGANISM: Artificial Sequence
<220> FEATURE:
<223> OTHER INFORMATION: Synthetic Primer, F734

<400> SEQUENCE: 1237
cucggagagg agccauacug                                          20

<210> SEQ ID NO 1238
<211> LENGTH: 26
<212> TYPE: RNA
<213> ORGANISM: Artificial Sequence
<220> FEATURE:
<223> OTHER INFORMATION: Synthetic Primer, F735

<400> SEQUENCE: 1238
uauaaugaca guuaacccug ccagga                                   26

<210> SEQ ID NO 1239
<211> LENGTH: 22
<212> TYPE: RNA

```
<213> ORGANISM: Artificial Sequence
<220> FEATURE:
<223> OTHER INFORMATION: Synthetic Primer, F736

<400> SEQUENCE: 1239
aggaagagca cagucacuuu ga                                            22

<210> SEQ ID NO 1240
<211> LENGTH: 22
<212> TYPE: RNA
<213> ORGANISM: Artificial Sequence
<220> FEATURE:
<223> OTHER INFORMATION: Synthetic Primer, F737

<400> SEQUENCE: 1240
caguggagcg aauuccuuug ga                                            22

<210> SEQ ID NO 1241
<211> LENGTH: 19
<212> TYPE: RNA
<213> ORGANISM: Artificial Sequence
<220> FEATURE:
<223> OTHER INFORMATION: Synthetic Primer, F738

<400> SEQUENCE: 1241
uugggucguu gggcauucc                                                19

<210> SEQ ID NO 1242
<211> LENGTH: 21
<212> TYPE: RNA
<213> ORGANISM: Artificial Sequence
<220> FEATURE:
<223> OTHER INFORMATION: Synthetic Primer, F739

<400> SEQUENCE: 1242
caguucacag ugcagcgaaa a                                             21

<210> SEQ ID NO 1243
<211> LENGTH: 28
<212> TYPE: RNA
<213> ORGANISM: Artificial Sequence
<220> FEATURE:
<223> OTHER INFORMATION: Synthetic Primer, F740

<400> SEQUENCE: 1243
aaauaucuac acacaggucu acaagguc                                      28

<210> SEQ ID NO 1244
<211> LENGTH: 22
<212> TYPE: RNA
<213> ORGANISM: Artificial Sequence
<220> FEATURE:
<223> OTHER INFORMATION: Synthetic Primer, F741

<400> SEQUENCE: 1244
cauccgggcu uuacgcaaau aa                                            22

<210> SEQ ID NO 1245
<211> LENGTH: 25
<212> TYPE: DNA
<213> ORGANISM: Artificial Sequence
<220> FEATURE:
<223> OTHER INFORMATION: Synthetic DNA/RNA primer, F742

<400> SEQUENCE: 1245
gccuccuuca ggaauucaau cuuct                                         25
```

```
<210> SEQ ID NO 1246
<211> LENGTH: 19
<212> TYPE: RNA
<213> ORGANISM: Artificial Sequence
<220> FEATURE:
<223> OTHER INFORMATION: Synthetic Primer, F743

<400> SEQUENCE: 1246
augaguucug ggcacuggg                                                  19

<210> SEQ ID NO 1247
<211> LENGTH: 24
<212> TYPE: DNA
<213> ORGANISM: Artificial Sequence
<220> FEATURE:
<223> OTHER INFORMATION: Synthetic DNA/RNA primer, F744

<400> SEQUENCE: 1247
gaugcaaacu cuugcacaaa ugct                                            24

<210> SEQ ID NO 1248
<211> LENGTH: 21
<212> TYPE: RNA
<213> ORGANISM: Artificial Sequence
<220> FEATURE:
<223> OTHER INFORMATION: Synthetic Primer, F745

<400> SEQUENCE: 1248
gaaccccgag ggcaaauaca g                                               21

<210> SEQ ID NO 1249
<211> LENGTH: 24
<212> TYPE: RNA
<213> ORGANISM: Artificial Sequence
<220> FEATURE:
<223> OTHER INFORMATION: Synthetic Primer, F746

<400> SEQUENCE: 1249
caguucgugg gcuuguuuug uauc                                            24

<210> SEQ ID NO 1250
<211> LENGTH: 22
<212> TYPE: RNA
<213> ORGANISM: Artificial Sequence
<220> FEATURE:
<223> OTHER INFORMATION: Synthetic Primer, F747

<400> SEQUENCE: 1250
uuaaagcugg cuauggcacc ug                                              22

<210> SEQ ID NO 1251
<211> LENGTH: 20
<212> TYPE: RNA
<213> ORGANISM: Artificial Sequence
<220> FEATURE:
<223> OTHER INFORMATION: Synthetic Primer, F748

<400> SEQUENCE: 1251
caucucucac caucccaagg                                                 20

<210> SEQ ID NO 1252
<211> LENGTH: 18
<212> TYPE: RNA
<213> ORGANISM: Artificial Sequence
<220> FEATURE:
```

<223> OTHER INFORMATION: Synthetic Primer, F749

<400> SEQUENCE: 1252
auacgcagcc uguaccca                                                       18

<210> SEQ ID NO 1253
<211> LENGTH: 24
<212> TYPE: RNA
<213> ORGANISM: Artificial Sequence
<220> FEATURE:
<223> OTHER INFORMATION: Synthetic Primer, F750

<400> SEQUENCE: 1253
caccucucuc aagaguuugg augg                                                24

<210> SEQ ID NO 1254
<211> LENGTH: 20
<212> TYPE: DNA
<213> ORGANISM: Artificial Sequence
<220> FEATURE:
<223> OTHER INFORMATION: Synthetic DNA/RNA primer, F751

<400> SEQUENCE: 1254
agauugcgag agagcugcat                                                     20

<210> SEQ ID NO 1255
<211> LENGTH: 22
<212> TYPE: RNA
<213> ORGANISM: Artificial Sequence
<220> FEATURE:
<223> OTHER INFORMATION: Synthetic Primer, F752

<400> SEQUENCE: 1255
cugugcugca uuucagagaa cg                                                  22

<210> SEQ ID NO 1256
<211> LENGTH: 19
<212> TYPE: RNA
<213> ORGANISM: Artificial Sequence
<220> FEATURE:
<223> OTHER INFORMATION: Synthetic Primer, F753

<400> SEQUENCE: 1256
aagacccaag cugccugac                                                      19

<210> SEQ ID NO 1257
<211> LENGTH: 24
<212> TYPE: RNA
<213> ORGANISM: Artificial Sequence
<220> FEATURE:
<223> OTHER INFORMATION: Synthetic Primer, F754

<400> SEQUENCE: 1257
gcuauuuuuc cucacagcuc guuc                                                24

<210> SEQ ID NO 1258
<211> LENGTH: 28
<212> TYPE: RNA
<213> ORGANISM: Artificial Sequence
<220> FEATURE:
<223> OTHER INFORMATION: Synthetic Primer, F755

<400> SEQUENCE: 1258
cuccuuccua gagaguuaga guaacuuc                                            28

```
<210> SEQ ID NO 1259
<211> LENGTH: 26
<212> TYPE: RNA
<213> ORGANISM: Artificial Sequence
<220> FEATURE:
<223> OTHER INFORMATION: Synthetic Primer, F756

<400> SEQUENCE: 1259
gagccuguuu ugugucuacu guucua                                          26

<210> SEQ ID NO 1260
<211> LENGTH: 19
<212> TYPE: DNA
<213> ORGANISM: Artificial Sequence
<220> FEATURE:
<223> OTHER INFORMATION: Synthetic DNA/RNA primer, F757

<400> SEQUENCE: 1260
cucuugcagc agccagact                                                  19

<210> SEQ ID NO 1261
<211> LENGTH: 20
<212> TYPE: RNA
<213> ORGANISM: Artificial Sequence
<220> FEATURE:
<223> OTHER INFORMATION: Synthetic Primer, F758

<400> SEQUENCE: 1261
ccaugggacu gacuuucugc                                                 20

<210> SEQ ID NO 1262
<211> LENGTH: 19
<212> TYPE: DNA
<213> ORGANISM: Artificial Sequence
<220> FEATURE:
<223> OTHER INFORMATION: Synthetic DNA/RNA primer, F759

<400> SEQUENCE: 1262
gcugaggacc ugguccuct                                                  19

<210> SEQ ID NO 1263
<211> LENGTH: 18
<212> TYPE: RNA
<213> ORGANISM: Artificial Sequence
<220> FEATURE:
<223> OTHER INFORMATION: Synthetic Primer, F760

<400> SEQUENCE: 1263
cugcaccagc agcuccua                                                   18

<210> SEQ ID NO 1264
<211> LENGTH: 23
<212> TYPE: DNA
<213> ORGANISM: Artificial Sequence
<220> FEATURE:
<223> OTHER INFORMATION: Synthetic DNA/RNA primer, F761

<400> SEQUENCE: 1264
cccggacgau auugaacaau ggt                                             23

<210> SEQ ID NO 1265
<211> LENGTH: 17
<212> TYPE: RNA
<213> ORGANISM: Artificial Sequence
<220> FEATURE:
<223> OTHER INFORMATION: Synthetic Primer, F762
```

<210> SEQ ID NO 1265 agccucacca cgagcug                                                    17

<210> SEQ ID NO 1266
<211> LENGTH: 23
<212> TYPE: RNA
<213> ORGANISM: Artificial Sequence
<220> FEATURE:
<223> OTHER INFORMATION: Synthetic Primer, F763

<400> SEQUENCE: 1266
caccuuuccu ugccucuuuc cua                                             23

<210> SEQ ID NO 1267
<211> LENGTH: 18
<212> TYPE: DNA
<213> ORGANISM: Artificial Sequence
<220> FEATURE:
<223> OTHER INFORMATION: Synthetic DNA/RNA primer, F764

<400> SEQUENCE: 1267
cucaaggaug cccaggct                                                   18

<210> SEQ ID NO 1268
<211> LENGTH: 21
<212> TYPE: RNA
<213> ORGANISM: Artificial Sequence
<220> FEATURE:
<223> OTHER INFORMATION: Synthetic Primer, F765

<400> SEQUENCE: 1268
ccucccugcu ucugucuccu a                                               21

<210> SEQ ID NO 1269
<211> LENGTH: 20
<212> TYPE: RNA
<213> ORGANISM: Artificial Sequence
<220> FEATURE:
<223> OTHER INFORMATION: Synthetic Primer, F766

<400> SEQUENCE: 1269
ccaguugcaa accagaccuc                                                 20

<210> SEQ ID NO 1270
<211> LENGTH: 22
<212> TYPE: RNA
<213> ORGANISM: Artificial Sequence
<220> FEATURE:
<223> OTHER INFORMATION: Synthetic Primer, F767

<400> SEQUENCE: 1270
acuccacacg caaauuuccu uc                                              22

<210> SEQ ID NO 1271
<211> LENGTH: 17
<212> TYPE: RNA
<213> ORGANISM: Artificial Sequence
<220> FEATURE:
<223> OTHER INFORMATION: Synthetic Primer, F768

<400> SEQUENCE: 1271
aggguggcaa guggcuc                                                    17

<210> SEQ ID NO 1272
<211> LENGTH: 18

```
<212> TYPE: RNA
<213> ORGANISM: Artificial Sequence
<220> FEATURE:
<223> OTHER INFORMATION: Synthetic Primer, F769

<400> SEQUENCE: 1272
gaggcucccc uuucuugc                                              18

<210> SEQ ID NO 1273
<211> LENGTH: 21
<212> TYPE: RNA
<213> ORGANISM: Artificial Sequence
<220> FEATURE:
<223> OTHER INFORMATION: Synthetic Primer, F770

<400> SEQUENCE: 1273
cugugacugc uuguagaugg c                                          21

<210> SEQ ID NO 1274
<211> LENGTH: 18
<212> TYPE: RNA
<213> ORGANISM: Artificial Sequence
<220> FEATURE:
<223> OTHER INFORMATION: Synthetic Primer, F771

<400> SEQUENCE: 1274
cugucgucuc uccagccc                                              18

<210> SEQ ID NO 1275
<211> LENGTH: 23
<212> TYPE: RNA
<213> ORGANISM: Artificial Sequence
<220> FEATURE:
<223> OTHER INFORMATION: Synthetic Primer, R498

<400> SEQUENCE: 1275
ugccaucauu cuugaggagg aag                                        23

<210> SEQ ID NO 1276
<211> LENGTH: 19
<212> TYPE: DNA
<213> ORGANISM: Artificial Sequence
<220> FEATURE:
<223> OTHER INFORMATION: Synthetic DNA/RNA primer, R499

<400> SEQUENCE: 1276
ugcaaucccu gccccggut                                             19

<210> SEQ ID NO 1277
<211> LENGTH: 21
<212> TYPE: DNA
<213> ORGANISM: Artificial Sequence
<220> FEATURE:
<223> OTHER INFORMATION: Synthetic DNA/RNA primer, R500

<400> SEQUENCE: 1277
ggauugcagg cucaccccaa t                                          21

<210> SEQ ID NO 1278
<211> LENGTH: 21
<212> TYPE: RNA
<213> ORGANISM: Artificial Sequence
<220> FEATURE:
<223> OTHER INFORMATION: Synthetic Primer, R501

<400> SEQUENCE: 1278
```
cuggauuucc ucauggaagc c                                         21

<210> SEQ ID NO 1279
<211> LENGTH: 21
<212> TYPE: RNA
<213> ORGANISM: Artificial Sequence
<220> FEATURE:
<223> OTHER INFORMATION: Synthetic Primer, R502

<400> SEQUENCE: 1279
aaauccaguu cguccuguuc a                                         21

<210> SEQ ID NO 1280
<211> LENGTH: 22
<212> TYPE: RNA
<213> ORGANISM: Artificial Sequence
<220> FEATURE:
<223> OTHER INFORMATION: Synthetic Primer, R503

<400> SEQUENCE: 1280
gaaacugccu cuugaccugu cc                                        22

<210> SEQ ID NO 1281
<211> LENGTH: 28
<212> TYPE: DNA
<213> ORGANISM: Artificial Sequence
<220> FEATURE:
<223> OTHER INFORMATION: Synthetic DNA/RNA primer, R504

<400> SEQUENCE: 1281
aggacaguca uguugccagu auuaaaat                                  28

<210> SEQ ID NO 1282
<211> LENGTH: 23
<212> TYPE: RNA
<213> ORGANISM: Artificial Sequence
<220> FEATURE:
<223> OTHER INFORMATION: Synthetic Primer, R505

<400> SEQUENCE: 1282
cuuccaugac uuuggcaauc ugg                                       23

<210> SEQ ID NO 1283
<211> LENGTH: 29
<212> TYPE: DNA
<213> ORGANISM: Artificial Sequence
<220> FEATURE:
<223> OTHER INFORMATION: Synthetic DNA/RNA primer, R506

<400> SEQUENCE: 1283
gaacaugucc uauuugaauu uuccgacut                                 29

<210> SEQ ID NO 1284
<211> LENGTH: 27
<212> TYPE: DNA
<213> ORGANISM: Artificial Sequence
<220> FEATURE:
<223> OTHER INFORMATION: Synthetic DNA/RNA primer, R507

<400> SEQUENCE: 1284
gacacaaaga cuggcuuaca uuuugat                                   27

<210> SEQ ID NO 1285
<211> LENGTH: 22
<212> TYPE: DNA
<213> ORGANISM: Artificial Sequence

```
<220> FEATURE:
<223> OTHER INFORMATION: Synthetic DNA/RNA primer, R508

<400> SEQUENCE: 1285
aggcugacca cuucuacucu gt                                                  22

<210> SEQ ID NO 1286
<211> LENGTH: 21
<212> TYPE: RNA
<213> ORGANISM: Artificial Sequence
<220> FEATURE:
<223> OTHER INFORMATION: Synthetic Primer, R509

<400> SEQUENCE: 1286
gcacucaggc uggaugaaca a                                                   21

<210> SEQ ID NO 1287
<211> LENGTH: 23
<212> TYPE: RNA
<213> ORGANISM: Artificial Sequence
<220> FEATURE:
<223> OTHER INFORMATION: Synthetic Primer, R510

<400> SEQUENCE: 1287
uguccagggc uaucuggaag auc                                                 23

<210> SEQ ID NO 1288
<211> LENGTH: 20
<212> TYPE: RNA
<213> ORGANISM: Artificial Sequence
<220> FEATURE:
<223> OTHER INFORMATION: Synthetic Primer, R511

<400> SEQUENCE: 1288
gcagcauuua cugcagcuug                                                     20

<210> SEQ ID NO 1289
<211> LENGTH: 27
<212> TYPE: RNA
<213> ORGANISM: Artificial Sequence
<220> FEATURE:
<223> OTHER INFORMATION: Synthetic Primer, R512

<400> SEQUENCE: 1289
ugacagaagu acaucugcua aacauga                                             27

<210> SEQ ID NO 1290
<211> LENGTH: 22
<212> TYPE: RNA
<213> ORGANISM: Artificial Sequence
<220> FEATURE:
<223> OTHER INFORMATION: Synthetic Primer, R513

<400> SEQUENCE: 1290
cucacaggau cuucagcuga cc                                                  22

<210> SEQ ID NO 1291
<211> LENGTH: 22
<212> TYPE: DNA
<213> ORGANISM: Artificial Sequence
<220> FEATURE:
<223> OTHER INFORMATION: Synthetic DNA/RNA primer, R514

<400> SEQUENCE: 1291
acuuuguugg cauggcagaa at                                                  22
```

<210> SEQ ID NO 1292
<211> LENGTH: 17
<212> TYPE: DNA
<213> ORGANISM: Artificial Sequence
<220> FEATURE:
<223> OTHER INFORMATION: Synthetic DNA/RNA primer, R515

<400> SEQUENCE: 1292
gccguggugc ugaccat                                                  17

<210> SEQ ID NO 1293
<211> LENGTH: 24
<212> TYPE: RNA
<213> ORGANISM: Artificial Sequence
<220> FEATURE:
<223> OTHER INFORMATION: Synthetic Primer, R516

<400> SEQUENCE: 1293
gugaugauug ggagauuccu gaug                                          24

<210> SEQ ID NO 1294
<211> LENGTH: 29
<212> TYPE: DNA
<213> ORGANISM: Artificial Sequence
<220> FEATURE:
<223> OTHER INFORMATION: Synthetic DNA/RNA primer, R517

<400> SEQUENCE: 1294
gcucugauag gaaaaugaga ucuacugut                                     29

<210> SEQ ID NO 1295
<211> LENGTH: 18
<212> TYPE: DNA
<213> ORGANISM: Artificial Sequence
<220> FEATURE:
<223> OTHER INFORMATION: Synthetic DNA/RNA primer, R518

<400> SEQUENCE: 1295
cuccagcagg gcuucgat                                                 18

<210> SEQ ID NO 1296
<211> LENGTH: 25
<212> TYPE: RNA
<213> ORGANISM: Artificial Sequence
<220> FEATURE:
<223> OTHER INFORMATION: Synthetic Primer, R519

<400> SEQUENCE: 1296
ggacuuugca acuucaacaa aacuc                                         25

<210> SEQ ID NO 1297
<211> LENGTH: 21
<212> TYPE: RNA
<213> ORGANISM: Artificial Sequence
<220> FEATURE:
<223> OTHER INFORMATION: Synthetic Primer, R520

<400> SEQUENCE: 1297
cuaggugucu cccccuguaa g                                             21

<210> SEQ ID NO 1298
<211> LENGTH: 18
<212> TYPE: DNA
<213> ORGANISM: Artificial Sequence
<220> FEATURE:
<223> OTHER INFORMATION: Synthetic DNA/RNA primer, R521

```
<400> SEQUENCE: 1298
agguucaggc cuugcact                                              18

<210> SEQ ID NO 1299
<211> LENGTH: 20
<212> TYPE: DNA
<213> ORGANISM: Artificial Sequence
<220> FEATURE:
<223> OTHER INFORMATION: Synthetic Primer, R522

<400> SEQUENCE: 1299
ccagcccagg aagcaaagag                                            20

<210> SEQ ID NO 1300
<211> LENGTH: 22
<212> TYPE: RNA
<213> ORGANISM: Artificial Sequence
<220> FEATURE:
<223> OTHER INFORMATION: Synthetic Primer, R523

<400> SEQUENCE: 1300
uuaaaacugg ucucgcucuc cc                                         22

<210> SEQ ID NO 1301
<211> LENGTH: 20
<212> TYPE: RNA
<213> ORGANISM: Artificial Sequence
<220> FEATURE:
<223> OTHER INFORMATION: Synthetic Primer, R524

<400> SEQUENCE: 1301
gaaagcggga aucgcagaaa                                            20

<210> SEQ ID NO 1302
<211> LENGTH: 22
<212> TYPE: DNA
<213> ORGANISM: Artificial Sequence
<220> FEATURE:
<223> OTHER INFORMATION: Synthetic DNA/RNA primer, R525

<400> SEQUENCE: 1302
ggaagaccuc uucuucgcac ut                                         22

<210> SEQ ID NO 1303
<211> LENGTH: 21
<212> TYPE: RNA
<213> ORGANISM: Artificial Sequence
<220> FEATURE:
<223> OTHER INFORMATION: Synthetic Primer, R526

<400> SEQUENCE: 1303
caaaagagcu cccccaucuc c                                          21

<210> SEQ ID NO 1304
<211> LENGTH: 25
<212> TYPE: RNA
<213> ORGANISM: Artificial Sequence
<220> FEATURE:
<223> OTHER INFORMATION: Synthetic Primer, R527

<400> SEQUENCE: 1304
agaagagaca ucuggacuua gccaa                                      25

<210> SEQ ID NO 1305
```

```
<211> LENGTH: 21
<212> TYPE: RNA
<213> ORGANISM: Artificial Sequence
<220> FEATURE:
<223> OTHER INFORMATION: Synthetic Primer, R528

<400> SEQUENCE: 1305
aucaucgacg guggguacau g                                              21

<210> SEQ ID NO 1306
<211> LENGTH: 20
<212> TYPE: RNA
<213> ORGANISM: Artificial Sequence
<220> FEATURE:
<223> OTHER INFORMATION: Synthetic Primer, R529

<400> SEQUENCE: 1306
cguugguccu gacgguacug                                                20

<210> SEQ ID NO 1307
<211> LENGTH: 25
<212> TYPE: RNA
<213> ORGANISM: Artificial Sequence
<220> FEATURE:
<223> OTHER INFORMATION: Synthetic Primer, R530

<400> SEQUENCE: 1307
ccauucugag gacugcuggu uuaua                                          25

<210> SEQ ID NO 1308
<211> LENGTH: 23
<212> TYPE: RNA
<213> ORGANISM: Artificial Sequence
<220> FEATURE:
<223> OTHER INFORMATION: Synthetic Primer, R531

<400> SEQUENCE: 1308
ccaggaccau cauccuacug uaa                                            23

<210> SEQ ID NO 1309
<211> LENGTH: 22
<212> TYPE: RNA
<213> ORGANISM: Artificial Sequence
<220> FEATURE:
<223> OTHER INFORMATION: Synthetic Primer, R532

<400> SEQUENCE: 1309
gaguguuugc uccucacucu uc                                             22

<210> SEQ ID NO 1310
<211> LENGTH: 25
<212> TYPE: DNA
<213> ORGANISM: Artificial Sequence
<220> FEATURE:
<223> OTHER INFORMATION: Synthetic DNA/RNA primer, R533

<400> SEQUENCE: 1310
cuucagguuu ccuucucuca uggut                                          25

<210> SEQ ID NO 1311
<211> LENGTH: 20
<212> TYPE: RNA
<213> ORGANISM: Artificial Sequence
<220> FEATURE:
<223> OTHER INFORMATION: Synthetic Primer, R534

<400> SEQUENCE: 1311
```
ggaugagcuc acagagcugc                                            20

<210> SEQ ID NO 1312
<211> LENGTH: 23
<212> TYPE: DNA
<213> ORGANISM: Artificial Sequence
<220> FEATURE:
<223> OTHER INFORMATION: Synthetic DNA/RNA primer, R535

<400> SEQUENCE: 1312
ucaaaaagca ugcccagacc uut                                        23

<210> SEQ ID NO 1313
<211> LENGTH: 23
<212> TYPE: RNA
<213> ORGANISM: Artificial Sequence
<220> FEATURE:
<223> OTHER INFORMATION: Synthetic Primer, R536

<400> SEQUENCE: 1313
acuuugagac uucugcuuug cuc                                        23

<210> SEQ ID NO 1314
<211> LENGTH: 24
<212> TYPE: RNA
<213> ORGANISM: Artificial Sequence
<220> FEATURE:
<223> OTHER INFORMATION: Synthetic Primer, R537

<400> SEQUENCE: 1314
aucgaaaaac ugugcaucua cacc                                       24

<210> SEQ ID NO 1315
<211> LENGTH: 18
<212> TYPE: DNA
<213> ORGANISM: Artificial Sequence
<220> FEATURE:
<223> OTHER INFORMATION: Synthetic DNA/RNA primer, R538

<400> SEQUENCE: 1315
agacccagca gugacugt                                              18

<210> SEQ ID NO 1316
<211> LENGTH: 24
<212> TYPE: DNA
<213> ORGANISM: Artificial Sequence
<220> FEATURE:
<223> OTHER INFORMATION: Synthetic DNA/RNA primer, R539

<400> SEQUENCE: 1316
acaaguauaa ugagcacccc uuct                                       24

<210> SEQ ID NO 1317
<211> LENGTH: 23
<212> TYPE: RNA
<213> ORGANISM: Artificial Sequence
<220> FEATURE:
<223> OTHER INFORMATION: Synthetic Primer, R540

<400> SEQUENCE: 1317
guggacacac cuguauuccu gag                                        23

<210> SEQ ID NO 1318
<211> LENGTH: 20
<212> TYPE: RNA

```
<213> ORGANISM: Artificial Sequence
<220> FEATURE:
<223> OTHER INFORMATION: Synthetic Primer, R541

<400> SEQUENCE: 1318
ccgaccaguu gggcaaaauc                                                  20

<210> SEQ ID NO 1319
<211> LENGTH: 25
<212> TYPE: DNA
<213> ORGANISM: Artificial Sequence
<220> FEATURE:
<223> OTHER INFORMATION: Synthetic DNA/RNA primer, R542

<400> SEQUENCE: 1319
gcagaagucu guuucuuca uggut                                             25

<210> SEQ ID NO 1320
<211> LENGTH: 20
<212> TYPE: RNA
<213> ORGANISM: Artificial Sequence
<220> FEATURE:
<223> OTHER INFORMATION: Synthetic Primer, R543

<400> SEQUENCE: 1320
aggccauguu ggguuaaagg                                                  20

<210> SEQ ID NO 1321
<211> LENGTH: 24
<212> TYPE: RNA
<213> ORGANISM: Artificial Sequence
<220> FEATURE:
<223> OTHER INFORMATION: Synthetic Primer, R544

<400> SEQUENCE: 1321
agaaucuaca gcuaccagau ggca                                             24

<210> SEQ ID NO 1322
<211> LENGTH: 24
<212> TYPE: RNA
<213> ORGANISM: Artificial Sequence
<220> FEATURE:
<223> OTHER INFORMATION: Synthetic Primer, R545

<400> SEQUENCE: 1322
ccuaguuucc agugcaucug uacc                                             24

<210> SEQ ID NO 1323
<211> LENGTH: 24
<212> TYPE: RNA
<213> ORGANISM: Artificial Sequence
<220> FEATURE:
<223> OTHER INFORMATION: Synthetic Primer, R546

<400> SEQUENCE: 1323
gguccccauc cauucuuccu auuc                                             24

<210> SEQ ID NO 1324
<211> LENGTH: 24
<212> TYPE: RNA
<213> ORGANISM: Artificial Sequence
<220> FEATURE:
<223> OTHER INFORMATION: Synthetic Primer, R547

<400> SEQUENCE: 1324
uguggagugu uggcuguauc uuug                                             24
```

-continued

<210> SEQ ID NO 1325
<211> LENGTH: 25
<212> TYPE: RNA
<213> ORGANISM: Artificial Sequence
<220> FEATURE:
<223> OTHER INFORMATION: Synthetic Primer, R548

<400> SEQUENCE: 1325
cucuguaagc gacuuuggu gauag                                          25

<210> SEQ ID NO 1326
<211> LENGTH: 25
<212> TYPE: RNA
<213> ORGANISM: Artificial Sequence
<220> FEATURE:
<223> OTHER INFORMATION: Synthetic Primer, R549

<400> SEQUENCE: 1326
gcccaaccaa uugagaaguu uguaa                                         25

<210> SEQ ID NO 1327
<211> LENGTH: 24
<212> TYPE: RNA
<213> ORGANISM: Artificial Sequence
<220> FEATURE:
<223> OTHER INFORMATION: Synthetic Primer, R550

<400> SEQUENCE: 1327
uuagucagga gucuaagcca acag                                          24

<210> SEQ ID NO 1328
<211> LENGTH: 23
<212> TYPE: RNA
<213> ORGANISM: Artificial Sequence
<220> FEATURE:
<223> OTHER INFORMATION: Synthetic Primer, R551

<400> SEQUENCE: 1328
cuugcccgca ucuauaguuu cca                                           23

<210> SEQ ID NO 1329
<211> LENGTH: 28
<212> TYPE: DNA
<213> ORGANISM: Artificial Sequence
<220> FEATURE:
<223> OTHER INFORMATION: Synthetic DNA/RNA primer, R552

<400> SEQUENCE: 1329
aacuuccguu uugaguguuu acugauut                                      28

<210> SEQ ID NO 1330
<211> LENGTH: 25
<212> TYPE: DNA
<213> ORGANISM: Artificial Sequence
<220> FEATURE:
<223> OTHER INFORMATION: Synthetic DNA/RNA primer, R553

<400> SEQUENCE: 1330
uuacuuggau aaaguuccag agcct                                         25

<210> SEQ ID NO 1331
<211> LENGTH: 25
<212> TYPE: DNA
<213> ORGANISM: Artificial Sequence
<220> FEATURE:

```
-continued

<223> OTHER INFORMATION: Synthetic DNA/RNA primer, R554

<400> SEQUENCE: 1331
gcuuauugcc accuacuuaa ccuct                                    25

<210> SEQ ID NO 1332
<211> LENGTH: 19
<212> TYPE: RNA
<213> ORGANISM: Artificial Sequence
<220> FEATURE:
<223> OTHER INFORMATION: Synthetic Primer, R555

<400> SEQUENCE: 1332
cuucagcccu gcagggaaa                                           19

<210> SEQ ID NO 1333
<211> LENGTH: 28
<212> TYPE: RNA
<213> ORGANISM: Artificial Sequence
<220> FEATURE:
<223> OTHER INFORMATION: Synthetic Primer, R556

<400> SEQUENCE: 1333
ggcaaguuca acauuauucc cuuuugua                                 28

<210> SEQ ID NO 1334
<211> LENGTH: 23
<212> TYPE: RNA
<213> ORGANISM: Artificial Sequence
<220> FEATURE:
<223> OTHER INFORMATION: Synthetic Primer, R557

<400> SEQUENCE: 1334
ucuuccucag gauugccuuu acc                                      23

<210> SEQ ID NO 1335
<211> LENGTH: 26
<212> TYPE: RNA
<213> ORGANISM: Artificial Sequence
<220> FEATURE:
<223> OTHER INFORMATION: Synthetic Primer, R558

<400> SEQUENCE: 1335
cauacagaga gggucaucag ugauac                                   26

<210> SEQ ID NO 1336
<211> LENGTH: 23
<212> TYPE: RNA
<213> ORGANISM: Artificial Sequence
<220> FEATURE:
<223> OTHER INFORMATION: Synthetic Primer, R559

<400> SEQUENCE: 1336
gaaagucucc cacaaaguaa ccc                                      23

<210> SEQ ID NO 1337
<211> LENGTH: 20
<212> TYPE: RNA
<213> ORGANISM: Artificial Sequence
<220> FEATURE:
<223> OTHER INFORMATION: Synthetic Primer, R560

<400> SEQUENCE: 1337
auagucauag ccgggccaca                                          20
```

-continued

```
<210> SEQ ID NO 1338
<211> LENGTH: 26
<212> TYPE: RNA
<213> ORGANISM: Artificial Sequence
<220> FEATURE:
<223> OTHER INFORMATION: Synthetic Primer, R561

<400> SEQUENCE: 1338
ccaguuuauu guauuugcau agcaca                                          26

<210> SEQ ID NO 1339
<211> LENGTH: 26
<212> TYPE: RNA
<213> ORGANISM: Artificial Sequence
<220> FEATURE:
<223> OTHER INFORMATION: Synthetic Primer, R562

<400> SEQUENCE: 1339
ggacccauua gaaccaacuc cauaaa                                          26

<210> SEQ ID NO 1340
<211> LENGTH: 21
<212> TYPE: RNA
<213> ORGANISM: Artificial Sequence
<220> FEATURE:
<223> OTHER INFORMATION: Synthetic Primer, R563

<400> SEQUENCE: 1340
uaccuuauac accgugccga a                                               21

<210> SEQ ID NO 1341
<211> LENGTH: 22
<212> TYPE: RNA
<213> ORGANISM: Artificial Sequence
<220> FEATURE:
<223> OTHER INFORMATION: Synthetic Primer, R564

<400> SEQUENCE: 1341
ccacacagca aagcagaaac uc                                              22

<210> SEQ ID NO 1342
<211> LENGTH: 20
<212> TYPE: RNA
<213> ORGANISM: Artificial Sequence
<220> FEATURE:
<223> OTHER INFORMATION: Synthetic Primer, R565

<400> SEQUENCE: 1342
uucuuucucu uccgcaccca                                                 20

<210> SEQ ID NO 1343
<211> LENGTH: 19
<212> TYPE: RNA
<213> ORGANISM: Artificial Sequence
<220> FEATURE:
<223> OTHER INFORMATION: Synthetic Primer, R566

<400> SEQUENCE: 1343
gugaggcaga ugcccagca                                                  19

<210> SEQ ID NO 1344
<211> LENGTH: 27
<212> TYPE: RNA
<213> ORGANISM: Artificial Sequence
<220> FEATURE:
<223> OTHER INFORMATION: Synthetic Primer, R567
```

-continued

<400> SEQUENCE: 1344
ccaauauugu cuuuguguuc ccggaca                                        27

<210> SEQ ID NO 1345
<211> LENGTH: 20
<212> TYPE: RNA
<213> ORGANISM: Artificial Sequence
<220> FEATURE:
<223> OTHER INFORMATION: Synthetic Primer, R568

<400> SEQUENCE: 1345
uguguuccuu uggagguggc                                                20

<210> SEQ ID NO 1346
<211> LENGTH: 24
<212> TYPE: RNA
<213> ORGANISM: Artificial Sequence
<220> FEATURE:
<223> OTHER INFORMATION: Synthetic Primer, R569

<400> SEQUENCE: 1346
gauccagagg aggaguaugu guga                                           24

<210> SEQ ID NO 1347
<211> LENGTH: 24
<212> TYPE: RNA
<213> ORGANISM: Artificial Sequence
<220> FEATURE:
<223> OTHER INFORMATION: Synthetic Primer, R570

<400> SEQUENCE: 1347
ucuuccucca ucucauagcu gucg                                           24

<210> SEQ ID NO 1348
<211> LENGTH: 20
<212> TYPE: RNA
<213> ORGANISM: Artificial Sequence
<220> FEATURE:
<223> OTHER INFORMATION: Synthetic Primer, R571

<400> SEQUENCE: 1348
cguccuguuu ucaggccaag                                                20

<210> SEQ ID NO 1349
<211> LENGTH: 24
<212> TYPE: RNA
<213> ORGANISM: Artificial Sequence
<220> FEATURE:
<223> OTHER INFORMATION: Synthetic Primer, R572

<400> SEQUENCE: 1349
auuagaggga cucuucccaa ugga                                           24

<210> SEQ ID NO 1350
<211> LENGTH: 20
<212> TYPE: RNA
<213> ORGANISM: Artificial Sequence
<220> FEATURE:
<223> OTHER INFORMATION: Synthetic Primer, R573

<400> SEQUENCE: 1350
ccacggugga auuguugcug                                                20

<210> SEQ ID NO 1351
<211> LENGTH: 27

```
<212> TYPE: RNA
<213> ORGANISM: Artificial Sequence
<220> FEATURE:
<223> OTHER INFORMATION: Synthetic Primer, R574

<400> SEQUENCE: 1351
auaccaggcu aguauagaug cuuaggg                                        27

<210> SEQ ID NO 1352
<211> LENGTH: 21
<212> TYPE: RNA
<213> ORGANISM: Artificial Sequence
<220> FEATURE:
<223> OTHER INFORMATION: Synthetic Primer, R575

<400> SEQUENCE: 1352
cagacaccaa cucccggaau c                                              21

<210> SEQ ID NO 1353
<211> LENGTH: 20
<212> TYPE: RNA
<213> ORGANISM: Artificial Sequence
<220> FEATURE:
<223> OTHER INFORMATION: Synthetic Primer, R576

<400> SEQUENCE: 1353
cagaacucuc uccccagcag                                                20

<210> SEQ ID NO 1354
<211> LENGTH: 19
<212> TYPE: RNA
<213> ORGANISM: Artificial Sequence
<220> FEATURE:
<223> OTHER INFORMATION: Synthetic Primer, R577

<400> SEQUENCE: 1354
cagcuucaug ucugugccg                                                 19

<210> SEQ ID NO 1355
<211> LENGTH: 20
<212> TYPE: RNA
<213> ORGANISM: Artificial Sequence
<220> FEATURE:
<223> OTHER INFORMATION: Synthetic Primer, R578

<400> SEQUENCE: 1355
ucacaccgcu guguuccauc                                                20

<210> SEQ ID NO 1356
<211> LENGTH: 21
<212> TYPE: RNA
<213> ORGANISM: Artificial Sequence
<220> FEATURE:
<223> OTHER INFORMATION: Synthetic Primer, R579

<400> SEQUENCE: 1356
guugugagcg augagcacgu a                                              21

<210> SEQ ID NO 1357
<211> LENGTH: 23
<212> TYPE: RNA
<213> ORGANISM: Artificial Sequence
<220> FEATURE:
<223> OTHER INFORMATION: Synthetic Primer, R580

<400> SEQUENCE: 1357
```

```
aaaaucgugu ccugguagca gag                                         23

<210> SEQ ID NO 1358
<211> LENGTH: 25
<212> TYPE: DNA
<213> ORGANISM: Artificial Sequence
<220> FEATURE:
<223> OTHER INFORMATION: Synthetic DNA/RNA primer, R581

<400> SEQUENCE: 1358
cccaccaaaa ugagaaaacu gugut                                       25

<210> SEQ ID NO 1359
<211> LENGTH: 20
<212> TYPE: RNA
<213> ORGANISM: Artificial Sequence
<220> FEATURE:
<223> OTHER INFORMATION: Synthetic Primer, R582

<400> SEQUENCE: 1359
uguccuccua gcaggagagg                                             20

<210> SEQ ID NO 1360
<211> LENGTH: 20
<212> TYPE: RNA
<213> ORGANISM: Artificial Sequence
<220> FEATURE:
<223> OTHER INFORMATION: Synthetic Primer, R583

<400> SEQUENCE: 1360
ccguggaugu caggcagaug                                             20

<210> SEQ ID NO 1361
<211> LENGTH: 24
<212> TYPE: RNA
<213> ORGANISM: Artificial Sequence
<220> FEATURE:
<223> OTHER INFORMATION: Synthetic Primer, R584

<400> SEQUENCE: 1361
auacuggacu caucucuccu uccc                                        24

<210> SEQ ID NO 1362
<211> LENGTH: 19
<212> TYPE: DNA
<213> ORGANISM: Artificial Sequence
<220> FEATURE:
<223> OTHER INFORMATION: Synthetic Primer, R585

<400> SEQUENCE: 1362
aaagaccacc cccaagacc                                              19

<210> SEQ ID NO 1363
<211> LENGTH: 23
<212> TYPE: DNA
<213> ORGANISM: Artificial Sequence
<220> FEATURE:
<223> OTHER INFORMATION: Synthetic DNA/RNA primer, R586

<400> SEQUENCE: 1363
auaacuccac acaucacucu ggt                                         23

<210> SEQ ID NO 1364
<211> LENGTH: 23
<212> TYPE: RNA
<213> ORGANISM: Artificial Sequence
```

```
<220> FEATURE:
<223> OTHER INFORMATION: Synthetic Primer, R587

<400> SEQUENCE: 1364
uugacauggu ugggacucuu gac                                            23

<210> SEQ ID NO 1365
<211> LENGTH: 22
<212> TYPE: RNA
<213> ORGANISM: Artificial Sequence
<220> FEATURE:
<223> OTHER INFORMATION: Synthetic Primer, R588

<400> SEQUENCE: 1365
uggcaaacuu cccaucguag ac                                             22

<210> SEQ ID NO 1366
<211> LENGTH: 24
<212> TYPE: RNA
<213> ORGANISM: Artificial Sequence
<220> FEATURE:
<223> OTHER INFORMATION: Synthetic Primer, R589

<400> SEQUENCE: 1366
guugaucauu guuccuuccc cuca                                           24

<210> SEQ ID NO 1367
<211> LENGTH: 21
<212> TYPE: RNA
<213> ORGANISM: Artificial Sequence
<220> FEATURE:
<223> OTHER INFORMATION: Synthetic Primer, R590

<400> SEQUENCE: 1367
ccaucuuguc aggaggacag g                                              21

<210> SEQ ID NO 1368
<211> LENGTH: 23
<212> TYPE: RNA
<213> ORGANISM: Artificial Sequence
<220> FEATURE:
<223> OTHER INFORMATION: Synthetic Primer, R591

<400> SEQUENCE: 1368
ggcaggaucu cuaacccauu gag                                            23

<210> SEQ ID NO 1369
<211> LENGTH: 22
<212> TYPE: RNA
<213> ORGANISM: Artificial Sequence
<220> FEATURE:
<223> OTHER INFORMATION: Synthetic Primer, R592

<400> SEQUENCE: 1369
cucagcaggu aacucacacu ug                                             22

<210> SEQ ID NO 1370
<211> LENGTH: 18
<212> TYPE: DNA
<213> ORGANISM: Artificial Sequence
<220> FEATURE:
<223> OTHER INFORMATION: Synthetic DNA/RNA primer, R593

<400> SEQUENCE: 1370
cuucccuggg ugcuccat                                                  18
```

<210> SEQ ID NO 1371
<211> LENGTH: 22
<212> TYPE: RNA
<213> ORGANISM: Artificial Sequence
<220> FEATURE:
<223> OTHER INFORMATION: Synthetic Primer, R594

<400> SEQUENCE: 1371
guggauaugg uccuucucuu cc                                              22

<210> SEQ ID NO 1372
<211> LENGTH: 19
<212> TYPE: RNA
<213> ORGANISM: Artificial Sequence
<220> FEATURE:
<223> OTHER INFORMATION: Synthetic Primer, R595

<400> SEQUENCE: 1372
ggcuaguggg cgcauguag                                                  19

<210> SEQ ID NO 1373
<211> LENGTH: 20
<212> TYPE: RNA
<213> ORGANISM: Artificial Sequence
<220> FEATURE:
<223> OTHER INFORMATION: Synthetic Primer, R596

<400> SEQUENCE: 1373
aucaaagucc agcaccagca                                                 20

<210> SEQ ID NO 1374
<211> LENGTH: 24
<212> TYPE: RNA
<213> ORGANISM: Artificial Sequence
<220> FEATURE:
<223> OTHER INFORMATION: Synthetic Primer, R597

<400> SEQUENCE: 1374
gggaauugca uucacacguu aaca                                            24

<210> SEQ ID NO 1375
<211> LENGTH: 29
<212> TYPE: RNA
<213> ORGANISM: Artificial Sequence
<220> FEATURE:
<223> OTHER INFORMATION: Synthetic Primer, R598

<400> SEQUENCE: 1375
uuuguuuugu uuuucuguuu cucccucug                                       29

<210> SEQ ID NO 1376
<211> LENGTH: 24
<212> TYPE: RNA
<213> ORGANISM: Artificial Sequence
<220> FEATURE:
<223> OTHER INFORMATION: Synthetic Primer, R599

<400> SEQUENCE: 1376 gagguuguu aguggagcau auga                                             24

<210> SEQ ID NO 1377
<211> LENGTH: 23
<212> TYPE: RNA
<213> ORGANISM: Artificial Sequence
<220> FEATURE:
<223> OTHER INFORMATION: Synthetic Primer, R600

-continued

<400> SEQUENCE: 1377
ugagacaggc caguguuuac aug                                         23

<210> SEQ ID NO 1378
<211> LENGTH: 26
<212> TYPE: DNA
<213> ORGANISM: Artificial Sequence
<220> FEATURE:
<223> OTHER INFORMATION: Synthetic DNA/RNA primer, R601

<400> SEQUENCE: 1378
gagacuggag aauguauaca caccut                                      26

<210> SEQ ID NO 1379
<211> LENGTH: 18
<212> TYPE: DNA
<213> ORGANISM: Artificial Sequence
<220> FEATURE:
<223> OTHER INFORMATION: Synthetic DNA/RNA primer, R602

<400> SEQUENCE: 1379
cgacaucucc ucgggcut                                               18

<210> SEQ ID NO 1380
<211> LENGTH: 18
<212> TYPE: RNA
<213> ORGANISM: Artificial Sequence
<220> FEATURE:
<223> OTHER INFORMATION: Synthetic Primer, R603

<400> SEQUENCE: 1380
cguagagcuc cggguguc                                               18

<210> SEQ ID NO 1381
<211> LENGTH: 20
<212> TYPE: DNA
<213> ORGANISM: Artificial Sequence
<220> FEATURE:
<223> OTHER INFORMATION: Synthetic DNA/RNA primer, R604

<400> SEQUENCE: 1381
cuacccaggg ccacuguuut                                             20

<210> SEQ ID NO 1382
<211> LENGTH: 22
<212> TYPE: RNA
<213> ORGANISM: Artificial Sequence
<220> FEATURE:
<223> OTHER INFORMATION: Synthetic Primer, R605

<400> SEQUENCE: 1382
gggacauuca ccacaucgac ua                                          22

<210> SEQ ID NO 1383
<211> LENGTH: 18
<212> TYPE: RNA
<213> ORGANISM: Artificial Sequence
<220> FEATURE:
<223> OTHER INFORMATION: Synthetic Primer, R606

<400> SEQUENCE: 1383
uggccucuuc uccugugc                                               18

<210> SEQ ID NO 1384

```
<211> LENGTH: 25
<212> TYPE: RNA
<213> ORGANISM: Artificial Sequence
<220> FEATURE:
<223> OTHER INFORMATION: Synthetic Primer, R607

<400> SEQUENCE: 1384
cuucuucuuc ccauagaugc ucucc                                           25

<210> SEQ ID NO 1385
<211> LENGTH: 24
<212> TYPE: RNA
<213> ORGANISM: Artificial Sequence
<220> FEATURE:
<223> OTHER INFORMATION: Synthetic Primer, R608

<400> SEQUENCE: 1385
gaggcauuau uugaccggau cuac                                            24

<210> SEQ ID NO 1386
<211> LENGTH: 23
<212> TYPE: RNA
<213> ORGANISM: Artificial Sequence
<220> FEATURE:
<223> OTHER INFORMATION: Synthetic Primer, R609

<400> SEQUENCE: 1386
cugaguauga gcuucccgaa gac                                             23

<210> SEQ ID NO 1387
<211> LENGTH: 19
<212> TYPE: RNA
<213> ORGANISM: Artificial Sequence
<220> FEATURE:
<223> OTHER INFORMATION: Synthetic Primer, R610

<400> SEQUENCE: 1387
ccugcuaaca cccuguucg                                                  19

<210> SEQ ID NO 1388
<211> LENGTH: 21
<212> TYPE: DNA
<213> ORGANISM: Artificial Sequence
<220> FEATURE:
<223> OTHER INFORMATION: Synthetic DNA/RNA primer, R611

<400> SEQUENCE: 1388
cugccugucu cucuuggcuu t                                               21

<210> SEQ ID NO 1389
<211> LENGTH: 26
<212> TYPE: RNA
<213> ORGANISM: Artificial Sequence
<220> FEATURE:
<223> OTHER INFORMATION: Synthetic Primer, R612

<400> SEQUENCE: 1389
uaugaacuuc cagaggaccc aaaaug                                          26

<210> SEQ ID NO 1390
<211> LENGTH: 24
<212> TYPE: RNA
<213> ORGANISM: Artificial Sequence
<220> FEATURE:
<223> OTHER INFORMATION: Synthetic Primer, R613

<400> SEQUENCE: 1390
```
ggaaaagaac ggcaguaaau acgg                                              24

<210> SEQ ID NO 1391
<211> LENGTH: 23
<212> TYPE: RNA
<213> ORGANISM: Artificial Sequence
<220> FEATURE:
<223> OTHER INFORMATION: Synthetic Primer, R614

<400> SEQUENCE: 1391
aauacggguc caucaaucac acg                                               23

<210> SEQ ID NO 1392
<211> LENGTH: 25
<212> TYPE: RNA
<213> ORGANISM: Artificial Sequence
<220> FEATURE:
<223> OTHER INFORMATION: Synthetic Primer, R615

<400> SEQUENCE: 1392
caguacuugg uauucugugc uagga                                             25

<210> SEQ ID NO 1393
<211> LENGTH: 25
<212> TYPE: RNA
<213> ORGANISM: Artificial Sequence
<220> FEATURE:
<223> OTHER INFORMATION: Synthetic Primer, R616

<400> SEQUENCE: 1393
ggaagcuguc caucaguaua cauuc                                             25

<210> SEQ ID NO 1394
<211> LENGTH: 23
<212> TYPE: RNA
<213> ORGANISM: Artificial Sequence
<220> FEATURE:
<223> OTHER INFORMATION: Synthetic Primer, R617

<400> SEQUENCE: 1394
ggcccuccuu caguuuaguu gag                                               23

<210> SEQ ID NO 1395
<211> LENGTH: 21
<212> TYPE: RNA
<213> ORGANISM: Artificial Sequence
<220> FEATURE:
<223> OTHER INFORMATION: Synthetic Primer, R618

<400> SEQUENCE: 1395
gguggaggcg auaguggaua g                                                 21

<210> SEQ ID NO 1396
<211> LENGTH: 26
<212> TYPE: RNA
<213> ORGANISM: Artificial Sequence
<220> FEATURE:
<223> OTHER INFORMATION: Synthetic Primer, R619

<400> SEQUENCE: 1396
agauggagau gaugaagaug auuggg                                            26

<210> SEQ ID NO 1397
<211> LENGTH: 22
<212> TYPE: RNA

```
<213> ORGANISM: Artificial Sequence
<220> FEATURE:
<223> OTHER INFORMATION: Synthetic Primer, R620

<400> SEQUENCE: 1397
gucaagugga uggcuccaga ag                                              22

<210> SEQ ID NO 1398
<211> LENGTH: 28
<212> TYPE: RNA
<213> ORGANISM: Artificial Sequence
<220> FEATURE:
<223> OTHER INFORMATION: Synthetic Primer, R621

<400> SEQUENCE: 1398
ccagaaaugu uuugguaaca gaaaacaa                                        28

<210> SEQ ID NO 1399
<211> LENGTH: 26
<212> TYPE: RNA
<213> ORGANISM: Artificial Sequence
<220> FEATURE:
<223> OTHER INFORMATION: Synthetic Primer, R622

<400> SEQUENCE: 1399
auucucucuu uagggagcuu cucuuc                                          26

<210> SEQ ID NO 1400
<211> LENGTH: 27
<212> TYPE: RNA
<213> ORGANISM: Artificial Sequence
<220> FEATURE:
<223> OTHER INFORMATION: Synthetic Primer, R623

<400> SEQUENCE: 1400
uggaagagaa aaggagauua cagcuuc                                         27

<210> SEQ ID NO 1401
<211> LENGTH: 23
<212> TYPE: RNA
<213> ORGANISM: Artificial Sequence
<220> FEATURE:
<223> OTHER INFORMATION: Synthetic Primer, R624

<400> SEQUENCE: 1401 auugguucucu cauucuccca ucc                                            23

<210> SEQ ID NO 1402
<211> LENGTH: 23
<212> TYPE: DNA
<213> ORGANISM: Artificial Sequence
<220> FEATURE:
<223> OTHER INFORMATION: Synthetic DNA/RNA primer, R625

<400> SEQUENCE: 1402
guuuagguuu uggcaacgug gat                                             23

<210> SEQ ID NO 1403
<211> LENGTH: 24
<212> TYPE: RNA
<213> ORGANISM: Artificial Sequence
<220> FEATURE:
<223> OTHER INFORMATION: Synthetic Primer, R626

<400> SEQUENCE: 1403
ucaccagaug cuaugugcua aucc                                            24
```

<210> SEQ ID NO 1404
<211> LENGTH: 19
<212> TYPE: RNA
<213> ORGANISM: Artificial Sequence
<220> FEATURE:
<223> OTHER INFORMATION: Synthetic Primer, R627

<400> SEQUENCE: 1404
uccuaccugu guccacacc                                                19

<210> SEQ ID NO 1405
<211> LENGTH: 19
<212> TYPE: DNA
<213> ORGANISM: Artificial Sequence
<220> FEATURE:
<223> OTHER INFORMATION: Synthetic DNA/RNA primer, R628

<400> SEQUENCE: 1405
ggcaugggac agagucgut                                                19

<210> SEQ ID NO 1406
<211> LENGTH: 22
<212> TYPE: RNA
<213> ORGANISM: Artificial Sequence
<220> FEATURE:
<223> OTHER INFORMATION: Synthetic Primer, R629

<400> SEQUENCE: 1406
uugugcaagg agagaaccuc ua                                            22

<210> SEQ ID NO 1407
<211> LENGTH: 25
<212> TYPE: RNA
<213> ORGANISM: Artificial Sequence
<220> FEATURE:
<223> OTHER INFORMATION: Synthetic Primer, R630

<400> SEQUENCE: 1407
ccuaucccag aacuggagac agaaa                                         25

<210> SEQ ID NO 1408
<211> LENGTH: 21
<212> TYPE: DNA
<213> ORGANISM: Artificial Sequence
<220> FEATURE:
<223> OTHER INFORMATION: Synthetic DNA/RNA primer, R631

<400> SEQUENCE: 1408
uguacaccuu gcaguggaac t                                             21

<210> SEQ ID NO 1409
<211> LENGTH: 18
<212> TYPE: RNA
<213> ORGANISM: Artificial Sequence
<220> FEATURE:
<223> OTHER INFORMATION: Synthetic Primer, R632

<400> SEQUENCE: 1409
agcccaggcc uuucuugg                                                 18

<210> SEQ ID NO 1410
<211> LENGTH: 17
<212> TYPE: RNA
<213> ORGANISM: Artificial Sequence
<220> FEATURE:

```
<223> OTHER INFORMATION: Synthetic Primer, R633

<400> SEQUENCE: 1410
acuggcauga cccccac                                                    17

<210> SEQ ID NO 1411
<211> LENGTH: 17
<212> TYPE: DNA
<213> ORGANISM: Artificial Sequence
<220> FEATURE:
<223> OTHER INFORMATION: Synthetic DNA/RNA primer, R634

<400> SEQUENCE: 1411
ugccacucac aggucgt                                                    17

<210> SEQ ID NO 1412
<211> LENGTH: 18
<212> TYPE: DNA
<213> ORGANISM: Artificial Sequence
<220> FEATURE:
<223> OTHER INFORMATION: Synthetic DNA/RNA primer, R635

<400> SEQUENCE: 1412
gcagaaacuc ccgcaggt                                                   18

<210> SEQ ID NO 1413
<211> LENGTH: 20
<212> TYPE: DNA
<213> ORGANISM: Artificial Sequence
<220> FEATURE:
<223> OTHER INFORMATION: Synthetic DNA/RNA primer, R636

<400> SEQUENCE: 1413
acuccagaua cugcaugcct                                                 20

<210> SEQ ID NO 1414
<211> LENGTH: 17
<212> TYPE: RNA
<213> ORGANISM: Artificial Sequence
<220> FEATURE:
<223> OTHER INFORMATION: Synthetic Primer, R637

<400> SEQUENCE: 1414
acucccgcag guuuccc                                                    17

<210> SEQ ID NO 1415
<211> LENGTH: 24
<212> TYPE: RNA
<213> ORGANISM: Artificial Sequence
<220> FEATURE:
<223> OTHER INFORMATION: Synthetic Primer, R638

<400> SEQUENCE: 1415
acgggaaagu ggugaagaua ugug                                            24

<210> SEQ ID NO 1416
<211> LENGTH: 26
<212> TYPE: RNA
<213> ORGANISM: Artificial Sequence
<220> FEATURE:
<223> OTHER INFORMATION: Synthetic Primer, R639

<400> SEQUENCE: 1416
agaaacauga uggaugucac guucuc                                          26
```

```
<210> SEQ ID NO 1417
<211> LENGTH: 24
<212> TYPE: DNA
<213> ORGANISM: Artificial Sequence
<220> FEATURE:
<223> OTHER INFORMATION: Synthetic DNA/RNA primer, R640

<400> SEQUENCE: 1417
uguuaaccuu gcagaauggu cgat                                              24

<210> SEQ ID NO 1418
<211> LENGTH: 19
<212> TYPE: RNA
<213> ORGANISM: Artificial Sequence
<220> FEATURE:
<223> OTHER INFORMATION: Synthetic Primer, R641

<400> SEQUENCE: 1418
augacuugga ccgcguagc                                                    19

<210> SEQ ID NO 1419
<211> LENGTH: 21
<212> TYPE: DNA
<213> ORGANISM: Artificial Sequence
<220> FEATURE:
<223> OTHER INFORMATION: Synthetic DNA/RNA primer, R642

<400> SEQUENCE: 1419
gcauccuacc guugaagcac t                                                 21

<210> SEQ ID NO 1420
<211> LENGTH: 25
<212> TYPE: DNA
<213> ORGANISM: Artificial Sequence
<220> FEATURE:
<223> OTHER INFORMATION: Synthetic DNA/RNA primer, R643

<400> SEQUENCE: 1420
caccuggaac uuggucucaa agaut                                             25

<210> SEQ ID NO 1421
<211> LENGTH: 19
<212> TYPE: DNA
<213> ORGANISM: Artificial Sequence
<220> FEATURE:
<223> OTHER INFORMATION: Synthetic DNA/RNA primer, R644

<400> SEQUENCE: 1421
auuccuaccg gaagcaggt                                                    19

<210> SEQ ID NO 1422
<211> LENGTH: 23
<212> TYPE: DNA
<213> ORGANISM: Artificial Sequence
<220> FEATURE:
<223> OTHER INFORMATION: Synthetic DNA/RNA primer, R645

<400> SEQUENCE: 1422
augacggaau auaagcuggu ggt                                               23

<210> SEQ ID NO 1423
<211> LENGTH: 22
<212> TYPE: RNA
<213> ORGANISM: Artificial Sequence
<220> FEATURE:
<223> OTHER INFORMATION: Synthetic Primer, R646
```

-continued

```
<400> SEQUENCE: 1423
aaaauauccc ccggcuugug ag                                                  22

<210> SEQ ID NO 1424
<211> LENGTH: 26
<212> TYPE: RNA
<213> ORGANISM: Artificial Sequence
<220> FEATURE:
<223> OTHER INFORMATION: Synthetic Primer, R647

<400> SEQUENCE: 1424
gaagaagaug uggaaaaguc ccaaug                                              26

<210> SEQ ID NO 1425
<211> LENGTH: 17
<212> TYPE: RNA
<213> ORGANISM: Artificial Sequence
<220> FEATURE:
<223> OTHER INFORMATION: Synthetic Primer, R648

<400> SEQUENCE: 1425
gucccuggcu ggaccaa                                                        17

<210> SEQ ID NO 1426
<211> LENGTH: 22
<212> TYPE: RNA
<213> ORGANISM: Artificial Sequence
<220> FEATURE:
<223> OTHER INFORMATION: Synthetic Primer, R649

<400> SEQUENCE: 1426
cacacauugg agcaugccau uc                                                  22

<210> SEQ ID NO 1427
<211> LENGTH: 27
<212> TYPE: DNA
<213> ORGANISM: Artificial Sequence
<220> FEATURE:
<223> OTHER INFORMATION: Synthetic DNA/RNA primer, R650

<400> SEQUENCE: 1427
agccuaaaca uccccuuaaa uuggaut                                             27

<210> SEQ ID NO 1428
<211> LENGTH: 20
<212> TYPE: RNA
<213> ORGANISM: Artificial Sequence
<220> FEATURE:
<223> OTHER INFORMATION: Synthetic Primer, R651

<400> SEQUENCE: 1428
cggcuuuacc uccaauggug                                                     20

<210> SEQ ID NO 1429
<211> LENGTH: 24
<212> TYPE: RNA
<213> ORGANISM: Artificial Sequence
<220> FEATURE:
<223> OTHER INFORMATION: Synthetic Primer, R652

<400> SEQUENCE: 1429
gcagagaaug gguacucacg uuuc                                                24

<210> SEQ ID NO 1430
<211> LENGTH: 21
```

```
<212> TYPE: DNA
<213> ORGANISM: Artificial Sequence
<220> FEATURE:
<223> OTHER INFORMATION: Synthetic DNA/RNA primer, R653

<400> SEQUENCE: 1430
ucagccuguu ucugggaaac t                                              21

<210> SEQ ID NO 1431
<211> LENGTH: 29
<212> TYPE: RNA
<213> ORGANISM: Artificial Sequence
<220> FEATURE:
<223> OTHER INFORMATION: Synthetic Primer, R654

<400> SEQUENCE: 1431
uggagagaga acaaauaaau gguuaccug                                      29

<210> SEQ ID NO 1432
<211> LENGTH: 27
<212> TYPE: DNA
<213> ORGANISM: Artificial Sequence
<220> FEATURE:
<223> OTHER INFORMATION: Synthetic DNA/RNA primer, R655

<400> SEQUENCE: 1432
gauucuuaua aagugcagcu ucugcat                                        27

<210> SEQ ID NO 1433
<211> LENGTH: 24
<212> TYPE: DNA
<213> ORGANISM: Artificial Sequence
<220> FEATURE:
<223> OTHER INFORMATION: Synthetic DNA/RNA primer, R656

<400> SEQUENCE: 1433
cagacgucac uuucaaacgu guat                                           24

<210> SEQ ID NO 1434
<211> LENGTH: 22
<212> TYPE: RNA
<213> ORGANISM: Artificial Sequence
<220> FEATURE:
<223> OTHER INFORMATION: Synthetic Primer, R657

<400> SEQUENCE: 1434
caggcucagg acuuagcaag aa                                             22

<210> SEQ ID NO 1435
<211> LENGTH: 24
<212> TYPE: RNA
<213> ORGANISM: Artificial Sequence
<220> FEATURE:
<223> OTHER INFORMATION: Synthetic Primer, R658

<400> SEQUENCE: 1435
uaaggccugc ugaaaaugac ugaa                                           24

<210> SEQ ID NO 1436
<211> LENGTH: 21
<212> TYPE: DNA
<213> ORGANISM: Artificial Sequence
<220> FEATURE:
<223> OTHER INFORMATION: Synthetic DNA/RNA primer, R659

<400> SEQUENCE: 1436
```
aguccucaug uacuggcccc t                                           21

<210> SEQ ID NO 1437
<211> LENGTH: 20
<212> TYPE: RNA
<213> ORGANISM: Artificial Sequence
<220> FEATURE:
<223> OTHER INFORMATION: Synthetic Primer, R660

<400> SEQUENCE: 1437
cugaucucgc caucgcugua                                             20

<210> SEQ ID NO 1438
<211> LENGTH: 24
<212> TYPE: DNA
<213> ORGANISM: Artificial Sequence
<220> FEATURE:
<223> OTHER INFORMATION: Synthetic DNA/RNA primer, R661

<400> SEQUENCE: 1438
guucauaccg acauguagga ccut                                        24

<210> SEQ ID NO 1439
<211> LENGTH: 23
<212> TYPE: RNA
<213> ORGANISM: Artificial Sequence
<220> FEATURE:
<223> OTHER INFORMATION: Synthetic Primer, R662

<400> SEQUENCE: 1439
ucaaagucgu cauccuucag uuc                                         23

<210> SEQ ID NO 1440
<211> LENGTH: 19
<212> TYPE: DNA
<213> ORGANISM: Artificial Sequence
<220> FEATURE:
<223> OTHER INFORMATION: Synthetic DNA/RNA primer, R663

<400> SEQUENCE: 1440
ccuccagaug ugaagccct                                              19

<210> SEQ ID NO 1441
<211> LENGTH: 19
<212> TYPE: DNA
<213> ORGANISM: Artificial Sequence
<220> FEATURE:
<223> OTHER INFORMATION: Synthetic DNA/RNA primer, R664

<400> SEQUENCE: 1441
gcuggaggag cuggaacut                                              19

<210> SEQ ID NO 1442
<211> LENGTH: 21
<212> TYPE: RNA
<213> ORGANISM: Artificial Sequence
<220> FEATURE:
<223> OTHER INFORMATION: Synthetic Primer, R665

<400> SEQUENCE: 1442
uaaacaggag cacgaggaug c                                           21

<210> SEQ ID NO 1443
<211> LENGTH: 19
<212> TYPE: DNA
<213> ORGANISM: Artificial Sequence

```
<220> FEATURE:
<223> OTHER INFORMATION: Synthetic DNA/RNA primer, R666

<400> SEQUENCE: 1443
uauucaucac ggcgcgcut                                                   19

<210> SEQ ID NO 1444
<211> LENGTH: 26
<212> TYPE: RNA
<213> ORGANISM: Artificial Sequence
<220> FEATURE:
<223> OTHER INFORMATION: Synthetic Primer, R667

<400> SEQUENCE: 1444
gaguccagga gaaaauucac augagg                                           26

<210> SEQ ID NO 1445
<211> LENGTH: 30
<212> TYPE: DNA
<213> ORGANISM: Artificial Sequence
<220> FEATURE:
<223> OTHER INFORMATION: Synthetic DNA/RNA primer, R668

<400> SEQUENCE: 1445
acaacccacu gagguauaug uauagguaut                                       30

<210> SEQ ID NO 1446
<211> LENGTH: 24
<212> TYPE: RNA
<213> ORGANISM: Artificial Sequence
<220> FEATURE:
<223> OTHER INFORMATION: Synthetic Primer, R669

<400> SEQUENCE: 1446
agcacaguga auuucuugc cauc                                              24

<210> SEQ ID NO 1447
<211> LENGTH: 25
<212> TYPE: RNA
<213> ORGANISM: Artificial Sequence
<220> FEATURE:
<223> OTHER INFORMATION: Synthetic Primer, R670

<400> SEQUENCE: 1447
ggugguaaac uuuugaguuu gcaga                                            25

<210> SEQ ID NO 1448
<211> LENGTH: 22
<212> TYPE: DNA
<213> ORGANISM: Artificial Sequence
<220> FEATURE:
<223> OTHER INFORMATION: Synthetic DNA/RNA primer, R671

<400> SEQUENCE: 1448
gggaaggagu gguacaacag at                                               22

<210> SEQ ID NO 1449
<211> LENGTH: 25
<212> TYPE: RNA
<213> ORGANISM: Artificial Sequence
<220> FEATURE:
<223> OTHER INFORMATION: Synthetic Primer, R672

<400> SEQUENCE: 1449
acagcuaguu ugccaguuag uaagc                                            25
```

```
<210> SEQ ID NO 1450
<211> LENGTH: 25
<212> TYPE: RNA
<213> ORGANISM: Artificial Sequence
<220> FEATURE:
<223> OTHER INFORMATION: Synthetic Primer, R673

<400> SEQUENCE: 1450
cacuuaauuu ggauuguggc acaga                                          25

<210> SEQ ID NO 1451
<211> LENGTH: 21
<212> TYPE: RNA
<213> ORGANISM: Artificial Sequence
<220> FEATURE:
<223> OTHER INFORMATION: Synthetic Primer, R674

<400> SEQUENCE: 1451
cucuugucau cagcucccag a                                              21

<210> SEQ ID NO 1452
<211> LENGTH: 20
<212> TYPE: RNA
<213> ORGANISM: Artificial Sequence
<220> FEATURE:
<223> OTHER INFORMATION: Synthetic Primer, R675

<400> SEQUENCE: 1452
gcgccagcau ccagagauac                                                20

<210> SEQ ID NO 1453
<211> LENGTH: 20
<212> TYPE: DNA
<213> ORGANISM: Artificial Sequence
<220> FEATURE:
<223> OTHER INFORMATION: Synthetic DNA/RNA primer, R676

<400> SEQUENCE: 1453
gagcguguga ugcagcucut                                                20

<210> SEQ ID NO 1454
<211> LENGTH: 26
<212> TYPE: RNA
<213> ORGANISM: Artificial Sequence
<220> FEATURE:
<223> OTHER INFORMATION: Synthetic Primer, R677

<400> SEQUENCE: 1454
guuugaccga agaaccaauu auaccc                                         26

<210> SEQ ID NO 1455
<211> LENGTH: 25
<212> TYPE: RNA
<213> ORGANISM: Artificial Sequence
<220> FEATURE:
<223> OTHER INFORMATION: Synthetic Primer, R678

<400> SEQUENCE: 1455
gaugcuucuc uccuucuucu cuugg                                          25

<210> SEQ ID NO 1456
<211> LENGTH: 26
<212> TYPE: RNA
<213> ORGANISM: Artificial Sequence
<220> FEATURE:
<223> OTHER INFORMATION: Synthetic Primer, R679
```

```
<400> SEQUENCE: 1456
uuccccaacc cacauuuccu uuauag                                          26

<210> SEQ ID NO 1457
<211> LENGTH: 23
<212> TYPE: RNA
<213> ORGANISM: Artificial Sequence
<220> FEATURE:
<223> OTHER INFORMATION: Synthetic Primer, R680

<400> SEQUENCE: 1457
ccaaaacccu ccugauguac acg                                             23

<210> SEQ ID NO 1458
<211> LENGTH: 21
<212> TYPE: RNA
<213> ORGANISM: Artificial Sequence
<220> FEATURE:
<223> OTHER INFORMATION: Synthetic Primer, R681

<400> SEQUENCE: 1458
gucacagcuc cagugucugu c                                               21

<210> SEQ ID NO 1459
<211> LENGTH: 24
<212> TYPE: RNA
<213> ORGANISM: Artificial Sequence
<220> FEATURE:
<223> OTHER INFORMATION: Synthetic Primer, R682

<400> SEQUENCE: 1459
gagauccagg cuaccuggua ugag                                            24

<210> SEQ ID NO 1460
<211> LENGTH: 20
<212> TYPE: DNA
<213> ORGANISM: Artificial Sequence
<220> FEATURE:
<223> OTHER INFORMATION: Synthetic DNA/RNA primer, R683

<400> SEQUENCE: 1460
aaggacgacc cagagcugat                                                 20

<210> SEQ ID NO 1461
<211> LENGTH: 25
<212> TYPE: RNA
<213> ORGANISM: Artificial Sequence
<220> FEATURE:
<223> OTHER INFORMATION: Synthetic Primer, R684

<400> SEQUENCE: 1461
aaauuaaaag gcaaguggac uucgg                                           25

<210> SEQ ID NO 1462
<211> LENGTH: 23
<212> TYPE: RNA
<213> ORGANISM: Artificial Sequence
<220> FEATURE:
<223> OTHER INFORMATION: Synthetic Primer, R685

<400> SEQUENCE: 1462
cuguugguga agcuaacguu gag                                             23

<210> SEQ ID NO 1463
```

```
<211> LENGTH: 22
<212> TYPE: RNA
<213> ORGANISM: Artificial Sequence
<220> FEATURE:
<223> OTHER INFORMATION: Synthetic Primer, R686

<400> SEQUENCE: 1463
aaaaugggaa agguauccag cc                                              22

<210> SEQ ID NO 1464
<211> LENGTH: 26
<212> TYPE: RNA
<213> ORGANISM: Artificial Sequence
<220> FEATURE:
<223> OTHER INFORMATION: Synthetic Primer, R687

<400> SEQUENCE: 1464
ccacagaaac aacaucgauu ucuucc                                          26

<210> SEQ ID NO 1465
<211> LENGTH: 18
<212> TYPE: DNA
<213> ORGANISM: Artificial Sequence
<220> FEATURE:
<223> OTHER INFORMATION: Synthetic DNA/RNA primer, R688

<400> SEQUENCE: 1465
acagggaugg ugguggut                                                   18

<210> SEQ ID NO 1466
<211> LENGTH: 25
<212> TYPE: RNA
<213> ORGANISM: Artificial Sequence
<220> FEATURE:
<223> OTHER INFORMATION: Synthetic Primer, R689

<400> SEQUENCE: 1466
uucuggauua gcuggauugu cagug                                           25

<210> SEQ ID NO 1467
<211> LENGTH: 23
<212> TYPE: DNA
<213> ORGANISM: Artificial Sequence
<220> FEATURE:
<223> OTHER INFORMATION: Synthetic DNA/RNA primer, R690

<400> SEQUENCE: 1467
ggcaaauaca cagaggaagc cut                                             23

<210> SEQ ID NO 1468
<211> LENGTH: 23
<212> TYPE: RNA
<213> ORGANISM: Artificial Sequence
<220> FEATURE:
<223> OTHER INFORMATION: Synthetic Primer, R691

<400> SEQUENCE: 1468
augucuauag ggaagggaag acg                                             23

<210> SEQ ID NO 1469
<211> LENGTH: 21
<212> TYPE: DNA
<213> ORGANISM: Artificial Sequence
<220> FEATURE:
<223> OTHER INFORMATION: Synthetic DNA/RNA primer, R692

<400> SEQUENCE: 1469
```
gucggugcug uagauauccc t                                      21

<210> SEQ ID NO 1470
<211> LENGTH: 26
<212> TYPE: RNA
<213> ORGANISM: Artificial Sequence
<220> FEATURE:
<223> OTHER INFORMATION: Synthetic Primer, R693

<400> SEQUENCE: 1470
acauugucaa guucuaugga gugugc                                 26

<210> SEQ ID NO 1471
<211> LENGTH: 22
<212> TYPE: DNA
<213> ORGANISM: Artificial Sequence
<220> FEATURE:
<223> OTHER INFORMATION: Synthetic DNA/RNA primer, R694

<400> SEQUENCE: 1471
cuggcugaag guggguuuga ut                                     22

<210> SEQ ID NO 1472
<211> LENGTH: 17
<212> TYPE: RNA
<213> ORGANISM: Artificial Sequence
<220> FEATURE:
<223> OTHER INFORMATION: Synthetic Primer, R695

<400> SEQUENCE: 1472
aagucacacg gcccucc                                           17

<210> SEQ ID NO 1473
<211> LENGTH: 28
<212> TYPE: RNA
<213> ORGANISM: Artificial Sequence
<220> FEATURE:
<223> OTHER INFORMATION: Synthetic Primer, R696

<400> SEQUENCE: 1473
uuguucucau uggcuucaaa gaucuuua                               28

<210> SEQ ID NO 1474
<211> LENGTH: 24
<212> TYPE: RNA
<213> ORGANISM: Artificial Sequence
<220> FEATURE:
<223> OTHER INFORMATION: Synthetic Primer, R697

<400> SEQUENCE: 1474
ucucuuggaa acucccaucu ugag                                   24

<210> SEQ ID NO 1475
<211> LENGTH: 18
<212> TYPE: RNA
<213> ORGANISM: Artificial Sequence
<220> FEATURE:
<223> OTHER INFORMATION: Synthetic Primer, R698

<400> SEQUENCE: 1475
ugagcccacc ugacuugg                                          18

<210> SEQ ID NO 1476
<211> LENGTH: 24
<212> TYPE: RNA

```
<213> ORGANISM: Artificial Sequence
<220> FEATURE:
<223> OTHER INFORMATION: Synthetic Primer, R699

<400> SEQUENCE: 1476
acaugagagc uuguuuuca cugg                                          24

<210> SEQ ID NO 1477
<211> LENGTH: 25
<212> TYPE: RNA
<213> ORGANISM: Artificial Sequence
<220> FEATURE:
<223> OTHER INFORMATION: Synthetic Primer, R700

<400> SEQUENCE: 1477
agagugaucu cuggaugucg gaaua                                        25

<210> SEQ ID NO 1478
<211> LENGTH: 21
<212> TYPE: RNA
<213> ORGANISM: Artificial Sequence
<220> FEATURE:
<223> OTHER INFORMATION: Synthetic Primer, R701

<400> SEQUENCE: 1478
accagugagg gaagugagga c                                            21

<210> SEQ ID NO 1479
<211> LENGTH: 28
<212> TYPE: DNA
<213> ORGANISM: Artificial Sequence
<220> FEATURE:
<223> OTHER INFORMATION: Synthetic DNA/RNA primer, R702

<400> SEQUENCE: 1479
uaagcaucag cauuugacuu uaccuuat                                     28

<210> SEQ ID NO 1480
<211> LENGTH: 27
<212> TYPE: RNA
<213> ORGANISM: Artificial Sequence
<220> FEATURE:
<223> OTHER INFORMATION: Synthetic Primer, R703

<400> SEQUENCE: 1480
caaacaaguu uauauuuccc caugcca                                      27

<210> SEQ ID NO 1481
<211> LENGTH: 28
<212> TYPE: DNA
<213> ORGANISM: Artificial Sequence
<220> FEATURE:
<223> OTHER INFORMATION: Synthetic DNA/RNA primer, R704

<400> SEQUENCE: 1481
gauuugaucc aguaacacca auagggut                                     28

<210> SEQ ID NO 1482
<211> LENGTH: 26
<212> TYPE: DNA
<213> ORGANISM: Artificial Sequence
<220> FEATURE:
<223> OTHER INFORMATION: Synthetic DNA/RNA primer, R705

<400> SEQUENCE: 1482
aaacacaaac uagagucaca caccut                                       26
```

<210> SEQ ID NO 1483
<211> LENGTH: 23
<212> TYPE: RNA
<213> ORGANISM: Artificial Sequence
<220> FEATURE:
<223> OTHER INFORMATION: Synthetic Primer, R706

<400> SEQUENCE: 1483
agcacuuacc ugugacucca uag                                                23

<210> SEQ ID NO 1484
<211> LENGTH: 27
<212> TYPE: RNA
<213> ORGANISM: Artificial Sequence
<220> FEATURE:
<223> OTHER INFORMATION: Synthetic Primer, R707

<400> SEQUENCE: 1484
uuguguggaa gauccaaucc auuuuug                                            27

<210> SEQ ID NO 1485
<211> LENGTH: 25
<212> TYPE: RNA
<213> ORGANISM: Artificial Sequence
<220> FEATURE:
<223> OTHER INFORMATION: Synthetic Primer, R708

<400> SEQUENCE: 1485
aaccauauca aauucacaca cuggc                                              25

<210> SEQ ID NO 1486
<211> LENGTH: 27
<212> TYPE: RNA
<213> ORGANISM: Artificial Sequence
<220> FEATURE:
<223> OTHER INFORMATION: Synthetic Primer, R709

<400> SEQUENCE: 1486
cucuugcuca guuuuaucua aggcuag                                            27

<210> SEQ ID NO 1487
<211> LENGTH: 30
<212> TYPE: RNA
<213> ORGANISM: Artificial Sequence
<220> FEATURE:
<223> OTHER INFORMATION: Synthetic Primer, R710

<400> SEQUENCE: 1487
cauaccaauu ucucgauuga ggaucuuuuc                                         30

<210> SEQ ID NO 1488
<211> LENGTH: 21
<212> TYPE: RNA
<213> ORGANISM: Artificial Sequence
<220> FEATURE:
<223> OTHER INFORMATION: Synthetic Primer, R711

<400> SEQUENCE: 1488
ccgcagaaau ggauacaggu c                                                  21

<210> SEQ ID NO 1489
<211> LENGTH: 30
<212> TYPE: RNA
<213> ORGANISM: Artificial Sequence
<220> FEATURE:

```
<223> OTHER INFORMATION: Synthetic Primer, R712

<400> SEQUENCE: 1489
agaaaaucaa agcauucuua ccuuacuaca                                            30

<210> SEQ ID NO 1490
<211> LENGTH: 25
<212> TYPE: DNA
<213> ORGANISM: Artificial Sequence
<220> FEATURE:
<223> OTHER INFORMATION: Synthetic DNA/RNA primer, R713

<400> SEQUENCE: 1490
uccaggaaga ggaaaggaaa aacat                                                 25

<210> SEQ ID NO 1491
<211> LENGTH: 27
<212> TYPE: RNA
<213> ORGANISM: Artificial Sequence
<220> FEATURE:
<223> OTHER INFORMATION: Synthetic Primer, R714

<400> SEQUENCE: 1491
auuugccccg auguaauaaa uaugcac                                               27

<210> SEQ ID NO 1492
<211> LENGTH: 26
<212> TYPE: RNA
<213> ORGANISM: Artificial Sequence
<220> FEATURE:
<223> OTHER INFORMATION: Synthetic Primer, R715

<400> SEQUENCE: 1492
gucaagaucu ucacaaaagg guuuga                                                26

<210> SEQ ID NO 1493
<211> LENGTH: 24
<212> TYPE: RNA
<213> ORGANISM: Artificial Sequence
<220> FEATURE:
<223> OTHER INFORMATION: Synthetic Primer, R716

<400> SEQUENCE: 1493
gccacugguc uauaauccag auga                                                  24

<210> SEQ ID NO 1494
<211> LENGTH: 25
<212> TYPE: RNA
<213> ORGANISM: Artificial Sequence
<220> FEATURE:
<223> OTHER INFORMATION: Synthetic Primer, R717

<400> SEQUENCE: 1494
gcaucuuguu cuguuugugg aagaa                                                 25

<210> SEQ ID NO 1495
<211> LENGTH: 23
<212> TYPE: DNA
<213> ORGANISM: Artificial Sequence
<220> FEATURE:
<223> OTHER INFORMATION: Synthetic DNA/RNA primer, R718

<400> SEQUENCE: 1495
ucaacaaccc ccacaaaaug uut                                                   23
```

```
<210> SEQ ID NO 1496
<211> LENGTH: 21
<212> TYPE: RNA
<213> ORGANISM: Artificial Sequence
<220> FEATURE:
<223> OTHER INFORMATION: Synthetic Primer, R719

<400> SEQUENCE: 1496
uggauuugac ggcuccucua c                                          21

<210> SEQ ID NO 1497
<211> LENGTH: 24
<212> TYPE: RNA
<213> ORGANISM: Artificial Sequence
<220> FEATURE:
<223> OTHER INFORMATION: Synthetic Primer, R720

<400> SEQUENCE: 1497
uuaacaccuc caguccucua ucug                                       24

<210> SEQ ID NO 1498
<211> LENGTH: 27
<212> TYPE: RNA
<213> ORGANISM: Artificial Sequence
<220> FEATURE:
<223> OTHER INFORMATION: Synthetic Primer, R721

<400> SEQUENCE: 1498
uaagaugucc acugcuguuc cuucaua                                    27

<210> SEQ ID NO 1499
<211> LENGTH: 20
<212> TYPE: RNA
<213> ORGANISM: Artificial Sequence
<220> FEATURE:
<223> OTHER INFORMATION: Synthetic Primer, R722

<400> SEQUENCE: 1499
cuucagccaa ggcagcaaug                                            20

<210> SEQ ID NO 1500
<211> LENGTH: 28
<212> TYPE: RNA
<213> ORGANISM: Artificial Sequence
<220> FEATURE:
<223> OTHER INFORMATION: Synthetic Primer, R723

<400> SEQUENCE: 1500
gauauggauu cacacagaca cuaucaca                                   28

<210> SEQ ID NO 1501
<211> LENGTH: 24
<212> TYPE: DNA
<213> ORGANISM: Artificial Sequence
<220> FEATURE:
<223> OTHER INFORMATION: Synthetic DNA/RNA primer, R724

<400> SEQUENCE: 1501
caagguguuu cuuugaugcu cugt                                       24

<210> SEQ ID NO 1502
<211> LENGTH: 23
<212> TYPE: RNA
<213> ORGANISM: Artificial Sequence
<220> FEATURE:
<223> OTHER INFORMATION: Synthetic Primer, R725
```

<400> SEQUENCE: 1502 ccguggaca uuggagaguu gac                                    23

<210> SEQ ID NO 1503
<211> LENGTH: 26
<212> TYPE: RNA
<213> ORGANISM: Artificial Sequence
<220> FEATURE:
<223> OTHER INFORMATION: Synthetic Primer, R726

<400> SEQUENCE: 1503
gaaccuuaaa ugucucuccu accuga                                26

<210> SEQ ID NO 1504
<211> LENGTH: 19
<212> TYPE: RNA
<213> ORGANISM: Artificial Sequence
<220> FEATURE:
<223> OTHER INFORMATION: Synthetic Primer, R727

<400> SEQUENCE: 1504
aaggcaccug acccaaaca                                        19

<210> SEQ ID NO 1505
<211> LENGTH: 20
<212> TYPE: RNA
<213> ORGANISM: Artificial Sequence
<220> FEATURE:
<223> OTHER INFORMATION: Synthetic Primer, R728

<400> SEQUENCE: 1505
gcacauaguc ccggaagcug                                       20

<210> SEQ ID NO 1506
<211> LENGTH: 24
<212> TYPE: RNA
<213> ORGANISM: Artificial Sequence
<220> FEATURE:
<223> OTHER INFORMATION: Synthetic Primer, R729

<400> SEQUENCE: 1506
uucuugaucu cacagucagg gaug                                  24

<210> SEQ ID NO 1507
<211> LENGTH: 17
<212> TYPE: DNA
<213> ORGANISM: Artificial Sequence
<220> FEATURE:
<223> OTHER INFORMATION: Synthetic DNA/RNA primer, R730

<400> SEQUENCE: 1507
augagcagcg uggccut                                          17

<210> SEQ ID NO 1508
<211> LENGTH: 20
<212> TYPE: RNA
<213> ORGANISM: Artificial Sequence
<220> FEATURE:
<223> OTHER INFORMATION: Synthetic Primer, R731

<400> SEQUENCE: 1508
uagcugugca uguccuggug                                       20

<210> SEQ ID NO 1509
<211> LENGTH: 23

```
<212> TYPE: RNA
<213> ORGANISM: Artificial Sequence
<220> FEATURE:
<223> OTHER INFORMATION: Synthetic Primer, R732

<400> SEQUENCE: 1509
uaggugagga ccacaaacca aac                                            23

<210> SEQ ID NO 1510
<211> LENGTH: 21
<212> TYPE: DNA
<213> ORGANISM: Artificial Sequence
<220> FEATURE:
<223> OTHER INFORMATION: Synthetic DNA/RNA primer, R733

<400> SEQUENCE: 1510
uggucuucac ucaccucgga t                                              21

<210> SEQ ID NO 1511
<211> LENGTH: 22
<212> TYPE: DNA
<213> ORGANISM: Artificial Sequence
<220> FEATURE:
<223> OTHER INFORMATION: Synthetic DNA/RNA primer, R734

<400> SEQUENCE: 1511
uuccuccaga agcuugaacu ct                                             22

<210> SEQ ID NO 1512
<211> LENGTH: 23
<212> TYPE: DNA
<213> ORGANISM: Artificial Sequence
<220> FEATURE:
<223> OTHER INFORMATION: Synthetic DNA/RNA primer, R735

<400> SEQUENCE: 1512
cccaagccug ggaccucuau uat                                            23

<210> SEQ ID NO 1513
<211> LENGTH: 19
<212> TYPE: RNA
<213> ORGANISM: Artificial Sequence
<220> FEATURE:
<223> OTHER INFORMATION: Synthetic Primer, R736

<400> SEQUENCE: 1513
caugcuggac cuucugcac                                                 19

<210> SEQ ID NO 1514
<211> LENGTH: 26
<212> TYPE: RNA
<213> ORGANISM: Artificial Sequence
<220> FEATURE:
<223> OTHER INFORMATION: Synthetic Primer, R737

<400> SEQUENCE: 1514
agacugcuaa ggcauaggaa uuuucg                                         26

<210> SEQ ID NO 1515
<211> LENGTH: 26
<212> TYPE: DNA
<213> ORGANISM: Artificial Sequence
<220> FEATURE:
<223> OTHER INFORMATION: Synthetic DNA/RNA primer, R738

<400> SEQUENCE: 1515
```
uuugacucug ucuccucuug ucuuct          26

<210> SEQ ID NO 1516
<211> LENGTH: 24
<212> TYPE: RNA
<213> ORGANISM: Artificial Sequence
<220> FEATURE:
<223> OTHER INFORMATION: Synthetic Primer, R739

<400> SEQUENCE: 1516
gagaugaagc aaacaacagu ggag          24

<210> SEQ ID NO 1517
<211> LENGTH: 30
<212> TYPE: RNA
<213> ORGANISM: Artificial Sequence
<220> FEATURE:
<223> OTHER INFORMATION: Synthetic Primer, R740

<400> SEQUENCE: 1517
auuucaugca aacuagauaa cuaccuguaa          30

<210> SEQ ID NO 1518
<211> LENGTH: 24
<212> TYPE: RNA
<213> ORGANISM: Artificial Sequence
<220> FEATURE:
<223> OTHER INFORMATION: Synthetic Primer, R741

<400> SEQUENCE: 1518
uggaguuugu cugcugaaug aacc          24

<210> SEQ ID NO 1519
<211> LENGTH: 26
<212> TYPE: RNA
<213> ORGANISM: Artificial Sequence
<220> FEATURE:
<223> OTHER INFORMATION: Synthetic Primer, R742

<400> SEQUENCE: 1519
agcucacaga aaugucugcu auacug          26

<210> SEQ ID NO 1520
<211> LENGTH: 24
<212> TYPE: RNA
<213> ORGANISM: Artificial Sequence
<220> FEATURE:
<223> OTHER INFORMATION: Synthetic Primer, R743

<400> SEQUENCE: 1520
augaggagug uguacucuug cauc          24

<210> SEQ ID NO 1521
<211> LENGTH: 22
<212> TYPE: DNA
<213> ORGANISM: Artificial Sequence
<220> FEATURE:
<223> OTHER INFORMATION: Synthetic DNA/RNA primer, R744

<400> SEQUENCE: 1521
gccaagaguu acgggauucc at          22

<210> SEQ ID NO 1522
<211> LENGTH: 22
<212> TYPE: RNA
<213> ORGANISM: Artificial Sequence

```
<220> FEATURE:
<223> OTHER INFORMATION: Synthetic Primer, R745

<400> SEQUENCE: 1522
aggaugccug accaguuaga gg                                        22

<210> SEQ ID NO 1523
<211> LENGTH: 26
<212> TYPE: RNA
<213> ORGANISM: Artificial Sequence
<220> FEATURE:
<223> OTHER INFORMATION: Synthetic Primer, R746

<400> SEQUENCE: 1523
aaaagacucg gaugauguac cuaugg                                    26

<210> SEQ ID NO 1524
<211> LENGTH: 21
<212> TYPE: RNA
<213> ORGANISM: Artificial Sequence
<220> FEATURE:
<223> OTHER INFORMATION: Synthetic Primer, R747

<400> SEQUENCE: 1524
cacucacccu ggaugucuuc g                                         21

<210> SEQ ID NO 1525
<211> LENGTH: 20
<212> TYPE: RNA
<213> ORGANISM: Artificial Sequence
<220> FEATURE:
<223> OTHER INFORMATION: Synthetic Primer, R748

<400> SEQUENCE: 1525
caccguagcu ccagacauca                                           20

<210> SEQ ID NO 1526
<211> LENGTH: 19
<212> TYPE: DNA
<213> ORGANISM: Artificial Sequence
<220> FEATURE:
<223> OTHER INFORMATION: Synthetic Primer, R749

<400> SEQUENCE: 1526
aaggagaaga ggacagcgg                                            19

<210> SEQ ID NO 1527
<211> LENGTH: 24
<212> TYPE: RNA
<213> ORGANISM: Artificial Sequence
<220> FEATURE:
<223> OTHER INFORMATION: Synthetic Primer, R750

<400> SEQUENCE: 1527
ccugcacuuc uaggcacuua cuaa                                      24

<210> SEQ ID NO 1528
<211> LENGTH: 20
<212> TYPE: DNA
<213> ORGANISM: Artificial Sequence
<220> FEATURE:
<223> OTHER INFORMATION: Synthetic DNA/RNA primer, R751

<400> SEQUENCE: 1528
ggcacuugca cagagaugat                                           20
```

```
<210> SEQ ID NO 1529
<211> LENGTH: 23
<212> TYPE: RNA
<213> ORGANISM: Artificial Sequence
<220> FEATURE:
<223> OTHER INFORMATION: Synthetic Primer, R752

<400> SEQUENCE: 1529
auuugaugac auguggugg uug                                              23

<210> SEQ ID NO 1530
<211> LENGTH: 17
<212> TYPE: DNA
<213> ORGANISM: Artificial Sequence
<220> FEATURE:
<223> OTHER INFORMATION: Synthetic DNA/RNA primer, R753

<400> SEQUENCE: 1530
ggagccguau uuggcgt                                                     17

<210> SEQ ID NO 1531
<211> LENGTH: 24
<212> TYPE: RNA
<213> ORGANISM: Artificial Sequence
<220> FEATURE:
<223> OTHER INFORMATION: Synthetic Primer, R754

<400> SEQUENCE: 1531
ccucuucacg uaggaauccu cuuc                                             24

<210> SEQ ID NO 1532
<211> LENGTH: 26
<212> TYPE: DNA
<213> ORGANISM: Artificial Sequence
<220> FEATURE:
<223> OTHER INFORMATION: Synthetic DNA/RNA primer, R755

<400> SEQUENCE: 1532
aucacuuugc gugguguaga uaugat                                           26

<210> SEQ ID NO 1533
<211> LENGTH: 25
<212> TYPE: DNA
<213> ORGANISM: Artificial Sequence
<220> FEATURE:
<223> OTHER INFORMATION: Synthetic DNA/RNA primer, R756

<400> SEQUENCE: 1533
aggacucuga agauguaccu auggt                                            25

<210> SEQ ID NO 1534
<211> LENGTH: 27
<212> TYPE: DNA
<213> ORGANISM: Artificial Sequence
<220> FEATURE:
<223> OTHER INFORMATION: Synthetic DNA/RNA primer, R757

<400> SEQUENCE: 1534
acaguuucca uaggucugaa aauguut                                          27

<210> SEQ ID NO 1535
<211> LENGTH: 20
<212> TYPE: RNA
<213> ORGANISM: Artificial Sequence
<220> FEATURE:
<223> OTHER INFORMATION: Synthetic Primer, R758
```

```
<400> SEQUENCE: 1535
agcccaaccc uuguccuuac                                          20

<210> SEQ ID NO 1536
<211> LENGTH: 24
<212> TYPE: RNA
<213> ORGANISM: Artificial Sequence
<220> FEATURE:
<223> OTHER INFORMATION: Synthetic Primer, R759

<400> SEQUENCE: 1536
gggacagcau caaaucaucc auug                                     24

<210> SEQ ID NO 1537
<211> LENGTH: 20
<212> TYPE: RNA
<213> ORGANISM: Artificial Sequence
<220> FEATURE:
<223> OTHER INFORMATION: Synthetic Primer, R760

<400> SEQUENCE: 1537
ccagacggaa accguagcug                                          20

<210> SEQ ID NO 1538
<211> LENGTH: 18
<212> TYPE: DNA
<213> ORGANISM: Artificial Sequence
<220> FEATURE:
<223> OTHER INFORMATION: Synthetic DNA/RNA primer, R761

<400> SEQUENCE: 1538
ggagcagccu cuggcaut                                            18

<210> SEQ ID NO 1539
<211> LENGTH: 28
<212> TYPE: DNA
<213> ORGANISM: Artificial Sequence
<220> FEATURE:
<223> OTHER INFORMATION: Synthetic DNA/RNA primer, R762

<400> SEQUENCE: 1539
ggcaaggaaa ggugauaaaa gugaauct                                 28

<210> SEQ ID NO 1540
<211> LENGTH: 27
<212> TYPE: DNA
<213> ORGANISM: Artificial Sequence
<220> FEATURE:
<223> OTHER INFORMATION: Synthetic DNA/RNA primer, R763

<400> SEQUENCE: 1540
acuugauaag aggucccaag acuuagt                                  27

<210> SEQ ID NO 1541
<211> LENGTH: 22
<212> TYPE: RNA
<213> ORGANISM: Artificial Sequence
<220> FEATURE:
<223> OTHER INFORMATION: Synthetic Primer, R764

<400> SEQUENCE: 1541
ccuauggcuu uccaaccuag ga                                       22

<210> SEQ ID NO 1542
```

-continued

```
<211> LENGTH: 25
<212> TYPE: DNA
<213> ORGANISM: Artificial Sequence
<220> FEATURE:
<223> OTHER INFORMATION: Synthetic DNA/RNA primer, R765

<400> SEQUENCE: 1542
cccuucuguc uugaacauga guuut                                              25

<210> SEQ ID NO 1543
<211> LENGTH: 26
<212> TYPE: RNA
<213> ORGANISM: Artificial Sequence
<220> FEATURE:
<223> OTHER INFORMATION: Synthetic Primer, R766

<400> SEQUENCE: 1543
uguggaguau uuggaugaca gaaaca                                             26

<210> SEQ ID NO 1544
<211> LENGTH: 22
<212> TYPE: DNA
<213> ORGANISM: Artificial Sequence
<220> FEATURE:
<223> OTHER INFORMATION: Synthetic DNA/RNA primer, R767

<400> SEQUENCE: 1544
aggccucuga uuccucacug at                                                 22

<210> SEQ ID NO 1545
<211> LENGTH: 20
<212> TYPE: DNA
<213> ORGANISM: Artificial Sequence
<220> FEATURE:
<223> OTHER INFORMATION: Synthetic DNA/RNA primer, R768

<400> SEQUENCE: 1545
ccuagguugg cucugacugt                                                    20

<210> SEQ ID NO 1546
<211> LENGTH: 22
<212> TYPE: DNA
<213> ORGANISM: Artificial Sequence
<220> FEATURE:
<223> OTHER INFORMATION: Synthetic DNA/RNA primer, R769

<400> SEQUENCE: 1546
ugccucuugc uucucuuuuc ct                                                 22

<210> SEQ ID NO 1547
<211> LENGTH: 20
<212> TYPE: RNA
<213> ORGANISM: Artificial Sequence
<220> FEATURE:
<223> OTHER INFORMATION: Synthetic Primer, R770

<400> SEQUENCE: 1547
uuccuacagu acuccccugc                                                    20

<210> SEQ ID NO 1548
<211> LENGTH: 19
<212> TYPE: RNA
<213> ORGANISM: Artificial Sequence
<220> FEATURE:
<223> OTHER INFORMATION: Synthetic Primer, R771

<400> SEQUENCE: 1548
```

-continued agucacagca caugacgga                                        19

<210> SEQ ID NO 1549
<211> LENGTH: 20
<212> TYPE: RNA
<213> ORGANISM: Artificial Sequence
<220> FEATURE:
<223> OTHER INFORMATION: Synthetic Primer, F772

<400> SEQUENCE: 1549
ggaggaggcg auggcuacua                                       20

<210> SEQ ID NO 1550
<211> LENGTH: 24
<212> TYPE: RNA
<213> ORGANISM: Artificial Sequence
<220> FEATURE:
<223> OTHER INFORMATION: Synthetic Primer, F773

<400> SEQUENCE: 1550
ggagaccuac aaacugaagu gcaa                                  24

<210> SEQ ID NO 1551
<211> LENGTH: 22
<212> TYPE: RNA
<213> ORGANISM: Artificial Sequence
<220> FEATURE:
<223> OTHER INFORMATION: Synthetic Primer, F774

<400> SEQUENCE: 1551
ccaugcagaa ugccaccaag ua                                    22

<210> SEQ ID NO 1552
<211> LENGTH: 19
<212> TYPE: RNA
<213> ORGANISM: Artificial Sequence
<220> FEATURE:
<223> OTHER INFORMATION: Synthetic Primer, F775

<400> SEQUENCE: 1552
caggcacucc uuggagcaa                                        19

<210> SEQ ID NO 1553
<211> LENGTH: 22
<212> TYPE: RNA
<213> ORGANISM: Artificial Sequence
<220> FEATURE:
<223> OTHER INFORMATION: Synthetic Primer, F776

<400> SEQUENCE: 1553
cuguuugaaa ugagcaggca cu                                    22

<210> SEQ ID NO 1554
<211> LENGTH: 19
<212> TYPE: RNA
<213> ORGANISM: Artificial Sequence
<220> FEATURE:
<223> OTHER INFORMATION: Synthetic Primer, F777

<400> SEQUENCE: 1554
acuggaggac ccgucuucu                                        19

<210> SEQ ID NO 1555
<211> LENGTH: 24
<212> TYPE: RNA

```
<213> ORGANISM: Artificial Sequence
<220> FEATURE:
<223> OTHER INFORMATION: Synthetic Primer, F778

<400> SEQUENCE: 1555
agaccuuaag ggaacagcuc ucau                                    24

<210> SEQ ID NO 1556
<211> LENGTH: 26
<212> TYPE: RNA
<213> ORGANISM: Artificial Sequence
<220> FEATURE:
<223> OTHER INFORMATION: Synthetic Primer, F779

<400> SEQUENCE: 1556
guggagucau gcuuauaugg agcaaa                                  26

<210> SEQ ID NO 1557
<211> LENGTH: 27
<212> TYPE: RNA
<213> ORGANISM: Artificial Sequence
<220> FEATURE:
<223> OTHER INFORMATION: Synthetic Primer, F780

<400> SEQUENCE: 1557
gacagaaaaa uaauucugug ggaucau                                 27

<210> SEQ ID NO 1558
<211> LENGTH: 28
<212> TYPE: RNA
<213> ORGANISM: Artificial Sequence
<220> FEATURE:
<223> OTHER INFORMATION: Synthetic Primer, F781

<400> SEQUENCE: 1558
uccugaaaga gaaauagagg uuccugau                                28

<210> SEQ ID NO 1559
<211> LENGTH: 18
<212> TYPE: DNA
<213> ORGANISM: Artificial Sequence
<220> FEATURE:
<223> OTHER INFORMATION: Synthetic Primer, F782

<400> SEQUENCE: 1559
ggtggccata ggaacgca                                           18

<210> SEQ ID NO 1560
<211> LENGTH: 25
<212> TYPE: RNA
<213> ORGANISM: Artificial Sequence
<220> FEATURE:
<223> OTHER INFORMATION: Synthetic Primer, F783

<400> SEQUENCE: 1560
uggaugcaga aaccagagau cuagu                                   25

<210> SEQ ID NO 1561
<211> LENGTH: 22
<212> TYPE: RNA
<213> ORGANISM: Artificial Sequence
<220> FEATURE:
<223> OTHER INFORMATION: Synthetic Primer, F784

<400> SEQUENCE: 1561
cuggucccca gacaacaagu au                                      22
```

<210> SEQ ID NO 1562
<211> LENGTH: 23
<212> TYPE: RNA
<213> ORGANISM: Artificial Sequence
<220> FEATURE:
<223> OTHER INFORMATION: Synthetic Primer, F785

<400> SEQUENCE: 1562
gaagaucaug uggccucagu gaa                                           23

<210> SEQ ID NO 1563
<211> LENGTH: 27
<212> TYPE: RNA
<213> ORGANISM: Artificial Sequence
<220> FEATURE:
<223> OTHER INFORMATION: Synthetic Primer, F786

<400> SEQUENCE: 1563
gucgaaaaua ccuucaacac ccaaauu                                       27

<210> SEQ ID NO 1564
<211> LENGTH: 27
<212> TYPE: RNA
<213> ORGANISM: Artificial Sequence
<220> FEATURE:
<223> OTHER INFORMATION: Synthetic Primer, F787

<400> SEQUENCE: 1564
ccaaaacugc agacaagcau aaagaug                                       27

<210> SEQ ID NO 1565
<211> LENGTH: 22
<212> TYPE: RNA
<213> ORGANISM: Artificial Sequence
<220> FEATURE:
<223> OTHER INFORMATION: Synthetic Primer, F788

<400> SEQUENCE: 1565
caggcagaag uugaucgacu cu                                            22

<210> SEQ ID NO 1566
<211> LENGTH: 27
<212> TYPE: RNA
<213> ORGANISM: Artificial Sequence
<220> FEATURE:
<223> OTHER INFORMATION: Synthetic Primer, F789

<400> SEQUENCE: 1566
aaagaagagu gcacaaaugu uagagga                                       27

<210> SEQ ID NO 1567
<211> LENGTH: 24
<212> TYPE: RNA
<213> ORGANISM: Artificial Sequence
<220> FEATURE:
<223> OTHER INFORMATION: Synthetic Primer, F790

<400> SEQUENCE: 1567
ccagcuuccu auaacuugga cgau                                          24

<210> SEQ ID NO 1568
<211> LENGTH: 23
<212> TYPE: RNA
<213> ORGANISM: Artificial Sequence
<220> FEATURE:

<223> OTHER INFORMATION: Synthetic Primer, F791

<400> SEQUENCE: 1568
gaaccacauc auggucucug ucu                                           23

<210> SEQ ID NO 1569
<211> LENGTH: 21
<212> TYPE: RNA
<213> ORGANISM: Artificial Sequence
<220> FEATURE:
<223> OTHER INFORMATION: Synthetic Primer, F792

<400> SEQUENCE: 1569
ucaucgggaa gaccuggcuu a                                             21

<210> SEQ ID NO 1570
<211> LENGTH: 23
<212> TYPE: RNA
<213> ORGANISM: Artificial Sequence
<220> FEATURE:
<223> OTHER INFORMATION: Synthetic Primer, F793

<400> SEQUENCE: 1570
gcugcaggac uaugaggaga aga                                           23

<210> SEQ ID NO 1571
<211> LENGTH: 20
<212> TYPE: RNA
<213> ORGANISM: Artificial Sequence
<220> FEATURE:
<223> OTHER INFORMATION: Synthetic Primer, F794

<400> SEQUENCE: 1571
cucccagaga ccaacguuca                                               20

<210> SEQ ID NO 1572
<211> LENGTH: 20
<212> TYPE: RNA
<213> ORGANISM: Artificial Sequence
<220> FEATURE:
<223> OTHER INFORMATION: Synthetic Primer, F795

<400> SEQUENCE: 1572
ggaccuggac cguguccuua                                               20

<210> SEQ ID NO 1573
<211> LENGTH: 20
<212> TYPE: RNA
<213> ORGANISM: Artificial Sequence
<220> FEATURE:
<223> OTHER INFORMATION: Synthetic Primer, F796

<400> SEQUENCE: 1573
ggaccuggac cguguccuua                                               20

<210> SEQ ID NO 1574
<211> LENGTH: 22
<212> TYPE: RNA
<213> ORGANISM: Artificial Sequence
<220> FEATURE:
<223> OTHER INFORMATION: Synthetic Primer, R772a

<400> SEQUENCE: 1574
cugcaguuag agguugguga ca                                            22

```
<210> SEQ ID NO 1575
<211> LENGTH: 19
<212> TYPE: RNA
<213> ORGANISM: Artificial Sequence
<220> FEATURE:
<223> OTHER INFORMATION: Synthetic Primer, R772b

<400> SEQUENCE: 1575
cccgccaagc acguauacu                                                    19

<210> SEQ ID NO 1576
<211> LENGTH: 20
<212> TYPE: RNA
<213> ORGANISM: Artificial Sequence
<220> FEATURE:
<223> OTHER INFORMATION: Synthetic Primer, R773a

<400> SEQUENCE: 1576
ccggaagagg aguagcugac                                                   20

<210> SEQ ID NO 1577
<211> LENGTH: 27
<212> TYPE: RNA
<213> ORGANISM: Artificial Sequence
<220> FEATURE:
<223> OTHER INFORMATION: Synthetic Primer, R773b

<400> SEQUENCE: 1577
cuccuagagu uuuccaaga accaagu                                            27

<210> SEQ ID NO 1578
<211> LENGTH: 26
<212> TYPE: RNA
<213> ORGANISM: Artificial Sequence
<220> FEATURE:
<223> OTHER INFORMATION: Synthetic Primer, R774

<400> SEQUENCE: 1578
auuugcagcu acuacucuga acugaa                                            26

<210> SEQ ID NO 1579
<211> LENGTH: 26
<212> TYPE: RNA
<213> ORGANISM: Artificial Sequence
<220> FEATURE:
<223> OTHER INFORMATION: Synthetic Primer, R775

<400> SEQUENCE: 1579
ucagugggau uguaacaacc agaaau                                            26

<210> SEQ ID NO 1580
<211> LENGTH: 20
<212> TYPE: RNA
<213> ORGANISM: Artificial Sequence
<220> FEATURE:
<223> OTHER INFORMATION: Synthetic Primer, R776

<400> SEQUENCE: 1580
gcacugucac cccuuccuug                                                   20

<210> SEQ ID NO 1581
<211> LENGTH: 19
<212> TYPE: RNA
<213> ORGANISM: Artificial Sequence
<220> FEATURE:
<223> OTHER INFORMATION: Synthetic Primer, R779
```

<400> SEQUENCE: 1581
gcuccaucug cauggcuug                                             19

<210> SEQ ID NO 1582
<211> LENGTH: 22
<212> TYPE: RNA
<213> ORGANISM: Artificial Sequence
<220> FEATURE:
<223> OTHER INFORMATION: Synthetic Primer, R780

<400> SEQUENCE: 1582
ggguuguagu cggucaugau gg                                         22

<210> SEQ ID NO 1583
<211> LENGTH: 19
<212> TYPE: RNA
<213> ORGANISM: Artificial Sequence
<220> FEATURE:
<223> OTHER INFORMATION: Synthetic Primer, R781

<400> SEQUENCE: 1583
ccuggcccuu gaagcacua                                             19

<210> SEQ ID NO 1584
<211> LENGTH: 20
<212> TYPE: RNA
<213> ORGANISM: Artificial Sequence
<220> FEATURE:
<223> OTHER INFORMATION: Synthetic Primer, R782

<400> SEQUENCE: 1584
accccaucuu ccccauccau                                            20

<210> SEQ ID NO 1585
<211> LENGTH: 24
<212> TYPE: RNA
<213> ORGANISM: Artificial Sequence
<220> FEATURE:
<223> OTHER INFORMATION: Synthetic Primer, R786

<400> SEQUENCE: 1585
cuaccucaca gugacugcag uuua                                       24

<210> SEQ ID NO 1586
<211> LENGTH: 21
<212> TYPE: RNA
<213> ORGANISM: Artificial Sequence
<220> FEATURE:
<223> OTHER INFORMATION: Synthetic Primer, R787

<400> SEQUENCE: 1586
agagaggauc agcgagagug g                                          21

<210> SEQ ID NO 1587
<211> LENGTH: 20
<212> TYPE: RNA
<213> ORGANISM: Artificial Sequence
<220> FEATURE:
<223> OTHER INFORMATION: Synthetic Primer, R788

<400> SEQUENCE: 1587
gucucguugc ccaaauugau                                            20

<210> SEQ ID NO 1588
<211> LENGTH: 27

-continued

<210> SEQ ID NO 1588
<211> LENGTH: 27
<212> TYPE: RNA
<213> ORGANISM: Artificial Sequence
<220> FEATURE:
<223> OTHER INFORMATION: Synthetic Primer, R789

<400> SEQUENCE: 1588
aguguuuuca uucgauuccu gucuucu                                    27

<210> SEQ ID NO 1589
<211> LENGTH: 20
<212> TYPE: RNA
<213> ORGANISM: Artificial Sequence
<220> FEATURE:
<223> OTHER INFORMATION: Synthetic Primer, R791

<400> SEQUENCE: 1589
ggugaugccg ugguugaugu                                            20

<210> SEQ ID NO 1590
<211> LENGTH: 20
<212> TYPE: RNA
<213> ORGANISM: Artificial Sequence
<220> FEATURE:
<223> OTHER INFORMATION: Synthetic Primer, R792

<400> SEQUENCE: 1590
aguucucgcu ucagcacgau                                            20

<210> SEQ ID NO 1591
<211> LENGTH: 20
<212> TYPE: RNA
<213> ORGANISM: Artificial Sequence
<220> FEATURE:
<223> OTHER INFORMATION: Synthetic Primer, R794

<400> SEQUENCE: 1591
uggccaagca aucugcguau                                            20

<210> SEQ ID NO 1592
<211> LENGTH: 23
<212> TYPE: RNA
<213> ORGANISM: Artificial Sequence
<220> FEATURE:
<223> OTHER INFORMATION: Synthetic Primer, R795

<400> SEQUENCE: 1592
ugccaggauc auagcguuua cag                                        23

<210> SEQ ID NO 1593
<211> LENGTH: 22
<212> TYPE: RNA
<213> ORGANISM: Artificial Sequence
<220> FEATURE:
<223> OTHER INFORMATION: Synthetic Primer, R796a

<400> SEQUENCE: 1593
cuggagcagg uccacuauag gu                                         22

<210> SEQ ID NO 1594
<211> LENGTH: 19
<212> TYPE: RNA
<213> ORGANISM: Artificial Sequence
<220> FEATURE:
<223> OTHER INFORMATION: Synthetic Primer, R796b

<400> SEQUENCE: 1594
uccucacacc ugcuccuca                                          19

<210> SEQ ID NO 1595
<211> LENGTH: 18
<212> TYPE: RNA
<213> ORGANISM: Artificial Sequence
<220> FEATURE:
<223> OTHER INFORMATION: Synthetic Primer, R796c

<400> SEQUENCE: 1595
gcugaugggu gggcacug                                           18

<210> SEQ ID NO 1596
<211> LENGTH: 20
<212> TYPE: RNA
<213> ORGANISM: Artificial Sequence
<220> FEATURE:
<223> OTHER INFORMATION: Synthetic Primer, R796d

<400> SEQUENCE: 1596
ggucuaccag gacuguccu                                          20

<210> SEQ ID NO 1597
<211> LENGTH: 25
<212> TYPE: RNA
<213> ORGANISM: Artificial Sequence
<220> FEATURE:
<223> OTHER INFORMATION: Synthetic Primer, R797

<400> SEQUENCE: 1597
ggaaggcagg aagauuuuca aucuc                                   25

<210> SEQ ID NO 1598
<211> LENGTH: 24
<212> TYPE: RNA
<213> ORGANISM: Artificial Sequence
<220> FEATURE:
<223> OTHER INFORMATION: Synthetic Primer, R798

<400> SEQUENCE: 1598
cguuuauaag cacgucacc ccuu                                     24

<210> SEQ ID NO 1599
<211> LENGTH: 21
<212> TYPE: RNA
<213> ORGANISM: Artificial Sequence
<220> FEATURE:
<223> OTHER INFORMATION: Synthetic Primer, R801

<400> SEQUENCE: 1599
aggaugaugg cacugaacuc c                                       21

<210> SEQ ID NO 1600
<211> LENGTH: 25
<212> TYPE: RNA
<213> ORGANISM: Artificial Sequence
<220> FEATURE:
<223> OTHER INFORMATION: Synthetic Primer, R802

<400> SEQUENCE: 1600
cacguuaguu agugagccag guaau                                   25

<210> SEQ ID NO 1601
<211> LENGTH: 19
<212> TYPE: RNA
<213> ORGANISM: Artificial Sequence

```
<220> FEATURE:
<223> OTHER INFORMATION: Synthetic Primer, R803

<400> SEQUENCE: 1601
cucagggcuc ugcagcucc                                               19

<210> SEQ ID NO 1602
<211> LENGTH: 19
<212> TYPE: RNA
<213> ORGANISM: Artificial Sequence
<220> FEATURE:
<223> OTHER INFORMATION: Synthetic Primer, R804

<400> SEQUENCE: 1602
ccuccggaag gucaucuca                                               19

<210> SEQ ID NO 1603
<211> LENGTH: 27
<212> TYPE: RNA
<213> ORGANISM: Artificial Sequence
<220> FEATURE:
<223> OTHER INFORMATION: Synthetic Primer, R806b

<400> SEQUENCE: 1603
cuccuagagu uuuccaaga accaagu                                       27

<210> SEQ ID NO 1604
<211> LENGTH: 23
<212> TYPE: RNA
<213> ORGANISM: Artificial Sequence
<220> FEATURE:
<223> OTHER INFORMATION: Synthetic Primer, R807

<400> SEQUENCE: 1604
gaaccaaguu cuuccgaggg aau                                          23

<210> SEQ ID NO 1605
<211> LENGTH: 18
<212> TYPE: RNA
<213> ORGANISM: Artificial Sequence
<220> FEATURE:
<223> OTHER INFORMATION: Synthetic Primer, R809

<400> SEQUENCE: 1605
acagcggcug cgaucacc                                                18

<210> SEQ ID NO 1606
<211> LENGTH: 19
<212> TYPE: RNA
<213> ORGANISM: Artificial Sequence
<220> FEATURE:
<223> OTHER INFORMATION: Synthetic Primer, R811

<400> SEQUENCE: 1606
gcugacugca caggacagg                                               19

<210> SEQ ID NO 1607
<211> LENGTH: 21
<212> TYPE: RNA
<213> ORGANISM: Artificial Sequence
<220> FEATURE:
<223> OTHER INFORMATION: Synthetic Primer, R813a

<400> SEQUENCE: 1607
cgagacccca aagguguuu c                                             21
```

```
<210> SEQ ID NO 1608
<211> LENGTH: 23
<212> TYPE: RNA
<213> ORGANISM: Artificial Sequence
<220> FEATURE:
<223> OTHER INFORMATION: Synthetic Primer, R813b

<400> SEQUENCE: 1608
uccacauuug uugagcacaa gga                                              23

<210> SEQ ID NO 1609
<211> LENGTH: 27
<212> TYPE: RNA
<213> ORGANISM: Artificial Sequence
<220> FEATURE:
<223> OTHER INFORMATION: Synthetic Primer, R815

<400> SEQUENCE: 1609
caccuuuaac ugcuucaggg ucaauau                                          27

<210> SEQ ID NO 1610
<211> LENGTH: 18
<212> TYPE: RNA
<213> ORGANISM: Artificial Sequence
<220> FEATURE:
<223> OTHER INFORMATION: Synthetic Primer, R816

<400> SEQUENCE: 1610
uguugucccg uggccauu                                                    18

<210> SEQ ID NO 1611
<211> LENGTH: 21
<212> TYPE: RNA
<213> ORGANISM: Artificial Sequence
<220> FEATURE:
<223> OTHER INFORMATION: Synthetic Primer, R817

<400> SEQUENCE: 1611
ggcaugaacc guucugagau g                                                21

<210> SEQ ID NO 1612
<211> LENGTH: 23
<212> TYPE: RNA
<213> ORGANISM: Artificial Sequence
<220> FEATURE:
<223> OTHER INFORMATION: Synthetic Primer, R818

<400> SEQUENCE: 1612
ccaaauucgc cuucuccuag agu                                              23

<210> SEQ ID NO 1613
<211> LENGTH: 22
<212> TYPE: RNA
<213> ORGANISM: Artificial Sequence
<220> FEATURE:
<223> OTHER INFORMATION: Synthetic Primer, R819

<400> SEQUENCE: 1613 cucccucugca ccaagguaaa ca                                              22

<210> SEQ ID NO 1614
<211> LENGTH: 25
<212> TYPE: RNA
<213> ORGANISM: Artificial Sequence
<220> FEATURE:
<223> OTHER INFORMATION: Synthetic Primer, R820
```

-continued

<400> SEQUENCE: 1614
ucccuucuag uaauuuggga augcc                                              25

<210> SEQ ID NO 1615
<211> LENGTH: 28
<212> TYPE: RNA
<213> ORGANISM: Artificial Sequence
<220> FEATURE:
<223> OTHER INFORMATION: Synthetic Primer, R823

<400> SEQUENCE: 1615
ucagcuuucu cccacuguau ugaauuuu                                           28

<210> SEQ ID NO 1616
<211> LENGTH: 20
<212> TYPE: RNA
<213> ORGANISM: Artificial Sequence
<220> FEATURE:
<223> OTHER INFORMATION: Synthetic Primer, R824

<400> SEQUENCE: 1616
ucggaagggc uguggaauug                                                    20

<210> SEQ ID NO 1617
<211> LENGTH: 22
<212> TYPE: RNA
<213> ORGANISM: Artificial Sequence
<220> FEATURE:
<223> OTHER INFORMATION: Synthetic Primer, R824b

<400> SEQUENCE: 1617
cguaggcaca cucaaacaac ga                                                 22

<210> SEQ ID NO 1618
<211> LENGTH: 24
<212> TYPE: RNA
<213> ORGANISM: Artificial Sequence
<220> FEATURE:
<223> OTHER INFORMATION: Synthetic Primer, R825

<400> SEQUENCE: 1618
cugauuucug aacauggacu gugg                                               24

<210> SEQ ID NO 1619
<211> LENGTH: 23
<212> TYPE: RNA
<213> ORGANISM: Artificial Sequence
<220> FEATURE:
<223> OTHER INFORMATION: Synthetic Primer, R826

<400> SEQUENCE: 1619
acgaagugca auggucuuua ggu                                                23

<210> SEQ ID NO 1620
<211> LENGTH: 25
<212> TYPE: RNA
<213> ORGANISM: Artificial Sequence
<220> FEATURE:
<223> OTHER INFORMATION: Synthetic Primer, R828

<400> SEQUENCE: 1620
gugagucauu ugucuugcuu uuggu                                              25

<210> SEQ ID NO 1621

-continued

<211> LENGTH: 25
<212> TYPE: RNA
<213> ORGANISM: Artificial Sequence
<220> FEATURE:
<223> OTHER INFORMATION: Synthetic Primer, F829

<400> SEQUENCE: 1621
gacagucuga aucauguccu ucagu                                                25

<210> SEQ ID NO 1622
<211> LENGTH: 18
<212> TYPE: RNA
<213> ORGANISM: Artificial Sequence
<220> FEATURE:
<223> OTHER INFORMATION: Synthetic Primer, F830

<400> SEQUENCE: 1622
gggcugccca ccaucuuc                                                        18

<210> SEQ ID NO 1623
<211> LENGTH: 25
<212> TYPE: RNA
<213> ORGANISM: Artificial Sequence
<220> FEATURE:
<223> OTHER INFORMATION: Synthetic Primer, F831

<400> SEQUENCE: 1623
ucagccugau agucgguac aaacu                                                 25

<210> SEQ ID NO 1624
<211> LENGTH: 20
<212> TYPE: RNA
<213> ORGANISM: Artificial Sequence
<220> FEATURE:
<223> OTHER INFORMATION: Synthetic Primer, R833

<400> SEQUENCE: 1624
ccuccaccuu gggcuacuca                                                      20

<210> SEQ ID NO 1625
<211> LENGTH: 19
<212> TYPE: RNA
<213> ORGANISM: Artificial Sequence
<220> FEATURE:
<223> OTHER INFORMATION: Synthetic Primer, R834

<400> SEQUENCE: 1625
gggugagccu ugacacaca                                                       19

<210> SEQ ID NO 1626
<211> LENGTH: 22
<212> TYPE: RNA
<213> ORGANISM: Artificial Sequence
<220> FEATURE:
<223> OTHER INFORMATION: Synthetic Primer, R835

<400> SEQUENCE: 1626
cagggaucag uucagcugua cc                                                   22

<210> SEQ ID NO 1627
<211> LENGTH: 21
<212> TYPE: RNA
<213> ORGANISM: Artificial Sequence
<220> FEATURE:
<223> OTHER INFORMATION: Synthetic Primer, F838

<400> SEQUENCE: 1627
ugggcucugu aaagaauagu g					21

<210> SEQ ID NO 1628
<211> LENGTH: 21
<212> TYPE: RNA
<213> ORGANISM: Artificial Sequence
<220> FEATURE:
<223> OTHER INFORMATION: Synthetic Primer, F839

<400> SEQUENCE: 1628
ugcacacuug gacagcauuu c					21

<210> SEQ ID NO 1629
<211> LENGTH: 26
<212> TYPE: RNA
<213> ORGANISM: Artificial Sequence
<220> FEATURE:
<223> OTHER INFORMATION: Synthetic Primer, F840

<400> SEQUENCE: 1629
ccaggaccaa ucuggucaca aacaua				26

<210> SEQ ID NO 1630
<211> LENGTH: 23
<212> TYPE: DNA
<213> ORGANISM: Artificial Sequence
<220> FEATURE:
<223> OTHER INFORMATION: Synthetic DNA/RNA primer, F841

<400> SEQUENCE: 1630
ggugggagga aaagacauag gat				23

<210> SEQ ID NO 1631
<211> LENGTH: 24
<212> TYPE: RNA
<213> ORGANISM: Artificial Sequence
<220> FEATURE:
<223> OTHER INFORMATION: Synthetic Primer, F842

<400> SEQUENCE: 1631
cuccagagag aaagaaucaa cagg				24

<210> SEQ ID NO 1632
<211> LENGTH: 20
<212> TYPE: RNA
<213> ORGANISM: Artificial Sequence
<220> FEATURE:
<223> OTHER INFORMATION: Synthetic Primer, F843

<400> SEQUENCE: 1632
gcauccguga cucucuggac					20

<210> SEQ ID NO 1633
<211> LENGTH: 28
<212> TYPE: RNA
<213> ORGANISM: Artificial Sequence
<220> FEATURE:
<223> OTHER INFORMATION: Synthetic Primer, F844

<400> SEQUENCE: 1633
ucagugagcc aauuccuugu aauaacuc				28

<210> SEQ ID NO 1634
<211> LENGTH: 22
<212> TYPE: DNA

```
<213> ORGANISM: Artificial Sequence
<220> FEATURE:
<223> OTHER INFORMATION: Synthetic DNA/RNA primer, F845

<400> SEQUENCE: 1634
cagaucccaa gcuuuccuc ut                                              22

<210> SEQ ID NO 1635
<211> LENGTH: 22
<212> TYPE: DNA
<213> ORGANISM: Artificial Sequence
<220> FEATURE:
<223> OTHER INFORMATION: Synthetic DNA/RNA primer, F846

<400> SEQUENCE: 1635
guucaugcca cugcacuuca ct                                             22

<210> SEQ ID NO 1636
<211> LENGTH: 20
<212> TYPE: DNA
<213> ORGANISM: Artificial Sequence
<220> FEATURE:
<223> OTHER INFORMATION: Synthetic DNA/RNA primer, F847

<400> SEQUENCE: 1636
ggugcaccca uuacccgaat                                                20

<210> SEQ ID NO 1637
<211> LENGTH: 25
<212> TYPE: DNA
<213> ORGANISM: Artificial Sequence
<220> FEATURE:
<223> OTHER INFORMATION: Synthetic DNA/RNA primer, F848

<400> SEQUENCE: 1637
uccccauaua aguucaagcc ugugt                                          25

<210> SEQ ID NO 1638
<211> LENGTH: 27
<212> TYPE: DNA
<213> ORGANISM: Artificial Sequence
<220> FEATURE:
<223> OTHER INFORMATION: Synthetic DNA/RNA primer, F849

<400> SEQUENCE: 1638
uuguauagcu acaguuuuc uguuggt                                         27

<210> SEQ ID NO 1639
<211> LENGTH: 27
<212> TYPE: RNA
<213> ORGANISM: Artificial Sequence
<220> FEATURE:
<223> OTHER INFORMATION: Synthetic Primer, F850

<400> SEQUENCE: 1639
uaaauaugug agucaauucc ccaagug                                        27

<210> SEQ ID NO 1640
<211> LENGTH: 27
<212> TYPE: DNA
<213> ORGANISM: Artificial Sequence
<220> FEATURE:
<223> OTHER INFORMATION: Synthetic DNA/RNA primer, F851

<400> SEQUENCE: 1640
ggcuagauuu uccccgauga uaguagt                                        27
```

<210> SEQ ID NO 1641
<211> LENGTH: 27
<212> TYPE: DNA
<213> ORGANISM: Artificial Sequence
<220> FEATURE:
<223> OTHER INFORMATION: Synthetic DNA/RNA primer, F852

<400> SEQUENCE: 1641
ggcuagauuu uccccuauga uaguagt                                        27

<210> SEQ ID NO 1642
<211> LENGTH: 24
<212> TYPE: RNA
<213> ORGANISM: Artificial Sequence
<220> FEATURE:
<223> OTHER INFORMATION: Synthetic Primer, F853

<400> SEQUENCE: 1642
caguaaguua aaggauugca ggag                                           24

<210> SEQ ID NO 1643
<211> LENGTH: 28
<212> TYPE: RNA
<213> ORGANISM: Artificial Sequence
<220> FEATURE:
<223> OTHER INFORMATION: Synthetic Primer, F854

<400> SEQUENCE: 1643
uguguauaug cauuuaccug ugaguaug                                       28

<210> SEQ ID NO 1644
<211> LENGTH: 24
<212> TYPE: DNA
<213> ORGANISM: Artificial Sequence
<220> FEATURE:
<223> OTHER INFORMATION: Synthetic DNA/RNA primer, F855

<400> SEQUENCE: 1644
uguaacaagg gcuacaggaa ucat                                           24

<210> SEQ ID NO 1645
<211> LENGTH: 27
<212> TYPE: RNA
<213> ORGANISM: Artificial Sequence
<220> FEATURE:
<223> OTHER INFORMATION: Synthetic Primer, F856

<400> SEQUENCE: 1645
gggcaucucu uauacucaug aaaucaa                                        27

<210> SEQ ID NO 1646
<211> LENGTH: 25
<212> TYPE: DNA
<213> ORGANISM: Artificial Sequence
<220> FEATURE:
<223> OTHER INFORMATION: Synthetic DNA/RNA primer, F857

<400> SEQUENCE: 1646
cuaugcagaa gaaugaacca gggat                                          25

<210> SEQ ID NO 1647
<211> LENGTH: 28
<212> TYPE: RNA
<213> ORGANISM: Artificial Sequence
<220> FEATURE:

```
<223> OTHER INFORMATION: Synthetic Primer, F858

<400> SEQUENCE: 1647
ugauucauuu ccauagggua agugaaaa                                          28

<210> SEQ ID NO 1648
<211> LENGTH: 26
<212> TYPE: RNA
<213> ORGANISM: Artificial Sequence
<220> FEATURE:
<223> OTHER INFORMATION: Synthetic Primer, F859

<400> SEQUENCE: 1648
gacauuauca ccaauuuuuc uagacg                                            26

<210> SEQ ID NO 1649
<211> LENGTH: 26
<212> TYPE: RNA
<213> ORGANISM: Artificial Sequence
<220> FEATURE:
<223> OTHER INFORMATION: Synthetic Primer, F860

<400> SEQUENCE: 1649
gacauucuca ccaauuuuuc uagacg                                            26

<210> SEQ ID NO 1650
<211> LENGTH: 22
<212> TYPE: RNA
<213> ORGANISM: Artificial Sequence
<220> FEATURE:
<223> OTHER INFORMATION: Synthetic Primer, F861

<400> SEQUENCE: 1650
ugugacaagg gugauuuucc uc                                                22

<210> SEQ ID NO 1651
<211> LENGTH: 25
<212> TYPE: DNA
<213> ORGANISM: Artificial Sequence
<220> FEATURE:
<223> OTHER INFORMATION: Synthetic DNA/RNA primer, F862

<400> SEQUENCE: 1651
cauaauugua ugagccacuu cccat                                             25

<210> SEQ ID NO 1652
<211> LENGTH: 26
<212> TYPE: DNA
<213> ORGANISM: Artificial Sequence
<220> FEATURE:
<223> OTHER INFORMATION: Synthetic DNA/RNA primer, F863

<400> SEQUENCE: 1652
agacucacaa uguacaaaag ccuaut                                            26

<210> SEQ ID NO 1653
<211> LENGTH: 33
<212> TYPE: RNA
<213> ORGANISM: Artificial Sequence
<220> FEATURE:
<223> OTHER INFORMATION: Synthetic Primer, F864

<400> SEQUENCE: 1653
aauauauaua aaggguauga uagaacacuu guc                                    33
```

<210> SEQ ID NO 1654
<211> LENGTH: 30
<212> TYPE: DNA
<213> ORGANISM: Artificial Sequence
<220> FEATURE:
<223> OTHER INFORMATION: Synthetic DNA/RNA primer, F865

<400> SEQUENCE: 1654
ggccuggcaa cuuauaugua uuuuguaut                                             30

<210> SEQ ID NO 1655
<211> LENGTH: 30
<212> TYPE: DNA
<213> ORGANISM: Artificial Sequence
<220> FEATURE:
<223> OTHER INFORMATION: Synthetic DNA/RNA primer, F866

<400> SEQUENCE: 1655
ggccugacaa cuuauaugua uuuuguaut                                             30

<210> SEQ ID NO 1656
<211> LENGTH: 33
<212> TYPE: RNA
<213> ORGANISM: Artificial Sequence
<220> FEATURE:
<223> OTHER INFORMATION: Synthetic Primer, F867

<400> SEQUENCE: 1656
ccauccuuau cucugugua ucauucauu caa                                          33

<210> SEQ ID NO 1657
<211> LENGTH: 25
<212> TYPE: RNA
<213> ORGANISM: Artificial Sequence
<220> FEATURE:
<223> OTHER INFORMATION: Synthetic Primer, F868

<400> SEQUENCE: 1657
gauuugucug uaauugccag caaaa                                                 25

<210> SEQ ID NO 1658
<211> LENGTH: 22
<212> TYPE: RNA
<213> ORGANISM: Artificial Sequence
<220> FEATURE:
<223> OTHER INFORMATION: Synthetic Primer, F869

<400> SEQUENCE: 1658
gagcaagaca ccaucucaag aa                                                    22

<210> SEQ ID NO 1659
<211> LENGTH: 28
<212> TYPE: DNA
<213> ORGANISM: Artificial Sequence
<220> FEATURE:
<223> OTHER INFORMATION: Synthetic DNA/RNA primer, F870

<400> SEQUENCE: 1659
caugauugau acauggaaag aauucuct                                              28

<210> SEQ ID NO 1660
<211> LENGTH: 24
<212> TYPE: RNA
<213> ORGANISM: Artificial Sequence
<220> FEATURE:
<223> OTHER INFORMATION: Synthetic Primer, F871

```
<400> SEQUENCE: 1660
acccaaauca acucaacucc agug                                          24

<210> SEQ ID NO 1661
<211> LENGTH: 28
<212> TYPE: DNA
<213> ORGANISM: Artificial Sequence
<220> FEATURE:
<223> OTHER INFORMATION: Synthetic DNA/RNA primer, F872

<400> SEQUENCE: 1661
uuagagcauu uaaaguaagc cacagugt                                      28

<210> SEQ ID NO 1662
<211> LENGTH: 21
<212> TYPE: DNA
<213> ORGANISM: Artificial Sequence
<220> FEATURE:
<223> OTHER INFORMATION: Synthetic DNA/RNA primer, F873

<400> SEQUENCE: 1662
cuguacacag ggcuuccgag t                                             21

<210> SEQ ID NO 1663
<211> LENGTH: 24
<212> TYPE: RNA
<213> ORGANISM: Artificial Sequence
<220> FEATURE:
<223> OTHER INFORMATION: Synthetic Primer, F874

<400> SEQUENCE: 1663
uuucagggcu gugaucacua gcac                                          24

<210> SEQ ID NO 1664
<211> LENGTH: 31
<212> TYPE: RNA
<213> ORGANISM: Artificial Sequence
<220> FEATURE:
<223> OTHER INFORMATION: Synthetic Primer, F875

<400> SEQUENCE: 1664
agauacauag guuagauaga gauaggacag a                                  31

<210> SEQ ID NO 1665
<211> LENGTH: 21
<212> TYPE: RNA
<213> ORGANISM: Artificial Sequence
<220> FEATURE:
<223> OTHER INFORMATION: Synthetic Primer, R838a

<400> SEQUENCE: 1665
aucagagcuu aaacugggaa g                                             21

<210> SEQ ID NO 1666
<211> LENGTH: 21
<212> TYPE: RNA
<213> ORGANISM: Artificial Sequence
<220> FEATURE:
<223> OTHER INFORMATION: Synthetic Primer, R838b

<400> SEQUENCE: 1666
aucagagcuu aaacugggaa a                                             21

<210> SEQ ID NO 1667
<211> LENGTH: 29
```

```
<212> TYPE: RNA
<213> ORGANISM: Artificial Sequence
<220> FEATURE:
<223> OTHER INFORMATION: Synthetic Primer, R839

<400> SEQUENCE: 1667
gucucaguuu uccuaccugu aaaaugaag                                    29

<210> SEQ ID NO 1668
<211> LENGTH: 28
<212> TYPE: DNA
<213> ORGANISM: Artificial Sequence
<220> FEATURE:
<223> OTHER INFORMATION: Synthetic DNA/RNA primer, R840

<400> SEQUENCE: 1668
acuuauucug acaguucucu uuuccct                                      28

<210> SEQ ID NO 1669
<211> LENGTH: 23
<212> TYPE: RNA
<213> ORGANISM: Artificial Sequence
<220> FEATURE:
<223> OTHER INFORMATION: Synthetic Primer, R841

<400> SEQUENCE: 1669
gguggcagug agcuguaaca gua                                          23

<210> SEQ ID NO 1670
<211> LENGTH: 22
<212> TYPE: RNA
<213> ORGANISM: Artificial Sequence
<220> FEATURE:
<223> OTHER INFORMATION: Synthetic Primer, R842

<400> SEQUENCE: 1670
ucagccucca uaucacuuga gc                                           22

<210> SEQ ID NO 1671
<211> LENGTH: 21
<212> TYPE: RNA
<213> ORGANISM: Artificial Sequence
<220> FEATURE:
<223> OTHER INFORMATION: Synthetic Primer, R843

<400> SEQUENCE: 1671
aacuuggguu gagccauagg c                                            21

<210> SEQ ID NO 1672
<211> LENGTH: 27
<212> TYPE: RNA
<213> ORGANISM: Artificial Sequence
<220> FEATURE:
<223> OTHER INFORMATION: Synthetic Primer, R844

<400> SEQUENCE: 1672
ccugguucca uggauuccac auuaaga                                      27

<210> SEQ ID NO 1673
<211> LENGTH: 20
<212> TYPE: DNA
<213> ORGANISM: Artificial Sequence
<220> FEATURE:
<223> OTHER INFORMATION: Synthetic DNA/RNA primer, R845

<400> SEQUENCE: 1673
```
gcguuugugu gugcaucugt           20

<210> SEQ ID NO 1674
<211> LENGTH: 23
<212> TYPE: RNA
<213> ORGANISM: Artificial Sequence
<220> FEATURE:
<223> OTHER INFORMATION: Synthetic Primer, R846

<400> SEQUENCE: 1674
ucuggugugu ggagaugucu uac           23

<210> SEQ ID NO 1675
<211> LENGTH: 25
<212> TYPE: RNA
<213> ORGANISM: Artificial Sequence
<220> FEATURE:
<223> OTHER INFORMATION: Synthetic Primer, R847a

<400> SEQUENCE: 1675
ggcugcaaaa agcuauaauu guacc           25

<210> SEQ ID NO 1676
<211> LENGTH: 25
<212> TYPE: RNA
<213> ORGANISM: Artificial Sequence
<220> FEATURE:
<223> OTHER INFORMATION: Synthetic Primer, R847b

<400> SEQUENCE: 1676
ggcugcaaaa agcuauaacu guacc           25

<210> SEQ ID NO 1677
<211> LENGTH: 25
<212> TYPE: RNA
<213> ORGANISM: Artificial Sequence
<220> FEATURE:
<223> OTHER INFORMATION: Synthetic Primer, R848

<400> SEQUENCE: 1677
uguguuaguc aggauucuuc agaga           25

<210> SEQ ID NO 1678
<211> LENGTH: 31
<212> TYPE: RNA
<213> ORGANISM: Artificial Sequence
<220> FEATURE:
<223> OTHER INFORMATION: Synthetic Primer, R849

<400> SEQUENCE: 1678
uucaguuaua uguguauaaa ugugugcauu g           31

<210> SEQ ID NO 1679
<211> LENGTH: 26
<212> TYPE: RNA
<213> ORGANISM: Artificial Sequence
<220> FEATURE:
<223> OTHER INFORMATION: Synthetic Primer, R850

<400> SEQUENCE: 1679
cuccagagac agacuaauag gaggua           26

<210> SEQ ID NO 1680
<211> LENGTH: 22
<212> TYPE: DNA
<213> ORGANISM: Artificial Sequence

```
<220> FEATURE:
<223> OTHER INFORMATION: Synthetic DNA/RNA primer, R851

<400> SEQUENCE: 1680
ccugugccca aguugagaga at                                                  22

<210> SEQ ID NO 1681
<211> LENGTH: 20
<212> TYPE: RNA
<213> ORGANISM: Artificial Sequence
<220> FEATURE:
<223> OTHER INFORMATION: Synthetic Primer, R853

<400> SEQUENCE: 1681
uaauccagcu gugggaggga                                                     20

<210> SEQ ID NO 1682
<211> LENGTH: 20
<212> TYPE: RNA
<213> ORGANISM: Artificial Sequence
<220> FEATURE:
<223> OTHER INFORMATION: Synthetic Primer, R854

<400> SEQUENCE: 1682
ggugcuaggu gugcucagga                                                     20

<210> SEQ ID NO 1683
<211> LENGTH: 27
<212> TYPE: RNA
<213> ORGANISM: Artificial Sequence
<220> FEATURE:
<223> OTHER INFORMATION: Synthetic Primer, R855

<400> SEQUENCE: 1683
cuucacucuc cuucccaaau guuuaug                                             27

<210> SEQ ID NO 1684
<211> LENGTH: 22
<212> TYPE: RNA
<213> ORGANISM: Artificial Sequence
<220> FEATURE:
<223> OTHER INFORMATION: Synthetic Primer, R856

<400> SEQUENCE: 1684
cuaugauucc cccacugcag uc                                                  22

<210> SEQ ID NO 1685
<211> LENGTH: 28
<212> TYPE: RNA
<213> ORGANISM: Artificial Sequence
<220> FEATURE:
<223> OTHER INFORMATION: Synthetic Primer, R857

<400> SEQUENCE: 1685
agaccccaaa auuacuugag ccaauuua                                            28

<210> SEQ ID NO 1686
<211> LENGTH: 27
<212> TYPE: RNA
<213> ORGANISM: Artificial Sequence
<220> FEATURE:
<223> OTHER INFORMATION: Synthetic Primer, R858

<400> SEQUENCE: 1686
acuucaacuu caauucaucc acugaaa                                             27
```

```
<210> SEQ ID NO 1687
<211> LENGTH: 24
<212> TYPE: RNA
<213> ORGANISM: Artificial Sequence
<220> FEATURE:
<223> OTHER INFORMATION: Synthetic Primer, R859

<400> SEQUENCE: 1687
ugcuugccug uaugaaaaua ucuc                                              24

<210> SEQ ID NO 1688
<211> LENGTH: 24
<212> TYPE: RNA
<213> ORGANISM: Artificial Sequence
<220> FEATURE:
<223> OTHER INFORMATION: Synthetic Primer, R861

<400> SEQUENCE: 1688
uccaaucaua gccacaguuu acaa                                              24

<210> SEQ ID NO 1689
<211> LENGTH: 26
<212> TYPE: DNA
<213> ORGANISM: Artificial Sequence
<220> FEATURE:
<223> OTHER INFORMATION: Synthetic DNA/RNA primer, R862

<400> SEQUENCE: 1689
gcacucuuau ucaucuaguu gccugt                                            26

<210> SEQ ID NO 1690
<211> LENGTH: 23
<212> TYPE: RNA
<213> ORGANISM: Artificial Sequence
<220> FEATURE:
<223> OTHER INFORMATION: Synthetic Primer, R863a

<400> SEQUENCE: 1690
caucauguga gccaauuccu cuc                                               23

<210> SEQ ID NO 1691
<211> LENGTH: 23
<212> TYPE: RNA
<213> ORGANISM: Artificial Sequence
<220> FEATURE:
<223> OTHER INFORMATION: Synthetic Primer, R863b

<400> SEQUENCE: 1691
caucauguga gccaaguccu cuc                                               23

<210> SEQ ID NO 1692
<211> LENGTH: 32
<212> TYPE: DNA
<213> ORGANISM: Artificial Sequence
<220> FEATURE:
<223> OTHER INFORMATION: Synthetic DNA/RNA primer, R864a

<400> SEQUENCE: 1692
uugcaccaaa uauuggvaau uaaauguuua ct                                     32

<210> SEQ ID NO 1693
<211> LENGTH: 32
<212> TYPE: DNA
<213> ORGANISM: Artificial Sequence
<220> FEATURE:
<223> OTHER INFORMATION: Synthetic DNA/RNA primer, R864b
```

<400> SEQUENCE: 1693
uugcaccaca uauugguaau uaaauguuua ct                          32

<210> SEQ ID NO 1694
<211> LENGTH: 22
<212> TYPE: RNA
<213> ORGANISM: Artificial Sequence
<220> FEATURE:
<223> OTHER INFORMATION: Synthetic Primer, R865

<400> SEQUENCE: 1694
cacuguaucg uaucccauug cg                                     22

<210> SEQ ID NO 1695
<211> LENGTH: 24
<212> TYPE: RNA
<213> ORGANISM: Artificial Sequence
<220> FEATURE:
<223> OTHER INFORMATION: Synthetic Primer, R867

<400> SEQUENCE: 1695
uugcaagcaa uugccauaga ggga                                   24

<210> SEQ ID NO 1696
<211> LENGTH: 33
<212> TYPE: RNA
<213> ORGANISM: Artificial Sequence
<220> FEATURE:
<223> OTHER INFORMATION: Synthetic Primer, R868

<400> SEQUENCE: 1696
acagauuaaa cuguaaccaa aauaaaauua ggc                         33

<210> SEQ ID NO 1697
<211> LENGTH: 22
<212> TYPE: RNA
<213> ORGANISM: Artificial Sequence
<220> FEATURE:
<223> OTHER INFORMATION: Synthetic Primer, R869a

<400> SEQUENCE: 1697
ugccuaaccu auggucauaa cg                                     22

<210> SEQ ID NO 1698
<211> LENGTH: 22
<212> TYPE: RNA
<213> ORGANISM: Artificial Sequence
<220> FEATURE:
<223> OTHER INFORMATION: Synthetic Primer, R869b

<400> SEQUENCE: 1698
ugccuaaccu auggucauac cg                                     22

<210> SEQ ID NO 1699
<211> LENGTH: 20
<212> TYPE: RNA
<213> ORGANISM: Artificial Sequence
<220> FEATURE:
<223> OTHER INFORMATION: Synthetic Primer, R870

<400> SEQUENCE: 1699
cccaggaggu ggagauugaa                                        20

<210> SEQ ID NO 1700

```
<211> LENGTH: 24
<212> TYPE: RNA
<213> ORGANISM: Artificial Sequence
<220> FEATURE:
<223> OTHER INFORMATION: Synthetic Primer, R871

<400> SEQUENCE: 1700
uccauguacu uuguccaaug cuga                                              24

<210> SEQ ID NO 1701
<211> LENGTH: 25
<212> TYPE: RNA
<213> ORGANISM: Artificial Sequence
<220> FEATURE:
<223> OTHER INFORMATION: Synthetic Primer, R872

<400> SEQUENCE: 1701
ugucaacacg auuaacaugc aaaga                                             25

<210> SEQ ID NO 1702
<211> LENGTH: 26
<212> TYPE: DNA
<213> ORGANISM: Artificial Sequence
<220> FEATURE:
<223> OTHER INFORMATION: Synthetic DNA/RNA primer, R873

<400> SEQUENCE: 1702
caaaauucaa aggguaucug ggcuct                                            26

<210> SEQ ID NO 1703
<211> LENGTH: 23
<212> TYPE: DNA
<213> ORGANISM: Artificial Sequence
<220> FEATURE:
<223> OTHER INFORMATION: Synthetic DNA/RNA primer, R874

<400> SEQUENCE: 1703
ugugcgcugg ucuuacuccu gut                                               23

<210> SEQ ID NO 1704
<211> LENGTH: 27
<212> TYPE: RNA
<213> ORGANISM: Artificial Sequence
<220> FEATURE:
<223> OTHER INFORMATION: Synthetic Primer, R875

<400> SEQUENCE: 1704
gcccuagugg augauaagaa uaaucag                                           27

<210> SEQ ID NO 1705
<211> LENGTH: 60
<212> TYPE: DNA
<213> ORGANISM: Artificial Sequence
<220> FEATURE:
<223> OTHER INFORMATION: Synthetic DNA/RNA, Rev Adaptor I
<220> FEATURE:
<221> NAME/KEY: misc_feature
<222> LOCATION: (21)..(23)
<223> OTHER INFORMATION: n is a, c, g, t or u
<220> FEATURE:
<221> NAME/KEY: misc_feature
<222> LOCATION: (27)..(29)
<223> OTHER INFORMATION: n is a, c, g, t or u

<400> SEQUENCE: 1705
tgacaaggcg tagtcacggu nnnactnnnt gauccttctg cauggtattc tttctctucc       60
```

<210> SEQ ID NO 1706
<211> LENGTH: 90
<212> TYPE: DNA
<213> ORGANISM: Artificial Sequence
<220> FEATURE:
<223> OTHER INFORMATION: Synthetic Primer, 5-01-Ah

<400> SEQUENCE: 1706
aatgatacgg cgaccaccga gatctacaca gcgctagtcg tcggcagcgt cagatgtgta    60
taagagacag tctgtacggt gacaaggcgt    90

<210> SEQ ID NO 1707
<211> LENGTH: 90
<212> TYPE: DNA
<213> ORGANISM: Artificial Sequence
<220> FEATURE:
<223> OTHER INFORMATION: Synthetic Primer, 5-02-Ah

<400> SEQUENCE: 1707
aatgatacgg cgaccaccga gatctacacg atatcgatcg tcggcagcgt cagatgtgta    60
taagagacag tctgtacggt gacaaggcgt    90

<210> SEQ ID NO 1708
<211> LENGTH: 90
<212> TYPE: DNA
<213> ORGANISM: Artificial Sequence
<220> FEATURE:
<223> OTHER INFORMATION: Synthetic Primer, 5-07-Ah

<400> SEQUENCE: 1708
aatgatacgg cgaccaccga gatctacaca catagcgtcg tcggcagcgt cagatgtgta    60
taagagacag tctgtacggt gacaaggcgt    90

<210> SEQ ID NO 1709
<211> LENGTH: 90
<212> TYPE: DNA
<213> ORGANISM: Artificial Sequence
<220> FEATURE:
<223> OTHER INFORMATION: Synthetic Primer, 5-08-Ah

<400> SEQUENCE: 1709
aatgatacgg cgaccaccga gatctacacg tgcgatatcg tcggcagcgt cagatgtgta    60
taagagacag tctgtacggt gacaaggcgt    90

<210> SEQ ID NO 1710
<211> LENGTH: 90
<212> TYPE: DNA
<213> ORGANISM: Artificial Sequence
<220> FEATURE:
<223> OTHER INFORMATION: Synthetic Primer, 5-09-Ah

<400> SEQUENCE: 1710
aatgatacgg cgaccaccga gatctacacc caacagatcg tcggcagcgt cagatgtgta    60
taagagacag tctgtacggt gacaaggcgt    90

<210> SEQ ID NO 1711
<211> LENGTH: 90
<212> TYPE: DNA
<213> ORGANISM: Artificial Sequence
<220> FEATURE:
<223> OTHER INFORMATION: Synthetic Primer, 5-010-Ah

<400> SEQUENCE: 1711

```
aatgatacgg cgaccaccga gatctacact tggtgagtcg tcggcagcgt cagatgtgta      60
taagagacag tctgtacggt gacaaggcgt                                       90

<210> SEQ ID NO 1712
<211> LENGTH: 90
<212> TYPE: DNA
<213> ORGANISM: Artificial Sequence
<220> FEATURE:
<223> OTHER INFORMATION: Synthetic Primer, 5-013-Ah

<400> SEQUENCE: 1712
aatgatacgg cgaccaccga gatctacaca accgcggtcg tcggcagcgt cagatgtgta      60
taagagacag tctgtacggt gacaaggcgt                                       90

<210> SEQ ID NO 1713
<211> LENGTH: 90
<212> TYPE: DNA
<213> ORGANISM: Artificial Sequence
<220> FEATURE:
<223> OTHER INFORMATION: Synthetic Primer, 5-014-Ah

<400> SEQUENCE: 1713
aatgatacgg cgaccaccga gatctacacg gttataatcg tcggcagcgt cagatgtgta      60
taagagacag tctgtacggt gacaaggcgt                                       90

<210> SEQ ID NO 1714
<211> LENGTH: 90
<212> TYPE: DNA
<213> ORGANISM: Artificial Sequence
<220> FEATURE:
<223> OTHER INFORMATION: Synthetic Primer, 01-Ih

<400> SEQUENCE: 1714
aatgatacgg cgaccaccga gatctacaca gcgctagtcg tcggcagcgt cagatgtgta      60
taagagacag tgacaaggcg tagtcacggt                                       90

<210> SEQ ID NO 1715
<211> LENGTH: 90
<212> TYPE: DNA
<213> ORGANISM: Artificial Sequence
<220> FEATURE:
<223> OTHER INFORMATION: Synthetic Primer, 02-Ih

<400> SEQUENCE: 1715
aatgatacgg cgaccaccga gatctacacg atatcgatcg tcggcagcgt cagatgtgta      60
taagagacag tgacaaggcg tagtcacggt                                       90

<210> SEQ ID NO 1716
<211> LENGTH: 90
<212> TYPE: DNA
<213> ORGANISM: Artificial Sequence
<220> FEATURE:
<223> OTHER INFORMATION: Synthetic Primer, 5-07-Ih

<400> SEQUENCE: 1716
aatgatacgg cgaccaccga gatctacaca catagcgtcg tcggcagcgt cagatgtgta      60
taagagacag tgacaaggcg tagtcacggt                                       90

<210> SEQ ID NO 1717
<211> LENGTH: 90
<212> TYPE: DNA
<213> ORGANISM: Artificial Sequence
```

<220> FEATURE:
<223> OTHER INFORMATION: Synthetic Primer, 5-08-Ih

<400> SEQUENCE: 1717
aatgatacgg cgaccaccga gatctacacg tgcgatatcg tcggcagcgt cagatgtgta    60
taagagacag tgacaaggcg tagtcacggt                                    90

<210> SEQ ID NO 1718
<211> LENGTH: 90
<212> TYPE: DNA
<213> ORGANISM: Artificial Sequence
<220> FEATURE:
<223> OTHER INFORMATION: Synthetic Primer, 5-09-Ih

<400> SEQUENCE: 1718
aatgatacgg cgaccaccga gatctacacc caacagatcg tcggcagcgt cagatgtgta    60
taagagacag tgacaaggcg tagtcacggt                                    90

<210> SEQ ID NO 1719
<211> LENGTH: 90
<212> TYPE: DNA
<213> ORGANISM: Artificial Sequence
<220> FEATURE:
<223> OTHER INFORMATION: Synthetic Primer, 5-010-Ih

<400> SEQUENCE: 1719
aatgatacgg cgaccaccga gatctacact tggtgagtcg tcggcagcgt cagatgtgta    60
taagagacag tgacaaggcg tagtcacggt                                    90

<210> SEQ ID NO 1720
<211> LENGTH: 90
<212> TYPE: DNA
<213> ORGANISM: Artificial Sequence
<220> FEATURE:
<223> OTHER INFORMATION: Synthetic Primer, 5-013-Ih

<400> SEQUENCE: 1720
aatgatacgg cgaccaccga gatctacaca accgcggtcg tcggcagcgt cagatgtgta    60
taagagacag tgacaaggcg tagtcacggt                                    90

<210> SEQ ID NO 1721
<211> LENGTH: 90
<212> TYPE: DNA
<213> ORGANISM: Artificial Sequence
<220> FEATURE:
<223> OTHER INFORMATION: Synthetic Primer, 5-014-Ih

<400> SEQUENCE: 1721
aatgatacgg cgaccaccga gatctacacg gttataatcg tcggcagcgt cagatgtgta    60
taagagacag tgacaaggcg tagtcacggt                                    90

<210> SEQ ID NO 1722
<211> LENGTH: 86
<212> TYPE: DNA
<213> ORGANISM: Artificial Sequence
<220> FEATURE:
<223> OTHER INFORMATION: Synthetic Primer, 7-1-Ah

<400> SEQUENCE: 1722
caagcagaag acggcatacg agatatattc acgtctcgtg ggctcggaga tgtgtataag    60
agacagtctg tacggtgaca aggcgt                                        86

<210> SEQ ID NO 1723
<211> LENGTH: 86
<212> TYPE: DNA
<213> ORGANISM: Artificial Sequence
<220> FEATURE:
<223> OTHER INFORMATION: Synthetic Primer, 7-2-Ah

<400> SEQUENCE: 1723
caagcagaag acggcatacg agatgcgcct gtgtctcgtg ggctcggaga tgtgtataag    60
agacagtctg tacggtgaca aggcgt    86

<210> SEQ ID NO 1724
<211> LENGTH: 86
<212> TYPE: DNA
<213> ORGANISM: Artificial Sequence
<220> FEATURE:
<223> OTHER INFORMATION: Synthetic Primer, 7-3-Ah

<400> SEQUENCE: 1724
caagcagaag acggcatacg agatactcta tggtctcgtg ggctcggaga tgtgtataag    60
agacagtctg tacggtgaca aggcgt    86

<210> SEQ ID NO 1725
<211> LENGTH: 86
<212> TYPE: DNA
<213> ORGANISM: Artificial Sequence
<220> FEATURE:
<223> OTHER INFORMATION: Synthetic Primer, 7-4-Ah

<400> SEQUENCE: 1725
caagcagaag acggcatacg agatgtctcg cagtctcgtg ggctcggaga tgtgtataag    60
agacagtctg tacggtgaca aggcgt    86

<210> SEQ ID NO 1726
<211> LENGTH: 86
<212> TYPE: DNA
<213> ORGANISM: Artificial Sequence
<220> FEATURE:
<223> OTHER INFORMATION: Synthetic Primer, 7-5-Ah

<400> SEQUENCE: 1726
caagcagaag acggcatacg agatagtaga gagtctcgtg ggctcggaga tgtgtataag    60
agacagtctg tacggtgaca aggcgt    86

<210> SEQ ID NO 1727
<211> LENGTH: 86
<212> TYPE: DNA
<213> ORGANISM: Artificial Sequence
<220> FEATURE:
<223> OTHER INFORMATION: Synthetic Primer, 7-6-Ah

<400> SEQUENCE: 1727
caagcagaag acggcatacg agatgacgag aggtctcgtg ggctcggaga tgtgtataag    60
agacagtctg tacggtgaca aggcgt    86

<210> SEQ ID NO 1728
<211> LENGTH: 86
<212> TYPE: DNA
<213> ORGANISM: Artificial Sequence
<220> FEATURE:
<223> OTHER INFORMATION: Synthetic Primer, 7-7-Ah

<400> SEQUENCE: 1728

```
caagcagaag acggcatacg agatagactt gggtctcgtg ggctcggaga tgtgtataag    60
agacagtctg tacggtgaca aggcgt                                         86

<210> SEQ ID NO 1729
<211> LENGTH: 86
<212> TYPE: DNA
<213> ORGANISM: Artificial Sequence
<220> FEATURE:
<223> OTHER INFORMATION: Synthetic Primer, 7-8-Ah

<400> SEQUENCE: 1729
caagcagaag acggcatacg agatgagtcc aagtctcgtg ggctcggaga tgtgtataag    60
agacagtctg tacggtgaca aggcgt                                         86

<210> SEQ ID NO 1730
<211> LENGTH: 86
<212> TYPE: DNA
<213> ORGANISM: Artificial Sequence
<220> FEATURE:
<223> OTHER INFORMATION: Synthetic Primer, 7-9-Ah

<400> SEQUENCE: 1730
caagcagaag acggcatacg agataattct gcgtctcgtg ggctcggaga tgtgtataag    60
agacagtctg tacggtgaca aggcgt                                         86

<210> SEQ ID NO 1731
<211> LENGTH: 86
<212> TYPE: DNA
<213> ORGANISM: Artificial Sequence
<220> FEATURE:
<223> OTHER INFORMATION: Synthetic Primer, 7-10-Ah

<400> SEQUENCE: 1731
caagcagaag acggcatacg agatggcctc atgtctcgtg ggctcggaga tgtgtataag    60
agacagtctg tacggtgaca aggcgt                                         86

<210> SEQ ID NO 1732
<211> LENGTH: 86
<212> TYPE: DNA
<213> ORGANISM: Artificial Sequence
<220> FEATURE:
<223> OTHER INFORMATION: Synthetic Primer, 7-1-Ah

<400> SEQUENCE: 1732
caagcagaag acggcatacg agatatctta gtgtctcgtg ggctcggaga tgtgtataag    60
agacagtctg tacggtgaca aggcgt                                         86

<210> SEQ ID NO 1733
<211> LENGTH: 86
<212> TYPE: DNA
<213> ORGANISM: Artificial Sequence
<220> FEATURE:
<223> OTHER INFORMATION: Synthetic Primer, 7-12-Ah

<400> SEQUENCE: 1733
caagcagaag acggcatacg agatgctccg acgtctcgtg ggctcggaga tgtgtataag    60
agacagtctg tacggtgaca aggcgt                                         86

<210> SEQ ID NO 1734
<211> LENGTH: 86
<212> TYPE: DNA
```

<213> ORGANISM: Artificial Sequence
<220> FEATURE:
<223> OTHER INFORMATION: Synthetic Primer, 7-1-Ih

<400> SEQUENCE: 1734
caagcagaag acggcatacg agatatattc acgtctcgtg ggctcggaga tgtgtataag    60
agacagtgac aaggcgtagt cacggt                                         86

<210> SEQ ID NO 1735
<211> LENGTH: 86
<212> TYPE: DNA
<213> ORGANISM: Artificial Sequence
<220> FEATURE:
<223> OTHER INFORMATION: Synthetic Primer, 7-2-Ih

<400> SEQUENCE: 1735
caagcagaag acggcatacg agatgcgcct gtgtctcgtg ggctcggaga tgtgtataag    60
agacagtgac aaggcgtagt cacggt                                         86

<210> SEQ ID NO 1736
<211> LENGTH: 86
<212> TYPE: DNA
<213> ORGANISM: Artificial Sequence
<220> FEATURE:
<223> OTHER INFORMATION: Synthetic Primer, 7-3-Ih

<400> SEQUENCE: 1736
caagcagaag acggcatacg agatactcta tggtctcgtg ggctcggaga tgtgtataag    60
agacagtgac aaggcgtagt cacggt                                         86

<210> SEQ ID NO 1737
<211> LENGTH: 86
<212> TYPE: DNA
<213> ORGANISM: Artificial Sequence
<220> FEATURE:
<223> OTHER INFORMATION: Synthetic Primer, 7-4-Ih

<400> SEQUENCE: 1737
caagcagaag acggcatacg agatgtctcg cagtctcgtg ggctcggaga tgtgtataag    60
agacagtgac aaggcgtagt cacggt                                         86

<210> SEQ ID NO 1738
<211> LENGTH: 86
<212> TYPE: DNA
<213> ORGANISM: Artificial Sequence
<220> FEATURE:
<223> OTHER INFORMATION: Synthetic Primer, 7-5-Ih

<400> SEQUENCE: 1738
caagcagaag acggcatacg agatagtaga gagtctcgtg ggctcggaga tgtgtataag    60
agacagtgac aaggcgtagt cacggt                                         86

<210> SEQ ID NO 1739
<211> LENGTH: 86
<212> TYPE: DNA
<213> ORGANISM: Artificial Sequence
<220> FEATURE:
<223> OTHER INFORMATION: Synthetic Primer, 7-6-Ih

<400> SEQUENCE: 1739
caagcagaag acggcatacg agatgacgag aggtctcgtg ggctcggaga tgtgtataag    60
agacagtgac aaggcgtagt cacggt                                         86

<210> SEQ ID NO 1740
<211> LENGTH: 86
<212> TYPE: DNA
<213> ORGANISM: Artificial Sequence
<220> FEATURE:
<223> OTHER INFORMATION: Synthetic Primer, 7-7-Ih

<400> SEQUENCE: 1740
caagcagaag acggcatacg agatagactt gggtctcgtg ggctcggaga tgtgtataag    60
agacagtgac aaggcgtagt cacggt                                         86

<210> SEQ ID NO 1741
<211> LENGTH: 86
<212> TYPE: DNA
<213> ORGANISM: Artificial Sequence
<220> FEATURE:
<223> OTHER INFORMATION: Synthetic Primer, 7-8-Ih

<400> SEQUENCE: 1741
caagcagaag acggcatacg agatgagtcc aagtctcgtg ggctcggaga tgtgtataag    60
agacagtgac aaggcgtagt cacggt                                         86

<210> SEQ ID NO 1742
<211> LENGTH: 86
<212> TYPE: DNA
<213> ORGANISM: Artificial Sequence
<220> FEATURE:
<223> OTHER INFORMATION: Synthetic Primer, 7-9-Ih

<400> SEQUENCE: 1742
caagcagaag acggcatacg agataattct gcgtctcgtg ggctcggaga tgtgtataag    60
agacagtgac aaggcgtagt cacggt                                         86

<210> SEQ ID NO 1743
<211> LENGTH: 86
<212> TYPE: DNA
<213> ORGANISM: Artificial Sequence
<220> FEATURE:
<223> OTHER INFORMATION: Synthetic Primer, 7-10-Ih

<400> SEQUENCE: 1743
caagcagaag acggcatacg agatggcctc atgtctcgtg ggctcggaga tgtgtataag    60
agacagtgac aaggcgtagt cacggt                                         86

<210> SEQ ID NO 1744
<211> LENGTH: 86
<212> TYPE: DNA
<213> ORGANISM: Artificial Sequence
<220> FEATURE:
<223> OTHER INFORMATION: Synthetic Primer, 7-11-Ih

<400> SEQUENCE: 1744
caagcagaag acggcatacg agatatctta gtgtctcgtg ggctcggaga tgtgtataag    60
agacagtgac aaggcgtagt cacggt                                         86

<210> SEQ ID NO 1745
<211> LENGTH: 86
<212> TYPE: DNA
<213> ORGANISM: Artificial Sequence
<220> FEATURE:
<223> OTHER INFORMATION: Synthetic Primer, 7-12-Ih -continued

<400> SEQUENCE: 1745
caagcagaag acggcatacg agatgctccg acgtctcgtg ggctcggaga tgtgtataag    60
agacagtgac aaggcgtagt cacggt                                         86

<210> SEQ ID NO 1746
<211> LENGTH: 18
<212> TYPE: RNA
<213> ORGANISM: Artificial Sequence
<220> FEATURE:
<223> OTHER INFORMATION: Synthetic Primer, F498

<400> SEQUENCE: 1746
gagugugcgu ggcucuca                                                  18

<210> SEQ ID NO 1747
<211> LENGTH: 18
<212> TYPE: RNA
<213> ORGANISM: Artificial Sequence
<220> FEATURE:
<223> OTHER INFORMATION: Synthetic Primer, F825

<400> SEQUENCE: 1747
cuggcuccgg gugacagc                                                  18

<210> SEQ ID NO 1748
<211> LENGTH: 19
<212> TYPE: RNA
<213> ORGANISM: Artificial Sequence
<220> FEATURE:
<223> OTHER INFORMATION: Synthetic Primer, F826

<400> SEQUENCE: 1748
gacucccaug acccccauc                                                 19

<210> SEQ ID NO 1749
<211> LENGTH: 28
<212> TYPE: RNA
<213> ORGANISM: Artificial Sequence
<220> FEATURE:
<223> OTHER INFORMATION: Synthetic Primer, F827

<400> SEQUENCE: 1749
aaaaauguua ugucagcguu uggcuuaa                                       28

<210> SEQ ID NO 1750
<211> LENGTH: 18
<212> TYPE: RNA
<213> ORGANISM: Artificial Sequence
<220> FEATURE:
<223> OTHER INFORMATION: Synthetic Primer, F828

<400> SEQUENCE: 1750
guaggcgcga gcuaagca                                                  18

<210> SEQ ID NO 1751
<211> LENGTH: 28
<212> TYPE: RNA
<213> ORGANISM: Artificial Sequence
<220> FEATURE:
<223> OTHER INFORMATION: Synthetic Primer, F829

<400> SEQUENCE: 1751
caggucauau ugaacauucc agauaccu                                       28

```
<210> SEQ ID NO 1752
<211> LENGTH: 18
<212> TYPE: RNA
<213> ORGANISM: Artificial Sequence
<220> FEATURE:
<223> OTHER INFORMATION: Synthetic Primer, F830

<400> SEQUENCE: 1752
gguccugacg caggcuuc                                                 18

<210> SEQ ID NO 1753
<211> LENGTH: 22
<212> TYPE: RNA
<213> ORGANISM: Artificial Sequence
<220> FEATURE:
<223> OTHER INFORMATION: Synthetic Primer, F831

<400> SEQUENCE: 1753
guaccugcau caaccccucu aa                                            22

<210> SEQ ID NO 1754
<211> LENGTH: 20
<212> TYPE: RNA
<213> ORGANISM: Artificial Sequence
<220> FEATURE:
<223> OTHER INFORMATION: Synthetic Primer, F832

<400> SEQUENCE: 1754
cagagacccg ugcugaguuu                                               20

<210> SEQ ID NO 1755
<211> LENGTH: 23
<212> TYPE: RNA
<213> ORGANISM: Artificial Sequence
<220> FEATURE:
<223> OTHER INFORMATION: Synthetic Primer, F833

<400> SEQUENCE: 1755
ggagagaaga gugcacaaua cca                                           23

<210> SEQ ID NO 1756
<211> LENGTH: 23
<212> TYPE: RNA
<213> ORGANISM: Artificial Sequence
<220> FEATURE:
<223> OTHER INFORMATION: Synthetic Primer, F834

<400> SEQUENCE: 1756
ccuguaaucc cugcacuuua gga                                           23

<210> SEQ ID NO 1757
<211> LENGTH: 25
<212> TYPE: RNA
<213> ORGANISM: Artificial Sequence
<220> FEATURE:
<223> OTHER INFORMATION: Synthetic Primer, F835

<400> SEQUENCE: 1757
acuuuccagu ugagcauccc aaauu                                         25

<210> SEQ ID NO 1758
<211> LENGTH: 28
<212> TYPE: RNA
<213> ORGANISM: Artificial Sequence
<220> FEATURE:
<223> OTHER INFORMATION: Synthetic Primer, F836
```

-continued

```
<400> SEQUENCE: 1758
cgucagcgug auauguaccg uauuuuau                                        28

<210> SEQ ID NO 1759
<211> LENGTH: 27
<212> TYPE: RNA
<213> ORGANISM: Artificial Sequence
<220> FEATURE:
<223> OTHER INFORMATION: Synthetic Primer, F837

<400> SEQUENCE: 1759
caccucagua auauggaagu ccaaguu                                         27

<210> SEQ ID NO 1760
<211> LENGTH: 26
<212> TYPE: RNA
<213> ORGANISM: Artificial Sequence
<220> FEATURE:
<223> OTHER INFORMATION: Synthetic Primer, F797

<400> SEQUENCE: 1760
cccuucguag acauauagcu guucuc                                          26

<210> SEQ ID NO 1761
<211> LENGTH: 23
<212> TYPE: RNA
<213> ORGANISM: Artificial Sequence
<220> FEATURE:
<223> OTHER INFORMATION: Synthetic Primer, F798

<400> SEQUENCE: 1761
uggugcuagu ugcaaagaca caa                                             23

<210> SEQ ID NO 1762
<211> LENGTH: 18
<212> TYPE: RNA
<213> ORGANISM: Artificial Sequence
<220> FEATURE:
<223> OTHER INFORMATION: Synthetic Primer, F799

<400> SEQUENCE: 1762
agcgacgcca uugcucau                                                   18

<210> SEQ ID NO 1763
<211> LENGTH: 21
<212> TYPE: RNA
<213> ORGANISM: Artificial Sequence
<220> FEATURE:
<223> OTHER INFORMATION: Synthetic Primer, F800

<400> SEQUENCE: 1763
ccucaaccau uuccggcaaa u                                               21

<210> SEQ ID NO 1764
<211> LENGTH: 18
<212> TYPE: RNA
<213> ORGANISM: Artificial Sequence
<220> FEATURE:
<223> OTHER INFORMATION: Synthetic Primer, F801

<400> SEQUENCE: 1764
ccagcucccu gcgaagag                                                   18

<210> SEQ ID NO 1765
<211> LENGTH: 26
```

```
<212> TYPE: RNA
<213> ORGANISM: Artificial Sequence
<220> FEATURE:
<223> OTHER INFORMATION: Synthetic Primer, F802

<400> SEQUENCE: 1765
aaucccugca guagauacga agacua                                            26

<210> SEQ ID NO 1766
<211> LENGTH: 25
<212> TYPE: RNA
<213> ORGANISM: Artificial Sequence
<220> FEATURE:
<223> OTHER INFORMATION: Synthetic Primer, F803

<400> SEQUENCE: 1766
agaccuugca gaaauaggaa uugcu                                             25

<210> SEQ ID NO 1767
<211> LENGTH: 27
<212> TYPE: RNA
<213> ORGANISM: Artificial Sequence
<220> FEATURE:
<223> OTHER INFORMATION: Synthetic Primer, F805

<400> SEQUENCE: 1767
aaagaaaaga caguuggagg aaucugu                                           27

<210> SEQ ID NO 1768
<211> LENGTH: 28
<212> TYPE: RNA
<213> ORGANISM: Artificial Sequence
<220> FEATURE:
<223> OTHER INFORMATION: Synthetic Primer, F806

<400> SEQUENCE: 1768
gaagaaaaug aaaaggaguu agcagcau                                          28

<210> SEQ ID NO 1769
<211> LENGTH: 27
<212> TYPE: RNA
<213> ORGANISM: Artificial Sequence
<220> FEATURE:
<223> OTHER INFORMATION: Synthetic Primer, F807

<400> SEQUENCE: 1769
aguggcaaaa gaacuucaga cuuuaca                                           27

<210> SEQ ID NO 1770
<211> LENGTH: 19
<212> TYPE: RNA
<213> ORGANISM: Artificial Sequence
<220> FEATURE:
<223> OTHER INFORMATION: Synthetic Primer, F808

<400> SEQUENCE: 1770
gcgcugcuca gaagcaaaa                                                    19

<210> SEQ ID NO 1771
<211> LENGTH: 25
<212> TYPE: RNA
<213> ORGANISM: Artificial Sequence
<220> FEATURE:
<223> OTHER INFORMATION: Synthetic Primer, F809

<400> SEQUENCE: 1771
```

```
guagaucgca uaaaggaagc aguca                                          25

<210> SEQ ID NO 1772
<211> LENGTH: 26
<212> TYPE: RNA
<213> ORGANISM: Artificial Sequence
<220> FEATURE:
<223> OTHER INFORMATION: Synthetic Primer, F810

<400> SEQUENCE: 1772
ggaagcaguc aggucaaaga auaugg                                         26

<210> SEQ ID NO 1773
<211> LENGTH: 27
<212> TYPE: RNA
<213> ORGANISM: Artificial Sequence
<220> FEATURE:
<223> OTHER INFORMATION: Synthetic Primer, F812

<400> SEQUENCE: 1773
caagcagaaa cacuguacaa agagauu                                        27

<210> SEQ ID NO 1774
<211> LENGTH: 18
<212> TYPE: RNA
<213> ORGANISM: Artificial Sequence
<220> FEATURE:
<223> OTHER INFORMATION: Synthetic Primer, F813

<400> SEQUENCE: 1774
gagggcgagc ugcaugau                                                  18

<210> SEQ ID NO 1775
<211> LENGTH: 25
<212> TYPE: RNA
<213> ORGANISM: Artificial Sequence
<220> FEATURE:
<223> OTHER INFORMATION: Synthetic Primer, F814

<400> SEQUENCE: 1775
cacaucuuca ggugcuggau uuuuc                                          25

<210> SEQ ID NO 1776
<211> LENGTH: 27
<212> TYPE: RNA
<213> ORGANISM: Artificial Sequence
<220> FEATURE:
<223> OTHER INFORMATION: Synthetic Primer, F815

<400> SEQUENCE: 1776 cuuugaaaa gccagugaug aucucaa                                         27

<210> SEQ ID NO 1777
<211> LENGTH: 24
<212> TYPE: RNA
<213> ORGANISM: Artificial Sequence
<220> FEATURE:
<223> OTHER INFORMATION: Synthetic Primer, F816

<400> SEQUENCE: 1777
gcaccuugac uuuaagugag agca                                           24

<210> SEQ ID NO 1778
<211> LENGTH: 28
<212> TYPE: RNA
<213> ORGANISM: Artificial Sequence
```

```
<220> FEATURE:
<223> OTHER INFORMATION: Synthetic Primer, F817

<400> SEQUENCE: 1778
acagcacugu uauuacuacu uggguuuu                                    28

<210> SEQ ID NO 1779
<211> LENGTH: 22
<212> TYPE: RNA
<213> ORGANISM: Artificial Sequence
<220> FEATURE:
<223> OTHER INFORMATION: Synthetic Primer, F818

<400> SEQUENCE: 1779
caagcuccuu acauacccag ca                                          22

<210> SEQ ID NO 1780
<211> LENGTH: 19
<212> TYPE: RNA
<213> ORGANISM: Artificial Sequence
<220> FEATURE:
<223> OTHER INFORMATION: Synthetic Primer, F819

<400> SEQUENCE: 1780 gcguuccuc gcuugcauu                                               19

<210> SEQ ID NO 1781
<211> LENGTH: 22
<212> TYPE: DNA
<213> ORGANISM: Artificial Sequence
<220> FEATURE:
<223> OTHER INFORMATION: Synthetic Primer, F820

<400> SEQUENCE: 1781
cgggcaggaa tctgatgact tt                                          22

<210> SEQ ID NO 1782
<211> LENGTH: 20
<212> TYPE: RNA
<213> ORGANISM: Artificial Sequence
<220> FEATURE:
<223> OTHER INFORMATION: Synthetic Primer, F821

<400> SEQUENCE: 1782
gcagggcagc aacaucuuug                                             20

<210> SEQ ID NO 1783
<211> LENGTH: 27
<212> TYPE: RNA
<213> ORGANISM: Artificial Sequence
<220> FEATURE:
<223> OTHER INFORMATION: Synthetic Primer, F822

<400> SEQUENCE: 1783
ggcuccugag accuuugaua acauaac                                     27

<210> SEQ ID NO 1784
<211> LENGTH: 26
<212> TYPE: RNA
<213> ORGANISM: Artificial Sequence
<220> FEATURE:
<223> OTHER INFORMATION: Synthetic Primer, F823

<400> SEQUENCE: 1784
cgugugcucc cuggauauuc uuagua                                      26
```

```
<210> SEQ ID NO 1785
<211> LENGTH: 18
<212> TYPE: RNA
<213> ORGANISM: Artificial Sequence
<220> FEATURE:
<223> OTHER INFORMATION: Synthetic Primer, F824

<400> SEQUENCE: 1785
cuggcuccgg gugacagc                                                 18
```

LIBRARY PREPARATION METHODS AND COMPOSITIONS AND USES THEREFOR

RELATED APPLICATIONS

This application claims priority to and the benefit under 35 USC § 119(e) of each of U.S. Provisional Application No. 62/527,893 filed Jun. 30, 2017, U.S. Provisional Application No. 62/614,362, filed Jan. 6, 2018, and U.S. Provisional Application No. 62/685,424, filed Jun. 15, 2018. The entire contents of each of the aforementioned applications are herein incorporated by reference in their entirety.

SEQUENCE LISTING

This application hereby incorporates by reference the material of the electronic Sequence Listing filed concurrently herewith. The material in the electronic Sequence Listing is submitted as a text (.txt) file entitled "20180627_LT01273_ST25.txt" created on Jun. 27, 2018 which has a file size of 359 KB and is herein incorporated by reference in its entirety.

FIELD OF THE INVENTION

The present invention relates to methods of preparing a library of target nucleic acid sequences and compositions and uses therefor.

BRIEF SUMMARY OF THE INVENTION

Provided are methods for preparing a library of target nucleic acid sequences, as well as compositions and uses therefor. Methods comprise contacting a nucleic acid sample with a plurality of adaptors capable of amplification of one or more target nucleic acid sequences under conditions wherein the target nucleic acid(s) undergo a first amplification; digesting the resulting first amplification products; repairing the digested target amplicons; and amplifying the repaired products in a second amplification, thereby producing a library of target nucleic acid sequence. Each of the plurality of adaptor compositions comprise a handle and a targeted nucleic acid sequence and optionally one or more tag sequences. Provided methods may be carried out in a single, addition only workflow reaction, allowing for rapid production of highly multiplexed targeted libraries, optionally including unique tag sequences. Resulting library compositions are useful for a variety of applications, including sequencing applications.

One aspect of the invention comprises methods for preparing a library of target nucleic acid sequences. In certain embodiments the methods comprise contacting a nucleic acid sample with a plurality of adaptors wherein each of a pair of adaptors are capable of amplification of one or more target nucleic acid sequences in the sample under conditions wherein the target nucleic acid(s) undergo a first amplification. The methods further comprise digesting the resulting first amplification products to reduce or eliminate any primer dimers resulting in the reaction and preparing partially digested amplicons, thereby preparing resulting gapped, double stranded partially digested amplicons. The methods further comprise repairing the partially digested target amplicons; then amplifying the repaired products in a second amplification using universal primers to thereby produce a library of target nucleic acid sequences. Each of the plurality of adaptors used in the provided methods comprise a 5' universal handle sequence and a 3' target nucleic acid sequence and a cleavable moiety. Two or more target specific adaptor pairs are included for use in provided methods, wherein each of the 3' target specific sequences comprise cleavable moieties. Optionally, one or more tag sequences are included.

In another aspect of the invention methods for preparing a library of target nucleic acid sequences having unique tag sequences is provided. In certain embodiments the methods comprise contacting a nucleic acid sample with a plurality of adaptors wherein each of a pair of adaptors are capable of amplification of one or more target nucleic acid sequences in the sample under conditions wherein the target nucleic acid(s) undergo a first amplification. The methods further comprise digesting the resulting first amplification products to reduce or eliminate any primer dimers resulting in the reaction and preparing partially digested amplicons, thereby preparing resulting gapped, double stranded partially digested amplicons. The methods further comprise repairing the partially digested target amplicons; then amplifying the repaired products in a second amplification using universal primers to thereby produce a library of target nucleic acid sequences. Each of the plurality of adaptors used in the provided methods comprise a 5' universal handle sequence, one or more unique tag sequences and a 3' target nucleic acid sequence and a cleavable moiety. Two or more target specific adaptor pairs are included for use in provided methods, wherein each of the 3' target specific sequences comprise cleavable moieties, each tag sequence is flanked by cleavable moieties, and each universal handle is without cleavable moieties.

In a further aspect, compositions are provided. In some embodiments provided are compositions comprising nucleic acid libraries generated by the methods described herein. In other embodiments, compositions comprising a plurality of nucleic acid adaptors are provided, wherein each of the plurality of adaptors comprise a 5' universal handle sequence, one or more unique tag sequences, and a 3' target nucleic acid sequence wherein each adaptor comprises a cleavable moiety. In certain embodiments the target nucleic acid sequence of the adaptor includes at least one cleavable moiety, cleavable moieties are included flanking either end of the tag sequence and the universal handle sequence does not include the cleavable moiety. In certain embodiments, compositions include at least two and up to one hundred thousand target specific adaptor pairs.

Still further, uses of provided compositions and kits comprising provided compositions for analysis of sequences of the nucleic acid libraries are additional aspects of the invention. In some embodiments, analysis of the sequences of the resulting libraries enables detection of low frequency alleles in a sample of interest.

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Efficient methods for production of targeted libraries from complex samples is desirable for a variety of nucleic acid analyses. The present invention provides, inter alia, methods of preparing libraries of target nucleic acid sequences, allowing for rapid production of highly multiplexed targeted libraries, optionally including unique tag sequences; and resulting library compositions are useful for a variety of applications, including sequencing applications. Novel features of the invention are set forth with particularity in the appended claims; and a complete understanding of the features and advantages of the present invention will be obtained by reference to the following detailed description that sets forth illustrative embodiments, in which the principles of the invention are utilized, and the accompanying drawings of which:

DESCRIPTION OF THE INVENTION

Figure 1:
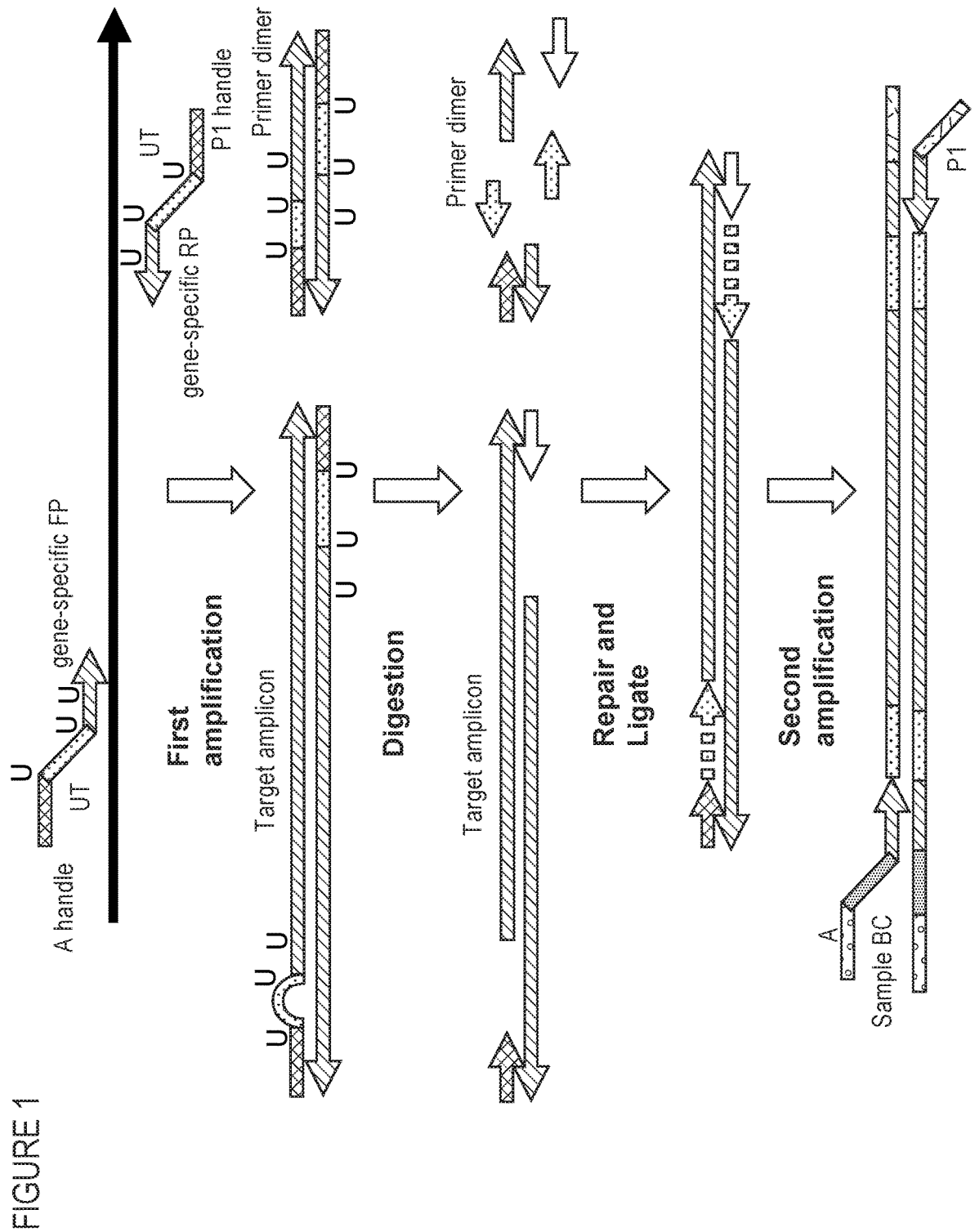
FIG. 1 depicts a workflow method of the invention that enables efficient rapid, highly multiplexed library preparation.

Section headings used herein are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc discussed in the present teachings, such that slight and insubstantial deviations are within the scope of the present teachings herein. In this application, the use of the singular includes the plural unless specifically stated otherwise. It is noted that, as used in this specification, singular forms "a," "an," and "the," and any singular use of a word, include plural referents unless expressly and unequivocally limited to one referent. Also, the use of "comprise", "comprises", "comprising", "contain", "contains", "containing", "include", "includes", and "including" are not intended to be limiting. It is to be understood that both the general description is exemplary and explanatory only and not restrictive of the invention.

Unless otherwise defined, scientific and technical terms used in connection with the invention described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization used herein are those well-known and commonly used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. Techniques and procedures described herein are generally performed according to conventional methods well known in the art and as described in various general and more specific references that are cited and discussed throughout the instant specification. See, e.g., Sambrook et al., *Molecular Cloning: A Laboratory Manual* (Third ed., Cold Spring Harbor Laboratory Press, Cold Spring Harbor, N.Y. 2000). Unless specifically provided, any nomenclature utilized in connection with, and laboratory procedures and techniques described herein are those well-known and commonly used in the art. As utilized in accordance with embodiments provided herein, the following terms, unless otherwise indicated, shall be understood to have the following meanings:

As used herein, "amplify", "amplifying" or "amplification reaction" and their derivatives, refer generally to an action or process whereby at least a portion of a nucleic acid molecule (referred to as a template nucleic acid molecule) is replicated or copied into at least one additional nucleic acid molecule. The additional nucleic acid molecule optionally includes sequence that is substantially identical or substantially complementary to at least some portion of the template nucleic acid molecule. A template target nucleic acid molecule may be single-stranded or double-stranded. The additional resulting replicated nucleic acid molecule may independently be single-stranded or double-stranded. In some embodiments, amplification includes a template-dependent in vitro enzyme-catalyzed reaction for the production of at least one copy of at least some portion of a target nucleic acid molecule or the production of at least one copy of a target nucleic acid sequence that is complementary to at least some portion of a target nucleic acid molecule. Amplification optionally includes linear or exponential replication of a nucleic acid molecule. In some embodiments, such amplification is performed using isothermal conditions; in other embodiments, such amplification can include thermocycling. In some embodiments, the amplification is a multiplex amplification that includes simultaneous amplification of a plurality of target sequences in a single amplification reaction. At least some target sequences can be situated on the same nucleic acid molecule or on different target nucleic acid molecules included in a single amplification reaction. In some embodiments, "amplification" includes amplification of at least some portion of DNA- and/or RNA-based nucleic acids, whether alone, or in combination. An amplification reaction can include single or double-stranded nucleic acid substrates and can further include any amplification processes known to one of ordinary skill in the art. In some embodiments, an amplification reaction includes polymerase chain reaction (PCR). In some embodiments, an amplification reaction includes isothermal amplification.

As used herein, "amplification conditions" and derivatives (e.g., conditions for amplification, etc.) generally refers to conditions suitable for amplifying one or more nucleic acid sequences. Amplification can be linear or exponential. In some embodiments, amplification conditions include isothermal conditions or alternatively include thermocycling conditions, or a combination of isothermal and thermocycling conditions. In some embodiments, conditions suitable for amplifying one or more target nucleic acid sequences includes polymerase chain reaction (PCR) conditions. Typically, amplification conditions refer to a reaction mixture that is sufficient to amplify nucleic acids such as one or more target sequences, or to amplify an amplified target sequence ligated or attached to one or more adaptors, e.g., an adaptor-attached amplified target sequence. Generally, amplification conditions include a catalyst for amplification or for nucleic acid synthesis, for example a polymerase; a primer that possesses some degree of complementarity to the nucleic acid to be amplified; and nucleotides, such as deoxyribonucleoside triphosphates (dNTPs) to promote extension of a primer once hybridized to a nucleic acid. Amplification conditions can require hybridization or annealing of a primer to a nucleic acid, extension of the primer and a denaturing step in which the extended primer is separated from the nucleic acid sequence undergoing amplification. Typically, though not necessarily, amplification conditions can include thermocycling. In some embodiments, amplification conditions include a plurality of cycles wherein steps of annealing, extending and separating are repeated. Typically, amplification conditions include cations such as $Mg^{++}$ or $Mn^{++}$ (e.g., $MgCl_2$, etc) and can also optionally include various modifiers of ionic strength.

As used herein, "target sequence" "target nucleic acid sequence" or "target sequence of interest" and derivatives, refers generally to any single or double-stranded nucleic acid sequence that can be amplified or synthesized according to the disclosure, including any nucleic acid sequence suspected or expected to be present in a sample. In some embodiments, the target sequence is present in double-stranded form and includes at least a portion of the particular nucleotide sequence to be amplified or synthesized, or its complement, prior to the addition of target-specific primers or appended adaptors. Target sequences can include the nucleic acids to which primers useful in the amplification or synthesis reaction can hybridize prior to extension by a polymerase. In some embodiments, the term refers to a nucleic acid sequence whose sequence identity, ordering or location of nucleotides is determined by one or more of the methods of the disclosure.

The term "portion" and its variants, as used herein, when used in reference to a given nucleic acid molecule, for example a primer or a template nucleic acid molecule, comprises any number of contiguous nucleotides within the length of the nucleic acid molecule, including the partial or entire length of the nucleic acid molecule.

As used herein, "contacting" and its derivatives, when used in reference to two or more components, refers generally to any process whereby the approach, proximity, mixture or commingling of the referenced components is promoted or achieved without necessarily requiring physical contact of such components, and includes mixing of solutions containing any one or more of the referenced components with each other. The referenced components may be contacted in any particular order or combination and the particular order of recitation of components is not limiting. For example, "contacting A with B and C" encompasses embodiments where A is first contacted with B then C, as well as embodiments where C is contacted with A then B, as well as embodiments where a mixture of A and C is contacted with B, and the like. Furthermore, such contacting does not necessarily require that the end result of the contacting process be a mixture including all of the referenced components, as long as at some point during the contacting process all of the referenced components are simultaneously present or simultaneously included in the same mixture or solution. For example, "contacting A with B and C" can include embodiments wherein C is first contacted with A to form a first mixture, which first mixture is then contacted with B to form a second mixture, following which C is removed from the second mixture; optionally A can then also be removed, leaving only B. Where one or more of the referenced components to be contacted includes a plurality (e.g., "contacting a target sequence with a plurality of target-specific primers and a polymerase"), then each member of the plurality can be viewed as an individual component of the contacting process, such that the contacting can include contacting of any one or more members of the plurality with any other member of the plurality and/or with any other referenced component (e.g., some but not all of the plurality of target specific primers can be contacted with a target sequence, then a polymerase, and then with other members of the plurality of target-specific primers) in any order or combination.

As used herein, the term "primer" and its derivatives refer generally to any polynucleotide that can hybridize to a target sequence of interest. In some embodiments, the primer can also serve to prime nucleic acid synthesis. Typically, a primer functions as a substrate onto which nucleotides can be polymerized by a polymerase; in some embodiments, however, a primer can become incorporated into a synthesized nucleic acid strand and provide a site to which another primer can hybridize to prime synthesis of a new strand that is complementary to the synthesized nucleic acid molecule. A primer may be comprised of any combination of nucleotides or analogs thereof, which may be optionally linked to form a linear polymer of any suitable length. In some embodiments, a primer is a single-stranded oligonucleotide or polynucleotide. (For purposes of this disclosure, the terms 'polynucleotide" and "oligonucleotide" are used interchangeably herein and do not necessarily indicate any difference in length between the two). In some embodiments, a primer is double-stranded. If double stranded, a primer is first treated to separate its strands before being used to prepare extension products. Preferably, the primer is an oligodeoxyribonucleotide. A primer must be sufficiently long to prime the synthesis of extension products. Lengths of the primers will depend on many factors, including temperature, source of primer and the use of the method. In some embodiments, a primer acts as a point of initiation for amplification or synthesis when exposed to amplification or synthesis conditions; such amplification or synthesis can occur in a template-dependent fashion and optionally results in formation of a primer extension product that is complementary to at least a portion of the target sequence. Exemplary amplification or synthesis conditions can include contacting the primer with a polynucleotide template (e.g., a template including a target sequence), nucleotides and an inducing agent such as a polymerase at a suitable temperature and pH to induce polymerization of nucleotides onto an end of the target-specific primer. If double-stranded, the primer can optionally be treated to separate its strands before being used to prepare primer extension products. In some embodiments, the primer is an oligodeoxyribonucleotide or an oligoribonucleotide. In some embodiments, the primer can include one or more nucleotide analogs. The exact length and/or composition, including sequence, of the target-specific primer can influence many properties, including melting temperature (Tm), GC content, formation of secondary structures, repeat nucleotide motifs, length of predicted primer extension products, extent of coverage across a nucleic acid molecule of interest, number of primers present in a single amplification or synthesis reaction, presence of nucleotide analogs or modified nucleotides within the primers, and the like. In some embodiments, a primer can be paired with a compatible primer within an amplification or synthesis reaction to form a primer pair consisting or a forward primer and a reverse primer. In some embodiments, the forward primer of the primer pair includes a sequence that is substantially complementary to at least a portion of a strand of a nucleic acid molecule, and the reverse primer of the primer of the primer pair includes a sequence that is substantially identical to at least of portion of the strand. In some embodiments, the forward primer and the reverse primer are capable of hybridizing to opposite strands of a nucleic acid duplex. Optionally, the forward primer primes synthesis of a first nucleic acid strand, and the reverse primer primes synthesis of a second nucleic acid strand, wherein the first and second strands are substantially complementary to each other, or can hybridize to form a double-stranded nucleic acid molecule. In some embodiments, one end of an amplification or synthesis product is defined by the forward primer and the other end of the amplification or synthesis product is defined by the reverse primer. In some embodiments, where the amplification or synthesis of lengthy primer extension products is required, such as amplifying an exon, coding region, or gene, several primer pairs can be created than span the desired length to enable sufficient amplification of the region. In some embodiments, a primer can include one or more cleavable groups. In some embodiments, primer lengths are in the range of about 10 to about 60 nucleotides, about 12 to about 50 nucleotides and about 15 to about 40 nucleotides in length. Typically, a primer is capable of hybridizing to a corresponding target sequence and undergoing primer extension when exposed to amplification conditions in the presence of dNTPS and a polymerase. In some instances, the particular nucleotide sequence or a portion of the primer is known at the outset of the amplification reaction or can be determined by one or more of the methods disclosed herein. In some embodiments, the primer includes one or more cleavable groups at one or more locations within the primer.

As used herein, "target-specific primer" and its derivatives, refers generally to a single stranded or double-stranded polynucleotide, typically an oligonucleotide, that includes at least one sequence that is at least 50% complementary, typically at least 75% complementary or at least 85% complementary, more typically at least 90% complementary, more typically at least 95% complementary, more typically at least 98% or at least 99% complementary, or identical, to at least a portion of a nucleic acid molecule that includes a target sequence. In such instances, the target-specific primer and target sequence are described as "corresponding" to each other. In some embodiments, the target-specific primer is capable of hybridizing to at least a portion of its corresponding target sequence (or to a complement of the target sequence); such hybridization can optionally be performed under standard hybridization conditions or under stringent hybridization conditions. In some embodiments, the target-specific primer is not capable of hybridizing to the target sequence, or to its complement, but is capable of hybridizing to a portion of a nucleic acid strand including the target sequence, or to its complement. In some embodiments, the target-specific primer includes at least one sequence that is at least 75% complementary, typically at least 85% complementary, more typically at least 90% complementary, more typically at least 95% complementary, more typically at least 98% complementary, or more typically at least 99% complementary, to at least a portion of the target sequence itself; in other embodiments, the target-specific primer includes at least one sequence that is at least 75% complementary, typically at least 85% complementary, more typically at least 90% complementary, more typically at least 95% complementary, more typically at least 98% complementary, or more typically at least 99% complementary, to at least a portion of the nucleic acid molecule other than the target sequence. In some embodiments, the target-specific primer is substantially non-complementary to other target sequences present in the sample; optionally, the target-specific primer is substantially non-complementary to other nucleic acid molecules present in the sample. In some embodiments, nucleic acid molecules present in the sample that do not include or correspond to a target sequence (or to a complement of the target sequence) are referred to as "non-specific" sequences or "non-specific nucleic acids". In some embodiments, the target-specific primer is designed to include a nucleotide sequence that is substantially complementary to at least a portion of its corresponding target sequence. In some embodiments, a target-specific primer is at least 95% complementary, or at least 99% complementary, or identical, across its entire length to at least a portion of a nucleic acid molecule that includes its corresponding target sequence. In some embodiments, a target-specific primer can be at least 90%, at least 95% complementary, at least 98% complementary or at least 99% complementary, or identical, across its entire length to at least a portion of its corresponding target sequence. In some embodiments, a forward target-specific primer and a reverse target-specific primer define a target-specific primer pair that can be used to amplify the target sequence via template-dependent primer extension. Typically, each primer of a target-specific primer pair includes at least one sequence that is substantially complementary to at least a portion of a nucleic acid molecule including a corresponding target sequence but that is less than 50% complementary to at least one other target sequence in the sample. In some embodiments, amplification can be performed using multiple target-specific primer pairs in a single amplification reaction, wherein each primer pair includes a forward target-specific primer and a reverse target-specific primer, each including at least one sequence that substantially complementary or substantially identical to a corresponding target sequence in the sample, and each primer pair having a different corresponding target sequence. In some embodiments, the target-specific primer can be substantially non-complementary at its 3' end or its 5' end to any other target-specific primer present in an amplification reaction. In some embodiments, the target-specific primer can include minimal cross hybridization to other target-specific primers in the amplification reaction. In some embodiments, target-specific primers include minimal cross-hybridization to non-specific sequences in the amplification reaction mixture. In some embodiments, the target-specific primers include minimal self-complementarity. In some embodiments, the target-specific primers can include one or more cleavable groups located at the 3' end. In some embodiments, the target-specific primers can include one or more cleavable groups located near or about a central nucleotide of the target-specific primer. In some embodiments, one of more targets-specific primers includes only non-cleavable nucleotides at the 5' end of the target-specific primer. In some embodiments, a target specific primer includes minimal nucleotide sequence overlap at the 3' end or the 5' end of the primer as compared to one or more different target-specific primers, optionally in the same amplification reaction. In some embodiments 1, 2, 3, 4, 5, 6, 7, 8, 9, 10 or more, target-specific primers in a single reaction mixture include one or more of the above embodiments. In some embodiments, substantially all of the plurality of target-specific primers in a single reaction mixture includes one or more of the above embodiments.

As used herein, the term "adaptor" denotes a nucleic acid molecule that can be used for manipulation of a polynucleotide of interest. In some embodiments, adaptors are used for amplification of one or more target nucleic acids. In some embodiments, the adaptors are used in reactions for sequencing. In some embodiments, an adaptor has one or more ends that lack a 5' phosphate residue. In some embodiments, an adaptor comprises, consists of, or consist essentially of at least one priming site. Such priming site containing adaptors can be referred to as "primer" adaptors. In some embodiments, the adaptor priming site can be useful in PCR processes. In some embodiments an adaptor includes a nucleic acid sequence that is substantially complementary to the 3' end or the 5' end of at least one target sequences within the sample, referred to herein as a gene specific target sequence, a target specific sequence, or target specific primer. In some embodiments, the adaptor includes nucleic acid sequence that is substantially non-complementary to the 3' end or the 5' end of any target sequence present in the sample. In some embodiments, the adaptor includes single stranded or double-stranded linear oligonucleotide that is not substantially complementary to an target nucleic acid sequence. In some embodiments, the adaptor includes nucleic acid sequence that is substantially non-complementary to at least one, and preferably some or all of the nucleic acid molecules of the sample. In some embodiments, suitable adaptor lengths are in the range of about 10-75 nucleotides, about 12-50 nucleotides and about 15-40 nucleotides in length. Generally, an adaptor can include any combination of nucleotides and/or nucleic acids. In some aspects, adaptors include one or more cleavable groups at one or more locations. In some embodiments, the adaptor includes sequence that is substantially identical, or substantially complementary, to at least a portion of a primer, for example a universal primer. In some embodiments, adaptors include a tag sequence to assist with cataloguing, identification or sequencing. In some embodiments, an adaptor acts as a substrate for amplification of a target sequence, particularly in the presence of a polymerase and dNTPs under suitable temperature and pH.

As used herein, "polymerase" and its derivatives, generally refers to any enzyme that can catalyze the polymerization of nucleotides (including analogs thereof) into a nucleic acid strand. Typically but not necessarily, such nucleotide polymerization can occur in a template-dependent fashion. Such polymerases can include without limitation naturally occurring polymerases and any subunits and truncations thereof, mutant polymerases, variant polymerases, recombinant, fusion or otherwise engineered polymerases, chemically modified polymerases, synthetic molecules or assemblies, and any analogs, derivatives or fragments thereof that retain the ability to catalyze such polymerization. Optionally, the polymerase can be a mutant polymerase comprising one or more mutations involving the replacement of one or more amino acids with other amino acids, the insertion or deletion of one or more amino acids from the polymerase, or the linkage of parts of two or more polymerases. Typically, the polymerase comprises one or more active sites at which nucleotide binding and/or catalysis of nucleotide polymerization can occur. Some exemplary polymerases include without limitation DNA polymerases and RNA polymerases. The term "polymerase" and its variants, as used herein, also refers to fusion proteins comprising at least two portions linked to each other, where the first portion comprises a peptide that can catalyze the polymerization of nucleotides into a nucleic acid strand and is linked to a second portion that comprises a second polypeptide. In some embodiments, the second polypeptide can include a reporter enzyme or a processivity-enhancing domain. Optionally, the polymerase can possess 5' exonuclease activity or terminal transferase activity. In some embodiments, the polymerase can be optionally reactivated, for example through the use of heat, chemicals or re-addition of new amounts of polymerase into a reaction mixture. In some embodiments, the polymerase can include a hot-start polymerase and/or an aptamer based polymerase that optionally can be reactivated.

The terms "identity" and "identical" and their variants, as used herein, when used in reference to two or more nucleic acid sequences, refer to similarity in sequence of the two or more sequences (e.g., nucleotide or polypeptide sequences). In the context of two or more homologous sequences, the percent identity or homology of the sequences or subsequences thereof indicates the percentage of all monomeric units (e.g., nucleotides or amino acids) that are the same (i.e., about 70% identity, preferably 75%, 80%, 85%, 90%, 95%, 98% or 99% identity). The percent identity can be over a specified region, when compared and aligned for maximum correspondence over a comparison window, or designated region as measured using a BLAST or BLAST 2.0 sequence comparison algorithms with default parameters described below, or by manual alignment and visual inspection. Sequences are said to be "substantially identical" when there is at least 85% identity at the amino acid level or at the nucleotide level. Preferably, the identity exists over a region that is at least about 25, 50, or 100 residues in length, or across the entire length of at least one compared sequence. A typical algorithm for determining percent sequence identity and sequence similarity are the BLAST and BLAST 2.0 algorithms, which are described in Altschul et al, Nuc. Acids Res. 25:3389-3402 (1977). Other methods include the algorithms of Smith & Waterman, Adv. Appl. Math. 2:482 (1981), and Needleman & Wunsch, J. Mol. Biol. 48:443 (1970), etc. Another indication that two nucleic acid sequences are substantially identical is that the two molecules or their complements hybridize to each other under stringent hybridization conditions.

The terms "complementary" and "complement" and their variants, as used herein, refer to any two or more nucleic acid sequences (e.g., portions or entireties of template nucleic acid molecules, target sequences and/or primers) that can undergo cumulative base pairing at two or more individual corresponding positions in antiparallel orientation, as in a hybridized duplex. Such base pairing can proceed according to any set of established rules, for example according to Watson-Crick base pairing rules or according to some other base pairing paradigm. Optionally there can be "complete" or "total" complementarity between a first and second nucleic acid sequence where each nucleotide in the first nucleic acid sequence can undergo a stabilizing base pairing interaction with a nucleotide in the corresponding antiparallel position on the second nucleic acid sequence. "Partial" complementarity describes nucleic acid sequences in which at least 20%, but less than 100%, of the residues of one nucleic acid sequence are complementary to residues in the other nucleic acid sequence. In some embodiments, at least 50%, but less than 100%, of the residues of one nucleic acid sequence are complementary to residues in the other nucleic acid sequence. In some embodiments, at least 70%, 80%, 90%, 95% or 98%, but less than 100%, of the residues of one nucleic acid sequence are complementary to residues in the other nucleic acid sequence. Sequences are said to be "substantially complementary" when at least 85% of the residues of one nucleic acid sequence are complementary to residues in the other nucleic acid sequence. In some embodiments, two complementary or substantially complementary sequences are capable of hybridizing to each other under standard or stringent hybridization conditions. "Non-complementary" describes nucleic acid sequences in which less than 20% of the residues of one nucleic acid sequence are complementary to residues in the other nucleic acid sequence. Sequences are said to be "substantially non-complementary" when less than 15% of the residues of one nucleic acid sequence are complementary to residues in the other nucleic acid sequence. In some embodiments, two non-complementary or substantially non-complementary sequences cannot hybridize to each other under standard or stringent hybridization conditions. A "mismatch" is present at any position in the two opposed nucleotides are not complementary. Complementary nucleotides include nucleotides that are efficiently incorporated by DNA polymerases opposite each other during DNA replication under physiological conditions. In a typical embodiment, complementary nucleotides can form base pairs with each other, such as the A-T/U and G-C base pairs formed through specific Watson-Crick type hydrogen bonding, or base pairs formed through some other type of base pairing paradigm, between the nucleobases of nucleotides and/or polynucleotides in positions antiparallel to each other. The complementarity of other artificial base pairs can be based on other types of hydrogen bonding and/or hydrophobicity of bases and/or shape complementarity between bases.

As used herein, "amplified target sequences" and its derivatives, refers generally to a nucleic acid sequence produced by the amplification of/amplifying the target sequences using target-specific primers and the methods provided herein. The amplified target sequences may be either of the same sense (the positive strand produced in the second round and subsequent even-numbered rounds of amplification) or antisense (i.e., the negative strand produced during the first and subsequent odd-numbered rounds of amplification) with respect to the target sequences. For the purposes of this disclosure, amplified target sequences are typically less than 50% complementary to any portion of another amplified target sequence in the reaction.

As used herein, terms "ligating", "ligation" and derivatives refer generally to the act or process for covalently linking two or more molecules together, for example, covalently linking two or more nucleic acid molecules to each other. In some embodiments, ligation includes joining nicks between adjacent nucleotides of nucleic acids. In some embodiments, ligation includes forming a covalent bond between an end of a first and an end of a second nucleic acid molecule. In some embodiments, for example embodiments wherein the nucleic acid molecules to be ligated include conventional nucleotide residues, the ligation can include forming a covalent bond between a 5' phosphate group of one nucleic acid and a 3' hydroxyl group of a second nucleic acid thereby forming a ligated nucleic acid molecule. In some embodiments, any means for joining nicks or bonding a 5'phosphate to a 3' hydroxyl between adjacent nucleotides can be employed. In an exemplary embodiment, an enzyme such as a ligase can be used.

As used herein, "ligase" and its derivatives, refers generally to any agent capable of catalyzing the ligation of two substrate molecules. In some embodiments, the ligase includes an enzyme capable of catalyzing the joining of nicks between adjacent nucleotides of a nucleic acid. In some embodiments, a ligase includes an enzyme capable of catalyzing the formation of a covalent bond between a 5' phosphate of one nucleic acid molecule to a 3' hydroxyl of another nucleic acid molecule thereby forming a ligated nucleic acid molecule. Suitable ligases may include, but not limited to, T4 DNA ligase; T7 DNA ligase; Taq DNA ligase, and *E. coli* DNA ligase.

As defined herein, a "cleavable group" generally refers to any moiety that once incorporated into a nucleic acid can be cleaved under appropriate conditions. For example, a cleavable group can be incorporated into a target-specific primer, an amplified sequence, an adaptor or a nucleic acid molecule of the sample. In an exemplary embodiment, a target-specific primer can include a cleavable group that becomes incorporated into the amplified product and is subsequently cleaved after amplification, thereby removing a portion, or all, of the target-specific primer from the amplified product. The cleavable group can be cleaved or otherwise removed from a target-specific primer, an amplified sequence, an adaptor or a nucleic acid molecule of the sample by any acceptable means. For example, a cleavable group can be removed from a target-specific primer, an amplified sequence, an adaptor or a nucleic acid molecule of the sample by enzymatic, thermal, photo-oxidative or chemical treatment. In one aspect, a cleavable group can include a nucleobase that is not naturally occurring. For example, an oligodeoxyribonucleotide can include one or more RNA nucleobases, such as uracil that can be removed by a uracil glycosylase. In some embodiments, a cleavable group can include one or more modified nucleobases (such as 7-methylguanine, 8-oxo-guanine, xanthine, hypoxanthine, 5,6-dihydrouracil or 5-methylcytosine) or one or more modified nucleosides (i.e., 7-methylguanosine, 8-oxo-deoxyguanosine, xanthosine, inosine, dihydrouridine or 5-methylcytidine). The modified nucleobases or nucleotides can be removed from the nucleic acid by enzymatic, chemical or thermal means. In one embodiment, a cleavable group can include a moiety that can be removed from a primer after amplification (or synthesis) upon exposure to ultraviolet light (i.e., bromodeoxyuridine). In another embodiment, a cleavable group can include methylated cytosine. Typically, methylated cytosine can be cleaved from a primer for example, after induction of amplification (or synthesis), upon sodium bisulfite treatment. In some embodiments, a cleavable moiety can include a restriction site. For example, a primer or target sequence can include a nucleic acid sequence that is specific to one or more restriction enzymes, and following amplification (or synthesis), the primer or target sequence can be treated with the one or more restriction enzymes such that the cleavable group is removed. Typically, one or more cleavable groups can be included at one or more locations with a target-specific primer, an amplified sequence, an adaptor or a nucleic acid molecule of the sample.

As used herein, "digestion", "digestion step" and its derivatives, generally refers to any process by which a cleavable group is cleaved or otherwise removed from a target-specific primer, an amplified sequence, an adaptor or a nucleic acid molecule of the sample. In some embodiments, the digestion step involves a chemical, thermal, photo-oxidative or digestive process.

As used herein, the term "hybridization" is consistent with its use in the art, and generally refers to the process whereby two nucleic acid molecules undergo base pairing interactions. Two nucleic acid molecule molecules are said to be hybridized when any portion of one nucleic acid molecule is base paired with any portion of the other nucleic acid molecule; it is not necessarily required that the two nucleic acid molecules be hybridized across their entire respective lengths and in some embodiments, at least one of the nucleic acid molecules can include portions that are not hybridized to the other nucleic acid molecule. The phrase "hybridizing under stringent conditions" and its variants refers generally to conditions under which hybridization of a target-specific primer to a target sequence occurs in the presence of high hybridization temperature and low ionic strength. As used herein, the phrase "standard hybridization conditions" and its variants refers generally to conditions under which hybridization of a primer to an oligonucleotide (i.e., a target sequence), occurs in the presence of low hybridization temperature and high ionic strength. In one exemplary embodiment, standard hybridization conditions include an aqueous environment containing about 100 mm magnesium sulfate, about 500 mM Tris-sulfate at pH 8.9, and about 200 mM ammonium sulfate at about 50-55° C., or equivalents thereof.

As used herein, the term "end" and its variants, when used in reference to a nucleic acid molecule, for example a target sequence or amplified target sequence, can include the terminal 30 nucleotides, the terminal 20 and even more typically the terminal 15 nucleotides of the nucleic acid molecule. A linear nucleic acid molecule comprised of linked series of contiguous nucleotides typically includes at least two ends. In some embodiments, one end of the nucleic acid molecule can include a 3' hydroxyl group or its equivalent, and can be referred to as the "3' end" and its derivatives. Optionally, the 3' end includes a 3' hydroxyl group that is not linked to a 5' phosphate group of a mononucleotide pentose ring. Typically, the 3' end includes one or more 5' linked nucleotides located adjacent to the nucleotide including the unlinked 3' hydroxyl group, typically the 30 nucleotides located adjacent to the 3' hydroxyl, typically the terminal 20 and even more typically the terminal 15 nucleotides. Generally, the one or more linked nucleotides can be represented as a percentage of the nucleotides present in the oligonucleotide or can be provided as a number of linked nucleotides adjacent to the unlinked 3' hydroxyl. For example, the 3' end can include less than 50% of the nucleotide length of the oligonucleotide. In some embodiments, the 3' end does not include any unlinked 3' hydroxyl group but can include any moiety capable of serving as a site for attachment of nucleotides via primer extension and/or nucleotide polymerization. In some embodiments, the term "3' end" for example when referring to a target-specific primer, can include the terminal 10 nucleotides, the terminal 5 nucleotides, the terminal 4, 3, 2 or fewer nucleotides at the 3'end. In some embodiments, the term "3' end" when referring to a target-specific primer can include nucleotides located at nucleotide positions 10 or fewer from the 3' terminus. As used herein, "5' end", and its derivatives, generally refers to an end of a nucleic acid molecule, for example a target sequence or amplified target sequence, which includes a free 5' phosphate group or its equivalent. In some embodiments, the 5' end includes a 5' phosphate group that is not linked to a 3' hydroxyl of a neighboring mononucleotide pentose ring. Typically, the 5' end includes to one or more linked nucleotides located adjacent to the 5' phosphate, typically the 30 nucleotides located adjacent to the nucleotide including the 5' phosphate group, typically the terminal 20 and even more typically the terminal 15 nucleotides. Generally, the one or more linked nucleotides can be represented as a percentage of the nucleotides present in the oligonucleotide or can be provided as a number of linked nucleotides adjacent to the 5' phosphate. For example, the 5' end can be less than 50% of the nucleotide length of an oligonucleotide. In another exemplary embodiment, the 5' end can include about 15 nucleotides adjacent to the nucleotide including the terminal 5' phosphate. In some embodiments, the 5' end does not include any unlinked 5' phosphate group but can include any moiety capable of serving as a site of attachment to a 3' hydroxyl group, or to the 3'end of another nucleic acid molecule. In some embodiments, the term "5' end" for example when referring to a target-specific primer, can include the terminal 10 nucleotides, the terminal 5 nucleotides, the terminal 4, 3, 2 or fewer nucleotides at the 5'end. In some embodiments, the term "5' end" when referring to a target-specific primer can include nucleotides located at positions 10 or fewer from the 5' terminus. In some embodiments, the 5' end of a target-specific primer can include only non-cleavable nucleotides, for example nucleotides that do not contain one or more cleavable groups as disclosed herein, or a cleavable nucleotide as would be readily determined by one of ordinary skill in the art. A "first end" and a "second end" of a polynucleotide refer to the 5' end or the 3'end of the polynucleotide. Either the first end or second end of a polynucleotide can be the 5' end or the 3' end of the polynucleotide; the terms "first" and "second" are not meant to denote that the end is specifically the 5' end or the 3' end.

As used herein "tag," "barcode," "unique tag" or "tag sequence" and its derivatives, refers generally to a unique short (6-14 nucleotide) nucleic acid sequence within an adaptor or primer that can act as a 'key' to distinguish or separate a plurality of amplified target sequences in a sample. For the purposes of this disclosure, a barcode or unique tag sequence is incorporated into the nucleotide sequence of an adaptor or primer. As used herein, "barcode sequence" denotes a nucleic acid fixed sequence that is sufficient to allow for the identification of a sample or source of nucleic acid sequences of interest. A barcode sequence can be, but need not be, a small section of the original nucleic acid sequence on which the identification is to be based. In some embodiments a barcode is 5-20 nucleic acids long. In some embodiments, the barcode is comprised of analog nucleotides, such as L-DNA, LNA, PNA, etc. As used herein, "unique tag sequence" denotes a nucleic acid sequence having at least one random sequence and at least one fixed sequence. A unique tag sequence, alone or in conjunction with a second unique tag sequence, is sufficient to allow for the identification of a single target nucleic acid molecule in a sample. A unique tag sequence can, but need not, comprise a small section of the original target nucleic acid sequence. In some embodiments a unique tag sequence is 2-50 nucleotides or base-pairs, or 2-25 nucleotides or base-pairs, or 2-10 nucleotides or base-pairs in length. A unique tag sequence can comprise at least one random sequence interspersed with a fixed sequence.

As used herein, "comparable maximal minimum melting temperatures" and its derivatives, refers generally to the melting temperature (Tm) of each nucleic acid fragment for a single adaptor or target-specific primer after digestion of a cleavable groups. The hybridization temperature of each nucleic acid fragment generated by an adaptor or target-specific primer is compared to determine the maximal minimum temperature required preventing hybridization of a nucleic acid sequence from the target-specific primer or adaptor or fragment or portion thereof to a respective target sequence. Once the maximal hybridization temperature is known, it is possible to manipulate the adaptor or target-specific primer, for example by moving the location of one or more cleavable group(s) along the length of the primer, to achieve a comparable maximal minimum melting temperature with respect to each nucleic acid fragment to thereby optimize digestion and repair steps of library preparation.

As used herein, "addition only" and its derivatives, refers generally to a series of steps in which reagents and components are added to a first or single reaction mixture. Typically, the series of steps excludes the removal of the reaction mixture from a first vessel to a second vessel in order to complete the series of steps. Generally, an addition only process excludes the manipulation of the reaction mixture outside the vessel containing the reaction mixture. Typically, an addition-only process is amenable to automation and high-throughput.

As used herein, "polymerizing conditions" and its derivatives, refers generally to conditions suitable for nucleotide polymerization. In typical embodiments, such nucleotide polymerization is catalyzed by a polymerase. In some embodiments, polymerizing conditions include conditions for primer extension, optionally in a template-dependent manner, resulting in the generation of a synthesized nucleic acid sequence. In some embodiments, the polymerizing conditions include polymerase chain reaction (PCR). Typically, the polymerizing conditions include use of a reaction mixture that is sufficient to synthesize nucleic acids and includes a polymerase and nucleotides. The polymerizing conditions can include conditions for annealing of a target-specific primer to a target sequence and extension of the primer in a template dependent manner in the presence of a polymerase. In some embodiments, polymerizing conditions can be practiced using thermocycling. Additionally, polymerizing conditions can include a plurality of cycles where the steps of annealing, extending, and separating the two nucleic strands are repeated. Typically, the polymerizing conditions include a cation such as $MgCl_2$. Generally, polymerization of one or more nucleotides to form a nucleic acid strand includes that the nucleotides be linked to each other via phosphodiester bonds, however, alternative linkages may be possible in the context of particular nucleotide analogs.

As used herein, the term "nucleic acid" refers to natural nucleic acids, artificial nucleic acids, analogs thereof, or combinations thereof, including polynucleotides and oligonucleotides. As used herein, the terms "polynucleotide" and "oligonucleotide" are used interchangeably and mean single-stranded and double-stranded polymers of nucleotides including, but not limited to, 2'-deoxyribonucleotides (nucleic acid) and ribonucleotides (RNA) linked by internucleotide phosphodiester bond linkages, e.g. 3'-5' and 2'-5', inverted linkages, e.g. 3'-3' and 5'-5', branched structures, or analog nucleic acids. Polynucleotides have associated counter ions, such as $H^+$, $NH_4^+$, trialkylammonium, $Mg^{2+}$, $Na^+$ and the like. An oligonucleotide can be composed entirely of deoxyribonucleotides, entirely of ribonucleotides, or chimeric mixtures thereof. Oligonucleotides can be comprised of nucleobase and sugar analogs. Polynucleotides typically range in size from a few monomeric units, e.g. 5-40, when they are more commonly frequently referred to in the art as oligonucleotides, to several thousands of monomeric nucleotide units, when they are more commonly referred to in the art as polynucleotides; for purposes of this disclosure, however, both oligonucleotides and polynucleotides may be of any suitable length. Unless denoted otherwise, whenever a oligonucleotide sequence is represented, it will be understood that the nucleotides are in 5' to 3' order from left to right and that "A" denotes deoxyadenosine, "C" denotes deoxycytidine, "G" denotes deoxyguanosine, "T" denotes thymidine, and "U" denotes deoxyuridine. As discussed herein and known in the art, oligonucleotides and polynucleotides are said to have "5' ends" and "3' ends" because mononucleotides are typically reacted to form oligonucleotides via attachment of the 5' phosphate or equivalent group of one nucleotide to the 3' hydroxyl or equivalent group of its neighboring nucleotide, optionally via a phosphodiester or other suitable linkage.

As used herein, the term "polymerase chain reaction" ("PCR") refers to the method of K. B. Mullis U.S. Pat. Nos. 4,683,195 and 4,683,202, hereby incorporated by reference, which describe a method for increasing the concentration of a segment of a polynucleotide of interest in a mixture of genomic DNA without cloning or purification. This process for amplifying the polynucleotide of interest consists of introducing a large excess of two oligonucleotide primers to the DNA mixture containing the desired polynucleotide of interest, followed by a precise sequence of thermal cycling in the presence of a DNA polymerase. The two primers are complementary to their respective strands of the double stranded polynucleotide of interest. To effect amplification, the mixture is denatured and the primers then annealed to their complementary sequences within the polynucleotide of interest molecule. Following annealing, the primers are extended with a polymerase to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired polynucleotide of interest. The length of the amplified segment of the desired polynucleotide of interest (amplicon) is determined by the relative positions of the primers with respect to each other, and therefore, this length is a controllable parameter. By virtue of repeating the process, the method is referred to as the "polymerase chain reaction" (hereinafter "PCR"). Because the desired amplified segments of the polynucleotide of interest become the predominant nucleic acid sequences (in terms of concentration) in the mixture, they are said to be "PCR amplified". As defined herein, target nucleic acid molecules within a sample including a plurality of target nucleic acid molecules are amplified via PCR. In a modification to the method discussed above, the target nucleic acid molecules can be PCR amplified using a plurality of different primer pairs, in some cases, one or more primer pairs per target nucleic acid molecule of interest, thereby forming a multiplex PCR reaction. Using multiplex PCR, it is possible to simultaneously amplify multiple nucleic acid molecules of interest from a sample to form amplified target sequences. It is also possible to detect the amplified target sequences by several different methodologies (e.g., quantitation with a bioanalyzer or qPCR, hybridization with a labeled probe; incorporation of biotinylated primers followed by avidin-enzyme conjugate detection; incorporation of $^{32}$P-labeled deoxynucleotide triphosphates, such as dCTP or dATP, into the amplified target sequence). Any oligonucleotide sequence can be amplified with the appropriate set of primers, thereby allowing for the amplification of target nucleic acid molecules from genomic DNA, cDNA, formalin-fixed paraffin-embedded DNA, fine-needle biopsies and various other sources. In particular, the amplified target sequences created by the multiplex PCR process as disclosed herein, are themselves efficient substrates for subsequent PCR amplification or various downstream assays or manipulations.

As defined herein "multiplex amplification" refers to selective and non-random amplification of two or more target sequences within a sample using at least one target-specific primer. In some embodiments, multiplex amplification is performed such that some or all of the target sequences are amplified within a single reaction vessel. The "plexy" or "plex" of a given multiplex amplification refers generally to the number of different target-specific sequences that are amplified during that single multiplex amplification. In some embodiments, the plexy can be about 12-plex, 24-plex, 48-plex, 96-plex, 192-plex, 384-plex, 768-plex, 1536-plex, 3072-plex, 6144-plex or higher.

Methods of Preparing Nucleic Acid Libraries

Provided methods of the invention comprise efficient procedures which enable rapid preparation of highly multiplexed libraries suitable for downstream analysis. See FIG. 1. The methods optionally allow for incorporation of one or more unique tag sequences, if so desired. Certain methods comprise streamlined, addition-only procedures conveying highly rapid library generation.

In one aspect of the invention, methods for preparing a library of target nucleic acid sequences are provided. In some embodiments, methods comprise contacting a nucleic acid sample with a plurality of adaptors capable of amplification of one or more target nucleic acid sequences in the sample under conditions wherein the target nucleic acid(s) undergo a first amplification; digesting resulting first amplification products to reduce or eliminate resulting primer dimers and prepare partially digested target amplicons, thereby producing gapped, double stranded amplicons. The methods further comprise repairing the partially digested target amplicons; then amplifying the repaired target amplicons in a second amplification using universal primers, thereby producing a library of target nucleic acid sequences. Each of the plurality of adaptors used in the methods herein comprise a universal handle sequence and a target nucleic acid sequence and a cleavable moiety and optionally one or more tag sequences. At least two and up to one hundred thousand target specific adaptor pairs are included in the provided methods, wherein the target nucleic acid sequence of each adaptor includes at least one cleavable moiety and the universal handle sequence does not include the cleavable moiety. In some embodiments where an optional tag sequence is included in at least one adaptor, the cleavable moieties are included in the adaptor sequence flanking either end of the tag sequence.

In one aspect of the invention, methods for preparing a tagged library of target nucleic acid sequences are provided. In some embodiments, methods comprise contacting a nucleic acid sample with a plurality of adaptors capable of amplification of one or more target nucleic acid sequences in the sample under conditions wherein the target nucleic acid(s) undergo a first amplification; digesting resulting first amplification products to reduce or eliminate resulting primer dimers and prepare partially digested target amplicons, thereby producing gapped, double stranded amplicons. The methods further comprise repairing the partially digested target amplicons; then amplifying the repaired target amplicons in a second amplification using universal primers, thereby producing a library of target nucleic acid sequences. Each of the plurality of adaptors used in the methods herein comprise a universal handle sequence and a target nucleic acid sequence and a cleavable moiety and one or more tag sequences. At least two and up to one hundred thousand target specific adaptor pairs are included in the provided methods, wherein the target nucleic acid sequence of each adaptor includes at least one cleavable moiety, the universal handle sequence does not include the cleavable moiety, and the cleavable moieties are included flanking either end of the tag sequence.

In certain embodiments, the comparable maximal minimum melting temperature of each universal sequence is higher than the comparable maximal minimum melting temperature of each target nucleic acid sequence and each tag sequence present in an adaptor.

In some embodiments, each of the adaptors comprise unique tag sequences as further described herein and each further comprise cleavable groups flanking either end of the tag sequence in each adaptor. In some embodiments wherein unique taq sequences are employed, each generated target specific amplicon sequence includes at least 1 different sequence and up to $10^7$ different sequences. In certain embodiments each target specific pair of the plurality of adaptors includes up to 16,777,216 different adaptor combinations comprising different tag sequences.

In some embodiments, methods comprise contacting the plurality of gapped polynucleotide products with digestion and repair reagents simultaneously. In some embodiments, methods comprise contacting the plurality of gapped polynucleotide products sequentially with the digestion then repair reagents.

A digestion reagent useful in the methods provided herein comprises any reagent capable of cleaving the cleavable site present in adaptors, and in some embodiments includes, but is not limited to, one or a combination of uracil DNA glycosylase (UDG). apurinic endonuclease (e.g., APE1), RecJf, formamidopyrimidine [fapy]-DNA glycosylase (fpg), Nth endonuclease III, endonuclease VIII, polynucleotide kinase (PNK), Taq DNA polymerase, DNA polymerase I and/or human DNA polymerase beta.

A repair reagent useful in the methods provided herein comprises any reagent capable of repair of the gapped amplicons, and in some embodiments includes, but is not limited to, any one or a combination of Phusion DNA polymerase, Phusion U DNA polymerase, SuperFi DNA polymerase, Taq DNA polymerase, Human DNA polymerase beta, T4 DNA polymerase and/or T7 DNA polymerase, SuperFiU DNA polymerase, E. coli DNA ligase, T3 DNA ligase, T4 DNA ligase, T7 DNA ligase, Taq DNA ligase, and/or 9° N DNA ligase.

Thus, in certain embodiments, a digestion and repair reagent comprises any one or a combination of one or a combination of uracil DNA glycosylase (UDG). apurinic endonuclease (e.g., APE1), RecJf, formamidopyrimidine [fapy]-DNA glycosylase (fpg), Nth endonuclease III, endonuclease VIII, polynucleotide kinase (PNK), Taq DNA polymerase, DNA polymerase I and/or human DNA polymerase beta; and any one or a combination of Phusion DNA polymerase, Phusion U DNA polymerase, SuperFi DNA polymerase, Taq DNA polymerase, Human DNA polymerase beta, T4 DNA polymerase and/or T7 DNA polymerase, SuperFiU DNA polymerase, E. coli DNA ligase, T3 DNA ligase, T4 DNA ligase, T7 DNA ligase, Taq DNA ligase, and/or 9° N DNA ligase. In certain embodiments, a digestion and repair reagent comprises any one or a combination of uracil DNA glycosylase (UDG), apurinic endonuclease (e.g., APE1), Taq DNA polymerase, Phusion U DNA polymerase, SuperFiU DNA polymerase, T7 DNA ligase. In certain embodiments, a digestion and repair reagent comprises any one or a combination of uracil DNA glycosylase (UDG), formamidopyrimidine [fapy]-DNA glycosylase (fpg), Phusion U DNA polymerase, Taq DNA polymerase, SuperFiU DNA polymerase, T4 PNK and T7 DNA ligase.

In some embodiments, methods comprise the digestion and repair steps carried out in a single step. In other embodiments, methods comprise the digestion and repair of steps carried out in a temporally separate manner at different temperatures.

In some embodiments methods of the invention are carried out wherein one or more of the method steps is conducted in manual mode. In particular embodiments, methods of the invention are carried out wherein each of the method steps is conducted manually. In some embodiments methods of the invention are carried out wherein one or more of the method steps is conducted in an automated mode. In particular embodiments, methods of the invention are carried wherein each of the method steps is automated. In some embodiments methods of the invention are carried out wherein one or more of the method steps is conducted in a combination of manual and automated modes.

In some embodiments, methods of the invention comprise at least one purification step. For example, in certain embodiments a purification step is carried out only after the second amplification of repaired amplicons. In some embodiments two purification steps are utilized, wherein a first purification step is carried out after the digestion and repair and a second purification step is carried out after the second amplification of repaired amplicons.

In some embodiments a purification step comprises conducting a solid phase adherence reaction, solid phase immobilization reaction or gel electrophoresis. In certain embodiments a purification step comprises separation conducted using Solid Phase Reversible Immobilization (SPRI) beads. In particular embodiments a purification step comprises separation conducted using SPRI beads wherein the SPRI beads comprise paramagnetic beads.

In some embodiments, methods comprise contacting a nucleic acid sample with a plurality of adaptors capable of amplification of one or more target nucleic acid sequences in the sample under conditions wherein the target nucleic acid(s) undergo a first amplification; digesting resulting first amplification products to reduce or eliminate resulting primer dimers and prepare partially digested target amplicons, thereby producing gapped, double stranded amplicons. The methods further comprise repairing the partially digested target amplicons, then purifying repaired amplicons; then amplifying the repaired target amplicons in a second amplification using universal primers, thereby producing a library of target nucleic acid sequences; and then purifying resulting library. Each of the plurality of adaptors used in the methods herein comprise a universal handle sequence and a target nucleic acid sequence and a cleavable moiety and optionally one or more tag sequences. At least two and up to one hundred thousand target specific adaptor pairs are included in the provided methods, wherein the target nucleic acid sequence of each adaptor includes at least one cleavable moiety and the universal handle sequence does not include the cleavable moiety. In some embodiments where an optional tag sequence is included in at least one adaptor, the cleavable moieties are included in the adaptor sequence flanking either end of the tag sequence.

In some embodiments, methods comprise contacting a nucleic acid sample with a plurality of adaptors capable of amplification of one or more target nucleic acid sequences in the sample under conditions wherein the target nucleic acid(s) undergo a first amplification; digesting resulting first amplification products to reduce or eliminate resulting primer dimers and prepare partially digested target amplicons, thereby producing gapped, double stranded amplicons. The methods further comprise repairing the partially digested target amplicons, and purifying repaired amplicons; then amplifying the repaired target amplicons in a second amplification using universal primers, thereby producing a library of target nucleic acid sequences; and then purifying resulting library. Each of the plurality of adaptors used in the methods herein comprise a universal handle sequence and a target nucleic acid sequence and a cleavable moiety and one or more tag sequences. At least two and up to one hundred thousand target specific adaptor pairs are included in the provided methods, wherein the target nucleic acid sequence of each adaptor includes at least one cleavable moiety, the universal handle sequence does not include the cleavable moiety, and cleavable moieties are included in the flanking either end of the tag sequence.

In some embodiments, methods comprise contacting a nucleic acid sample with a plurality of adaptors capable of amplification of one or more target nucleic acid sequences in the sample under conditions wherein the target nucleic acid(s) undergo a first amplification; digesting resulting first amplification products to reduce or eliminate resulting primer dimers and prepare partially digested target amplicons, thereby producing gapped, double stranded amplicons. The methods further comprise repairing the partially digested target amplicons, then purifying repaired amplicons; then amplifying the repaired target amplicons in a second amplification using universal primers, thereby producing a library of target nucleic acid sequences; and then purifying resulting library. Each of the plurality of adaptors used in the methods herein comprise a universal handle sequence and a target nucleic acid sequence and a cleavable moiety and optionally one or more tag sequences. At least two and up to one hundred thousand target specific adaptor pairs are included in the provided methods, wherein the target nucleic acid sequence of each adaptor includes at least one cleavable moiety and the universal handle sequence does not include the cleavable moiety. In some embodiments where an optional tag sequence is included in at least one adaptor, the cleavable moieties are included in the adaptor sequence flanking either end of the tag sequence. In some embodiments a digestion and repair reagent comprises any one or a combination of one or a combination of uracil DNA glycosylase (UDG). apurinic endonuclease (e.g., APE1), RecJf, formamidopyrimidine [fapy]-DNA glycosylase (fpg), Nth endonuclease III, endonuclease VIII, polynucleotide kinase (PNK), Taq DNA polymerase, DNA polymerase I and/or human DNA polymerase beta; and any one or a combination of Phusion DNA polymerase, Phusion U DNA polymerase, SuperFi DNA polymerase, Taq DNA polymerase, Human DNA polymerase beta, T4 DNA polymerase and/or T7 DNA polymerase, SuperFiU DNA polymerase, *E. coli* DNA ligase, T3 DNA ligase, T4 DNA ligase, T7 DNA ligase, Taq DNA ligase, and/or 9° N DNA ligase. In certain embodiments, a digestion and repair reagent comprises any one or a combination of uracil DNA glycosylase (UDG), apurinic endonuclease (e.g., APE1), Taq DNA polymerase, Phusion U DNA polymerase, SuperFiU DNA polymerase, T7 DNA ligase. In certain embodiments, a digestion and repair reagent comprises any one or a combination of uracil DNA glycosylase (UDG), formamidopyrimidine [fapy]-DNA glycosylase (fpg), Phusion U DNA polymerase, Taq DNA polymerase, SuperFiU DNA polymerase, T4 PNK and T7 DNA ligase.

In some embodiments, methods comprise contacting a nucleic acid sample with a plurality of adaptors capable of amplification of one or more target nucleic acid sequences in the sample under conditions wherein the target nucleic acid(s) undergo a first amplification; digesting resulting first amplification products to reduce or eliminate resulting primer dimers and prepare partially digested target amplicons, thereby producing gapped, double stranded amplicons. The methods further comprise repairing the partially digested target amplicons, and purifying repaired amplicons; then amplifying the repaired target amplicons in a second amplification using universal primers, thereby producing a library of target nucleic acid sequences; and then purifying resulting library. Each of the plurality of adaptors used in the methods herein comprise a universal handle sequence and a target nucleic acid sequence and a cleavable moiety and one or more tag sequences. At least two and up to one hundred thousand target specific adaptor pairs are included in the provided methods, wherein the target nucleic acid sequence of each adaptor includes at least one cleavable moiety, the universal handle sequence does not include the cleavable moiety, and cleavable moieties are included in the flanking either end of the tag sequence. In some embodiments a digestion and repair reagent comprises any one or a combination of one or a combination of uracil DNA glycosylase (UDG). apurinic endonuclease (e.g., APE1), RecJf, formamidopyrimidine [fapy]-DNA glycosylase (fpg), Nth endonuclease III, endonuclease VIII, polynucleotide kinase (PNK), Taq DNA polymerase, DNA polymerase I and/or human DNA polymerase beta; and any one or a combination of Phusion DNA polymerase, Phusion U DNA polymerase, SuperFi DNA polymerase, Taq DNA polymerase, Human DNA polymerase beta, T4 DNA polymerase and/or T7 DNA polymerase, SuperFiU DNA polymerase, *E. coli* DNA ligase, T3 DNA ligase, T4 DNA ligase, T7 DNA ligase, Taq DNA ligase, and/or 9° N DNA ligase. In certain embodiments, a digestion and repair reagent comprises any one or a combination of uracil DNA glycosylase (UDG), apurinic endonuclease (e.g., APE1), Taq DNA polymerase, Phusion U DNA polymerase, SuperFiU DNA polymerase, T7 DNA ligase. In certain embodiments, a digestion and repair reagent comprises any one or a combination of uracil DNA glycosylase (UDG), formamidopyrimidine [fapy]-DNA glycosylase (fpg), Phusion U DNA polymerase, Taq DNA polymerase, SuperFiU DNA polymerase, T4 PNK and T7 DNA ligase.

In certain embodiments methods of the invention are carried out in a single, addition only workflow reaction, allowing for rapid production of highly multiplexed targeted libraries. For example, in one embodiment, methods for preparing a library of target nucleic acid sequences comprise contacting a nucleic acid sample with a plurality of adaptors capable of amplification of one or more target nucleic acid sequences in the sample under conditions wherein the target nucleic acid(s) undergo a first amplification; digesting resulting first amplification products to reduce or eliminate resulting primer dimers and prepare partially digested target amplicons, thereby producing gapped, double stranded amplicons. The methods further comprise repairing the partially digested target amplicons; then amplifying the repaired target amplicons in a second amplification using universal primers, thereby producing a library of target nucleic acid sequences, and purifying the resulting library. In certain embodiments the purification comprises a single or repeated separating step that is carried out following production of the library following the second amplification; and wherein the other method steps are conducted in a single reaction vessel without requisite transferring of a portion (aliquot) of any of the products generated in steps to another reaction vessel. Each of the plurality of adaptors used in the methods herein comprise a universal handle sequence and a target nucleic acid sequence and a cleavable moiety and optionally one or more tag sequences. At least two and up to one hundred thousand target specific adaptor pairs are included in the provided methods, wherein the target nucleic acid sequence of each adaptor includes at least one cleavable moiety and the universal handle sequence does not include the cleavable moiety. In some embodiments where an optional tag sequence is included in at least one adaptor, the cleavable moieties are included in the adaptor sequence flanking either end of the tag sequence.

In another embodiment, methods for preparing a tagged library of target nucleic acid sequences are provided comprising contacting a nucleic acid sample with a plurality of adaptors capable of amplification of one or more target nucleic acid sequences in the sample under conditions wherein the target nucleic acid(s) undergo a first amplification; digesting resulting first amplification products to reduce or eliminate resulting primer dimers and prepare partially digested target amplicons, thereby producing gapped, double stranded amplicons. The methods further comprise repairing the partially digested target amplicons; then amplifying the repaired target amplicons in a second amplification using universal primers, thereby producing a library of target nucleic acid sequences, and purifying the resulting library. In certain embodiments the purification comprises a single or repeated separating step; and wherein the other method steps are optionally conducted in a single reaction vessel without requisite transferring of a portion of any of the products generated in steps to another reaction vessel. Each of the plurality of adaptors used in the methods herein comprise a universal handle sequence and a target nucleic acid sequence and a cleavable moiety and one or more tag sequences. At least two and up to one hundred thousand target specific adaptor pairs are included in the provided methods, wherein the target nucleic acid sequence of each adaptor includes at least one cleavable moiety, the universal handle sequence does not include the cleavable moiety, and the cleavable moieties are included flanking either end of the tag sequence.

In one embodiment, methods for preparing a library of target nucleic acid sequences comprise contacting a nucleic acid sample with a plurality of adaptors capable of amplification of one or more target nucleic acid sequences in the sample under conditions wherein the target nucleic acid(s) undergo a first amplification; digesting resulting first amplification products to reduce or eliminate resulting primer dimers and prepare partially digested target amplicons, thereby producing gapped, double stranded amplicons. The methods further comprise repairing the partially digested target amplicon; then amplifying the repaired target amplicons in a second amplification using universal primers, thereby producing a library of target nucleic acid sequences, and purifying the resulting library.

In some embodiments a digestion reagent comprises any one or any combination of: uracil DNA glycosylase (UDG). AP endonuclease (APE1), RecJf, formamidopyrimidine [fapy]-DNA glycosylase (fpg), Nth endonuclease III, endonuclease VIII, polynucleotide kinase, Taq DNA polymerase, DNA polymerase I and/or human DNA polymerase beta. In certain embodiments a digestion reagent comprises any one or any combination of: uracil DNA glycosylase (UDG). AP endonuclease (APE1), RecJf, formamidopyrimidine [fapy]-DNA glycosylase (fpg), Nth endonuclease III, endonuclease VIII, polynucleotide kinase, Taq DNA polymerase, DNA polymerase I and/or human DNA polymerase beta wherein the digestion reagent lacks formamidopyrimidine [fapy]-DNA glycosylase (fpg).

In some embodiments a digestion reagent comprises a single-stranded DNA exonuclease that degrades in a 5'-3' direction. In some embodiments a cleavage reagent comprises a single-stranded DNA exonuclease that degrades abasic sites. In some embodiments herein the digestions reagent comprises an RecJf exonuclease. In particular embodiments a digestion reagent comprises APE1 and RecJf, wherein the cleavage reagent comprises an apurinic/apyrimidinic endonuclease. In certain embodiments the digestion reagent comprises an AP endonuclease (APE1).

In some embodiments a repair reagent comprises at least one DNA polymerase; wherein the gap-filling reagent comprises: any one or any combination of: Phusion DNA polymerase, Phusion U DNA polymerase, SuperFi DNA polymerase, Taq DNA polymerase, Human DNA polymerase beta, T4 DNA polymerase and/or T7 DNA polymerase and/or SuperFi U DNA polymerase. In some embodiments a repair reagent further comprises a plurality of nucleotides.

In some embodiment a repair reagent comprises an ATP-dependent or an ATP-independent ligase; wherein the repair reagent comprises any one or any combination of: E. coli DNA ligase, T3 DNA ligase, T4 DNA ligase, T7 DNA ligase, Taq DNA ligase. 9° N DNA ligase In certain embodiments a digestion and repair reagent comprises any one or a combination of one or a combination of uracil DNA glycosylase (UDG). apurinic endonuclease (e.g., APE1), RecJf, formamidopyrimidine [fapy]-DNA glycosylase (fpg), Nth endonuclease III, endonuclease VIII, polynucleotide kinase (PNK), Taq DNA polymerase, DNA polymerase I and/or human DNA polymerase beta; and any one or a combination of Phusion DNA polymerase, Phusion U DNA polymerase, SuperFi DNA polymerase, Taq DNA polymerase, Human DNA polymerase beta, T4 DNA polymerase and/or T7 DNA polymerase, SuperFiU DNA polymerase, E. coli DNA ligase, T3 DNA ligase, T4 DNA ligase, T7 DNA ligase, Taq DNA ligase, and/or 9° N DNA ligase. In particular embodiments, a digestion and repair reagent comprises any one or a combination of uracil DNA glycosylase (UDG), apurinic endonuclease (e.g., APE1), Taq DNA polymerase, Phusion U DNA polymerase, SuperFiU DNA polymerase, T7 DNA ligase. In certain embodiments a purification comprises a single or repeated separating step that is carried out following production of the library following the second amplification; and wherein method steps are conducted in a single reaction vessel without requisite transferring of a portion of any of the products generated in steps to another reaction vessel until a first purification. Each of the plurality of adaptors used in the methods herein comprise a universal handle sequence and a target nucleic acid sequence and a cleavable moiety and optionally one or more tag sequences. At least two and up to one hundred thousand target specific adaptor pairs are included in the provided methods, wherein the target nucleic acid sequence of each adaptor includes at least one cleavable moiety and the universal handle sequence does not include the cleavable moiety. In some embodiments where an optional tag sequence is included in at least one adaptor, the cleavable moieties are included in the adaptor sequence flanking either end of the tag sequence.

In another embodiment, methods for preparing a tagged library of target nucleic acid sequences are provided comprising contacting a nucleic acid sample with a plurality of adaptors capable of amplification of one or more target nucleic acid sequences in the sample under conditions wherein the target nucleic acid(s) undergo a first amplification; digesting resulting first amplification products to reduce or eliminate resulting primer dimers and prepare partially digested target amplicons, thereby producing gapped, double stranded amplicons. The methods further comprise repairing the partially digested target amplicons; then amplifying the repaired target amplicons in a second amplification using universal primers, thereby producing a library of target nucleic acid sequences, and purifying the resulting library. In certain embodiments a digestion and repair reagent comprises any one or a combination of one or a combination of uracil DNA glycosylase (UDG). apurinic endonuclease (e.g., APE1), RecJf, formamidopyrimidine [fapy]-DNA glycosylase (fpg), Nth endonuclease III, endonuclease VIII, polynucleotide kinase (PNK), Taq DNA polymerase, DNA polymerase I and/or human DNA polymerase beta; and any one or a combination of Phusion DNA polymerase, Phusion U DNA polymerase, SuperFi DNA polymerase, Taq DNA polymerase, Human DNA polymerase beta, T4 DNA polymerase and/or T7 DNA polymerase, SuperFiU DNA polymerase, E. coli DNA ligase, T3 DNA ligase, T4 DNA ligase, T7 DNA ligase, Taq DNA ligase, and/or 9° N DNA ligase. In particular embodiments, a digestion and repair reagent comprises any one or a combination of uracil DNA glycosylase (UDG), apurinic endonuclease (e.g., APE1), Taq DNA polymerase, Phusion U DNA polymerase, SuperFiU DNA polymerase, T7 DNA ligase. In certain embodiments the purification comprises a single or repeated separating step that is carried out following production of the library following the second amplification; and wherein steps the other method steps are conducted in a single reaction vessel without requisite transferring of a portion (aliquot) of any of the products generated in steps to another reaction vessel. Each of the plurality of adaptors used in the methods herein comprise a universal handle sequence and a target nucleic acid sequence and a cleavable moiety and one or more tag sequences. At least two and up to one hundred thousand target specific adaptor pairs are included in the provided methods, wherein the target nucleic acid sequence of each adaptor includes at least one cleavable moiety, the universal handle sequence does not include the cleavable moiety, and the cleavable moieties are included flanking either end of the tag sequence.

In some embodiments, adaptor-dimer byproducts resulting from the first amplification of step of the methods are largely removed from the resulting library. In certain embodiments the enriched population of amplified target nucleic acids contains a reduced amount of adaptor-dimer byproduct. In particular embodiments adaptor dimer byproducts are eliminated.

In some embodiments, the library is prepared in less than 4 hours. In some embodiments, the library is prepared, enriched and sequenced in less than 3 hours. In some embodiments, the library is prepared, enriched and sequenced in 2 to 3 hours. In some embodiments, the library is prepared in approximately 2.5 hours. In some embodiments, the library is prepared in approximately 2.75 hours. In some embodiments, the library is prepared in approximately 3 hours.

Compositions

Additional aspects of the invention comprise composition comprising a plurality of nucleic acid adaptors, as well as library compositions prepared according to the methods of the invention. Provided compositions are useful in conjunction with the methods described herein as well as for additional analysis and applications known in the art.

Thus, provided are composition comprising a plurality of nucleic acid adaptors, wherein each of the plurality of adaptors comprises a 5' universal handle sequence, optionally one or more tag sequences, and a 3' target nucleic acid sequence wherein each adaptor comprises a cleavable moiety, wherein the target nucleic acid sequence of the adaptor includes at least one cleavable moiety, and when tag sequences are present cleavable moieties are included flanking either end of the tag sequence and wherein the universal handle sequence does not include the cleavable moiety. At least two and up to one hundred thousand target specific adaptor pairs are included in provided compositions. Provided composition allow for rapid production of highly multiplexed targeted libraries.

In some embodiments, provided compositions comprise plurality of nucleic acid adaptors, wherein each of the plurality of adaptors comprise a 5' universal handle sequence, one or more tag sequences, and a 3' target nucleic acid sequence wherein each adaptor comprises a cleavable moiety; wherein the target nucleic acid sequence of the adaptor includes at least one cleavable moiety, cleavable moieties are included flanking either end of the tag sequence and the universal handle sequence does not include the cleavable moiety. At least two and up to one hundred thousand target specific adaptor pairs are included in provided compositions. Provided composition allow for rapid production of highly multiplexed, tagged, targeted libraries.

Primer/adaptor compositions may be single stranded or double stranded. In some embodiments adaptor compositions comprise are single stranded adaptors. In some embodiments adaptor compositions comprise double stranded adaptors. In some embodiments adaptor compositions comprise a mixture of single stranded and double stranded adaptors.

In some embodiments, compositions include a plurality of adaptors capable of amplification of one or more target nucleic acid sequences comprising a multiplex of adaptor pairs capable of amplification of at least two different target nucleic acid sequences wherein the target-specific primer sequence is substantially non-complementary to other target specific primer sequences in the composition. In some embodiments, the composition comprises at least 25, 50, 75, 100, 150, 200, 250, 300, 350, 400, 450, 500, 750, 1000, 1250, 1500, 1750, 2000, 2250, 2500, 2750, 3000, 3250, 3500, 3750, 4000, 4500, 5000, 5500, 6000, 7000, 8000, 9000, 10000, 11000, or 12000, or more target-specific adaptor pairs. In some embodiments, target-specific adaptor pairs comprise about 15 nucleotides to about 40 nucleotides in length, wherein at least one nucleotide is replaced with a cleavable group. In some embodiments the cleavable group is a uridine nucleotide. In some embodiments, the target-specific adaptor pairs are designed to amplify an exon, gene, exome or region of the genome associated with a clinical or pathological condition, e.g., amplification of one or more sites comprising one or more mutations (e.g., driver mutation) associated with a cancer, e.g., lung, colon, breast cancer, etc., or amplification of mutations associated with an inherited disease, e.g., cystic fibrosis, muscular dystrophies, etc. In some embodiments, the target-specific adaptor pairs when hybridized to a target sequence and amplified as provided herein generates a library of adaptor-ligated amplified target sequences that are about 100 to about 600 base pairs in length. In some embodiments, no one adaptor-ligated amplified target sequence is overexpressed in the library by more than 30% as compared to the remainder of other adaptor-ligated amplified target sequences in the library. In some embodiments, an adaptor-ligated amplified target sequence library is substantially homogenous with respect to GC content, amplified target sequence length or melting temperature (Tm) of the respective target sequences.

In some embodiments, the target-specific primer sequences of adaptor pairs in the compositions of the invention are target-specific sequences that can amplify specific regions of a nucleic acid molecule. In some embodiments, the target-specific adaptors can amplify genomic DNA or cDNA. In some embodiments, target-specific adaptors can amplify mammalian nucleic acid, such as, but not limited to human DNA or RNA, murine DNA or RNA, bovine DNA or RNA, canine DNA or RNA, equine DNA or RNA, or any other mammal of interest. In other embodiments, target specific adaptors include sequences directed to amplify plant nucleic acids of interest. In other embodiments, target specific adaptors include sequences directed to amplify infectious agents, e.g., bacterial and/or viral nucleic acids. In some embodiments, the amount of nucleic acid required for selective amplification is from about 1 ng to 1 microgram. In some embodiments, the amount of nucleic acid required for selective amplification of one or more target sequences is about 1 ng, about 5 ng or about 10 ng. In some embodiments, the amount of nucleic acid required for selective amplification of target sequence is about 10 ng to about 200 ng.

As described herein, each of the plurality of adaptors comprises a 5' universal handle sequence. In some embodiments a universal handle sequence comprises any one or any combination of an amplification primer binding sequence, a sequencing primer binding sequence and/or a capture primer binding sequence. In some embodiments the comparable maximal minimum melting temperatures of each adaptor universal handle sequence is higher than the comparable maximal minimum melting temperatures of each target nucleic acid sequence and each tag sequence present in the same adaptor. Preferably, the universal handle sequences of provided adaptors do not exhibit significant complementarity and/or hybridization to any portion of a unique tag sequence and/or target nucleic acid sequence of interest. In some embodiments a first universal handle sequence comprises any one or any combination of an amplification primer binding sequence, a sequencing primer binding sequence and/or a capture primer binding sequence. In some embodiments a second universal handle sequence comprises any one or any combination of an amplification primer binding sequence, a sequencing primer binding sequence and/or a capture primer binding sequence. In certain embodiments first and second universal handle sequences correspond to forward and reverse universal handle sequences and in certain embodiments the same first and second universal handle sequences are included for each of the plurality of target specific adaptor pairs. Such forward and reverse universal handle sequences are targeted in conjunction with universal primers to carry out a second amplification of repaired amplicons in production of libraries according to methods of the invention. In certain embodiments a first 5' universal handle sequence comprises two universal handle sequences (e.g., a combination of an amplification primer binding sequence, a sequencing primer binding sequence and/or a capture primer binding sequence); and a second 5' universal sequence comprises two universal handle sequences (e.g., a combination of an amplification primer binding sequence, a sequencing primer binding sequence and/or a capture primer binding sequence), wherein the 5' first and second universal handle sequences do not exhibit significant hybridization to any portion of a target nucleic acid sequence of interest.

The structure and properties of universal amplification primers or universal primers are well known to those skilled in the art and can be implemented for utilization in conjunction with provided methods and compositions to adapt to specific analysis platforms. Universal handle sequences of the adaptors provided herein are adapted accordingly to accommodate a preferred universal primer sequences. For example, e.g., as described herein universal P1 and A primers with optional barcode sequences have been described in the art and utilized for sequencing on Ion Torrent sequencing platforms (Ion Xpress™ Adapters, Thermo Fisher Scientific). Similarly, additional and other universal adaptor/primer sequences described and known in the art (e.g., Illumina universal adaptor/primer sequences can be found, e.g., at //supportillumina.com/content/dam/ illumina-support/documents/documentation/chemistry_documentation/experiment-design/illumina-adapter-sequences_1000000002694-01.pdf; PacBio universal adaptor/ primer sequences, can be found, e.g., at //s3.ama-zonaws.com/files.pacb.com/pdf/Guide_Pacific_Biosciences_Template_Preparation_and_Sequencing.pdf; etc.) can be used in conjunction with the methods and compositions provided herein. Suitable universal primers of appropriate nucleotide sequence for use with adaptors of the invention are readily prepared using standard automated nucleic acid synthesis equipment and reagents in routine use in the art. One single type of universal primer or separate types (or even a mixture) of two different universal primers, for example a pair of universal amplification primers suitable for amplification of repaired amplicons in a second amplification are included for use in the methods of the invention. Universal primers optionally include a different tag (barcode) sequence, where the tag (barcode) sequence does not hybridize to the adaptor. Barcode sequences incorporated into amplicons in a second universal amplification can be utilized e.g., for effective identification of sample source.

In some embodiments adaptors further comprise a unique tag sequence located between the 5' first universal handle sequence and the 3' target-specific sequence, and wherein the unique tag sequence does not exhibit significant complementarity and/or hybridization to any portion of a unique tag sequence and/or target nucleic acid sequence of interest. In some embodiments the plurality of primer adaptor pairs has $10^4$-$10^9$ different tag sequence combinations. Thus in certain embodiments each generated target specific adaptor pair comprises $10^4$-$10^9$ different tag sequences. In some embodiments the plurality of primer adaptors comprise each target specific adaptor comprising at least 1 different unique tag sequence and up to $10^5$ different unique tag sequences. In some embodiments the plurality of primer adaptors comprise each target specific adaptor comprising at least 1 different unique tag sequence and up to $10^5$ different unique tag sequences. In certain embodiments each generated target specific amplicon generated comprises at least two and up to $10^9$ different adaptor combinations comprising different tag sequences, each having two different unique tag sequences. In some embodiments the plurality of primer adaptors comprise each target specific adaptor comprising 4096 different tag sequences. In certain embodiments each generated target specific amplicon generated comprises up to 16,777,216 different adaptor combinations comprising different tag sequences, each having two different unique tag sequences.

In some embodiments individual primer adaptors in the plurality of adaptors include a unique tag sequence (e.g., contained in a tag adaptor) comprising different random tag sequences alternating with fixed tag sequences. In some embodiments, the at least one unique tag sequence comprises a at least one random sequence and at least one fixed sequence, or comprises a random sequence flanked on both sides by a fixed sequence, or comprises a fixed sequence flanked on both sides by a random sequence. In some embodiments a unique tag sequence includes a fixed sequence that is 2-2000 nucleotides or base-pairs in length. In some embodiments a unique tag sequence includes a random sequence that is 2-2000 nucleotides or base-pairs in length.

In some embodiments, unique tag sequences include a sequence having at least one random sequence interspersed with fixed sequences. In some embodiments, individual tag sequences in a plurality of unique tags have the structure $(N)_n(X)_x(M)_m(Y)_y$, wherein "N" represents a random tag sequence that is generated from A, G, C, T, U or I, and wherein "n" is 2-10 which represents the nucleotide length of the "N" random tag sequence; wherein "X" represents a fixed tag sequence, and wherein "x" is 2-10 which represents the nucleotide length of the "X" random tag sequence; wherein "M" represents a random tag sequence that is generated from A, G, C, T, U or I, wherein the random tag sequence "M" differs or is the same as the random tag sequence "N", and wherein "m" is 2-10 which represents the nucleotide length of the "M" random tag sequence; and wherein "Y" represents a fixed tag sequence, wherein the fixed tag sequence of "Y" is the same or differs from the fixed tag sequence of "X", and wherein "y" is 2-10 which represents the nucleotide length of the "Y" random tag sequence. In some embodiments, the fixed tag sequence "X" is the same in a plurality of tags. In some embodiments, the fixed tag sequence "X" is different in a plurality of tags. In some embodiments, the fixed tag sequence "Y" is the same in a plurality of tags. In some embodiments, the fixed tag sequence "Y" is different in a plurality of tags. In some embodiments, the fixed tag sequences "$(X)_x$" and "$(Y)_y$" within the plurality of adaptors are sequence alignment anchors.

In some embodiments, the random sequence within a unique tag sequence is represented by "N", and the fixed sequence is represented by "X". Thus, a unique tag sequence is represented by $N_1N_2N_3X_1X_2X_3$ or by $N_1N_2N_3X_1X_2X_3N_4N_5N_6X_4X_5X_6$. Optionally, a unique tag sequence can have a random sequence in which some or all of the nucleotide positions are randomly selected from a group consisting of A, G, C, T, U and I. For example, a nucleotide for each position within a random sequence is independently selected from any one of A, G, C, T, U or I, or is selected from a subset of these six different types of nucleotides. Optionally, a nucleotide for each position within a random sequence is independently selected from any one of A, G, C or T. In some embodiments, the first fixed tag sequence "$X_1X_2X_3$" is the same or different sequence in a plurality of tags. In some embodiments, the second fixed tag sequence "$X_4X_5X_6$" is the same or different sequence in a plurality of tags. In some embodiments, the first fixed tag sequence "$X_1X_2X_3$" and the second fixed tag sequence "$X_4X_5X_6$" within the plurality of adaptors are sequence alignment anchors.

In some embodiments, a unique tag sequence comprises the sequence 5'-NNNACTNNNTGA-3', where "N" represents a position within the random sequence that is generated randomly from A, G, C or T, the number of possible distinct random tags is calculated to be $4^6$ (or 4^6) is about 4096, and the number of possible different combinations of two unique tags is $4^{12}$ (or 4^12) is about 16.78 million. In some embodiments, the underlined portions of 5'-NNNACTNNNTGA-3' are a sequence alignment anchor.

In some embodiments, the fixed sequences within the unique tag sequence is a sequence alignment anchor that can be used to generate error-corrected sequencing data. In some embodiments fixed sequences within the unique tag sequence is a sequence alignment anchor that can be used to generate a family of error-corrected sequencing reads.

Adaptors provided herein comprise at least one cleavable moiety. In some embodiments a cleavable moiety is within the 3' target-specific sequence. In some embodiments a cleavable moiety is at or near the junction between the 5' first universal handle sequence and the 3' target-specific sequence. In some embodiments a cleavable moiety is at or near the junction between the 5' first universal handle sequence and the unique tag sequence, and at or near the junction between the unique tag sequence and the 3' target-specific sequence. The cleavable moiety can be present in a modified nucleotide, nucleoside or nucleobase. In some embodiments, the cleavable moiety can include a nucleobase not naturally occurring in the target sequence of interest.

In some embodiments the at least one cleavable moiety in the plurality of adaptors is a uracil base, uridine or a deoxyuridine nucleotide. In some embodiments a cleavable moiety is within the 3' target-specific sequence and the junctions between the 5' universal handle sequence and the unique tag sequence and/or the 3'target specific sequence wherein the at least one cleavable moiety in the plurality of adaptors is cleavable with uracil DNA glycosylase (UDG). In some embodiments, a cleavable moiety is cleaved, resulting in a susceptible abasic site, wherein at least one enzyme capable of reacting on the abasic site generates a gap comprising an extendible 3' end. In certain embodiments the resulting gap comprises a 5'-deoxyribose phosphate group. In certain embodiments the resulting gap comprises an extendible 3' end and a 5' ligatable phosphate group.

In another embodiment, inosine can be incorporated into a DNA-based nucleic acid as a cleavable group. In one exemplary embodiment, EndoV can be used to cleave near the inosine residue. In another exemplary embodiment, the enzyme hAAG can be used to cleave inosine residues from a nucleic acid creating abasic sites.

Where a cleavable moiety is present, the location of the at least one cleavable moiety in the adaptors does not significantly change the melting temperature (Tm) of any given double-stranded adaptor in the plurality of double-stranded adaptors. The melting temperatures (Tm) of any two given double-stranded adaptors from the plurality of double-stranded adaptors are substantially the same, wherein the melting temperatures (Tm) of any two given double-stranded adaptors does not differ by more than 10° C. of each other. However, within each of the plurality of adaptors, the melting temperatures of sequence regions differs, such that the comparable maximal minimum melting temperature of, for example, the universal handle sequence, is higher than the comparable maximal minimum melting temperatures of either the unique tag sequence and/or the target specific sequence of any adaptor. This localized differential in comparable maximal minimum melting temperatures can be adjusted to optimize digestion and repair of amplicons and ultimately improved effectiveness of the methods provided herein.

Further provided are compositions comprising a nucleic acid library generated by methods of the invention. Thus, provided are composition comprising a plurality of amplified target nucleic acid amplicons, wherein each of the plurality of amplicons comprises a 5' universal handle sequence, optionally a first unique tag sequences, an intermediate target nucleic acid sequence, optionally a second unique tag sequences and a 3' universal handle sequence. At least two and up to one hundred thousand target specific amplicons are included in provided compositions. Provided compositions include highly multiplexed targeted libraries. In some embodiments, provided compositions comprise a plurality of nucleic acid amplicons, wherein each of the plurality of amplicons comprise a 5' universal handle sequence, a first unique tag sequences, an intermediate target nucleic acid sequence, a second unique tag sequences and a 3' universal handle sequence. At least two and up to one hundred thousand target specific tagged amplicons are included in provided compositions. Provided compositions include highly multiplexed tagged targeted libraries.

In some embodiments, library compositions include a plurality of target specific amplicons comprising a multiplex of at least two different target nucleic acid sequences. In some embodiments, the composition comprises at least 25, 50, 75, 100, 150, 200, 250, 300, 350, 400, 450, 500, 750, 1000, 1250, 1500, 1750, 2000, 2250, 2500, 2750, 3000, 3250, 3500, 3750, 4000, 4500, 5000, 5500, 6000, 7000, 8000, 9000, 10000, 11000, or 12000, or more target-specific amplicons. In some embodiments, the target-specific amplicons comprise one or more exon, gene, exome or region of the genome associated with a clinical or pathological condition, e.g., amplicons comprising one or more sites comprising one or more mutations (e.g., driver mutation) associated with a cancer, e.g., lung, colon, breast cancer, etc., or amplicons comprising mutations associated with an inherited disease, e.g., cystic fibrosis, muscular dystrophies, etc. In some embodiments, the target-specific amplicons comprise a library of adaptor-ligated amplicon target sequences that are about 100 to about 750 base pairs in length.

As described herein, each of the plurality of amplicons comprises a 5' universal handle sequence. In some embodiments a universal handle sequence comprises any one or any combination of an amplification primer binding sequence, a sequencing primer binding sequence and/or a capture primer binding sequence. Preferably, the universal handle sequences of provided adaptors do not exhibit significant complementarity and/or hybridization to any portion of a unique tag sequence and/or target nucleic acid sequence of interest. In some embodiments a first universal handle sequence comprises any one or any combination of an amplification primer binding sequence, a sequencing primer binding sequence and/or a capture primer binding sequence. In some embodiments a second universal handle sequence comprises any one or any combination of an amplification primer binding sequence, a sequencing primer binding sequence and/or a capture primer binding sequence. In certain embodiments first and second universal handle sequences correspond to forward and reverse universal handle sequences and in certain embodiments the same first and second universal handle sequences are included for each of the plurality of target specific amplicons. Such forward and reverse universal handle sequences are targeted in conjunction with universal primers to carry out a second amplification of a preliminary library composition in production of resulting amplified according to methods of the invention. In certain embodiments a first 5' universal handle sequence comprises two universal handle sequences (e.g., a combination of an amplification primer binding sequence, a sequencing primer binding sequence and/or a capture primer binding sequence); and a second 5' universal sequence comprises two universal handle sequences (e.g., a combination of an amplification primer binding sequence, a sequencing primer binding sequence and/or a capture primer binding sequence), wherein the 5' first and second universal handle sequences do not exhibit significant hybridization to any portion of a target nucleic acid sequence of interest.

The structure and properties of universal amplification primers or universal primers are well known to those skilled in the art and can be implemented for utilization in conjunction with provided methods and compositions to adapt to specific analysis platforms. Universal handle sequences of the adaptors and amplicons provided herein are adapted accordingly to accommodate a preferred universal primer sequences. For example, e.g., as described herein universal P1 and A primers with optional barcode sequences have been described in the art and utilized for sequencing on Ion Torrent sequencing platforms (Ion Xpress™ Adapters, Thermo Fisher Scientific). Similarly, additional and other universal adaptor/primer sequences described and known in the art (e.g., Illumina universal adaptor/primer sequences can be found, e.g., at //support.illumina.com/content/dam/illumina-support/documents/documentation/chemistry_documentation/experiment-design/illumina-adapter-sequences_1000000002694-01.pdf; PacBio universal adaptor/primer sequences, can be found, e.g., at //s3.amazonaws.com/files.pacb.com/pdf/Guide_Pacific_Biosciences_Template_Preparation_and_Sequencing.pdf; etc.) can be used in conjunction with the methods and compositions provided herein. Suitable universal primers of appropriate nucleotide sequence for use with libraries of the invention are readily prepared using standard automated nucleic acid synthesis equipment and reagents in routine use in the art. One single type or separate types (or even a mixture) of two different universal primers, for example a pair of universal amplification primers suitable for amplification of a preliminary library may be used in production of the libraries of the invention. Universal primers optionally include a tag (barcode) sequence, where the tag (barcode) sequence does not hybridize to adaptor sequence or to target nucleic acid sequences. Barcode sequences incorporated into amplicons in a second universal amplification can be utilized e.g., for effective identification of sample source to thereby generate a barcoded library. Thus provided compositions include highly multiplexed barcoded targeted libraries. Provided compositions also include highly multiplexed barcoded tagged targeted libraries.

In some embodiments amplicon libraries comprise a unique tag sequence located between the 5' first universal handle sequence and the 3' target-specific sequence, and wherein the unique tag sequence does not exhibit significant complementarity and/or hybridization to any portion of a unique tag sequence and/or target nucleic acid sequence. In some embodiments the plurality of amplicons has $10^4$-$10^9$ different tag sequence combinations. Thus in certain embodiments each of the plurality of amplicons in a library comprises $10^4$-$10^9$ different tag sequences. In some embodiments each of the plurality of amplicons in a library comprises at least 1 different unique tag sequence and up to $10^5$ different unique tag sequences. In certain embodiments each target specific amplicon in a library comprises at least two and up to $10^9$ different combinations comprising different tag sequences, each having two different unique tag sequences. In some embodiments each of the plurality of amplicons in a library comprise a tag sequence comprising 4096 different tag sequences. In certain embodiments each target specific amplicon of a library comprises up to 16,777,216 different combinations comprising different tag sequences, each having two different unique tag sequences.

In some embodiments individual amplicons in the plurality of amplicons of a library include a unique tag sequence (e.g., contained in a tag adaptor sequence) comprising different random tag sequences alternating with fixed tag sequences. In some embodiments, the at least one unique tag sequence comprises a at least one random sequence and at least one fixed sequence, or comprises a random sequence flanked on both sides by a fixed sequence, or comprises a fixed sequence flanked on both sides by a random sequence. In some embodiments a unique tag sequence includes a fixed sequence that is 2-2000 nucleotides or base-pairs in length.

In some embodiments a unique tag sequence includes a random sequence that is 2-2000 nucleotides or base-pairs in length.

In some embodiments, unique tag sequences include a sequence having at least one random sequence interspersed with fixed sequences. In some embodiments, individual tag sequences in a plurality of unique tags have the structure $(N)_n(X)_x(M)_m(Y)_y$, wherein "N" represents a random tag sequence that is generated from A, G, C, T, U or I, and wherein "n" is 2-10 which represents the nucleotide length of the "N" random tag sequence; wherein "X" represents a fixed tag sequence, and wherein "x" is 2-10 which represents the nucleotide length of the "X" random tag sequence; wherein "M" represents a random tag sequence that is generated from A, G, C, T, U or I, wherein the random tag sequence "M" differs or is the same as the random tag sequence "N", and wherein "m" is 2-10 which represents the nucleotide length of the "M" random tag sequence; and wherein "Y" represents a fixed tag sequence, wherein the fixed tag sequence of "Y" is the same or differs from the fixed tag sequence of "X", and wherein "y" is 2-10 which represents the nucleotide length of the "Y" random tag sequence. In some embodiments, the fixed tag sequence "X" is the same in a plurality of tags. In some embodiments, the fixed tag sequence "X" is different in a plurality of tags. In some embodiments, the fixed tag sequence "Y" is the same in a plurality of tags. In some embodiments, the fixed tag sequence "Y" is different in a plurality of tags. In some embodiments, the fixed tag sequences "$(X)_x$" and "$(Y)_y$" within the plurality of amplicons are sequence alignment anchors.

In some embodiments, the random sequence within a unique tag sequence is represented by "N", and the fixed sequence is represented by "X". Thus, a unique tag sequence is represented by $N_1N_2N_3X_1X_2X_3$ or by $N_1N_2N_3X_1X_2X_3N_4N_5N_6X_4X_5X_6$. Optionally, a unique tag sequence can have a random sequence in which some or all of the nucleotide positions are randomly selected from a group consisting of A, G, C, T, U and I. For example, a nucleotide for each position within a random sequence is independently selected from any one of A, G, C, T, U or I, or is selected from a subset of these six different types of nucleotides. Optionally, a nucleotide for each position within a random sequence is independently selected from any one of A, G, C or T. In some embodiments, the first fixed tag sequence "$X_1X_2X_3$" is the same or different sequence in a plurality of tags. In some embodiments, the second fixed tag sequence "$X_4X_5X_6$" is the same or different sequence in a plurality of tags. In some embodiments, the first fixed tag sequence "$X_1X_2X_3$" and the second fixed tag sequence "$X_4X_5X_6$" within the plurality of amplicons are sequence alignment anchors.

In some embodiments, a unique tag sequence comprises the sequence 5'-NNNACTNNNTGA-3', where "N" represents a position within the random sequence that is generated randomly from A, G, C or T, the number of possible distinct random tags is calculated to be $4^6$ (or 4^6) is about 4096, and the number of possible different combinations of two unique tags is $4^{12}$ (or 4^12) is about 16.78 million. In some embodiments, the underlined portions of 5'-NNNACTNNNTGA-3' are a sequence alignment anchor.

In some embodiments, the fixed sequences within the unique tag sequence is a sequence alignment anchor that can be used to generate error-corrected sequencing data. In some embodiments fixed sequences within the unique tag sequence is a sequence alignment anchor that can be used to generate a family of error-corrected sequencing reads.

Kits, Systems

Further provided herein are kits for use in preparing libraries of target nucleic acids using methods of the first or second aspects of the invention. Embodiments of a kit comprise a supply of at least a pair of target specific adaptors as defined herein which are capable of producing a first amplification product; as well as optionally a supply of at least one universal pair of amplification primers capable of annealing to the universal handle(s) of the adaptor and priming synthesis of an amplification product, which amplification product would include a target sequence of interest ligated to a universal sequence. Adaptors and/or primers may be supplied in kits ready for use, or more preferably as concentrates requiring dilution before use, or even in a lyophilized or dried form requiring reconstitution prior to use. In certain embodiments kits further include a supply of a suitable diluent for dilution or reconstitution of the components. Optionally, kits further comprise supplies of reagents, buffers, enzymes, dNTPs, etc., for use in carrying out amplification, digestion, repair, and/or purification in the generation of library as provided herein. Non-limiting examples of such reagents are as described in the Materials and Methods sections of the accompanying Exemplification. Further components which optionally are supplied in the kit include components suitable for purification of libraries prepared using the provided methods. In some embodiments, provided is a kit for generating a target-specific library comprising a plurality of target-specific adaptors having a 5' universal handle sequence, a 3' target specific sequence and a cleavable group, a DNA polymerase, an adaptor, dATP, dCTP, dGTP, dTTP, and a digestion reagent. In some embodiments, the kit further comprises one or more antibodies, a repair reagent, universal primers optionally comprising nucleic acid barcodes, purification solutions or columns.

Particular features of adaptors for inclusion in kits are as described elsewhere herein in relation to other aspects of the invention. The structure and properties of universal amplification primers are well known to those skilled in the art and can be implemented for utilization in conjunction with provided methods and compositions to adapt to specific analysis platforms (e.g., as described herein universal P1 and A primers have been described in the art and utilized for sequencing on Ion Torrent sequencing platforms). Similarly, additional and other universal adaptor/primer sequences described and known in the art (e.g., Illumina universal adaptor/primer sequences, PacBio universal adaptor/primer sequences, etc.) can be used in conjunction with the methods and compositions provided herein. Suitable primers of appropriate nucleotide sequence for use with adaptors included in the kit is readily prepared using standard automated nucleic acid synthesis equipment and reagents in routine use in the art. A kit may include a supply of one single type of universal primer or separate types (or even a mixture) of two different universal primers, for example a pair of amplification primers suitable for amplification of templates modified with adaptors in a first amplification. A kit may comprise at least a pair of adaptors for first amplification of a sample of interest according to the methods of the invention, plus at least two different amplification primers that optionally carry a different tag (barcode) sequence, where the tag (barcode) sequence does not hybridize to the adaptor. A kit can be used to amplify at least two different samples where each sample is amplified according to methods of the invention separately and a second amplification comprises using a single universal primer having a barcode, and then pooling prepared sample libraries after library preparations. In some embodiments a kit includes different universal primer-pairs for use in second amplification step described herein. In this context the 'universal' primer-pairs may be of substantially identical nucleotide sequence but differ with respect to some other feature or modification.

Further provided are systems, e.g., systems used to practice methods provided herein, and/or comprising compositions provided herein. In some embodiments, systems facilitate methods carried out in automated mode. In certain embodiments, systems facilitate high throughput mode. In certain embodiments, systems include, e.g., a fluid handling element, a fluid containing element, a heat source and/or heat sink for achieving and maintaining a desired reaction temperature, and/or a robotic element capable of moving components of the system from place to place as needed (e.g., a multiwell plate handling element).

Samples

As defined herein, "sample" and its derivatives, is used in its broadest sense and includes any specimen, culture and/or the like that is suspected of including a target nucleic acid. In some embodiments, a sample comprises DNA, RNA, chimeric nucleic acid, hybrid nucleic acid, multiplex-forms of nucleic acids or any combination of two or more of the foregoing. In some embodiments a sample useful in conjunction with methods of the invention includes any biological, clinical, surgical, agricultural, atmospheric or aquatic-based specimen containing one or more target nucleic acid of interest. In some embodiments, a sample includes nucleic acid molecules obtained from an animal such as a human or mammalian source. In another embodiment, a sample includes nucleic acid molecules obtained from a non-mammalian source such as a plant, bacteria, virus or fungus. In some embodiments, the source of the nucleic acid molecules may be an archived or extinct sample or species. In some embodiments a sample includes isolated nucleic acid sample prepared, for example, from a source such as genomic DNA, RNA or a prepared sample such as, e.g., fresh-frozen or formalin-fixed paraffin-embedded (FFPE) nucleic acid specimen. It is also envisioned that a sample is from a single individual, a collection of nucleic acid samples from genetically related members, multiple nucleic acid samples from genetically unrelated members, multiple nucleic acid samples (matched) from a single individual such as a tumor sample and normal tissue sample, or genetic material from a single source that contains two distinct forms of genetic material such as maternal and fetal DNA obtained from a maternal subject, or the presence of contaminating bacteria DNA in a sample that contains plant or animal DNA. In some embodiments, a source of nucleic acid material includes nucleic acids obtained from a newborn (e.g., a blood sample for newborn screening). In some embodiments, provided methods comprise amplification of multiple target-specific sequences from a single nucleic acid sample. In some embodiments, provided methods comprise target-specific amplification of two or more target sequences from two or more nucleic acid samples or species. In certain embodiments, provided methods comprise amplification of highly multiplexed target nucleic acid sequences from a single sample. In particular embodiments, provided methods comprise amplification of highly multiplexed target nucleic acid sequences from more than one sample, each from the same source organism.

In some embodiments a sample comprises a mixture of target nucleic acids and non-target nucleic acids. In certain embodiments a sample comprises a plurality of initial polynucleotides which comprises a mixture of one or more target nucleic acids and may include one or more non-target nucleic acids. In some embodiments a sample comprising a plurality of polynucleotides comprises a portion or aliquot of an originating sample; in some embodiments, a sample comprises a plurality of polynucleotides which is the entire originating sample. In some embodiments a sample comprises a plurality of initial polynucleotides is isolated from the same source or from the same subject at different time points.

In some embodiments, a nucleic acid sample includes cell-free nucleic acids from a biological fluid, nucleic acids from a tissue, nucleic acids from a biopsied tissue, nucleic acids from a needle biopsy, nucleic acids from a single cell or nucleic acids from two or more cells. In certain embodiments, a single reaction mixture contains 1-100 ng of the plurality of initial polynucleotides. In some embodiments a plurality of initial polynucleotides comprises a formalin fixed paraffin-embedded (FFPE) sample; genomic DNA; RNA; cell free DNA or RNA; circulating tumor DNA or RNA; fresh frozen sample, or a mixture of two or more of the foregoing; and in some embodiments a the plurality of initial polynucleotides comprises a nucleic acid reference standard. In some embodiments, a sample includes nucleic acid molecules obtained from biopsies, tumors, scrapings, swabs, blood, mucus, urine, plasma, semen, hair, laser capture micro-dissections, surgical resections, and other clinical or laboratory obtained sample. In some embodiments, a sample is an epidemiological, agricultural, forensic or pathogenic sample. In certain embodiments, a sample includes a reference. In some embodiments a sample is a normal tissue or well documented tumor sample. In certain embodiments a reference is a standard nucleic acid sequence (e.g., Hg19).

Target Nucleic Acid Sequence Analysis

Provided methods and compositions of the invention are particularly suitable for amplifying, optionally tagging, and preparing target sequences for subsequent analysis. Thus, in some embodiments, methods provided herein include analyzing resulting library preparations. For example, methods comprise analysis of a polynucleotide sequence of a target nucleic acid, and, where applicable, analysis of any tag sequence(s) added to a target nucleic acid. In some embodiments wherein multiple target nucleic acid regions are amplified, provided methods include determining polynucleotide sequences of multiple target nucleic acids. Provided methods further optionally include using a second tag sequence(s), e.g., barcode sequence, to identify the source of the target sequence (or to provide other information about the sample source). In certain embodiments, use of prepared library composition is provided for analysis of the sequences of the nucleic acid library.

In particular embodiments, use of prepared tagged library compositions is provided for further analyzing the sequences of the target nucleic acid library. In some embodiments determination of sequences comprises determining the abundance of at least one of the target sequences in the sample. In some embodiments determination of a low frequency allele in a sample is comprised in determination of sequences of a nucleic acid library. In certain embodiments, determination of the presence of a mutant target nucleic acid in the plurality of polynucleotides is comprised in determination of sequences of a nucleic acid library. In some embodiments, determination of the presence of a mutant target nucleic acid comprises detecting the abundance level of at least one mutant target nucleic acid in the plurality of polynucleotides. For example, such determination comprises detecting at least one mutant target nucleic acid is present at 0.05% to 1% of the original plurality of polynucleotides in the sample, detecting at least one mutant target nucleic acid is present at about 1% to about 5% of the polynucleotides in the sample, and/or detecting at least 85%-100% of target nucleic acids in sample. In some embodiments, determination of the presence of a mutant target nucleic acid comprises detecting and identification of copy number variation and/or genetic fusion sequences in a sample.

In some embodiments, nucleic acid sequencing of the amplified target sequences produced by the teachings of this disclosure include de novo sequencing or targeted re-sequencing. In some embodiments, nucleic acid sequencing further includes comparing the nucleic acid sequencing results of the amplified target sequences against a reference nucleic acid sequence. In some embodiments, nucleic acid sequencing of the target library sequences further includes determining the presence or absence of a mutation within a nucleic acid sequence. In some embodiments, nucleic acid sequencing includes the identification of genetic markers associated with disease (e.g., cancer and/or inherited disease).

In some embodiments, prepared library of target sequences of the disclosed methods is used in various downstream analysis or assays with, or without, further purification or manipulation. In some embodiments analysis comprises sequencing by traditional sequencing reactions, high throughput next generation sequencing, targeted multiplex array sequence detection, or any combination of two or more of the foregoing. In certain embodiments analysis is carried out by high throughput next generation sequencing. In particular embodiments sequencing is carried out in a bidirectional manner, thereby generating sequence reads in both forward and reverse strands for any given amplicon.

In some embodiments, library prepared according to the methods provided herein is then further manipulated for additional analysis. For example, \ prepared library sequences is used in downstream enrichment techniques known in the art, such a bridge amplification or emPCR to generate a template library that is then used in next generation sequencing. In some embodiments, the target nucleic acid library is used in an enrichment application and a sequencing application. For example, sequence determination of a provided target nucleic acid library is accomplished using any suitable DNA sequencing platform. In some embodiments, the library sequences of the disclosed methods or subsequently prepared template libraries is used for single nucleotide polymorphism (SNP) analysis, genotyping or epigenetic analysis, copy number variation analysis, gene expression analysis, analysis of gene mutations including but not limited to detection, prognosis and/or diagnosis, detection and analysis of rare or low frequency allele mutations, nucleic acid sequencing including but not limited to de novo sequencing, targeted resequencing and synthetic assembly analysis. In one embodiment, prepared library sequences are used to detect mutations at less than 5% allele frequency. In some embodiments, the methods disclosed herein is used to detect mutations in a population of nucleic acids at less than 4%, 3%, 2% or at about 1% allele frequency. In another embodiment, libraries prepared as described herein are sequenced to detect and/or identify germline or somatic mutations from a population of nucleic acid molecules. In certain embodiments, sequencing adaptors are ligated to the ends of the prepared libraries generate a plurality of libraries suitable for nucleic acid sequencing.

In some embodiments, methods for preparing a target-specific amplicon library are provided for use in a variety of downstream processes or assays such as nucleic acid sequencing or clonal amplification. In some embodiments, the library is amplified using bridge amplification or emPCR to generate a plurality of clonal templates suitable for nucleic acid sequencing. For example, optionally following target-specific amplification a secondary and/or tertiary amplification process including, but not limited to, a library amplification step and/or a clonal amplification step is performed. "Clonal amplification" refers to the generation of many copies of an individual molecule. Various methods known in the art is used for clonal amplification. For example, emulsion PCR is one method, and involves isolating individual DNA molecules along with primer-coated beads in aqueous bubbles within an oil phase. A polymerase chain reaction (PCR) then coats each bead with clonal copies of the isolated library molecule and these beads are subsequently immobilized for later sequencing. Emulsion PCR is used in the methods published by Marguilis et al. and Shendure and Porreca et al. (also known as "polony sequencing", commercialized by Agencourt and recently acquired by Applied Biosystems). Margulies, et al. (2005) *Nature* 437: 376-380; Shendure et al., *Science* 309 (5741): 1728-1732. Another method for clonal amplification is "bridge PCR," where fragments are amplified upon primers attached to a solid surface. These methods, as well as other methods of clonal amplification, both produce physically isolated locations that each contain many copies derived from a single molecule polynucleotide fragment. Thus, in some embodiments, the one or more target specific amplicons are amplified using for example, bridge amplification or emPCR to generate a plurality of clonal templates suitable for nucleic acid sequencing.

In some embodiments, at least one of the library sequences to be clonally amplified are attached to a support or particle. A support can be comprised of any suitable material and have any suitable shape, including, for example, planar, spheroid or particulate. In some embodiments, the support is a scaffolded polymer particle as described in U.S. Published App. No. 20100304982, hereby incorporated by reference in its entirety. In certain embodiments methods comprise depositing at least a portion of an enriched population of library sequences onto a support (e.g., a sequencing support), wherein the support comprises an array of sequencing reaction sites. In some embodiments, an enriched population of library sequences are attached to the sequencing reaction sites on the support. wherein the support comprises an array of $10^2$-$10^{10}$ sequencing reaction sites.

Sequence determination means determination of information relating to the sequence of a nucleic acid and may include identification or determination of partial as well as full sequence information of the nucleic acid. Sequence information may be determined with varying degrees of statistical reliability or confidence. In some embodiments sequence analysis includes high throughput, low depth detection such as by qPCR, rtPCR, and/or array hybridization detection methodologies known in the art. In some embodiments, sequencing analysis includes the determination of the in depth sequence assessment, such as by Sanger sequencing or other high throughput next generation sequencing methods. Next-generation sequencing means sequence determination using methods that determine many (typically thousands to billions) nucleic acid sequences in an intrinsically massively parallel manner, e.g. where many sequences are read out, e.g., in parallel, or alternatively using an ultra-high throughput serial process that itself may be parallelized. Thus, in certain embodiments, methods of the invention include sequencing analysis comprising massively parallel sequencing. Such methods include but are not limited to pyrosequencing (for example, as commercialized by 454 Life Sciences, Inc., Branford, Conn.); sequencing by ligation (for example, as commercialized in the SOLiD™ technology, Life Technologies, Inc., Carlsbad, Calif.); sequencing by synthesis using modified nucleotides (such as commercialized in TruSeq™ and HiSeq™. technology by Illumina, Inc., San Diego, Calif.; HeliScope™ by Helicos Biosciences Corporation, Cambridge, Mass.; and PacBio Sequel® or RS systems by Pacific Biosciences of California, Inc., Menlo Park, Calif.), sequencing by ion detection technologies (e.g., Ion Torrent™ technology, Life Technologies, Carlsbad, Calif.); sequencing of DNA nanoballs (Complete Genomics, Inc., Mountain View, Calif.); nanopore-based sequencing technologies (for example, as developed by Oxford Nanopore Technologies, LTD, Oxford, UK), and like highly parallelized sequencing methods.

For example, in certain embodiments, libraries produced by the teachings of the present disclosure are sufficient in yield to be used in a variety of downstream applications including the Ion Xpress™ Template Kit using an Ion Torrent™ PGM system (e.g., PCR-mediated addition of the nucleic acid fragment library onto Ion Sphere™ Particles) (Life Technologies, Part No. 4467389) or Ion Torrent Proton™ system). For example, instructions to prepare a template library from the amplicon library can be found in the Ion Xpress Template Kit User Guide (Life Technologies, Part No. 4465884), hereby incorporated by reference in its entirety. Instructions for loading the subsequent template library onto the Ion Torrent™ Chip for nucleic acid sequencing are described in the Ion Sequencing User Guide (Part No. 4467391), hereby incorporated by reference in its entirety. Similarly, sequencing using other platforms (e.g., PacBio, Illumina, Helicos, Complete Genomics, Oxford Nanopore) may be carried out using adapted methodologies to incorporate the relevant template preparation according to the instructions and guidance provided with each of the respective platforms.

The initiation point for the sequencing reaction may be provided by annealing a sequencing primer to a product of a solid-phase amplification reaction. In this regard, one or both of the adaptors added during formation of template library may include a nucleotide sequence which permits annealing of a sequencing primer to amplified products derived by whole genome or solid-phase amplification of the template library. Depending on implementation of an embodiment of the invention, a tag sequence and/or target nucleic acid sequence may be determined in a single read from a single sequencing primer, or in multiple reads from two different sequencing primers. In the case of two reads from two sequencing primers, a 'tag read' and a 'target sequence read' are performed in either order, with a suitable denaturing step to remove an annealed primer after the first sequencing read is completed.

In some embodiments, a sequencer is coupled to server that applies parameters or software to determine the sequence of the amplified target nucleic acid molecules. In certain embodiments, the sequencer is coupled to a server that applies parameters or software to determine the presence of a low frequency mutation allele present in a sample.

EMBODIMENTS

In one embodiment, a method for preparing a library of target nucleic acid sequences is provided comprising contacting a nucleic acid sample with a plurality of adaptors capable of amplification of one or more target nucleic acid sequences in the sample under conditions wherein the target nucleic acid(s) undergo a first amplification; digesting resulting first amplification products to reduce or eliminate resulting primer dimers and prepare partially digested target amplicons, producing gapped, double stranded amplicons, then repairing the partially digested target amplicons; and amplifying the repaired target amplicons in a second amplification using universal primers, wherein each of the plurality of adaptors comprise a universal handle sequence and a target nucleic acid sequence and a cleavable moiety, wherein at least two and up to one hundred thousand target specific adaptor pairs are included, and wherein the target nucleic acid sequence of the adaptor includes at least one cleavable moiety and the universal handle sequence does not include the cleavable moiety. Optionally one or more tag sequences are comprised in each of the plurality of adaptors. Such methods thereby produce a library of target nucleic acid sequence. In some embodiments, the digestion and repair is carried out in a single step. In particular embodiments the plurality of gapped polynucleotide products in digestion are contacted with the digestion and repair reagents simultaneously. In other embodiments the digestion and repair step is carried out in a temporally separate manner at different temperatures. In particular embodiments the plurality of gapped polynucleotide products in digestion are contacted sequentially with the digestion and repair reagents. In some embodiments one or more of the method steps is conducted in manual mode or in an automated mode or a combination thereof. In particular embodiments each of the method steps is carried out in automated mode. In some embodiments the foregoing methods further comprise at least one purification step. In particular embodiments a purification step is carried out only after the second universal amplification step. In other particular embodiments a purification is carried out after the digestion and repair step and an additional purification is carried out after the second universal amplification. In some of the embodiments adaptor-dimer by products resulting from the first amplification are removed from the resulting library, and in some embodiments an enriched population of amplified target nucleic acids contains a reduced amount of adaptor-dimer byproduct. In certain embodiments, adaptor-dimer byproducts are eliminated. In the foregoing methods the plurality of adaptors capable of amplification of one or more target nucleic acid sequences comprises a multiplex of adaptor pairs capable of amplification of at least two different target nucleic acid sequences. In some embodiments, each target specific pair of the plurality of adaptors includes up to 16,777,216 different adaptor combinations comprising different tag sequences. In certain embodiments each generated target specific amplicon sequence includes at least 1 different sequence and up to $10^7$ different sequences. In some embodiments, the foregoing methods further comprise analyzing the sequence of the resulting library of target nucleic acid sequences. Such analyzing comprises sequencing by traditional sequencing reactions, high throughput next generation sequencing, targeted multiplex array sequence detection, or any combination of two or more of the foregoing. In other embodiments, the foregoing methods further comprise determining the abundance of at least one of the target nucleic acid sequences in the sample. Such determining is carried out by high throughput next generation sequencing in certain embodiments. In particular embodiments, such sequencing is carried out in a bidirectional manner, thereby generating sequence reads in both forward and reverse strands for any given amplicon. In some embodiments the foregoing methods comprise digestion reagent selected from any one or a combination of uracil DNA glycosylase (UDG) apurinic endonuclease (e.g., APE1), RecJf, formamidopyrimidine [fapy]-DNA glycosylase (fpg), Nth endonuclease III, endonuclease VIII, polynucleotide kinase (PNK), Taq DNA polymerase, DNA polymerase I and/or human DNA polymerase beta. In some embodiments, the foregoing methods comprise repair reagent selected from any one or a combination of Phusion DNA polymerase, Phusion U DNA polymerase, SuperFi DNA polymerase, Taq DNA polymerase, Human DNA polymerase beta, T4 DNA polymerase and/or T7 DNA polymerase, SuperFiU DNA polymerase, E. coli DNA ligase, T3 DNA ligase, T4 DNA ligase, T7 DNA ligase, Taq DNA ligase, and/or 9° N DNA ligase. In particular embodiments the foregoing methods comprise digestion and repair reagent selected from any one or a combination of uracil DNA glycosylase (UDG), apurinic endonuclease (e.g., APE1), Taq DNA polymerase, Phusion U DNA polymerase, SuperFiU DNA polymerase, 7 DNA ligase. In more particular embodiments the foregoing methods comprise digestion and repair reagent selected from any one or a combination of uracil DNA glycosylase (UDG) formamidopyrimidine [fapy]-DNA glycosylase (fpg), Phusion U DNA polymerase, Taq DNA polymerase, SuperFiU DNA polymerase, T4 PNK and T7 DNA ligase. In preferred embodiments, the foregoing methods generate compositions comprising nucleic acid library. In particularly preferred embodiments, generated compositions comprising nucleic acid library are useful for analysis of sequences. In specific embodiments, use comprises determination of low frequency allele(s) in a sample.

In one embodiment, a method for preparing a library of target nucleic acid sequences is provided comprising contacting a nucleic acid sample with a plurality of adaptors capable of amplification of one or more target nucleic acid sequences in the sample under conditions wherein the target nucleic acid(s) undergo a first amplification; digesting resulting first amplification products to reduce or eliminate resulting primer dimers and prepare partially digested target amplicons, producing gapped, double stranded amplicons, then repairing the partially digested target amplicons; and amplifying the repaired target amplicons in a second amplification using universal primers, wherein each of the plurality of adaptors comprise a universal handle sequence and a target nucleic acid sequence and a cleavable moiety and a tag sequence is included in at least one adaptor, and the cleavable moieties are included flanking either end of the tag sequence, wherein at least two and up to one hundred thousand target specific adaptor pairs are included, and wherein the target nucleic acid sequence of the adaptor includes at least one cleavable moiety and the universal handle sequence does not include the cleavable moiety. Such methods thereby produce a library of target nucleic acid sequence. In some embodiments, the digestion and repair is carried out in a single step. In particular embodiments the plurality of gapped polynucleotide products in digestion are contacted with the digestion and repair reagents simultaneously. In other embodiments the digestion and repair step is carried out in a temporally separate manner at different temperatures. In particular embodiments the plurality of gapped polynucleotide products in digestion are contacted sequentially with the digestion and repair reagents. In some embodiments one or more of the method steps is conducted in manual mode or in an automated mode or a combination thereof. In particular embodiments each of the method steps is carried out in automated mode. In some embodiments the foregoing methods further comprise at least one purification step. In particular embodiments a purification step is carried out only after the second universal amplification step. In other particular embodiments a purification is carried out after the digestion and repair step and an additional purification is carried out after the second universal amplification. In some of the embodiments adaptor-dimer by products resulting from the first amplification are removed from the resulting library, and in some embodiments an enriched population of amplified target nucleic acids contains a reduced amount of adaptor-dimer byproduct. In certain embodiments, adaptor-dimer byproducts are eliminated. In the foregoing methods the plurality of adaptors capable of amplification of one or more target nucleic acid sequences comprises a multiplex of adaptor pairs capable of amplification of at least two different target nucleic acid sequences. In some embodiments, each target specific pair of the plurality of adaptors includes up to 16,777,216 different adaptor combinations comprising different tag sequences. In certain embodiments each generated target specific amplicon sequence includes at least 1 different sequence and up to $10^7$ different sequences. In some embodiments, the foregoing methods further comprise analyzing the sequence of the resulting library of target nucleic acid sequences. Such analyzing comprises sequencing by traditional sequencing reactions, high throughput next generation sequencing, targeted multiplex array sequence detection, or any combination of two or more of the foregoing. In other embodiments, the foregoing methods further comprise determining the abundance of at least one of the target nucleic acid sequences in the sample. Such determining is carried out by high throughput next generation sequencing in certain embodiments. In particular embodiments, such sequencing is carried out in a bidirectional manner, thereby generating sequence reads in both forward and reverse strands for any given amplicon. In some embodiments the foregoing methods comprise digestion reagent selected from any one or a combination of uracil DNA glycosylase (UDG) apurinic endonuclease (e.g., APE1), RecJf, formamidopyrimidine [fapy]-DNA glycosylase (fpg), Nth endonuclease III, endonuclease VIII, polynucleotide kinase (PNK), Taq DNA polymerase, DNA polymerase I and/or human DNA polymerase beta. In some embodiments, the foregoing methods comprise repair reagent selected from any one or a combination of Phusion DNA polymerase, Phusion U DNA polymerase, SuperFi DNA polymerase, Taq DNA polymerase, Human DNA polymerase beta, T4 DNA polymerase and/or T7 DNA polymerase, SuperFiU DNA polymerase, E. coli DNA ligase, T3 DNA ligase, T4 DNA ligase, T7 DNA ligase, Taq DNA ligase, and/or 9° N DNA ligase. In particular embodiments the foregoing methods comprise digestion and repair reagent selected from any one or a combination of uracil DNA glycosylase (UDG), apurinic endonuclease (e.g., APE1), Taq DNA polymerase, Phusion U DNA polymerase, SuperFiU DNA polymerase, 7 DNA ligase. In more particular embodiments the foregoing methods comprise digestion and repair reagent selected from any one or a combination of uracil DNA glycosylase (UDG) formamidopyrimidine [fapy]-DNA glycosylase (fpg), Phusion U DNA polymerase, Taq DNA polymerase, SuperFiU DNA polymerase, T4 PNK and T7 DNA ligase. In preferred embodiments, the foregoing methods generate compositions comprising nucleic acid library. In particularly preferred embodiments, generated compositions comprising nucleic acid library are useful for analysis of sequences. In specific embodiments, use comprises determination of low frequency allele(s) in a sample.

In one embodiment, a method for preparing a library of target nucleic acid sequences is provided comprising contacting a nucleic acid sample with a plurality of adaptors capable of amplification of one or more target nucleic acid sequences in the sample under conditions wherein the target nucleic acid(s) undergo a first amplification; digesting resulting first amplification products to reduce or eliminate resulting primer dimers and prepare partially digested target amplicons, producing gapped, double stranded amplicons, then repairing the partially digested target amplicons; and amplifying the repaired target amplicons in a second amplification using universal primers, wherein each of the plurality of adaptors comprise a universal handle sequence and a target nucleic acid sequence and a cleavable moiety, wherein at least two and up to one hundred thousand target specific adaptor pairs are included, and wherein the target nucleic acid sequence of the adaptor includes at least one cleavable moiety and the universal handle sequence does not include the cleavable moiety and the melting temperature of each universal sequence is higher than the melting temperature of each target nucleic acid sequence and each tag sequence present. Optionally one or more tag sequences are comprised in each of the plurality of adaptors. Such methods thereby produce a library of target nucleic acid sequence. In some embodiments, the digestion and repair is carried out in a single step. In particular embodiments the plurality of gapped polynucleotide products in digestion are contacted with the digestion and repair reagents simultaneously. In other embodiments the digestion and repair step is carried out in a temporally separate manner at different temperatures. In particular embodiments the plurality of gapped polynucleotide products in digestion are contacted sequentially with the digestion and repair reagents. In some embodiments one or more of the method steps is conducted in manual mode or in an automated mode or a combination thereof. In particular embodiments each of the method steps is carried out in automated mode. In some embodiments the foregoing methods further comprise at least one purification step. In particular embodiments a purification step is carried out only after the second universal amplification step. In other particular embodiments a purification is carried out after the digestion and repair step and an additional purification is carried out after the second universal amplification. In some of the embodiments adaptor-dimer by products resulting from the first amplification are removed from the resulting library, and in some embodiments an enriched population of amplified target nucleic acids contains a reduced amount of adaptor-dimer byproduct. In certain embodiments, adaptor-dimer byproducts are eliminated. In the foregoing methods the plurality of adaptors capable of amplification of one or more target nucleic acid sequences comprises a multiplex of adaptor pairs capable of amplification of at least two different target nucleic acid sequences. In some embodiments, each target specific pair of the plurality of adaptors includes up to 16,777,216 different adaptor combinations comprising different tag sequences. In certain embodiments each generated target specific amplicon sequence includes at least 1 different sequence and up to $10^7$ different sequences. In some embodiments, the foregoing methods further comprise analyzing the sequence of the resulting library of target nucleic acid sequences. Such analyzing comprises sequencing by traditional sequencing reactions, high throughput next generation sequencing, targeted multiplex array sequence detection, or any combination of two or more of the foregoing. In other embodiments, the foregoing methods further comprise determining the abundance of at least one of the target nucleic acid sequences in the sample. Such determining is carried out by high throughput throughput next generation sequencing in certain embodiments. In particular embodiments, such sequencing is carried out in a bidirectional manner, thereby generating sequence reads in both forward and reverse strands for any given amplicon. In some embodiments the foregoing methods comprise digestion reagent selected from any one or a combination of uracil DNA glycosylase (UDG) apurinic endonuclease (e.g., APE1), RecJf, formamidopyrimidine [fapy]-DNA glycosylase (fpg), Nth endonuclease III, endonuclease VIII, polynucleotide kinase (PNK), Taq DNA polymerase, DNA polymerase I and/or human DNA polymerase beta. In some embodiments, the foregoing methods comprise repair reagent selected from any one or a combination of Phusion DNA polymerase, Phusion U DNA polymerase, SuperFi DNA polymerase, Taq DNA polymerase, Human DNA polymerase beta, T4 DNA polymerase and/or T7 DNA polymerase, SuperFiU DNA polymerase, E. coli DNA ligase, T3 DNA ligase, T4 DNA ligase, T7 DNA ligase, Taq DNA ligase, and/or 9° N DNA ligase. In particular embodiments the foregoing methods comprise digestion and repair reagent selected from any one or a combination of uracil DNA glycosylase (UDG), apurinic endonuclease (e.g., APE1), Taq DNA polymerase, Phusion U DNA polymerase, SuperFiU DNA polymerase, 7 DNA ligase. In more particular embodiments the foregoing methods comprise digestion and repair reagent selected from any one or a combination of uracil DNA glycosylase (UDG) formamidopyrimidine [fapy]-DNA glycosylase (fpg), Phusion U DNA polymerase, Taq DNA polymerase, SuperFiU DNA polymerase, T4 PNK and T7 DNA ligase. In preferred embodiments, the foregoing methods generate compositions comprising nucleic acid library. In particularly preferred embodiments, generated compositions comprising nucleic acid library are useful for analysis of sequences. In specific embodiments, use comprises determination of low frequency allele(s) in a sample.

In one embodiment, a method for preparing a library of target nucleic acid sequences is provided comprising contacting a nucleic acid sample with a plurality of adaptors capable of amplification of one or more target nucleic acid sequences in the sample under conditions wherein the target nucleic acid(s) undergo a first amplification; digesting resulting first amplification products to reduce or eliminate resulting primer dimers and prepare partially digested target amplicons, producing gapped, double stranded amplicons, then repairing the partially digested target amplicons; and amplifying the repaired target amplicons in a second amplification using universal primers, wherein each of the plurality of adaptors comprise a universal handle sequence and a target nucleic acid sequence and a cleavable moiety, wherein at least two and up to one hundred thousand target specific adaptor pairs are included, and wherein the target nucleic acid sequence of the adaptor includes at least one cleavable moiety and the universal handle sequence does not include the cleavable moiety. Optionally one or more tag sequences are comprised in each of the plurality of adaptors. Such methods are carried out in a single, addition only workflow reaction, allowing for rapid production of highly multiplexed targeted libraries thereby produce a library of target nucleic acid sequence. In some embodiments, the digestion and repair is carried out in a single step. In particular embodiments the plurality of gapped polynucleotide products in digestion are contacted with the digestion and repair reagents simultaneously. In other embodiments the digestion and repair step is carried out in a temporally separate manner at different temperatures. In particular embodiments the plurality of gapped polynucleotide products in digestion are contacted sequentially with the digestion and repair reagents. In some embodiments one or more of the method steps is conducted in manual mode or in an automated mode or a combination thereof. In particular embodiments each of the method steps is carried out in automated mode. In some embodiments the foregoing methods further comprise at least one purification step. In particular embodiments a purification step is carried out only after the second universal amplification step. In other particular embodiments a purification is carried out after the digestion and repair step and an additional purification is carried out after the second universal amplification. In some of the embodiments adaptor-dimer by products resulting from the first amplification are removed from the resulting library, and in some embodiments an enriched population of amplified target nucleic acids contains a reduced amount of adaptor-dimer byproduct. In certain embodiments, adaptor-dimer byproducts are eliminated. In the foregoing methods the plurality of adaptors capable of amplification of one or more target nucleic acid sequences comprises a multiplex of adaptor pairs capable of amplification of at least two different target nucleic acid sequences. In some embodiments, each target specific pair of the plurality of adaptors includes up to 16,777,216 different adaptor combinations comprising different tag sequences. In certain embodiments each generated target specific amplicon sequence includes at least 1 different sequence and up to $10^7$ different sequences. In some embodiments, the foregoing methods further comprise analyzing the sequence of the resulting library of target nucleic acid sequences. Such analyzing comprises sequencing by traditional sequencing reactions, high throughput next generation sequencing, targeted multiplex array sequence detection, or any combination of two or more of the foregoing. In other embodiments, the foregoing methods further comprise determining the abundance of at least one of the target nucleic acid sequences in the sample. Such determining is carried out by high throughput next generation sequencing in certain embodiments. In particular embodiments, such sequencing is carried out in a bidirectional manner, thereby generating sequence reads in both forward and reverse strands for any given amplicon. In some embodiments the foregoing methods comprise digestion reagent selected from any one or a combination of uracil DNA glycosylase (UDG) apurinic endonuclease (e.g., APE1), RecJf, formamidopyrimidine [fapy]-DNA glycosylase (fpg), Nth endonuclease III, endonuclease VIII, polynucleotide kinase (PNK), Taq DNA polymerase, DNA polymerase I and/or human DNA polymerase beta. In some embodiments, the foregoing methods comprise repair reagent selected from any one or a combination of Phusion DNA polymerase, Phusion U DNA polymerase, SuperFi DNA polymerase, Taq DNA polymerase, Human DNA polymerase beta, T4 DNA polymerase and/or T7 DNA polymerase, SuperFiU DNA polymerase, E. coli DNA ligase, T3 DNA ligase, T4 DNA ligase, T7 DNA ligase, Taq DNA ligase, and/or 9° N DNA ligase. In particular embodiments the foregoing methods comprise digestion and repair reagent selected from any one or a combination of uracil DNA glycosylase (UDG), apurinic endonuclease (e.g., APE1), Taq DNA polymerase, Phusion U DNA polymerase, SuperFiU DNA polymerase, 7 DNA ligase. In more particular embodiments the foregoing methods comprise digestion and repair reagent selected from any one or a combination of uracil DNA glycosylase (UDG) formamidopyrimidine [fapy]-DNA glycosylase (fpg), Phusion U DNA polymerase, Taq DNA polymerase, SuperFiU DNA polymerase, T4 PNK and T7 DNA ligase. In preferred embodiments, the foregoing methods generate compositions comprising nucleic acid library. In particularly preferred embodiments, generated compositions comprising nucleic acid library are useful for analysis of sequences. In specific embodiments, use comprises determination of low frequency allele(s) in a sample.

In one embodiment, a method for preparing a library of target nucleic acid sequences is provided comprising contacting a nucleic acid sample with a plurality of adaptors capable of amplification of one or more target nucleic acid sequences in the sample under conditions wherein the target nucleic acid(s) undergo a first amplification; digesting resulting first amplification products to reduce or eliminate resulting primer dimers and prepare partially digested target amplicons, producing gapped, double stranded amplicons, then repairing the partially digested target amplicons; and amplifying the repaired target amplicons in a second amplification using universal primers, wherein each of the plurality of adaptors comprise a universal handle sequence and a target nucleic acid sequence and a cleavable moiety and all of the adaptors comprise tag sequences having cleavable groups flanking either end of the tag sequence, wherein at least two and up to one hundred thousand target specific adaptor pairs are included, and wherein the target nucleic acid sequence of the adaptor includes at least one cleavable moiety and the universal handle sequence does not include the cleavable moiety. Such methods thereby produce a library of target nucleic acid sequence. In some embodiments, the digestion and repair is carried out in a single step. In particular embodiments the plurality of gapped polynucleotide products in digestion are contacted with the digestion and repair reagents simultaneously. In other embodiments the digestion and repair step is carried out in a temporally separate manner at different temperatures. In particular embodiments the plurality of gapped polynucleotide products in digestion are contacted sequentially with the digestion and repair reagents. In some embodiments one or more of the method steps is conducted in manual mode or in an automated mode or a combination thereof. In particular embodiments each of the method steps is carried out in automated mode. In some embodiments the foregoing methods further comprise at least one purification step. In particular embodiments a purification step is carried out only after the second universal amplification step. In other particular embodiments a purification is carried out after the digestion and repair step and an additional purification is carried out after the second universal amplification. In some of the embodiments adaptor-dimer by products resulting from the first amplification are removed from the resulting library, and in some embodiments an enriched population of amplified target nucleic acids contains a reduced amount of adaptor-dimer byproduct. In certain embodiments, adaptor-dimer byproducts are eliminated. In the foregoing methods the plurality of adaptors capable of amplification of one or more target nucleic acid sequences comprises a multiplex of adaptor pairs capable of amplification of at least two different target nucleic acid sequences. In some embodiments, each target specific pair of the plurality of adaptors includes up to 16,777,216 different adaptor combinations comprising different tag sequences. In certain embodiments each generated target specific amplicon sequence includes at least 1 different sequence and up to $10^7$ different sequences. In some embodiments, the foregoing methods further comprise analyzing the sequence of the resulting library of target nucleic acid sequences. Such analyzing comprises sequencing by traditional sequencing reactions, high throughput next generation sequencing, targeted multiplex array sequence detection, or any combination of two or more of the foregoing. In other embodiments, the foregoing methods further comprise determining the abundance of at least one of the target nucleic acid sequences in the sample. Such determining is carried out by high throughput next generation sequencing in certain embodiments. In particular embodiments, such sequencing is carried out in a bidirectional manner, thereby generating sequence reads in both forward and reverse strands for any given amplicon. In some embodiments the foregoing methods comprise digestion reagent selected from any one or a combination of uracil DNA glycosylase (UDG) apurinic endonuclease (e.g., APE1), RecJf, formamidopyrimidine [fapy]-DNA glycosylase (fpg), Nth endonuclease III, endonuclease VIII, polynucleotide kinase (PNK), Taq DNA polymerase, DNA polymerase I and/or human DNA polymerase beta. In some embodiments, the foregoing methods comprise repair reagent selected from any one or a combination of Phusion DNA polymerase, Phusion U DNA polymerase, SuperFi DNA polymerase, Taq DNA polymerase, Human DNA polymerase beta, T4 DNA polymerase and/or T7 DNA polymerase, SuperFiU DNA polymerase, *E. coli* DNA ligase, T3 DNA ligase, T4 DNA ligase, T7 DNA ligase, Taq DNA ligase, and/or 9° N DNA ligase. In particular embodiments the foregoing methods comprise digestion and repair reagent selected from any one or a combination of uracil DNA glycosylase (UDG), apurinic endonuclease (e.g., APE1), Taq DNA polymerase, Phusion U DNA polymerase, SuperFiU DNA polymerase, 7 DNA ligase. In more particular embodiments the foregoing methods comprise digestion and repair reagent selected from any one or a combination of uracil DNA glycosylase (UDG) formamidopyrimidine [fapy]-DNA glycosylase (fpg), Phusion U DNA polymerase, Taq DNA polymerase, SuperFiU DNA polymerase, T4 PNK and T7 DNA ligase. In preferred embodiments, the foregoing methods generate compositions comprising nucleic acid library. In particularly preferred embodiments, generated compositions comprising nucleic acid library are useful for analysis of sequences. In specific embodiments, use comprises determination of low frequency allele(s) in a sample.

In one embodiment, provided is a method for preparing a library of target nucleic acid sequences comprising contacting a nucleic acid sample with a plurality of adaptors capable of amplification of one or more target nucleic acid sequences in the sample under conditions wherein the target nucleic acid(s) undergo a first amplification, digesting resulting first amplification products to reduce or eliminate resulting primer dimers and prepare partially digested target amplicons, producing gapped, double stranded amplicons, then repairing the partially digested target amplicons, and amplifying the repaired target amplicons in a second amplification using universal primers; wherein each of the plurality of adaptors comprises a universal handle sequence, one or more tag sequences, a target nucleic acid sequence and a cleavable moiety; and wherein at least two and up to one hundred thousand target specific adaptor pairs are included and wherein the target nucleic acid sequence of the adaptor includes at least one cleavable moiety, cleavable moieties are included in the flanking either end of the tag sequence and the universal handle sequence does not include the cleavable moiety. In certain embodiments the melting temperature of each universal sequence is higher than the melting temperature of each target nucleic acid sequence and each tag sequence present. Such methods thereby produce a library of target nucleic acid sequence. In particular embodiments such methods are carried out in a single, addition only workflow reaction, allowing for rapid production of highly multiplexed targeted libraries. In some embodiments, the digestion and repair is carried out in a single step. In particular embodiments the plurality of gapped polynucleotide products in digestion are contacted with the digestion and repair reagents simultaneously. In other embodiments the digestion and repair step is carried out in a temporally separate manner at different temperatures. In particular embodiments the plurality of gapped polynucleotide products in digestion are contacted sequentially with the digestion and repair reagents. In some embodiments one or more of the method steps is conducted in manual mode or in an automated mode or a combination thereof. In particular embodiments each of the method steps is carried out in automated mode. In some embodiments the foregoing methods further comprise at least one purification step. In particular embodiments a purification step is carried out only after the second universal amplification step. In other particular embodiments a purification is carried out after the digestion and repair step and an additional purification is carried out after the second universal amplification. In some of the embodiments adaptor-dimer by products resulting from the first amplification are removed from the resulting library, and in some embodiments an enriched population of amplified target nucleic acids contains a reduced amount of adaptor-dimer byproduct. In certain embodiments, adaptor-dimer byproducts are eliminated. In the foregoing methods the plurality of adaptors capable of amplification of two or more target nucleic acid sequences comprises a multiplex of adaptor pairs capable of amplification of target nucleic acid sequences. In certain embodiments all of the adaptors comprise tag sequences having cleavable groups flanking either end of the tag sequences. In some embodiments, each target specific pair of the plurality of adaptors includes up to 16,777,216 different adaptor combinations comprising different tag sequences. In certain embodiments each generated target specific amplicon sequence includes at least 1 different sequence and up to $10^7$ different sequences. In some embodiments, the foregoing methods further comprise analyzing the sequence of the resulting library of target nucleic acid sequences. Such analyzing comprises sequencing by traditional sequencing reactions, high throughput next generation sequencing, targeted multiplex array sequence detection, or any combination of two or more of the foregoing. In other embodiments, the foregoing methods further comprise determining the abundance of at least one of the target nucleic acid sequences in the sample. Such determining is carried out by high throughput next generation sequencing in certain embodiments. In particular embodiments, such sequencing is carried out in a bidirectional manner, thereby generating sequence reads in both forward and reverse strands for any given amplicon. In some embodiments the foregoing methods comprise digestion reagent selected from any one or a combination of uracil DNA glycosylase (UDG) apurinic endonuclease (e.g., APE1), RecJf, formamidopyrimidine [fapy]-DNA glycosylase (fpg), Nth endonuclease III, endonuclease VIII, polynucleotide kinase (PNK), Taq DNA polymerase, DNA polymerase I and/or human DNA polymerase beta. In some embodiments, the foregoing methods comprise repair reagent selected from any one or a combination of Phusion DNA polymerase, Phusion U DNA polymerase, SuperFi DNA polymerase, Taq DNA polymerase, Human DNA polymerase beta, T4 DNA polymerase and/or T7 DNA polymerase, SuperFiU DNA polymerase, E. coli DNA ligase, T3 DNA ligase, T4 DNA ligase, T7 DNA ligase, Taq DNA ligase, and/or 9° N DNA ligase. In particular embodiments the foregoing methods comprise digestion and repair reagent selected from any one or a combination of uracil DNA glycosylase (UDG), apurinic endonuclease (e.g., APE1), Taq DNA polymerase, Phusion U DNA polymerase, SuperFiU DNA polymerase, 7 DNA ligase. In more particular embodiments the foregoing methods comprise digestion and repair reagent selected from any one or a combination of uracil DNA glycosylase (UDG) formamidopyrimidine [fapy]-DNA glycosylase (fpg), Phusion U DNA polymerase, Taq DNA polymerase, SuperFiU DNA polymerase, T4 PNK and T7 DNA ligase. In preferred embodiments, the foregoing methods generate compositions comprising nucleic acid library. In particularly preferred embodiments, generated compositions comprising nucleic acid library are useful for analysis of sequences. In specific embodiments, use comprises determination of low frequency allele(s) in a sample.

In one embodiment provided is a composition comprising a plurality of nucleic acid adaptors, wherein each of the plurality of adaptors comprise a 5' universal handle sequence, one or more tag sequences, and a 3' target nucleic acid sequence wherein each adaptor comprises a cleavable moiety, the target nucleic acid sequence of the adaptor includes at least one cleavable moiety, cleavable moieties are included flanking either end of the tag sequence and the universal handle sequence does not include the cleavable moiety, and at least two and up to one hundred thousand target specific adaptor pairs are included. In some embodiments the melting temperature of each adaptor universal sequence is higher than the melting temperature of each target nucleic acid sequence and each tag sequence present in the same adaptor. The provided compositions allow for rapid production of highly multiplexed targeted libraries. In particular embodiments, the composition comprises multiplex of adaptor pairs capable of amplification of at least two different target nucleic acid sequences. In certain embodiments, each target specific pair of the plurality of adaptors includes up to 16,777,216 different adaptor combinations comprising different tag sequences In certain embodiments, compositions each generated target specific amplicon produced by target specific pairs of the plurality of adaptors produces at least 1 different sequence and up to $10^7$ different sequences. The foregoing compositions comprise adaptors wherein they are single stranded or double stranded. Yet additional embodiments provide kits comprising the adaptor compositions of any of the foregoing embodiments. In some embodiments such kits further comprise any one or more of an amplification reagent, a digestion reagent and a repair reagent. In certain embodiments such kits further comprise an amplification reagent, a digestion reagent and a repair reagent.

EXEMPLIFICATION

Example 1

Provided methods of the invention comprise streamlined procedures enabling rapid, highly multiplexed PCR. See FIG. 1. The invention optionally allows for the incorporation of one or more unique tag sequences, if so desired. Exemplary methods of the invention comprise the following protocols:

Example 1A

Materials and Method
Optional Reverse Transcription (RT) Reaction method (10 uL reaction) may be carried out in samples where RNA and DNA are analyzed:
Materials
2 uL 5× SuperScript™ VILO™ (Thermo Fisher Scientific) mix into a microtube or microwell, ≤8 uL volume of DNA+RNA sample for ≤20 ng total amount of DNA+RNA sample (~1% RNA sample of the total nucleic acid (TNA)); nuclease-free H2O to the above tube/well to make 10 uL total reaction volume;

Method:
42 C for 30 min
85 C for 1 min
4 C hold (indefinitely)

Amplification:
Materials

| ul | dH$_2$O (to 30 ul final) |
| ul | 20 ng genomic DNA sample |
| 48 nM | Panel of Adaptors |
| 15 ul | PhusionU multiplex PCR master mix |
| 2.4 ul | 2 u/ul Phusion U DNA polymerase |

Amplification:
98 C for 2 min
3 cycles of the following:
    98 C for 30 s
    64 C for 2 min
    62 C for 2 min
    60 C for 4 min
    58 C for 2 min
    72 C for 30 s
72 C for 2 min
4 C hold (indefinitely).

Digestion, Fill-in, Ligation:
Materials

| 2 ul | (5 u/ul) UDG, |
| 4 ul | (10 u/ul) FPG |
| 0.5 ul | (10 u/ul) T4 PNK |
| 1 ul | (3000 u/ul) T7 ligase |
| 1 ul | (10 mM) ATP. |

Method
Mix the materials above, add to reaction mixture.
Incubate:
30 C for 20 min
55 C for 20 min
25 C for 10 min
98 C for 2 min
4 C hold (indefinitely)

The resulting repaired sample is purified using 35 ul Ampure® beads (Beckman Coulter, Inc.) according to the manufacturer instructions.

Amplification:
Materials
1 ul for each P1 and A-universal primers, optionally containing barcode sequence (Ion
Xpress™ Adapters, Thermo Fisher Scientific)

Method
Incubate:
98 C for 2 min
22 cycles of
98 C for 15 s
64 C for 15 s
72 C for 15 s
72 C for 5 min
4 C hold (indefinitely)

The resulting sample is purified using 35 ul Ampure® beads (Beckman Coulter, Inc.) according to the manufacturer instructions. Optionally, the purification step is repeated 1× to 2×.

Example 1B

Materials and Method
Optional Reverse Transcription (RT) Reaction method (10 uL reaction) may be carried out in samples where RNA and DNA are analyzed:

Materials
2 uL 5× SuperScript™ VILO™ (Thermo Fisher Scientific) mix into a microtube or microwell, ≤8 uL volume of DNA+RNA sample for ≤20 ng total amount of DNA+RNA sample (~1% RNA sample of the total nucleic acid (TNA)); nuclease-free H2O to the above tube/well to make 10 uL total reaction volume;

Method:
42 C for 30 min
85 C for 1 min
4 C hold (indefinitely)

Amplification:
Materials

| ul | dH$_2$O (to 30 ul final) |
| ul | 20 ng genomic DNA sample |
| 48 nM | Panel of Adaptors |
| 15 ul | PhusionU multiplex PCR master mix |
| 2.4 ul | 2 u/ul Phusion U DNA polymerase |

Amplification:
98 C for 2 min
3 cycles of the following:
    98 C for 30 s
    64 C for 2 min
    62 C for 2 min
    60 C for 4 min
    58 C for 2 min
    72 C for 30 s
72 C for 2 min
4 C hold (indefinitely).

Digestion, Fill-in, Ligation:
Materials

| 2 ul | (5 u/ul) UDG, |
| 4 ul | (10 u/ul) APE1 |
| 0.5 ul | (1 u/ul) Taq polymerase |
| 1 ul | (3000 u/ul) T7 ligase |
| 1 ul | (10 mM) ATP. |

Method
Mix the materials above, add to reaction mixture.
Incubate:
30 C for 20 min
55 C for 20 min
25 C for 10 min
98 C for 2 min
4 C hold (indefinitely)

Amplification:
Materials
1 ul for each P1 and A-universal primers, optionally
    containing barcode sequence (Ion Xpress™ Adapters,
    Thermo Fisher Scientific)

Method
Incubate:
98 C for 2 min
22 cycles of
98 C for 15 s
64 C for 15 s
72 C for 15 s
72 C for 5 min
4 C hold (indefinitely)

The resulting sample is purified using 35 ul Ampure® beads (Beckman Coulter, Inc.) according to the manufacturer instructions. Optionally, purification step may be repeated 1× to 2×.

Example 1C

Materials and Method

Optional Reverse Transcription (RT) Reaction method (10 uL reaction) may be carried out in samples where RNA and DNA are analyzed:

Materials 2 uL 5× SuperScript™ VILO™ (Thermo Fisher Scientific) mix into a microtube or microwell, ≤8 uL volume of DNA+RNA sample for ≤20 ng total amount of DNA+RNA sample (~1% RNA sample of the total nucleic acid (TNA)); nuclease-free H2O to the above tube/well to make 10 uL total reaction volume;

Method:
42 C for 30 min
85 C for 1 min
4 C hold (indefinitely)

Amplification:
Materials

| _ul | dH$_2$O (to 30 ul final) |
| _ul | Genomic DNA sample (~20 ng) |
| 6 ul | Adaptor Panel 250 nM |
| 15 ul | PhusionU multiplex PCR master mix (F-562) |
| 3.0 ul | 2 u/ul SuperFiU DNA Polymerase |

Amplification
Assemble mixture of materials in reaction in 96-well plate wells, amplify using method:
99 C for 2 min
3 cycles of the following:
  99 C for 30 s
  64 C for 2 min
  62 C for 2 min
  60 C for 4 min
  58 C for 2 min
  72 C for 30 s
72 C for 2 min
4 C hold (indefinitely)

Digestion, Fill-in, Ligation:
Materials

| 0.1 ul | VIP Oligo 10 uM (P/N 4385451 Thermo Fisher Scientific, Inc.) |
| 2 ul | (5 u/ul) UDG |
| 4 ul | (10 u/ul) APE1 (NEB, M0282L) |
| 0.5 ul | (1 u/ul) Taq polymerase (EP0404) |
| 1 ul | (3000 u/ul) T7 ligase (NEB M0318L) |
| 1 ul | (10 mM) ATP |

Method
Mix the above materials, add into reaction mixture
Incubate:
30 C for 15 min
50 C for 15 min
55 C for 15 min
25 C for 10 min
98 C for 2 min
4 C hold (indefinitely)

Amplification
Materials
1 ul for each P1 and A-Barcode-universal primers optionally containing barcode sequence (Ion Xpress™ Adapters, Thermo Fisher Scientific)

Method
Add into the reaction wells the above materials, amplify:
99 C for 2 min
20 cycles:
  99 C for 20 s
  64 C for 20 s
  72 C for 20 s
72 C for 5 min
4 C hold (indefinitely)

The resulting sample is purified using 1× Ampure® beads (Beckman Coulter, Inc.) according to the manufacturer instructions. Optionally, purification step may be repeated 1× to 2×.

Example 1D

Materials and Method

Optional Reverse Transcription (RT) Reaction method (10 uL reaction) may be carried out in samples where RNA and DNA are analyzed:

Materials 2 uL 5× SuperScript™ VILO™ (Thermo Fisher Scientific) mix into a microtube or microwell, ≤8 uL volume of DNA+RNA sample for ≤20 ng total amount of DNA+RNA sample (~1% RNA sample of the total nucleic acid (TNA)); nuclease-free H2O to the above tube/well to make 10 uL total reaction volume;

Method:
42 C for 30 min
85 C for 1 min
4 C hold (indefinitely)

Amplification:
Materials

| _x_ul | nuclease free dH$_2$O (x to 30 ul final) |
| _y_ul | Genomic DNA sample (y ~20 ng) or y 10 uL of RT reaction for DNA + RNA sample |
| 12.5 ul | Adaptor Panel for ~50 nM each primer concentration |
| 7.5 ul | Platinum ™ SuperFi ™ PCR master mix, replacing SuperFi enzyme with 0.96 U/μL SuperFiU ™ DNA Polymerase |
| 3.0 ul | 2 U/ul SuperFiU ™ DNA Polymerase | optionally, an control may be included in reaction, (e.g, Acrometrix Oncology Hotspot Control (Thermo Fisher Scientific))

Amplification
Assemble mixture of materials in reaction in 96-well plate wells, seal, vortex and centrifuge plate, amplify using method:
99 C for 1 s
3 cycles of the following:
  99 C for 30 s
  64 C for 2 min
  60 C for 6 min
  72 C for 30 s
then 72 C for 2 min
4 C hold (indefinitely)

Digestion, Fill-in, Ligation:
Materials

| | | |
|---|---|---|
| 0.1 ul | VIP Oligo 0.2 uM (P/N 4385451 Thermo Fisher Scientific, Inc.) | |
| 2 ul | (5 u/ul) UDG | |
| 4 ul | (8 U/ul) APE1 (NEB, M0282L) | |
| 0.5 ul | (0.1 U/ul) Taq polymerase (EP0404) | |
| 1 ul | (6000 U/ul) T7 ligase (NEB M0318L) | |
| 1 ul | (2 mM) ATP | |
| 0.5 ul | mAB2A7 (0.6 mg/mL) | |
| 0.25 ul | mAB5D3 (0.25 mg/mL) | |

Method

Mix the above materials, add into reaction mixture, seal plate, vortex and centrifuge Incubate:
30 C for 15 min
50 C for 15 min
55 C for 15 min
25 C for 10 min
98 C for 2 min
4 C hold (indefinitely)

Amplification
Materials 1 ul for each P1 and A-Barcode-universal primers optionally barcoded sequence (Ion Xpress™ Adapters, Thermo Fisher Scientific); or 1 uL each of 10 uM BC1-Ah, and 1 uL of 10 uM P1-P1 h (IonCode™ Barcode Adapters, Thermo Fisher Scientific), for uni-directional library Method Add into the reaction wells the above materials, seal plate, vortex and centrifuge, then amplify:

99 C for 15s
5 cycles:
99 C for 15 s
62 C for 20 s
72 C for 20 s
15 cycles:
99 C for 15 s
70 C for 40 s
72 C for 5 min
4 C hold (indefinitely)

The resulting sample is purified using 1× Ampure® beads (Beckman Coulter, Inc.) according to the manufacturer instructions.

Optionally, purification may be repeated 1× to 2×.

Example 1E

Materials and Method
Amplification:
Materials

| | |
|---|---|
| x_ul | dH$_2$O (x to 30 ul final) |
| y_ul | Genomic DNA sample (y ~20 ng) or y 10 uL of RT reaction for DNA + RNA sample |
| 12.5 ul | Adaptor Panel for ~50 nM each primer concentration |
| 7.5 ul | Platinum ™ SuperFi ™ PCR master mix, replacing SuperFi enzyme with 0.96 U/μL SuperFiU ™ DNA Polymerase |
| 3.0 ul | 2 u/ul SuperFiU ™ DNA Polymerase |

Amplification

Assemble mixture of materials in reaction in 96-well plate wells, seal plate, vortex and centrifuge, then amplify using method:

99 C for 1 s 3 cycles of the following:
99 C for 30 s
64 C for 2 min
60 C for 6 min
72 C for 30 s
72 C for 2 min
4 C hold (indefinitely)

Digestion, Fill-in, Ligation:
Materials

| | |
|---|---|
| 0.1 ul | VIP Oligo 0.2 uM (P/N 4385451 Thermo Fisher Scientific, Inc.) |
| 2 ul | (5 u/ul) UDG |
| 4 ul | (8 U/ul) APE1 (NEB, M0282L) |
| 0.5 ul | (0.1 U/ul) Taq polymerase (EP0404) |
| 1 ul | (6000 U/ul) T7 ligase (NEB M0318L) |
| 1 ul | (2 mM) ATP |
| 0.5 ul | mAB2A7 (0.6 mg/mL) |
| 0.25 ul | mAB5D3 (0.25 mg/mL) |

Method

Mix the above materials, add into reaction mixture, seal plate, vortex and centrifuge Incubate:
30 C for 15 min
50 C for 15 min
55 C for 15 min
25 C for 10 min
98 C for 2 min
4 C hold (indefinitely)

Figure 7:
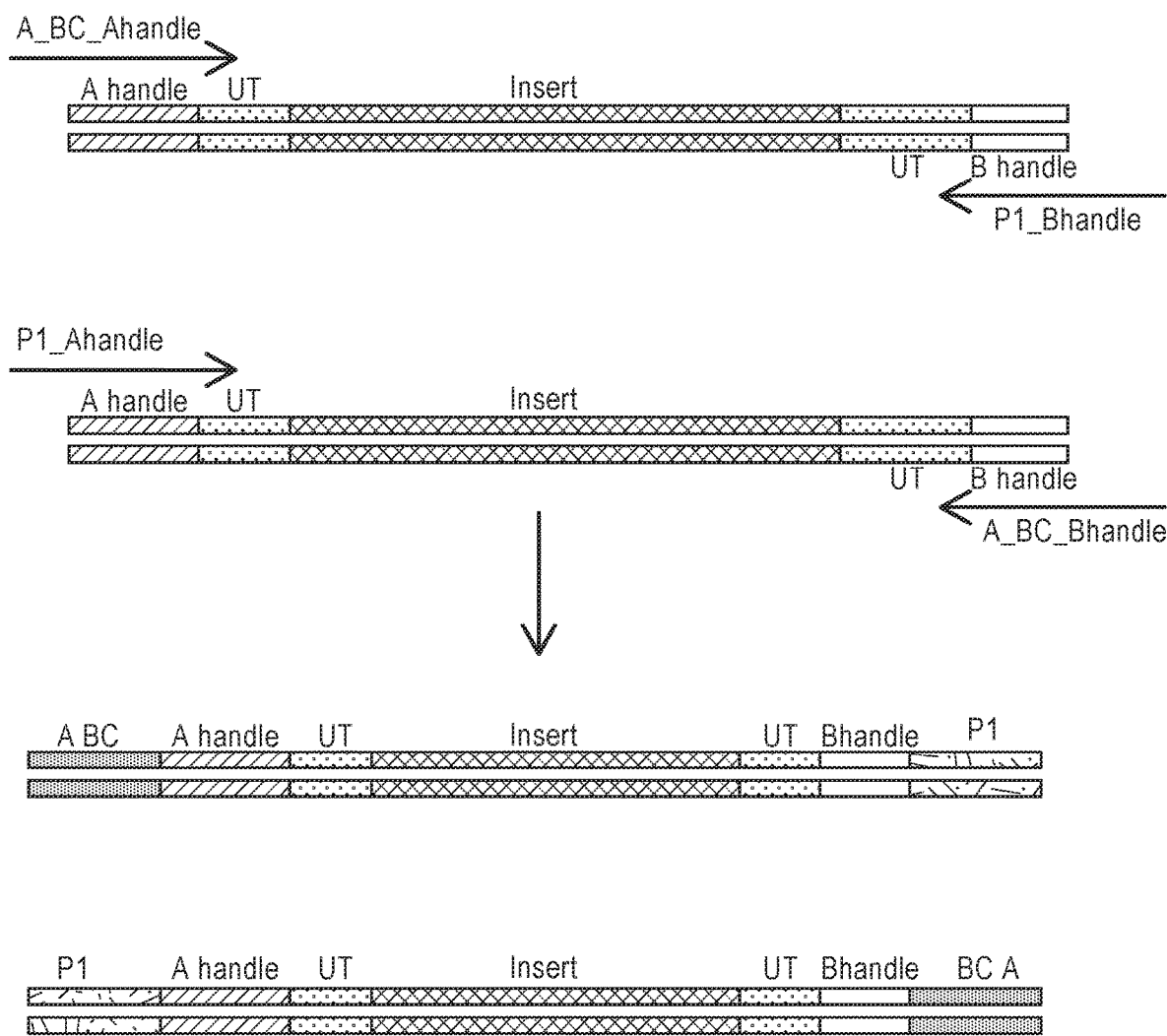
FIG. 7 depicts an additional aspect of the workflow of the invention that enables addition of adaptor sequences to facilitate bidirectional sequencing

Amplification
Materials 1 uL of 10 uM BC1-Ah, 1 uL of 10 uM P1-Uh, 1.5 uL of 10 uM BC1-Uh, and 1.5 uL of 10 uM P1-Ah. herein for bi-directional library preparation. BC1-Ah comprises barcode sequence and complementary sequence to universal A handle of forward adapters herein; BC1-Uh comprises barcode sequence and complementary sequence to universal handle of any of reverse adapters B, C, D, or E herein; P1-Uh comprises Ion adapter P1 adapter sequence, barcode sequence, and complementary sequence to universal B, C, D, or E handle of any of reverse adapters B, C, D, or E herein; P1-Ah comprises Ion adapter P1 adapter sequence, barcode sequence, and complementary sequence to universal handle of A handle of forward adapters herein. See FIG. 7.

Method

Add into the reaction wells the above materials, seal plate, vortex, centrifuge then amplify:

99 C for 15 s
5 cycles:
99 C for 15 s
62 C for 20 s
72 C for 20 s
15 cycles:
99 C for 15 s
70 C for 40 s
72 C for 5 min
4 C hold (indefinitely)

The resulting sample is purified using 1× Ampure® beads (Beckman Coulter, Inc.) according to the manufacturer instructions.

Optionally, purification may be repeated 1× to 2×.

Example 1F

Materials and Method
Optional Reverse Transcription (RT) Reaction method (10 uL reaction) may be carried out in samples where RNA and DNA are analyzed:
Materials
2 uL 5× SuperScript™ VILO™ (Thermo Fisher Scientific) mix into a microtube or microwell, ≤8 uL volume of DNA+RNA sample for ≤20 ng total amount of DNA+RNA sample (~1% RNA sample of the total nucleic acid (TNA)); nuclease-free H2O to the above tube/well to make 10 uL total reaction volume;
Method:
42 C for 30 min
85 C for 1 min
4 C hold (indefinitely)
Amplification:
Materials

| | |
|---|---|
| _x_ul | nuclease free dH$_2$O (x to 30 ul final) |
| _y_ul | Genomic DNA sample (y ~20 ng) or y 10 uL of RT reaction for DNA + RNA sample |
| 12.5 ul | Adaptor Panel for ~50 nM each primer concentration |
| 7.5 ul | Platinum ™ SuperFi ™ PCR master mix, replacing SuperFi enzyme with 0.96 U/μL SuperFiU ™ DNA Polymerase |
| 3.0 ul | 2 U/ul SuperFiU ™ DNA Polymerase | optionally, a control may be included in reaction, (e.g, Acrometrix Oncology Hotspot Control (Thermo Fisher Scientific))
Amplification
Assemble mixture of materials in reaction in 96-well plate wells, seal, vortex and centrifuge plate, amplify using method:
99 C for 1 s
3 cycles of the following:
  99 C for 30 s
  64 C for 2 min
  60 C for 6 min
  72 C for 30 s
then 72 C for 2 min
4 C hold (indefinitely)
Digestion, Fill-in, Ligation:
Materials

| | |
|---|---|
| 0.1 ul | VIP Oligo 0.2 uM (P/N 4385451 Thermo Fisher Scientific, Inc.) |
| 2 ul | (5 u/ul) UDG |
| 4 ul | (8 U/ul) APE1 (NEB, M0282L) |
| 0.5 ul | (0.1 U/ul) Taq polymerase (EP0404) |
| 1 ul | (6000 U/ul) T7 ligase (NEB M0318L) |
| 1 ul | (2 mM) ATP |
| 0.5 ul | mAB2A7 (0.6 mg/mL) |
| 0.25 ul | mAB5D3 (0.25 mg/mL) |

Method
Mix the above materials, add into reaction mixture, seal plate, vortex and centrifuge
Incubate:
30 C for 15 min
50 C for 15 min
55 C for 15 min
25 C for 10 min
98 C for 2 min
4 C hold (indefinitely)

Amplification
Materials
1 ul for each of (1) P5-index-A-handle primer; (2) P5-index-I-handle primer; (3) P7-index-A-handle primer; and (4) P7-index-I-handle primer. See Table F.
Method
Add into the reaction wells the above materials, seal plate, vortex and centrifuge, then amplify:
99 C for 15 s
5 cycles:
99 C for 15 s
62 C for 20 s
72 C for 20 s
15 cycles:
99 C for 15 s
70 C for 40 s
72 C for 5 min
4 C hold (indefinitely)
The resulting sample is purified using 1× Ampure® beads (Beckman Coulter, Inc.) according to the manufacturer instructions.

Optionally, purification may be repeated 1× to 2×.

Example 2

The first step of provided methods comprises a few rounds of amplification, for example, three to six cycles of amplification, and in certain instances, three cycles of amplification using forward and reverse adaptors to each gene specific target sequence. Each adaptor contains a 5'universal sequence, and a 3' gene specific target sequence. In some embodiments adaptors optionally comprise a unique tag sequence located between the 5' universal and the 3' gene specific target sequences.

In specific embodiments wherein unique tag sequences are utilized, each gene specific target adaptor pair includes a multitude of different unique tag sequences in each adaptor. For example, each gene specific target adaptor comprises up to 4096 TAGS. Thus, each target specific adaptor pair comprises at least four and up to 16,777,216 possible combinations.

Each of the provided adaptors comprises a cleavable uracil in place of thymine at specific locations in the forward and reverse adaptor sequences. Positions of uracils (Us) are consistent for all forward and reverse adaptors having unique tag sequences, wherein uracils (Us) are present flanking the 5' and 3' ends of the unique tag sequence when present; and Us are present in each of the gene specific target sequence regions, though locations for each gene specific target sequence will inevitably vary. Uracils flanking each unique tag sequence (UT) and in gene-specific sequence regions are designed in conjunction with sequences and calculated Tm of such sequences, to promote fragment dissociation at a temperature lower than melting temperature of the universal handle sequences, which are designed to remain hybridized at a selected temperature. Variations in Us in the flanking sequences of the UT region are possible, however designs keep the melting temperature below that of the universal handle sequences on each of the forward and reverse adaptors. Exemplary adaptor sequence structures comprise:

```
Forward Adaptor:
                                                            SEQ ID NO: 1
------A Handle-----  ------*UT*------  --Gene Specific--
TCTGTACGGTGACAAGGCG-U-NNNACTNNNTGA-U-GAGGACCGUCGCTUGGT Rev Adaptor B
                                                            SEQ ID NO: 2
CTCTATGGGCAGTCGGTGAT-U-NNNACTNNNTGA-U-CCTTCTGCAUGGTATTCTTTCTCTUCC
-----B Handle-------  --------*UT*----  -------Gene Specific-------

Rev Adaptor C
                                                            SEQ ID NO: 3
TCTAGTCGGTCAGTCACGG-U-NNNACTNNNTGA-U-CCTTCTGCAUGGTATTCTTTCTCTUCC
-----C Handle-------  ------UT-------  -------Gene Specific-------

Rev Adaptor D
                                                            SEQ ID NO: 4
TCTAGTGCTGCAGTCACGG-U-NNNACTNNNTGA-U-CCTTCTGCAUGGTATTCTTTCTCTUCC
-----D Handle-------  ------UT-------  -------Gene Specific-------

Rev Adaptor E
                                                            SEQ ID NO: 5
TGACAAGGCGTAGTCACGG-U-NNNACTNNNTGA-U-CCTTCTGCAUGGTATTCTTTCTCTUCC
-----E Handle-------  ------UT-------  -------Gene Specific-------
```

Wherein each N is a base selected from A, C, G, or T and the constant sections of the UT region are used as anchor sequences to ensure correct identification of variable (N) portion. The constant and variable regions of the UT can be significantly modified (e.g., alternative constant sequence, >3 Ns per section) as long as the Tm of the UT region remains below that of the universal handle regions. Importantly, cleavable uracils are absent from each forward (e.g., TCTGTACGGTGACAAGGCG (SEQ ID NO:6) and reverse (e.g., CTCTATGGGCAGTCGGTGAT (SEQ ID NO:7) universal handle sequence.

Enzymes used for amplification include (but are not limited to): Phusion U DNA polymerase; SuperFi U DNA polymerase; Taq DNA polymerase; Veraseq Ultra DNA polymerase. SuperFi U DNA Polymerase is a modified version of high fidelity SuperFi DNA Polymerase, available from Thermo Fisher Scientific. SuperFiU DNA comprises a modification in the uracil-binding pocket (e.g., AA 36) and a family B polymerase catalytic domain (e.g., AA 762). SuperFiU is described in U.S. Provisional patent application No. 62/524,730 filed Jun. 26, 2017, and International Patent application no. PCT/EP2018/066896, filed Jun. 25, 2018 which are each hereby incorporated by reference. Polymerase enzymes may be limited in their ability to utilize uracil and/or any alternative cleavable residues (e.g., inosine, etc.) included into adaptor sequences. In certain embodiments, it may also be advantageous to use a mixture of polymerases to reduce enzyme specific PCR errors.

The second step of methods involves partial digestion of resulting amplicons, as well as any unused uracil-containing adaptors. For example, where uracil is incorporated as a cleavable site, digestion and repair includes enzymatic cleavage of the uridine monophosphate from resulting primers, primer dimers and amplicons, and melting DNA fragments, then repairing gapped amplicons by polymerase fill-in and ligation. This step reduces and potentially eliminates primer-dimer products that occur in multiplex PCR. In some instances, digestion and repair are carried out in a single step. In certain instances, it may be desirable to separate digestion and repair-steps temporally. For example, thermolabile polymerase inhibitors may be utilized in conjunction with methods, such that digestion occurs at lower temperatures (25-40° C.), then repair is activated by increasing temperature enough to disrupt a polymerase-inhibitor interaction (e.g., polymerase-Ab), though not high enough to melt the universal handle sequences.

Uracil-DNA Glycosylase (UDG) enzyme can be used to remove uracils, leaving abasic sites which can be acted upon by several enzymes or enzyme combinations including (but not limited to): APE 1-Apurinic/apyrimidinic endonuclease; FPG-Formamidopyrimidine [fapy]-DNA glycosylase; Nth-Endonuclease III; Endo VIII-Endonuclease VIII; PNK-Polynucleotide Kinase; Taq- *Thermus aquaticus* DNA polymerase; DNA pol I-DNA polymerase I; Pol beta-Human DNA polymerase beta. In a particular implementation, the method uses Human apurinic/apyrimidinic endonuclease, APE1. APE1 activity leaves a 3'-OH and a 5'deoxyribose-phosphate (5'-dRP). Removal of the 5'-dRP can be accomplished by a number of enzymes including recJ, Polymerase beta, Taq, DNA pol I, or any DNA polymerase with 5'-3' exonuclease activity. Removal of the 5'-dRP by any of these enzymes creates a ligatable 5'-phosphate end. In another implementations, UDG activity removes the Uracil and leaves and abasic site which is removed by FPG, leaving a 3' and 5'-phosphate. The 3'-phosphate is then removed by T4 PNK, leaving a polymerase extendable 3'-OH. The 5'-deoxyribose phosphate can then be removed by Polymerase beta, fpg, Nth, Endo VIII, Taq, DNA pol I, or any other DNA polymerase with 5'-3' exonuclease activity. In a particular implementation Taq DNA polymerase is utilized.

Repair fill-in process can be accomplished by almost any polymerase, possibly the amplification polymerase used for amplification in step 1 or by any polymerase added in step 2 including (but not limited to): Phusion DNA polymerase; Phusion U DNA polymerase; SuperFi DNA polymerase; SuperFi U DNA polymerase; TAQ; Pol beta; T4 DNA polymerase; and T7 DNA polymerase. Ligation repair of amplicons can be performed by many ligases including (but not limited to): T4 DNA ligase; T7 DNA ligase; Taq DNA ligase. In a particular implementation of the methods, Taq DNA polymerase is utilized and ligation repaired in accomplished by T7 DNA ligase.

A last step of library preparation involves amplification of the repaired amplicons by standard PCR protocols using universal primers that contain sequences complementary to the universal handle sequences on the 5' and 3' ends of prepared amplicons. For example, an A-universal primer, and a P1 universal primer, each part of the Ion Express Adaptor Kit (Thermo Fisher Scientific, Inc.) may optionally contain a sample specific barcode. The last library amplification step may be performed by many polymerases including, but not limited to: Phusion DNA polymerase; Phusion U DNA polymerase; SuperFi DNA polymerase; SuperFi U DNA polymerase; Taq DNA polymerase; Veraseq Ultra DNA polymerase.

2A, In one specific implementation, adaptors were designed using the composition design approach provided herein, including universal handle-unique tag-gene specific target sequence described in Example 2 above, and targeted to genes using the ONCOMINE™ Focus Research Panel (Thermo Fisher Scientific, Inc.) target sequences and ION AMPLISEQ™ Designer (Thermo Fisher Scientific, Inc). Forward and reverse adaptors described above were utilized comprising

```
Forward Adaptor:
                                                 SEQ ID NO: 1
------A Handle----- ------*UT*------ --Gene Specific--
TCTGTACGGTGACAAGGCG-U-NNNACTNNNTGA-U-GAGGACCGUCGCTUGGT Rev Adaptor B
                                                 SEQ ID NO: 2
CTCTATGGGCAGTCGGTGAT-U-NNNACTNNNTGA-U-CCTTCTGCAUGGTATTCTTTCTCTUCC
-----B Handle------- --------*UT*---- -------Gene Specific-------
```

Figure 2:
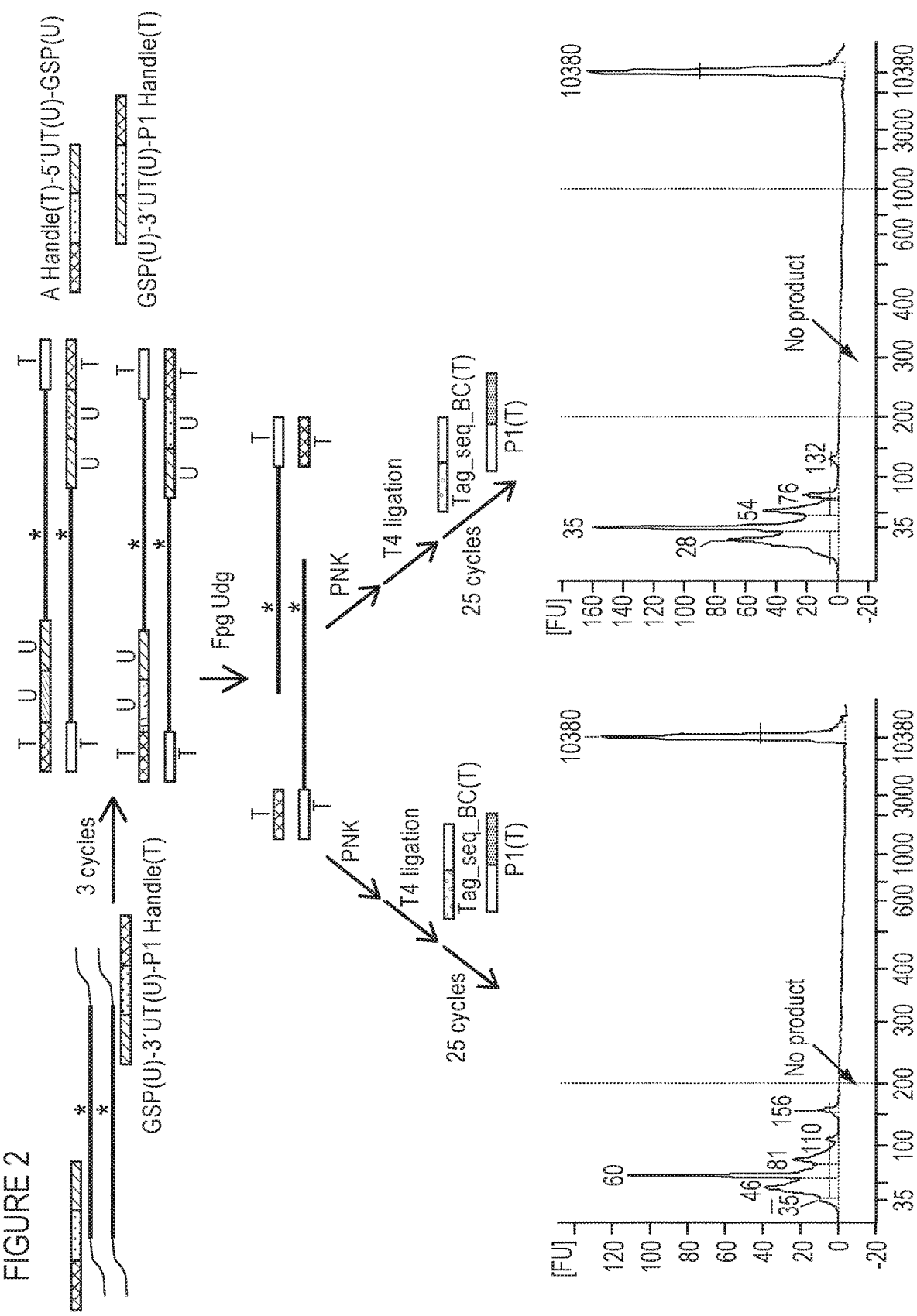
FIG. 2 depicts results from the experimental description in Example 2A.

With target sequences specific to targets as in Table A, and adaptors each comprise 4096 unique tag sequences for each gene specific target sequence, resulting in an estimate of 16,777,216 different unique tag combinations for each gene specific target sequence pair. Preparation of library was carried out according to the method described above for Example 1A. Formamidopyrimidine [fapy]-DNA glycosylase (FPG)/UDG enzyme is utilized for digestion, which is expected to create abasic sites at all uracil positions, FPG is expected to cleave on the 5' and 3' side of the abasic site (leaving a 3'-phosphate and a 5' phosphate) and removal of the 3'phosphate (by T4 PNK for example) should produce an extendable 3'-OH and a ligatable 5'-phosphate. However, as shown by the BioAnalyzer trace (See FIG. 2), this process consistently failed to generate recoverable product. The process can be rescued however by the addition of an additional purification step post-repair. The purification process can be anything inactivates and removes the repair enzymes prior to the next amplification step. Similar results were obtained if endoVIII was utilized.

Figure 3:
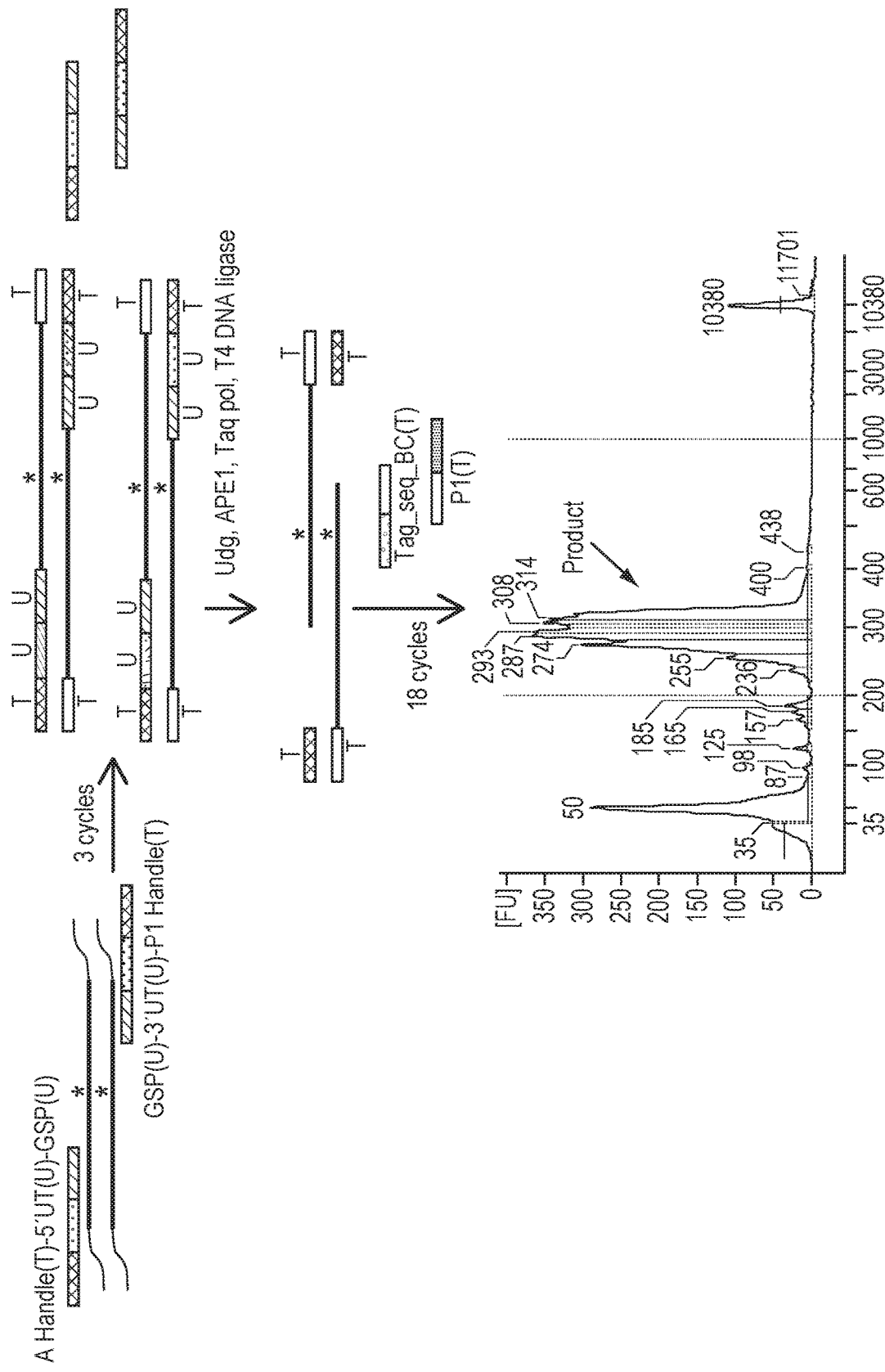
FIG. 3 depicts results from the experimental description in Example 2B.

2B. In another specific implementation, adaptors were prepared as described in section 2A for targets of the ONCOMINE™ Focus Assay. See Table B. Forward and reverse adaptors described above were utilized comprising With target sequences specific to targets as in Table B, and adaptors each comprise 4096 unique tag sequences for each gene specific target sequence, resulting in an estimate of 16,777,216 different unique tag combinations for each gene specific target sequence pair. Preparation of library was carried out according to the method described above for 1C. See FIG. 3, Table 1. Similar successful sequencing results were generated with each of the reverse adaptor pairings.

Example 3

Prepared libraries are sequenced, and analyzed. Sequencing can be carried out by a variety of known methods, including, but not limited to sequencing by synthesis, sequencing by ligation, and/or sequencing by hybridization. Sequencing has been carried out in the examples herein using the Ion Torrent platform (Thermo Fisher Scientific, Inc.), however, libraries can be prepared and adapted for analysis, e.g., sequencing, using any other platforms, e.g., Illumina, PacBio, etc. Result may be analyzed using a number of metrics to assess performance, for example:

of families (with ng input DNA captured) The median #of families is a measure of the number of families that maps to an individual target. In this case, each unique molecular tag is a family.

Uniformity is a measure of the percentage of target bases covered by at least 0.2× the average read depth. This metric is used to ensure that the technology does not selectively under-amplify certain targets.

Positives/Negatives: When a control sample with known mutations is utilized is analyzed (e.g., Acrometrix Oncology Hotspot Control DNA, Thermo Fisher Scientific, Inc.), the number of True Positives can be tracked.

```
Forward Adaptor:
                                                 SEQ ID NO: 1
------A Handle----- ------*UT*------ --Gene Specific--
TCTGTACGGTGACAAGGCG-U-NNNACTNNNTGA-U-GAGGACCGUCGCTUGGT Reverse Adaptor was any of Rev Adaptor B, Rev Adaptor C,
Rev Adaptor D, Rev Adaptor E:
Rev Adaptor B
                                                 SEQ ID NO: 2
CTCTATGGGCAGTCGGTGAT-U-NNNACTNNNTGA-U-CCTTCTGCAUGGTATTCTTTCTCTUCC
-----B Handle------- --------*UT*---- -------Gene Specific-------

Rev Adaptor C
                                                 SEQ ID NO: 3
TCTAGTCGGTCAGTCACGG-U-NNNACTNNNTGA-U-CCTTCTGCAUGGTATTCTTTCTCTUCC
-----C Handle------- ------UT------- -------Gene Specific-------

Rev Adaptor D
                                                 SEQ ID NO: 4
TCTAGTGCTGCAGTCACGG-U-NNNACTNNNTGA-U-CCTTCTGCAUGGTATTCTTTCTCTUCC
-----D Handle------- ------UT------- -------Gene Specific-------

Rev Adaptor E
                                                 SEQ ID NO: 5
TGACAAGGCGTAGTCACGG-U-NNNACTNNNTGA-U-CCTTCTGCAUGGTATTCTTTCTCTUCC
-----E Handle------- ------UT------- -------Gene Specific-------
```

True Positives: The number of True Positives informs on the number of mutations that were present and correctly identified.

False positives (FP): (Hot spot and Whole Target) The number of False Positives informs on the number of mutations that are determined to be present, but known not to be in the sample.

False negatives (FN) (if acrometrix spike-in is used) The number of False Negatives informs on the number of mutations that were present but not identified.

On/Off Target is the percentage of mapped reads that were aligned/not aligned over a target region. This metric is used to ensure the technology amplifies predominantly the targets to which the panel was designed.

Low quality is tracked to ensure the data is worth analyzing. This metric is a general system metric and isn't directly related to this technology.

Example 4

One benefit of the instant invention is the ability to use Ampliseq.com designer in conjunction with the provided methodology. Adaptors were designed using the composition design approach provided herein, including universal handle-unique tag-gene specific target sequence described in Example 2 above, and targeted to genes using the ONCOMINE™ Focus Research Panel (Thermo Fisher Scientific, Inc.) target sequences and ION AMPLISEQ™ Designer (Thermo Fisher Scientific, Inc). Forward and reverse adaptors described above were utilized comprising

```
Forward Adaptor:
                                                     SEQ ID NO: 1
------A Handle-----  ------*UT*------  --Gene Specific--
TCTGTACGGTGACAAGGCG-U-NNNACTNNNTGA-U-GAGGACCGUCGCTUGGT Rev Adaptor B
                                                     SEQ ID NO: 2
CTCTATGGGCAGTCGGTGAT-U-NNNACTNNNTGA-U-CCTTCTGCAUGGTATTCTTTCTCTUCC
-----B Handle-------  --------*UT*----  -------Gene Specific-------
```

Figure 4A:
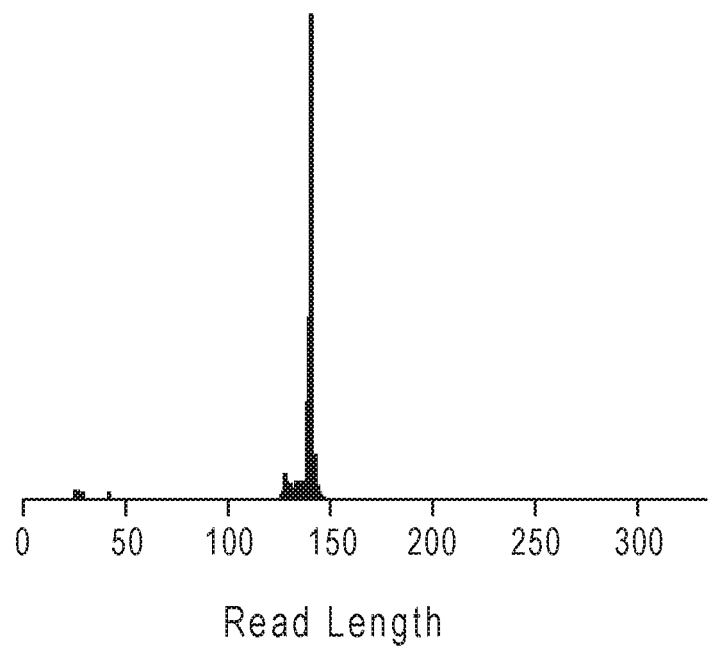
FIG. 4A-4C depicts results from the experimental description in Example 4.
Figure 4B:
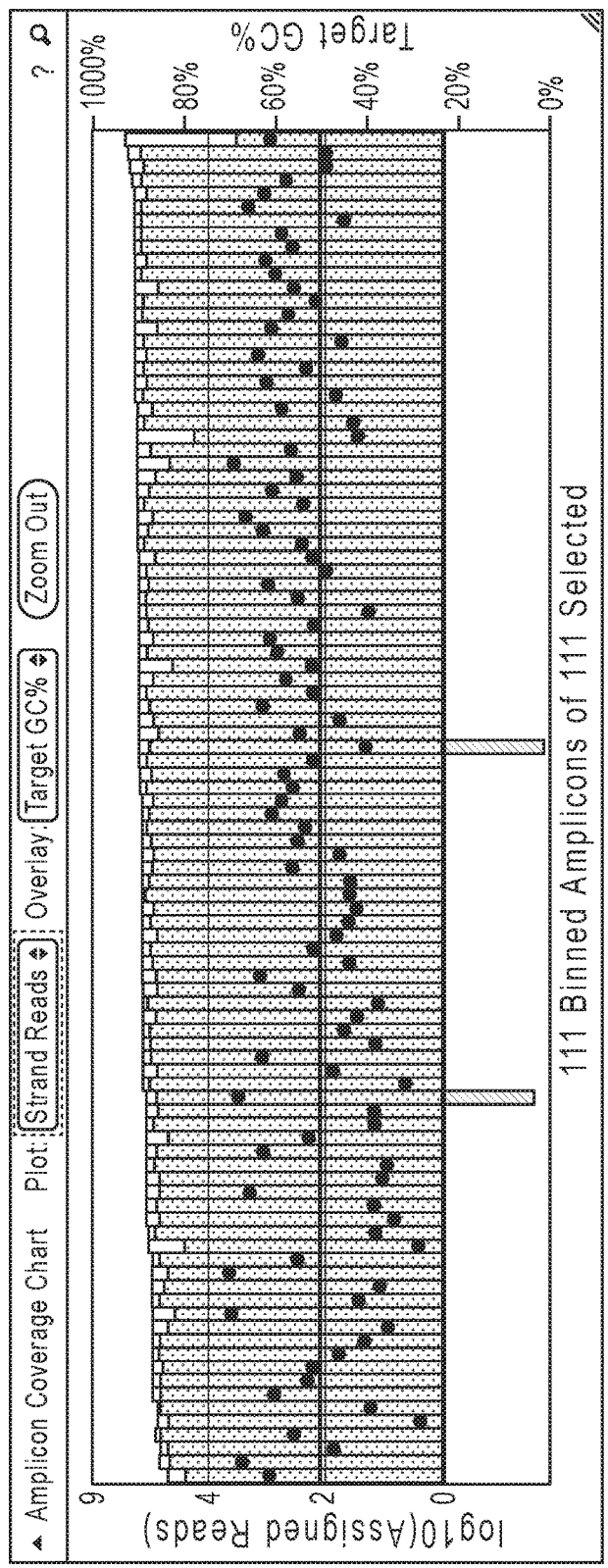
Figure 4C:
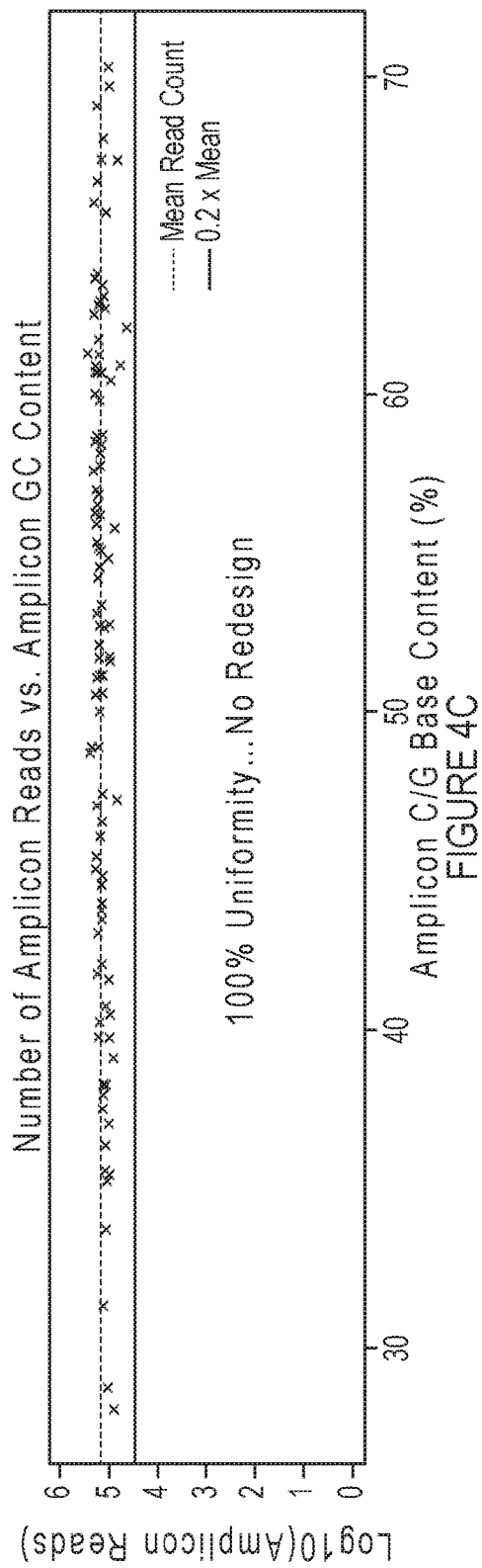

With target sequences specific to targets as in Table A, and adaptors each comprise 4096 unique tag sequences for each gene specific target sequence, resulting in an estimate of 16,777,216 different unique tag combinations for each gene specific target sequence pair. Library was prepared using 20 ng of genomic DNA and ~1% Acrometrix Oncomine™ Hotspot Control (AOHC) DNA (Thermo Fisher Scientific, Inc.), according to the protocol described above in Example 1C. Prepared library was sequenced using Ion 520/530 Templating/Sequencing kits and instrumentation (Thermo Fisher Scientific, Inc.). Performance with the panel (eg., yield, uniformity) indicates the technology is able to effectively make use of the designer pipeline. See FIG. 4A-4C.

Results using the AOHC DNA (shown in Table 1) demonstrate that, using this protocol, we effectively identify most of the True Positives (71 or 75) present in the AOHC and importantly did not generate any False positives.

TABLE 1

|  | Oncology Panel (Ex 4) | BRCA Panel (Ex 5) | Oncology HotSpot Panel (Ex 3) | Oncology HotSpot Bidirectional (ex 6) |
| --- | --- | --- | --- | --- |
| True Positives | 75 | NA | NA | NA |
| TP in SNP, INDEL | 71; 4 | NA | NA | NA |
| False Negatives | 3 | NA | NA | NA |
| False Positives | 0 | 0 | 0 | 0 |
| Uniformity | 98.60% | 100% | 100% | 100% |
| Low Quality | 15% | 28% | 31% | 26% |
| On Target | 98% | 95% | 96% | 95% |
| # of Families | 4398 | 5208 | 8755 | 6391 |

Example 5

Adaptors were designed according to the composition design approach provided herein, including universal handle-unique tag-gene specific target sequence described in Example 2 above, and targeted to genes using the BRCA Research Panel (Thermo FisherScientific, Inc.) target sequences and ION AMPLISEQ™ Designer (Thermo Fisher Scientific, Inc). Forward and reverse adaptors described above were utilized comprising

```
Forward Adaptor:
                                                        SEQ ID NO: 1
------A Handle-----  ------*UT*------  --Gene Specific--
TCTGTACGGTGACAAGGCG-U-NNNACTNNNTGA-U-GAGGACCGUCGCUGGT Rev Adaptor B
                                                        SEQ ID NO: 2
CTCTATGGGCAGTCGGTGAT-U-NNNACTNNNTGA-U-CCTTCTGCAUGGTATTCTTTCTCTUCC
-----B Handle-------  --------*UT*----  -------Gene Specific-------
```

Figure 5:
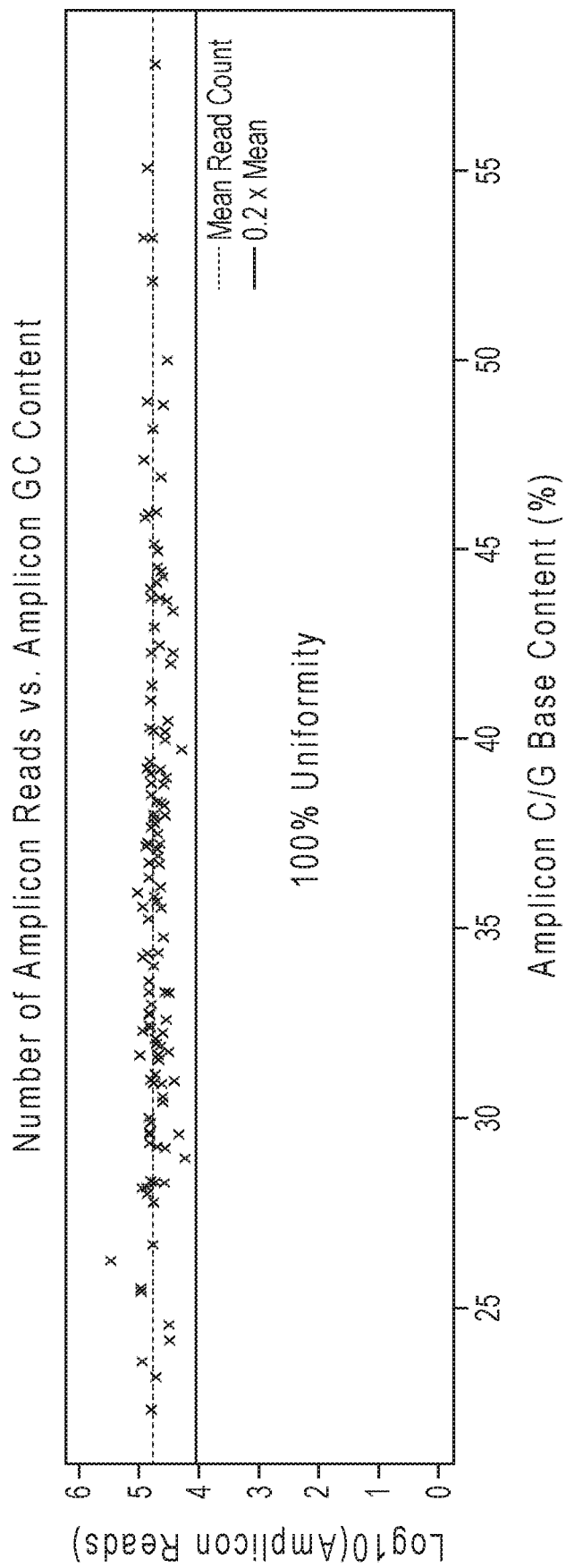
FIG. 5 depicts results from the experimental description in Example 5.

With target sequences specific to targets as in Table C, and adaptors each comprise 4096 unique tag sequences for each gene specific target sequence, resulting in an estimate of 16,777,216 different unique tag combinations for each gene specific target sequence pair. Library was prepared using 20 ng genomic DNA according to the protocol described above in Example 1C Prepared library was sequenced using Ion 520/530 Templating/Sequencing kits and instrumentation (Thermo Fisher Scientific, Inc.). Similar to Example 5, performance (e.g., yield, uniformity) with the panel indicates the technology is able to use the designer pipeline. See FIG. 5 and Table 1.

Example 6

Figure 6A:
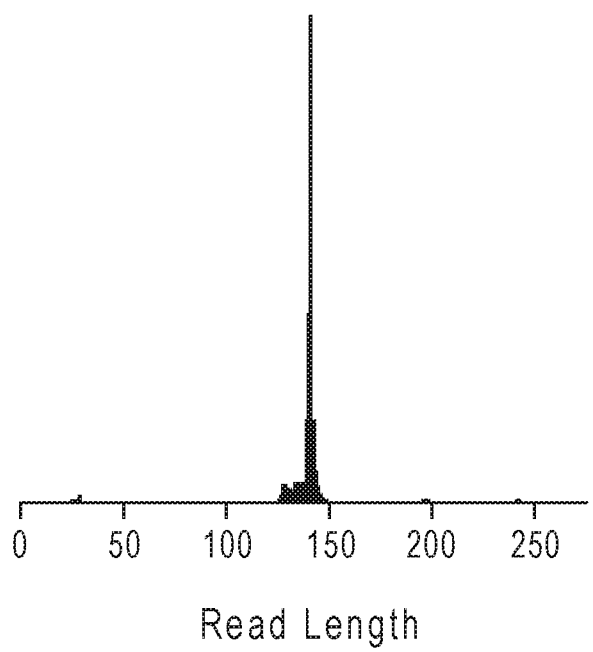
FIG. 6A-6C depicts results from the experimental description in Example 6.
Figure 6B:
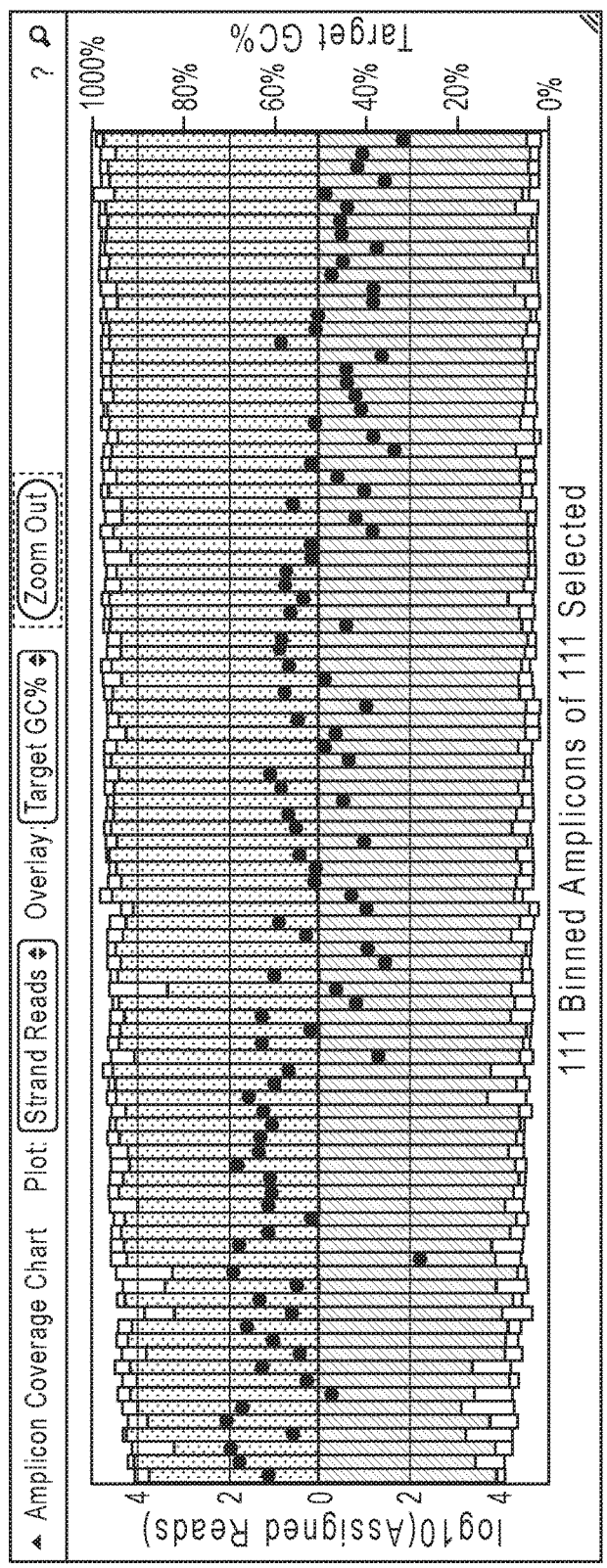
Figure 6C:
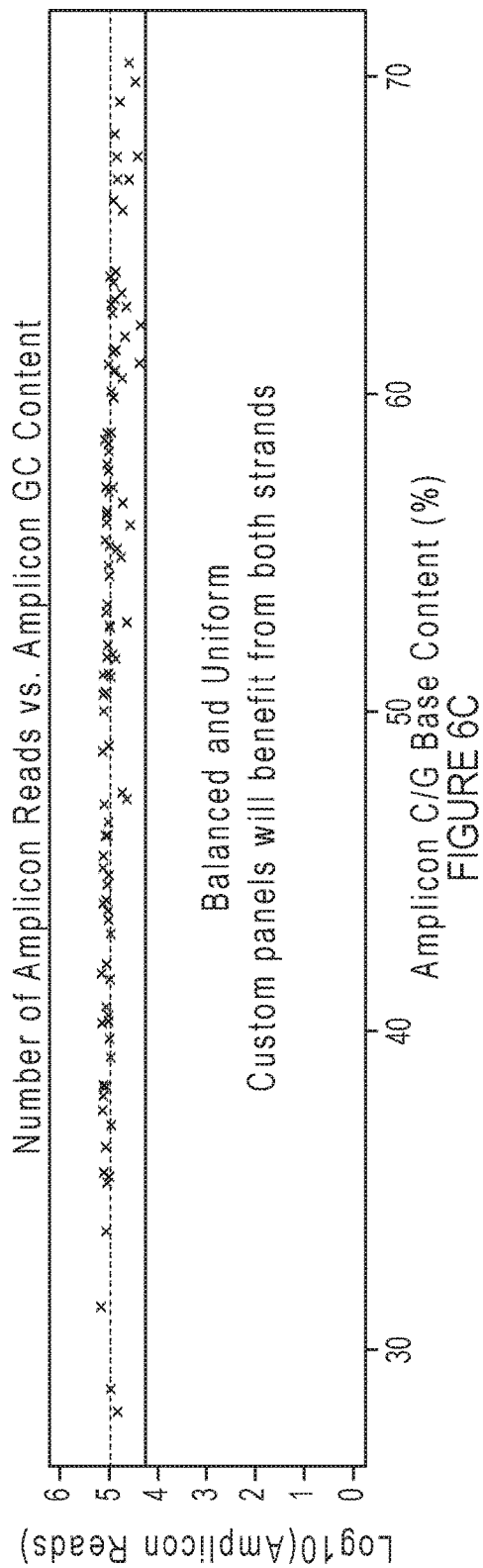

Primers were designed using the composition design approach provided herein and targeted to oncology genes using those of the panel target sequences as described above in Example 4, except that the library amplification step utilized two primer pairs (to put the two universal sequences on each end of amplicons, e.g., an A-universal handle and a P1-universal handle on each end) to enable bi-directional sequencing. Prepared library was sequenced using Ion 520/530 Templating/Sequencing kits and instrumentation (Thermo Fisher Scientific, Inc.). See FIG. 7. Performance (e.g., yield, uniformity) with the instant panel indicates the technology is able to use the designer pipeline and effectively generate sequencing data for both strands of DNA. See FIG. 6A-6C and Table 1.

Example 7

Primers were designed using the composition design approach provided herein and targeted to a wide variety of oncology target sequences. Forward and reverse adaptors described above were utilized comprising

```
Forward Adaptor:
                                                        SEQ ID NO: 1
------A Handle-----  ------*UT*------  --Gene Specific--
TCTGTACGGTGACAAGGCG-U-NNNACTNNNTGA-U-GAGGACCGUCGCUGGT Rev Adaptor C
                                                        SEQ ID NO: 3
TCTAGTCGGTCAGTCACGG-U-NNNACTNNNTGA-U-CCTTCTGCAUGGTATTCTTTCTCTUCC
-----C Handle-------  ------UT-------  -------Gene Specific-------
```

TABLE 2A

Family Generation, Coverage, and Uniformity

| | | AmpliSeq HD | | | | |
|---|---|---|---|---|---|---|
| Sample | Input | Median Read Counts per Target | Uniformity (U50) | Median # Families Size >= 3 | Molecular Conversion | Median # Families Size >= 3 |
| cfDNA 2016B | 20 ng | 61,939 | 95.9% | 5794 | 48% | 5794 |
| | | 63,679 | 95.9% | 5879 | 49% | 5879 |
| cfDNA 416G | 20 ng | 79,004 | 98.6% | 7676 | 64% | 7676 |
| | | 61,694 | 98.6% | 7322 | 61% | 7322 |
| 0.5% fMM | 6000 copies | 61,458 | 98.6% | 5466 | 46% | 5466 |
| | | 62,019 | 98.6% | 5685 | 47% | 5685 |
| 0.1% fMM | 6000 copies | 70,397 | 98.6% | 6278 | 52% | 6278 |
| | | 60,879 | 98.6% | 5946 | 50% | 5946 |
| gDNA | 292 copies | 22,650 | 97.3% | 340 | 57% | 340 |
| | | 79,746 | 98.6% | 354 | 59% | 354 |

TABLE 2B

Sensitivity, Specificity, and FPs/lib, Hot Spots Only

| | | AmpliSeq HD | | |
|---|---|---|---|---|
| Sample | Input | Sensitivity (%) | Specificity (%) | FP |
| cfDNA 2016B | 20 ng | | 100.00 | 0 |
| | | | 99.70 | 1 |
| cfDNA 416G | 20 ng | | 100.00 | 0 |
| | | | 100.00 | 0 |
| 0.5% allelic Frequency | 6000 copies | 100.0 100.0 | 100.00 100.00 | 0 0 |
| 0.1% allelic Frequency | 6000 copies | 85.14 94.60 | 100.00 100.00 | 0 0 |
| gDNA | 292 copies | | 100.00 100.00 | 0 0 |

With target sequences specific to targets as in Table D and adaptors each comprise 4096 unique tag sequences for each gene specific target sequence, resulting in an estimate of 16,777,216 different unique tag combinations for each gene specific target sequence pair. Samples containing 19.8 ng of cell free DNA and 0.2 ng of total RNA were processed as described in example 1D, starting with the optional reverse transcriptase step. Total RNA for some samples listed contained 5 spiked in fusion constructs. See Table D. Prepared library was sequenced using Ion 520/530 Templating/Sequencing kits and instrumentation (Thermo Fisher Scientific, Inc.). Performance (e.g., yield, uniformity, molecular conversion, sensitivity) with the instant panel indicates the technology can efficiently convert input DNA into library and detect mutations present at frequencies as low as 0.1% to 0.5%. See Table 2A-2B. Additionally, results confirm the technology can efficiently convert input DNA and cDNA into library and detect fusions present at frequencies of ~1%. See Table 3A-3B.

TABLE 3A

| Fusions | | |
|---|---|---|
| LRIG3-ROS1 | EZR-ROS1 | KLC1-ALK |
| CCDC6-RET | GOPC-ROS1 | SDC4-ROS1 |
| CD74-ROS1 | HIP1-ALK | SLC34A2-ROS1 |
| CUX1-RET | KIF5B-ALK | TPM3-ROS1 |
| EML4-ALK | KIF5B-RET | TPR-ALK |

TABLE 3B

Family Generation, Coverage, and Uniformity (No Activation)

| Sample | Input | FP | U50 | Conversion |
|---|---|---|---|---|
| cfDNA 5022 | 10 ng | 0 (343) 0 (323) | 98.5 | 44% |
| cfDNA 5022 + total RNA | 10 ng | 0 (343) 2 (323) | 99.25 | 51% |

TABLE 3B-continued

Family Generation, Coverage, and Uniformity (No Activation)

| Sample | Input | FP | U50 | Conversion |
|---|---|---|---|---|
| cfDNA 5022 + Trifusion | 10 ng | 0 (343) 1 (323) | 98.5 | 50% |
| gDNA | 10 ng | 0 (343) 2 (323) | 93.98 | 45% |
| gDNA + total RNA | 10 ng | 0 (343) 0 (323) | 93.98 | 54% |
| gDNA + Trifusion | 10 ng | 1 (343) 1 (323) | 95.49 | 53% |

Example 8

Primers were designed using the composition design approach provided herein and targeted to genes using those of short tandem repeats (STRs), which are useful for high resolution genotyping and analysis of complex mixtures. Forward and reverse adaptors described above were utilized comprising

```
Forward Adaptor:
                                                SEQ ID NO: 1
------A Handle-----  ------*UT*------  --Gene Specific--
TCTGTACGGTGACAAGGCG-U-NNNACTNNNTGA-U-GAGGACCGUCGCTUGGT Rev Adaptor E
                                                SEQ ID NO: 5
TGACAAGGCGTAGTCACGG-U-NNNACTNNNTGA-U-CCTTCTGCAUGGTATTCTTTCTCTUCC
-----E Handle-------  ------UT-------  -------Gene Specific-------
```

With target sequences specific to targets as in Table E and adaptors each comprise 4096 unique tag sequences for each gene specific target sequence, resulting in an estimate of 16,777,216 different unique tag combinations for each gene specific target sequence pair. Samples containing 1 to 10 ng of genomic DNA were processed as described in example 1D without the optional reverse transcriptase step. Prepared library was sequenced using Ion 520/530 Templating/Sequencing kits and instrumentation (Thermo Fisher Scientific, Inc.). Performance (e.g., yield, uniformity) with the instant panel indicates that even challenging STR targets (which are often shortened by 1 or more repeats during amplification) can be efficiently converted into a library. Results were consistent across titration levels of input DNA. See Table 4. When results were compared to standard operating procedure according to manufacturer instructions using Torrent Suite Molecular Diagnostics plugin to evaluate the same targets, results generated using compositions and methods provided herein yielded more consistent signal over each of the repeat regions, with less stutter (data not shown).

TABLE 4

| Barcode Name | Input DNA | Median Read Counts per Target | Median # Families Size >= 3 | Half-Double Uniformity (Families Size >= 3) | 80% Uniformity (Families Size >= 3) |
|---|---|---|---|---|---|
| BC_0102 | 1 ng | 37,727 | 257 | 77.78% | 63.89% |
| BC_0105 | 2 ng | 35,056 | 412 | 83.33% | 63.89% |
| BC_0108 | 5 ng | 32,478 | 1021 | 80.56% | 69.44% |
| BC_0120 | 10 ng | 30,915 | 1646 | 86.11% | 63.89% |

Example 9

Primers were designed using the composition design approach provided herein and targeted to oncology genes target sequences as described above in Example 6, where two primer pairs were utilized in library amplification (to put the two universal sequences on each end of amplicons, e.g., an A-universal handle and a P1-universal handle on each end) to enable bi-directional sequencing. Library preparation was carried out on samples containing spiked in AOHC control as described according to methods of Example 1E above without optional RT step. See FIG. 7. Prepared library was sequenced using Ion 520/530 Templating/Sequencing kits and instrumentation (Thermo Fisher Scientific, Inc.), then analyzed separately for unidirectional sequence results as well as results analyzed from bidirectional sequencing. Performance (e.g., yield, uniformity, sensitivity) with the instant panel indicates the technology is able to use the designer pipeline and effectively generate sequencing data for both strands of DNA, and bidirectional sequence analysis results in reduction of indel False Positives measured. See Table 5.

TABLE 5

|  | Bidirectional, Analyzed Unidirectional | Bidirectional, Analyzed Bidirectional |
|---|---|---|
| True Positives | 67 | 67 |
| Sensitivity | 91.8 | 91.8 |
| TP in SNP, INDEL | 65; 2 | 65; 2 |
| False Negatives | 6 | 6 |
| False Positives in SNP, INDEL | 1:2 | 1:0 |

TABLE 6

| Reverse Barcode | Reads Detected | % Total |
|---|---|---|
| bc1 | 332 | 0.001% |
| bc2 | 54 | 0.000% |
| bc3 | 261 | 0.001% |
| bc4 | 481 | 0.001% |
| bc5 | 9,908 | 0.019% |
| bc6 | 8,532 | 0.016% |
| bc7 | 2,656 | 0.005% |
| bc8 | 52,089,480 | 99.941% |
| bc9 | 1,403 | 0.003% |
| bc10 | 7,131 | 0.014% |

Example 10

For each of the Ion barcode adaptors, a single barcode is included in an A adapter. Addition of a second set of barcodes on the P1 adapter can effectively reduce the level of contamination artifacts in results by filtering out identified contamination reads. Primers were designed using the composition design approach provided herein and targeted to a wide variety of oncology target sequences. Samples containing 20 ng of genomic DNA were processed similarly to those described in Example 7 above and using the method of example 1D, however, additionally barcoded P1 adapters were also utilized, wherein a barcode 12mer sequence was inserted into the P1 adapter sequence of the reverse adaptor. Sample containing genomic DNA for library preparation was processed with barcode 8 in both A and P1 adapters. Additional samples were also processed with barcodes 1, 2, 3, 4, 5, 6, 7 and 9 (each in both P1 and A barcoded adapters), but without genomic DNA. Performance (e.g., yield, uniformity, Conversion) with the instant panel indicates that additional barcodes can effectively identify contamination. See Table 6.

Example 11

In another specific implementation, adaptors were prepared as described in example 2A for targets of the ONCOMINE™ Focus Assay, as in Table B, as well as described in example 6 with target sequences specific to targets as in Table D and adaptors each comprise 4096 unique tag sequences for each gene specific target sequence, resulting in an estimate of 16,777,216 different unique tag combinations for each gene specific target sequence pair. Forward and reverse adaptors utilized comprising

```
Forward Adaptor:
                                                  SEQ ID NO: 1
------A Handle------ ------*UT*---- ---Gene Specific--
TCTGTACGGTGACAAGGCG-U-NNNACTNNNTGA-U-GAGGACCGUCGCTUGGT Rev Adaptor I:
                                                  SEQ ID NO: 1705
TGACAAGGCGTAGTCACGG -U-NNNACTNNNTGA-U-CCTTCTGCAUGGTATTCTTTCTCTUCC
-----I Handle---------------*UT*---- -------Gene Specific-------
```

Figure 8:
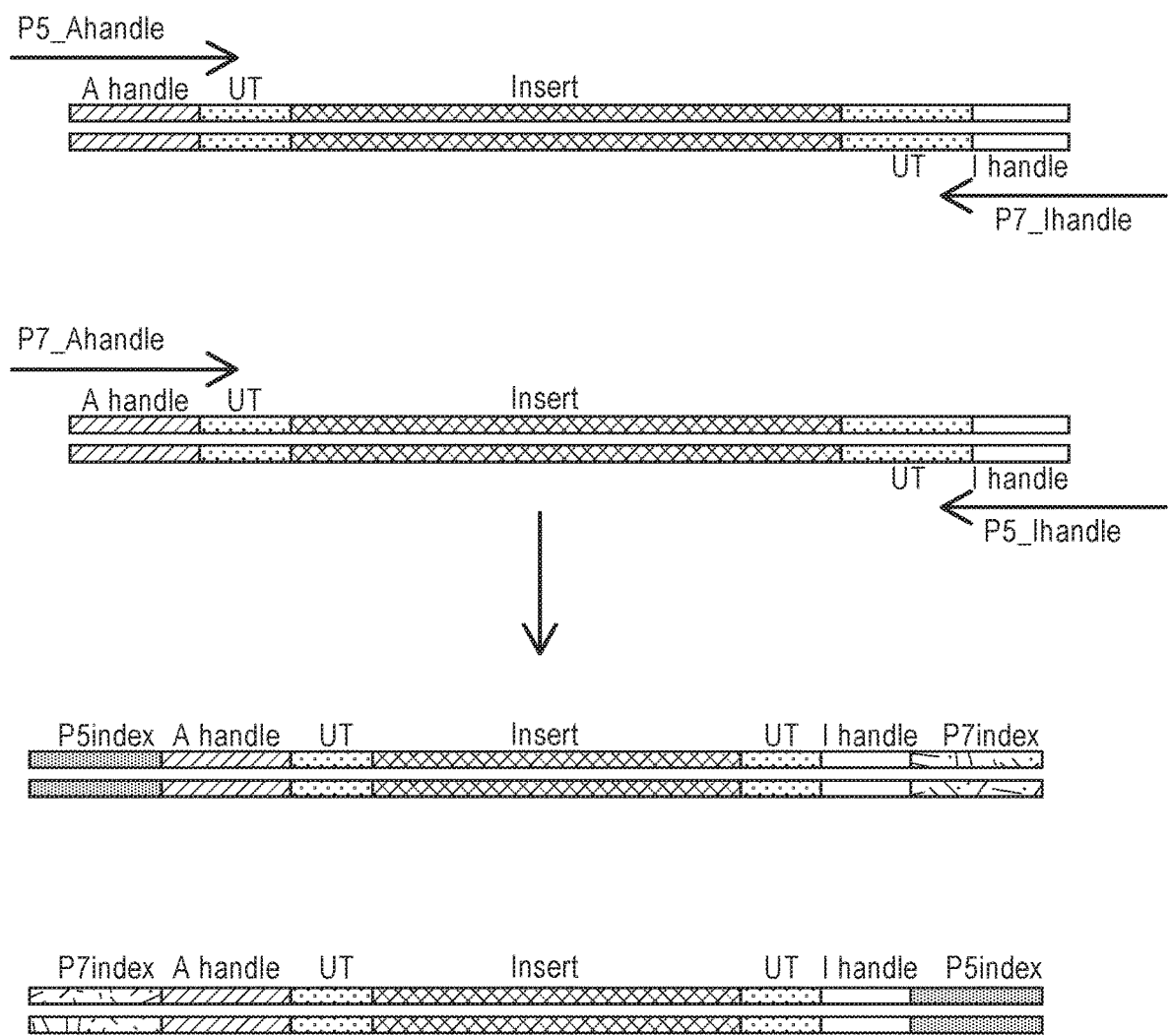
FIG. 8 depicts an additional aspect of the workflow of the invention that enables sequencing on Illumina platforms

Preparation of library was carried out according to the method described above for 1F. See also FIG. 8. The workflow has been adapted to use amplification primers to enable libraries to carry out sequencing runs on the Illumina platform. The design (shown schematically in FIG. 8) contains: (1) P5 grafting primer region; (2) P5 index (A-H) region; (3) P5 sequencing/index read primer region; (4) A-handle region; (5) UT region; (6) gene specific insert; (7) UT region; (8) I-handle region; (9) P7 sequencing/index read primer region; (10) P7 index (1-12) region; and (11) P7 grafting primer region. 3 libraries were made with an oncology panel comprising targets of Table D having idex5-01-idex7-5, idex5-02-index7-6 and idex5-7-idex7-7 respectively. 2 libraries were made with Focus panel comprising targets of Table B having idex5-01-idex7-5, and idex5-7-idex7-7 respectively. See Table F. All libraries are made with 19.6 ng of g24385 with 0.4 ng spike-in AOHC so we could detect 0.1% allele frequency.

TABLE F

| Name | Sequence (5' to 3') | SEQ ID |
|---|---|---|
| 5-01-Ah | AATGATACGGCGACCACCGAGATCTACAC AGCGCTAG TCGTCGGCAGCGTC AGATGTGTATAAGAGACAG TCTGTACGGTGACAAGGCGT | 1706 |
| 5-02-Ah | AATGATACGGCGACCACCGAGATCTACAC GATATCGA TCGTCGGCAGCGTC AGATGTGTATAAGAGACAG TCTGTACGGTGACAAGGCGT | 1707 |
| 5-07-Ah | AATGATACGGCGACCACCGAGATCTACAC ACATAGCG TCGTCGGCAGCGTC AGATGTGTATAAGAGACAG TCTGTACGGTGACAAGGCGT | 1708 |
| 5-08-Ah | AATGATACGGCGACCACCGAGATCTACAC GTGCGATA TCGTCGGCAGCGTC AGATGTGTATAAGAGACAG TCTGTACGGTGACAAGGCGT | 1709 |
| 5-09-Ah | AATGATACGGCGACCACCGAGATCTACAC CCAACAGA TCGTCGGCAGCGTC AGATGTGTATAAGAGACAG TCTGTACGGTGACAAGGCGT | 1710 |
| 5-010-Ah | AATGATACGGCGACCACCGAGATCTACAC TTGGTGAG TCGTCGGCAGCGTC AGATGTGTATAAGAGACAG TCTGTACGGTGACAAGGCGT | 1711 |
| 5-013-Ah | AATGATACGGCGACCACCGAGATCTACAC AACCGCGG TCGTCGGCAGCGTC AGATGTGTATAAGAGACAG TCTGTACGGTGACAAGGCGT | 1712 |
| 5-014-Ah | AATGATACGGCGACCACCGAGATCTACAC GGTTATAA TCGTCGGCAGCGTC AGATGTGTATAAGAGACAG TCTGTACGGTGACAAGGCGT | 1713 |
| 01-Ih | AATGATACGGCGACCACCGAGATCTACAC AGCGCTAG TCGTCGGCAGCGTC AGATGTGTATAAGAGACAG TGACAAGGCGTAGTCACGGT | 1714 |
| 02-Ih | AATGATACGGCGACCACCGAGATCTACAC GATATCGA TCGTCGGCAGCGTC AGATGTGTATAAGAGACAG TGACAAGGCGTAGTCACGGT | 1715 |
| 5-07-Ih | AATGATACGGCGACCACCGAGATCTACAC ACATAGCG TCGTCGGCAGCGTC AGATGTGTATAAGAGACAG TGACAAGGCGTAGTCACGGT | 1716 |
| 5-08-Ih | AATGATACGGCGACCACCGAGATCTACAC GTGCGATA TCGTCGGCAGCGTC AGATGTGTATAAGAGACAG TGACAAGGCGTAGTCACGGT | 1717 |
| 5-09-Ih | AATGATACGGCGACCACCGAGATCTACAC CCAACAGA TCGTCGGCAGCGTC AGATGTGTATAAGAGACAG TGACAAGGCGTAGTCACGGT | 1718 |
| 5-010-Ih | AATGATACGGCGACCACCGAGATCTACAC TTGGTGAG TCGTCGGCAGCGTC AGATGTGTATAAGAGACAG TGACAAGGCGTAGTCACGGT | 1719 |
| 5-013-Ih | AATGATACGGCGACCACCGAGATCTACAC AACCGCGG TCGTCGGCAGCGTC AGATGTGTATAAGAGACAG TGACAAGGCGTAGTCACGGT | 1720 |
| 5-014-Ih | AATGATACGGCGACCACCGAGATCTACAC GGTTATAA TCGTCGGCAGCGTC AGATGTGTATAAGAGACAG TGACAAGGCGTAGTCACGGT | 1721 |
| 7-1-Ah | CAAGCAGAAGACGGCATACGAGAT ATATTCAC GTCTCGTGGGCTCGG AGATGTGTATAAGAGACAG TCTGTACGGTGACAAGGCGT | 1722 |
| 7-2-Ah | CAAGCAGAAGACGGCATACGAGAT GCGCCTGT GTCTCGTGGGCTCGG AGATGTGTATAAGAGACAG TCTGTACGGTGACAAGGCGT | 1723 |
| 7-3-Ah | CAAGCAGAAGACGGCATACGAGAT ACTCTATG GTCTCGTGGGCTCGG AGATGTGTATAAGAGACAG TCTGTACGGTGACAAGGCGT | 1724 |
| 7-4-Ah | CAAGCAGAAGACGGCATACGAGAT GTCTCGCA GTCTCGTGGGCTCGG AGATGTGTATAAGAGACAG TCTGTACGGTGACAAGGCGT | 1725 |
| 7-5-Ah | CAAGCAGAAGACGGCATACGAGAT AGTAGAGA GTCTCGTGGGCTCGG AGATGTGTATAAGAGACAG TCTGTACGGTGACAAGGCGT | 1726 |
| 7-6-Ah | CAAGCAGAAGACGGCATACGAGAT GACGAGAG GTCTCGTGGGCTCGG AGATGTGTATAAGAGACAG TCTGTACGGTGACAAGGCGT | 1727 |
| 7-7-Ah | CAAGCAGAAGACGGCATACGAGAT AGACTTGG GTCTCGTGGGCTCGG AGATGTGTATAAGAGACAG TCTGTACGGTGACAAGGCGT | 1728 |
| 7-8-Ah | CAAGCAGAAGACGGCATACGAGAT GAGTCCAA GTCTCGTGGGCTCGG AGATGTGTATAAGAGACAG TCTGTACGGTGACAAGGCGT | 1729 |
| 7-9-Ah | CAAGCAGAAGACGGCATACGAGAT AATTCTGC GTCTCGTGGGCTCGG AGATGTGTATAAGAGACAG TCTGTACGGTGACAAGGCGT | 1730 |
| 7-10-Ah | CAAGCAGAAGACGGCATACGAGAT GGCCTCAT GTCTCGTGGGCTCGG AGATGTGTATAAGAGACAG TCTGTACGGTGACAAGGCGT | 1731 |

TABLE F-continued

| Name | Sequence (5' to 3') | SEQ ID |
|---|---|---|
| 7-1-Ah | CAAGCAGAAGACGGCATACGAGAT ATCTTAGT GTCTCGTGGGCTCGG AGATGTGTATAAGAGACAG TCTGTACGGTGACAAGGCGT | 1732 |
| 7-12-Ah | CAAGCAGAAGACGGCATACGAGAT GCTCCGAC GTCTCGTGGGCTCGG AGATGTGTATAAGAGACAG TCTGTACGGTGACAAGGCGT | 1733 |
| 7-1-Ih | CAAGCAGAAGACGGCATACGAGAT ATATTCAC GTCTCGTGGGCTCGG AGATGTGTATAAGAGACAG TGACAAGGCGTAGTCACGGT | 1734 |
| 7-2-Ih | CAAGCAGAAGACGGCATACGAGAT GCGCCTGT GTCTCGTGGGCTCGG AGATGTGTATAAGAGACAG TGACAAGGCGTAGTCACGGT | 1735 |
| 7-3-Ih | CAAGCAGAAGACGGCATACGAGAT ACTCTATG GTCTCGTGGGCTCGG AGATGTGTATAAGAGACAG TGACAAGGCGTAGTCACGGT | 1736 |
| 7-4-Ih | CAAGCAGAAGACGGCATACGAGAT GTCTCGCA GTCTCGTGGGCTCGG AGATGTGTATAAGAGACAG TGACAAGGCGTAGTCACGGT | 1737 |
| 7-5-Ih | CAAGCAGAAGACGGCATACGAGAT AGTAGAGA GTCTCGTGGGCTCGG AGATGTGTATAAGAGACAG TGACAAGGCGTAGTCACGGT | 1738 |
| 7-6-Ih | CAAGCAGAAGACGGCATACGAGAT GACGAGAG GTCTCGTGGGCTCGG AGATGTGTATAAGAGACAG TGACAAGGCGTAGTCACGGT | 1739 |
| 7-7-Ih | CAAGCAGAAGACGGCATACGAGAT AGACTTGG GTCTCGTGGGCTCGG AGATGTGTATAAGAGACAG TGACAAGGCGTAGTCACGGT | 1740 |
| 7-8-Ih | CAAGCAGAAGACGGCATACGAGAT GAGTCCAA GTCTCGTGGGCTCGG AGATGTGTATAAGAGACAG TGACAAGGCGTAGTCACGGT | 1741 |
| 7-9-Ih | CAAGCAGAAGACGGCATACGAGAT AATTCTGC GTCTCGTGGGCTCGG AGATGTGTATAAGAGACAG TGACAAGGCGTAGTCACGGT | 1742 |
| 7-10-Ih | CAAGCAGAAGACGGCATACGAGAT GGCCTCAT GTCTCGTGGGCTCGG AGATGTGTATAAGAGACAG TGACAAGGCGTAGTCACGGT | 1743 |
| 7-11-Ih | CAAGCAGAAGACGGCATACGAGAT ATCTTAGT GTCTCGTGGGCTCGG AGATGTGTATAAGAGACAG TGACAAGGCGTAGTCACGGT | 1744 |
| 7-12-Ih | CAAGCAGAAGACGGCATACGAGAT GCTCCGAC GTCTCGTGGGCTCGG AGATGTGTATAAGAGACAG TGACAAGGCGTAGTCACGGT | 1745 |

To mimic low level of mutant variants (0.1%) presence in DNA samples, we used purified genomic DNA and spiked in small quantity of AcroMetrix Oncology Hotpot Control plasmid. These samples are used as our control samples for the purpose of demonstrating the library preparation method and assessing the sensitivity and specificity for low levels mutant variants detection by this assay method. Bioanalyzer results matched library structure designs, and yield and purity of libraries were on par with those prepared on other methods described above. Similar successful sequencing results were generated with each of the adaptor pairings.

A MiSeq sequencing run successfully generated clusters, and produced sequencing and indexing reads. Sequencing results of the panel run on the Illumina MiSeq indicate similar performance as compared to the standard AmpliSeq HD version run on the Ion S5 using a 540 chip. See Table 7.

TABLE 7

|  | MiSeq | S5 540 |
|---|---|---|
| Raw Read Accuracy (%) | 99.31 | 99.27 |
| Mapped Reads | 12,994,280 | 17,855,575 |

TABLE 7-continued

|  | MiSeq | S5 540 |
|---|---|---|
| Mean Depth | 46,674 | 62,429 |
| On-Target (%) | 98.91 | 98.64 |
| coverageAnalysis Uniformity (%) | 97.86 | 97.98 |
| Half-Double Uniformity (%) | 86.62 | 83.64 |
| 0.1% MegaMix TP | 140 | 138 |
| 0.1% MegaMix FN | 11 | 13 |
| 0.1% MegaMix FP | 58 | 38 |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

TABLE A

| Primer Name | SEQ ID | Primer Sequence (target of primer A) | Primer Name | SEQ ID | Primer Sequence (target seq of primer B) |
|---|---|---|---|---|---|
| F1 | 8 | GCTCCCAGGCACUTGATGAUAC | R1 | 104 | ACAGAAUCACAUGCCACACAGT |
| F2 | 9 | TGTTGCCATTCAGGGTTTCUGA | R2 | 105 | TTCCTTCUAAAAGGCCATGAAGATCUG |
| F3 | 10 | ACCAAUGCGAGGAAGAAAAACAAUC | R3 | 106 | TCTGAAGAACAUGTGUGAGCACA |
| F4 | 11 | TCTTCAGAAUCTTGTTGGCUGCAT | R4 | 107 | CCCAACCCACAUTTCCTTTATAGATGTUT |
| F5 | 12 | AGAGTTGCAUCCTTCCCTTCUCT | R5 | 108 | TGTTCCAACAGGAUCTGUCCAAAA |
| F6 | 13 | CTGGCAUGACGCAGTTTCTUC | R6 | 109 | CCAGTGTCTGUCCTTGCCTTUC |
| F7 | 14 | GATCAAAGAGACGAAGUCTCTUGCA | R7 | 110 | CUATGACAAGAAAAUGGACACCAACAAG |
| F8 | 15 | CTTGCCUAGACAGCACCGUAAT | R8 | 111 | AGGAGGAUAAAGACCTGGUCCAT |
| F9 | 16 | TGGTTTCTGGUGGGACCATTAUG | R9 | 112 | GTCCTCUGGATCTCTTCAUGCA |
| F10 | 17 | TTGAAAGAGAACACACUTACTCUCCAC | R10 | 113 | CTGAGACATTCCUATGTCCTGCUC |
| F11 | 18 | CTCTACCAGAGUTAATCAACTGAUGCA | R11 | 114 | TUGAUACAAAACAAGCCCACGAACT |
| F12 | 19 | TATCAACTGTCCUTGTTGGCAAAUCA | R12 | 115 | CCAGCCTAATCTUGTTTTTCTTATGTTCUG |
| F13 | 20 | GCAAATGACTUGCTATTATTGAUGGCA | R13 | 116 | GTTATAGATGGUGAAACCTGTTTGTUGG |
| F14 | 21 | GTGGGATCATAUTCATCTACAAAGUGGT | R14 | 117 | GATTACTGGTTUCCAACAGGTTCTUG |
| F15 | 22 | GGAGGTCAUGGCATCGAGUT | R15 | 118 | TATGGTCTGGACATCCAGGAUCT |
| F16 | 23 | GTGAGGCAGUCTTTACUCACCT | R16 | 119 | TAGGAAATGCAUTTCCTTTCTUCCCA |
| F17 | 24 | GGGAAATGUGAGCCCUGAGAT | R17 | 120 | CCTGTGGCUGTCAGTATTUGGA |
| F18 | 25 | ACTCTTGCUCCTTCCATCCTUG | R18 | 121 | GTTCATCCUGCTGGAGCUCAT |
| F19 | 26 | CCCAAUGCAGCGAACAATGTUC | R19 | 122 | GTAGCTGCTGAAAAUGTAACTTTGTAUCC |
| F20 | 27 | GATCAGGGCUTCCAUGAGGAAA | R20 | 123 | ACTCTGTAGGCUGCAGTTCUCA |
| F21 | 28 | CTCAAGAGUGAGCCACTTCTUACC | R21 | 124 | CTCCTCTTGUCTTCTCCTTUGCA |
| F22 | 29 | AGAATAAAACACAUACAAGTTGGAAATTTCUGG | R22 | 125 | CTTGTGAGTGGAUGGGTAAAACCUAT |
| F23 | 30 | ACCUGAGCCAAGGACTTTUACC | R23 | 126 | CGGACTGAAAGUATAACCTTCTTCTTUCC |
| F24 | 31 | TGTCAATTAGCUGGAACATCUGAAACT | R24 | 127 | GCATGTGAACAUTCTGCTTTTCAUGG |
| F25 | 32 | GTGCCCTATUACCTCAATCAUCCT | R25 | 128 | ACGCCTTCACCUTTAACACCUC |
| F26 | 33 | CCAGACAGAAAAGCGGCUGTUA | R26 | 129 | ACTTGGGAGGUATCCACAUCCT |
| F27 | 34 | CCTAGTAGAATGTTUACTACCAAATGGAAUGA | R27 | 130 | AGATTCATCTUGAAGAAGTTGAUGGAGG |
| F28 | 35 | TTTTTGAUGAAACAAGACGACTTTGUG | R28 | 131 | GAATAGGATATTGUATCATACCAATTTCUCGAT |
| F29 | 36 | CACAGCUACACCATATATGAAUGGAGA | R29 | 132 | CAGCATTTGACTUACCTTATCAATGTCUC |
| F30 | 37 | GATCTATGTUCGAACAGGTATCUACCATG | R30 | 133 | ACTGCTAAACACTAAUATAACCTTTGGAAAUAT |
| F31 | 38 | GGGAAGAAAAGUGTTTTGAAATGTGTUT | R31 | 134 | CATTTTTCCAGATACUAGAGTGTCTGTGUA |
| F32 | 39 | TTTGAATCTTUGGCCAGTACCUCA | R32 | 135 | CATAAGAGAGAAGGUUTGACTGCCAUAAA |
| F33 | 40 | GACTAGCUAGAGACAATGAAUAAGGGAAAA | R33 | 136 | GAATCTCCATTTUAGCACTTACCTGUGA |
| F34 | 41 | CTGAGATGCACAAUAAAACAGTUAGCC | R34 | 137 | AGAATGTCAGTUAAGTTAATGAGCTTUCCAT |
| F35 | 42 | GACAUTCUCAAACAGGAGAAGAAGGA | R35 | 138 | GCTTGATCCAAGGACCATGATCUG |
| F36 | 43 | TCTTTTCTCAAGUTGGCCTGAAUCA | R36 | 139 | CAATTCCCAAAAUGAAGGTAGCUACAC |
| F37 | 44 | CAATCTTTTGAUGACATTGCATACAUCGA | R37 | 140 | GGAAGATCCAAUCCATTTTTGTUGCC |
| F38 | 45 | GTATGCAGGCAUCCCTCAGCUA | R38 | 141 | CGGGAAGCGGGAGAUCTUG |
| F39 | 46 | CUGGUGACCGAGGACAACGT | R39 | 142 | GGCGTCCUACTGGCAUGA |

TABLE A-continued

| Primer Name | SEQ ID | Primer Sequence (target of primer A) | Primer Name | SEQ ID | Primer Sequence (target seq of primer B) |
|---|---|---|---|---|---|
| F40 | 47 | GTCCUGGGAGTCUCAGGACA | R40 | 143 | CCTUCAGCAGCTUGAAGAGCT |
| F41 | 48 | CCAGTTACCUGTCCTGGTCAUT | R41 | 144 | GGAAACTCCCAUCTTGAGTCAUAAGG |
| F42 | 49 | AGTGAAAAACAAGCUCTCATGTCUGA | R42 | 145 | CATGTGTCCAGUGAAAATCCUCACT |
| F43 | 50 | GGAAAAATTGUGAAGATCTGTGACTTUGG | R43 | 146 | CTGACTUTAGAGATTAAAGUGAAGGAGGAT |
| F44 | 51 | AGCACTCTGACAUATGGCCATUT | R44 | 147 | CCTGGACAAAAAUACCAATCTATTGUGG |
| F45 | 52 | GGCACGGTUGAATGTAAGGCTUA | R45 | 148 | ACTGATATGGUAGACAGAGCCUAAACAT |
| F46 | 53 | CCCACAGAAACCCAUGTAUGAAGT | R46 | 149 | ACTGACCAAAACUCAGCCTGUT |
| F47 | 54 | TUGACAGAACGGGAAGCCCUCAT | R47 | 150 | CCTGACAGACAAUAAAAGGCAGCUT |
| F48 | 55 | CCTTACTCAUGGTCGGAUCACAA | R48 | 151 | GTTGAAACUAAAAATCCTTGCAGGACT |
| F49 | 56 | CCAATATTATGGAUCCCAACTGCCUA | R49 | 152 | ACATTCTGAAGCAGCUGGAGTUT |
| F50 | 57 | GCTACTTTGAUTTCTCCACTUCCAAC | R50 | 153 | GAGGAGATTGAAAAUCTTCCTGCCUT |
| F51 | 58 | AAAGGCAUGGAGCATCTGUACA | R51 | 154 | TTGGTCCGUCTCCUCCACGG |
| F52 | 59 | GTTATGTCCUCATTGCCCUCAACA | R52 | 155 | CTTCAGTCCGGUTTTATTTGCATCAUAG |
| F53 | 60 | CGAGGGCAAAUACAGCTTUGGT | R53 | 156 | GACTCTCCAAGAUGGGATACUCCA |
| F54 | 61 | TGATGGAGAUGTGATAATTUCAGGAAACA | R54 | 157 | CGGTGACTUACTGCAGCTGTUT |
| F55 | 62 | GAGACATGCAUGAACATTTTTCUCCA | R55 | 158 | TCCAGACCAGGGUGTTGTTTUC |
| F56 | 63 | GCCTCTUACACCCAGUGGAGAA | R56 | 159 | TGTGCCAGGGACCUTACCTTAUA |
| F57 | 64 | CCTTCTCUCTCTGTCAUAGGGACT | R57 | 160 | CACAGCAAAGCAGAAACUCACAUC |
| F58 | 65 | CTCCAGGAAGCCUACGTGAUG | R58 | 161 | TGTGTUCCCGGACATAGUCCA |
| F59 | 66 | CAGGAACGUACTGGUGAAAACAC | R59 | 162 | GAAAATGCUGGCTGACCUAAAGC |
| F60 | 67 | GCTTGTAAGUGCCCGAAGTGUA | R60 | 163 | CACAACCCACUGAGGTATATGTATAGGUAT |
| F61 | 68 | CGCAGTGCUAACCAAGTTCTTUC | R61 | 164 | CCATGGTTAAATAAAAUGCCACTTACTGUT |
| F62 | 69 | CAGTCAAGGUTGCTGATTTUGGT | R62 | 165 | CTTGGTGGUAAACTTTTGAGTTUGCA |
| F63 | 70 | CGAATCGCUACCCTGCTGUT | R63 | 166 | CCAAGCCUCATGGTGCCAT |
| F64 | 71 | TACCGAUACCGUGCGGG | R64 | 167 | TACUGGCAGCAAGUGCCCAG |
| F65 | 72 | CTGTCCUCCACAGGCATTTTUG | R65 | 168 | CCCTCACUCACAGCACATAGUC |
| F66 | 73 | CCATCCCUGACTGTGAGAUCAA | R66 | 169 | CCAGGUACGCCTCCAGAUGA |
| F67 | 74 | TCAGTGGAAAAAUAGCCTCAATTCTUACC | R67 | 170 | CTTCATGAAGACCUCACAGTAAAAAUAGGT |
| F68 | 75 | TATTATGACTUGTCACAATGUCACCACAT | R68 | 171 | GACTCGAGTGAUGATTGGGAGAUC |
| F69 | 76 | TTCCUTAGTCTTTCTTGAAGCAGCA | R69 | 172 | AGATGCTCUGAGAAAGGCAUAGAAAG |
| F70 | 77 | TCTGACUCCACGAGAACTTGAUCATA | R70 | 173 | TATTGTTAACCUTGCAGAATGGUCGA |
| F71 | 78 | CAAGGCAUAAAAGCTGGGAAAUAGG | R71 | 174 | CUACCTGCCUACGCAACAAGAT |
| F72 | 79 | GGCTAUGGCACCUGCAACT | R72 | 175 | GGGACCUCAGATGTGCTGTUG |
| F73 | 80 | CCACAGAUCCACTGUGCGAC | R73 | 176 | GTGGCTTGUGGGCAAACTUG |
| F74 | 81 | CCATCCTGACCUGGTATGGUCA | R74 | 177 | CCTGCTUCAGGACGTTGAACUC |
| F75 | 82 | CAGCTCGUCATCGGGACUT | R75 | 178 | ACCTGGCUCCTCTTCACGUA |
| F76 | 83 | CCTCCTTCCUAGAGAGTTAGAGUAACT | R76 | 179 | CACCCACACUACACATCACTTUG |
| F77 | 84 | CACTGTGTTACUGCCATCGACTUA | R77 | 180 | TCGAGATTUAGCAGCCAGAAATGTUT |

TABLE A-continued

| Primer Name | SEQ ID | Primer Sequence (target of primer A) | Primer Name | SEQ ID | Primer Sequence (target seq of primer B) |
|---|---|---|---|---|---|
| F78 | 85 | GATTCAATCAAACUGCAGAGTATTUGGG | R78 | 181 | TGATCTGGUGTCAGAGAUGGAGAT |
| F79 | 86 | GGCTTCTTGGUCGTGTTCTUCA | R79 | 182 | CUAGCGCCUGGAAGAGAAAAGGAGAT |
| F80 | 87 | CCCAGCGUCCTCAAAAGTUACA | R80 | 183 | CCCTCCACAAUCATTCCTGUGT |
| F81 | 88 | CTCTACGUCTCCUCCGACCA | R81 | 184 | CTTATTTATTGGTCUCTCATTCTCCCAUCC |
| F82 | 89 | CCTGTACTGGUGGATGTCCUCA | R82 | 185 | GCCTGTUGGACATCCTGGAUAC |
| F83 | 90 | CGCCAGGCUCACCTCTAUAG | R83 | 186 | AGGAGCGAUGACGGAATAUAAGC |
| F84 | 91 | TGTCTTTGCUGATGTTTCAAUAAAAGGAA | R84 | 187 | AGTTAAGGACTCUGAAGATGTACCTAUGG |
| F85 | 92 | CATGTACTGGUCCCTCATUGCA | R85 | 188 | GTAATAATCCAGACUGTGTTTCTCCCUT |
| F86 | 93 | TACCTCTATTGTUGGATCATATTCGUCCA | R86 | 189 | TATTATAAGGCCUGCTGAAAATGACUGAAT |
| F87 | 94 | CAGACACTGUACAAGCTCUACGA | R87 | 190 | GAAUAAAGAGGAGCAGGTUGAGGAA |
| F88 | 95 | CTCTGUCACAGTGGATCGAGA | R88 | 191 | CAACATGACGAAGAUGGCAAACTUC |
| F89 | 96 | TCCUTCCATAGUGACCAAGACCA | R89 | 192 | GGGTACAUACAAAGCAGTCTGUGT |
| F90 | 97 | GGTTCCATGGUAGCTGGUGAT | R90 | 193 | GCCCATTTTTATCUACTTCCATCTTGUCA |
| F91 | 98 | TGTAAAGAGACAGCCUTTCCTCUGA | R91 | 194 | AGTTCACAAAUCCATCAATGTTGCUC |
| F92 | 99 | ACACUCTUGAGGGCCACAAAG | R92 | 195 | TGTGATTGUAGGGTCTCCCTUGAT |
| F93 | 100 | CCGCTCCUTGTAGCCAAUGA | R93 | 196 | GGGTCUGACGGGTAGAGUGT |
| F94 | 101 | CCACUTUGGAACAGGACCAAC | R94 | 197 | TCAAAGTCGTCAUCCTTCAGTTCUC |
| F95 | 102 | CTTTCTTCCACCUTTCTCCAGCUA | R95 | 198 | CATCGCTGUAGAACGCACCAUA |
| F96 | 103 | TCAAGCCCUCCAACATCCUAGT | R96 | 199 | GGAAACTTCTGTUCATACCGACATGUAG |

TABLE B

| Primer Name | SEQ ID | Primer Sequence (target seq of Primer A) | Primer Name | SEQ ID | Primer Sequence (target seq of Primer B/C/D/E) |
|---|---|---|---|---|---|
| F97 | 200 | GAGGTCGTATCGTCCACAAAAUGGT | R97 | 469 | GAGGCAGGAGACCCUGUAGGAG |
| F98 | 201 | GAAACTGCTTAGUAACTAGCAGAAGTGTUC | R98 | 470 | GAGGATAUATGCCAUACCCCAGCAAA |
| F99 | 202 | GACAAAGTTGUGTGTTGTAAGUGGAACA | R99 | 471 | GACCAAGAAAGGCUTGTGTCTACATTTUT |
| F100 | 203 | GAGCACCAATCUTTCTTCTGCCTTTUG | R100 | 472 | GACCAAAUCAAGAAACCTGTTUGAGAGAA |
| F101 | 204 | GAGGGAUCCCAAGGAAGAGAAGUGA | R101 | 473 | GACACTTCCCUGTGGGAATGUCAA |
| F102 | 205 | GAGCTACTCTCCUGAACTCTCTCACUC | R102 | 474 | GATGCATCAGAACCCUCCTTGAAUC |
| F103 | 206 | GACTCCCAGUGCAACGTUAGGT | R103 | 475 | GAGGUCCACGGAUCCAGAAACAAG |
| F104 | 207 | GATCACGUGTCCCCCTUCCA | R104 | 476 | GAGGTTCCTCCUCTCCTGGUCUC |
| F105 | 208 | GAACATTTGGCUGTGACTTCUAAGAAGAAA | R105 | 477 | GAGCTCACTAACUAACGTGAAAGCCUAC |
| F106 | 209 | GAGATGAUCCAGATGTUAGGGCAGT | R106 | 478 | GAGGTTTTGCACAAGUTAGGTTTGTTUG |
| F107 | 210 | GAGCCCAAATUGATTTCGATGATCUCA | R107 | 479 | GAACCTTTATATCGTUACTCTGAATCTTATCTCC |
| F108 | 211 | GAGCTCAAGAGUGAGCCACTUCT | R108 | 480 | GATGACTCTGTCUCCTCTTGTCTTCUC |
| F109 | 212 | GAATTAACACACAUCAGTGGAACTUCGT | R109 | 481 | GAAAACGTTTTUCACCTTAGCATTTUGT |
| F110 | 213 | GAGCAAUCCAAAAGAAUAGCAGCCAAA | R110 | 482 | GACACCATCUCCCATATCATUGAGACCAAAT |
| F111 | 214 | GACTTTGTGGAAUAGCCCATGAAGAGUA | R111 | 483 | GACGACAGACUACTTTGGTTCTCTTTUGT |
| F112 | 215 | GAACAGGAAGAGCACAGUCACTTUG | R112 | 484 | GACTCACUGACAAGCTCCUCGT |

TABLE B-continued

| Primer Name | SEQ ID | Primer Sequence (target seq of Primer A) | Primer Name | SEQ ID | Primer Sequence (target seq of Primer B/C/D/E) |
|---|---|---|---|---|---|
| F113 | 216 | GACCATGCAGAGUGAAAGGATAUCCC | R113 | 485 | GAGCCTTTTCTTUTGCTTCCCTTGUT |
| F114 | 217 | GATGGAGCCGCUGACACCUA | R114 | 486 | GACAGGACCUGGCCCUGAC |
| F115 | 218 | GAGGTGUCTAGCCCAUGGGAGAA | R115 | 487 | GACCCAUCACACACCAUAACUCCAC |
| F116 | 219 | GAGTCTGGUCCACATTGCTCUCA | R116 | 488 | GAGCTGUCCCCTCACCATUCAG |
| F117 | 220 | GAGCAAGAGUACACACTCCTCATTUGG | R117 | 489 | GATCACAACCCACUGAGGTATATGTAUAGG |
| F118 | 221 | GACTGGTTTCUGGTGGGACCATUA | R118 | 490 | GACAUGCACCGGAAAAGCGAUG |
| F119 | 222 | GACTCCCAGGCACUTGATGATACUC | R119 | 491 | GACATTTCTAGGUTACAGGCCUGGAT |
| F120 | 223 | GAGGGCTUGGTAACGTCCUGT | R120 | 492 | GACTCCAUGCCCCTCACUCA |
| F121 | 224 | GATGTGTCAAGGAGUTCGAAGATUCAC | R121 | 493 | GAATTGAAAATCUTCCTGCCTUCCCT |
| F122 | 225 | GAGUACAGCCAGTGTGUCCGA | R122 | 494 | GAGCAAAAGTGGUCCTCTCTGAAUCT |
| F123 | 226 | GACCATCCGGGCUTTACGCAAAUA | R123 | 495 | GAATATCAUCCAGCCTGTGTCTTUCC |
| F124 | 227 | GACCCCACUGAACCTCTCTTACATUT | R124 | 496 | GAGAGGGAAGGCAGGAUCTCUAAC |
| F125 | 228 | GACCCUAACAGCCATGCTTTCUC | R125 | 497 | GACCAGGCAAUGGAAAGGGTACAUA |
| F126 | 229 | GACGGCGAUGCTGAGAACCAAUA | R126 | 498 | GAGAAUAAAGAGGAGCAGGTUGAGGAA |
| F127 | 230 | GACCGACGUTGACCGCAUC | R127 | 499 | GAGGGCAAAUGAGCCTCUCAGT |
| F128 | 231 | GAAAATATTCAGTGTCCGTUCACACACAA | R128 | 500 | GATCCAGATTGAUCTTGGGAGTGUAAAAA |
| F129 | 232 | GACCACACUGACGTGCCTCUC | R129 | 501 | GAGTCTTTGTGUTCCCGGACAUAGT |
| F130 | 233 | GAGCGCCACAGAGAAGUTGTUGA | R130 | 502 | GAGGGTCUGACGGGTAGAGUGT |
| F131 | 234 | GACCACAAAAUGGATCCAGACAACUGT | R131 | 503 | GAGCTTGCTCTGAUAGGAAAATGAGATCUA |
| F132 | 235 | GAACTGTTTCGTAUTTATAGCTGATTTGAUGGA | R132 | 504 | GACCTCTTCCUCAGGATTGCCTUT |
| F133 | 236 | GACCTCAUTGCCCUCAACACAGT | R133 | 505 | GATCAGTCCGGTUTTATTTGCATCATAGUT |
| F134 | 237 | GACACCACGUACCAGATGGAUGT | R134 | 506 | GACCCAAAGACUCTCCAAGATGGGAUA |
| F135 | 238 | GAAGACATGCAUGAACATTTTTCUCCAC | R135 | 507 | GATCCAGACCAGGGUGTTGTTUC |
| F136 | 239 | GATGUGGAGCCTCTUACACCCA | R136 | 508 | GAGTGCCAGGGACCUTACCTTAUAC |
| F137 | 240 | GAACGTCTTCCUTCTCTCTCTGUCA | R137 | 509 | GACTGAGGUTCAGAGCCAUGGA |
| F138 | 241 | GAGAATGTGAAAAUTCCAGTGGCCAUC | R138 | 510 | GAGUCATATCUCCCCAAACCCCAAT |
| F139 | 242 | GAGGGTGTGUGGTCTCCCAUAC | R139 | 511 | GAGCCATAGGGCAUAAGCTGTGUC |
| F140 | 243 | GAGGATGAGCUACCTGGAGGAUGT | R140 | 512 | GACCTTGGTCCUTCACCTAACCTUG |
| F141 | 244 | GAGGTCACTGUACACCTTACACAUGAA | R141 | 513 | GACCCTCUTTAGCCAUGGCAAGG |
| F142 | 245 | GACATCACUGTAAACCTGCAGACAAAC | R142 | 514 | GATGGTCTCUCATTCTCCCAUCCC |
| F143 | 246 | GAGCTTCTTGGUCGTGTTCTTCAUT | R143 | 515 | GACTCCTCCUGTGATCTGCAAUCT |
| F144 | 247 | GAUGGAAGCCCAGCCATTUCTAAA | R144 | 516 | GAGATGAUGAAGATGATUGGGAAACACAAG |
| F145 | 248 | GAGCCCCUGAGCGTCAUCT | R145 | 517 | GAGGGCTGUGCGTCACTGUA |
| F146 | 249 | GAGAGCTGGUGGAGGCUGA | R146 | 518 | GAGGAGCCCAGGCCUTTCUT |
| F147 | 250 | GAGUGACCGAGGACAACGUGAT | R147 | 519 | GAGCGTCCUACTGGCAUGACC |
| F148 | 251 | GACTCUGGGAGATCTUCACGCT | R148 | 520 | GACCACUCACAGGTCGTGUGT |
| F149 | 252 | GAGGATTGCAGAUTGGGCCUTG | R149 | 521 | GAACATGATGGAUGTCACGTTCUCAAA |
| F150 | 253 | GAATAATCCAUTGCCTGTCUAAAGAACACT | R150 | 522 | GATGTTAACCUTGCAGAATGGUCGAT |

TABLE B-continued

| Primer Name | SEQ ID | Primer Sequence (target seq of Primer A) | Primer Name | SEQ ID | Primer Sequence (target seq of Primer B/C/D/E) |
|---|---|---|---|---|---|
| F151 | 254 | GAGACTTGGUGTTGTTGAUGGCAAA | R151 | 523 | GACUGCAGGATTCCUACCGGAA |
| F152 | 255 | GACCAACAUGACTTACTTGAUCCCCAT | R152 | 524 | GAATCACCAAAUGGCACCAUACGA |
| F153 | 256 | GAACCCUGGCCTACCTGGUC | R153 | 525 | GAAGTTCAAGCUGAAGAAGATGUGGAA |
| F154 | 257 | GATGAAGCAGCAAGUATGAUGAGCAA | R154 | 526 | GACTGACACCUAGCTGTGATCCUG |
| F155 | 258 | GAGGCACGGTUGAATGTAAGGCTUA | R155 | 527 | GAACTGATATGGUAGACAGAGCCUAAACAT |
| F156 | 259 | GACCACACCCUGTTCACTCCTUT | R156 | 528 | GAGTCTCAGTCAUTAGAGCACTCUGG |
| F157 | 260 | GAAAGGTGATCUATTTTTCCCTTTCUCC | R157 | 529 | GATTTCATACUGACCAAAACUCAGCCT |
| F158 | 261 | GAGCTTTTTGCUAAAATGCATGTTUCCAA | R158 | 530 | GAGACACGGCUTTACCTCCAAUG |
| F159 | 262 | GACAAAGAATGGUCCTGCACCAGTAAUAT | R159 | 531 | GAAGGCCTGCUGAAAATGACTGAATAUAA |
| F160 | 263 | GATCCTCATGUACTGGTCCCTCAUT | R160 | 532 | GAGTAAAAGGUGCACTGTAATAAUCCAGACT |
| F161 | 264 | GACAGATCTGTATUTATTTCAGTGTTACTUACCT | R161 | 533 | GAGACTCTGAAGAUGTACCTATGGTCCUA |
| F162 | 265 | GACATGTCAACAUCGCTCTAATUCAGAGA | R162 | 534 | GAGCTTTCAAAAGGCTUAAACACAGGAT |
| F163 | 266 | GATGTTACGCAGUGCTAACCAAGUT | R163 | 535 | GAGCAAACCACAAAAGUATACTCCAUGGT |
| F164 | 267 | GAGCTGAUTTTGGTCTUGCCAGAG | R164 | 536 | GATCTGACTTGGUGGTAAACTTTTGAGUT |
| F165 | 268 | GACCTCACCTCUATGGTGGGATCAUAT | R165 | 537 | GAGTTCTTGCUGGTGTGAAATGACUG |
| F166 | 269 | GATTCGCCTGUCCTCATGTATUGG | R166 | 538 | GACACCCCCAGGAUTCTUACAGAAAA |
| F167 | 270 | GAGCACUGGGACTTTGGTAATUCAC | R167 | 539 | GACATCTCTGGAAACTCCCATCTUGA |
| F168 | 271 | GACAGTGAAAAACAAGCUCTCATGTCUG | R168 | 540 | GACCACATGUGTCCAGTGAAAAUCCT |
| F169 | 272 | GACAGTGTGUCCACCGTGAUCT | R169 | 541 | GAAGTGAAGGAGGAUGAGCCUGA |
| F170 | 273 | GATGGAATGCCAGAACUACAATCTTTUGAT | R170 | 542 | GAGTGGAAGATCCAAUCCATTTTTGTTGUC |
| F171 | 274 | GAGACGCAUTTCCACAGCUACAC | R171 | 543 | GAAGCATCAGCAUTTGACTTTACCTTAUCA |
| F172 | 275 | GAGCTTTGAAUCTTTGGCCAGUACCT | R172 | 544 | GACATAAGAGAGAAGGUTTGACTGCCAUA |
| F173 | 276 | GAGATGCAGCCAUTGACCTGTTUAC | R173 | 545 | GAAGAAAACCATUACTTGTCCATCGUCT |
| F174 | 277 | GAGGGATUAAAGCTGGCTAUGGCA | R174 | 546 | GACCTTGTUGGGACCTCAGAUGT |
| F175 | 278 | GAAGCAUACGCAGCCTGUACC | R175 | 547 | GAGTGGUAGCAGTGGAUGCAGAA |
| F176 | 279 | GAGCTUCCAGGAGCGATCGTUT | R176 | 548 | GAAGGCCCCAUACAATTTGAUGACA |
| F177 | 280 | GAAGCTCGTUCATCGGGACTUG | R177 | 549 | GACCATGGUGCACCUGGGAT |
| F178 | 281 | GACTGGTUACTGAAAGCUCAGGGAT | R178 | 550 | GAACTTTGCGUGGTGTAGATATGAUCAA |
| F179 | 282 | GAGGACTCTGUGAGTGGGATTTGTTUT | R179 | 551 | GAGTCTTCACUCACCTCGGAUGA |
| F180 | 283 | GACATCCCUGACTGTGAGAUCAAGAA | R180 | 552 | GACAGGUACGCCTCCAGAUGAG |
| F181 | 284 | GAATCAACCUGCTTGGTGTCUG | R181 | 553 | GAAACUCCCGCAGGTTCCCT |
| F182 | 285 | GAACGAGGACCUGTGGGACUC | R182 | 554 | GAGTGCCUUGCCCTTTTTGUGG |
| F183 | 286 | GACATUCCCCAACAGCTGUGGT | R183 | 555 | GACCGGGAUGCCAGGAUACG |
| F184 | 287 | GACCTTCCUCCTGAAGGCCUGA | R184 | 556 | GAGGGCUGTACCTCCUCAGAGA |
| F185 | 288 | GAAAGTGCUGTGTGCCCUGCAT | R185 | 557 | GAACAGGCUGCCCAAGGGCUA |
| F186 | 289 | GACCCCTCTUGGACCTTAGAUGC | R186 | 558 | GACAGUGATCAGAUGAGCAGCAG |
| F187 | 290 | GACGCAUGGAGAAGAAACTGCAUG | R187 | 559 | GAACGGUCTGGAACCCAGAGA |
| F188 | 291 | GATCCCCUAUGTGCAAGTCCUAAAG | R188 | 560 | GAGCTATTGAUGTCTGCAGTCUGG |
| F189 | 292 | GACCACTGUGCAGAAGCTCUCC | R189 | 561 | GATUGACTUGCCGGAAGAGCCT |

TABLE B-continued

| Primer Name | SEQ ID | Primer Sequence (target seq of Primer A) | Primer Name | SEQ ID | Primer Sequence (target seq of Primer B/C/D/E) |
|---|---|---|---|---|---|
| F190 | 293 | GACGCCGGCCUCGTGAGUC | R190 | 562 | GAAGACCUCCGAGTCACTCCUG |
| F191 | 294 | GACAAATGCUGAAAGCTGTACCAUACC | R191 | 563 | GAAAAAGACTCGGAUGATGTACCTAUGG |
| F192 | 295 | GATGAGGCAGUCTTTACTCACCUG | R192 | 564 | GATTCCTTTCTUCCCAGAGACAUGC |
| F193 | 296 | GAGCAAAGACUGGTTCTCACUCACC | R193 | 565 | GAACATCCCUCTCTGCTCUGCA |
| F194 | 297 | GACGAUCTGTTCUACACGGAACCC | R194 | 566 | GAGGCTGGTTAUTGAAACCTTGTTTUACAT |
| F195 | 298 | GACCAGACAAGCCUACAGTAGGAAUC | R195 | 567 | GACTACCCCCGUACCAAGUACAAAC |
| F196 | 299 | GACTCCACAGACCCUCTCCTUGC | R196 | 568 | GATCGUCGAAGCGGCUGAC |
| F197 | 300 | GAAGGGTGTCUCTCTGTGGCTTUA | R197 | 569 | GAGACTCTGUAGGCTGCAGTTCUC |
| F198 | 301 | GAGTTTCUGCAGATTGACTUGCACA | R198 | 570 | GACTTCTTCCUACCTGTTTCCCAUGAC |
| F199 | 302 | GATCAGGAAACAAAAAUTTGTGCTAUGCAA | R199 | 571 | GAGGACCCAUTAGAACCAACUCCAT |
| F200 | 303 | GAGCTGGAGGAGCUAGAGCTUGAT | R200 | 572 | GAGGCTTGUGGGAGACCTUGAAC |
| F201 | 304 | GAGGGCTGUCGTGGTAGACTUAGA | R201 | 573 | GACCTGGTAGTCUCAAGCAGATGTUAAUG |
| F202 | 305 | GAAAGACTTCUCAAATTGTTGCCATTUCAG | R202 | 574 | GAAACGGACATGAGUTTGTTTTCCTTCUA |
| F203 | 306 | GACGAGGAAGAAAAACAAUCCCACTUG | R203 | 575 | GACAGCCAACAAGAUCTGAAGAACAUG |
| F204 | 307 | GAGAGATCCTTCGAAGTCATCGTCUT | R204 | 576 | GATCCCTAGGUAGCTAACCCCUAC |
| F205 | 308 | GAGGGCAAUGTCAATTAGCUGGAAC | R205 | 577 | GAAAAACACGGCAUGTGAACATTCUG |
| F206 | 309 | GACACTGTGTTACUGCCATCGACUAC | R206 | 578 | GAGTATTCAUCGAGATTUAGCAGCCAGA |
| F207 | 310 | GACTTTTACCCUCTTCAGCTCAGTTUCT | R207 | 579 | GAGAGAGAGGACUGACTATCGGACUG |
| F208 | 311 | GATCTCCTCCAACCUAATAGTGTATUCACA | R208 | 580 | GAGACTGUCAAGCAGAGAATGGGUAC |
| F209 | 312 | GATTTCGUAAGTGTTACUCAAGAAGCAGAA | R209 | 581 | GAGAATAGGATATTGUATCATACCAATTTCUCGAT |
| F210 | 313 | GAATGCCCCCAAGAAUCCTAGUAGAA | R210 | 582 | GAACGAAAATGUAAGAAGATTCATCUGAAGAAG |
| F211 | 314 | GAAGAGATGATTGUTGAATTTTCCTTTUGGG | R211 | 583 | GAAAAGCCATTTUCCAGATACTAGAGUGT |
| F212 | 315 | GACGGAACUCGAATCGCUACCCT | R212 | 584 | GAGGGUCCCCAAGACACCUACG |
| F213 | 316 | GACTCGATGCUGTTCCCAGGUAC | R213 | 585 | GACCGAGAACUGAGGGTGGUACA |
| F214 | 317 | GATCATACAGACACUTCATTTGGAGUACC | R214 | 586 | GATACTAGAACUCAAAACACTGGCTGUT |
| F215 | 318 | GAAAAAATAAAGCUGGCTTCAAGTTGUCT | R215 | 587 | GAGTAAGTCTTCACUTTCAGATTTTAGTUGGG |
| F216 | 319 | GAACATTGTGACCUAATTTTGTGATCTCUG | R216 | 588 | GATGCTTCCTGGUCTTTAGGATTUCUT |
| F217 | 320 | GACCCCACTCAUGTTTAGCAGATGUA | R217 | 589 | GATTTTACTTCUGCTTGGTGGCAUG |
| F218 | 321 | GAGGACAGGUTTTGTTGTUGAGGAAG | R218 | 590 | GATTTACCCTCAUGGCTTAGTAGCATTATUT |
| F219 | 322 | GAAGCAAGGTCAUAAATTATTCTCCATATTUCCA | R219 | 591 | GAAAAAATATCCATCCAGCTUCAGGAAAAGG |
| F220 | 323 | GATCTTTTTACCUUATAGATGGGAAACAUGAGAG | R220 | 592 | GAATCAGTCUGGTGGATGGGUAACA |
| F221 | 324 | GAATGTGTCTTUCAUGAGAAAAACAAGATCAUT | R221 | 593 | GACTAATAATGAATAAUTGGGTATGAGGCUACAGT |
| F222 | 325 | GATAGTAGCTGAUCCACAGAAGTTCAGUA | R222 | 594 | GATGTGAGAGAGCAAUCAAGGAGUG |
| F223 | 326 | GAAAGACTCTGAAUACCACCATCAAGAATAAUAAA | R223 | 595 | GAGTCTGAGAGUAGAAGGCAGATTCTGUA |
| F224 | 327 | GAATCTACAGGCCAAUGGTTCCTUC | R224 | 596 | GAAACTTGCGGAGATCUGAAAACCA |
| F225 | 328 | GAGCCAGTAGUCACAAAGATTTCUACCA | R225 | 597 | GACTCTAAAGAAGGAAGUGAGAACTTCUCC |
| F226 | 329 | GAAGAAGAUGGGUGGGCAGAC | R226 | 598 | GACTTCTTCACUCAAAGTGCCTATTUGAC |
| F227 | 330 | GAAACCACTGATACAUTTTTCTACTTTCCUGAA | R227 | 599 | GATTCTTTTGAGAACUGAGTGATTTAUGACCT |

TABLE B-continued

| Primer Name | SEQ ID | Primer Sequence (target seq of Primer A) | Primer Name | SEQ ID | Primer Sequence (target seq of Primer B/C/D/E) |
|---|---|---|---|---|---|
| F228 | 331 | GAAGACTTCTTUGAGATATTTCCATAGCTCAC | R228 | 600 | GAAGAAGTAGAAACAGAACTGTATGUAAGCAT |
| F229 | 332 | GACATTTTTGTTTATGUTATTCTCTCTACCUCAGC | R229 | 601 | GAGCTATACGAACTAGAAGTGAGAAATAATCUT |
| F230 | 333 | GAAGTTATAGGTAAUCGATGCATATAGCTCAUCT | R230 | 602 | GATTTCTCCAGGUCCAAAATGAATAACTATTUGA |
| F231 | 334 | GAAATTGTTTGTAGGGUTGGTTATTAGTGACUAT | R231 | 603 | GAATCCAGGAUAGGAAGCACACAUG |
| F232 | 335 | GACCACTATGUAAGACAAAGGCUGGT | R232 | 604 | GATTTTATAACTAGATUTTCCTTCTCTCCATCC |
| F233 | 336 | GAGTTTCTGUAGCCCATACTTTGGAUGA | R233 | 605 | GAAATTCATACAUTTTTCTCTAACUGCAAACAT |
| F234 | 337 | GACACTGUGAAGGCCCTTTCTTCUG | R234 | 606 | GAGCAGTTGUGAGATTATCTTTTCAUGGC |
| F235 | 338 | GAGCATAGGAGATAAUCATAGGAATCCCAAAUT | R235 | 607 | GATGTTTTTCTAAUGTGTTAAAGTTCATGGAAC |
| F236 | 339 | GAAGTCACTGGAAUTGTTGGGCUAC | R236 | 608 | GACCATGACTGUCACAGTGACCUT |
| F237 | 340 | GACTCCAGGAGCCGUAGAGTTT | R237 | 609 | GATTGUGGCCCAAACAAAGCUC |
| F238 | 341 | GAACTCTTCCTATTUTTGTAGTGACCTGTUT | R238 | 610 | GAGTGCTTGGAAAUGGAATGGTTTAGAAT |
| F239 | 342 | GATTCCTGAUAAAGCACAGCTGTAGUG | R239 | 611 | GACTACTGUAACCAAGAGGTGACTUCAG |
| F240 | 343 | GATTGTUCAAGCAGCGAGUCC | R240 | 612 | GAAGCCGAUATCCCUGCAGAC |
| F241 | 344 | GACATGAACUACCTGGACCGCUT | R241 | 613 | GAGTCGGUGTAGAUGCACAGCT |
| F242 | 345 | GAGGTGCTGUCTGGGAAGAUGT | R242 | 614 | GATGCCCAAGGUACTGCAUGGT |
| F243 | 346 | GAAAAGAGGCAGUAGCATCTTCCC | R243 | 615 | GACUCACGCCUAAACCAGAACC |
| F244 | 347 | GAAATCCTGGAGCUTTGGTGTCTAATUC | R244 | 616 | GATAGCTGGCUCCGCACCUT |
| F245 | 348 | GATGCAGAAGCGGUTTCTGUG | R245 | 617 | GACTGCUGGGCGCCGUAAC |
| F246 | 349 | GAGCCTCAGAGAUAAAGGCAAAGATUG | R246 | 618 | GAACCCACACAAGCGAAUCTCUG |
| F247 | 350 | GAACCATTATTTCTTUGTTTTGTTTTTCCTGUAT | R247 | 619 | GAACTTTGCUGCCTTAATGACATUCC |
| F248 | 351 | GATACCAACCAAGUTTCATUAACCACAGT | R248 | 620 | GAGGTACCUGAGATGGAGGAGUC |
| F249 | 352 | GACCATGTTGGUCACTTACTCAAAGATUT | R249 | 621 | GATTGAGCCACUAAGCAGTAACCATUC |
| F250 | 353 | GAAATGGGCAAGGUATGGATGUGG | R250 | 622 | GACCCGAAGUCTTCTGCAGUCC |
| F251 | 354 | GATGGCGCAUCAGATCCTAGTUT | R251 | 623 | GAGCCGAAACGAUCAAGGUGAGT |
| F252 | 355 | GATGTAACAACCUAAAGGGAATAGGAAGAAUG | R252 | 624 | GATCAGTAGAAAGAUGGUACCAAAAUGGGT |
| F253 | 356 | GAGGCACTGGUTCTCATTCCUG | R253 | 625 | GAGACCGAGCUCGGGTGUAT |
| F254 | 357 | GAATGACTCAAUACCAACCCCUCCA | R254 | 626 | GAGCCTTTGTGGUCATGGGAAAGTAUA |
| F255 | 358 | GACATAACCATGAUATTAATAGGACTCCUGCT | R255 | 627 | GAATTTGCCTGAAATACACATAGAACTTTCUG |
| F256 | 359 | GATGAACGCAAAACCUGTTGAAGTUAAAA | R256 | 628 | GAGGGATGGGUGACTGAGAUGGT |
| F257 | 360 | GACTTAAAAATGTCAAUATCTGGCCTCAAAUACG | R257 | 629 | GAGTGGACAUGCGAAUGGAGGA |
| F258 | 361 | GAGGGAAGCAATUTGCTACACTTTAATTUAAAC | R258 | 630 | GATTTACTCTGACAGCUAAATGAACTCAAATGUA |
| F259 | 362 | GAACAGAAGCUTCTAATCCUCAACGT | R259 | 631 | GAAGGCTCAGAACACUTTACTGAATTTUG |
| F260 | 363 | GAAGTTGAUGCCAATTCACAAUCACCA | R260 | 632 | GATTACTTAGAAGAAAAUGCTCCTTGUCAGA |
| F261 | 364 | GACTGAGGTCTATCACTTTCTTTTCATCTTUG | R261 | 633 | GAGTGAAGGAAACCAUCGTGAUAAAGC |
| F262 | 365 | GACTATTTGTTTCTCCCCATGGAATTGUC | R262 | 634 | GAGAAAATGGACCCAGTTCTCUGCT |
| F263 | 366 | GATAATCTTGAACTGCCTGUGCACT | R263 | 635 | GAATCTTTCAACUGTAAAATTCACTGUGGGT |
| F264 | 367 | GAAAGCAAUGGCTTGGGAAGUAAGA | R264 | 636 | GACCATTCTCAUATCCTAGGTCUGCCT |
| F265 | 368 | GATCTAAAGGTTTTTCUGATTTCCTCATTAGGAUT | R265 | 637 | GAGCACUCCATTUGGACAGCAA |
| F266 | 369 | GATCCAGTCATTTUGAGAAAGACAACTUACT | R266 | 638 | GAGTTTATTTTCTGGUTTCAATAGAACAAGTUGA |

TABLE B-continued

| Primer Name | SEQ ID | Primer Sequence (target seq of Primer A) | Primer Name | SEQ ID | Primer Sequence (target seq of Primer B/C/D/E) |
|---|---|---|---|---|---|
| F267 | 370 | GATTCATTAATATTTCAGATCACCAGTTGATUG | R267 | 639 | GATTTGAAAGGTAGAUTGCCATAATGTATCATUG |
| F268 | 371 | GAATTAACTGTACCUCCAACTTTCTTACTATAUGC | R268 | 640 | GAATGTGGAATCTUTGTTTAGTTTTACTCUGGT |
| F269 | 372 | GATTAAGAAACUAGAAACTGTTTAGACUGCCT | R269 | 641 | GAATGGTTTAGTCUGACACATATTTAACACUT |
| F270 | 373 | GATGGTTCTGUCGACTAAACUGC | R270 | 642 | GATTTTCAAGTTAUAGAAACATGTCATGTTGUCA |
| F271 | 374 | GAACGGACACUATGTCCTTAAGCUGA | R271 | 643 | GACTAGACTTUGAGACCTGCTAAATAATUAGATG |
| F272 | 375 | GATTGGCAUGGCTTCTCUAGCT | R272 | 644 | GACAGGUCCAAGUGAACCAGGGA |
| F273 | 376 | GACACCTTCUACCGCTCACUGC | R273 | 645 | GAAGGGCACUGACCCTGGUA |
| F274 | 377 | GAATTGACUCTGAATGUCGGCCAA | R274 | 646 | GATCTGCAGGAGGGUGCTCTUA |
| F275 | 378 | GACTCTGCCCCUAAGAAACCUGGA | R275 | 647 | GAGGGCAACUACACCTGCAUGT |
| F276 | 379 | GAATTACTCUAACTTTCGCAUGCACAC | R276 | 648 | GATGCCAAGACAGUGAAGTTCAAAUG |
| F277 | 380 | GAAGUGGGCAGCAGTTTCUGA | R277 | 649 | GAGACACCACCUACTTCTCCGUCA |
| F278 | 381 | GAAACCAACTGCUTGTATGCTTTCUGG | R278 | 650 | GAAAGACCAAAAGAGAAUGGAAAGTACUGAC |
| F279 | 382 | GAGCAGCCUTACCTGGTUGGA | R279 | 651 | GAAGAGUATCCATCUCCAGGAGACG |
| F280 | 383 | GATTACAGCUCGTTGGUGCAGT | R280 | 652 | GATGTGGCUCTCCGCCCAUT |
| F281 | 384 | GAATGGAAACCCUGACAGAGTCTTUG | R281 | 653 | GAGCTACACCATUAGCTTCACTGATTUT |
| F282 | 385 | GATGTTATGAGCUTAGCACCTUGCAG | R282 | 654 | GACTGGATGGUAAGAGGAGTTTCTTCAUC |
| F283 | 386 | GACCAGTTCUGCAGTTAGAGGTUG | R283 | 655 | GACCTTTCCCCUCCCCTACCUAG |
| F284 | 387 | GATTTGATTCTTAAUCACCTAAGGAUGGCT | R284 | 656 | GACAAAACAAAGUCAAAGAGAATTATGAAATGUG |
| F285 | 388 | GAATCCGTACCUTCCACCAATCUG | R285 | 657 | GACAGGGATTTUGGTTACTACTTTGCUAAGA |
| F286 | 389 | GATATAACAATGAAUGACCAAAAGGAAATUAACAA | R286 | 658 | GATTGTCTTCUGGACACGTTCUGAAA |
| F287 | 390 | GATAACTTTCCATAUGCAAACCTACTGGCUA | R287 | 659 | GATATTAAGCTTTCUTGGAAAATTCTCTTUCCCT |
| F288 | 391 | GACCUGGACGTCTUGGAAAAGGG | R288 | 660 | GATTCAGAAGUAGGAAAGGAGUCCAG |
| F289 | 392 | GATCTGGGUCAAGGAUGGCACA | R289 | 661 | GACACCUGTCACCCGCACAC |
| F290 | 393 | GAGCCCACUTCCCATCUGGGT | R290 | 662 | GACAGTCAGUAACGCCAGUGAGT |
| F291 | 394 | GATCCCCGCUGCTGUGCAAC | R291 | 663 | GAGUCCCGTGGUGCAAAGGC |
| F292 | 395 | GACCCACATGUCCAGCACCUT | R292 | 664 | GAATGTACACTAGTTUCCGGAATAAACCTTUT |
| F293 | 396 | GAGCTGGUGAAACAGGTAGUGAGT | R293 | 665 | GACTUGACCCCUGCGAGCCA |
| F294 | 397 | GACTCCAGGUCCTTGTGUGAGC | R294 | 666 | GACCCACUCAAGCTCAGCUGUAA |
| F295 | 398 | GACCTCACGAACUGTGCTGAUGG | R295 | 667 | GACTGAGAATGGCUACCTCTCGAUAUG |
| F296 | 399 | GAGGATTCGAGAAGUGACAGGCUAUG | R296 | 668 | GAGGCTGGAGUTGGTGTTATAGTUCAA |
| F297 | 400 | GAATTGGTAGCUGGTGATGTTCCUC | R297 | 669 | GACTCACACATCUGAGCCCATTTTTAUC |
| F298 | 401 | GACAGCTAATUCATCTGGAGAUCAAACCC | R298 | 670 | GACTGAGAGGGUGTCACATACCAUG |
| F299 | 402 | GATGTCAGTTCCCUCCTTTTCTATTTUCUC | R299 | 671 | GATTCATACCGACAUGTAGGACCTUGT |
| F300 | 403 | GATGGGCACGGUAATGCUGCT | R300 | 672 | GAACTTCUCACACCGCTGTGUT |
| F301 | 404 | GACTCUGCGGTGGUGGCAT | R301 | 673 | GACCTCACCUCCGTTTCCUGCA |
| F302 | 405 | GACTCCACCUCCAGGAACTUACUC | R302 | 674 | GATCUGGCCCCCUAGGAGGA |
| F303 | 406 | GAGGGATCTTGUGAAATGUCATCTGACUC | R303 | 675 | GATCATCCTCUCCCCATAGAAAAGUCC |
| F304 | 407 | GATCAACCCTGUTTTCTCCCTCTTAUG | R304 | 676 | GATCTCUGCCATCATTUCCGGAAAG |

TABLE B-continued

| Primer Name | SEQ ID | Primer Sequence (target seq of Primer A) | Primer Name | SEQ ID | Primer Sequence (target seq of Primer B/C/D/E) |
|---|---|---|---|---|---|
| F305 | 408 | GACTGUACAGCATGAAGUGCAAGAAC | R305 | 677 | GATGCAAGGAAUGCGATGAAGUAGA |
| F306 | 409 | GACCATTAACAUGGCCTACCAGAGUT | R306 | 678 | GAGTCGCUAACACGTGTGTGTUC |
| F307 | 410 | GATTGCCUAGACAGCACCGTAAUG | R307 | 679 | GATGGCTAAACTUGACCTTTTTACTCUGC |
| F308 | 411 | GAGACGCAGUTTCTTCTTCTCAUCG | R308 | 680 | GATTCCTCAGCAUCGACCTUGC |
| F309 | 412 | GATATCGAGTGTGUGCATATGTGTATGTUG | R309 | 681 | GAAATCTATATACTUCCTTACCTGGGATUGGA |
| F310 | 413 | GAAGGGAAAAUGACAAAGAACAGCUCA | R310 | 682 | GAACATGCTGAGAUCAGCCAAATUC |
| F311 | 414 | GAGGCCTGCUTTTGGAGTCCUAT | R311 | 683 | GAGCAGUGAAAAGAGTCUCAAACACAA |
| F312 | 415 | GAGAAGAGCCUCCACCATCUCCA | R312 | 684 | GACCCACAGGCCUCTCUCGAG |
| F313 | 416 | GACACACAUGCCATCATTCUAGGAAG | R313 | 685 | GACTGGUATGAGAAACUGCACGAGT |
| F314 | 417 | GAGAGGTTTCCAGCACTCTGACAUAT | R314 | 686 | GAAATACCAATCUATTGTGGGCTCUGG |
| F315 | 418 | GATCTTCTCTGUTTCAGGGCAUGAAC | R315 | 687 | GACCTCCTTCUGCATGGTATTCTTUCT |
| F316 | 419 | GAAGATTCUGCCGAACCAATGGAUC | R316 | 688 | GAATTAAAGCAGUGCTCATGATUGGG |
| F317 | 420 | GATATGACTUGTCACAATGUCACCACAT | R317 | 689 | GACGGGACUCGAGTGATGATUGG |
| F318 | 421 | GAGTGCCCUATUACCTCAATCATCCUG | R318 | 690 | GACTTCACCTTUAACACCTCCAGUCC |
| F319 | 422 | GATCAGTTACTACCUGAAAATGACACTTUGT | R319 | 691 | GACTCCTCTAGCUATCTTAATGACTUGGAC |
| F320 | 423 | GATAAAGACCTUCTTCCGTGTGUCCT | R320 | 692 | GACTGCTTTCATUCATAGGGAAATACAUAAGAAA |
| F321 | 424 | GATACATTTATTUGAGAAACTTGAGAGAACUTCA | R321 | 693 | GATTCAATATTTTAAAUAGTCTGGCCUAAACGGT |
| F322 | 425 | GAAGATGGTGATAGAUCTTTAAGAGAATTGCUT | R322 | 694 | GATGATTTCCAGUATTAATTGGCAAUAAGAGAAT |
| F323 | 426 | GAAGCTTTTGATAAGAGUTAGGAAATCACTAGUC | R323 | 695 | GAATGAAAGCUAAAACATAAGATGAAUGGGAAAA |
| F324 | 427 | GAAGGAUAAAAACCAGCATTATTTATTUGAGCA | R324 | 696 | GAATTATTTCTTACCACUTTTCCTTTCTCCUGT |
| F325 | 428 | GACTGACCCAUAATCTTGCACCATTUACC | R325 | 697 | GAATTGTGAGATAACAGCAGGGAUACC |
| F326 | 429 | GATTTGAAATGAAUGTTCACGACAAAUGC | R326 | 698 | GAGCTTCATTGTCTUGATAAAATTTATGGTATCUT |
| F327 | 430 | GAACAACCAAAACAAUACACACAGAGATTUT | R327 | 699 | GACCAGCTCTTUCATATCTTAACATTUAGCAACA |
| F328 | 431 | GAACGGAGGGUCATGTGTATATTAAGUAAG | R328 | 700 | GAGCCAAAACATTTGTCCCTTTCTATAATTUG |
| F329 | 432 | GAGAATTAAGUGTGTACTACUCCCAAGAGAAAA | R329 | 701 | GATGGACTTCAAGUGATCACTTGUG |
| F330 | 433 | GATATAGGATGAGUAGCTCCAAATTAATGAAUGT | R330 | 702 | GAAGCCTGUGGTGCTTTTGCG |
| F331 | 434 | GAGCTGTAGAAUAGTCAAGAGGAATUGCA | R331 | 703 | GAAAGTCAAACUACACTCAGAACCUGAAT |
| F332 | 435 | GACTCAGTGCUCTAAATCCAGAGCUG | R332 | 704 | GAGCAAAGGCCAAAGAUAAAATGCTTACUG |
| F333 | 436 | GAATGAAATATUGTCAACTCTCTUAGGCAAAAT | R333 | 705 | GAAAGCTACAGAAUGTGAACAGTCTTCUAAA |
| F334 | 437 | GATACTTUGCAAAGCTGAATUAGACAGCA | R334 | 706 | GAGAGGTAGAUGCTGTAATTGCTGAUACAA |
| F335 | 438 | GAACATGAGCAUCACATTTTCCTUGG | R335 | 707 | GACAAACACCTCCUGATAAATTGGCTTUG |
| F336 | 439 | GATGCCTTATGAAUATATTCACGCUGACT | R336 | 708 | GACCCTACUCCAAGGAGCUCAGG |
| F337 | 440 | GAACCAGGUAAGCACCGAAGUC | R337 | 709 | GACCCAGTUACCATAACTACTCUGAGAAAA |
| F338 | 441 | GAACCAAGCCGCUGGTUCA | R338 | 710 | GACTTGCAGAGCUATCCCCUAAAGC |
| F339 | 442 | GAAGACCCCUTTAACTCAAGACUGC | R339 | 711 | GAGCTGCACCGAGUCGTAGUC |
| F340 | 443 | GAGCGAGGAUATCTGGAAGAAATUCGA | R340 | 712 | GAGTCGUTGTCUCCCCGAAGG |
| F341 | 444 | GAUTCUCCACGGCCGACCA | R341 | 713 | GAATACAGTCCUGGATGATGATGTTTUGA |
| F342 | 445 | GAAAGTCCCUCAAAAATAGGAGGUGCT | R342 | 714 | GAGGACAAGAAAAGUGCAACTUCCCA |
| F343 | 446 | GAGACAGAUCAGCAACAACCGAAAAUG | R343 | 715 | GATTTCATTGUTTTCCAACUCCGGGAT |

TABLE B-continued

| Primer Name | SEQ ID | Primer Sequence (target seq of Primer A) | Primer Name | SEQ ID | Primer Sequence (target seq of Primer B/C/D/E) |
|---|---|---|---|---|---|
| F344 | 447 | GATTTGTCCAGAGACCTTCTAACGTAUT | R344 | 716 | GATTCCACAGAAACAACAUCGATTTCTTC |
| F345 | 448 | GATTTCUGAAGAGGACTTGTUGCG | R345 | 717 | GATGCATTUGATCATGCATTUGAAACAAGT |
| F346 | 449 | GAGATTTUCAGTTAATAATAUCCCCCGAGCT | R346 | 718 | GAAGTCTGUGCGCGCTUGC |
| F347 | 450 | GAAATCGCCUCCGGAUCCC | R347 | 719 | GAGTGCGCACGUCGCAAUC |
| F348 | 451 | GAGTCATTCCTTCUTTTTAAAATGGTGCTUAAGT | R348 | 720 | GAGGATGTAUACAAAAGGCGGATGUG |
| F349 | 452 | GAGGTCCCCCACCUCTCTTTUG | R349 | 721 | GAGCCAGAGAGUCCCTTUCACC |
| F350 | 453 | GACTCUCCAGGAAGGCTCACAUC | R350 | 722 | GATGCCACTCUTTGGGTTGAGUT |
| F351 | 454 | GATGGCATUGCCTTGTCCTUG | R351 | 723 | GATTTCAAACUGGAGGCTTAUCACCAA |
| F352 | 455 | GAGGCAGAAAACCAAAACAUGGCTUA | R352 | 724 | GAATACAAGCATGAAAAUCAAAACATATCTTCUGC |
| F353 | 456 | GAAATTGTTCCTCAAGUTTGTTTAAGGACTUAAAA | R353 | 725 | GAGTAAATGGTAGCTUTTATCATAATCACCAGUC |
| F354 | 457 | GAAGTGGTATCAUCCCCATTTAATAGCUG | R354 | 726 | GATCCATTCAAGACUTTAGCAGGTGGUA |
| F355 | 458 | GAACAAATACAAAACUGTCCACATCTATGTUG | R355 | 727 | GAGTTACTCTCATGUGAGAACCATTTGAAUGA |
| F356 | 459 | GAAACAAACCATAGCUATAATGAAGAACTTGCUA | R356 | 728 | GAGTTTTTCTTATCUCTTAAAATGTTTCTGCUACA |
| F257 | 460 | GAAATAGTTGATCAUACTTTGTAACAGAAUCACA | R257 | 729 | GAAAGGUACAAGTUAAGGCACACAGAAG |
| F358 | 461 | GACTCATCTCCCTUTAATTTTGGCACATTAUT | R358 | 730 | GATGGATCTUGGCACAATGAUAACAGG |
| F359 | 462 | GAAACTATCTUCTTTGGACTTCUGAAGAGAC | R359 | 731 | GATGCTATAGTACCAGUACCTTTTAAGGTUCA |
| F360 | 463 | GAAGTAAATAATGGTTUCTCCTTCTCTTACTTUG | R360 | 732 | GACCGTAAGGUGGCCTACTTUGC |
| F361 | 464 | GATTCCTGGUGGCATTCAAUAAAGCA | R361 | 733 | GACAGCGTTTTCUTGTATTCCTGTATTUAGC |
| F362 | 465 | GAAGGAGCAACUAGGGATCUGGT | R362 | 734 | GAGGAACTGTGAAUGAACTTGTAGGUG |
| F363 | 466 | GAACCCCTAAUCTGGTCAACCUG | R363 | 735 | GACCUGACCAGGGCGUCAAA |
| F364 | 467 | GAAGAAATAGAAAACUACAGGACGTTAUCCAG | R364 | 736 | GAAGTTCATCTUCGAAGCTCAAATTUCAG |
| F365 | 468 | GATCCGCTTTCUAAAATGTCAGTTGUC | R365 | 737 | GATACAACAAAAUGTTTGACTTCAUGCAGGT |

TABLE C

| Primer Name | SEQ ID | Primer Sequence | Primer Name | SEQ ID | Primer Sequence |
|---|---|---|---|---|---|
| F366 | 738 | AAAACTCAGTAUCAACAACTACCGGUAC | R366 | 870 | TCCCGTGGCUGGTAAATCTGAAAUA |
| F367 | 739 | CTCAGAAAUGGAAAAAACCTGCAGUAAA | R367 | 871 | CCAAAACATGAAUGTTCTCAACAAGUG |
| F368 | 740 | GTTCCCTCUGCGTGTTCTCAUAA | R368 | 872 | ATTCCTGCACUAATGTGTTCATUCT |
| F369 | 741 | AAGAACCTGUGTGAAAGTATCUAGCAC | R369 | 873 | GUCCAAAGCGAGCAAGAGAAUCC |
| F370 | 742 | AUAAACCAAACCCAUGCAAAAGGAC | R370 | 874 | AGTTCCAGUAGTCCTACTTGACACT |
| F371 | 743 | GCATTGAUGGAAGGAAGCAAAUACA | R371 | 875 | AGAGCACGTUCTTCTGCTGTAUG |
| F372 | 744 | CCAGCTTCAUAGACAAAGGTTCUCT | R372 | 876 | AGTTGAATATCTGTTUTTCAACAAGTACATTUT |
| F373 | 745 | GTGGTTTCUCCATTGACCACAUC | R373 | 877 | GCCTGGCCUGAATGCCUAAA |
| F374 | 746 | CAAAUGGGCAGGACTCTUAGGT | R374 | 878 | CAATTTCAACACAAGCUAAACTAGUAGGAT |
| F375 | 747 | GUGAGGAAACTUCTGCAGAGGT | R375 | 879 | TCAACAAAAGUGCCAGTAGUCATTTC |
| F376 | 748 | GGAAGCAGGGAAGCUCTTCAUC | R376 | 880 | CTGTTTTUAGCAAAAGCGUCCAGA |
| F377 | 749 | TGGTTUGAAGAACTTTCTUCAGAAGCT | R377 | 881 | AGTCAGCCCUTGCTCTTUGAAT |

TABLE C-continued

| Primer Name | SEQ ID | Primer Sequence | Primer Name | SEQ ID | Primer Sequence |
|---|---|---|---|---|---|
| F378 | 750 | AGGGAGACUGUGTGTAATATTTGCG | R378 | 882 | TTGGCCAUACAAAGTGAUAAAGGACTT |
| F379 | 751 | GCCAGTATGAAGAATGTTGAAGAUCAAAA | R379 | 883 | TTTGCAGGGUGAAGAGCTAGUC |
| F380 | 752 | GCCAAAAGGAAGUCTGTTUCCAC | R380 | 884 | TGTACAAAUGGGACTAACAGGUGGA |
| F381 | 753 | CATGCCACACAUTCTCTTTTTACAUGT | R381 | 885 | AGCATACCAAGTCUACTGAATAAACACTUT |
| F382 | 754 | GTAGAGUGCTACACTGUCCAACA | R382 | 886 | CCTGGAGTCGAUTGATTAGAGCCUA |
| F383 | 755 | CTCTGAGAAAGAAUGAAATGGAGTUGGA | R383 | 887 | AATGTGTTATGUGGCTCCATTATAGCT |
| F384 | 756 | AAACAAATTTUCCAGCGCTTCUGA | R384 | 888 | GCATTTTTACCUACGATATTCCTCCAAUG |
| F385 | 757 | AGCAATAAAAGTGUATAAATGCCTGTAUGC | R385 | 889 | ACCAGTAAAAAUAAAGAACCAGGAGUGG |
| F386 | 758 | TCAACAAGTTGACUAAATCTCGTACTTUCT | R386 | 890 | TTATAGAGGTTTUCTACTGTTGCUGCAT |
| F387 | 759 | CATTCTTACAUAAAGGACACTGUGAAGG | R387 | 891 | GCAGTTGTGAGAUTATCTTTTCAUGGC |
| F388 | 760 | CCCTTACAGAUGGAGTCTTTUGGC | R388 | 892 | CATCATTCACCCUTGGCACAGUAA |
| F389 | 761 | AAAGACCTTTUGGTAACTCAGACUCAG | R389 | 893 | AAAUATTTTCTAGGAATUGCGGGAGGA |
| F390 | 762 | ACATTCACUGAAAATUGTAAAGCCTATAATTG | R390 | 894 | CAGGUAAUCGGCTCTAAAGAAACATG |
| F391 | 763 | GGTTGTGCTTTTUAAATTTCAATTTTATTTTUGCT | R391 | 895 | CAGAGAGATCGAGGCAGAGUG |
| F392 | 764 | GGATGUCACAACCGUGTGG | R392 | 896 | AGTAGUGGATTTUGCTTCTCTGATATAAACT |
| F393 | 765 | AGTGAAAACUAAAATGGAUCAAGCAGATG | R393 | 897 | GCTCTUAGCCAAAATATAGCATAAAAATCAG |
| F394 | 766 | AAACTAGTTTTUGCCAGTTTTTUAAAATAACCT | R394 | 898 | AAAAAGCATUGTTTTTAATCAUACCTGACTT |
| F395 | 767 | TTTTTACCCCCAGUGGTATGUGG | R395 | 899 | GGTACAGAUTTGTAAATCUCAGGGCAA |
| F396 | 768 | GAAAACACAAAUCAAAGAGAAGCUGCA | R396 | 900 | GAGAUCACGGGUGACAGAGC |
| F397 | 769 | ATATTTAGUAGCCAGGACAGUAGAAGGA | R397 | 901 | ACCTACCTGAUACCCCAGAUCCC |
| F398 | 770 | AAATATTTCAGUGTCCGTUCACACACAA | R398 | 902 | TCCAGATTGAUCTTGGGAGTGUAAAAA |
| F399 | 771 | GCAGAUGCAAGGTATTCTGUAAAGG | R399 | 903 | GTGTGCTAGAGGUAACTCATGATAAUGG |
| F400 | 772 | ACCTACATAAAACUCTTTCCAGAATGTUGT | R400 | 904 | GAAAGGGUCAACAAAAGAATGUCCAT |
| F401 | 773 | CCCTTTCTGTUGAAGCTGTCAAUC | R401 | 905 | GAAAGTTCCCCAAUTGAAAGTUGCAG |
| F402 | 774 | AGAUGGTATGTUGCCAACACGAG | R402 | 906 | AACTTTGTAATCAACATTCATCGTTGUGT |
| F403 | 775 | GATGTTTCCGUCAAATCGTGUGG | R403 | 907 | TAGATGATAGGUGGTACATGCACAGUT |
| F404 | 776 | GTAGAACTATCUGCAGACACCUCAAAC | R404 | 908 | ACCUGAATTATCACTAUCAGAACAAAGCA |
| F405 | 777 | CCAGAACCACCAUCTTTCAGTAATTUG | R405 | 909 | GAACAGUACCCGTTCCCTUGA |
| F406 | 778 | ATCATAAAATGTUGGAGCTAGGTCCUT | R406 | 910 | CTTGAGGACCUGCGAAAUCCAG |
| F407 | 779 | TATGATGGAAGGGUAGCTGTUAGAAGG | R407 | 911 | TGGAAAGCTTCUCAAAGTATTTCATTTUCT |
| F408 | 780 | GGTTAAAATGTCACUCTGAGAGGAUAGC | R408 | 912 | GCAGCGTTTAUAGTCTGCTTTTACAUC |
| F409 | 781 | GGAAATTTGUAAAATGTGCUCCCCAAA | R409 | 913 | AACGGGCTGGAAGAAAATAAUCAAG |
| F410 | 782 | AATTCCTTGTCACUCAGACCAACUC | R410 | 914 | TCTGCTAGCUGTTTTCTUCACAGT |
| F411 | 783 | ACTAAGGTGAUGTTCCTGAGAUGC | R411 | 915 | AACAATATACCTUCTCAGTCTACUAGGCAT |
| F412 | 784 | ACTTTCCUTAATGTCATTTUCAGCAAAACT | R412 | 916 | CAGATAACTAGAACAGCCUAUGGGAAG |
| F413 | 785 | CAGTCTGAACUACTTCTTCATATTCTUGCT | R413 | 917 | GGCCAAAATUGAATGCTATGCTUAGAT |
| F414 | 786 | CTAGTTCTGCUTGAATGTTTTCAUCACT | R414 | 918 | AGCACAATAGCCGTAATAACAUAGAGAA |
| F415 | 787 | TGGAATGTTCTCAUTTCCCATTTCTCUT | R415 | 919 | TGGACTCATTACUCCAAATAAACAUGGA |
| F416 | 788 | GTTTCGTUGCCTCTGAACUGAGAT | R416 | 920 | GTCTAATATCAAGCCUGTACAGACAGUT |

TABLE C-continued

| Primer Name | SEQ ID | Primer Sequence | Primer Name | SEQ ID | Primer Sequence |
|---|---|---|---|---|---|
| F417 | 789 | CCTTGATTTTCTUCCTTTTGTTCACATUCA | R417 | 921 | TGCAGAATACAUTCAAGGTTUCAAAGC |
| F418 | 790 | TTTCTATGCTUGTTTCCCGACUGT | R418 | 922 | AATAAATGTGUGAGTCAGTGUGCAG |
| F419 | 791 | GAUGAAAGCTCCTUCACCACAGAA | R419 | 923 | AAGCCTTCAUCCGGAGAGTGUA |
| F420 | 792 | CCTAGAGTGCUAACTTCCAGUAACG | R420 | 924 | TAATGCUGAAGACCCCAAAGATCUC |
| F421 | 793 | CTTGGAAGGCUAGGATTGACAAATUCT | R421 | 925 | GCCAAAUGAACAGACAAGUAAAAGACA |
| F422 | 794 | TTGTTACTCTTCUTGGCTCCAGTUG | R422 | 926 | GCAAATTGATAGUTGTTCTAGCAGUGAA |
| F423 | 795 | TTAGGTGGGCUTAGATTTCTACUGACT | R423 | 927 | CAGCAGTAUAAGCAATATGGAACUCGAA |
| F424 | 796 | TGCTTATAGGTUCAGCTTTCGTTTUG | R424 | 928 | GGAGCAGAATGGUCAAGTGATGAAUA |
| F425 | 797 | CCACTATGUAAGACAAAGGCUGGT | R425 | 929 | TTTTATAACTAGATTTCCTTCTCTCCATUCC |
| F426 | 798 | TCCGTTTGGTUAGTTCCCTGATTTAUC | R426 | 930 | AGAGCGTCCCCUCACAAATAAAUT |
| F427 | 799 | GTATTATCTGUGGCTCAGTAACAAAUGC | R427 | 931 | GAAAGAGTTCACUCCAAATCAGUAGAGA |
| F428 | 800 | TTAAAGCCTCAUGAGGATCACUGG | R428 | 932 | GGTTCTGAUGACTCACATGAUGGG |
| F429 | 801 | AGTTCATCACTUCTGGAAAACCACUC | R429 | 933 | CCCTGTGUGAGAGAAAAGAATGGAAUAA |
| F430 | 802 | GGGATCAGCATUCAGATCTACCTTTUT | R430 | 934 | AGGCUGAATTCTGTAAUAAAAGCAAACA |
| F431 | 803 | TTCAGCCTTTTCUACATTCATTCTGUCT | R431 | 935 | AGGGTAGTTCUGTTTCAAACTUGCAT |
| F432 | 804 | TACCCTGAUACTTTTCTGGAUGCCT | R432 | 936 | TGTATATTTTCAGCUGCTTGTGAATTTUCT |
| F433 | 805 | GAATCCAAACUGATTTCATCCCUGGT | R433 | 937 | GACAGTTCTGCAUACATGTAACTAGUGT |
| F434 | 806 | AGCTGCCUACCACAAATACAAATTAUG | R434 | 938 | GCGGAUACAACCUCAAAAGACG |
| F435 | 807 | CAGAGTTCUCACAGTTCCAAGGTUAG | R435 | 939 | TGUCAAGTTTCTCUCAGGAGGAAAAG |
| F436 | 808 | GAAGAAGAAGAAAACAAAUGGTTUACCAAG | R436 | 940 | AAGGAAAATAACUCCTGAACATCUAAAGA |
| F437 | 809 | ATCACCACGTCAUAGAAAGTAATTGUGC | R437 | 941 | TGTTGAAGAGCUATTGAAAATCATTTGUGC |
| F438 | 810 | CATTCAAACTTACTUGCAAAATATGTGGUC | R438 | 942 | ACAGCTCAAAGUTGAACTTATTCACUAAGA |
| F439 | 811 | GCATAGGAGATAAUCATAGGAATCCCAAAUT | R439 | 943 | ATGTTTTTCTAATGUGTTAAAGTTCATUGGA |
| F440 | 812 | AGTTGTAGTTGTUGAATTCAGTATCAUCCT | R440 | 944 | GCCAGTTTCCAUATGATCCATCTAUAGT |
| F441 | 813 | TGTGCCTTTCCUAAGGAATTTGCTAAUA | R441 | 945 | AGAAACCTTAACCAUCACTGCCGTATAUG |
| F442 | 814 | AAAAGATAAUGGAAAGGGAUGACACAGC | R442 | 946 | GCCACTTTTUGGGTATCTGCACUA |
| F443 | 815 | CTGTTAAGGCCCAGUTAGATCCUC | R443 | 947 | TTCAAGAGGUGTACAGGCAUCAG |
| F444 | 816 | AGGCAGTTCUAGAAGAATGAAAACTCUT | R444 | 948 | GGTCAGGAAAGAAUCCAAGTTTGGTAUA |
| F445 | 817 | TGTACCTAGCAUCTGCCTCAUAC | R445 | 949 | CCTCAGCTCCUAGACTTTCAGAAAUAUG |
| F446 | 818 | TAGACCTTTTCCUCTGCCCTTAUCA | R446 | 950 | AAACTCCATCUCAAACAAACAAAUAAT |
| F447 | 819 | CACATUATTACAGTGGAUGGAGAAGACA | R447 | 951 | CCTCCTGAATTTAGTGAATAAGGCUCT |
| F448 | 820 | CTTCTTTGGGUGTTTTATGCTTGGUT | R448 | 952 | GCAAAGCACGAACUGCUGT |
| F449 | 821 | GCAGAGCTUTATGAAGCAGUGAAGA | R449 | 953 | GTGAUGGCCAGAGAGTCUAAAACAG |
| F450 | 822 | TCTTAAATGGUCACAGGGTTATTCAGT | R450 | 954 | TGACATCCCUGATAAACCTTGUCC |
| F451 | 823 | TTCCATTGCATCUTTCTCATCTTTCUC | R451 | 955 | TTTTTGTCGCUGCTAACTGTATGUA |
| F452 | 824 | TTCACTUCAGCAAATTTTTAGAUCCAGAC | R452 | 956 | GCTCCAACTAAUCATAAGAGATTTUAAAAGAC |
| F453 | 825 | TGCCCCTTUCGTCTATTTGUCAG | R453 | 957 | AAGTAAGAAGGCCUGATTTGGATCT |
| F454 | 826 | GGAGATTTTCTGUGTTTTCTGCTAGUC | R454 | 958 | GCTATTTCCTUGATACTGGACTGUCAAA |

TABLE C-continued

| Primer Name | SEQ ID | Primer Sequence | Primer Name | SEQ ID | Primer Sequence |
|---|---|---|---|---|---|
| F455 | 827 | TGACAUACTTTGCAAUGAAGCAGAAAA | R455 | 959 | ATTCCTTGAGUTTACATTAACTUACCAGAAG |
| F456 | 828 | GGATCCTGATAUGTCTTGGTCAAGTUC | R456 | 960 | ATGACAATTATCAACCUCATCTGCTCUT |
| F457 | 829 | GGCACCAAAUACGAAACACCCAUA | R457 | 961 | TAAATTGUTTTCTCCTGTUGAACCAGACA |
| F458 | 830 | ATATCTGTCAGTGAAUCCACTAGGACUG | R458 | 962 | CCTGCTTATTTUTCTCACATTCTUCCG |
| F459 | 831 | TGAAGAAGCAUCUGAAACTGTATTTCCT | R459 | 963 | GGTTUAGAGACTTTCUCAAAGGCTTAGAT |
| F460 | 832 | GGACTACTACTATAUGTGCATTGAGAGTTUT | R460 | 964 | GTGTTUCACTGTCTGUCACAGAAG |
| F461 | 833 | TGGCTTATAAAATATUAATGTGCTTCTGTTUT | R461 | 965 | AAAACTATCTTCUTCAGAGGTATCUACAACT |
| F462 | 834 | GGTAAAAAUGCCTATTGGAUCCAAAGAG | R462 | 966 | GTGACGUACGGGGTTTUAGCAAG |
| F463 | 835 | AATCTACAAAAAGUAAGAACUAGCAAGACT | R463 | 967 | GGCTTCTGATTUGCTACATTTGAAUCT |
| F464 | 836 | AAGTGACAAAATCUCCAAGGAAGTTGUA | R464 | 968 | AGGTCTTTTTCTGAAAUATTTTGGTCACAUG |
| F465 | 837 | GAATTCTTUGCCACGTATTTCUAGCC | R465 | 969 | AGATATTGCCUGCTTTACUGCAAGAA |
| F466 | 838 | GGCTTCTTCAUTTCAGGGTAUCAAAAA | R466 | 970 | TGTATTTCCAGUCCACTTCAGAGG |
| F467 | 839 | AATACAUACTGTTTGCUCACAGAAGGAG | R467 | 971 | TTGTTTTCTTTTUCAAAGTGGATATUAAACCT |
| F468 | 840 | ACCGAAAGACCAAAAAUCAGAACTAATUAAC | R468 | 972 | CAGAAGGAATCGUCATCTATAAAACTATAUGT |
| F469 | 841 | TCACAGAAUGATTCUGAAGAACCAACT | R469 | 973 | CTGTAGTTTTTCCTUATTCATTTTGCTTCUT |
| F470 | 842 | ATTACCCCAGAAGCUGATTCTCUGT | R470 | 974 | TGGGATTGAAAGUCAGTATCACTGTAUT |
| F471 | 843 | TATATGATCATGAAAAUGCCAGCACUCT | R471 | 975 | GTTACCTTTGAGCUGTCTGACATTTUG |
| F472 | 844 | TTCCCATGGAAAAGAAUCAAGATGTAUG | R472 | 976 | TTGGATTACTCTUAGATTTGTGTTTTGGTUG |
| F473 | 845 | ACTGTCAATCCAGACUCTGAAGAACUT | R473 | 977 | ATGGTAGAGTTCUTGAAAATGGGTUC |
| F474 | 846 | CAGGUGAUAAACAAGCAACCCAAGT | R474 | 978 | GTATTTATCTATATUCAAGGAGATGTCCGAUT |
| F475 | 847 | TGGCATTAGAUAATCAAAGAAACUGAGC | R475 | 979 | GCCTTTTGGCUAGGTGTTAAATTAUGG |
| F476 | 848 | GAATCAGGAAGUCAGTTTGAATTTACUCAG | R476 | 980 | GTCTACCUGACCAATCGAUGGG |
| F477 | 849 | GCCTGTUGAAAAATGACTGUAACAAAAG | R477 | 981 | AGCTTTTUGCAGAGCTTCAGUAGA |
| F478 | 850 | TGAAGATAACAAAUATACTGCUGCCAGT | R478 | 982 | GGCCAGATAATTUAAGACATATGTTGUGC |
| F479 | 851 | AGGAGGGAAACACUCAGATAAAGAAGA | R479 | 983 | GCTCCGTTUAGTAGCAGTTAACUGT |
| F480 | 852 | TTTCAGACTGCAAGUGGGAAAAATAUT | R480 | 984 | GTCTGTTTCCUCATAACTTAGAATGUCCAT |
| F481 | 853 | TCTTCTTACAACUCCCTATACATTCUCAUT | R481 | 985 | TCACTGTGCGAAGACUTTTATGTCUA |
| F482 | 854 | CCAGTTGGTACUGGAAATCAACTAGUG | R482 | 986 | TTTCACTTTGUCCAAAGATTCCTTUGC |
| F483 | 855 | AAAAGAGCAAGGUACTAGTGAAAUCACC | R483 | 987 | AGAATTCTGCAUTTCTTTACACTTUGGG |
| F484 | 856 | AAAAACCTTGTTUCTATTGAGACTGUGG | R484 | 988 | GGACTGATTUGTGTAACAAGTUGCAG |
| F485 | 857 | AATTCAGCCTUAGCTTTTTACACAAGUT | R485 | 989 | TCATACAAATAATUTCCTACATAATCUGCAGT |
| F486 | 858 | TGACAAAAUCATCTCUCCGAAAAACAA | R486 | 990 | CAATACTGGCUCAATACCAGAAUCAAGT |
| F487 | 859 | AATAATTTTGAGGUAGGGCCACCUG | R487 | 991 | AACCTGCCAUAATTTTCGTTGGC |
| F488 | 860 | TCATAACTCTCUAGATAATGATGAATGUAGCA | R488 | 992 | GAAGTTTCCAAACUAACATCACAAGGUG |
| F489 | 861 | GTATAGGGAAGCUCATAAGTCAGTCUC | R489 | 993 | ATTTCAGAAAACACUTGTCTTGCGUT |
| F490 | 862 | AGAAGATAGUACCAAGCAAGTCTTTUCC | R490 | 994 | ACCACATTATAUGAAAAGCCTTTTUGGG |
| F491 | 863 | TAGTACAGCAAGUGGAAAGCAAGUT | R491 | 995 | GGUTCTCTTAUCAACACGAGGAAGT |
| F492 | 864 | CAGGCTTCACCUAAAAACGUAAAAAUG | R492 | 996 | CTGTCAGTTCAUCATCTTCCAUAAAAGC |
| F493 | 865 | ATGAAATAUTTCTTTTUAGGAGAACCCTCAAT | R493 | 997 | TATACCAUACCUAUAGAGGGAGAACAGATAT |

TABLE C-continued

| Primer Name | SEQ ID | Primer Sequence | Primer Name | SEQ ID | Primer Sequence |
|---|---|---|---|---|---|
| F494 | 866 | ATATATTUTCTCCCCATUGCAGCACAA | R494 | 998 | GCTTGAAGATTTUTCCAAAGTCAGAUGT |
| F495 | 867 | AGGACATCCAUTTTATCAAGTTTCUGCT | R495 | 999 | GTTTTGCTTTUGTCTGTTTTCCUCCAA |
| F496 | 868 | TGGCTCTGATGAUAGTAAAAATAAGATTAAUGA | R496 | 1000 | AGGCAAAAATTCAUCACACAAATTGUCA |
| F497 | 869 | GCTGTATACGUATGGCGTTTCUAAACAT | R497 | 1001 | TCATTGGAGGGUATGAGCCAUCC |

TABLE D

| Primer Name | SEQ ID | Primer Sequence | Primer Name | SEQ ID | Primer Sequence (target of PrimerC) |
|---|---|---|---|---|---|
| F498 | 1746 | GAGUGUGCGUGGCUCUCA | R498 | 1275 | UGCCAUCAUUCUUGAGGAGGAAG |
| F499 | 1002 | ACAACUGCAGCAAAGACUGGT | R499 | 1276 | UGCAAUCCCUGCCCCGGUT |
| F500 | 1003 | AGUUAAUUUUGGUUACAUCCCUCUCUGC | R500 | 1277 | GGAUUGCAGGCUCACCCCAAT |
| F501 | 1004 | AUCGAUCUGUUAGAAACCUCUCCAG | R501 | 1278 | CUGGAUUCCUCAUGGAAGCC |
| F502 | 1005 | GGACUCUGUAGGCUGCAGT | R502 | 1279 | AAAUCCAGUUCGUCCUGUUCA |
| F503 | 1006 | UGAGGCAGUCUUUACUCACCUG | R503 | 1280 | GAAACUGCCUCUUGACCUGUCC |
| F504 | 1007 | ACAAGCAAAGUCUCUAUGGUGAUUAUGT | R504 | 1281 | AGGACAGUCAUGUUGCCAGUAUUAAAAT |
| F505 | 1008 | CAACUACCAUCCAGCAACAGAAAAT | R505 | 1282 | CUUCCAUGACUUUGGCAAUCUGG |
| F506 | 1009 | GACAGAUGAGAGAAAUGCACUUAGAAGA | R506 | 1283 | GAACAUGUCCUAUUUGAAUUUUCCGACUT |
| F507 | 1010 | AGGAAUGUGUUUCUCCAUACAGGUC | R507 | 1284 | GACACAAAGACUGGCUUACAUUUUGAT |
| F508 | 1011 | CUUCAAGCAGUGAAAUACGUCCA | R508 | 1285 | AGGCUGACCACUUCUACUCUGT |
| F509 | 1012 | AGGGUCCAGGUUCUUCCAGA | R509 | 1286 | GCACUCAGGCUGGAUGAACAA |
| F510 | 1013 | GAUAGUUUGAGAGUCGUUCGAUUGC | R510 | 1287 | UGUCCAGGGCUAUCUGGAAGAUC |
| F511 | 1014 | CUCCACCACCUCCUCAAACAG | R511 | 1288 | GCAGCAUUUACUGCAGCUUG |
| F512 | 1015 | AUCAGCCAGGCACAAAGC | R512 | 1289 | UGACAGAAGUACAUCUGCUAAACAUGA |
| F513 | 1016 | CAUCUUUGUCAUCAGCUGAAGAUGAAAT | R513 | 1290 | CUCACAGGAUCUUCAGCUGACC |
| F514 | 1017 | GCCUAAAGAAUCAAAUGAAAACCAAGAGA | R514 | 1291 | ACUUUGUUGGCAUGGCAGAAAAT |
| F515 | 1018 | GUGACCCGGAGCACUUCC | R515 | 1292 | GCCGUGGUGCUGACCAT |
| F516 | 1019 | CCACAUUACAUACUUACCAUGCCACT | R516 | 1293 | GUGAUGAUUGGGGAGAUUCCUGAUG |
| F517 | 1020 | AUGGGACCCACUCCAUCG | R517 | 1294 | GCUCUGAUAGGAAAAUGAGAUCUACUGUT |
| F518 | 1021 | CCCUUCUAAGGACCCCCUCUUC | R518 | 1295 | CUCCAGCAGGGCUUCGAT |
| F519 | 1022 | CUCUGCCGGGCUUUGAUCUT | R519 | 1296 | GGACUUUGCAACUUCAACAAAACUC |
| F520 | 1023 | UACUACCGCCUCACACGCT | R520 | 1297 | CUAGGUGUCUCCCCCUGUAAG |
| F521 | 1024 | UUCCCUCUCUCCUUCUGCCUC | R521 | 1298 | AGGUUCAGGCCUUGCACT |
| F522 | 1025 | CCAGCAGAAGACAAAAAGACAAACA | R522 | 1299 | CCAGCCCAGGAAGCAAAGAG |
| F523 | 1026 | GGAGAGGGAGGAGAGCUAACT | R523 | 1300 | UUAAAACUGGUCUCGCUCUCCC |
| F524 | 1027 | AGAAGCUGUGCAUUUACACCGA | R524 | 1301 | GAAAGCGGGAAUCGCAGAAA |
| F525 | 1028 | UUUUGCUGAUGCUAUGCUCUCCAC | R525 | 1302 | GGAAGACCUCUUCUUCGCACUT |
| F526 | 1029 | CUGAUCCGCAAGCAUGCUC | R526 | 1303 | CAAAGAGCUCCCCCAUCUCC |
| F527 | 1030 | UGAGCUCGCUCACUUGUGAUG | R527 | 1304 | AGAAGAGCAUCUGGACUUAGCCAA |
| F528 | 1031 | CAGGAUCCAAAUUCGUUCUGUGC | R528 | 1305 | AUCAUCGACGGUGGGUACAUG |

TABLE D-continued

| Primer Name | SEQ ID | Primer Sequence | Primer Name | SEQ ID | Primer Sequence (target of PrimerC) |
|---|---|---|---|---|---|
| F529 | 1032 | UACUAACAACUCUGGUCUGGACCAT | R529 | 1306 | CGUUGGUCCUGACGGUACUG |
| F530 | 1033 | AUGCUAUUUGGACAAUAAACUCACCUUG | R530 | 1307 | CCAUUCUGAGGACUGCUGGUUUAUA |
| F531 | 1034 | CUCCUUACCUCAUACAGUGCAGAAA | R531 | 1308 | CCAGGACCAUCAUCCUACUGUAA |
| F532 | 1035 | CCCUGAGUGCAGCUUCGAUC | R532 | 1309 | GAGUGUUUGCUCCUCACUCUUC |
| F533 | 1036 | CGAUCAUGGAUGGCGGGUAC | R533 | 1310 | CUUCAGGUUUCCUUCUCUCAUGGUT |
| F534 | 1037 | UUUAUGAAUGGAGAGGCUGCUG | R534 | 1311 | GGAUGAGCUCACAGAGCUGC |
| F535 | 1038 | ACCUCUCACCCUUAUAAGUCUUCUGA | R535 | 1312 | UCAAAAGCAUGCCCAGACCUUT |
| F536 | 1039 | ACUUGAGCUUCCCUAGGACCA | R536 | 1313 | ACUUUGAGACUUCUGCUUUGCUC |
| F537 | 1040 | GGGAGACAAUACGUGUCGGG | R537 | 1314 | AUCGAAAACUGUGCAUCUACACC |
| F538 | 1041 | AAGACAGGUAGCGAUCCAGGUAG | R538 | 1315 | AGACCCAGCAGUGACUGT |
| F539 | 1042 | CUAGGUGCCCAUGUCCAUCUG | R539 | 1316 | ACAAGUAUAAUGAGCACCCCUUCT |
| F540 | 1043 | GAUGUCCAAUGUACCUGAGGCAA | R540 | 1317 | GUGGACACACCUGUAUUCCUGAG |
| F541 | 1044 | CAGCAGAAAGAGGACUCAGAAUAGAAAAUC | R541 | 1318 | CCGACCAGUUGGGCAAAAUC |
| F542 | 1045 | AGAGAUUCGCUUGUGUGGGUUAAA | R542 | 1319 | GCAGAAGUCUGUUUUCUUCAUGGUT |
| F543 | 1046 | ACCAGGGUUACCUUGAUCUCC | R543 | 1320 | AGGCCAUGUUGGGUUAAAGG |
| F544 | 1047 | ACUUCUCAAUUGCUACGGGCAAUC | R544 | 1321 | AGAAUCUACAGCUACCAGAUGGCA |
| F545 | 1048 | AGAUCUCGUGAACGAUGCAAT | R545 | 1322 | CCUAGUUUCCAGUGCAUCUGUACC |
| F546 | 1049 | UAUGUGGACUGCAGAAGAACUUCG | R546 | 1323 | GGUCCCCAUCCAUUCUUCCUAUUC |
| F547 | 1050 | UGUGGUUUAUGAACAAGCGAUUUGG | R547 | 1324 | UGUGGAGUGUUGGCUGUAUCUUUG |
| F548 | 1051 | GCUCAUAUCGAGAGGUAGCCAUUC | R548 | 1325 | CUCUGUAAGCGACUUUUGGUGAUAG |
| F549 | 1052 | GCAGACGAGCUUGACAUCAGAAA | R549 | 1326 | GCCCAACCAAUUGAGAAGUUUGUAA |
| F550 | 1053 | AAGACUUCGGGUGCUCUGUAC | R550 | 1327 | UUAGUCAGGAGUCUAAGCCAACAG |
| F551 | 1054 | GGGACAGACUGUCAUUCAAAAUAGGA | R551 | 1328 | CUUGCCCGCAUCUAUAGUUUCCA |
| F552 | 1055 | UGAAGAAAGUCCAGACCUCGGA | R552 | 1329 | AACUUCCGUUUUGAGUGUUUACUGAUUT |
| F553 | 1056 | GUCGACUGCCUGAUAAGACAUGA | R553 | 1330 | UUACUUGGAUAAAGUUCCAGAGCCT |
| F554 | 1057 | UAGUUUGGUUUCUCUGUCUGUUCGUG | R554 | 1331 | GCUUAUUGCCACCUACUUAACCUCT |
| F555 | 1058 | AAGCCUCCAUCGCUACCCT | R555 | 1332 | CUUCAGCCCUGCAGGGAAA |
| F556 | 1059 | UCAGGCGCCAAGUAGGT | R556 | 1333 | GGCAAGUUCAACAUUAUUCCCUUUUGUA |
| F557 | 1060 | AAAGCGGCUGUUAGUCACUGG | R557 | 1334 | UCUUCCUCAGGAUUGCCUUUACC |
| F558 | 1061 | UAAAGAUCAUGUCUCGGCUCAAGGA | R558 | 1335 | CAUACAGAGAGGGUCAUCAGUGAUAC |
| F559 | 1062 | GUGCACAGGUUAUUCUGAUUCCC | R559 | 1336 | GAAAGUCUCCCACAAAGUAACCC |
| F560 | 1063 | AGAAGGGCUAGGCCAAUUGAC | R560 | 1337 | AUAGUCAUAGCCGGGCCACA |
| F561 | 1064 | GUCAGCCUGAACAUAACAUCCUUG | R561 | 1338 | CCAGUUUAUUGUAUUUGCAUAGCACA |
| F562 | 1065 | GGGACCUCCGGUCAGAAAAC | R562 | 1339 | GGACCCAUUAGAACCAACUCCAUAAA |
| F563 | 1066 | CUCCCAACCAAGCUCUCUUGA | R563 | 1340 | UACCUUAUACACCGUGCCGAA |
| F564 | 1067 | CCCAGAAGGUGAGAAAGUUAAAAUUCC | R564 | 1341 | CCACACAGCAAAGCAGAAACUC |
| F565 | 1068 | AGGGCAUGAACUACUGGAGG | R565 | 1342 | UUCUUUCUCUUCCGCACCCA |
| F566 | 1069 | GCCUCUCCCUCCCUCCAGGAA | R566 | 1343 | GUGAGGCAGAUGCCCAGCA |
| F567 | 1070 | UGCCUCACCUCCACCGT | R567 | 1344 | CCAAUAUUGUCUUUGUGUUCCCGGACA |

TABLE D-continued

| Primer Name | SEQ ID | Primer Sequence | Primer Name | SEQ ID | Primer Sequence (target of PrimerC) |
|---|---|---|---|---|---|
| F568 | 1071 | AAGUGUAAGAAGUGCGAAGGG | R568 | 1345 | UGUGUUCCUUUGGAGGUGGC |
| F569 | 1072 | GCCUUUUUAACUGGUAGAGAUUGGUG | R569 | 1346 | GAUCCAGAGGAGGAGUAUGUGUGA |
| F570 | 1073 | UCAUCACCUUCCUUUCAUGCUCUC | R570 | 1347 | UCUUCCUCCAUCUCAUAGCUGUCG |
| F571 | 1074 | UCCUACGUGGUGUGUCUGAA | R571 | 1348 | CGUCCUGUUUCAGGCCAAG |
| F572 | 1075 | UGAUCAUCGAAUUCUCCAAAAUGGC | R572 | 1349 | AUUAGAGGGACUCUUCCCAAUGGA |
| F573 | 1076 | GAUGAGAUGUGGUACAAGCAUUCCA | R573 | 1350 | CCACGGUGGAAUUGUUGCUG |
| F574 | 1077 | CCCCUACAGCAUUGUUAAGAAAGUAUUT | R574 | 1351 | AUACCAGGCUAGUAUAGAUGCUUAGGG |
| F575 | 1078 | CUGGGACUAGCAUGCUGACC | R575 | 1352 | CAGACACCAACUCCCGGAAUC |
| F576 | 1079 | CUGCCUGUCUCUGGUUCUGT | R576 | 1353 | CAGAACUCUCUCCCCAGCAG |
| F577 | 1080 | ACUUGGAGUGAGUUUGGAUGGG | R577 | 1354 | CAGCUUCAUGUCUGUGCCG |
| F578 | 1081 | UCCUGAUCUCCUUAGACAACUACCUT | R578 | 1355 | UCACACCGCUGUGUUCCAUC |
| F579 | 1082 | UGUUCCUAUUUCAGCCCCACUC | R579 | 1356 | GUUGUGAGCGAUGAGCACGUA |
| F580 | 1083 | GGAAAGGGUCCUCUGAUCAUUGC | R580 | 1357 | AAAAUCGUGUCCUGGUAGCAGAG |
| F581 | 1084 | CGAGGGCCGGUAUACAUUCG | R581 | 1358 | CCCACCAAAAUGAGAAAACUGUGUT |
| F582 | 1085 | GAAUGUGAAAAUUCCAGUGGCCAT | R582 | 1359 | UGUCCUCCUAGCAGGAGAGG |
| F583 | 1086 | AUACCCUCUCAGCGUACCCUT | R583 | 1360 | CCGUGGAUGUCAGGCAGAUG |
| F584 | 1087 | AGCGCUUUGUGGUCAUCCA | R584 | 1361 | AUACUGGACUCAUCUCUCCUUCCC |
| F585 | 1088 | AAACUAGCCCUCAAUCCCUGAC | R585 | 1362 | AAAGACCACCCCAAGACC |
| F586 | 1089 | CACAGUUGGAGGACUUCCUCUUC | R586 | 1363 | AUAACUCCACACAUCACUCUGGT |
| F587 | 1090 | CUACAUGGGUGCUUCCCAUUCC | R587 | 1364 | UUGACAUGGUUGGGACUCUUGAC |
| F588 | 1091 | GUCCUCGUGGCCAUGAAUGAA | R588 | 1365 | UGGCAAACUUCCCAUCGUAGAC |
| F589 | 1092 | CCCAAUCCCCACACCAAGUAUC | R589 | 1366 | GUUGAUCAUUGUUCCUUCCCUCA |
| F590 | 1093 | AUGUUCCUCCCUCAUCUCUAAUGGT | R590 | 1367 | CCAUCUUGUCAGGAGGACAGG |
| F591 | 1094 | UGGACUCGAGCAACAUUGAUGG | R591 | 1368 | GGCAGGAUCUCUAACCCAUUGAG |
| F592 | 1095 | GCUGAAGUACCAGACCUGCUA | R592 | 1369 | CUCAGCAGGUAACUCACACUUG |
| F593 | 1096 | GGAUUUGACCCUCCAUGAUCAGG | R593 | 1370 | CUUCCCUGGGUGCUCCAT |
| F594 | 1097 | UCACUCUCUCUCUGCGCAUUC | R594 | 1371 | GUGGAUAUGGUCCUUCUCUUCC |
| F595 | 1098 | CAUGAAGUGCAAGAACGUGGT | R595 | 1372 | GGCUAGUGGGCGCAUGUAG |
| F596 | 1099 | GCGGAUCAGAGCCUCAAAC | R596 | 1373 | AUCAAAGUCCAGCACCAGCA |
| F597 | 1100 | ACUGUCCUGUUUUGAUAUCCCAGAUUUT | R597 | 1374 | GGGAAUUGCAUUCACACGUUAACA |
| F598 | 1101 | CUGUCUCAAUAUCCCAAACCCUAAG | R598 | 1375 | UUUGUUUUGUUUUUCUGUUUCUCCCUCUG |
| F599 | 1102 | UAUUAGUAUGCCCCUGCAACGUG | R599 | 1376 | GAGGGUUGUUAGUGGAGCAUAUGA |
| F600 | 1103 | CAACCUCCUGCCAUCAUAUUGA | R600 | 1377 | UGAGACAGGCCAGUGUUUACAUG |
| F601 | 1104 | CAACCAUGACAAGAUUUUCCCUUACC | R601 | 1378 | GAGACUGGAGAAUGUAUACACACCUT |
| F602 | 1105 | UGCCUGUGGAGGAACUUUUCA | R602 | 1379 | CGACAUCUCCUCGGGCUT |
| F603 | 1106 | CUUCCUCUCGCCCAUCACA | R603 | 1380 | CGUAGAGCUCCGGGUGUC |
| F604 | 1107 | AGUGCCUCCUCUCCCAUCUT | R604 | 1381 | CUACCCAGGGCCACUGUUUT |
| F605 | 1108 | CACUCCUUGCUUCUCAGAUGAAACC | R605 | 1382 | GGGACAUUCACCACAUCGACUA |
| F606 | 1109 | CAGGUACUCCCGCAGGUUG | R606 | 1383 | UGGCCUCUUCUCCUGUGC |

TABLE D-continued

| Primer Name | SEQ ID | Primer Sequence | Primer Name | SEQ ID | Primer Sequence (target of PrimerC) |
|---|---|---|---|---|---|
| F607 | 1110 | CACGCAUACGGUUUGGUUUGG | R607 | 1384 | CUUCUUCUUCCCAUAGAUGCUCUCC |
| F608 | 1111 | CUAGAAGCUCUCUAUCCCACACCT | R608 | 1385 | GAGGCAUUAUUUGACCGGAUCUAC |
| F609 | 1112 | CAAGGAAUGCCUUCAAAAAGUUGGG | R609 | 1386 | CUGAGUAUGAGCUUCCCGAAGAC |
| F610 | 1113 | AGAUGAUGAUCUCCAGGUACAGG | R610 | 1387 | CCUGCUAACACCCUGUUCG |
| F611 | 1114 | CGGCACUGCAUGCAAUUUCUT | R611 | 1388 | CUGCCUGUCUCUCUUGGCUUT |
| F612 | 1115 | CCAUUUAUAGCUGAGUCUCCAUCCUG | R612 | 1389 | UAUGAACUUCCAGAGGACCCAAAUG |
| F613 | 1116 | CCCAGUUGUGGGUACCUUUAGAT | R613 | 1390 | GGAAAAGAACGGCAGUAAAUACGG |
| F614 | 1117 | CUUUCAAACGAGUCAAGCAAGAAUGG | R614 | 1391 | AAUACGGGUCCAUCAAUCACACG |
| F615 | 1118 | ACCACACUUUCCAUAAUGAGGCT | R615 | 1392 | CAGUACUUGGUAUUCUGUGCUAGGA |
| F616 | 1119 | CUUUUCCAUCUUUUCUGUGUUGGUC | R616 | 1393 | GGAAGCUGUCCAUCAGUAUACAUUC |
| F617 | 1120 | CAGACAAAUCCCAAAACAAACCUGA | R617 | 1394 | GGCCCUCCUUCAGUUUAGUUGAG |
| F618 | 1121 | GUAGCUACAGGACUCAGAUACGUG | R618 | 1395 | GGUGGAGGCGAUAGUGGAUAG |
| F619 | 1122 | GUAUUUGGGCGAAUGCAGUUUUUC | R619 | 1396 | AGAUGGAGAUGAUGAAGAUGAUUGGG |
| F620 | 1123 | CCAGAGAAAAGAGAGUUACUCACACA | R620 | 1397 | GUCAAGUGGAUGGCUCCAGAAG |
| F621 | 1124 | ACUGUGUUACUGCCAUCGACUUAC | R621 | 1398 | CCAGAAAUGUUUUGGUAACAGAAAACAA |
| F622 | 1125 | GGUAUUCUCGGAGGUUGCCUUT | R622 | 1399 | AUUCUCUCUUUAGGGAGCUUCUCUUC |
| F623 | 1126 | CUUGGUCGUGUUCUUCAUUCGG | R623 | 1400 | UGGAAGAGAAAAGGAGAUUACAGCUUC |
| F624 | 1127 | ACCACUGUGGAGGCAUUUG | R624 | 1401 | AUUGGUCUCUCAUUCUCCCAUCC |
| F625 | 1128 | AGUGAAGAUCUCCCACAUUAACACC | R625 | 1402 | GUUUAGGUUUUGGCAACGUGGAT |
| F626 | 1129 | CUUGCCCAAAGCAACCUUCUC | R626 | 1403 | UCACCAGAUGCUAUGUGCUAAUCC |
| F627 | 1130 | AUUGGUUGCGGCCAUCUCT | R627 | 1404 | UCCUACCGUGUCCACACC |
| F628 | 1131 | ACCAAUUUCAUAGGCGUGGC | R628 | 1405 | GGCAUGGGACAGAGUCGUT |
| F629 | 1132 | GCCUAUCGCUCUGCUCUCUC | R629 | 1406 | UUGUGCAAGGAGAGAACCUCUA |
| F630 | 1133 | UAACCCAGCGACGAACUUUCC | R630 | 1407 | CCUAUCCCAGAACUGGAGACAGAAA |
| F631 | 1134 | GCCCCUGAGCGUCAUCUG | R631 | 1408 | UGUACACCUUGCAGUGGAACT |
| F632 | 1135 | CUGGUGGAGGCUGACGA | R632 | 1409 | AGCCCAGGCCUUUCUUGG |
| F633 | 1136 | ACAACGUGAUGAAGAUCGCAGA | R633 | 1410 | ACUGGCAUGACCCCCAC |
| F634 | 1137 | GGGAGAUCUUCACGCUGGG | R634 | 1411 | UGCCACUCACAGGUCGT |
| F635 | 1138 | GUCUGAGGAGCCCGUGT | R635 | 1412 | GCAGAAACUCCCGCAGGT |
| F636 | 1139 | UCCUCGGAGCAGUGAGGG | R636 | 1413 | ACUCCAGAUACUGCAUGCCT |
| F637 | 1140 | AGCCUCUCCACGCUCCCUC | R637 | 1414 | ACUCCCGCAGGUUUCCC |
| F638 | 1141 | CUCACAUUGCCCCUGACAACAUA | R638 | 1415 | ACGGGAAAGUGGUGAAGAUAUGUG |
| F639 | 1142 | GUGUCCUUUCAGGAUGGUGGAUG | R639 | 1416 | AGAAACAUGUGGAUGUCACGUUCUC |
| F640 | 1143 | GGUGACAUUUUCAAAGCAGUGUAUCC | R640 | 1417 | UGUUAACCUUGCAGAAUGGUCGAT |
| F641 | 1144 | GGGUAUUCGAUGAUCCCUGUGG | R641 | 1418 | AUGACUUGGACCGCGUAGC |
| F642 | 1145 | CCUCCCCACCAGCAUGUUT | R642 | 1419 | GCAUCCUACCGUUGAAGCACT |
| F643 | 1146 | GGCUUUGGUGAGAUCCAUUGAC | R643 | 1420 | CACCUGGAACUUGGUCUCAAAGAUT |
| F644 | 1147 | GCAUGUACUGGUCCCGCAT | R644 | 1421 | AUUCCUACCGGAAGCAGGT |
| F645 | 1148 | UGGUUCUGGAUCAGCUGGAUG | R645 | 1422 | AUGACGGAAUAUAAGCUGGUGGT |

TABLE D-continued

| Primer Name | SEQ ID | Primer Sequence | Primer Name | SEQ ID | Primer Sequence (target of PrimerC) |
|---|---|---|---|---|---|
| R646 | 1149 | UGCCAACAUGACUUACUUGAUCC | R646 | 1423 | AAAAUAUCCCCCGGCUUGUGAG |
| F647 | 1150 | GGACUAGGCGUGGGAUGUUUUT | R647 | 1424 | GAAGAAGAUGUGGAAAAGUCCCAAUG |
| F648 | 1151 | AGUGGAUCCCCUCUCCACC | R648 | 1425 | GUCCCUGGCUGGACCAA |
| F649 | 1152 | GAGGUUUUCCAGCACUCUGACAUAT | R649 | 1426 | CACACAUUGGAGCAUGCCAUUC |
| F650 | 1153 | CGGUUGAAUGUAAGGCUUACAACG | R650 | 1427 | AGCCUAAACAUCCCCUUAAAUUGGAUT |
| F651 | 1154 | GAACGGGAAGCCCUCAUGUC | R651 | 1428 | CGGCUUUACCUCCAAUGGUG |
| F652 | 1155 | CCUUACUCAUGGUCGGAUCACAAAG | R652 | 1429 | GCAGAGAAUGGGUACUCACGUUUC |
| F653 | 1156 | CCCUUUCUCCCCACAGAAAC | R653 | 1430 | UCAGCCUGUUUCUGGGAAACT |
| F654 | 1157 | GUAGAGCAAAUCCAUCCCCACA | R654 | 1431 | UGGAGAGAACAAAUAAAUGGUUACCUG |
| F655 | 1158 | UGUGCUUUUAGGGCCCACC | R655 | 1432 | GAUUCUUAUAAAGUGCAGCUUCUGCAT |
| F656 | 1159 | UCUGUUCAAUUUUGUUGAGCUUCUGAAUT | R656 | 1433 | CAGACGUCACUUUCAAACGUGUAT |
| F657 | 1160 | UCAGUGUUACUUACCUGUCUUGUCUUT | R657 | 1434 | CAGGCUCAGGACUUAGCAAGAA |
| F658 | 1161 | UGAAUUAGCUGUAUCGUCAAGGCA | R658 | 1435 | UAAGGCCUGCUGAAAAUGACUGAA |
| F659 | 1162 | UGUUUCUCCCUUCUCAGGAUUCCUA | R659 | 1436 | AGUCCUCAUGUACUGGUCCCT |
| F660 | 1163 | AAACCCGCAAUCCGGAAC | R660 | 1437 | CUGAUCUCGCCAUCGCUGUA |
| F661 | 1164 | CCCUCCAACAUCCUAGUCAACUC | R661 | 1438 | GUUCAUACCGACAUGUAGGACCUT |
| F662 | 1165 | GCUAGAGCUUGAUGAGCAGCAG | R662 | 1439 | UCAAAGUCGUCAUCCUUCAGUUC |
| F663 | 1166 | CCAUGGAGUCGAUGAGCUGG | R663 | 1440 | CCUCCAGAUGUGAAGCCCT |
| F664 | 1167 | GCCCAGCUCUGAGAUCCUUUC | R664 | 1441 | GCUGGAGGAGCUGGAACUT |
| F665 | 1168 | CAUUUCUGACAACUGAACUGCUCUC | R665 | 1442 | UAAACAGGAGCACGAGGAUGC |
| F666 | 1169 | UUACCAGCUUGUUCAUGUCUGGAUUC | R666 | 1443 | UAUUCAUCACGGCGCGCUT |
| F667 | 1170 | ACUGAGCUUGUUGGAAUAAGGAUGUT | R667 | 1444 | GAGUCCAGGAGAAAAUUCACAUGAGG |
| F668 | 1171 | UUGUAAGUGCCCGAAGUGUAAG | R668 | 1445 | ACAACCCACUGAGGUAUAUGUAUAGGUAUT |
| F669 | 1172 | UACGCAGUGCUAACCAAGUUCUUUC | R669 | 1446 | AGCACAGUGAAUUUCUUGCCAUC |
| F670 | 1173 | CAGUCAAGGUUGCUGAUUUUGGUC | R670 | 1447 | GGUGGUAAACUUUUGAGUUUGCAGA |
| F671 | 1174 | UAUGGAUGUUGCCAAGCUGUAUUCUG | R671 | 1448 | GGGAAGGAGUGGUACAACAGAT |
| F672 | 1175 | GGUGGUCCUACCAUACAUGAAACAT | R672 | 1449 | ACAGCUAGUUUGCCAGUUAGUAAGC |
| F673 | 1176 | GCAAGCAAAAAGUUUGUCCACAGAG | R673 | 1450 | CACUUAAUUUGGAUUGUGGCACAGA |
| F674 | 1177 | ACAUCUCUCACCUCAUCUGUCCT | R674 | 1451 | CUCUUGUCAUCAGCUCCCAGA |
| F675 | 1178 | UCCCUGUAGUCCCGGAUGAG | R675 | 1452 | GCGCCAGCAUCCAGAGAUAC |
| F676 | 1179 | AAUUGUUGCCAUUUCAGGGUUUCUG | R676 | 1453 | GAGCGUGUGAUGCAGCUCUT |
| F677 | 1180 | CUCACCUAUCUCCCAGGCCUAAAAUA | R677 | 1454 | GUUUGACCGAAGAACCAAUUAUACCC |
| F678 | 1181 | ACAAACGAGAUGCCUCUUCCAG | R678 | 1455 | GAUGCUUCUCUCCUUCUUCUCUUGG |
| F679 | 1182 | GGCUGUCGUGGUAGACUUAGA | R679 | 1456 | UUCCCCAACCCACAUUUCCUUUAUAG |
| F680 | 1183 | CUGAGUGUAUCCUGGAGGUUGUUG | R680 | 1457 | CCAAAACCCUCCUGAUGUACACG |
| F681 | 1184 | GCUUGGUUCUGAUGUUUGUAGUGUAG | R681 | 1458 | GUCACAGCUCCAGUGUCUGUC |
| F682 | 1185 | UCCUUGUUGGUGUCCAUUUUCUUGT | R682 | 1459 | GAGAUCCAGGCUACCUGGUAUGAG |
| F683 | 1186 | ACAUGCCAUCAUUCUAGGAAGCUC | R683 | 1460 | AAGGACGACCCAGAGCUGAT |
| F684 | 1187 | CAGGACCCGCUUCUCUGAAAG | R684 | 1461 | AAAUUAAAGGCAAGUGGACUUCGG |

TABLE D-continued

| Primer Name | SEQ ID | Primer Sequence | Primer Name | SEQ ID | Primer Sequence (target of PrimerC) |
|---|---|---|---|---|---|
| F685 | 1188 | AAGACCCCUUUAACUCAAGACUGC | R685 | 1462 | CUGUUGGUGAAGCUAACGUUGAG |
| F686 | 1189 | UGCUCCAUGAGGAGACACC | R686 | 1463 | AAAAUGGGAAAGGUAUCCAGCC |
| F687 | 1190 | AAUGUAACCUUGCUAAAGGAGUGAUUUCT | R687 | 1464 | CCACAGAAACAACAUCGAUUUCUUCC |
| F688 | 1191 | AACUGGCAAAUAUAUCAUUGAGCCAAAUC | R688 | 1465 | ACAGGGAUGGUGGUGGUT |
| F689 | 1192 | GGUGUGAAAUGACUGAGUACAAACUG | R689 | 1466 | UUCUGGAUUAGCUGGAUUGUCAGUG |
| F690 | 1193 | AUGGUGAAACCUGUUUGUUGGACAT | R690 | 1467 | GGCAAAUACACAGAGGAAGCCUT |
| F691 | 1194 | CCUGCUCAUGGUCUUUGAGUAUAUG | R691 | 1468 | AUGUCUAUAGGGAAGGGAAGACG |
| F692 | 1195 | GCCACACGCAACUGUCUAG | R692 | 1469 | GUCGGUGCUGUAGAUAUCCCT |
| F693 | 1196 | GACAAUCCUUGCUUACCUGAGGAAC | R693 | 1470 | ACAUUGUCAAGUUCUAUGGAGUGUGC |
| F694 | 1197 | GCUCGGGAUCCAUAUGUGGUAAT | R694 | 1471 | CUGGCUGAAGGUGGGUUUGAUT |
| F695 | 1198 | GGCCCUAUACUUAGGCCCUUUT | R695 | 1472 | AAGUCACACGGCCCUCC |
| F696 | 1199 | AACUCACGGUGGCUGCT | R696 | 1473 | UUGUUCUCAUUGGCUUCAAAGAUCUUUA |
| F697 | 1200 | UGUCCUGGUCAUUUAUAGAAACCGA | R697 | 1474 | UCUCUUGGAAACUCCCAUCUUGAG |
| F698 | 1201 | UCUCAUGUCUGAACUGAAGAUAAUGACT | R698 | 1475 | UGAGCCCACCUGACUUGG |
| F699 | 1202 | UUGGUAGCUCAGCUGGACUGAUAT | R699 | 1476 | ACAUGAGAGCUUGUUUUUCACUGG |
| F700 | 1203 | AUGAAGCAGGCUGAUACUACACAG | R700 | 1477 | AGAGUGAUCUCUGGAUGUCGGAAUA |
| F701 | 1204 | UUGUGAAGAUCUGUGACUUUGGC | R701 | 1478 | ACCAGUGAGGGAAGUGAGGAC |
| F702 | 1205 | CCUUUGGGUUAUAAAUAGUGCACUCAGA | R702 | 1479 | UAAGCAUCAGCAUUUGACUUUACCUUAT |
| F703 | 1206 | GGGAAGAAAAGUGUUUUGAAAUGUGUT | R703 | 1480 | CAAACAAGUUUAUAUUUCCCCAUGCCA |
| F704 | 1207 | UGGCUUUGAAUCUUUGGCCAGUA | R704 | 1481 | GAUUUGAUCCAGUAACACCAAUAGGGUT |
| F705 | 1208 | GUCGAGGCAAUGGAAAAGCUC | R705 | 1482 | AAACACAAACUAGAGUCACACCCUT |
| F706 | 1209 | AGAACAGCUCAAAGCAAUUUCUACA | R706 | 1483 | AGCACUUACCUGUGACUCCAUAG |
| F707 | 1210 | AGCAAGAGGCUUUGGAGUAUUUCAUG | R707 | 1484 | UUGUGUGGAAGAUCCAAUCCAUUUUUG |
| F708 | 1211 | UGUUCAUGCUGUGUAUGUAAUAGAAUGUT | R708 | 1485 | AACCAUAUCAAAUUCACACUGGC |
| F709 | 1212 | CUGGAAUGCCAGAACUACAAUCUUUUGA | R709 | 1486 | CUCUUGCUCAGUUUUAUCUAAGGCUAG |
| F710 | 1213 | CUCAAGAAGCAGAAAGGGAAGAAUUUUT | R710 | 1487 | CAUACCAAUUUCUCGAUUGAGGAUCUUUUC |
| F711 | 1214 | UGACAGCCAUCAUCAAAGAGAUCG | R711 | 1488 | CCGCAGAAAUGGAUACAGGUC |
| F712 | 1215 | GGGAUUUCCUGCAGAAAGACUUGA | R712 | 1489 | AGAAAAUCAAAGCAUUCUUACCUUACUACA |
| F713 | 1216 | AAGGCACAAGAGGCCCUAG | R713 | 1490 | UCCAGGAAGAGGAAAGGAAAAACAT |
| F714 | 1217 | ACCAAUGGCUAAGUGAAGAUGACAAT | R714 | 1491 | AUUUGCCCCGAUGUAAUAAAUAUGCAC |
| F715 | 1218 | AGGUUAUCUUUUUACCACAGUUGCAC | R715 | 1492 | GUCAAGAUCUUCACAAAAGGGUUUGA |
| F716 | 1219 | UUUUCUGUCCACCAGGGAGUAACUA | R716 | 1493 | GCCACUGGUCUAUAAUCCAGAUGA |
| F717 | 1220 | GACAAGUUCAUGUACUUUGAGUUCCC | R717 | 1494 | GCAUCUUGUUCUGUUUGUGGAAGAA |
| F718 | 1221 | AGCAAAUAAAGACAAAGCCAACCG | R718 | 1495 | UCAACAACCCCCACAAAAUGUUT |
| F719 | 1222 | AGUUUAAGAUGAGUCAUAUUUGUGGGUUUT | R719 | 1496 | UGGAUUUGACGGCUCCUCUAC |
| F720 | 1223 | CUGACCAUGUGGACAUUAGGUGUG | R720 | 1497 | UUAACACCUCCAGUCCCUCAUCUG |
| F721 | 1224 | CCUUCCCUCGGGAAAACUGAC | R721 | 1498 | UAAGAUGUCCACUGCUGUUCCUUCAUA |
| F722 | 1225 | GUUUGGUUUUGUAGGUCUUGUGGAUG | R722 | 1499 | CUUCAGCCAAGGCAGCAAUG |
| F723 | 1226 | GAGGUGGCCUGAUCUUCACAA | R723 | 1500 | GAUAUGGAUUCACACAGACACUAUCACA |

TABLE D-continued

| Primer Name | SEQ ID | Primer Sequence | Primer Name | SEQ ID | Primer Sequence (target of PrimerC) |
|---|---|---|---|---|---|
| F724 | 1227 | CGCUUAUGCAUACUCAGGAUGAGUT | R724 | 1501 | CAAGGUGUUUCUUUGAUGCUCUGT |
| F725 | 1228 | UAAGGUUCCUUCAAGCUGCCCUA | R725 | 1502 | CCUGUGGACAUUGGAGAGUUGAC |
| F726 | 1229 | CAUGGGAGGAUGUUCUUUCCCAUUT | R726 | 1503 | GAACCUUAAAUGUCUCUCCUACCUGA |
| F727 | 1230 | UUUUCUUCCUAAGGUUGCACAUAGG | R727 | 1504 | AAGGCACCUGACCCAAACA |
| F728 | 1231 | AUUUUUGGCUUCCUGGCCUUT | R728 | 1505 | GCACAUAGUCCCGGAAGCUG |
| F729 | 1232 | GGAAAGCCUCACCUGUCUACG | R729 | 1506 | UUCUUGAUCUCACAGUCAGGGAUG |
| F730 | 1233 | UCAAGAAUCGCCCGAGCC | R730 | 1507 | AUGAGCAGCGUGGCCUT |
| F731 | 1234 | UUGGUUCGGACAGACAACCC | R731 | 1508 | UAGCUGUGCAUGUCCUGGUG |
| F732 | 1235 | CUCUGCACAGCUCCAAUGAGAC | R732 | 1509 | UAGGUGAGGACCACAAACCAAAC |
| F733 | 1236 | GCUACAAGAACUACCGAUACCGT | R733 | 1510 | UGGUCUUCACUCACCUCGGAT |
| F734 | 1237 | CUCGGAGAGGAGCCAUACUG | R734 | 1511 | UUCCUCCAGAAGCUUGAACUCT |
| F735 | 1238 | UAUAAUGACAGUUAACCCUGCCAGGA | R735 | 1512 | CCCAAGCCUGGGACCUCUAUUAT |
| F736 | 1239 | AGGAAGAGCACAGUCACUUUGA | R736 | 1513 | CAUGCUGGACCUUCUGCAC |
| F737 | 1240 | CAGUGGAGCGAAUUCCUUUGGA | R737 | 1514 | AGACUGCUAAGGCAUAGGAAUUUCG |
| F738 | 1241 | UUGGGUCGUUGGGCAUUCC | R738 | 1515 | UUUGACUCUGUCUCCUCUUGUCUUCT |
| F739 | 1242 | CAGUUCACAGUGCAGCGAAAA | R739 | 1516 | GAGAUGAAGCAAACAACAGUGGAG |
| F740 | 1243 | AAAUAUCUACACACAGGUCUACAAGGUC | R740 | 1517 | AUUUCAUGCAAACUAGAUAACUACCUGUAA |
| F741 | 1244 | CAUCCGGGCUUUACGCAAAUAA | R741 | 1518 | UGGAGUUUGUCUGCUGAAUGAACC |
| F742 | 1245 | GCCUCCUUCAGGAAUUCAAUCUUCT | R742 | 1519 | AGCUCACAGAAAUGUCUGCUAUACUG |
| F743 | 1246 | AUGAGUUCUGGGCACUGGG | R743 | 1520 | AUGAGGAGUGUGUACUCUUGCAUC |
| F744 | 1247 | GAUGCAAACUCUUGCACAAAUGCT | R744 | 1521 | GCCAAGAGUUACGGGAUUCCAT |
| F745 | 1248 | GAACCCCGAGGGCAAAUACAG | R745 | 1522 | AGGAUGCCUGACCAGUUAGAGG |
| F746 | 1249 | CAGUUCGUGGGCUUGUUUUGUAUC | R746 | 1523 | AAAAGACUCGGAUGAUGUACCUAUGG |
| F747 | 1250 | UUAAAGCUGGCUAUGGCACCUG | R747 | 1524 | CACUCACCCUGGAUGUCUUCG |
| F748 | 1251 | CAUCUCUCACCAUCCCAAGG | R748 | 1525 | CACCGUAGCUCCAGACAUCA |
| F749 | 1252 | AUACGCAGCCUGUACCCA | R749 | 1526 | AAGGAGAAGAGGACAGCGG |
| F750 | 1253 | CACCUCUCUCAAGAGUUUGGAUGG | R750 | 1527 | CCUGCACUUCUAGGCACUUACUAA |
| F751 | 1254 | AGAUUGCGAGAGAGCUGCAT | R751 | 1528 | GGCACUUGCACAGAGAUGAT |
| F752 | 1255 | CUGUGCUGCAUUUCAGAGAACG | R752 | 1529 | AUUUGAUGACAUGUGGGUGGUUG |
| F753 | 1256 | AAGACCCAAGCUGCCUGAC | R753 | 1530 | GGAGCCGUAUUUGGCGT |
| F754 | 1257 | GCUAUUUUCCUCACAGCUCGUUC | R754 | 1531 | CCUCUUCACGUAGGAAUCCUCUUC |
| F755 | 1258 | CUCCUUCCUAGAGAGUUAGAGUAACUUC | R755 | 1532 | AUCACUUUGCGUGGUGUAGAUAUGAT |
| F756 | 1259 | GAGCCUGUUUUGUGUCUACUGUUCUA | R756 | 1533 | AGGACUCUGAAGAUGUACCUAUGGT |
| F757 | 1260 | CUCUUGCAGCAGCCAGACT | R757 | 1534 | ACAGUUUCCAUAGGUCUGAAAAUGUUT |
| F758 | 1261 | CCAUGGGACUGACUUUCUGC | R758 | 1535 | AGCCCAACCCUUGUCCUUAC |
| F759 | 1262 | GCUGAGGACCUGGUCCUCT | R759 | 1536 | GGGACAGCAUCAAAUCAUCCAUUG |
| F760 | 1263 | CUGCACCAGCAGCUCCUA | R760 | 1537 | CCAGACGGAAACCGUAGCUG |
| F761 | 1264 | CCCGGACGAUAUUGAACAAUGGT | R761 | 1538 | GGAGCAGCCUCUGGCAUT |
| F762 | 1265 | AGCCUCACCACGAGCUG | R762 | 1539 | GGCAAGGAAAGGUGAUAAAAGUGAAUCT |

TABLE D-continued

| Primer Name | SEQ ID | Primer Sequence | Primer Name | SEQ ID | Primer Sequence (target of PrimerC) |
|---|---|---|---|---|---|
| F763 | 1266 | CACCUUUCCUUGCCUCUUUCCUA | R763 | 1540 | ACUUGAUAAGAGGUCCCAAGACUUAGT |
| F764 | 1267 | CUCAAGGAUGCCCAGGCT | R764 | 1541 | CCUAUGGCUUUCCAACCUAGGA |
| F765 | 1268 | CCUCCCUGCUUCUGUCUCCUA | R765 | 1542 | CCCUUCUGUCUUGAACAUGAGUUUT |
| F766 | 1269 | CCAGUUGCAAACCAGACCUC | R766 | 1543 | UGUGGAGUAUUUGGAUGACAGAAACA |
| F767 | 1270 | ACUCCACACGCAAAUUUCCUUC | R767 | 1544 | AGGCCUCUGAUUCCUCACUGAT |
| F768 | 1271 | AGGGUGGCAAGUGGCUC | R768 | 1545 | CCUAGGUUGGCUCUGACUGT |
| F769 | 1272 | GAGGCUCCCCUUUCUUGC | R769 | 1546 | UGCCUCUUGCUUCUCUUUUCCT |
| F770 | 1273 | CUGUGACUGCUUGUAGAUGGC | R770 | 1547 | UUCCUACAGUACUCCCCUGC |
| F771 | 1274 | CUGUCGUCUCUCCAGCCC | R771 | 1548 | AGUCACAGCACAUGACGGA |
| F772 | 1549 | GGAGGAGGCGAUGGCUACUA | R772a | 1574 | CUGCAGUUAGAGGUUGGUGACA |
|  |  |  | R772b | 1575 | CCCGCCAAGCACGUAUACU |
| F773 | 1550 | GGAGACCUACAAACUGAAGUGCAA | R773a | 1576 | CCGGAAGAGGAGUAGCUGAC |
|  |  |  | R773b | 1577 | CUCCUAGAGUUUUUCCAAGAACCAAGU |
| F774 | 1551 | CCAUGCAGAAUGCCACCAAGUA | R774 | 1578 | AUUUGCAGCUACUACUCUGAACUGAA |
| F775 | 1552 | CAGGCACUCCUUGGAGCAA | R775 | 1579 | UCAGUGGGAUUGUAACAACCAGAAAU |
| F776 | 1553 | CUGUUUGAAAUGAGCAGGCACU | R776 | 1580 | GCACUGUCACCCCUUCCUUG |
| F777 | 1554 | ACUGGAGGACCCGUCUUCU |  |  |  |
| F778 | 1555 | AGACCUUAAGGGAACAGCUCUCAU |  |  |  |
| F779 | 1556 | GUGGAGUCAUGCUUAUAUGGAGCAAA | R779 | 1581 | GCUCCAUCUGCAUGGCUUG |
| F780 | 1557 | GACAGAAAAUAAUUCUGUGGGAUCAU |  |  |  |
| F781 | 1558 | UCCUGAAAGAGAAAUAGAGGUUCCUGAU |  |  |  |
| F782 | 1559 | GGTGGCCATAGGAACGCA |  |  |  |
| F783 | 1560 | UGGAUGCAGAAACCAGAGAUCUAGU |  |  |  |
| F784 | 1561 | CUGGUCCCCAGACAACAAGUAU |  |  |  |
| F785 | 1562 | GAAGAUCAUGUGGCCUCAGUGAA | R780 | 1582 | GGGUUGUAGUCGGUCAUGAUGG |
| F786 | 1563 | GUCGAAAAUACCUUCAACACCCAAAUU | R781 | 1583 | CCUGGCCCUUGAAGCACUA |
|  |  |  | R782 | 1584 | ACCCCAUCUUCCCCAUCCAU |
| F787 | 1564 | CCAAAACUGCAGACAAGCAUAAAGAUG | R786 | 1585 | CUACCUCACAGUGACUGCAGUUUA |
|  |  |  | R787 | 1586 | AGAGAGGAUCAGCGAGAGUGG |
| F788 | 1565 | CAGGCAGAAGUUGAUCGACUCU | R788 | 1587 | GUCUCGUUGCCCAAAUUGAU |
| F789 | 1566 | AAAGAAGAGUGCACAAAUGUUAGAGGA | R789 | 1588 | AGUGUUUUCAUUCGAUUCCUGUCUUCU |
| F790 | 1567 | CCAGCUUCCUAUAACUUGGACGAU |  |  |  |
| F791 | 1568 | GAACCACAUCAUGGUCUCUGUCU | R791 | 1589 | GGUGAUGCCGUGGUUGAUGU |
| F792 | 1569 | UCAUCGGGAAGACCUGGCUUA | R792 | 1590 | AGUUCUCGCUUCAGCACGAU |
| F793 | 1570 | GCUGCAGGACUAUGAGGAGAAGA |  |  |  |
| F794 | 1571 | CUCCCAGAGACCAACGUUCA | R794 | 1591 | UGGCCAAGCAAUCUGCGUAU |
| F795 | 1572 | GGACCUGGACCGUGUCCUUA | R795 | 1592 | UGCCAGGAUCAUAGCGUUACAG |
| F796 | 1573 | GGACCUGGACCGUGUCCUUA | R796a | 1593 | CUGGAGCAGGUCCACUAUAGGU |
|  |  |  | R796b | 1594 | UCCUCACACCUGCUCCUCA |
|  |  |  | R796c | 1595 | GCUGAUGGGUGGGCACUG |
|  |  |  | R796d | 1596 | GGUCUACCAGGACUGUCCCU |
| F797 | 1760 | CCCUUCGUAGACAUAUAGCUGUUCUC | R797 | 1597 | GGAAGGCAGGAAGAUUUUCAAUCUC |

TABLE D-continued

| Primer Name | SEQ ID | Primer Sequence | Primer Name | SEQ ID | Primer Sequence (target of PrimerC) |
|---|---|---|---|---|---|
| F798 | 1761 | UGGUGCUAGUUGCAAAGACACAA | R798 | 1598 | CGUUUAUAAGCACUGUCACCCCUU |
| F799 | 1762 | AGCGACGCCAUUGCUCAU | | | |
| F800 | 1763 | CCUCAACCAUUUCCGGCAAAU | | | |
| F801 | 1764 | CCAGCUCCCUGCGAAGAG | R801 | 1599 | AGGAUGAUGGCACUGAACUCC |
| F802 | 1765 | AAUCCCUGCAGUAGAUACGAAGACUA | R802 | 1600 | CACGUUAGUUAGUGAGCCAGGUAAU |
| F803 | 1766 | AGACCUUGCAGAAAUAGGAAUUGCU | R803 | 1601 | CUCAGGGCUCUGCAGCUCC |
| F804 | | | R804 | 1602 | CCUCCGGAAGGUCAUCUCA |
| F805 | 1767 | AAAGAAAAGACAGUUGGAGGAAUCUGU | R805 | | |
| F806 | 1768 | GAAGAAAAUGAAAAGGAGUUAGCAGCAU | R806b | 1603 | CUCCUAGAGUUUUCCAAGAACCAAGU |
| | | | R807 | 1604 | GAACCAAGUUCUUCCGAGGGAAU |
| F807 | 1769 | AGUGGCAAAAGAACUUCAGACUUUACA | | | |
| F808 | 1770 | GCGCUGCUCAGAAGCAAAA | | | |
| F809 | 1771 | GUAGAUCGCAUAAAGGAAGCAGUCA | R809 | 1605 | ACAGCGGCUGCGAUCACC |
| F810 | 1772 | GGAAGCAGUCAGGUCAAAGAAUAUGG | | | |
| F811 | | | R811 | 1606 | GCUGACUGCACAGGACAGG |
| F812 | 1773 | CAAGCAGAAACACUGUACAAAGAGAUU | | | |
| F813 | 1774 | GAGGGCGAGCUGCAUGAU | R813a | 1607 | CGAGACCCCAAAAGGUGUUUC |
| | | | R813b | 1608 | UCCACAUUUGUUGAGCACAAGGA |
| F814 | 1775 | CACAUCUUCAGGUGCUGGAUUUUUC | | | |
| F815 | 1776 | CUUUUGAAAAGCCAGUGAUGAUCUCAA | R815 | 1609 | CACCUUUAACUGCUUCAGGGUCAAUAU |
| F816 | 1777 | GCACCUUGACUUUAAGUGAGAGCA | R816 | 1610 | UGUUGUCCCGUGGCCAUU |
| F817 | 1778 | ACAGCACUGUUAUUACUACUUGGGUUUU | R817 | 1611 | GGCAUGAACCGUUCUGAGAUG |
| F818 | 1779 | CAAGCUCCUUACAUACCCAGCA | R818 | 1612 | CCAAAUUCGCCUUCUCCUAGAGU |
| F819 | 1780 | GCGUUCCUCGCUUGCAUU | R819 | 1613 | CUCCUCUGCACCAAGGUAAACA |
| F820 | 1781 | CGGGCAGGAAUCUGAUGACUUU | R820 | 1614 | UCCCUUCUAGUAAUUUGGGAAUGCC |
| F821 | 1782 | GCAGGGCAGCAACAUCUUUG | | | |
| F822 | 1783 | GGCUCCUGAGACCUUUGAUAACAUAAC | | | |
| F823 | 1784 | CGUGUGCUCCCUGGAUAUUCUUAGUA | R823 | 1615 | UCAGCUUUCUCCCACUGUAUUGAAUUUU |
| F824 | 1785 | CUGGCUCCGGGUGACAGC | R824 | 1616 | UCGGAAGGGCUGUGGAAUUG |
| | | | R824b | 1617 | CGUAGGCACACUCAAACAACGA |
| F825 | 1747 | CUGGCUCCGGGUGACAGC | R825 | 1618 | CUGAUUUCUGAACAUGGACUGUGG |
| F826 | 1748 | GACUCCCAUGACCCCCAUC | R826 | 1619 | ACGAAGUGCAAUGGUCUUUAGGU |
| F827 | 1749 | AAAAAUGUUAUGUCAGCGUUUGGCUUAA | | | |
| F828 | 1750 | GUAGGCGCGAGCUAAGCA | R828 | 1620 | GUGAGUCAUUUGUCUUGCUUUUGGU |
| F829 | 1751 | CAGGUCAUAUUGAACAUUCCAGAUACCU | | | |
| F830 | 1752 | GGUCCUGACGCAGGCUUC | | | |
| | | | F829 | 1621 | GACAGUCUGAAUCAUGUCCUUCAGU |
| | | | F830 | 1622 | GGGCUGCCCACCAUCUUC |
| | | | F831 | 1623 | UCAGCCUGAUAGUCUGGUACAAACU |
| F831 | 1753 | GUACCUGCAUCAACCCCUCUAA | | | |
| F832 | 1754 | CAGAGACCCGUGCUGAGUUU | | | |
| F833 | 1755 | GGAGAGAAGAGUGCACAAUACCA | R833 | 1624 | CCUCCACCUUGGGCUACUCA |

TABLE D-continued

| Primer Name | SEQ ID | Primer Sequence | Primer Name | SEQ ID | Primer Sequence (target of PrimerC) |
|---|---|---|---|---|---|
| F834 | 1756 | CCUGUAAUCCCUGCACUUUAGGA | R834 | 1625 | GGGUGAGCCUUGACACACA |
| F835 | 1757 | ACUUUCCAGUUGAGCAUCCCAAAUU | R835 | 1626 | CAGGGAUCAGUUCAGCUGUACC |
| F836 | 1758 | CGUCAGCGUGAUAUGUACCGUAUUUAU | | | |
| F837 | 1759 | CACCUCAGUAAUAUGGAAGUCCAAGUU | | | |

TABLE E

| Primer Name | SEQ ID | Primer Sequence | Primer Name | SEQ ID | Primer Sequence |
|---|---|---|---|---|---|
| F838 | 1627 | UGGGCUCUGUAAAGAAUAGUG | R838a | 1665 | AUCAGAGCUUAAACUGGGAAG |
|  |  |  | R838b | 1666 | AUCAGAGCUUAAACUGGGAAA |
| F839 | 1628 | UGCACACUUGGACAGCAUUUC | R839 | 1667 | GUCUCAGUUUCCUACCUGUAAAAUGAAG |
| F840 | 1629 | CCAGGACCAAUCUGGUCACAAACAUA | R840 | 1668 | ACUUAUUCUGACAGUUCUCUUUUUCCCT |
| F841 | 1630 | GGUGGGAGGAAAAGACAUAGGAT | R841 | 1669 | GGUGGCAGUGAGCUGUAACAGUA |
| F842 | 1631 | CUCCAGAGAGAAAGAAUCAACAGG | R842 | 1670 | UCAGCCUCCAUAUCACUUGAGC |
| F843 | 1632 | GCAUCCGUGACUCUCUGGAC | R843 | 1671 | AACUUGGGUUGAGCCAUAGGC |
| F844 | 1633 | UCAGUGACCAAUUCCUUGUAAUAACUC | R844 | 1672 | CCUGGUUCCAUGGAUUCCACAUUAAGA |
| F845 | 1634 | CAGAUCCCAAGCUCUUCCUCUT | R845 | 1673 | GCGUUUGUGUGUGCAUCUGT |
| F846 | 1635 | GUUCAUGCCACUGCACUUCACT | R846 | 1674 | UCUGGUGUGUGGAGAUGUCUUAC |
| F847 | 1636 | GGUGCACCCAUUACCCGAAT | R847a | 1675 | GGCUGCAAAAAGCUAUAAUUGUACC |
|  |  |  | R847b | 1676 | GGCUGCAAAAAGCUAUAACUGUACC |
| F848 | 1637 | UCCCCAUAUAAGUUCAAGCCUGUGT | R848 | 1677 | UGUGUUAGUCAGGAUUCUUCAGAGA |
| F849 | 1638 | UUGUAUAGCUACAGUUUUUCUGUUGGT | R849 | 1678 | UUCAGUUAUAUGUGUAUAAAUGUGUGCAUUG |
| F850 | 1639 | UAAAUAUGUGAGUCAAUUCCCCAAGUG | R850 | 1679 | CUCCAGAGACAGACUAAUAGGAGGUA |
| F851 | 1640 | GGCUAGAUUUUCCCCGAUGAUAGUAGT | R851 | 1680 | CCUGUGCCCAAGUUGAGAGAAT |
| F852 | 1641 | GGCUAGAUUUUCCCCUAUGAUAGUAGT | | | |
| F853 | 1642 | CAGUAAGUUAAAGGAUUGCAGGAG | R853 | 1681 | UAAUCCAGCUGUGGGAGGGA |
| F854 | 1643 | UGUGUAUAUGCAUUUACCUGUGAGUAUG | R854 | 1682 | GGUGCUAGGUGUGCUCAGGA |
| F855 | 1644 | UGUAACAAGGGCUACAGGAAUCAT | R855 | 1683 | CUUCACUCUCCUUCCCAAAUGUUUAUG |
| F856 | 1645 | GGGCAUCUCUUAUACUCAUGAAAUCAA | R856 | 1684 | CUAUGAUUCCCCCACUGCAGUC |
| F857 | 1646 | CUAUGCAGAAGAAUGAACCAGGGAT | R857 | 1685 | AGACCCCAAAAUUACUUGAGCCAAUUUA |
| F858 | 1647 | UGAUUCAUUUCCAUAGGGUAAGUGAAAA | R858 | 1686 | ACUUCAACUUCAAUUCAUCCACUGAAA |
| F859 | 1648 | GACAUUAUCACCAAUUUUUCUAGACG | R859 | 1687 | UGCUUGCCUGUAUGAAAAUAUCUC |
| F860 | 1649 | GACAUUCUCACCAAUUUUUCUAGACG | | | |
| F861 | 1650 | UGUGACAAGGGUGAUUUUCCUC | R861 | 1688 | UCCAAUCAUAGCCACAGUUUACAA |
| F862 | 1651 | CAUAAUUGUAUGAGCCACUUCCCAT | R862 | 1689 | GCACUCUUAUUCAUCUAGUUGCCGUT |
| F863 | 1652 | AGACUCACAAUGUACAAAAGCCUAUT | R863a | 1690 | CAUCAUGUGAGCCAAUUCCUCUC |
|  |  |  | R863b | 1691 | CAUCAUGUGAGCCAAGUCCUCUC |
| F864 | 1653 | AAUAUAUAUAAAGGGUAUGAUAGAACACUUGUC | R864a | 1692 | UUGCACCAAAUAUUGGUAAUUAAAUGUUUACT |
|  |  |  | R864b | 1693 | UUGCACCACAUAUUGGUAAUUAAAUGUUUACT |
| F865 | 1654 | GGCCUGGCAACUUAUAUGUAUUUUUGUAUT | R865 | 1694 | CACUGUAUCGUAUCCCAUUGCG |
| F866 | 1655 | GGCCUGACAACUUAUAUGUAUUUUUGUAUT | | | |

TABLE E-continued

| Primer Name | SEQ ID | Primer Sequence | Primer Name | SEQ ID | Primer Sequence |
|---|---|---|---|---|---|
| F867 | 1656 | CCAUCCUUAUCUCUUGUGUAUCUAUUCAUUCAA | R867 | 1695 | UUGCAAGCAAUUGCCAUAGAGGGA |
| F868 | 1657 | GAUUUGUCUGUAAUUGCCAGCAAAA | R868 | 1696 | ACAGAUUAAACUGUAACCAAAAUAAAAUUAGGC |
| F869 | 1658 | GAGCAAGACACCAUCUCAAGAA | R869a | 1697 | UGCCUAACCUAUGGUCAUAACG |
|  |  |  | R869b | 1698 | UGCCUAACCUAUGGUCAUACCG |
| F870 | 1659 | CAUGAUUGAUACAUGGAAAGAAUUCUCT | R870 | 1699 | CCCAGGAGGUGGAGAUUGAA |
| F871 | 1660 | ACCCAAAUCAACUCAACUCCAGUG | R871 | 1700 | UCCAUGUACUUUGUCCAAUGCUGA |
| F872 | 1661 | UUAGAGCAUUUAAAGUAAGCCACAGUGT | R872 | 1701 | UGUCAACACGAUUAACAUGCAAAGA |
| F873 | 1662 | CUGUACACAGGGCUUCCGAGT | R873 | 1702 | CAAAAUUCAAAGGGUAUCUGGGCUCT |
| F874 | 1663 | UUUCAGGGCUGUGAUCACUAGCAC | R874 | 1703 | UGUGCGCUGGUCUUACUCCUGUT |
| F875 | 1664 | AGAUACAUAGGUUAGAUAGAGAUAGGACAGA | R875 | 1704 | GCCCUAGUGGAUGAUAAGAAUAAUCAG |

What is claimed is:

1. A method for preparing a library of target nucleic acid sequences comprising
   (a) contacting a nucleic acid sample with a plurality of adaptors capable of amplification of one or more target nucleic acid sequences in the sample under conditions wherein the target nucleic acid(s) undergo a first amplification;
   (b) digesting resulting first amplification products to reduce or eliminate resulting primer dimers and prepare partially digested target amplicons, producing gapped, double stranded amplicons, then repairing the partially digested target amplicons; and
   (c) amplifying the repaired target amplicons in a second amplification using universal primers,
   thereby producing a library of target nucleic acid sequences;
   wherein each of the plurality of adaptors comprises a universal handle sequence and a target nucleic acid sequence and a cleavable moiety and optionally one or more tag sequences; wherein at least two and up to one hundred thousand target specific adaptor pairs are included; and
   wherein the target nucleic acid sequence of the adaptor includes at least one cleavable moiety and the universal handle sequence does not include the cleavable moiety.

2. The method of claim 1 wherein an optional tag sequence is included in at least one adaptor, and the cleavable moieties are included in the adaptor sequence flanking either end of the tag sequence.

3. The method of claim 2 wherein all of the adaptors comprise tag sequences having cleavable groups flanking either end of the tag sequences.

4. The method of claim 2 wherein each target specific pair of the plurality of adaptors includes up to 16,777,216 different adaptor combinations comprising different tag sequences.

5. The method of claim 1 carried out in a single, addition only workflow reaction, allowing for rapid production of highly multiplexed targeted libraries.

6. The method of claim 1 wherein the digestion and repair of step (b) is carried out in a single step or is carried out in a temporally separate manner at different temperatures.

7. The method of claim 6, wherein the plurality of gapped polynucleotide products in step (b) are contacted simultaneously with a digestion reagent and a repair reagent.

8. The method of claim 6, wherein the plurality of gapped polynucleotide products in step (b) are contacted sequentially with a digestion reagent and a repair reagent.

9. The method of claim 6, wherein a digestion and repair reagent comprises any one or a combination of one or a combination of uracil DNA glycosylase (UDG), apurinic endonuclease (APE1), RecJf, formamidopyrimidine [fapy]-DNA glycosylase (fpg), Nth endonuclease III, endonuclease VIII, polynucleotide kinase (PNK), Taq DNA polymerase, DNA polymerase I and/or human DNA polymerase beta; and any one or a combination of Phusion DNA polymerase, Phusion U DNA polymerase, SuperFi DNA polymerase, Taq DNA polymerase, Human DNA polymerase beta, T4 DNA polymerase and/or T7 DNA polymerase, SuperFiU DNA polymerase, E. coli DNA ligase, T3 DNA ligase, T4 DNA ligase, T7 DNA ligase, Taq DNA ligase, and/or 9° N DNA ligase.

10. The method of claim 9 wherein a digestion and repair reagent comprises any one or a combination of uracil DNA glycosylase (UDG), apurinic endonuclease (APE1), Taq DNA polymerase, Phusion U DNA polymerase, SuperFiU DNA polymerase, and T7 DNA ligase.

11. The method claim 1 wherein one or more of the method steps is conducted in an automated mode.

12. The method of claim 1 further comprising at least one purification step.

13. The method of claim 12 wherein a purification step is carried out only after step (c) or wherein a first purification step is carried out after step (b) and a second purification step is carried out after step (c).

14. The method of claim 1, further comprising analyzing the sequence of the resulting library of target nucleic acid sequences.

15. The method of claim 14 wherein analyzing comprises sequencing by traditional sequencing reactions, high throughput next generation sequencing, targeted multiplex array sequence detection, or any combination of two or more of the foregoing.

16. The method of claim 15 wherein sequencing is carried out in a bidirectional manner, thereby generating sequence reads in both forward and reverse strands for any given amplicon.

17. The method of claim 14 further comprising determining the abundance of at least one of the target nucleic acid sequences in the sample.

18. The method of claim 1, wherein a digestion reagent comprises any one or a combination of uracil DNA glycosylase (UDG), apurinic endonuclease (APE1), RecJf, formamidopyrimidine [fapy]-DNA glycosylase (fpg), Nth endonuclease III, endonuclease VIII, polynucleotide kinase (PNK), Taq DNA polymerase, DNA polymerase I and/or human DNA polymerase beta.

19. The method of claim 1 wherein a repair reagent comprises any one or a combination of Phusion DNA polymerase, Phusion U DNA polymerase, SuperFi DNA polymerase, Taq DNA polymerase, Human DNA polymerase beta, T4 DNA polymerase and/or T7 DNA polymerase, SuperFiU DNA polymerase, E. coli DNA ligase, T3 DNA ligase, T4 DNA ligase, T7 DNA ligase, Taq DNA ligase, and/or 9° N DNA ligase.

20. A method for preparing a library of target nucleic acid sequences comprising
- (d) contacting a nucleic acid sample with a plurality of adaptors capable of amplification of one or more target nucleic acid sequences in the sample under conditions wherein the target nucleic acid(s) undergo a first amplification;
- (e) digesting resulting first amplification products to reduce or eliminate resulting primer dimers and prepare partially digested target amplicons, producing gapped, double stranded amplicons, then repairing the partially digested target amplicons; and
- (f) amplifying the repaired target amplicons in a second amplification using universal primers,
- thereby producing a library of target nucleic acid sequences;
- wherein each of the plurality of adaptors comprise a universal handle sequence, one or more tag sequences, a target nucleic acid sequence and a cleavable moiety; and wherein at least two and up to one hundred thousand target specific adaptor pairs are included;
- wherein the target nucleic acid sequence of the adaptor includes at least one cleavable moiety, cleavable moieties are included in the flanking either end of the tag sequence and the universal handle sequence does not include the cleavable moiety.

* * * * *